US012747271B2

(12) United States Patent
Bao et al.

(10) Patent No.: US 12,747,271 B2
(45) Date of Patent: Sep. 29, 2026

(54) Av3 MUTANT POLYPEPTIDES FOR PEST CONTROL

(71) Applicant: SUTERRA LLC, Bend, OR (US)

(72) Inventors: Lin Bao, Portage, MI (US); Breck Davis, Kalamazoo, MI (US); Kyle Douglas Schneider, Kalamazoo, MI (US)

(73) Assignee: SUTERRA LLC, Bend, OR (US)

( * ) Notice: Subject to any disclaimer, the term of this patent is extended or adjusted under 35 U.S.C. 154(b) by 136 days.

(21) Appl. No.: 18/552,830

(22) PCT Filed: Mar. 31, 2022

(86) PCT No.: PCT/US2022/022939
§ 371 (c)(1),
(2) Date: Sep. 27, 2023

(87) PCT Pub. No.: WO2022/212777
PCT Pub. Date: Oct. 6, 2022

(65) Prior Publication Data
US 2025/0188136 A1 Jun. 12, 2025

Related U.S. Application Data

(60) Provisional application No. 63/169,643, filed on Apr. 1, 2021.

(51) Int. Cl.

| | |
|---|---|
| ***C12N 15/82*** | (2006.01) |
| ***A01N 63/50*** | (2020.01) |
| ***A01P 7/04*** | (2006.01) |
| ***C07K 14/435*** | (2006.01) |

(52) U.S. Cl.
CPC ........ *C07K 14/43595* (2013.01); *A01N 63/50* (2020.01); *A01P 7/04* (2021.08); *C12N 15/8286* (2013.01)

(58) Field of Classification Search
CPC ................................................ C07K 14/43595
USPC ......................................................... 800/279
See application file for complete search history.

(56) References Cited

U.S. PATENT DOCUMENTS

| | | | |
|---|---|---|---|
| 4,945,050 | A | 7/1990 | Sanford et al. |
| 4,996,155 | A | 2/1991 | Sick et al. |
| 5,045,469 | A | 9/1991 | Payne et al. |
| 5,055,294 | A | 10/1991 | Gilroy |
| 5,073,632 | A | 12/1991 | Donovan |
| 5,104,974 | A | 4/1992 | Sick et al. |
| 5,135,867 | A | 8/1992 | Payne et al. |
| 5,187,091 | A | 2/1993 | Donovan et al. |
| 5,236,843 | A | 8/1993 | Narva et al. |
| 5,281,530 | A | 1/1994 | Sick et al. |
| 5,322,687 | A | 6/1994 | Donovan et al. |
| 5,356,623 | A | 10/1994 | Von Tersch et al. |
| 5,378,625 | A | 1/1995 | Donovan et al. |
| 5,407,825 | A | 4/1995 | Payne et al. |
| 5,424,409 | A | 6/1995 | Ely et al. |
| 5,530,195 | A | 6/1996 | Kramer et al. |
| 5,593,881 | A | 1/1997 | Thompson et al. |
| 5,616,319 | A | 4/1997 | Donovan et al. |
| 5,670,365 | A | 9/1997 | Feitelson |
| 5,679,343 | A | 10/1997 | Donovan et al. |
| 5,683,691 | A | 11/1997 | Peferoen et al. |
| 5,723,756 | A | 3/1998 | Peferoen et al. |
| 5,723,758 | A | 3/1998 | Payne et al. |
| 5,743,477 | A | 4/1998 | Walsh et al. |
| 5,753,492 | A | 5/1998 | Schnepf et al. |
| 5,763,568 | A | 6/1998 | Atkinson et al. |
| 5,824,792 | A | 10/1998 | Payne et al. |
| 5,831,011 | A | 11/1998 | Payne et al. |
| 5,837,237 | A | 11/1998 | Peferoen et al. |
| 5,874,288 | A | 2/1999 | Thompson et al. |
| 5,932,209 | A | 8/1999 | Thompson et al. |
| 5,942,664 | A | 8/1999 | Baum et al. |
| 5,959,182 | A | 9/1999 | Atkinson et al. |
| 5,973,231 | A | 10/1999 | Bradfisch et al. |
| 5,985,831 | A | 11/1999 | Bradfisch et al. |
| 6,028,246 | A | 2/2000 | Lambert et al. |
| 6,043,415 | A | 3/2000 | Strizhov et al. |

(Continued)

FOREIGN PATENT DOCUMENTS

| | | | |
|---|---|---|---|
| AU | 2001285900 | B2 | 2/2005 |
| AU | 784649 | B2 | 5/2006 |

(Continued)

OTHER PUBLICATIONS

Witkowski et al. Biochemistry 38: 11643-11650 (Year: 1999).*
NCBI Accession No. AAF65230.1; Flare11-S3 [Plastid transformation vector pMSK49]; Apr. 24, 2000.
NCBI Accession No. AAL07474.1; lectin GNA-1 [Galanthus nivalis]; Sep. 26, 2001.
NCBI Accession No. P81295.1; RecName: Full=Pathogenesis-related 5 protein Jun a 3.0101; Short=PR-5 protein Jun a 3.0101; AltName: Full=Pollen allergen Jun a 3; AltName: Allergen=Jun a 3.0101; Flags: Precursor; May 25, 2022.
NCBI, UniProtKB/Swiss-Prot. S0F209.1, Omega/Kappa-hexatoxin-Hv1h [Hydronyche versuta], Oct. 2014, 2 pages.

(Continued)

*Primary Examiner* — Li Zheng
(74) *Attorney, Agent, or Firm* — Michael Best & Friedrich LLP

(57) ABSTRACT

New insecticidal peptides, polypeptides, proteins, and nucleotides; their expression in culture and plants; methods of producing the peptides, polypeptides, proteins, and nucleotides; new processes; new production techniques; new formulations; and new organisms, are disclosed. The present disclosure is also related to mutants named Av3 mutant polypeptides (AMPs) that are non-naturally occurring, modified-form of the peptide, Av3, isolated from the sea anemone, *Anemonia viridis*. Here we describe: polynucleotides encoding AMPs; various formulations and combinations of both polynucleotides and peptides; and methods for using the same that are useful for the control of insects.

24 Claims, 73 Drawing Sheets

Specification includes a Sequence Listing.

(56) References Cited

U.S. PATENT DOCUMENTS

| | | | |
|---|---|---|---|
| 6,048,839 | A | 4/2000 | Bradfisch et al. |
| 6,063,605 | A | 5/2000 | Ely et al. |
| 6,063,756 | A | 5/2000 | Donovan et al. |
| 6,077,937 | A | 6/2000 | Payne et al. |
| 6,096,708 | A | 8/2000 | Payne et al. |
| 6,107,278 | A | 8/2000 | Schnepf et al. |
| 6,143,550 | A | 11/2000 | Lambert et al. |
| 6,150,165 | A | 11/2000 | Payne et al. |
| 6,150,589 | A | 11/2000 | Payne et al. |
| 6,156,573 | A | 12/2000 | Malvar et al. |
| 6,166,195 | A | 12/2000 | Schnepf et al. |
| 6,172,281 | B1 | 1/2001 | Van Mellaert et al. |
| 6,320,100 | B1 | 11/2001 | Koziel et al. |
| 6,326,351 | B1 | 12/2001 | Donovan et al. |
| 6,399,330 | B1 | 6/2002 | Donovan et al. |
| 6,448,226 | B1 | 9/2002 | Lambert et al. |
| 6,468,523 | B1 | 10/2002 | Mettus et al. |
| 6,537,756 | B1 | 3/2003 | Rupar et al. |
| 6,570,005 | B1 | 5/2003 | Schnepf et al. |
| 6,573,240 | B1 | 6/2003 | Payne et al. |
| 6,583,264 | B2 | 6/2003 | King et al. |
| 6,686,452 | B2 | 2/2004 | Rupar et al. |
| 6,727,409 | B1 | 4/2004 | Lambert et al. |
| 6,780,408 | B1 | 8/2004 | Bosch et al. |
| 6,784,337 | B1 | 8/2004 | Atkinson et al. |
| 6,831,062 | B2 | 12/2004 | Thompson et al. |
| 6,855,873 | B1 | 2/2005 | Van Mellaert et al. |
| 6,949,626 | B2 | 9/2005 | Donovan et al. |
| 6,962,705 | B2 | 11/2005 | Malvar et al. |
| 7,019,197 | B1 | 3/2006 | Christou et al. |
| 7,208,474 | B2 | 4/2007 | Bermudez et al. |
| 7,214,788 | B2 | 5/2007 | Guzov et al. |
| 7,244,880 | B2 | 7/2007 | Arnaut et al. |
| 7,250,501 | B2 | 7/2007 | Malvar et al. |
| 7,279,547 | B2 | 10/2007 | King et al. |
| 7,304,206 | B2 | 12/2007 | Malvar et al. |
| 7,355,099 | B2 | 4/2008 | Carozzi et al. |
| 7,361,808 | B2 | 4/2008 | Boets et al. |
| 7,595,173 | B2 | 9/2009 | Krebs et al. |
| 7,943,819 | B2 | 5/2011 | Baum et al. |
| 8,575,070 | B2 | 11/2013 | Watt et al. |
| 8,993,295 | B2 | 3/2015 | Seed et al. |
| 9,567,373 | B2 | 2/2017 | Watt et al. |
| 9,567,381 | B2 | 2/2017 | Kennedy et al. |
| 10,669,319 | B2 | 6/2020 | Kennedy et al. |
| 2001/0010932 | A1 | 8/2001 | Schnepf et al. |
| 2001/0026939 | A1 | 10/2001 | Rice et al. |
| 2001/0026941 | A1 | 10/2001 | Held et al. |
| 2002/0015066 | A1 | 2/2002 | Siwinski et al. |
| 2002/0152496 | A1 | 10/2002 | Fischhoff et al. |
| 2003/0017967 | A1 | 1/2003 | Asano et al. |
| 2003/0046726 | A1 | 3/2003 | Koziel et al. |
| 2003/0054391 | A1 | 3/2003 | Bulla, Jr. |
| 2003/0134310 | A1 | 7/2003 | Cujec |
| 2003/0144192 | A1 | 7/2003 | Donovan et al. |
| 2003/0167517 | A1 | 9/2003 | Arnaut et al. |
| 2003/0167522 | A1 | 9/2003 | Narva et al. |
| 2003/0229919 | A1 | 12/2003 | Isaac et al. |
| 2004/0018982 | A1 | 1/2004 | Schnepf et al. |
| 2004/0033523 | A1 | 2/2004 | English et al. |
| 2004/0058860 | A1 | 3/2004 | Payne et al. |
| 2004/0093637 | A1 | 5/2004 | Malvar et al. |
| 2004/0123343 | A1 | 6/2004 | La Rosa et al. |
| 2004/0194165 | A1 | 9/2004 | Payne et al. |
| 2005/0091714 | A1 | 4/2005 | Sunchis et al. |
| 2005/0097635 | A1 | 5/2005 | Lambert et al. |
| 2005/0227321 | A1 | 10/2005 | Krebs et al. |
| 2006/0051822 | A1 | 3/2006 | Donovan et al. |
| 2006/0174372 | A1 | 8/2006 | Malvar et al. |
| 2006/0218666 | A1 | 9/2006 | Isaac et al. |
| 2006/0242734 | A1 | 10/2006 | King et al. |
| 2007/0061919 | A1 | 3/2007 | Baum et al. |
| 2007/0074308 | A1 | 3/2007 | Boets et al. |
| 2007/0163000 | A1 | 7/2007 | Rupar et al. |
| 2007/0208168 | A1 | 9/2007 | Guzov et al. |
| 2007/0245430 | A1 | 10/2007 | Abad et al. |
| 2007/0277263 | A1 | 11/2007 | Anderson et al. |
| 2008/0016596 | A1 | 1/2008 | Abad et al. |
| 2008/0020968 | A1 | 1/2008 | Abad et al. |
| 2008/0040827 | A1 | 2/2008 | Donovan et al. |
| 2008/0047034 | A1 | 2/2008 | Arnaut et al. |
| 2009/0099081 | A1 | 4/2009 | Carozzi et al. |
| 2009/0183278 | A1 | 7/2009 | Abad et al. |
| 2010/0055761 | A1 | 3/2010 | Seed et al. |
| 2015/0148288 | A1 | 5/2015 | Kennedy et al. |
| 2017/0174731 | A1 | 6/2017 | Kennedy et al. |
| 2017/0183374 | A1 | 6/2017 | Watt et al. |
| 2018/0362598 | A1 | 12/2018 | Carlson et al. |
| 2019/0261634 | A1 | 8/2019 | Carlson et al. |
| 2019/0264197 | A1 | 8/2019 | Barkan et al. |
| 2020/0207818 | A1 | 7/2020 | Schneider et al. |
| 2020/0255482 | A1 | 8/2020 | Kennedy et al. |
| 2020/0277345 | A1 | 9/2020 | Kennedy et al. |
| 2020/0315001 | A1 | 10/2020 | Khan et al. |

FOREIGN PATENT DOCUMENTS

| | | | |
|---|---|---|---|
| CA | 2410153 | A1 | 6/2004 |
| CN | 1199569 | A | 11/1998 |
| CN | 1260397 | A | 7/2000 |
| CN | 1366822 | A | 9/2002 |
| CN | 1401772 | A | 3/2003 |
| CN | 1942582 | A | 4/2007 |
| CN | 1952151 | A | 4/2007 |
| CN | 101003789 | A | 7/2007 |
| CN | 106367361 | A | 2/2017 |
| EP | 1681351 | A1 | 7/2006 |
| EP | 1987178 | B1 | 3/2015 |
| JP | 2005139167 | A | 6/2005 |
| JP | 2007006895 | A | 1/2007 |
| JP | 2008518624 | A | 6/2008 |
| JP | 2009286708 | A | 12/2009 |
| JP | 2012504623 | A | 2/2012 |
| MX | 9606262 | A | 1/1998 |
| MX | PA01004361 | A | 6/2003 |
| MX | PA02008705 | A | 12/2004 |
| MX | PA03006130 | A | 2/2005 |
| RU | 2278161 | C1 | 6/2006 |
| UA | 75317 | C2 | 4/2006 |
| UA | 75570 | C2 | 5/2006 |
| WO | 9100915 | A1 | 1/1991 |
| WO | 9534656 | A1 | 12/1995 |
| WO | 199840490 | A1 | 9/1998 |
| WO | 199840491 | A2 | 9/1998 |
| WO | 2000026371 | A1 | 5/2000 |
| WO | 2000026378 | A1 | 5/2000 |
| WO | 2001014562 | A1 | 3/2001 |
| WO | 2001034811 | A2 | 5/2001 |
| WO | 2001047952 | A2 | 7/2001 |
| WO | 2002014517 | A1 | 2/2002 |
| WO | 2002015701 | A2 | 2/2002 |
| WO | 2002057664 | A2 | 7/2002 |
| WO | 2003042369 | A2 | 5/2003 |
| WO | 2003082910 | A1 | 10/2003 |
| WO | 2004016653 | A2 | 2/2004 |
| WO | 2004020636 | A1 | 3/2004 |
| WO | 2005066202 | A2 | 7/2005 |
| WO | 2005082077 | A2 | 9/2005 |
| WO | 2006052806 | A2 | 5/2006 |
| WO | 2006053473 | A1 | 5/2006 |
| WO | 2007027776 | A2 | 3/2007 |
| WO | 2007045160 | A1 | 4/2007 |
| WO | 2007062064 | A2 | 5/2007 |
| WO | 2007087567 | A2 | 8/2007 |
| WO | 2007107302 | A2 | 9/2007 |
| WO | 2008036138 | A2 | 3/2008 |
| WO | 2008132743 | A2 | 11/2008 |
| WO | 2008153551 | A1 | 12/2008 |
| WO | 2009155557 | A2 | 12/2009 |
| WO | 2010/039652 | A2 | 4/2010 |
| WO | 2010133644 | A2 | 11/2010 |
| WO | 2011084634 | A1 | 7/2011 |
| WO | 2012038950 | A1 | 3/2012 |
| WO | 2013040142 | A2 | 3/2013 |

(56) References Cited

FOREIGN PATENT DOCUMENTS

| | | | | |
|---|---|---|---|---|
| WO | 2013134734 A2 | | 9/2013 | |
| WO | 2013166211 A2 | | 11/2013 | |
| WO | 2014200910 A2 | | 12/2014 | |
| WO | 2018207036 A1 | | 11/2018 | |
| WO | WO-2020056315 A1 | * | 3/2020 | ............ A01N 63/50 |

OTHER PUBLICATIONS

Norton et al., "The Cystine Knot Structure of lon Channel Toxins and Related Polypeptides", Toxicon, vol. 36, No. 11, pp. 1573-1583, 1998.

PCT International Search Report, PCT/US2017/055596, mailed Feb. 23, 2018 (6 pages).

Pena et al., "Molecular mechanism of histone H3K4me3 recognition by plant homeodomain of ING2." Nature 442, 100-103 (2006).

Pence, "The antimetabolite imidazole as a pesticide", California Agric., Jan. 1965, pp. 13-15.

Peña et al., "A Bacillus thuringiensis S-Layer Protein Involved in Toxicity against Epilachna varivestis (Coleoptera: Coccinellidae)", App & Environ Microbiology, Jan. 2006, vol. 72, No. 1, pp. 353-360.

Pogue et al., "Production of Pharmaceutical-Grade Recombinant Aprotinin and a Monoclonal Antibody Product Using Plant-Based Transient Expression Systems", Plant Biotechnology Journal, 2010, vol. 8, pp. 638-654.

Quintero-Hernandez et al., "Scorpion and Spider Venom Peptides: Gene Cloning and Peptide Expression", Toxicon, 2011, vol. 58, pp. 644-663.

Rose R. I., "Pesticides and public health: integrated methods of mosquito management," Emerg. Infect. Dis., Jan.-Feb. 2001, vol. 7, No. 1, pp. 17-23.

Rowell et al., "Bt Basics for Vegetable Integrated Pest Management", University of Kentucky—College of Agriculture, UK Cooperative Extension Service, Jul. 2005.

Sambrook and Russell, Molecular Cloning: A Laboratory Manual, 2001, Table of Contents.

Sathasivan et al., "Nucleotide sequence of a mutant acetolactate synthase gene from an imidazolinone-resistant *Arabidopsis thaliana* var. Columbia", Nucl. Acids Res., (1990), vol. 18, No. 8, p. 2188.

Shi et al., "Construction of Plant Expression Vector of Fusion Gene Ubiquitin and Signal peptide Sequence of Pathogenesis-related Protein 1a", Journal of Shihezi University (Natural Science), 2006, vol. 24, No. 3, pp. 265-269.

Shim et al., "NeuroBactrus, a Novel, Highly Effective, and Environmentally Friendly Recombinant Baculovirus Insecticide," Applied and Environmental Microbiology, 2013, vol. 79, No. 1, pp. 141-149.

Stalker et al., Purification and Properties of a Nitrilase Specific for the Herbicide Bromoxynil and Corresponding Nucleotide Sequence Analysis of the bxn Gene, J. Biol. Chem., May 5, 1988, vol. 263, No. 13, pp. 6310-6314.

Staub, J.M. and Maliga, P., "Accumulation of D1 polypeptidde in tobacco plastids is regulated via the untranslated region of the psbA mRNA", The EMBO J. (1993) vol. 12 No. 2, pp. 601-606.

Svab, et al., High-frequency plastid transformation in tobacco by selection for a chimeric aadA gene, Proc. Natl. Acad. Sci., Feb. 1993, vol. 90, pp. 913-917.

Svab, et al., Stable Transformation of Plastids in Higher Plants, Proc. Natl. Acad. Sci., Nov. 1990, vol. 87, pp. 8526-8530.

Tabashnik et al., "Insect resistance to Bt crops: lessons from the first billion acres", Nature Biotechnology, 31 (6):510-521, 2013.

Takahashi et al., "Solution structure of hanatoxin1, a gating modifier of voltage-dependent K+ channels: common surface features of gating modifier toxins", Journal of Molecular Biology, Mar. 31, 2000, vol. 297, Issue 3, pp. 771-780.

UniProt entry MYPU_2440, 2001.

UniProt entry X1P169, 2014.

UniProt P04824, Alpha-glactosidase 1, MEL1, Retrieved from < https://www.uniprot.org/uniprot/P04824 > on Apr. 6, 2022.

Van Damme, E.J.M., et al., "Biosynthesis, primary structure and molecular cloning of snowdrop (*Galanthus nivalis* L.) lectin", European Journal of Biochemistry, 1991, vol. 202, pp. 23-30.

Yan, F. et al., "Improved Insecticidal Toxicity by Fusing Cry1Ac of Bacillus thuringiensis with Av3 of Anemonia viridis", Current Microbiology, Published online Dec. 29, 2013 (May 2014), vol. 68, No. 5, p. 604-609.

Yokoyama et al., "Chain-growth polymerization for poly(3-hexylthiophene) with a defined molecular weight and a low polydispersity." Macromolecules 37.4 (2004): 1169-1171.

Yokoyama et al., "Novel cry gene from *Paenibacillus lentimorbus* strain Semadara inhibits ingestion and promotes insecticidal activity in *Anomala cuprea* larvae", J of Invertebrate Pathology, 2004, vol. 85, pp. 25-32.

Yu et al., "Glutathionylation-triggered conformational changes of glutaredoxin Grx1 from the yeast *Saccharomyces cerevisiae*", Proteins, 2008, vol. 72, No. 3, pp. 1077-1083.

Zhang et al., "Cloning and Analysis of the First cry Gene from *Bacillus popilliae*", J of Bacteriology, Jul. 1997, vol. 179, No. 13, pp. 4336-4341.

Zhu et al., "Evolutionary origin of inhibitor cystine knot peptides", FASEB Jour., Sep. 2003, vol. 17, pp. 1765-1767.

Zimmermann, et al., "Protein translocation across the ER membrane", Biochimica et Biophysica Acta, (Jun. 27, 2010) Elsevier, Amsterdam, vol. 1808, No. 3, pp. 912-924.

European Extended Search Report, EP Application No. 20191154.2, dated Oct. 21, 2020, 9 pages.

European Extended Search Report, EP Application No. 17862582.8, dated Oct. 26, 2020, pp. 22.

Lambert et al., "A Bacillus thuringiensis Insecticidal Crystal Protein with a High Activity against Members of the Family Noctuidae", Applied & Environmental Microbiology, Jan. 1996, vol. 62, No. 1, pp. 80-86.

McCormick et al., "Leaf Disc Transformation of Cultivated Tomato (L. *esculentum*) using Agrobacterium Trumefaciens", Plant Cell Reports, 1986, vol. 5, pp. 81-84.

Ostergaard et al., "Increasing galactose consumption by *Saccharomyces cerevisiae* through metabolic engineering of the GAL gene regulatory network," Nature Biotechnology, 2000, vol. 18, pp. 1283-1286.

Ostergaard et al., "Physiological Studies in Aerobic Batch Cultivations of *Saccharomyces cerevisiae* Strains Harboring the MEL1," Biotechnology and Bioengineering, 2000, vol. 68, No. 3, pp. 252-259.

Gill, G. et al., "Mutants of GAL4 Protein Altered in an Activation Function", Cell, 1987, vol. 51, pp. 121-126.

Angsuthanasombat, C. et al., "Directed Mutagenesis of the Bacillus Thuringiensis Cry11A Toxin Reveals a Crucial Role in Larvicidal Activity of Arginine-136 in Helix 4," Journal of Biochemistry and Molecular Biology, Sep. 2001, vol. 34, No. 5, pp. 402-407.

BBC New Article: May 10, 2016, "Kew report makes new tally for nmber of world's plants", Retrieved from < https://www.bbc.com/ news/science-environment-36230858 on Sep. 23, 2019.

Crickmore et al., "Revision of the Nomenclature for the Bacillus thuringiensis Pesticidal Crystal Proteins", Microbiology and Molecular Biology Reviews, vol. 62, No. 3, Sep. 1998, pp. 807-813.

Czapla, T.H. et al., Effect of Plant Lectins on the Larval Development of Europran Corn Borer (Lepidoptera: Pyralidae) and Southern Corn Rootworm (Coleoptera: Chrysomelidae) J. Econ. Entomol., Dec. 1990, vol. 83, No. 6, pp. 2480-2485. cited byapplicant.

Anthony Shelton, Ph.D., "Biological Control A Guide to Natural Enemies in North America", as an update dated "Last updated Feb. 25, 2015" by Zachary P. Cohen, Cornell University.

De Maagd et al., "How Bacillus thuringiensis has evolved specific toxins to colonize the insect world," Trends in Genetics, Apr. 2001, vol. 17, No. 4, pp. 193-199.

De Maagd et al., "Identification of Bacillus Thuringiensis Delta-Endotoxin Cry1C Domain III Amino Acid Residues Involved in Insect Specificity," Applied and Environmental Microbiology, Oct. 1999, vol. 65, No. 10, pp. 4369-4374.

Guo, H. et al., "Protein tolerance to random amino acid change," PNAS, Jun. 2004, Vo. 101, No. 25, pp. 9205-9210.

(56) References Cited

OTHER PUBLICATIONS

Guo, L. et al., "Fractionation and identification of Alaska pollock skin collagen-derived mineral chelating peptides" Food Chemistry 173: 536-542, 2015.
International Search Report and Written Opinion issued in related PCT Application No. PCT/US2022/022939, dated Nov. 9, 2022.
Andrews et al., "Characterizatino of the lipid acyl hydrolase activity of the major potato (*Solanum tuberosum*) tuber protein, patatin, by cloning and abundant expression in a baculovirus vector", Biochem. J., (1988), vol. 252, pp. 199-206.
Ayres, Nicola M. et al., Genetic Transformation of Rice, Critical Reviews in Plant Science, 1994, vol. 13, No. 3 pp. 219-239.
Barloy, F. et al., Cloning and Expression of the First Anaerobic Toxin Gene from *Clostridium bifermentans* subsp. Malaysia, Encoding a New Mosquitocidal Protein with Homologies to Bscillus thuringiensis Delta-Endotoxins, J of Bacteriology, Jun. 1996, vol. 178, No. 11, pp. 3099-3105.
Barloy, F. et al., Distribution of Clostridial cry-Like Genes Among Bacillus thuringiensis and Clostridium Strains, Current Microbiology, 1998, vol. 36, pp. 232-237.
Benchabane, Meriem, et al. Preventing unintended proteolysis in plant protein biofactories, Plant Biotechnology Journal, No. 6, 2008, pp. 633-648.
Blumenthal et al., Voltage-gated sodium channel toxins: poisons, probes, and future promise. Cell Biochem Biophys. 2003; 38(2):215-38.
Bommineni, V.R., et al., An Evaluation of Target Cells and Tissues used in Genetic Transformation of Cereals, Maydica, Apr. 1997, vol. 42, pp. 107-120.
Borovsky, D., et al., Expression of Aedes trypsin-modulating oostatic factor on the virion of TMV: A potential larvicide, Proc Natl Acad Sci, Dec. 12, 2006, vol. 103, No. 50, pp. 18963-18968.
Borovsky, D., Trypsin-modulating oostatic factor: a potential new larvicide for mosquito control, Journal of Experimental Biology, 2003 vol. 206, No. 21, pp. 3869-3875.
Bosmans, Frank et al, Sea Anemone Venom as a Source of Insecticidal Peptides Acting on Voltage-Gated Na+ Channels, Toxicon, V 49, No. 4, pp. 550-560, Mar. 2007; XP002705659, ISN:0041-0101.
Broderick, N.A. et al., Midgut Bacteria Required for Bacillus Thuringiensis Insecticidal Activity, PNAS, Oct. 10, 2006, vol. 103, No. 41., pp. 15196-15199.
Brogdon WG, McAllister JC, "Insecticide Resistance and Vector Control", Emerg Infect Dis 1998, 4(4):605-613.
Cavallini, C., Biological Action of Two Tomato Cysteine-Rich Miniproteins, Ph.D. Thesis; Dept of Biotechnology; University of Verona, 2010; XP002705655, retrieved from the internet: URL:http://www.univr.it/documenti/AllegaiOA/allegatooa.sub.--5484.pdf.
Chambaud, I. et al. "The complete genome sequence of the murine respiratory pathogen Mycoplasma pulmonis", Nucleic Acids Research, Information Retrieval Ltd, vol. 29, No. 10, Jan. 1, 2001 (Jan. 1, 2001), pp. 2145-2153.
Chang, H.C., et al., De novo folding of GFP fusion proteins: high efficiency in eukaryotes but not in bacteria, Journal of Molecular Biology, Oct. 21, 2005, vol. 353, No. 2, pp. 397-409.
Chen, M.H., et al., Signal peptide-dependent targeting of a rice alpha-amylase and cargo proteins to plastids and extracellular compartments of plant cells, Plant Physiology, Jul. 2004, vol. 135, No. 3, pp. 1367-1377.
Daskalova et al., "Engineering of *N. benthamiana* L. plants for production of N-acetylgalactosamine-glycosylated proteins", BMC Biotechnology, Aug. 24, 2010, vol. 10, No. 62.
De Loose et al., "The extensin signal peptide allows secretion of a heterologous protein from protoplasts", Gene, 1991, vol. 99, pp. 95-100.
Down et al., "Insecticidal Spider Venom Toxin Fused to Snowdrop Lectin is Toxic to the Peach-potato Aphid, *Myzus persicae* (Hemiptera: Aphididae) and the Rice Brown Planthopper, *Nilaparvata Lugens* (Hemiptera: Delphacidae)", Pest Manag. Sci., Jan. 2006, vol. 62, pp. 77-85.
Escoubas et al., "Structure and pharmacology of spider venom neurotoxins", Biochimie, vol. 82, Issues 9-10, Sep. 10, 2000, pp. 893-907.
Figueiredo et al., "Heterologous Expression of an Insecticidal Gene from the Armed Spider (*Phoneutria nigriventer*)", Journal of Venomous Animals and Toxins Including Tropical Diseases, vol. 14, No. 2, pp. 274-293, 2008 XP002705657, ISSN: 1678-9199.
Fitches et al., "An evaluation of garlic lectin as an alternative carrier domain for insecticidal fusion proteins", Insect Science, 2008, vol. 15, pp. 483-495.
Fitches et al., "Fusion proteins containing insect-specific toxins as pest control agents: snowdrop lectin delivers fused insecticidal spider venom toxin to insect haemolymph following oral ingestion", J. Insect Physiol., Feb. 2004, vol. 50, pp. 61-71.
Fitches et al., "The insecticidal activity of recombinant garlic lectins towards aphids", Insect Biochem. Mol. Biol., 2008, vol. 38, pp. 905-915.
Fletcher et al., "The Structure of a Novel Insecticidal Neurotoxin, w-atracotoxin-HV1, from the venom of an Australian funnel web spider", Nature Structural Biology vol. 4, No. 7, pp. 559-566, 1997.
Galvez et al., "Purification and characterization of a unique, potent, peptidyl probe for the high conductance calcium-activated potassium channel from venom of the scorpion *Buthus tamulus*", Journal of Biological Chemistry, Jul. 5, 1990; vol. 265, No. 19, pp. 11083-11090.
Gimenez-Gallego et al., "Purification, sequence, and model structure of charybdotoxin, a potent selective inhibitor of calcium-activated potassium channels", Proc. Natl. Acad. Sci., May 1988, vol. 85, No. 10, pp. 3329-3333.
Gressent et al., "Pea Albumin 1 Subunit b (PA1b), a Promising Bioinsecticide of Plant Origin", Toxins, vol. 3, No. 12, pp. 1502-1517, Dec. 2011; XP002705656, ISSN: 2072-6651.
Guardia et al., "Structural basis of redox-dependent modulation of galectin-1 dynamics and function", Glycobiology, 2014, vol. 24, No. 5, pp. 424-441.
Heath et al., "Characterization of the protease processing sites in a multidomain proteinase inhibitor precursor from Nicotiana alata", European Journal of Biochemistry, (1995), vol. 230, pp. 250-257.
Hernandez-Campuzano et al., Expression of a spider venom peptide in transgenic tobacco confers insect resistance, Toxicon, 2009, vol. 53, No. 1, pp. 122-128.
Hofte et al., "Insecticidal Crystal Proteins of Bacillus thuringiensis", Microbiological Reviews, vol. 53, No. 2, Jun. 1989, pp. 242-255.
International Search Report and Written Opinion for PCT application No. PCT/US2019/051093, mailed Feb. 4, 2020, 18 pages.
Ishida et al., "High efficiency transformation of maize (*Zea mays* L.) mediated by Agrobacterium tumefaciens", Nature Biotechnology, Jun. 1996, vol. 14, pp. 745-750.
Jennings et al., "Biosynthesis and insecticidal properties of plant cyclotides: The cyclic knotted proteins from Oldenlandia affinis", PNAS, 98(19):10614-10619, 2001.
Jones et al., "Global trends in emerging infectious diseases." Nature 451.7181 (2008): 990-993.
Jones et al., "The Cys-Loop Ligand-Gated Ion Channel Gene Superfamily of the Nematode, Caenorhabditis Elegans", Invert Neurosci, 2008, vol. 8, pp. 41-47.
Khan et al., "Spider venom toxin protects plants from insect attack", Transgenic Research, 2006, vol. 15, pp. 349-357.
Kramer, K.J. et al., "Sequence of a cDNA and expression of the gene encoding epidermal and gut chitinases of Manduca sexta", Insects Biochemistry and Molecular Biology, (Sep. 1, 1993) Elsevier Ltd, vol. 23, No. 6, pp. 691-701.
Kumari et al., "Cysteine-Rich Peptide Family with Unusual Disulfide Connectivity from Jasminum sambac", Journal of Natural Products, 78:2791-2799, 2015.
Kwok et al., "GFP-labelled Rubisco and aspartate aminotransferase are present in plastid stromules and traffic between plastids", Journal of Experimental Botany, Mar. 2004, vol. 55, No. 397, pp. 595-604.
Lew et al., "Structure-Function Relationships of ?-Conotoxin GVIA" Journal of Biological Chemistry, 1997, vol. 272, No. 18, pp. 12014-12023.

(56) References Cited

OTHER PUBLICATIONS

Marrone et al., "Improvements in laboratory rearing of the southern corn rootworm, *Diabrotica undecimpuncta howardi* Barber (Coleoptera: Chrysomelidae), on an artificial diet and corn", J. of Economic Entomology, (1985), vol. 78, pp. 290-293.
Martinez et al., "Toxin III From Anemonia-Sulcata Primary Structure", Febs Letters, V 84, No. 2, pp. 247-252; 1977; XP002705658, ISSN: 0014-5793.
McBride et al., "Controlled expression of plastid transgenes in plants based on a nuclear DNA-encoded and plastid-targeted T7 RNA polymerase", Proc. Natl. Acad. Sci. USA, (Jul. 1, 1994), vol. 91, pp. 7301-7305.
Memelink et al., "Structure and regulation of tobacco extensin", Plant Journal, (1993), vol. 4, No. 6, pp. 1011-1022.
Midoro-Horiuti et al., "Variable Expression of Pathogenesis-Related Protein Allergen in Mountain Cedar (*Juniperas ashei*) Pollen", J Immunol, 164(4):2188-2192, 2000.
Moran et al., Sea anemone toxins affecting voltage-gated sodium channels—molecular and evolutionary features, Toxicon. Dec. 15, 2009; 54(8): 1089-1101.
Mukherjee et al., "Orally active acaricidal peptide toxins from spider venom", Toxicon, 2006, vol. 47, pp. 182-187.
De Dianous, S. et al., "The Effect of the Mode of Application on the Toxicity of Androctonus australis Hector Insect Toxin", Pestic. Sci., 23:35-40, 1988.
Dauplais, M., et al., "On the convergent evolution of animal toxins", Journal of Biological Chemistry, Feb. 14, 1997; vol. 272, No. 7, pp. 4302-4309.
Aronson, A. et al., "Why Bacillus thuringiensis insecticidal toxins are so effective: unique features of their mode of action," FEMS Microbiology Letters, 2001, vol. 195, pp. 1-8.
Li, WP et al., Expression and Characterization of a Recombinant Cry1Ac Crystal Protein Fused with an Insect-Specific Neurotoxin Omega-ACTX-Hv1a in Bacillus Thuringiensis, Gene (Amsterdam), V 498, No. 2, pp. 323-327, Feb. 2012, XP002705660. cited byapplicant.
Tounsi, S. et al., "Cloning and study of the expression of a novel cry1la-type gene from *Bacillus thuringiensis* subsp. Kurstaki," J. Appl. Microbial., 2003, vol. 95, No. 1, pp. 23-28.
Hallquiist, N. et al., "Lipopolysaccharide regulates cysteine-rich intestinal protein, a zincfinger protein, in immune cells and plasma", Journal of Leukocyte Biology, 59(2):172-177, 1996 (abstract only).
Walters, F. et al., "An Engineered Chymotrypsin/Cathepsin G Site in Domain I Renders Bacillus thuringiensis Cry3A Active against Western Corn Rootworm Larvae", Applied and Environmental Microbiology, 74(2):367-374, 2008.
Harris, J. et al., "Rapid and general profiling of protease specificity by using combinatorial fluorogenic substrate libraries", PNAS, 97(14):7754-7759, 2000.
Hellens et al., "A Guide to Agrobacterium Binary Ti Vectors", Trends in Plant Science, Oct. 2000, vol. 5, No. 10 pp. 446-451.
Helting, T. et al., "Structure of Tetanus Toxin," The Journal of Biological Chemistry, Jan. 1977, vol. 252, No. 1, pp. 187-193.
Hiei et al., "Efficient transformation of rice (*Oryza sativa* L.) mediated by Agrobacterium and sequence analysis of the boundaries of the T-NDA", The Plant Journal, 1994, vol. 6, No. 2, pp. 271-282.
Tyndall, J. et al., "Proteases Universally Recognize Beta Strands In Their Active Sites", Chem. Rev., 105:973-999, 2005.
Moran et al., "Molecular analysis of the sea anemone toxin Av3 reveals selectivity to insects and demonstrates the heterogeneity of receptor site-3 on voltage-gated Na+ channels", Biochem. J., 406:41-48, 2007.
Anonymous: GSP: BAY44659, Retrieved from the Internet: 1-4 URL:http://ibis.internal.epo.org/exam/dbfetch.jsp?id=GSP:BAY44659 [retrieved on Oct. 15, 2020], 1 page.
Petit et al., Etude Structure/Fonction d'une Albumine Entomotoxique de Type Alb du Pois Chez le rix: ApplicationGBP a la Protection Contre le Ravageur Sitophilus Oryzae. ["Structure-function study of an Alb-type entomotoxic albumin, isolated from garden pea, in rice : application to post-harvest protection again"], Ph.D. Dissertation. Etude Struction/Fonctition D'une Albumine Entomotoxique De Type A1B Du Pois Chez Le Riz: Application GBP a La Protection Contre Le Ravageur Sitophilus Oryzae, Universite.
Raymond, Ben et al., "The impact of strain diversity and mixed infections on the evolution of resistance to Bacillus thuringiensis", Proceedings of the Royal Society B, 280:1-9 (http://dx.doi.org/10.1098/rspb.2013.1497), 2013. cited byapplicant.
Pineda, S. et al., "Diversification of a single ancestral gene into a successful toxin superfamily in highly venomous Australian funnel-web spiders," BCM Genomics, 2014, vol. 15, pp. 177-177.
Sainsbury, F. et al., "Multimodal Protein Constructs for Herbivore Insect Control", Toxins, vol. 4, Jun. 12, 2012 (Jun. 12, 2012), pp. 455-475.
Seltzer, J. et al., "Cleavage Specificity of Human Skin Type IV Collagenase (Gelatinase)," The Journal of Biological Chemistry 265(33): 20409-20413, 1990.
Shu, C. et al., "Current Patents Related to Bacillus thuringiensis Insecticidal Crystal Proteins", Recent Patents on DNA Gene Sequences, 2009, vol. 3, No. 1, pp. 26-28.
PCT International Search Report for PCT/US2013/030042, mailed Oct. 28, 2013, 6 pages.

* cited by examiner

*Fractions are not accurately portrayed in profile due to issue with fraction collector

Kl prc1-from NRRL Y-1140
3207 bp

Time [min]

Av3 MUTANT POLYPEPTIDES FOR PEST CONTROL

CROSS REFERENCE TO RELATED APPLICATIONS

This application is a 35 U.S.C. § 371 United States National Phase Application which claims the benefit of, and priority to, PCT Application No. PCT/US2022/022939, filed Mar. 31, 2022, which claims the benefit of, and priority to, U.S. Provisional Application Ser. No. 63/169,643, filed on Apr. 1, 2021. The entire contents of the aforementioned applications are incorporated by reference herein.

SEQUENCE

This application incorporates by reference in its entirety the Sequence Listing entitled "277702-541489.txt" (91,103 bytes), which was created on May 9, 2024, and filed electronically herewith.

TECHNICAL FIELD

New insecticidal proteins, nucleotides, peptides, their expression in plants, methods of producing the peptides, new processes, production techniques, new peptides, new formulations, and combinations of new and known organisms that produce greater yields than would be expected of related peptides for the control of insects are described and claimed.

BACKGROUND

Deleterious insects represent a worldwide threat to human health and food security. Insects pose a threat to human health because they are a vector for disease. One of the most notorious insect-vectors of disease is the mosquito. Mosquitoes in the genus *Anopheles* are the principal vectors of Zika virus, Chikungunya virus, and malaria—a disease caused by protozoa in the genus *Trypanosoma*. Another mosquito, *Aedes aegypti*, is the main vector of the viruses that cause Yellow fever and Dengue. And, *Aedes* spp. mosquitos are also the vectors for the viruses responsible for various types of encephalitis. *Wuchereria bancrofti* and *Brugia malayi*, parasitic roundworms that cause filariasis, are usually spread by mosquitoes in the genera *Culex, Mansonia*, and *Anopheles.*

Similar to the mosquito, other members of the Diptera order have likewise plagued humankind since time immemorial. In addition to producing painful bites, Horseflies and deerflies transmit the bacterial pathogens of tularemia (*Pasteurella tularensis*) and anthrax (*Bacillus anthracis*), as well as a parasitic roundworm (*Loa loa*) that causes loiasis in tropical Africa.

Blowflies (*Chrysomya megacephala*) and houseflies (*Musca domestica*) will in one moment take off from carrion and dung, and in the next moment alight in our homes and on our food-spreading dysentery, typhoid fever, cholera, poliomyelitis, yaws, leprosy, and tuberculosis in their wake.

Eye gnats in the genus *Hippelates* can carry the spirochaete pathogen that causes yaws (*Treponema* pertenue), and may also spread conjunctivitis (pinkeye). Tsetse flies in the genus *Glossina* transmit the protozoan pathogens that cause African sleeping sickness (*Trypanosoma* gambiense and T. rhodesiense). Sand flies in the genus *Phlebotomus* are vectors of a bacterium (*Bartonella bacilliformis*) that causes Carrion's disease (Oroyo fever) in South America. In parts of Asia and North Africa, they spread a viral agent that causes sand fly fever (Pappataci fever) as well as protozoan pathogens (*Leishmania* spp.) that cause Leishmaniasis.

Human food security is also threatened by insects. Insect pests indiscriminately target food crops earmarked for commercial purposes and personal use alike; indeed, the damage caused by insect pests can run the gamut from mere inconvenience to financial ruin in the former, to extremes such as malnutrition or starvation in the latter. Insect pests also cause stress and disease in domesticated animals. And, insect pests once limited by geographical and climate boundaries have expanded their range due to global travel and climate change.

SUMMARY

The present disclosure describes an Av3 mutant polypeptide (AMP) having insecticidal activity against one or more insect species, said AMP comprising an amino acid sequence that is at least 95% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-X-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or an agriculturally acceptable salt thereof.

In addition, the present disclosure describes combination or mixture, comprising, consisting essentially of, or consisting of, one or more AMPs.

In addition, the present disclosure describes a composition comprising, consisting essentially of, or consisting of, one or more AMPs, and further comprising an excipient.

Furthermore, the present disclosure describes a polynucleotide operable to encode an AMP, said AMP comprising, consisting essentially of, or consisting of, an amino acid sequence that is at least 95% identical to the amino acid sequence according to Formula (I): $X_1$-S-C-C-P-C-Y-W-$X_2$-$X_3$-C-P-W-G-Q-$X_4$-C-Y-P-X-G-C-$X_6$-G-$X_7$-X-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or an agriculturally acceptable salt thereof.

In addition, the present disclosure describes a method of producing an AMP, said method comprising: (a) preparing a vector comprising a first expression cassette comprising, consisting essentially of, or consisting of, a polynucleotide operable to encode an AMP, or a complementary nucleotide sequence thereof, said AMP comprising an amino acid sequence that is at least 95% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-X-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; introducing the vector into a host cell; and (c) growing the host cell in a growth medium under conditions operable to enable expression of the AMP and secretion into the growth medium.

In addition, the present disclosure describes a method for protecting a plant from insects, the method comprising: providing a plant that expresses an AMP, or a polynucleotide encoding the same.

In addition, the present disclosure describes a method for controlling insects comprising, providing to said insect a transgenic plant that comprises in its genome a stably incorporated expression cassette, wherein said stably incorporated expression cassette comprises a polynucleotide operable to encode an AMP.

In addition, the present disclosure describes a method of combating, controlling, or inhibiting a pest comprising, applying a pesticidally effective amount of the combination, mixture, or composition of one or more AMPs, or one or more agriculturally acceptable salts thereof, or a combination or composition comprising the same, to the pest, a locus of the pest, a food supply of the pest, a habitat of the pest, or a breeding ground of the pest; a plant, a seed, a plant part, a locus of a plant, or an environment of a plant that is susceptible to an attack by the pest; an animal, a locus of an animal, or an environment of an animal susceptible to an attack by the pest; or a combination thereof.

In addition, the present disclosure describes a vector comprising a polynucleotide operable to encode an AMP having an amino acid that is at least 90%, 90%, 95%, 96%, 97%, 98%, 99% or 100% identical to an amino acid sequence as set forth in any one of SEQ ID NOs: 6, 20, 24-26, 28-36, 38-42, 48, 54, 58, 60, 62-63, 69, 108, 116, 119, and 168-169.

In addition, the present disclosure provides AMPs having an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence as follows:

(SEQ ID NO: 20)
"KSCCPCYWGGCPWGQDCYPDGCDGPK";

(SEQ ID NO: 24)
"KSCCPCYWGGCPWGQNCYPNGCSGPK";

(SEQ ID NO: 25)
"KSCCPCYWGGCPWGQNCYPEGCDGPK";

(SEQ ID NO: 26)
"KSCCPCYWPGCPWGQNCYPEGCSGPK";

(SEQ ID NO: 35)
"KSCCPCYWPGCPWGQNCYPEGCRGPD"

(SEQ ID NO: 36)
"KSCCPCYWGGCPWGQNCYPEGCSGPG";

(SEQ ID NO: 38)
"KSCCPCYWGGCPWGQNCYPEGCGGPG";
and (SEQ ID NO: 40)
"KSCCPCYWGGCPWGQNCYPEGCSGPKVG".

In addition, the present disclosure describes a vector comprising a polynucleotide operable to encode an AMP having an amino acid that is at least 90% identical to an amino acid sequence as set forth in any one of SEQ ID NOs: 25, 36, 38, and 40.

In addition, the present disclosure describes a yeast strain comprising: a first expression cassette comprising a polynucleotide operable to encode an AMP, said AMP comprising an amino acid sequence that is at least 90%, 90%, 95%, 96%, 97%, 98%, 99% or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or a complementary nucleotide sequence thereof.

In addition, the present disclosure describes an Av3 mutant polypeptide (AMP) having insecticidal activity against one or more insect species, said AMP comprising an amino acid sequence that is at least 95% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; $X_6$ is G or absent; or an agriculturally acceptable salt thereof.

In addition, the present disclosure describes a combination or mixture, comprising, consisting essentially of, or consisting of, one or more AMPs comprising an amino acid sequence that is at least 95% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; $X_6$ is G or absent; or an agriculturally acceptable salt thereof.

In addition, the present disclosure describes a composition comprising, consisting essentially of, or consisting of, one or more AMPs, said AMPs comprising an amino acid sequence that is at least 95% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; $X_6$ is G or absent; or an agriculturally acceptable salt thereof, wherein the composition further comprises an excipient.

In addition, the present disclosure describes an Av3 mutant polypeptide (AMP) having insecticidal activity against one or more insect species, said AMP comprising, consisting essentially of, or consisting of, an amino acid sequence that is at least 90%, 95%, 96%, 97%, 98%, 99% or 100% identical to the amino acid sequence set forth in any one of SEQ ID NOs: 6, 20, 24-26, 28-36, 38-42, 48, 54, 58, 60, 62-63, 69, 108, 116, 119, and 168-169.

In addition, the present disclosure describes an Av3 mutant polypeptide (AMP) having insecticidal activity against one or more insect species, said AMP comprising, consisting essentially of, or consisting of, an amino acid sequence that is at least 95% identical to the amino acid sequence set forth in any one of SEQ ID NOs: 20, 24-26, 35-36, 38, and 40.

In addition, the present disclosure describes an Av3 mutant polypeptide (AMP) having insecticidal activity against one or more insect species, said AMP comprising, consisting essentially of, or consisting of, an amino acid sequence that is at least 95% identical to the amino acid sequence set forth in any one of SEQ ID NOs: 25, 36, 38, and 40.

In addition, the present disclosure describes an Av3 mutant polypeptide (AMP) having insecticidal activity against one or more insect species, said AMP comprising, consisting essentially of, or consisting of, an amino acid sequence set forth in any one of SEQ ID NOs: 6, 20, 24-26, 28-36, 38-42, 48, 54, 58, 60, 62-63, 69, 108, 116, 119, and 168-169.

In addition, the present disclosure describes an Av3 mutant polypeptide (AMP) having insecticidal activity against one or more insect species, said AMP comprising, consisting essentially of, or consisting of, an amino acid sequence set forth in any one of SEQ ID NOs: 20, 24-26, 35-36, 38, and 40.

In addition, the present disclosure describes an Av3 mutant polypeptide (AMP) having insecticidal activity against one or more insect species, said AMP comprising, consisting essentially of, or consisting of, an amino acid sequence set forth in any one of SEQ ID NOs: 25, 36, 38, and 40.

In addition, the present disclosure describes an Av3 mutant polypeptide (AMP) having insecticidal activity against one or more insect species, said AMP comprising, consisting essentially of, or consisting of, an amino acid sequence set forth in SEQ ID NO: 38.

DETAILED DESCRIPTION

Definitions

Figure 1:
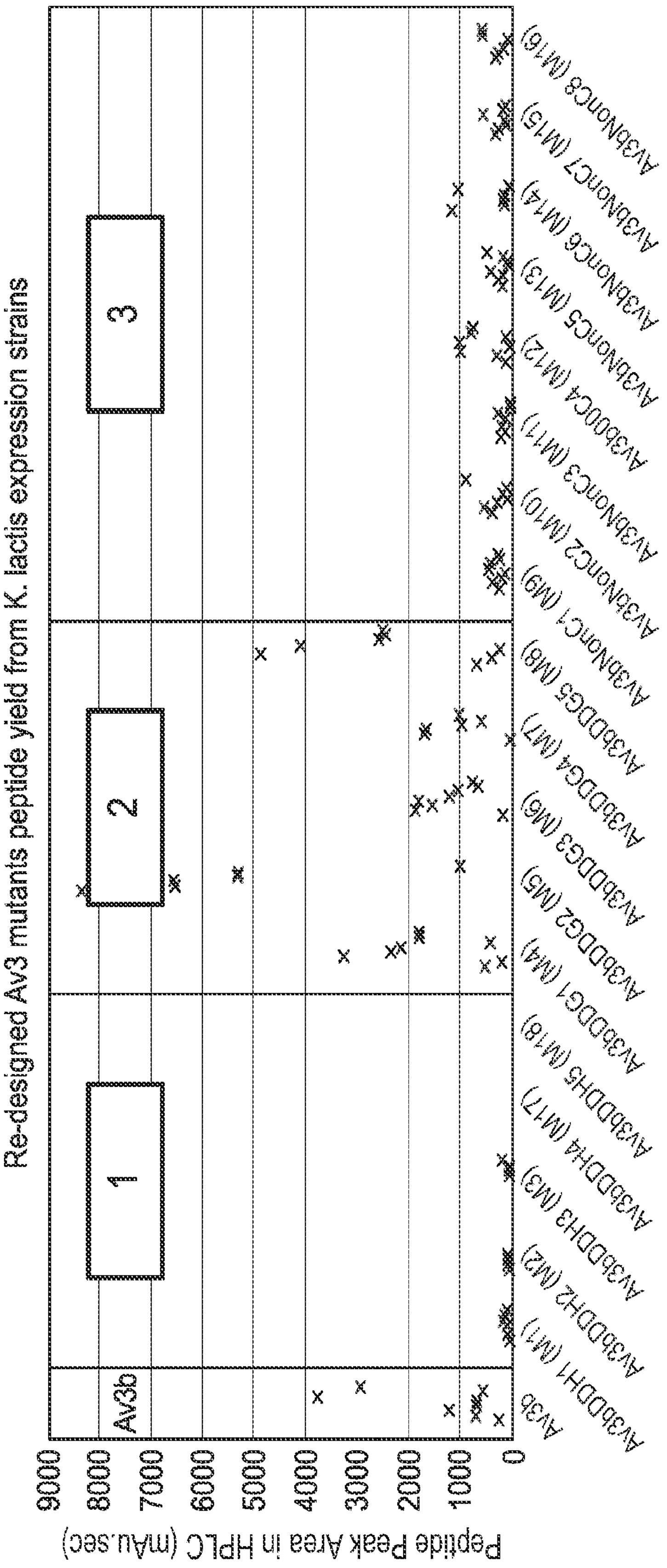
FIG. 1 depicts the yield of Av3b mutant strains, Av3bM1-Av3bM18, which were based on the designs of (1) change disulfide bonds pattern from inhibitor cystine knot (ICK) motif to disulfide-directed $-hairpin (DDH) motif (shown in the section of the graph indicated by box 1); (2) an energy efficient design based on Rosetta protein modeling software (shown in the section of the graph indicated by box 2); and (3) a most energy efficient mutation design focusing on non-essential residues based on Rosetta protein modeling software (shown in the section of the graph indicated by box 3). Each of the mutant strains are identified in the parenthesis (e.g., "M1"=Av3bM1, etc.).

"5'-end" and "3'-end" refers to the directionality, i.e., the end-to-end orientation of a nucleotide polymer (e.g., DNA). The 5'-end of a polynucleotide is the end of the polynucleotide that has the fifth carbon.

"5'- and 3'-homology arms" or "5' and 3' arms" or "left and r'ght arms" refers to the polynucleotide sequences in a vector and/or targeting vector that homologously recombine with the target genome sequence and/or endogenous gene of interest in the host organism in order to achieve successful genetic modification of the host organism's chromosomal locus.

"Additive" refers to any agriculturally acceptable additive. Agriculturally acceptable additives include, without limitation, disintegrants, dispersing additives, coating additives, diluents, surfactants, absorption promoting additives, anti-caking additives, anti-microbial agents (e.g., preservatives), colorants, desiccants, plasticizers and dyes.

"Alignment" refers to a method of comparing two or more sequences (e.g., nucleotide, polynucleotide, amino acid, peptide, polypeptide, or protein sequences) for the purpose of determining their relationship to each other. Alignments are typically performed by computer programs that apply various algorithms, however, it is also possible to perform an alignment by hand. Alignment programs typically iterate through potential alignments of sequences and score the alignments using substitution tables, employing a variety of strategies to reach a potential optimal alignment score. Commonly-used alignment algorithms include, but are not limited to, CLUSTALW (see Thompson J. D., Higgins D. G., Gibson T. J., CLUSTAL W: improving the sensitivity of progressive multiple sequence alignment through sequence weighting, position-specific gap penalties and weight matrix choice, Nucleic Acids Research 22: 4673-4680, 1994); CLUSTALV (see Larkin M. A., et al., CLUSTALW2, ClustalW and ClustalX version 2, Bioinformatics 23(21): 2947-2948, 2007); Mafft; Kalign; ProbCons; and T-Coffee (see Notredame et al., T-Coffee: A novel method for multiple sequence alignments, Journal of Molecular Biology 302: 205-217, 2000). Exemplary programs that implement one or more of the foregoing algorithms include, but are not limited to, MegAlign from DNAStar (DNAStar, Inc. 3801 Regent St. Madison, Wis. 53705), MUSCLE, T-Coffee, CLUSTALX, CLUSTALV, JalView, Phylip, and Discovery Studio from Accelrys (Accelrys, Inc., 10188 Telesis Ct, Suite 100, San Diego, Calif 92121). In some embodiments, an alignment will introduce "phase shifts" and/or "gaps" into one or both of the sequences being compared in order to maximize the similarity between the two sequences, and scoring refers to the process of quantitatively expressing the relatedness of the aligned sequences.

"Agent" refers to one or more chemical substances, molecules, nucleotides, polynucleotides, peptides, polypeptides, proteins, poisons, insecticides, pesticides, organic compounds, inorganic compounds, prokaryote organisms, or eukaryote organisms, and agents produced therefrom.

"Agriculturally-acceptable carrier" covers all adjuvants, inert components, dispersants, surfactants, tackifiers, binders, etc. that are ordinarily used in pesticide formulation technology; these are well known to those skilled in pesticide formulation.

"Agriculturally acceptable salt" is synonymous with pharmaceutically acceptable salt, and as used herein refers to a compound that is modified by making acid or base salts thereof.

"Agroinfection" means a plant transformation method where DNA is introduced into a plant cell by using Agrobacteria *A. tumefaciens* or *A. rhizogenes.*

"Alpha-MF signal" or "αMF secretion signal" refers to a protein that directs nascent recombinant polypeptides to the secretory pathway.

"AMP" or "Av3 mutant polypeptide" or "Av3b mutant polypeptide" or "Av3b mutant peptide" refers to peptides having one or more mutations relative to the amino acid sequence set forth in SEQ ID NO: 1. In some embodiments, an AMP can have an amino acid sequence according to Formula (I):

$$X_1\text{-S-C-C-P-C-Y-W-}X_2\text{-}X_3\text{-C-P-W-G-Q-}X_4\text{-C-Y-P-}X_5\text{-G-C-X-G-}X_7\text{-}X_8\text{-}X_9\text{-}X_{10} \quad \text{Formula (I)}$$

wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent.

In yet other embodiments, an AMP has an amino acid sequence according to Formula (II):

$$\text{K-S-C-C-P-C-Y-W-G-G-C-P-W-G-Q-}X_1\text{-C-Y-P-}X_2\text{-G-C-}X_3\text{-G-P-}X_4\text{-}X_5\text{-}X_6 \quad \text{Formula (H)}$$

wherein $X_1$ is N or D; $X_2$ is E, D, or N; $X_3$ is S, D, R, or G; $X_4$ is K, G, or D; $X_5$ is V or absent; $X_6$ is G or absent.

"AMP expression cassette" refers to one or more regulatory elements such as promoters; enhancer elements; mRNA stabilizing polyadenylation signal; an internal ribosome entry site (IRES); introns; post-transcriptional regulatory elements; and a polynucleotide operable to encode an AMP, e.g., an AMP ORF. For example, one example of an AMP expression cassette is one or more segments of DNA that contains a polynucleotide segment operable to express an AMP, a ADH1 promoter, a LAC4 terminator, and an alpha-MF secretory signal. An AMP expression cassette contains all of the nucleic acids necessary to encode an AMP or an AMP-insecticidal protein.

"AMP ORF" refers to a polynucleotide operable to encode an AMP, or an AMP-insecticidal protein.

"AMP ORF diagram" refers to the composition of one or more AMP ORFs, as written out in diagram or equation form. For example, a "AMP ORF diagram" can be written out as using acronyms or short-hand references to the DNA segments contained within the expression ORF. Accordingly, in one example, a "AMP ORF diagram" may describe the polynucleotide segments encoding the ERSP, LINKER, STA, and AMP, by diagramming in equation form the DNA segments as "ersp" (i.e., the polynucleotide sequence that encodes the ERSP polypeptide); "linker" or "L" (i.e., the polynucleotide sequence that encodes the LINKER polypeptide); "sta" (i.e., the polynucleotide sequence that encodes the STA polypeptide), and "amp" (i.e., the polynucleotide sequence encoding an AMP), respectively.

An example of an AMP ORF diagram is "ersp-sta-(linker$_i$-amp$_j$)$_N$," or "ersp-(amp$_j$-linker$_i$)$_N$-sta" and/or any combination of the DNA segments thereof.

"AMP-insecticidal protein" or "AMP-insecticidal polypeptide" or "insecticidal protein" or "insecticidal polypeptide" refers to any protein, peptide, polypeptide, amino acid sequence, configuration, or arrangement, comprising: (1) at least one AMP, or two or more AMPs; and (2) additional peptides, polypeptides, or proteins. For example, in some embodiments, these additional peptides, polypeptides, or proteins have the ability to increase the mortality and/or inhibit the growth of insects when the insects are exposed to an AMP-insecticidal protein, relative to an AMP alone; increase the expression of said AMP-insecticidal protein, e.g., in a host cell or an expression system; and/or affect the post-translational processing of the AMP-insecticidal protein. In some embodiments, an AMP-insecticidal protein can be a polymer comprising two or more AMPs. In some embodiments, an AMP-insecticidal protein can be a polymer comprising two or more AMPs, wherein the AMPs are operably linked via a linker peptide, e.g., a cleavable and/or non-cleavable linker.

In some embodiments, an AMP-insecticidal protein can refer to a one or more AMPs operably linked with one or more proteins such as a stabilizing domain (STA); an endoplasmic reticulum signaling protein (ERSP); an insect cleavable or insect non-cleavable linker (L); and/or any other combination thereof. In some embodiments, an AMP-insecticidal protein can be a non-naturally occurring protein comprising (1) an AMP; and (2) additional peptides, polypeptides, or proteins, e.g., an ERSP; a linker; a STA; a UBI; or a histidine tag or similar marker.

"AMP construct" refers to the three-dimensional arrangement/orientation of peptides, polypeptides, and/or motifs of operably linked polypeptide segments (e.g., an AMP-insecticidal protein). For example, an AMP ORF can include one or more of the following components or motifs: an AMP; an endoplasmic reticulum signal peptide (ERSP); a linker peptide (L); a translational stabilizing protein (STA); or any combination thereof. And, as used herein, the term "AMP construct" is used to describe the designation and/or orientation of the structural motif. In other words, the AMP construct describes the arrangement and orientation of the components or motifs contained within a given AMP ORF. For example, in some embodiments, an AMP construct describes, without limitation, the orientation of one of the following AMP-insecticidal proteins: ERSP-AMP; ERSP-(AMP)$_N$; ERSP-AMP-L; ERSP-(AMP)$_N$-L; ERSP-(AMP-L)$_N$; ERSP-L-AMP; ERSP-L-(AMP)$_N$; ERSP-(L-AMP)$_N$; ERSP-STA-AMP; ERSP-STA-(AMP)$_N$; ERSP-AMP-STA; ERSP-(AMP)$_N$-STA; ERSP-(STA-AMP)$_N$; ERSP-(AMP-STA)$_N$; ERSP-L-AMP-STA; ERSP-L-STA-AMP; ERSP-L-(AMP-STA)$_N$; ERSP-L-(STA-AMP)$_N$; ERSP-L-(AMP)$_N$-STA; ERSP-(L-AMP)$_N$-STA; ERSP-(L-STA-AMP)$_N$; ERSP-(L-AMP-STA)$_N$; ERSP-(L-STA)$_N$-AMP; ERSP-(L-AMP)$_N$-STA; ERSP-STA-L-AMP; ERSP-STA-AMP-L; ERSP-STA-L-(AMP)$_N$; ERSP-(STA-L)$_N$-AMP; ERSP-STA-(L-AMP)$_N$; ERSP-(STA-L-AMP)$_N$; ERSP-STA-(AMP)$_N$-L; ERSP-STA-(AMP-L)$_N$; ERSP-(STA-AMP)$_N$-L; ERSP-(STA-AMP-L)$_N$; ERSP-AMP-L-STA; ERSP-AMP-STA-L; ERSP-(AMP)$_N$-STA-L ERSP-(AMP-L)$_N$-STA; ERSP-(AMP-STA)$_N$-L; ERSP-(AMP-L-STA)$_N$; or ERSP-(AMP-STA-L)$_N$; wherein N is an integer ranging from 1 to 200. See also "Structural motif".

"Av3 mutant polynucleotide" refers to the polynucleotide sequence that encodes any AMP. The term "Av3 mutant polynucleotide" when used to describe the Av3 mutant polynucleotide sequence, e.g., such as one contained in an AMP open reading frame (ORF), its inclusion in a vector, and/or when describing the polynucleotides encoding an insecticidal protein, is written in lowercase and italicized, e.g., "amp" and/or "Amp".

"Applying" or "application" or "apply" or "administering" or "administration" or "administer" means to dispense and/or otherwise provide, and refers to any method of application or route of administration. For example, applying can refer to, e.g., application of an AMP or an agriculturally acceptable salt thereof; or application of an AMP or agriculturally acceptable salt thereof, and one or more excipients, e.g., a sprayable composition, a foam; a burning formulation; a fabric treatment; a surface-treatment; a dispersant; a microencapsulation, and the like. By "co-application" or "co-administer" it is meant that two or more components are applied or administered at the same time; or a one or more components are applied or administered just prior to, or just after the application the other one or more components. For example, in some embodiments, a first AMP and a second AMP, wherein the first and second AMP can be the same or different, can be applied or administered simultaneously or sequentially.

"Av3b" refers to an AMP having an N-terminal mutation and a C-terminal mutation to the wild type Av3 peptide, wherein the N-terminal mutation results in an amino acid substitution of RIK relative to SEQ ID NO:172, and the C-terminal mutation results in an amino acid deletion relative to SEQ ID NO: 172; thus, in an Av3b peptide, the wild-type Av3 peptide amino acid sequence is changed from "RSCCPCYWGGCPWGQNCYPEGCSGPKV" (SEQ ID NO: 172), to the amino acid sequence: "KSCCPCYWGGCPWGQNCYPEGCSGPK" (SEQ ID NO:1).

"Binary vector" or "binary expression vector" means an expression vector which can replicate itself in both *E. coli* strains and *Agrobacterium* strains. Also, the vector contains a region of DNA (often referred to as t-DNA) bracketed by left and right border sequences that is recognized by virulence genes to be copied and delivered into a plant cell by *Agrobacterium.*

"bp" or "base pair" refers to a molecule comprising two chemical bases bonded to one another forming a. For example, a DNA molecule consists of two winding strands, wherein each strand has a backbone made of an alternating deoxyribose and phosphate groups. Attached to each deoxyribose is one of four bases, i.e., adenine (A), cytosine (C), guanine (G), or thymine (T), wherein adenine forms a base pair with thymine, and cytosine forms a base pair with guanine.

"C-terminus" or "C-terminal" refers to the free carboxyl group (i.e., —COOH) that is positioned on the terminal end of a polypeptide.

"cDNA" or "copy DNA" or "complementary DNA" refers to a molecule that is complementary to a molecule of RNA. In some embodiments, cDNA may be either single-stranded or double-stranded. In some embodiments, cDNA can be a double-stranded DNA synthesized from a single stranded RNA template in a reaction catalyzed by a reverse transcriptase. In yet other embodiments, "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. In some embodiments, "cDNA" refers to a DNA that is complementary to and derived from an mRNA template.

"CEW" refers to Corn earworm.

"Cleavable Linker" see Linker.

"Cloning" refers to the process and/or methods concerning the insertion of a DNA segment (e.g., usually a gene of interest, for example amp) from one source and recombining it with a DNA segment from another source (e.g., usually a vector, for example, a plasmid) and directing the recombined DNA, or "recombinant DNA" to replicate, usually by transforming the recombined DNA into a bacteria or yeast host.

"Coding sequence" or "CDS" refers to a polynucleotide or nucleic acid sequence that can be transcribed (e.g., in the case of DNA) or translated (e.g., in the case of mRNA) into a peptide, polypeptide, or protein, when placed under the control of appropriate regulatory sequences and in the presence of the necessary transcriptional and/or translational molecular factors. The boundaries of the coding sequence are determined by a translation start codon at the 5' (amino) terminus and a translation stop codon at the 3' (carboxy) terminus. A transcription termination sequence will usually be located 3' to the coding sequence. In some embodiments, a coding sequence may be flanked on the 5' and/or 3' ends by untranslated regions. In some embodiments, a coding sequence can be used to produce a peptide, a polypeptide, or a protein product. In some embodiments, the coding sequence may or may not be fused to another coding sequence or localization signal, such as a nuclear localization signal. In some embodiments, the coding sequence may be cloned into a vector or expression construct, may be integrated into a genome, or may be present as a DNA fragment.

"Codon optimization" refers to the production of a gene in which one or more endogenous, native, and/or wild-type codons are replaced with codons that ultimately still code for the same amino acid, but that are of preference in the corresponding host.

"Combination" refers to the result of combining two or more separate components. Thus, as used herein, a "combination" refers to an association of two or more separate components, e.g., an AMP and an additional component. Accordingly, in some embodiments, a combination can refer to the association of a first AMP, and one or more additional AMPs; wherein the first AMP and one or more additional AMPs are the same or different. In some embodiments, the combination can be, e.g., a mixture, or as part of a composition further comprising one or more excipients. In some embodiments, a combination can refer to the simultaneous, separate, or sequential application of two or more separate components (e.g., a first AMP, and one or more additional AMPs; wherein the first AMP and one or more additional AMPs are the same or different). For example, in some embodiments, a "combination" refers to the result of a simultaneous application of both a first AMP, and one or more additional AMPs; wherein the first AMP and one or more additional AMPs are the same or different. In another embodiment, a "combination" refers to the result of a separate application of a first AMP, and one or more additional AMPs; wherein the first AMP and one or more additional AMPs are the same or different. In a further embodiments, a "combination" refers to the result of a sequential application of two or more separate components, e.g., a first application of a first AMP, followed by a second application of one or more additional AMPs (wherein the first AMP and one or more additional AMPs are the same or different), or vice versa. Where the application is sequential or separate, the delay in applying the second component should not be such as to lose the beneficial effect of the combination.

"Complementary" refers to the topological compatibility or matching together of interacting surfaces of two polynucleotides as understood by those of skill in the art. Thus, two sequences are "complementary" to one another if they are capable of hybridizing to one another to form a stable anti-parallel, double-stranded nucleic acid structure. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions. Thus, the polynucleotide whose sequence 5'-TATAC-3' is complementary to a polynucleotide whose sequence is 5'-GTATA-3'.

"Conditioned medium" means the cell culture medium which has been used by cells and is enriched with cell derived materials but does not contain cells.

"Copy number" refers to the number of identical copies of a vector, an expression cassette, an amplification unit, a gene or indeed any defined nucleotide sequence, that are present in a host cell at any time. For example, in some embodiments, a gene or another defined chromosomal nucleotide sequence may be present in one, two, or more copies on the chromosome. An autonomously replicating vector may be present in one, or several hundred copies per host cell.

"Culture" or "cell culture" refers to the maintenance of cells in an artificial, in vitro environment.

"Culturing" refers to the propagation of organisms on or in various kinds of media. For example, the term "culturing" can mean growing a population of cells under suitable conditions in a liquid or solid medium. In some embodiments, culturing refers to fermentative recombinant production of a heterologous polypeptide of interest and/or other desired end products (typically in a vessel or reactor).

"Cystine" refers to an oxidized cysteine-dimer. Cystines are sulfur-containing amino acids obtained via the oxidation of two cysteine molecules, and are linked with a disulfide bond.

"Defined medium" means a medium that is composed of known chemical components but does not contain crude proteinaceous extracts or by-products such as yeast extract or peptone.

"Degeneracy" or "codon degeneracy" refers to the phenomenon that one amino acid can be encoded by different nucleotide codons. Thus, the nucleic acid sequence of a nucleic acid molecule that encodes a protein or polypeptide can vary due to degeneracies. As a result of the degeneracy of the genetic code, many nucleic acid sequences can encode a given polypeptide with a particular activity; such functionally equivalent variants are contemplated herein.

"Disulfide bond" or "disulfide bridges" refers to a covalent bond between two cysteine amino acids derived by the coupling of two thiol groups on their side chains. In some embodiments, a disulfide bond occurs via the oxidative folding of two different thiol groups (—SH) present in a polypeptide. In some embodiments, a polypeptide can comprise at least six different thiol groups (i.e., six cysteine residues each containing a thiol group); thus, in some embodiments, a polypeptide can form zero, one, two, three, or more intramolecular disulfide bonds.

"Double expression cassette" refers to two AMP expression cassettes contained on the same vector.

"Double transgene peptide expression vector" or "double transgene expression vector" means a yeast expression vector that contains two copies of the AMP expression cassette.

"DNA" refers to deoxyribonucleic acid, comprising a polymer of one or more deoxyribonucleotides or nucleotides (i.e., adenine [A], guanine [G], thymine [T], or cytosine [C]), which can be arranged in single-stranded or double-stranded form. For example, one or more nucleotides creates a polynucleotide.

"dNTPs" refers to the nucleoside triphosphates that compose DNA and RNA.

"Endogenous" refers to a polynucleotide, peptide, polypeptide, protein, or process that naturally occurs and/or exists in an organism, e.g., a molecule or activity that is already present in the host cell before a particular genetic manipulation.

"Enhancer element" refers to a DNA sequence operably linked to a promoter, which can exert increased transcription activity on the promoter relative to the transcription activity that results from the promoter in the absence of the enhancer element.

"ER" or "Endoplasmic reticulum" is a subcellular organelle common to all eukaryotes where some post translation modification processes occur.

"ERSP" or "Endoplasmic reticulum signal peptide" is an N-terminus sequence of amino acids that—during protein translation of the mRNA molecule encoding an AMP—is recognized and bound by a host cell signal-recognition particle, which moves the protein translation ribosome/mRNA complex to the ER in the cytoplasm. The result is the protein translation is paused until it docks with the ER where it continues and the resulting protein is injected into the ER.

"ersp" refers to a polynucleotide encoding the peptide, ERSP.

"ER trafficking" means transportation of a cell expressed protein into ER for post-translational modification, sorting and transportation.

"Excipient" refers to any agriculturally or pharmaceutically acceptable additive, carrier, surfactant, emulsifier, thickener, preservative, solvent, disintegrant, glidant, lubricant, diluent, filler, bulking agent, binder, emollient, stiffening agent, chelating agent, stabilizer, solubilizing agents, dispersing agent, suspending agent, antioxidant, antiseptic, wetting agent, humectant, fragrant, suspending agents, pigments, colorants, isotonic agents, viscosity enhancing agents, mucoadhesive agents, and/or any combination thereof, that can be added to an agricultural composition, preparation, and/or formulation, which may be useful in achieving a desired modification to the characteristics of the agricultural composition, preparation, and/or formulation. Such modifications include, but are not limited to, physical stability, chemical stability, pesticidal efficacy, and/or any combination thereof.

"Expression cassette" refers to (1) a DNA sequence of interest, e.g., a polynucleotide operable to encode an AMP; and one or more of the following: (2) promoters, terminators, and/or enhancer elements; (3) an appropriate mRNA stabilizing polyadenylation signal; (4) an internal ribosome entry site (IRES); (5) introns; and/or (6) post-transcriptional regulatory elements. The combination (1) with at least one of (2)-(6) is called an "expression cassette." In some embodiments, there can be numerous expression cassettes cloned into a vector. For example, in some embodiments, there can be a first expression cassette comprising a polynucleotide operable to encode an AMP. In alternative embodiments, there are two expression cassettes, each comprising a polynucleotide operable to encode an AMP (i.e., a double expression cassette). In other embodiments, there are three expression cassettes operable to encode an AMP (i.e., a triple expression cassette). In some embodiments, a double expression cassette can be generated by subcloning a second expression cassette into a vector containing a first expression cassette. In some embodiments, a triple expression cassette can be generated by subcloning a third expression cassette into a vector containing a first and a second expression cassette. Methods concerning expression cassettes and cloning techniques are well-known in the art and described herein. See also AMP expression cassette.

"FECT" means a transient plant expression system using Foxtail mosaic virus with elimination of coating protein gene and triple gene block.

"Fermentation beer" refers to spent fermentation medium, i.e., fermentation medium supernatant after removal of organisms, that has been inoculated with and consumed by a transformed host cell (e.g., a yeast cell operable to express an AMP of the present disclosure). In some embodiments, fermentation beer refers to the solution that is recovered following the fermentation of the transformed host cell. The term "fermentation" refers broadly to the enzymatic and anaerobic or aerobic breakdown of organic substances (e.g., a carbon substrate) nutrient substances by microorganisms under controlled conditions (e.g., temperature, oxygen, pH, nutrients, and the like) to produce fermentation products (e.g., one or more peptides of the present disclosure). While fermentation typically describes processes that occur under anaerobic conditions, as used herein it is not intended that the term be solely limited to strict anaerobic conditions, as the term "fermentation" used herein may also occur processes that occur in the presence of oxygen.

"GFP" means green fluorescent protein from the jellyfish, *Aequorea victoria*.

"Growth medium" refers to a nutrient medium used for growing cells in vitro.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. Thus, in some embodiments, the term "homologous" refers to the sequence similarity between two polypeptide molecules, or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, if 6 of 10 of the positions in two sequences are matched or homologous then the two sequences are 60% homologous. By way of example, the DNA sequences ATTGCC and TATGGC share 50% homology.

There may be partial homology, or complete homology and thus identical. "Sequence identity" refers to a measure of relatedness between two or more nucleic acid sequences or two or more polypeptide sequences, and is given as a percentage with reference to the total comparison length. The identity calculation takes into account those nucleotide residues or amino acid residues that are identical and in the same relative positions in their respective larger sequences.

"Homologous recombination" refers to the event of substitution of a segment of DNA by another one that possesses identical regions (homologous) or nearly so. For example, in some embodiments, "homologous recombination" refers to a type of genetic recombination in which nucleotide sequences are exchanged between two similar or identical molecules of DNA. Briefly, homologous recombination is most widely used by cells to accurately repair harmful breaks that occur on both strands of DNA, known as double-strand breaks. Although homologous recombination varies widely among different organisms and cell types, most forms involve the same basic steps: after a double-strand break occurs, sections of DNA around the 5' ends of the break are cut away in a process called resection. In the strand invasion step that follows, an overhanging 3' end of the broken DNA molecule then "invades" a similar or identical DNA molecule that is not broken. After strand invasion, the further sequence of events may follow either of two main pathways, i.e., the double-strand break repair pathway, or the synthesis-dependent strand annealing pathway.

Homologous recombination is conserved across all three domains of life as well as viruses, suggesting that it is a nearly universal biological mechanism. For example, in some embodiments, homologous recombination can occur using a site-specific integration (SSI) sequence, whereby there is a strand exchange crossover event between nucleic acid sequences substantially similar in nucleotide composition. These crossover events can take place between sequences contained in the targeting construct of the invention (i.e., the SSI sequence) and endogenous genomic nucleic acid sequences (e.g., the polynucleotide encoding the peptide subunit). In addition, in some embodiments, it is possible that more than one site-specific homologous recombination event can occur, which would result in a replacement event in which nucleic acid sequences contained within the targeting construct have replaced specific sequences present within the endogenous genomic sequences.

"Hybridize" refers to the annealing of one single-stranded polynucleotide to another polynucleotide based on the well-understood principle of sequence complementarity. In some embodiments, the other polynucleotide is a single-stranded polynucleotide. The propensity for hybridization between polynucleotides depends on the temperature and ionic strength of their milieu, the length of the polynucleotides, and the degree of complementarity. The effect of these parameters on hybridization are well known in the art.

"Hybridization" refers to any process by which a strand of polynucleotide binds with a complementary strand through base pairing. Two single-stranded polynucleotides "hybridize" when they form a double-stranded duplex. Thus, as used herein, the term "hybridize" refers to the annealing of one single-stranded polynucleotide to another polynucleotide based on the well-understood principle of sequence complementarity. In some embodiments, the other polynucleotide is a single-stranded polynucleotide. The propensity for hybridization between polynucleotides depends on the temperature and ionic strength of their milieu, the length of the polynucleotides, and the degree of complementarity. The effect of these parameters on hybridization are well known in the art. When two single-stranded polynucleotides hybridize and form a double-stranded duplex, the region of double-strandedness can include the full-length of one or both of the single-stranded polynucleotides, or all of one single stranded polynucleotide and a subsequence of the other single stranded polynucleotide, or the region of double-strandedness can include a subsequence of each polynucleotide. Hybridization also includes the formation of duplexes which contain certain mismatches, provided that the two strands are still forming a double stranded helix. See "Stringent hybridization conditions" below.

"$IC_{50}$" or "IC50" refers to half-maximal inhibitory concentration, which is a measurement of how much of an agent is needed to inhibit a biological process by half, thus providing a measure of potency of said agent.

"Identity" refers to a relationship between two or more polypeptide sequences or two or more polynucleotide sequences, as determined by comparing said sequences. The term "identity" also means the degree of sequence relatedness between polypeptide or polynucleotide sequences, as the case may be, as determined by the match between strings of such sequences. "Identity" and "similarity" can be readily calculated by any one of the myriad methods known to those having ordinary skill in the art, including but not limited to those described in: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994:, Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988), the disclosures of which are incorporated herein by reference in their entireties. Furthermore, methods to determine identity and similarity are codified in publicly available computer programs. For example in some embodiments, methods to determine identity and similarity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990), the disclosures of which are incorporated herein by reference in their entireties.

"in vivo" refers to in the living body of a plant or animal (e.g., an animal, plant or a cell) and to processes or reactions that occur within the living body of a plant or animal.

"Inactive" refers to a condition wherein something is not in a state of use, e.g., lying dormant and/or not working. For example, when used in the context of a gene or when referring to a gene, the term inactive means said gene is no longer actively synthesizing a gene product, having said gene product translated into a protein, or otherwise having the gene perform its normal function. For example, in some embodiments, the term inactive can refer the failure of a gene to transcribe RNA, a failure of RNA processing (e.g., pre-mRNA processing; RNA splicing; or other post-transcriptional modifications); interference with non-coding RNA maturation; interference with RNA export (e.g., from the nucleus to the cytoplasm); interference with translation; protein folding; translocation; protein transport; and/or inhibition and/or interference with any of the molecules polynucleotides, peptides, polypeptides, proteins, transcription factors, regulators, inhibitors, or other factors that take part in any of the aforementioned processes.

"Inhibiting" or "inhibit" or "combating" or "combat" or "controlling" or "control," or any variation of these terms, refers to making something (e.g., the number of pests, the functions and/or activities of the pest, and/or the deleterious effect of the pest on a plant or animal susceptible to attack thereof) less in size, amount, intensity, or degree. For example, in some embodiments, the application of a pesticidally effective amount of an AMP or agriculturally acceptable salt thereof, or an agricultural composition comprising an AMP or agriculturally acceptable salt thereof, to (i) the pest, a locus of the pest, a food supply of the pest, a habitat of the pest, or a breeding ground of the pest; (ii) a plant, a seed, a plant part, a locus of a plant, or an environment of a plant that is susceptible to an attack by the pest; (iii) an animal, a locus of an animal, or an environment of an animal susceptible to an attack by the pest; or (iv) a combination thereof, results in the following effect: a decrease in the number of pests, or inhibition of the pest's activities (e.g., the pest dies stops or slows its movement; stops or slows its feeding; stops or slows its growth; becomes confused, e.g., with regard to navigation, locating food, sleeping behaviors, and/or mating; fails to pupate if applicable; interferes with reproduction of the pest; and/or precludes the pest from producing offspring and/or precludes the insect from producing fertile offspring) relative to the number of pests or activities thereof that had not been exposed to a pesticidally effective amount of an AMP or agriculturally acceptable salt thereof, or an agricultural composition comprising an AMP or agriculturally acceptable salt thereof.

In some embodiments, combating, controlling, or inhibiting a pest, includes any measurable decrease or complete inhibition to achieve a desired result. For example, there may be a decrease of about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or more, in the number of pests or the activities thereof treated with peptides and/or compositions of the present disclosure, compared to untreated pests. About as used herein means within ±10%, preferably ±5% of a given value.

Thus, in some embodiments, the terms "combating, controlling, or inhibiting a pest," refers to a decrease in the number of pests, or an inhibition of the activities of the pests (e.g., movement; feeding; growth; level of awareness or alertness, e.g., with regard to navigation, locating food, sleeping behaviors, and/or mating; pupation if applicable; reproduction; ability to produce offspring and/or ability to produce fertile offspring) that have received a pesticidally effective amount of an AMP of the present disclosure, or an agricultural composition thereof, that is at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.25%, at least about 1.5%, at least about 1.75%, at least about 2%, at least about 20.25%, at least about 2.5%, at least about 20.75%, at least about 3%, at least about 30.25%, at least about 3.5%, at least about 30.75%, at least about 4%, at least about 40.25%, at least about 4.5%, at least about 40.75%, at least about 5%, at least about 5.25%, at least about 5.5%, at least about 5.75%, at least about 6%, at least about 60.25%, at least about 6.5%, at least about 60.75%, at least about 7%, at least about 70.25%, at least about 7.5%, at least about 70.75%, at least about 8%, at least about 80.25%, at least about 8.5%, at least about 80.75%, at least about 9%, at least about 90.25%, at least about 9.5%, at least about 90.75%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 80%, at least about 85%, at least about 90%, at least about 95%, at least about 100%, or a greater than a 100%, relative to the number of pests, or the inhibition of activities of the pests (e.g., movement; feeding; growth; level of awareness or alertness, e.g., with regard to navigation, locating food, sleeping behaviors, and/or mating; pupation if applicable; reproduction; ability to produce offspring and/or ability to produce fertile offspring) that have not received a pesticidally effective amount of an AMP of the present disclosure, or an agricultural composition thereof.

"Inoperable" refers to the condition of a thing not functioning, malfunctioning, or no longer able to function. For example, when used in the context of a gene or when referring to a gene, the term inoperable means said gene is no longer able to operate as it normally would, either permanently or transiently. For example, "inoperable," in some embodiments, means that a gene is no longer able to synthesize a gene product, having said gene product translated into a protein, or is otherwise unable to gene perform its normal function. For example, in some embodiments, the term inoperable can refer the failure of a gene to transcribe RNA, a failure of RNA processing (e.g., pre-mRNA processing; RNA splicing; or other post-transcriptional modifications); interference with non-coding RNA maturation; interference with RNA export (e.g., from the nucleus to the cytoplasm); interference with translation; protein folding; translocation; protein transport; and/or inhibition and/or interference with any of the molecules polynucleotides, peptides, polypeptides, proteins, transcription factors, regulators, inhibitors, or other factors that take part in any of the aforementioned processes.

"Insect" includes all organisms in the class "Insecta." The term "pre-adult" insects refers to any form of an organism prior to the adult stage, including, for example, eggs, larvae, and nymphs. As used herein, the term "insect refers to any arthropod and nematode, including acarids, and insects known to infest all crops, vegetables, and trees and includes insects that are considered pests in the fields of forestry, horticulture and agriculture. Examples of specific crops that might be protected with the methods disclosed herein are soybean, corn, cotton, alfalfa and the vegetable crops. A list of specific crops and insects is enclosed herein.

"Insect gut environment" or "gut environment" means the specific pH and proteinase conditions found within the fore, mid or hind gut of an insect or insect larva.

"Insect hemolymph environment" means the specific pH and proteinase conditions of found within an insect or insect larva.

"Insecticidal activity" means that upon or after exposing the insect to compounds, agents, or peptides, the insect either dies stops or slows its movement; stops or slows its feeding; stops or slows its growth; becomes confused (e.g., with regard to navigation, locating food, sleeping behaviors, and/or mating); fails to pupate; interferes with reproduction; and/or precludes the insect from producing offspring and/or precludes the insect from producing fertile offspring.

"Intervening linker" refers to a short peptide sequence in the protein separating different parts of the protein, or a short DNA sequence that is placed in the reading frame in the ORF to separate the upstream and downstream DNA sequences. For example, in some embodiments, an intervening linker may be used allowing proteins to achieve their independent secondary and tertiary structure formation during translation. In some embodiments, the intervening linker can be either resistant or susceptible to cleavage in plant cellular environments, in the insect and/or lepidopteran gut environment, and in the insect hemolymph and lepidopteran hemolymph environment.

"Isolated" refers to separating a thing and/or a component from its natural environment, e.g., a toxin isolated from a given genus or species means that toxin is separated from its natural environment.

"kb" refers to kilobase, i.e., 1000 bases. As used herein, the term "kb" means a length of nucleic acid molecules. For example, 1 kb refers to a nucleic acid molecule that is 1000 nucleotides long. A length of double-stranded DNA that is 1 kb long, contains two thousand nucleotides (i.e., one thousand on each strand). Alternatively, a length of single-stranded RNA that is 1 kb long, contains one thousand nucleotides.

"kDa" refers to kilodalton, a unit equaling 1,000 daltons; a "dalton" or "Da" is a unit of molecular weight (MW).

"$KD_{50}$" or "Knockdown dose 50" or "paralytic dose 50" or "$PD_{50}$" refers to the median dose required to cause paralysis or cessation of movement in 50% of a population, for example, and without limitation, a population of *Musca domestica* (common housefly), or a population of *Aedes aegypti* (mosquito).

"Knock in" or "knock-in" or "knocks-in" or "knocking-in" refers to the replacement of an endogenous gene with an exogenous or heterologous gene, or part thereof,. For example, in some embodiments, the term "knock-in" refers to the introduction of a nucleic acid sequence encoding a desired protein to a target gene locus by homologous recombination, thereby causing the expression of the desired protein. In some embodiments, a "knock-in" mutation can modify a gene sequence to create a loss-of-function or gain-of-function mutation. The term "knock-in" can refer to the procedure by which a exogenous or heterologous polynucleotide sequence or fragment thereof is introduced into the genome, (e.g., "they performed a knock-in" or "they knocked-in the heterologous gene"), or the resulting cell and/or organism (e.g., "the cell is a "knock-in" or "the animal is a "knock-in").

"Knock out" or "knockout" or "knock-out" or "knocks-out" or "knocking-out" refers to a partial or complete suppression of the expression gene product (e.g., mRNA) of a protein encoded by an endogenous DNA sequence in a cell. In some embodiments, the "knock-out" can be effectuated by targeted deletion of a whole gene, or part of a gene encoding a peptide, polypeptide, or protein. As a result, the deletion may render a gene inactive, partially inactive, inoperable, partly inoperable, or otherwise reduce the expression of the gene or its products in any cell in the whole organism and/or cell in which it is normally expressed. The term "knock-out" can refer to the procedure by which an endogenous gene is made completely or partially inactive or inoperable (e.g., "they performed a knock-out" or "they knocked-out the endogenous gene"), or the resulting cell and/or organism (e.g., "the cell is a "knock-out" or "the animal is a "knock-out").

"l" or "linker" refers to a nucleotide encoding intervening linker peptide.

"L" or "LINKER" in the proper context refers to an intervening linker peptide, which links a translational stabilizing protein (STA) with an additional polypeptide, e.g., an AMP, and/or multiple AMP. When referring to amino acids, "L" can also mean leucine.

"LAC4 terminator" or "Lac4 terminator" refers to a DNA segment comprised of the transcriptional terminator sequence derived from the *K. lactis* β-galactosidase gene.

"Lepidopteran gut environment" means the specific pH and proteinase conditions of found within the fore, mid or hind gut of a lepidopteran insect or larva.

"Lepidopteran hemolymph environment" means the specific pH and proteinase conditions of found within lepidopteran insect or larva.

"$LD_{20}$" refers to a dose required to kill 20% of a population.

"$LD_{50}$" refers to lethal dose 50 which means the dose required to kill 50% of a population.

"Linker" or "LINKER" or "peptide linker" or "L" or "intervening linker" refers to a short peptide sequence operable to link two peptides together. Linker can also refer to a short DNA sequence that is placed in the reading frame of an ORF to separate an upstream and downstream DNA sequences. In some embodiments, a linker can be cleavable by an insect protease. In some embodiments, a linker may allow proteins to achieve their independent secondary and tertiary structure formation during translation. In some embodiments, the linker can be either resistant or susceptible to cleavage in plant cellular environments, in the insect and/or lepidopteran gut environment, and/or in the insect hemolymph and lepidopteran hemolymph environment. In some embodiments, a linker can be cleaved by a protease, e.g., in some embodiments, a linker can be cleaved by a plant protease (e.g., papain, bromelain, ficin, actinidin, zingibain, and/or cardosins), an insect protease, a fungal protease, a vertebrate protease, an invertebrate protease, a bacteria protease, a mammal protease, a reptile protease, or an avian protease. In some embodiments, a linker can be cleavable or non-cleavable. In some embodiments, a linker comprises a binary or tertiary region, wherein each region is cleavable by at least two types of proteases: one of which is an insect and/or nematode protease and the other one of which is a human protease. In some embodiments, a linker can have one of (at least) three roles: to cleave in the insect gut environment, to cleave in the plant cell, or to be designed not to intentionally cleave.

"Locus of a pest" refers to the habitat of a pest; food supply of a pest; breeding ground of a pest; area traveled by or inhabited by a pest; material infested, eaten, used by a pest; and/or any environment in which a pest inhabits, uses, is present in, or is expected to be. In some embodiments, the locus of a pest includes, without limitation, a pest habitat; a pest food supply; a pest breeding ground; a pest area; a pest environment; any surface or location that may be frequented and/or infested by a pest; any plant or animal, or a locus of a plant or animal, susceptible to attack by a pest; and/or any surface or location where a pest may be found, may be expected to be found, or is likely to be attacked by a pest.

"Locus of a plant" refers to any place in which a plant is growing; any place where plant propagation materials of a plant are sown; any place where plant propagation materials of a plant will be placed into the soil; or any area where plants are stored, including without limitation, live plants and/or harvested plants, leaves, seeds, fruits, or parts thereof.

"Locus of an animal" refers to any place where animals live, eat, breed, sleep, or otherwise are present in.

"Medium" (plural "media") refers to a nutritive solution for culturing cells in cell culture.

"MOA" refers to mechanism of action.

"Molecular weight (MW)" refers to the mass or weight of a molecule, and is typically measured in "daltons (Da)" or kilodaltons (kDa). In some embodiments, MW can be calculated using sodium dodecyl sulfate polyacrylamide gel electrophoresis (SDS-PAGE), analytical ultracentrifugation, or light scattering. In some embodiments, the SDS-PAGE method is as follows: the sample of interest is separated on a gel with a set of molecular weight standards. The sample is run, and the gel is then processed with a desired stain, followed by destaining for about 2 to 14 hours. The next step is to determine the relative migration distance (Rf) of the standards and protein of interest. The migration distance can be determined using the following equation:

$$Rf = \frac{\text{Migration distance of the protein}}{\text{Migration distance of the dye front}} \qquad \text{Formula (III)}$$

Next, the logarithm of the MW can be determined based on the values obtained for the bands in the standard; e.g., in some embodiments, the logarithm of the molecular weight of an SDS-denatured polypeptide and its relative migration distance (Rf) is plotted into a graph. After plotting the graph, interpolating the value derived will provide the molecular weight of the unknown protein band.

"Motif" refers to a polynucleotide or polypeptide sequence that is implicated in having some biological significance and/or exerts some effect or is involved in some biological process.

"Multiple cloning site" or "MCS" refers to a segment of DNA found on a vector that contains numerous restriction sites in which a DNA sequence of interest can be inserted.

"Mutant" refers to an organism, DNA sequence, amino acid sequence, peptide, polypeptide, or protein, that has an alteration or variation (for example, in the nucleotide sequence or the amino acid sequence), which causes said organism and/or sequence to be different from the naturally occurring or wild-type organism, wild-type sequence, and/or reference sequence with which the mutant is being compared. In some embodiments, this alteration or variation can be one or more nucleotide and/or amino acid substitutions or modifications (e.g., deletion or addition). In some embodiments, the one or more amino acid substitutions or modifications can be conservative; here, such a conservative amino acid substitution and/or modification in a "mutant" does not substantially diminish the activity of the mutant in relation to its non-mutant form. For example, in some embodiments, a "mutant" possesses one or more conservative amino acid substitutions when compared to a peptide with a disclosed and/or claimed sequence, as indicated by a SEQ ID NO.

"N-terminus" or "N-terminal" refers to the free amine group (i.e., —$NH_2$) that is positioned on beginning or start of a polypeptide.

"NCBI" refers to the National Center for Biotechnology Information.

"nm" refers to nanometers.

"Non-Polar amino acid" is an amino acid that is weakly hydrophobic and includes glycine, alanine, proline, valine, leucine, isoleucine, phenylalanine and methionine. Glycine or gly is the most preferred non-polar amino acid for the dipeptides of this invention.

"Normalized peptide yield" means the peptide yield in the conditioned medium divided by the corresponding cell density at the point the peptide yield is measured. The peptide yield can be represented by the mass of the produced peptide in a unit of volume, for example, mg per liter or mg/L, or by the UV absorbance peak area of the produced peptide in the HPLC chromatograph, for example, mAu·sec. The cell density can be represented by visible light absorbance of the culture at wavelength of 600 nm (OD600).

"OD" refers to optical density. Typically, OD is measured using a spectrophotometer. When measuring growth over time of a cell population, OD600 is preferable to UV spectroscopy; this is because at a 600 nm wavelength, the cells will not be harmed as they would under too much UV light.

"OD660 nm" or "OD660.m" refers to optical densities of a liquid sample measured (for example, yeast cell culture) when measured in a spectrophotometer at 660 nanometers (nm).

"One letter code" means the peptide sequence which is listed in its one letter code to distinguish the various amino acids in the primary structure of a protein: alanine=A, arginine=R, asparagine=N, aspartic acid=D, asparagine or aspartic acid=B, cysteine=C, glutamic acid=E, glutamine=Q, glutamine or glutamic acid=Z, glycine=G, histidine=H, isoleucine=I, leucine=L, lysine=K, methionine=M, phenylalanine=F, proline=P, serine=S, threonine=T, tryptophan=W, tyrosine=Y, and valine=V.

"Open reading frame" or "ORF" refers to a length of RNA or DNA sequence, between a translation start signal (e.g., AUG or ATG, respectively) and any one or more of the known termination codons, which encodes one or more polypeptide sequences. Put another way, the ORF describes the frame of reference as seen from the point of view of a ribosome translating the RNA code, insofar that the ribosome is able to keep reading (i.e., adding amino acids to the nascent protein) because it has not encountered a stop codon. Thus, "open reading frame" or "ORF" refers to the amino acid sequence encoded between translation initiation and termination codons of a coding sequence. Here, the terms "initiation codon" and "termination codon" refer to a unit of three adjacent nucleotides (i.e., a codon) in a coding sequence that specifies initiation and chain termination, respectively, of protein synthesis (mRNA translation).

In some embodiments, an ORF is a continuous stretch of codons that begins with a start codon (usually ATG for DNA, and AUG for RNA) and ends at a stop codon (usually UAA, UAG or UGA). In other embodiments, an ORF can be length of RNA or DNA sequence, between a translation start signal (e.g., AUG or ATG) and any one or more of the known termination codons, wherein said length of RNA or DNA sequence encodes one or more polypeptide sequences. In some other embodiments, an ORF can be a DNA sequence encoding a protein which begins with an ATG start codon and ends with a TGA, TAA or TAG stop codon. ORF can also mean the translated protein that the DNA encodes. Generally, those having ordinary skill in the art distinguish the terms "open reading frame" and "ORF," from the term "coding sequence," based upon the fact that the broadest definition of "open reading frame" simply contemplates a series of codons that does not contain a stop codon. Accordingly, while an ORF may contain introns, the coding sequence is distinguished by referring to those nucleotides (e.g., concatenated exons) that can be divided into codons that are actually translated into amino acids by the ribosomal translation machinery (i.e., a coding sequence does not contain introns); however, as used herein, the terms "coding sequence"; "CDS"; "open reading frame"; and "ORF,' are used interchangeably.

"Operable" refers to the ability to be used, the ability to do something, and/or the ability to accomplish some function or result. For example, in some embodiments, "operable" refers to the ability of a polynucleotide, DNA sequence, RNA sequence, or other nucleotide sequence or gene to encode a peptide, polypeptide, and/or protein. For example, in some embodiments, a polynucleotide may be operable to encode a protein, which means that the polynucleotide contains information that imbues it with the ability to create a protein (e.g., by transcribing mRNA, which is in turn translated to protein).

"Operably linked" refers to a juxtaposition wherein the components so described are in a relationship permitting them to function in their intended manner. For example, in some embodiments, operably linked can refer to two or more DNA, peptide, or polypeptide sequences. In other embodiments, operably linked can mean that the two adjacent DNA sequences are placed together such that the transcriptional activation of one DNA sequence can act on the other DNA sequence. In yet other embodiments, the term "operably linked" can refer to two or more peptides and/or polypeptides, wherein said two or more peptides and/or polypeptides are connected in such a way as to yield a single polypeptide chain; alternatively, the term operably linked can refer to two or more peptides that are connected in such a way that one peptide exerts some effect on the other. In yet other embodiments, operably linked can refer to two adjacent DNA sequences are placed together such that the transcriptional activation of one can act on the other.

"Out-recombined" or "out-recombination" refers to the removal of a gene and/or polynucleotide sequence (e.g., an endogenous gene, a transgene, a heterologous polynucleotide, etc.) that is flanked by two site-specific recombination sites (e.g., the 5'- and 3'-nucleotide sequence of a target gene that is homologous to the homology arms of a target vector) during in vivo homologous recombination. In some embodiments, the term "out-recombined" refers to the process wherein an endogenous gene is removed, e.g., during homologous recombination. In other embodiments, the term "out-recombined" refers to the process wherein a heterologous polynucleotide is removed via molecular mechanisms intrinsic to the host cell.

"Pest" includes, but is not limited to: insects, fungi, bacteria, nematodes, mites, ticks, and the like.

"Pesticidally-effective amount" refers to an amount of the pesticide that is able to do one or more of the following: bring about death to at least one pest; or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

"Pharmaceutically acceptable salt" is synonymous with agriculturally acceptable salt, and as used herein refers to a compound that is modified by making acid or base salts thereof.

"Plant" shall mean whole plants, plant tissues, plant cells, plant parts, plant organs (e.g., leaves, stems, roots, etc.), seeds, propagules, embryos and progeny of the same. Plant cells can be differentiated or undifferentiated (e.g. callus, suspension culture cells, protoplasts, leaf cells, root cells, phloem cells, and pollen).

"Plant transgenic protein" means a protein from a heterologous species that is expressed in a plant after the DNA or RNA encoding it was delivered into one or more of the plant cells.

"Plant-incorporated protectant" or "PIP" means an insecticidal protein produced by transgenic plants, and the genetic material necessary for the plant to produce the protein.

"Plant cleavable linker" means a cleavable linker peptide, or a nucleotide encoding a cleavable linker peptide, which contains a plant protease recognition site and can be cleaved during the protein expression process in the plant cell.

"Plant regeneration media" means any media that contains the necessary elements and vitamins for plant growth and plant hormones necessary to promote regeneration of a cell into an embryo which can germinate and generate a plantlet derived from tissue culture. Often the media contains a selectable agent to which the transgenic cells express a selection gene that confers resistance to the agent.

"Plasmid" refers to a DNA segment that acts as a carrier for a gene of interest, and, when transformed or transfected into an organism, can replicate and express the DNA sequence contained within the plasmid independently of the host organism. Plasmids are a type of vector, and can be "cloning vectors" (i.e., simple plasmids used to clone a DNA fragment and/or select a host population carrying the plasmid via some selection indicator) or "expression plasmids" (i.e., plasmids used to produce large amounts of polynucleotides and/or polypeptides).

"Polar amino acid" is an amino acid that is polar and includes serine, threonine, cysteine, asparagine, glutamine, histidine, tryptophan and tyrosine; preferred polar amino acids are serine, threonine, cysteine, asparagine and glutamine; with serine being most highly preferred.

"Polynucleotide" refers to a polymeric-form of nucleotides (e.g., ribonucleotides, deoxyribonucleotides, or analogs thereof) of any length; e.g., a sequence of two or more ribonucleotides or deoxyribonucleotides. As used herein, the term "polynucleotide" includes double- and single-stranded DNA, as well as double- and single-stranded RNA; it also includes modified and unmodified forms of a polynucleotide (modifications to and of a polynucleotide, for example, can include methylation, phosphorylation, and/or capping). In some embodiments, a polynucleotide can be one of the following: a gene or gene fragment (for example, a probe, primer, EST, or SAGE tag); genomic DNA; genomic DNA fragment; exon; intron; messenger RNA (mRNA); transfer RNA; ribosomal RNA; ribozyme; cDNA; recombinant polynucleotide; branched polynucleotide; plasmid; vector; isolated DNA of any sequence; isolated RNA of any sequence; nucleic acid probe; primer or amplified copy of any of the foregoing.

In yet other embodiments, a polynucleotide can refer to a polymeric-form of nucleotides operable to encode the open reading frame of a gene.

In some embodiments, a polynucleotide can refer to cDNA.

In some embodiments, polynucleotides can have any three-dimensional structure and may perform any function, known or unknown. The structure of a polynucleotide can also be referenced to by its 5'- or 3'-end or terminus, which indicates the directionality of the polynucleotide. Adjacent nucleotides in a single-strand of polynucleotides are typically joined by a phosphodiester bond between their 3' and 5' carbons. However, different intemucleotide linkages could also be used, such as linkages that include a methylene, phosphoramidate linkages, etc. This means that the respective 5' and 3' carbons can be exposed at either end of the polynucleotide, which may be called the 5' and 3' ends or termini. The 5' and 3' ends can also be called the phosphoryl ($PO_4$) and hydroxyl (OH) ends, respectively, because of the chemical groups attached to those ends. The term polynucleotide also refers to both double- and single-stranded molecules. Unless otherwise specified or required, any embodiment that makes or uses a polynucleotide encompasses both the double-stranded form and each of two complementary single-stranded forms known or predicted to make up the double-stranded form.

In some embodiments, a polynucleotide can include modified nucleotides, such as methylated nucleotides and nucleotide analogs (including nucleotides with non-natural bases, nucleotides with modified natural bases such as aza- or deaza-purines, etc.). If present, modifications to the nucleotide structure can be imparted before or after assembly of the polynucleotide.

In some embodiments, a polynucleotide can also be further modified after polymerization, such as by conjugation with a labeling component. Additionally, the sequence of nucleotides in a polynucleotide can be interrupted by non-nucleotide components. One or more ends of the polynucleotide can be protected or otherwise modified to prevent that end from interacting in a particular way (e.g. forming a covalent bond) with other polynucleotides.

In some embodiments, a polynucleotide can be composed of a specific sequence of four nucleotide bases: adenine (A); cytosine (C); guanine (G); and thymine (T). Uracil (U) can also be present, for example, as a natural replacement for thymine when the polynucleotide is RNA. Uracil can also be used in DNA. Thus, the term "sequence" refers to the alphabetical representation of a polynucleotide or any nucleic acid molecule, including natural and non-natural bases.

The term "RNA molecule" or ribonucleic acid molecule refers to a polynucleotide having a ribose sugar rather than deoxyribose sugar and typically uracil rather than thymine as one of the pyrimidine bases. An RNA molecule of the invention is generally single-stranded, but can also be double-stranded. In the context of an RNA molecule from an RNA sample, the RNA molecule can include the single-stranded molecules transcribed from DNA in the cell nucleus, mitochondrion or chloroplast, which have a linear sequence of nucleotide bases that is complementary to the DNA strand from which it is transcribed.

In some embodiments, a polynucleotide can further comprise one or more heterologous regulatory elements. For example, in some embodiments, the regulatory element is one or more promoters; enhancers; silencers; operators; splicing signals; polyadenylation signals; termination signals; RNA export elements, internal ribosomal entry sites (IRES); poly-U sequences; or combinations thereof.

"Post-transcriptional regulatory elements" are DNA segments and/or mechanisms that affect mRNA after it has been transcribed. Mechanisms of post-transcriptional mechanisms include splicing events; capping, splicing, and addition of a Poly (A) tail, and other mechanisms known to those having ordinary skill in the art.

"Promoter" refers to a region of DNA to which RNA polymerase binds and initiates the transcription of a gene.

"Protein" has the same meaning as "peptide" and/or "polypeptide" in this document.

"Ratio" refers to the quantitative relation between two amounts showing the number of times one value contains or is contained within the other.

"Reading frame" refers to one of the six possible reading frames, three in each direction, of the double stranded DNA molecule. The reading frame that is used determines which codons are used to encode amino acids within the coding sequence of a DNA molecule. In some embodiments, a reading frame is a way of dividing the sequence of nucleotides in a polynucleotide and/or nucleic acid (e.g., DNA or RNA) into a set of consecutive, non-overlapping triplets.

"Recombinant DNA" or "rDNA" refers to DNA that is comprised of two or more different DNA segments.

"Recombinant vector" means a DNA plasmid vector into which foreign DNA has been inserted.

"Regulatory elements" refers to a genetic element that controls some aspect of the expression and/or processing of nucleic acid sequences. For example, in some embodiments, a regulatory element can be found at the transcriptional and post-transcriptional level. Regulatory elements can be cis-regulatory elements (CREs), or trans-regulatory elements (TREs). In some embodiments, a regulatory element can be one or more promoters; enhancers; silencers; operators; splicing signals; polyadenylation signals; termination signals; RNA export elements, internal ribosomal entry sites (IRES); poly-U sequences; and/or other elements that influence gene expression, for example, in a tissue-specific manner; temporal-dependent manner; to increase or decrease expression; and/or to cause constitutive expression.

"Restriction enzyme" or "restriction endonuclease" refers to an enzyme that cleaves DNA at a specified restriction site. For example, a restriction enzyme can cleave a plasmid at an EcoRI, SacII or BstXI restriction site allowing the plasmid to be linearized, and the DNA of interest to be ligated.

"Restriction site" refers to a location on DNA comprising a sequence of 4 to 8 nucleotides, and whose sequence is recognized by a particular restriction enzyme.

"Selection gene" means a gene which confers an advantage for a genetically modified organism to grow under the selective pressure.

"sp." or "sp." refers to species.

"ssp." or "subsp." or "ssp." or "subsp." refers to subspecies.

"Subcloning" or "subcloned" refers to the process of transferring DNA from one vector to another, usually advantageous vector. For example, polynucleotide encoding a mutant AMP can be subcloned into a pLB102 plasmid subsequent to selection of yeast colonies transformed with pKLAC1 plasmids.

"SSI" is an acronym that is context dependent. In some contexts, it can refer to "site-specific integration," which is used to refer to a sequence that will permit in vivo homologous recombination to occur at a specific site within a host organism's genome. Thus, in some embodiments, the term "site-specific integration" refers to the process directing a transgene to a target site in a host-organism's genome, allowing the integration of genes of interest into pre-selected genome locations of a host-organism. However, in other contexts, SSI can refer to "surface spraying indoors," which is a technique of applying a variable volume sprayable volume of an insecticide onto surfaces where vectors rest, such as on walls, windows, floors and ceilings.

"STA" or "Translational stabilizing protein" or "stabilizing domain" or "stabilizing protein" (used interchangeably herein) means a peptide or protein with sufficient tertiary structure that it can accumulate in a cell without being targeted by the cellular process of protein degradation. The protein can be between 5 and 50 amino acids long. The translational stabilizing protein is coded by a DNA sequence for a protein that is operably linked with a sequence encoding an insecticidal protein or an AMP in the ORF. The operably-linked STA can either be upstream or downstream of the AMP and can have any intervening sequence between the two sequences (STA and AMP) as long as the intervening sequence does not result in a frame shift of either DNA sequence. The translational stabilizing protein can also have an activity which increases delivery of the AMP across the gut wall and into the hemolymph of the insect.

"sta" means a nucleotide encoding a translational stabilizing protein.

"Stringent hybridization" or "stringent hybridization conditions" refers to conditions under which a polynucleotide (e.g., a nucleic acid probe, primer or oligonucleotide) will hybridize to its target sequence, typically in a complex mixture of nucleic acids, but not to other sequences. Stringent hybridization conditions are sequence-and length-dependent, and depend on % (percent)-identity (or %-mismatch) over a certain length of nucleotide residues. Longer sequences hybridize specifically at higher temperatures than shorter sequences. Generally, stringent conditions are selected to be about 5° C. lower than the thermal melting point (Tm) for the specific sequence at a defined ionic strength and pH. Stringent conditions may also be achieved with the addition of destabilizing agents, such as formamide. In some embodiments, a polynucleotide of the present disclosure can stringently hybridize to a polynucleotide encoding an AMP, or a complementary nucleotide sequence thereof. For example, in some embodiments, a polynucleotide of the present disclosure can stringently hybridize to a polynucleotide operable to encode an AMP having an amino acid sequence as set forth in any one of SEQ ID NOs: 6, 20, 24-26, 28-36, 38-42, 48, 54, 58, 60, 62-63, 69, 108, 116, 119, and 168-169, or a complementary nucleotide sequence thereof.

"Structural motif" refers to the three-dimensional arrangement of peptides and/or polypeptides, and/or the arrangement of operably linked polypeptide segments. For example, the polypeptide comprising ERSP-STA-L-AMP has an ERSP motif, an STA motif, a LINKER motif, and an AMP polypeptide motif.

"Susceptible to attack by a pest(s)," refer to plants, or human or animal patients or subjects, susceptible to a pest or a pest infections.

"Toxin" refers to a venom and/or a poison, especially a protein or conjugated protein produced by certain animals, higher plants, and pathogenic bacteria. Generally, the term "toxin" is reserved natural products, e.g., molecules and peptides found in scorpions, spiders, snakes, poisonous mushrooms, etc., whereas the term "toxicant" is reserved for man-made products and/or artificial products e.g., man-made chemical pesticides. However, as used herein, the terms "toxin" and "toxicant" are used synonymously "Transfection" and "transformation" both refer to the process of introducing exogenous and/or heterologous DNA or RNA (e.g., a vector containing a polynucleotide that encodes a CRIP) into a host organism (e.g., a prokaryote or a eukaryote). Generally, those having ordinary skill in the art sometimes reserve the term "transformation" to describe processes where exogenous and/or heterologous DNA or RNA are introduced into a bacterial cell; and reserve the term "transfection" for processes that describe the introduction of exogenous and/or heterologous DNA or RNA into eukaryotic cells. However, as used herein, the term "transformation" and "transfection" are used synonymously, regardless of whether a process describes the introduction exogenous and/or heterologous DNA or RNA into a prokaryote (e.g., bacteria) or a eukaryote (e.g., yeast, plants, or animals).

"Transgene" means a heterologous and/or exogenous polynucleotide sequence that is transformed into an organism and/or a cell therefrom.

"Transgenic host cell" or "host cell" means a cell which is transformed with a gene and has been selected for its transgenic status via an additional selection gene.

"Transgenic plant" means a plant that has been derived from a single cell that was transformed with foreign DNA such that every cell in the plant contains that transgene.

"Transient expression system" means an *Agrobacterium tumefaciens*-based system which delivers DNA encoding a disarmed plant virus into a plant cell where it is expressed. The plant virus has been engineered to express a protein of interest at high concentrations, up to 40% of the total soluble protein (TSP).

"Triple expression cassette refers to three AMP expression cassettes contained on the same vector.

"TRBO" means a transient plant expression system using Tobacco mosaic virus with removal of the viral coating protein gene.

"Trypsin cleavage" means an in vitro assay that uses the protease enzyme trypsin (which recognizes exposed lysine and arginine amino acid residues) to separate a cleavable linker at that cleavage site. It also means the act of the trypsin enzyme cleaving that site.

"TSP" or "total soluble protein" means the total amount of protein that can be extracted from a plant tissue sample and solubilized into the extraction buffer.

"var." refers to varietas or variety. The term "var." is used to indicate a taxonomic category that ranks below the species level and/or subspecies (where present). In some embodiments, the term "var." represents members differing from others of the same subspecies or species in minor but permanent or heritable characteristics.

"Vector" refers to the DNA segment that accepts a heterologous polynucleotide operable to encode a peptide of interest (e.g., amp). The heterologous polynucleotide is known as an "insert" or "transgene."

"Wild type" or "WT" or "wild-type" or "wildtype" refer to the phenotype and/or genotype (i.e., the appearance or sequence) of an organism, polynucleotide sequence, and/or polypeptide sequence, as it is found and/or observed in its naturally occurring state or condition.

"Yield" refers to the production of a peptide, and increased yields can mean increased amounts of production, increased rates of production, and an increased average or median yield and increased frequency at higher yields. The term "yield" when used in reference to plant crop growth and/or production, as in "yield of the plant" refers to the quality and/or quantity of biomass produced by the plant.

Throughout this specification, unless specifically stated otherwise or the context requires otherwise, reference to a single step, composition of matter, group of steps or group of compositions of matter shall be taken to encompass one and a plurality (i.e., one or more) of those steps, compositions of matter, groups of steps or group of compositions of matter.

The present disclosure is performed without undue experimentation using, unless otherwise indicated, conventional techniques of molecular biology, microbiology, virology, recombinant DNA technology, solid phase and liquid nucleic acid synthesis, peptide synthesis in solution, solid phase peptide synthesis, immunology, cell culture, and formulation. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp1-22; Atkinson et al, pp35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). Biochem. Biophys. Res. Commun. 73 336-342; Merrifield, R. B. (1963). J. Am. Chem. Soc. 85, 2149-2154; Barany, G. and Merrifield, R. B. (1979) in The Peptides (Gross, E. and Meienhofer, 3. eds.), vol. 2, pp. 1-284, Academic Press, New York. 12. Wiinsch, E., ed. (1974) Synthese von Peptiden in Houben-Weyls Metoden der Organischen Chemie (Muler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) Int. J. Peptide Protein Res. 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000); each of these references are incorporated herein by reference in their entireties.

Although the disclosure of the invention has been described in detail for purposes of clarity and understanding, it will be obvious to those with skill in the art that certain modifications can be practiced within the scope of the appended claims. All publications and patent documents cited herein are hereby incorporated by reference in their entirety for all purposes to the same extent as if each were so individually denoted.

Throughout this specification, unless the context requires otherwise, the word "comprise," or variations such as "comprises" or "comprising," will be understood to imply the inclusion of a stated step or element or integer or group of steps or elements or integers but not the exclusion of any other step or element or integer or group of elements or integers.

All patent applications, patents, and printed publications referred to herein are incorporated by reference in their entirety to the same extent as if each individual publication, patent, or patent application was specifically and individually indicated to be incorporated by reference in its entirety. And, all patent applications, patents, and printed publications cited herein are incorporated herein by reference in the entireties, except for any definitions, subject matter disclaimers, or disavowals, and except to the extent that the incorporated material is inconsistent with the express disclosure herein, in which case the language in this disclosure controls.

Av3b Mutant Peptides (AMPs)

The sea anemone, *Anemonia viridis*, possesses a variety of toxins that it uses to defend itself: one of these toxins is the neurotoxin "Av3." Av3 is a type III sea anemone toxin that inhibits the inactivation of voltage-gated sodium ($Na^+$) channels at receptor site 3, resulting in contractile paralysis. The binding of an Av3 toxin to site 3 results in the inactivated state of the sodium channel to become destabilized, which in turn causes the channel to remain in the open position (see Blumenthal et al., Voltage-gated sodium channel toxins: poisons, probes, and future promise. Cell Biochem Biophys. 2003; 38(2):215-38). Av3 shows high selectivity for crustacean and insect sodium channels, and low selectivity for mammalian sodium channels (see Moran et al., Sea anemone toxins affecting voltage-gated sodium channels—molecular and evolutionary features, Toxicon. 2009 Dec. 15; 54(8): 1089-1101). An exemplary Av3 polypeptide from *Anemonia viridis* is provided having the amino acid sequence of "RSCCPCYWGGCPWGQNCYPEGCSGPKV" (SEQ ID NO:172) (NCBI Accession No. P01535.1).

In some embodiments, wild-type Av3 can be mutated, e.g., a wild-type Av3 can have an N-terminal mutation and a C-terminal mutation, wherein the N-terminal mutation results in an amino acid substitution of RIK relative to SEQ ID NO:172, and the C-terminal mutation results in an amino acid deletion relative to SEQ ID NO:172; thus, the wild-type Av3 peptide amino acid sequence is changed from "RSCCPCYWGGCPWGQNCYPEGCSGPKV" (SEQ ID NO: 172), to the amino acid sequence: "KSCCPCYWGGCPWGQNCYPEGCSGPK" (SEQ ID NO:1).

When wild-type Av3 has an RIK mutation and a C-terminal deletion, resulting in the peptide having an amino acid sequence of SEQ ID NO: 1, the resulting peptide is called, "Av3b." An exemplary method of obtaining Av3b is disclosed in PCT Application No. PCT/US2019/051093, the disclosure of which is incorporated herein by reference in its entirety.

The Av3b peptide has characteristics that make it superior to wild-type Av3. See PCT/US2019/051093. However, the inventors have developed novel and inventive mutations to Av3b that result in peptides having desirable and unexpected properties; these mutant peptides are called Av3 mutant polypeptides (AMPs).

Exemplary AMPs

In some embodiments, an Av3 mutant polypeptide (AMP) can be a mutant or variant that differs from wild type Av3 (SEQ ID NO:172), e.g., in some embodiments, this variance can be an amino acid substitution, amino acid deletion/insertion, or a change to the polynucleotide encoding the AMP. The result of this variation is a non-naturally occurring polypeptide and/or polynucleotide sequence encoding the same, relative to WT Av3, that possesses insecticidal activity against one or more insect species.

In some embodiments, an AMP can be a mutant or variant that differs from the Av3b peptide having an amino acid sequence as set forth in SEQ ID NO: 1. In some embodiments, an Av3b peptide can be made by creating an N-terminal mutation and a C-terminal mutation to the wild type Av3 peptide, wherein the N-terminal mutation results in an amino acid substitution of RIK relative to SEQ ID NO:172, and the C-terminal mutation results in an amino acid deletion relative to SEQ ID NO:172; thus, the wild-type Av3 peptide amino acid sequence can be changed from "RSCCPCYWGGCPWGQNCYPEGCSGPKV" (SEQ ID NO: 172), to the amino acid sequence:

(SEQ ID NO: 1)
"KSCCPCYWGGCPWGQNCYPEGCSGPK".

In some embodiments, an Av3 mutant polypeptide (AMP) having insecticidal activity against one or more insect species, comprises, consists essentially of, or consists of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-X-G-C-$X_6$-G-$X_7$-X-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or an agriculturally acceptable salt thereof.

In some embodiments, an Av3 mutant polypeptide (AMP) having insecticidal activity against one or more insect species, comprises, consists essentially of, or consists of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; $X_6$ is G or absent; or an agriculturally acceptable salt thereof.

The inventors evaluated 172 mutations to the Av3b peptide. A summary of the AMPs evaluated here possessing mutations that confer novel and unexpected properties are provided in the tables below. Table 1 provides a summary of AMPs that confer at least one novel property relative to Av3b. Table 2 provides a summary of AMPs that confer two or more novel properties relative to Av3b. A complete listing of all of the mutants evaluated is provided at the end of the application.

TABLE 1

Summary of Av3b mutants possessing mutations that confer novel and unexpected properties relative to Av3b. Table 1 provides a summary of AMPs that confer at least one novel property relative to Av3b. The properties include: Y = yield; A = activity; S = general stability; D = resistance to proteolytic degradation in fermentation media (fermentation beer); F = similar protein folding relative to Av3b (as determined via circular dichroism); T = thermostable at 54° C.; P = stable under diverse pH conditions; G = stable in insect gut extract. Here, yield and activity are scored when a given peptide's yield or activity comparable to, or better than, the yield or activity of Av3b under the same conditions.

| Name | SEQ ID NO. | Sequence | Desirable property |
|---|---|---|---|
| Av3b | 1 | KSCCPCYWGGCPWGQNCYPEGCSGPK | — |
| Av3bM5 | 6 | KSCCPCYWPNCPWGQNCYPEGCSGPK | Y |
| Av3bM19 | 20 | KSCCPCYWGGCPWGQDCYPDGCDGPK | Y, A, S, D |
| Av3bM23 | 24 | KSCCPCYWGGCPWGQNCYPNGCSGPK | Y, A |
| Av3bM24 | 25 | KSCCPCYWGGCPWGQNCYPEGCDGPK | Y, A, S, D, G |
| Av3bM25 | 26 | KSCCPCYWPGCPWGQNCYPEGCSGPK | Y, A, |
| Av3bM27 | 28 | KSCCPCYWAGCPWGQNCYPEGCSGPK | A |

TABLE 1-continued

Summary of Av3b mutants possessing mutations that confer novel and unexpected properties relative to Av3b. Table 1 provides a summary of AMPs that confer at least one novel property relative to Av3b. The properties include: Y = yield; A = activity; S = general stability; D = resistance to proteolytic degradation in fermentation media (fermentation beer); F = similar protein folding relative to Av3b (as determined via circular dichroism); T = thermostable at 54° C.; P = stable under diverse pH conditions; G = stable in insect gut extract. Here, yield and activity are scored when a given peptide's yield or activity comparable to, or better than, the yield or activity of Av3b under the same conditions.

| Name | SEQ ID NO. | Sequence | Desirable property |
|---|---|---|---|
| Av3bM28 | 29 | HSCCPCYWGGCPWGQNCYPEGCSGPK | Y |
| Av3bM29 | 30 | QSCCPCYWGGCPWGQNCYPEGCSGPK | Y |
| Av3bM30 | 31 | QSCCPCYWGGCPWGQNCYPEGCSGPH | Y |
| Av3bM31 | 32 | TSCCPCYWGGCPWGQNCYPEGCSGPK | Y |
| Av3bM32 | 33 | SSCCPCYWGGCPWGQNCYPEGCSGPK | Y |
| Av3bM33 | 34 | SSCCPCYWGGCPWGQNCYPEGCSGPT | Y |
| Av3bM35 | 58 | NSCCPCYWGGCPWGQNCYPEGCSGPK | Y |
| Av3bM37 | 60 | ESCCPCYWGGCPWGQNCYPEGCSGPK | Y |
| Av3bM39 | 62 | ISCCPCYWGGCPWGQNCYPEGCSGPK | A |
| Av3bM40 | 63 | LSCCPCYWGGCPWGQNCYPEGCSGPK | A |
| Av3bM46 | 69 | VSCCPCYWGGCPWGQNCYPEGCSGPK | A |
| Av3bM85 | 108 | KSCCPCYWGGCPWGQNCYPEGCGGPK | A |
| Av3bM93 | 116 | KSCCPCYWGGCPWGQNCYPEGCTGPK | A |
| Av3bM96 | 119 | KSCCPCYWGGCPWGQNCYPEGCVGPK | A |
| Av3bM97 | 41 | KSCCPCYWGGCPWGQNCYPEGCSGPA | A |
| Av3bM98 | 42 | KSCCPCYWGGCPWGQNCYPEGCSGPR | D |
| Av3bM103 | 36 | KSCCPCYWGGCPWGQNCYPEGCSGPG | D, F, T, P, G |
| Av3bM111 | 48 | KSCCPCYWGGCPWGQNCYPEGCSGPT | A |
| Av3bM125 | 35 | KSCCPCYWPGCPWGQNCYPEGCRGPD | Y, D |
| Av3bM148 | 39 | KSCCPCYWGGCPWGQNCYPEGCSGPKG | D |
| Av3bM163 | 168 | KSCCPCYWGGCPWGQNCYPEGCSGP | A |
| Av3bM164 | 169 | KSCCPCYWGGCPWGQNCYPEGCSG | A |
| Av3bM165 | 40 | KSCCPCYWGGCPWGQNCYPEGCSGPKVG | A, D, F, T, P |
| Av3bM168 | 54 | KSCCPCYWGGCPWGQNCYPEGCSGPKVI | A |
| Av3bM170 | 38 | KSCCPCYWGGCPWGQNCYPEGCGGPG | A, D, F, T, P, G |

TABLE 2

Summary of Av3b mutants possessing mutations that confer novel and unexpected properties relative to Av3b. Table 2 provides a summary of AMPs that confer two or more novel properties relative to Av3b The properties include: Y = yield; A = activity; S = general stability; D = resistance to proteolytic degradation in fermentation beer; F = similar protein folding relative to Av3b (as determined via circular dichroism); T = thermostable at 54° C.; P = stable under diverse pH conditions; G = stable in insect gut extract. Here, yield and activity are scored when a given peptide's yield or activity comparable to, or better than, the yield or activity of Av3b under the same conditions.

| Name | SEQ ID NO. | Sequence | Desirable property |
|---|---|---|---|
| Av3b | 1 | KSCCPCYWGGCPWGQNCYPEGCSGPK | — |
| Av3bM19 | 20 | KSCCPCYWGGCPWGQDCYPDGCDGPK | Y, A, S, D |

TABLE 2-continued

Summary of Av3b mutants possessing mutations that confer novel and unexpected properties relative to Av3b. Table 2 provides a summary of AMPs that confer two or more novel properties relative to Av3b The properties include: Y = yield; A = activity; S = general stability; D = resistance to proteolytic degradation in fermentation beer; F = similar protein folding relative to Av3b (as determined via circular dichroism); T = thermostable at 54° C.; P = stable under diverse pH conditions; G = stable in insect gut extract. Here, yield and activity are scored when a given peptide's yield or activity comparable to, or better than, the yield or activity of Av3b under the same conditions.

| Name | SEQ ID NO. | Sequence | Desirable property |
|---|---|---|---|
| Av3bM23 | 24 | KSCCPCYWGGCPWGQNCYPNGCSGPK | Y, A |
| Av3bM24 | 25 | KSCCPCYWGGCPWGQNCYPEGCDGPK | Y, A, S, D, G |
| Av3bM25 | 26 | KSCCPCYWPGCPWGQNCYPEGCSGPK | Y, A, |
| Av3bM103 | 36 | KSCCPCYWGGCPWGQNCYPEGCSGPG | D, F, T, P, G |
| Av3bM125 | 35 | KSCCPCYWPGCPWGQNCYPEGCRGPD | Y, D |
| Av3bM165 | 40 | KSCCPCYWGGCPWGQNCYPEGCSGPKVG | A, D, F, T, P |
| Av3bM170 | 38 | KSCCPCYWGGCPWGQNCYPEGCGGPG | A, D, F, T, P, G |

In some embodiments, the present disclosure comprises, consists essentially of, or consists of, an Av3 mutant polypeptide (AMP) having insecticidal activity against one or more insect species, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences provided in the foregoing Table 1.

In some embodiments, the present disclosure comprises, consists essentially of, or consists of, an Av3 mutant polypeptide (AMP) having insecticidal activity against one or more insect species, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences provided in the foregoing Table 2.

In some embodiments, the present disclosure comprises, consists essentially of, or consists of, an Av3 mutant polypeptide (AMP) having insecticidal activity against one or more insect species, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or an agriculturally acceptable salt thereof.

In some embodiments, the present disclosure comprises, consists essentially of, or consists of, an Av3 mutant polypeptide (AMP) having insecticidal activity against one or more insect species, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; $X_6$ is G or absent; or an agriculturally acceptable salt thereof.

In some embodiments, the AMP comprises, consists essentially of, or consists of, an amino sequence as set forth in any one of SEQ ID NOs: 6, 20, 24-26, 28-36, 38-42, 48, 54, 58, 60, 62-63, 69, 108, 116, 119, and 168-169, or an agriculturally acceptable salt thereof.

In some embodiments, the AMP comprises, consists essentially of, or consists of, an amino sequence as set forth in any one of SEQ ID NOs: 20, 24-26, 35-36, 38, and 40, or an agriculturally acceptable salt thereof.

In some embodiments, the AMP comprises, consists essentially of, or consists of, an amino sequence as set forth in any one of SEQ ID NOs: 25, 36, 38, and 40, or an agriculturally acceptable salt thereof.

In some embodiments, an AMP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQDCYPDGCDGPK" (SEQ ID NO: 20), or an agriculturally acceptable salt thereof.

In some embodiments, an AMP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPNGCSGPK" (SEQ ID NO: 24), or an agriculturally acceptable salt thereof.

In some embodiments, an AMP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCDGPK" (SEQ ID NO: 25), or an agriculturally acceptable salt thereof.

In some embodiments, an AMP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWPGCPWGQNCYPEGCSGPK" (SEQ ID NO: 26), or an agriculturally acceptable salt thereof.

In some embodiments, an AMP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWPGCPWGQNCYPEGCRGPD" (SEQ ID NO: 35), or an agriculturally acceptable salt thereof.

In some embodiments, an AMP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCSGPG" (SEQ ID NO: 36), or an agriculturally acceptable salt thereof.

In some embodiments, an AMP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCGGPG" (SEQ ID NO: 38), or an agriculturally acceptable salt thereof.

In some embodiments, an AMP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCSGPKVG" (SEQ ID NO: 40), or an agriculturally acceptable salt thereof.

In some embodiments, an AMP of the present disclosure can comprise, consist essentially of, or consist of, a homopolymer or heteropolymer of two or more AMPs, wherein the amino acid sequence of each AMP is the same or different.

In some embodiments, an AMP of the present disclosure can comprise, consist essentially of, or consist of, an AMP that is a fused protein comprising two or more AMPs separated by a cleavable or non-cleavable linker, and wherein the amino acid sequence of each AMP may be the same or different.

In some embodiments, the linker is a cleavable linker.

In some embodiments, the linker has an amino acid sequence as set forth in any one of SEQ ID NOs: 184-193.

In some embodiments, the linker is cleavable inside at least one of (i) the gut or hemolymph of an insect, and (ii) cleavable inside the gut of a mammal.

Detailed methods concerning linkers are described below.

Polynucleotides Encoding AMPs

In some embodiments, the present disclosure comprises, consists essentially of, or consists of, a polynucleotide operable to encode an Av3 mutant polypeptide (AMP).

In some embodiments, the present disclosure comprises, consists essentially of, or consists of, a polynucleotide operable to encode an AMP, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or a complementary nucleotide sequence thereof.

In some embodiments, the present disclosure comprises, consists essentially of, or consists of, a polynucleotide operable to encode an AMP, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; $X_6$ is G or absent; or a complementary nucleotide sequence thereof.

In some embodiments, the polynucleotide is operable to encode an AMP that comprises, consists essentially of, or consists of, an amino sequence as set forth in any one of SEQ ID NOs: 6, 20, 24-26, 28-36, 38-42, 48, 54, 58, 60, 62-63, 69, 108, 116, 119, and 168-169, or a complementary nucleotide sequence thereof.

In some embodiments, the polynucleotide is operable to encode an AMP that comprises, consists essentially of, or consists of, an amino sequence as set forth in any one of SEQ ID NOs: 20, 24-26, 35-36, 38, and 40, or a complementary nucleotide sequence thereof.

In some embodiments, polynucleotides of the present disclosure encode an AMP, wherein the polynucleotide hybridizes under stringent conditions to a polynucleotide which encodes an AMP having an amino acid sequence of SEQ ID NOs: 20, 24-26, 35-36, 38, and 40, or a complementary nucleotide sequence thereof.

In some embodiments, the polynucleotide is operable to encode an AMP that comprises, consists essentially of, or consists of, an amino sequence as set forth in any one of SEQ ID NOs: 25, 36, 38, and 40, or a complementary nucleotide sequence thereof.

Nucleotide sequence homologs, e.g., AMPs encoded by polynucleotides that hybridize to each or any of the sequences disclosed in this application under stringent hybridization conditions, are also an embodiment of the present disclosure. The present disclosure also provides a method for detecting a first polynucleotide that hybridizes to a second polynucleotide, wherein the first polynucleotide (or its reverse complement sequence) encodes an AMP or fragment thereof, and hybridizes to the second polynucleotide. In such case, the second polynucleotide can be any of the polynucleotides operable to encode an AMP of the present disclosure, under stringent hybridization conditions.

In some embodiments, a polynucleotide of the present disclosure can stringently hybridize to a polynucleotide encoding an AMP, or a complementary sequence thereof, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent.

In some embodiments, a polynucleotide of the present disclosure can stringently hybridize to a polynucleotide encoding an AMP, or a complementary sequence thereof, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; $X_6$ is G or absent.

In some embodiments, a polynucleotide of the present disclosure comprises, consists essentially of, or consists of, a polynucleotide segment encoding an AMP or fragment thereof, wherein: (a) said AMP comprises an amino acid sequence set forth in SEQ ID NOs: 6, 20, 24-26, 28-36, 38-42, 48, 54, 58, 60, 62-63, 69, 108, 116, 119, or 168-169; or (b) said AMP comprises an amino acid sequence having at least 80%, or 85%, or 90%, or 95%, or 98%, or 99%, or about 100% amino acid sequence identity to SEQ ID NOs: 6, 20, 24-26, 28-36, 38-42, 48, 54, 58, 60, 62-63, 69, 108, 116, 119, or 168-169; or (c) said polynucleotide segment hybridizes to a polynucleotide having a polynucleotide segment operable to encode an AMP having an amino acid sequence as set forth in SEQ ID NOs: 6, 20, 24-26, 28-36, 38-42, 48, 54, 58, 60, 62-63, 69, 108, 116, 119, or 168-169.

In one embodiment, the present disclosure provides a method comprising contacting a sample of nucleic acids with a nucleic acid probe that hybridizes under stringent hybridization conditions with a polynucleotide comprising a polynucleotide segment encoding an AMP or fragment thereof as provided herein, and does not hybridize under such hybridization conditions with a polynucleotide that does not comprise the segment, wherein the probe is homologous or complementary to a polynucleotide encoding any one of SEQ ID NOs: 6, 20, 24-26, 28-36, 38-42, 48, 54, 58, 60, 62-63, 69, 108, 116, 119, or 168-169, or a polynucleotide encoding an AMP comprising an amino acid sequence having at least 80%, or 85%, or 90%, or 95%, or 98%, or 99%, or about 100% amino acid sequence identity to SEQ ID NOs: 6, 20, 24-26, 28-36, 38-42, 48, 54, 58, 60, 62-63, 69, 108, 116, 119, or 168-169. The method may further comprise (a) subjecting the sample and probe to stringent hybridization conditions; and (b) detecting hybridization of the probe with polynucleotide of the sample.

In some embodiments, the polynucleotide is operable to encode an AMP that can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQDCYPDGCDGPK" (SEQ ID NO: 20), or a complementary nucleotide sequence thereof.

In some embodiments, the polynucleotide is operable to encode an AMP that can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPNGCSGPK" (SEQ ID NO: 24), or a complementary nucleotide sequence thereof.

In some embodiments, the polynucleotide is operable to encode an AMP that can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCDGPK" (SEQ ID NO: 25), or a complementary nucleotide sequence thereof.

In some embodiments, the polynucleotide is operable to encode an AMP that can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWPGCPWGQNCYPEGCSGPK" (SEQ ID NO: 26), or a complementary nucleotide sequence thereof.

In some embodiments, the polynucleotide is operable to encode an AMP that can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWPGCPWGQNCYPEGCRGPD" (SEQ ID NO: 35), or a complementary nucleotide sequence thereof.

In some embodiments, the polynucleotide is operable to encode an AMP that can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCSGPG" (SEQ ID NO: 36), or a complementary nucleotide sequence thereof.

In some embodiments, the polynucleotide is operable to encode an AMP that can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCGGPG" (SEQ ID NO: 38), or a complementary nucleotide sequence thereof.

In some embodiments, the polynucleotide is operable to encode an AMP that can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCY-PEGCSGPKVG" (SEQ ID NO: 40), or a complementary nucleotide sequence thereof.

In some embodiments, the polynucleotide is operable to encode an AMP that can comprise, consist essentially of, or consist of, a homopolymer or heteropolymer of two or more AMPs, wherein the amino acid sequence of each AMP is the same or different.

In some embodiments, the polynucleotide is operable to encode an AMP that can comprise, consist essentially of, or consist of, an AMP that is a fused protein comprising two or more AMPs separated by a cleavable or non-cleavable linker, and wherein the amino acid sequence of each AMP may be the same or different.

In some embodiments, the linker is a cleavable linker.

In some embodiments, the linker has an amino acid sequence as set forth in any one of SEQ ID NOs: 184-193.

In some embodiments, the linker is cleavable inside at least one of (i) the gut or hemolymph of an insect, and (ii) cleavable inside the gut of a mammal.

AMP-Insecticidal Proteins

In some embodiments, an AMP-insecticidal protein can be any protein, peptide, polypeptide, amino acid sequence, configuration, construct, or arrangement, comprising: (1) at least one AMP, or two or more AMPs; and (2) one or more additional non-AMP peptides, polypeptides, or proteins. For example, in some embodiments, these additional non-AMP peptides, polypeptides, or proteins may have the ability to increase the mortality and/or inhibit the growth of insects exposed to the AMP-insecticidal protein, relative to the AMP alone; increase the expression of the AMP-insecticidal protein, e.g., in a host cell; and/or affect the post-translational processing of the AMP-insecticidal protein.

In some embodiments, an AMP-insecticidal protein can be a polymer comprising two or more AMPs. In yet other embodiments, an AMP-insecticidal protein can be a polymer comprising two or more AMPs, wherein the AMPs are operably linked via a linker peptide, e.g., a cleavable and/or a non-cleavable linker. Here, the linker peptide falls under the category of the additional non-AMP peptide described above.

In some embodiments, an AMP-insecticidal protein can refer to a one or more AMPs operably linked with one or more proteins such as a stabilizing domain (STA); an endoplasmic reticulum signaling protein (ERSP); an insect cleavable or insect non-cleavable linker (L); and/or any other combination thereof.

In some embodiments, an AMP-insecticidal protein can be a polymer of amino acids that, when properly folded or in its most natural thermodynamic state, exerts an insecticidal activity against one or more insects.

In some embodiments, an AMP-insecticidal protein can be a polymer comprising two or more AMPs that are different. In other embodiments, an insecticidal protein can be a polymer of two or more AMPs that are the same.

In yet other embodiments, an AMP-insecticidal protein can comprise one or more AMPs, and one or more peptides, polypeptides, or proteins, that may assist in the AMP-insecticidal protein's folding.

In some embodiments, an AMP-insecticidal protein can comprise one or more AMPs, and one or more peptides, polypeptides, or proteins, wherein the one or more peptides, polypeptides, or proteins are protein tags that help stability or solubility. In other embodiments, the peptides, polypeptides, or proteins can be protein tags that aid in affinity purification.

In some embodiments, an AMP-insecticidal protein can refer to a one or more AMPs operably linked with one or more proteins such as a stabilizing domain (STA); an endoplasmic reticulum signaling protein (ERSP); an insect cleavable or insect non-cleavable linker; one or more heterologous peptides; one or more additional polypeptides; and/or any other combination thereof. In some embodiments, an insecticidal protein can comprise a one or more AMPs as disclosed herein.

In some embodiments, an AMP-insecticidal protein can comprise an AMP homopolymer, e.g., two or more AMP monomers that are the same AMP. In some embodiments, the insecticidal protein can comprise an AMP heteropolymer, e.g., two or more AMP monomers, wherein the AMP monomers are different.

In some embodiments, an AMP-insecticidal protein can comprise, consist essentially of, or consist of one or more AMPs having an amino acid sequence set forth in SEQ ID NOs: 6, 20, 24-26, 28-36, 38-42, 48, 54, 58, 60, 62-63, 69, 108, 116, 119, and 168-169, or an agriculturally acceptable salt thereof. In some embodiments, the AMP-insecticidal protein may comprise an AMP having an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to of SEQ ID NOs: 6, 20, 24-26, 28-36, 38-42, 48, 54, 58, 60, 62-63, 69, 108, 116, 119, and 168-169, or an agriculturally acceptable salt thereof.

In some embodiments, an AMP-insecticidal protein can comprise, consist essentially of, or consist of one or more AMPs having an amino acid sequence set forth in SEQ ID NOs: 20, 24-26, 35-36, 38, and 40, or an agriculturally acceptable salt thereof. In some embodiments, the AMP-insecticidal protein may comprise an AMP having an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to of SEQ ID NOs: 20, 24-26, 35-36, 38, and 40, or an agriculturally acceptable salt thereof.

In some embodiments, an AMP-insecticidal protein can comprise, consist essentially of, or consist of one or more AMPs having an amino acid sequence set forth in SEQ ID NOs: 25, 36, 38, and 40, or an agriculturally acceptable salt thereof. In some embodiments, the AMP-insecticidal protein may comprise an AMP having an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to of SEQ ID NOs: 25, 36, 38, and 40, or an agriculturally acceptable salt thereof.

Examples of linkers include, but not limited to, the following sequences: IGER (SEQ ID NO:181), EEKKN, (SEQ ID NO:182), and ETMFKHGL (SEQ ID NO:183), or combinations thereof.

In some embodiments, the linker can be one or more of the following: ALKFLV (SEQ ID NO: 184), ALKLFV (SEQ ID NO: 185), IFVRLR (SEQ ID NO: 186), LFAAPF (SEQ ID NO: 187), ALKFLVGS (SEQ ID NO: 188), ALKLFVGS (SEQ ID NO: 189), IFVRLRGS (SEQ ID NO: 190), LFAAPFGS (SEQ ID NO: 191), LFVRLRGS (SEQ ID NO: 192), and/or LGERGS (SEQ ID NO: 193).

Exemplary methods for the generation of cleavable and non-cleavable linkers can be found in U.S. patent application Ser. No. 15/727,277; and PCT Application No. PCT/US2013/030042, the disclosure of which are incorporated herein by reference in their entireties.

Exemplary ERSPs and STAs and their methods of use are provided in U.S. Pat. No. 9,567,381, the disclosure of which is incorporated herein by reference in its entirety.

Detailed methods concerning ERSPs, STAs, and linkers, are described below.

Methods for Producing an AMP

Methods of producing proteins are well known in the art, and there are a variety of techniques available. For example, in some embodiments, proteins can be produced using recombinant methods, or chemically synthesized.

In some embodiments, an AMP of the present disclosure can be created using any known method for producing a protein. For example, in some embodiments, and without limitation, an AMP can be created using a recombinant expression system, such as yeast expression system or an bacterial expression system. However, those having ordinary skill in the art will recognize that other methods of protein production are available.

In some embodiments, the present disclosure comprises, consists essentially of, or consists of, a method of producing an AMP using a recombinant expression system.

In some embodiments, the present disclosure comprises, consists essentially of, or consists of, a method of producing an AMP, said method comprising: (a) preparing a vector comprising a first expression cassette comprising, consisting essentially of, or consisting of, a polynucleotide operable to encode an AMP, or a complementary nucleotide sequence thereof, (b) introducing the vector into a host cell, for example a bacteria or a yeast, or an insect, or a plant cell, or an animal cell; and (c) growing the yeast strain in a growth medium under conditions operable to enable expression of the AMP and secretion into the growth medium. In some related embodiments, the host cell, is a yeast cell.

The invention is practicable in a wide variety of host cells (see host cell section below). Indeed, an end-user of the invention can practice the teachings thereof in any host cell of his or her choosing. Thus, in some embodiments, the host cell can be any host cell that satisfies the requirements of the end-user; i.e., in some embodiments, the expression of an AMP may be accomplished using a variety of host cells, and pursuant to the teachings herein. For example, in some embodiments, a user may desire to use one specific type of host cell (e.g., a yeast cell or a bacteria cell) as opposed to another; the preference of a given host cell can range from availability to cost.

For example, in some embodiments, in some embodiments, the present disclosure comprises, consists essentially of, or consists of, a method of producing an AMP, said method comprising: (a) preparing a vector comprising a first expression cassette comprising, consisting essentially of, or consisting of, a polynucleotide operable to encode an AMP, or a complementary nucleotide sequence thereof, (b) introducing the vector into a host cell, for example a bacteria or a yeast, or an insect, or a plant cell, or an animal cell; and (c) growing the yeast strain in a growth medium under conditions operable to enable expression of the AMP and secretion into the growth medium. In some related embodiments, the host cell, is a yeast cell.

In some embodiments, the present disclosure comprises, consists essentially of, or consists of, a method of producing an AMP, said method comprising: (a) preparing a vector comprising a first expression cassette comprising, consisting essentially of, or consisting of, a polynucleotide operable to encode an AMP, or a complementary nucleotide sequence thereof, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; (b) introducing the vector into a host cell, for example a bacteria or a yeast, or an insect, or a plant cell, or an animal cell; and (c) growing the yeast strain in a growth medium under conditions operable to enable expression of the AMP and secretion into the growth medium. In some related embodiments, the host cell, is a yeast cell.

In some embodiments, the present disclosure comprises, consists essentially of, or consists of, a method of producing an AMP, said method comprising: (a) preparing a vector comprising a first expression cassette comprising, consisting essentially of, or consisting of, a polynucleotide operable to encode an AMP, or a complementary nucleotide sequence thereof, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; (b) introducing the vector into a host cell, for example a bacteria or a yeast, or an insect, or a plant cell, or an animal cell; and (c) growing the yeast strain in a growth medium under conditions operable to enable expression of the AMP and secretion into the growth medium. In some related embodiments, the host cell, is a yeast cell.

In some embodiments, the present disclosure comprises, consists essentially of, or consists of, a method of producing an AMP, said method comprising: (a) preparing a vector comprising a first expression cassette comprising, consisting essentially of, or consisting of, a polynucleotide operable to encode an AMP, or a complementary nucleotide sequence thereof, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences set forth in any one of SEQ ID NOs: 6, 20, 24-26, 28-36, 38-42, 48, 54, 58, 60, 62-63, 69, 108, 116, 119, and 168-169; (b) introducing the vector into a host cell, for example a bacteria or a yeast, or an insect, or a plant cell, or an animal cell; and (c) growing the yeast strain in a growth medium under conditions operable to enable expression of the AMP and secretion into the growth medium. In some related embodiments, the host cell, is a yeast cell.

In some embodiments, the present disclosure comprises, consists essentially of, or consists of, a method of producing an AMP, said method comprising: (a) preparing a vector comprising a first expression cassette comprising, consisting essentially of, or consisting of, a polynucleotide operable to encode an AMP, or a complementary nucleotide sequence thereof, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences set forth in any one of SEQ ID NOs: 20, 24-26, 35-36, 38, and 40; (b) introducing the vector into a host cell, for example a bacteria or a yeast, or an insect, or a plant cell, or an animal cell; and (c) growing the yeast strain in a growth medium under conditions operable to enable expression of the AMP and secretion into the growth medium.

In some related embodiments, the host cell, is a yeast cell. In some embodiments, the present disclosure comprises, consists essentially of, or consists of, a method of producing an AMP, said method comprising: (a) preparing a vector comprising a first expression cassette comprising, consisting essentially of, or consisting of, a polynucleotide operable to encode an AMP, or a complementary nucleotide sequence thereof, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences set forth in any one of SEQ ID NOs: 25, 36, 38, and 40; (b) introducing the vector into a host cell, for example a bacteria or a yeast, or an insect, or a plant cell, or an animal cell; and (c) growing the yeast strain in a growth medium under conditions operable to enable expression of the AMP and secretion into the growth medium. In some related embodiments, the host cell, is a yeast cell.

In some embodiments, the method of producing an AMP produces a homopolymer, wherein each AMP has the same amino acid sequence.

In some embodiments, the method of producing an AMP produces a homopolymer, wherein each AMP has a different amino acid sequence.

In some embodiments, the method of producing an AMP, wherein the AMP is a fused protein comprising two or more AMPs separated by a cleavable or non-cleavable linker, and wherein the amino acid sequence of each AMP may be the same or different.

In some embodiments, the method of producing an AMP, wherein the linker is a cleavable linker.

In some embodiments, the method of producing an AMP, wherein the linker has an amino acid sequence as set forth in any one of SEQ ID NOs: 184-193.

In some embodiments, the method of producing an AMP, wherein the linker is cleavable inside at least one of (i) the gut or hemolymph of an insect, and (ii) cleavable inside the gut of a mammal.

In some embodiments, the method of producing an AMP provides for a vector, wherein the vector is a plasmid. In some embodiments, the plasmid my comprise an alpha-MF signal.

In some embodiments, the present disclosure comprises, consists essentially of, or consists of, a method of producing an AMP, said method comprising: (a) preparing a vector comprising a first expression cassette comprising, consisting essentially of, or consisting of, a polynucleotide operable to encode an AMP, or a complementary nucleotide sequence thereof, (b) introducing the vector into a host cell; and (c) growing the host cell in a growth medium under conditions operable to enable expression of the AMP and secretion into the growth medium, wherein the vector is transformed into a microorganism, e.g., a yeast or a bacteria.

In some embodiments, the host cell can be a yeast strain.

In some embodiments, the yeast strain is selected from any species belonging to the genera *Saccharomyces, Pichia, Kluyveromyces, Hansenula, Yarrowia*, or *Schizosaccharomyces.*

In some embodiments, the yeast strain is selected from the group consisting of *Kluyveromyces lactis, Kluyveromyces marxianus, Saccharomyces cerevisiae*, and *Pichia pastoris.*

In some embodiments, the yeast strain is *Kluyveromyces lactis.*

In some embodiments, the yeast strain is *Kluyveromyces marxianus.*

In some embodiments, the AMP is secreted into the growth medium.

In some embodiments, the AMP is secreted into the growth medium in a cell culture or fermentation of a suitably transformed host cell incorporating a polynucleotide operable to encode the AMP, wherein expression of the AMP provides a yield of: at least 70 mg/L, at least 80 mg/L, at least 90 mg/L, at least 100 mg/L, at least 110 mg/L, at least 120 mg/L, at least 130 mg/L, at least 140 mg/L, at least 150 mg/L, at least 160 mg/L, at least 170 mg/L, at least 180 mg/L, at least 190 mg/L, at least 200 mg/L, at least 500 mg/L, at least 750 mg/L, at least 1,000 mg/L, at least 1,250 mg/L, at least 1,500 mg/L, at least 1,750 mg/L, at least 2,000 mg/L, at least 2,500 mg/L, at least 3,000 mg/L, at least 3,500 mg/L, at least 4,000 mg/L, at least 4,500 mg/L, at least 5,000 mg/L, at least 5,500 mg/L, at least at least 6,000 mg/L, at least 6,500 mg/L, at least 7,000 mg/L, at least 7,500 mg/L, at least 8,000 mg/L, at least 8,500 mg/L, at least 9,000 mg/L, at least 9,500 mg/L, at least 10,000 mg/L, at least 11,000 mg/L, at least 12,000 mg/L, at least 12,500 mg/L, at least 13,000 mg/L, at least 14,000 mg/L, at least 15,000 mg/L, at least 16,000 mg/L, at least 17,000 mg/L, at least 17,500 mg/L, at least 18,000 mg/L, at least 19,000 mg/L, at least 20,000 mg/L, at least 25,000 mg/L, at least 30,000 mg/L, at least 40,000 mg/L, at least 50,000 mg/L, at least 60,000 mg/L, at least 70,000 mg/L, at least 80,000 mg/L, at least 90,000 mg/L, or at least 100,000 mg/L of AMP per liter of yeast culture medium.

In some embodiments, the expression of the AMP in the medium results in the expression of a single AMP in the medium.

In some embodiments, the expression of the AMP in the medium results in the expression of an AMP polymer comprising two or more AMP polypeptides in the medium.

In some embodiments, the vector comprises two or three expression cassettes, each expression cassette operable to encode the AMP of the first expression cassette.

In some embodiments, the vector comprises two or three expression cassettes, each expression cassette operable to encode the AMP of the first expression cassette, or an AMP of a different expression cassette.

In some embodiments, an expression cassette of the present disclosure is operable to encode an AMP as set forth in any one of SEQ ID NOs: 6, 20, 24-26, 28-36, 38-42, 48, 54, 58, 60, 62-63, 69, 108, 116, 119, and 168-169.

In some embodiments, an expression cassette of the present disclosure is operable to encode an AMP as set forth in any one of SEQ ID NOs: 20, 24-26, 35-36, 38, and 40.

In some embodiments, an expression cassette of the present disclosure is operable to encode an AMP as set forth in any one of SEQ ID NOs: 25, 36, 38, and 40.

Isolating and Mutating Wild-Type Av3 Proteins

In various illustrative embodiments, an AMP can be obtained by creating an AMP polynucleotide sequence, which in turn can be created by generating a mutation in the wild-type Av3 polynucleotide sequence, e.g., "RSCCPCYWGGCPWGQNCYPEGCSGPKV" (SEQ ID NO: 172) or an Av3b polynucleotide sequence, e.g., "KSCCPCYWGGCPWGQNCYPEGCSGPK" (SEQ ID NO:1) (i.e., creating an AMP polynucleotide sequence); inserting that AMP polynucleotide (amp) sequence into the appropriate vector; transforming a host organism in such a way that the polynucleotide encoding an AMP is expressed; culturing the host organism to generate the desired amount of AMP; and then purifying the AMP from in and/or around host organism.

Wild-type *Anemonia viridis* toxins, e.g., Av3 can be isolated from sea anemones obtained in the wild using any of the techniques known to those having ordinary skill in the art. For example, in some embodiments, the toxins and/or venom of animals can be isolated according to the methods described in U.S. Patent Application No. US20200207818A1; U.S. Pat. No. 5,989,857; and Moran et al., Molecular analysis of the sea anemone toxin Av3 reveals selectivity to insects and demonstrates the heterogeneity of receptor site-3 on voltage-gated $Na^+$ channels. Biochem. J. 2007; 406:41-48; the disclosures of which are incorporated herein by reference in their entireties.

In some embodiments, a wild-type Av3 polynucleotide sequence can be obtained by screening a genomic library using primer probes directed to the Av3 polynucleotide sequence. Alternatively, wild-type Av3 polynucleotide sequence and/or AMP polynucleotide sequences can be chemically synthesized. For example, a wild-type Av3 polynucleotide sequence and/or AMP polynucleotide sequence can be generated using the oligonucleotide synthesis methods such as the phosphoramidite; triester, phosphite, or H-Phosphonate methods (see Engels, J. W. and Uhlmann, E. (1989), Gene Synthesis [New Synthetic Methods (77)]. Angew. Chem. Int. Ed. Engl., 28: 716-734, the disclosure of which is incorporated herein by reference in its entirety).

Chemically synthesizing AMP polynucleotides

In some embodiments, the polynucleotide sequence encoding the AMP can be chemically synthesized using commercially available polynucleotide synthesis services such as those offered by Genewiz® (e.g., TurboGENE™; PriorityGENE; and FragmentGENE), or Sigma-Aldrich® (e.g., Custom DNA and RNA Oligos Design and Order Custom DNA Oligos). Exemplary method for generating DNA and or custom chemically synthesized polynucleotides are well known in the art, and are illustratively provided in U.S. Pat. No. 5,736,135, Ser. No. 08/389,615, filed on Feb. 13, 1995, the disclosure of which is incorporated herein by reference in its entirety. See also Agarwal, et al., Chemical synthesis of polynucleotides. Angew Chem Int Ed Engl. 1972 June; 11(6):451-9; Ohtsuka et al., Recent developments in the chemical synthesis of polynucleotides. Nucleic Acids Res. 1982 Nov. 11; 10(21): 6553-6570; Sondek & Shortle. A general strategy for random insertion and substitution mutagenesis: substoichiometric coupling of trinucleotide phosphoramidites. Proc Natl Acad Sci USA. 1992 Apr. 15; 89(8): 3581-3585; Beaucage S. L., et al., Advances in the Synthesis of Oligonucleotides by the Phosphoramidite Approach. Tetrahedron, Elsevier Science Publishers, Amsterdam, NL, vol. 48, No. 12, 1992, pp. 2223-2311; Agrawal (1993) Protocols for Oligonucleotides and Analogs: Synthesis and Properties; Methods in Molecular Biology Vol. 20, the disclosures of which are incorporated herein by reference in their entireties.

Producing a mutation in a wild-type Av3 polynucleotide sequence and/or an Av3b polynucleotide sequence can be achieved by various means that are well known to those having ordinary skill in the art. Methods of mutagenesis include Kunkel's method; cassette mutagenesis; PCR site-directed mutagenesis; the "perfect murder" technique (delitto perfetto); direct gene deletion and site-specific mutagenesis with PCR and one recyclable marker; direct gene deletion and site-specific mutagenesis with PCR and one recyclable marker using long homologous regions; transplacement "pop-in pop-out" method; and CRISPR-Cas 9. Exemplary methods of site-directed mutagenesis can be found in Ruvkun & Ausubel, A general method for site-directed mutagenesis in prokaryotes. Nature. 1981 Jan. 1; 289(5793):85-8; Wallace et al., Oligonucleotide directed mutagenesis of the human beta-globin gene: a general method for producing specific point mutations in cloned DNA. Nucleic Acids Res. 1981 Aug. 11; 9(15):3647-56; Dalbadie-McFarland et al., Oligonucleotide-directed mutagenesis as a general and powerful method for studies of protein function. Proc Natl Acad Sci USA. 1982 November; 79(21):6409-13; Bachman. Site-directed mutagenesis. Methods Enzymol. 2013; 529:241-8; Carey et al., PCR-mediated site-directed mutagenesis. Cold Spring Harb Protoc. 2013 Aug. 1; 2013(8):738-42; and Cong et al., Multiplex genome engineering using CRISPR/Cas systems. Science. 2013 Feb. 15; 339(6121):819-23, the disclosures of all of the aforementioned references are incorporated herein by reference in their entireties.

Chemically synthesizing polynucleotides allows for a DNA sequence to be generated that is tailored to produce a desired polypeptide based on the arrangement of nucleotides within said sequence (i.e., the arrangement of cytosine [C], guanine [G], adenine [A] or thymine [T] molecules); the mRNA sequence that is transcribed from the chemically synthesized DNA polynucleotide can be translated to a sequence of amino acids, each amino acid corresponding to a codon in the mRNA sequence. Accordingly, the amino acid composition of a polypeptide chain that is translated from an mRNA sequence can be altered by changing the underlying codon that determines which of the 20 amino acids will be added to the growing polypeptide; thus, mutations in the DNA such as insertions, substitutions, deletions, and frame-shifts may cause amino acid insertions, substitutions, or deletions, depending on the underlying codon.

In some embodiments, a polynucleotide can be chemically synthesized, wherein said polynucleotide harbors one or more mutations. In some embodiments, an mRNA can be created from the template DNA sequence. In yet other embodiments, the mRNA can be cloned and transformed into a competent cell.

Recombinant Expression, Vectors and Transformation

Obtaining an AMP from a chemically synthesized DNA polynucleotide sequence and/or a wild-type DNA polynucleotide sequence that has been altered via mutagenesis can be achieved by cloning the DNA sequence into an appropriate vector. There are a variety of expression vectors available, host organisms, and cloning strategies known to those having ordinary skill in the art. For example, the vector can be a plasmid, which can introduce a heterologous gene and/or expression cassette into yeast cells to be transcribed and translated. The term "vector" is used to refer to a carrier nucleic acid molecule into which a nucleic acid sequence can be inserted for introduction into a cell where it can be replicated. A vector may contain "vector elements" such as an origin of replication (ORI); a gene that confers antibiotic resistance to allow for selection; multiple cloning sites; a promoter region; a selection marker for non-bacterial transfection; and a primer binding site. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference in their entireties. In addition to encoding an AMP polynucleotide, a vector may encode a targeting molecule. A targeting molecule is one that directs the desired nucleic acid to a particular tissue, cell, or other location.

In some embodiments, the present disclosure comprises, consists essentially of, or consists of, a vector comprising a polynucleotide operable to encode an AMP of the present disclosure.

In some embodiments, the present disclosure comprises, consists essentially of, or consists of, a vector comprising a polynucleotide operable to encode an AMP, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or a complementary nucleotide sequence thereof.

In some embodiments, the present disclosure comprises, consists essentially of, or consists of, a vector comprising a polynucleotide or complementary sequence thereof, that can stringently hybridize to a polynucleotide or segment thereof operable to encode an AMP, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-X-G-C-$X_6$-G-$X_7$-X-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent.

In some embodiments, the present disclosure comprises, consists essentially of, or consists of, a vector comprising a polynucleotide or complementary sequence thereof, that can stringently hybridize to a polynucleotide or segment thereof operable to encode an AMP, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent.

In some embodiments, the present disclosure comprises, consists essentially of, or consists of, a vector comprising a polynucleotide operable to encode an AMP, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; or a complementary nucleotide sequence thereof.

In some embodiments, the present disclosure comprises, consists essentially of, or consists of, a vector comprising a polynucleotide operable to encode an AMP, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence as set forth in any one of SEQ ID NOs: 6, 20, 24-26, 28-36, 38-42, 48, 54, 58, 60, 62-63, 69, 108, 116, 119, and 168-169; or a complementary nucleotide sequence thereof.

In some embodiments, the present disclosure comprises, consists essentially of, or consists of, a vector comprising a polynucleotide operable to encode an AMP, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence as set forth in any one of SEQ ID NOs: 20, 24-26, 35-36, 38, and 40; or a complementary nucleotide sequence thereof.

In some embodiments, the present disclosure comprises, consists essentially of, or consists of, a vector comprising a polynucleotide operable to encode an AMP, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence as set forth in any one of SEQ ID NOs: 25, 36, 38, and 40; or a complementary nucleotide sequence thereof.

In some embodiments, the polynucleotide is operable to encode an AMP that comprises, consists essentially of, or consists of, an amino sequence as set forth in any one of SEQ ID NOs: 6, 20, 24-26, 28-36, 38-42, 48, 54, 58, 60, 62-63, 69, 108, 116, 119, and 168-169, or a complementary nucleotide sequence thereof.

In some embodiments, the polynucleotide is operable to encode an AMP that comprises, consists essentially of, or consists of, an amino sequence as set forth in any one of SEQ ID NOs: 20, 24-26, 35-36, 38, and 40, or a complementary nucleotide sequence thereof.

In some embodiments, the polynucleotide is operable to encode an AMP that comprises, consists essentially of, or consists of, an amino sequence as set forth in any one of SEQ ID NOs: 25, 36, 38, and 40, or a complementary nucleotide sequence thereof.

In some embodiments, a polynucleotide operable to encode an AMP or an AMP-insecticidal protein, or a complementary nucleotide sequence thereof, can be transformed into a host cell.

In some embodiments, a polynucleotide operable to encode an AMP or an AMP-insecticidal protein, or a complementary nucleotide sequence thereof, can be cloned into a vector, and transformed into a host cell.

In some embodiments, an AMP ORF can be transformed into a host cell. In some embodiments, an AMP ORF can be cloned into a vector (e.g., a plasmid) and subsequently transformed into a host cell.

In addition to a polynucleotide sequence operable to encode an AMP (e.g., an AMP ORF) or an AMP-insecticidal protein, additional DNA segments known as regulatory elements can be cloned into a vector that allow for enhanced expression of the foreign DNA or transgene; examples of such additional DNA segments include (1) promoters, terminators, and/or enhancer elements; (2) an appropriate mRNA stabilizing polyadenylation signal; (3) an internal ribosome entry site (IRES); (4) introns; and (5) post-transcriptional regulatory elements. The combination of a DNA segment of interest (e.g., amp) with any one of the foregoing cis-acting elements is called an "expression cassette."

In some embodiments, an expression cassette or AMP expression cassette can contain one or more polynucleotides operable to encode one or more AMPs, and/or one or more AMP-insecticidal proteins.

In some embodiments, an expression cassette or AMP expression cassette can contain one or more polynucleotides operable to encode one or more AMPs, and/or one or more AMP-insecticidal proteins; and, optionally, one or more additional regulatory elements such as: (1) promoters, terminators, and/or enhancer elements; (2) an appropriate mRNA stabilizing polyadenylation signal; (3) an internal ribosome entry site (IRES); (4) introns; and (5) post-transcriptional regulatory elements.

In some embodiments, a single expression cassette can contain one or more of the aforementioned regulatory elements, and a polynucleotide operable to express an AMP.

For example, in some embodiments, an AMP expression cassette can comprise polynucleotide operable to encode an AMP, and an α-MF signal; Kex2 site; LAC4 terminator; ADN1 promoter; and an acetamidase (amdS) selection marker-flanked by LAC4 promoters on the 5'-end and 3'-end.

In some embodiments, there can be numerous expression cassettes cloned into a vector. For example, in some embodiments, there can be a first expression cassette comprising a polynucleotide operable to express an AMP. In alternative embodiments, there are two expression cassettes operable to encode an AMP (i.e., a double expression cassette).

In other embodiments, there are three expression cassettes operable to encode an AMP (i.e., a triple expression cassette).

In some embodiments, a double expression cassette can be generated by subcloning a second AMP expression cassette into a vector containing a first AMP expression cassette.

In some embodiments, a triple expression cassette can be generated by subcloning a third AMP expression cassette into a vector containing a first and a second AMP expression cassette.

In some embodiments, one, two, three, or more expression cassettes can be cloned into a vector, wherein each expression cassette comprises: (1) a DNA sequence of interest, e.g., a polynucleotide operable to encode an AMP; and one or more of the following: (2) promoters, terminators, and/or enhancer elements; (3) an appropriate mRNA stabilizing polyadenylation signal; (4) an internal ribosome entry site (IRES); (5) introns; and/or (6) post-transcriptional regulatory elements.

In some embodiments, one, two, three, or more expression cassettes can be cloned into a vector, wherein each expression cassette comprises a polynucleotide encoding an AMP, wherein each of the AMPs are the same or different.

In some embodiments, one, two, three, or more expression cassettes can be cloned into a vector, wherein each expression cassette comprises a polynucleotide encoding an AMP ORF, wherein each of the AMP ORFs are the same or different.

In some embodiments, an AMP polynucleotide can be cloned into a vector (for example, a cloning vector or an expression vector known in the art) using a variety of cloning strategies, and commercial cloning kits and materials readily available to those having ordinary skill in the art. For example, the AMP polynucleotide can be cloned into a vector using such strategies as the SnapFast; Gateway; TOPO; Gibson; LIC; InFusionHD; or Electra strategies. There are numerous commercially available vectors that can be used to produce AMP. For example, an AMP polynucleotide can be generated using polymerase chain reaction (PCR), and combined with a pCR™II-TOPO vector, or a PCR™2.1-TOPO® vector (commercially available as the TOPO® TA Cloning® Kit from Invitrogen) for 5 minutes at room temperature; the TOPO® reaction can then be transformed into competent cells, which can subsequently be selected based on color change (see Janke et al., A versatile toolbox for PCR-based tagging of yeast genes: new fluorescent proteins, more markers and promoter substitution cassettes. Yeast. 2004 August; 21(11):947-62; see also, Adams et al. Methods in Yeast Genetics. Cold Spring Harbor, NY, 1997, the disclosure of which is incorporated herein by reference in its entirety).

In some embodiments, a polynucleotide encoding an AMP or multiple copies of AMPs (either the same or different) can be cloned into a vector such as a plasmid, cosmid, virus (bacteriophage, animal viruses, and plant viruses), and/or artificial chromosome (e.g., YACs).

In some embodiments, a polynucleotide encoding an AMP can be inserted into a vector, for example, a plasmid vector using *E. coli* as a host, by performing the following: digesting about 2 to 5 μg of vector DNA using the restriction enzymes necessary to allow the DNA segment of interest to be inserted, followed by overnight incubation to accomplish complete digestion (alkaline phosphatase may be used to dephosphorylate the 5'-end in order to avoid self-ligation/recircularization); gel purify the digested vector. Next, amplify the DNA segment of interest, for example, a polynucleotide encoding an AMP, via PCR, and remove any excess enzymes, primers, unincorporated dNTPs, short-failed PCR products, and/or salts from the PCR reaction using techniques known to those having ordinary skill in the art (e.g., by using a PCR clean-up kit). Ligate the DNA segment of interest to the vector by creating a mixture comprising: about 20 ng of vector; about 100 to 1,000 ng or DNA segment of interest; 2 μL 10× buffer (i.e., 30 mM Tris-HCl 4 mM $MgCl_2$, 26 μM NAD, 1 mM DTT, 50 μg/ml BSA, pH 8, stored at 25° C.); 1 μL T4 DNA ligase; all brought to a total volume of 20 μL by adding $H_2O$. The ligation reaction mixture can then be incubated at room temperature for 2 hours, or at 16° C. for an overnight incubation. The ligation reaction (i.e., about 1 μL) can then be transformed to competent cell, for example, by using electroporation or chemical methods, and a colony PCR can then be performed to identify vectors containing the DNA segment of interest.

In some embodiments a polynucleotide encoding an AMP (e.g., an AMP ORF), along with other DNA segments together composing an AMP expression cassette can be designed for secretion from host yeast cells. An illustrative method of designing an AMP expression cassette is as follows: the cassette can begin with a signal peptide sequence, followed by a DNA sequence encoding a Kex2 cleavage site (Lysine-Arginine), and subsequently followed by the AMP polynucleotide transgene (AMP ORF), with the addition of glycine-serine codons at the 5'-end, and finally a stop codon at the 3'-end. All these elements will then be expressed to a fusion peptide in yeast cells as a single open reading frame (ORF). An α-mating factor (αMF) signal sequence is most frequently used to facilitate metabolic processing of the recombinant insecticidal peptides through the endogenous secretion pathway of the recombinant yeast, i.e. the expressed fusion peptide will typically enter the Endoplasmic Reticulum, wherein the α-mating factor signal sequence is removed by signal peptidase activity, and then the resulting pro-insecticidal peptide will be trafficked to the Golgi Apparatus, in which the Lysine-Arginine dipeptide mentioned above is completely removed by Kex2 endoprotease, after which the mature, polypeptide (i.e., AMP), is secreted out of the cells.

In some embodiments, polypeptide expression levels in recombinant yeast cells can be enhanced by optimizing the codons based on the specific host yeast species. Naturally occurring frequencies of codons observed in endogenous open reading frames of a given host organism need not necessarily be optimized for high efficiency expression. Furthermore, different yeast species (for example, *Kluyveromyces lactis, Pichia pastoris, Saccharomyces cerevisiae*, etc.) have different optimal codons for high efficiency expression. Hence, codon optimization should be considered for the AMP expression cassette, including the sequence elements encoding the signal sequence, the Kex2 cleavage site and the AMP, because they are initially translated as one fusion peptide in the recombinant yeast cells.

In some embodiments, a codon-optimized AMP expression cassette can be ligated into a yeast-specific expression vectors for yeast expression. There are many expression vectors available for yeast expression, including episomal vectors and integrative vectors, and they are usually designed for specific yeast strains. One should carefully choose the appropriate expression vector in view of the specific yeast expression system which will be used for the peptide production. In some embodiments, integrative vectors can be used, which integrate into chromosomes of the transformed yeast cells and remain stable through cycles of cell division and proliferation. The integrative DNA sequences are homologous to targeted genomic DNA loci in the transformed yeast species, and such integrative sequences include pLAC4, 25S rDNA, pAOX1, and TRP2, etc. The locations of insecticidal peptide transgenes can be adjacent to the integrative DNA sequence (Insertion vectors) or within the integrative DNA sequence (replacement vectors).

In some embodiments, the expression vectors or cloning vectors can contain *E. coli* elements for DNA preparation in *E. coli*, for example, *E. coli* replication origin, antibiotic selection marker, etc. In some embodiments, vectors can contain an array of the sequence elements needed for expression of the transgene of interest, for example, transcriptional promoters, terminators, yeast selection markers, integrative DNA sequences homologous to host yeast DNA, etc. There are many suitable yeast promoters available, including natural and engineered promoters, for example, yeast promoters such as pLAC4, pAOX1, pUPP, pADH1, pTEF, pGal1, etc., and others, can be used in some embodiments.

In some embodiments, selection methods such as acetamide prototrophy selection; zeocin-resistance selection; geneticin-resistance selection; nourseothricin-resistance selection; uracil deficiency selection; and/or other selection methods may be used. For example, in some embodiments, the *Aspergillus nidulans* amdS gene can be used as selectable marker. Exemplary methods for the use of selectable markers can be found in U.S. Pat. No. 6,548,285 (filed Apr. 3, 1997); U.S. Pat. No. 6,165,715 (filed Jun. 22, 1998); and 6,110,707 (filed Jan. 17, 1997), the disclosures of which are incorporated herein by reference in its entirety.

In some embodiments, a polynucleotide encoding an AMP can be inserted into a pKLAC1 vector. The pKLAC1 is commercially available from New England Biolabs® Inc., (item no. NEB #E1000). The pKLAC1 vector is designed to accomplish high-level expression of recombinant protein (e.g., AMP) in the yeast *Kluyveromyces lactis*. The pKLAC1 plasmid can be ordered alone, or as part of a *K. lactis* Protein Expression Kit. The pKLAC1 plasmid can be linearized using the SacII or BstXI restriction enzymes, and possesses a MCS downstream of an αMF secretion signal. The αMF secretion signal directs recombinant proteins to the secretory pathway, which is then subsequently cleaved via Kex2 resulting in peptide of interest, for example, an AMP. Kex2 is a calcium-dependent serine protease, which is involved in activating proproteins of the secretory pathway, and is commercially available (PeproTech®; item no. 450-45).

In some embodiments, a polynucleotide encoding an AMP can be inserted into a pLB102 plasmid, or subcloned into a pLB102 plasmid subsequent to selection of yeast colonies transformed with pKLAC1 plasmids ligated with polynucleotide encoding an AMP. Yeast, for example *K. lactis*, transformed with a pKLAC1 plasmids ligated with polynucleotide encoding an AMP can be selected based on acetamidase (amdS), which allows transformed yeast cells to grow in YCB medium containing acetamide as its only nitrogen source.

In some embodiments, a polynucleotide encoding an AMP can be inserted into other commercially available plasmids and/or vectors that are readily available to those having skill in the art, e.g., plasmids are available from Addgene (a non-profit plasmid repository); GenScript®; Takara®; Qiagen®; and Promega™.

In some embodiments, a yeast cell transformed with one or more AMP expression cassettes can produce an AMP in a yeast culture with a yield of, at least 70 mg/L, at least 80 mg/L, at least 90 mg/L, at least 100 mg/L, at least 110 mg/L, at least 120 mg/L, at least 130 mg/L, at least 140 mg/L, at least 150 mg/L, at least 160 mg/L, at least 170 mg/L, at least 180 mg/L, at least 190 mg/L 200 mg/L, at least 500 mg/L, at least 750 mg/L, at least 1,000 mg/L, at least 1,250 mg/L, at least 1,500 mg/L, at least 1,750 mg/L, at least 2,000 mg/L, at least 2,500 mg/L, at least 3,000 mg/L, at least 3,500 mg/L, at least 4,000 mg/L, at least 4,500 mg/L, at least 5,000 mg/L, at least 5,500 mg/L, at least at least 6,000 mg/L, at least 6,500 mg/L, at least 7,000 mg/L, at least 7,500 mg/L, at least 8,000 mg/L, at least 8,500 mg/L, at least 9,000 mg/L, at least 9,500 mg/L, at least 10,000 mg/L, at least 11,000 mg/L, at least 12,000 mg/L, at least 12,500 mg/L, at least 13,000 mg/L, at least 14,000 mg/L, at least 15,000 mg/L, at least 16,000 mg/L, at least 17,000 mg/L, at least 17,500 mg/L, at least 18,000 mg/L, at least 19,000 mg/L, at least 20,000 mg/L, at least 25,000 mg/L, at least 30,000 mg/L, at least 40,000 mg/L, at least 50,000 mg/L, at least 60,000 mg/L, at least 70,000 mg/L, at least 80,000 mg/L, at least 90,000 mg/L, or at least 100,000 mg/L of AMP per liter of medium.

In some embodiments, one or more expression cassettes comprising a polynucleotide operable to express an AMP can be inserted into a vector, resulting in a yield ranging from about 100 mg/L of AMP to about 100,000 mg/L; from about 110 mg/L to about 100,000 mg/L; from about 120 mg/L to about 100,000 mg/L; from about 130 mg/L to about 100,000 mg/L; from about 140 mg/L to about 100,000 mg/L; from about 150 mg/L to about 100,000 mg/L; from about 160 mg/L to about 100,000 mg/L; from about 170 mg/L to about 100,000 mg/L; from about 180 mg/L to about 100,000 mg/L; from about 190 mg/L to about 100,000 mg/L; from about 200 mg/L to about 100,000 mg/L; from about 250 mg/L to about 100,000 mg/L; from about 500 mg/L to about 100,000 mg/L; from about 750 mg/L to about 100,000 mg/L; from about 1000 mg/L to about 100,000 mg/L; from about 1000 mg/L to about 100,000 mg/L; from about 1500 mg/L to about 100,000 mg/L; from about 2000 mg/L to about 100,000 mg/L; from about 2500 mg/L to about 100,000 mg/L; from about 3000 mg/L to about 100,000 mg/L; from about 3500 mg/L to about 100,000 mg/L; from about 4000 mg/L to about 100,000 mg/L; from about 4500 mg/L to about 100,000 mg/L; from about 5000 mg/L to about 100,000 mg/L; from about 5500 mg/L to about 100,000 mg/L; from about 6000 mg/L to about 100,000 mg/L; from about 6500 mg/L to about 100,000 mg/L; from about 7000 mg/L to about 100,000 mg/L; from about 7500 mg/L to about 100,000 mg/L; from about 8000 mg/L to about 100,000 mg/L; from about 8500 mg/L to about 100,000 mg/L; from about 9000 mg/L to about 100,000 mg/L; from about 9500 mg/L to about 100,000 mg/L; from about 10000 mg/L to about 100,000 mg/L; from about 10500 mg/L to about 100,000 mg/L; from about 11000 mg/L to about 100,000 mg/L; from about 11500 mg/L to about 100,000 mg/L; from about 12000 mg/L to about 100,000 mg/L; from about 12500 mg/L to about 100,000 mg/L; from about 13000 mg/L to about 100,000 mg/L; from about 13500 mg/L to about 100,000 mg/L; from about 14000 mg/L to about 100,000 mg/L; from about 14500 mg/L to about 100,000 mg/L; from about 15000 mg/L to about 100,000 mg/L; from about 15500 mg/L to about 100,000 mg/L; from about 16000 mg/L to about 100,000 mg/L; from about 16500 mg/L to about 100,000 mg/L; from about 17000 mg/L to about 100,000 mg/L; from about 17500 mg/L to about 100,000 mg/L; from about 18000 mg/L to about 100,000 mg/L; from about 18500 mg/L to about 100,000 mg/L; from about 19000 mg/L to about 100,000 mg/L; from about 19500 mg/L to about 100,000 mg/L; from about 20000 mg/L to about 100,000 mg/L; from about 20500 mg/L to about 100,000 mg/L; from about 21000 mg/L to about 100,000 mg/L; from about 21500 mg/L to about 100,000 mg/L; from about 22000 mg/L to about 100,000 mg/L; from about 22500 mg/L to about 100,000 mg/L; from about 23000 mg/L to about 100,000 mg/L; from about 23500 mg/L to about 100,000 mg/L; from about 24000 mg/L to about 100,000 mg/L; from about 24500 mg/L to about 100,000 mg/L; from about 25000 mg/L to about 100,000 mg/L; from about 25500 mg/L to about 100,000 mg/L; from about 26000 mg/L to about 100,000 mg/L; from about 26500 mg/L to about 100,000 mg/L; from about 27000 mg/L to about 100,000 mg/L; from about 27500 mg/L to about 100,000 mg/L; from about 28000 mg/L to about 100,000 mg/L; from about 28500 mg/L to about 100,000 mg/L; from about 29000 mg/L to about 100,000 mg/L; from about 29500 mg/L to about 100,000 mg/L; from about 30000 mg/L to about 100,000 mg/L; from about 30500 mg/L to about 100,000 mg/L; from about 31000 mg/L to about 100,000 mg/L; from about 31500 mg/L to about 100,000 mg/L; from about 32000 mg/L to about 100,000 mg/L; from about 32500 mg/L to about 100,000 mg/L; from about 33000 mg/L to about 100,000 mg/L; from about 33500 mg/L to about 100,000 mg/L; from about 34000 mg/L to about 100,000 mg/L; from about 34500 mg/L to about 100,000 mg/L; from about 35000 mg/L to about 100,000 mg/L; from about 35500 mg/L to about 100,000 mg/L; from about 36000 mg/L to about 100,000 mg/L; from about 36500 mg/L to about 100,000 mg/L; from about 37000 mg/L to about 100,000 mg/L; from about 37500 mg/L to about 100,000 mg/L; from about 38000 mg/L to about 100,000 mg/L; from about 38500 mg/L to about 100,000 mg/L; from about 39000 mg/L to about 100,000 mg/L; from about 39500 mg/L to about 100,000 mg/L; from about 40000 mg/L to about 100,000 mg/L; from about 40500 mg/L to about 100,000 mg/L; from about 41000 mg/L to about 100,000 mg/L; from about 41500 mg/L to about 100,000 mg/L; from about 42000 mg/L to about 100,000 mg/L; from about 42500 mg/L to about 100,000 mg/L; from about 43000 mg/L to about 100,000 mg/L; from about 43500 mg/L to about 100,000 mg/L; from about 44000 mg/L to about 100,000 mg/L; from about 44500 mg/L to about 100,000 mg/L; from about 45000 mg/L to about 100,000 mg/L; from about 45500 mg/L to about 100,000 mg/L; from about 46000 mg/L to about 100,000 mg/L; from about 46500 mg/L to about 100,000 mg/L; from about 47000 mg/L to about 100,000 mg/L; from about 47500 mg/L to about 100,000 mg/L; from about 48000 mg/L to about 100,000 mg/L; from about 48500 mg/L to about 100,000 mg/L; from about 49000 mg/L to about 100,000 mg/L; from about 49500 mg/L to about 100,000 mg/L; from about 50000 mg/L to about 100,000 mg/L; from about 50500 mg/L to about 100,000 mg/L; from about 51000 mg/L to about 100,000 mg/L; from about 51500 mg/L to about 100,000 mg/L; from about 52000 mg/L to about 100,000 mg/L; from about 52500 mg/L to about 100,000 mg/L; from about 53000 mg/L to about 100,000 mg/L; from about 53500 mg/L to about 100,000 mg/L; from about 54000 mg/L to about 100,000 mg/L; from about 54500 mg/L to about 100,000 mg/L; from about 55000 mg/L to about 100,000 mg/L; from about 55500 mg/L to about 100,000 mg/L; from about 56000 mg/L to about 100,000 mg/L; from about 56500 mg/L to about 100,000 mg/L; from about 57000 mg/L to about 100,000 mg/L; from about 57500 mg/L to about 100,000 mg/L; from about 58000 mg/L to about 100,000 mg/L; from about 58500 mg/L to about 100,000 mg/L; from about 59000 mg/L to about 100,000 mg/L; from about 59500 mg/L to about 100,000 mg/L; from about 60000 mg/L to about 100,000 mg/L; from about 60500 mg/L to about 100,000 mg/L; from about 61000 mg/L to about 100,000 mg/L; from about 61500 mg/L to about 100,000 mg/L; from about 62000 mg/L to about 100,000 mg/L; from about 62500 mg/L to about 100,000 mg/L; from about 63000 mg/L to about 100,000 mg/L; from about 63500 mg/L to about 100,000 mg/L; from about 64000 mg/L to about 100,000 mg/L; from about 64500 mg/L to about 100,000 mg/L; from about 65000 mg/L to about 100,000 mg/L; from about 65500 mg/L to about 100,000 mg/L; from about 66000 mg/L to about 100,000 mg/L; from about 66500 mg/L to about 100,000 mg/L; from about 67000 mg/L to about 100,000 mg/L; from about 67500 mg/L to about 100,000 mg/L; from about 68000 mg/L to about 100,000 mg/L; from about 68500 mg/L to about 100,000 mg/L; from about 69000 mg/L to about 100,000 mg/L; from about 69500 mg/L to about 100,000 mg/L; from about 70000 mg/L to about 100,000 mg/L; from about 70500 mg/L to about 100,000 mg/L; from about 71000 mg/L to about 100,000 mg/L; from about 71500 mg/L to about 100,000 mg/L; from about 72000 mg/L to about 100,000 mg/L; from about 72500 mg/L to about 100,000 mg/L; from about 73000 mg/L to about 100,000 mg/L; from about 73500 mg/L to about 100,000 mg/L; from about 74000 mg/L to about 100,000 mg/L; from about 74500 mg/L to about 100,000 mg/L; from about 75000 mg/L to about 100,000 mg/L; from about 75500 mg/L to about 100,000 mg/L; from about 76000 mg/L to about 100,000 mg/L; from about 76500 mg/L to about 100,000 mg/L; from about 77000 mg/L to about 100,000 mg/L; from about 77500 mg/L to about 100,000 mg/L; from about 78000 mg/L to about 100,000 mg/L; from about 78500 mg/L to about 100,000 mg/L; from about 79000 mg/L to about 100,000 mg/L; from about 79500 mg/L to about 100,000 mg/L; from about 80000 mg/L to about 100,000 mg/L; from about 80500 mg/L to about 100,000 mg/L; from about 81000 mg/L to about 100,000 mg/L; from about 81500 mg/L to about 100,000 mg/L; from about 82000 mg/L to about 100,000 mg/L; from about 82500 mg/L to about 100,000 mg/L; from about 83000 mg/L to about 100,000 mg/L; from about 83500 mg/L to about 100,000 mg/L; from about 84000 mg/L to about 100,000 mg/L; from about 84500 mg/L to about 100,000 mg/L; from about 85000 mg/L to about 100,000 mg/L; from about 85500 mg/L to about 100,000 mg/L; from about 86000 mg/L to about 100,000 mg/L; from about 86500 mg/L to about 100,000 mg/L; from about 87000 mg/L to about 100,000 mg/L; from about 87500 mg/L to about 100,000 mg/L; from about 88000 mg/L to about 100,000 mg/L; from about 88500 mg/L to about 100,000 mg/L; from about 89000 mg/L to about 100,000 mg/L; from about 89500 mg/L to about 100,000 mg/L; from about 90000 mg/L to about 100,000 mg/L; from about 90500 mg/L to about 100,000 mg/L; from about 91000 mg/L to about 100,000 mg/L; from about 91500 mg/L to about 100,000 mg/L; from about 92000 mg/L to about 100,000 mg/L; from about 92500 mg/L to about 100,000 mg/L; from about 93000 mg/L to about 100,000 mg/L; from about 93500 mg/L to about 100,000 mg/L; from about 94000 mg/L to about 100,000 mg/L; from about 94500 mg/L to about 100,000 mg/L; from about 95000 mg/L to about 100,000 mg/L; from about 95500 mg/L to about 100,000 mg/L; from about 96000 mg/L to about 100,000 mg/L; from about 96500 mg/L to about 100,000 mg/L; from about 97000 mg/L to about 100,000 mg/L; from about 97500 mg/L to about 100,000 mg/L; from about 98000 mg/L to about 100,000 mg/L; from about 98500 mg/L to about 100,000 mg/L; from about 99000 mg/L to about 100,000 mg/L; or from about 99500 mg/L to about 100,000 mg/L of AMP per liter of medium (supernatant of yeast fermentation broth).

In some In some embodiments, one or more expression cassettes comprising a polynucleotide operable to express an AMP can be inserted into a vector, resulting in a yield ranging from about 100 mg/L of AMP to about 100,000 mg/L; from about 100 mg/L to about 99500 mg/L; from about 100 mg/L to about 99000 mg/L; from about 100 mg/L to about 98500 mg/L; from about 100 mg/L to about 98000 mg/L; from about 100 mg/L to about 97500 mg/L; from about 100 mg/L to about 97000 mg/L; from about 100 mg/L to about 96500 mg/L; from about 100 mg/L to about 96000 mg/L; from about 100 mg/L to about 95500 mg/L; from about 100 mg/L to about 95000 mg/L; from about 100 mg/L to about 94500 mg/L; from about 100 mg/L to about 94000 mg/L; from about 100 mg/L to about 93500 mg/L; from about 100 mg/L to about 93000 mg/L; from about 100 mg/L to about 92500 mg/L; from about 100 mg/L to about 92000 mg/L; from about 100 mg/L to about 91500 mg/L; from about 100 mg/L to about 91000 mg/L; from about 100 mg/L to about 90500 mg/L; from about 100 mg/L to about 90000 mg/L; from about 100 mg/L to about 89500 mg/L; from about 100 mg/L to about 89000 mg/L; from about 100 mg/L to about 88500 mg/L; from about 100 mg/L to about 88000 mg/L; from about 100 mg/L to about 87500 mg/L; from about 100 mg/L to about 87000 mg/L; from about 100 mg/L to about 86500 mg/L; from about 100 mg/L to about 86000 mg/L; from about 100 mg/L to about 85500 mg/L; from about 100 mg/L to about 85000 mg/L; from about 100 mg/L to about 84500 mg/L; from about 100 mg/L to about 84000 mg/L; from about 100 mg/L to about 83500 mg/L; from about 100 mg/L to about 83000 mg/L; from about 100 mg/L to about 82500 mg/L; from about 100 mg/L to about 82000 mg/L; from about 100 mg/L to about 81500 mg/L; from about 100 mg/L to about 81000 mg/L; from about 100 mg/L to about 80500 mg/L; from about 100 mg/L to about 80000 mg/L; from about 100 mg/L to about 79500 mg/L; from about 100 mg/L to about 79000 mg/L; from about 100 mg/L to about 78500 mg/L; from about 100 mg/L to about 78000 mg/L; from about 100 mg/L to about 77500 mg/L; from about 100 mg/L to about 77000 mg/L; from about 100 mg/L to about 76500 mg/L; from about 100 mg/L to about 76000 mg/L; from about 100 mg/L to about 75500 mg/L; from about 100 mg/L to about 75000 mg/L; from about 100 mg/L to about 74500 mg/L; from about 100 mg/L to about 74000 mg/L; from about 100 mg/L to about 73500 mg/L; from about 100 mg/L to about 73000 mg/L; from about 100 mg/L to about 72500 mg/L; from about 100 mg/L to about 72000 mg/L; from about 100 mg/L to about 71500 mg/L; from about 100 mg/L to about 71000 mg/L; from about 100 mg/L to about 70500 mg/L; from about 100 mg/L to about 70000 mg/L; from about 100 mg/L to about 69500 mg/L; from about 100 mg/L to about 69000 mg/L; from about 100 mg/L to about 68500 mg/L; from about 100 mg/L to about 68000 mg/L; from about 100 mg/L to about 67500 mg/L; from about 100 mg/L to about 67000 mg/L; from about 100 mg/L to about 66500 mg/L; from about 100 mg/L to about 66000 mg/L; from about 100 mg/L to about 65500 mg/L; from about 100 mg/L to about 65000 mg/L; from about 100 mg/L to about 64500 mg/L; from about 100 mg/L to about 64000 mg/L; from about 100 mg/L to about 63500 mg/L; from about 100 mg/L to about 63000 mg/L; from about 100 mg/L to about 62500 mg/L; from about 100 mg/L to about 62000 mg/L; from about 100 mg/L to about 61500 mg/L; from about 100 mg/L to about 61000 mg/L; from about 100 mg/L to about 60500 mg/L; from about 100 mg/L to about 60000 mg/L; from about 100 mg/L to about 59500 mg/L; from about 100 mg/L to about 59000 mg/L; from about 100 mg/L to about 58500 mg/L; from about 100 mg/L to about 58000 mg/L; from about 100 mg/L to about 57500 mg/L; from about 100 mg/L to about 57000 mg/L; from about 100 mg/L to about 56500 mg/L; from about 100 mg/L to about 56000 mg/L; from about 100 mg/L to about 55500 mg/L; from about 100 mg/L to about 55000 mg/L; from about 100 mg/L to about 54500 mg/L; from about 100 mg/L to about 54000 mg/L; from about 100 mg/L to about 53500 mg/L; from about 100 mg/L to about 53000 mg/L; from about 100 mg/L to about 52500 mg/L; from about 100 mg/L to about 52000 mg/L; from about 100 mg/L to about 51500 mg/L; from about 100 mg/L to about 51000 mg/L; from about 100 mg/L to about 50500 mg/L; from about 100 mg/L to about 50000 mg/L; from about 100 mg/L to about 49500 mg/L; from about 100 mg/L to about 49000 mg/L; from about 100 mg/L to about 48500 mg/L; from about 100 mg/L to about 48000 mg/L; from about 100 mg/L to about 47500 mg/L; from about 100 mg/L to about 47000 mg/L; from about 100 mg/L to about 46500 mg/L; from about 100 mg/L to about 46000 mg/L; from about 100 mg/L to about 45500 mg/L; from about 100 mg/L to about 45000 mg/L; from about 100 mg/L to about 44500 mg/L; from about 100 mg/L to about 44000 mg/L; from about 100 mg/L to about 43500 mg/L; from about 100 mg/L to about 43000 mg/L; from about 100 mg/L to about 42500 mg/L; from about 100 mg/L to about 42000 mg/L; from about 100 mg/L to about 41500 mg/L; from about 100 mg/L to about 41000 mg/L; from about 100 mg/L to about 40500 mg/L; from about 100 mg/L to about 40000 mg/L; from about 100 mg/L to about 39500 mg/L; from about 100 mg/L to about 39000 mg/L; from about 100 mg/L to about 38500 mg/L; from about 100 mg/L to about 38000 mg/L; from about 100 mg/L to about 37500 mg/L; from about 100 mg/L to about 37000 mg/L; from about 100 mg/L to about 36500 mg/L; from about 100 mg/L to about 36000 mg/L; from about 100 mg/L to about 35500 mg/L; from about 100 mg/L to about 35000 mg/L; from about 100 mg/L to about 34500 mg/L; from about 100 mg/L to about 34000 mg/L; from about 100 mg/L to about 33500 mg/L; from about 100 mg/L to about 33000 mg/L; from about 100 mg/L to about 32500 mg/L; from about 100 mg/L to about 32000 mg/L; from about 100 mg/L to about 31500 mg/L; from about 100 mg/L to about 31000 mg/L; from about 100 mg/L to about 30500 mg/L; from about 100 mg/L to about 30000 mg/L; from about 100 mg/L to about 29500 mg/L; from about 100 mg/L to about 29000 mg/L; from about 100 mg/L to about 28500 mg/L; from about 100 mg/L to about 28000 mg/L; from about 100 mg/L to about 27500 mg/L; from about 100 mg/L to about 27000 mg/L; from about 100 mg/L to about 26500 mg/L; from about 100 mg/L to about 26000 mg/L; from about 100 mg/L to about 25500 mg/L; from about 100 mg/L to about 25000 mg/L; from about 100 mg/L to about 24500 mg/L; from about 100 mg/L to about 24000 mg/L; from about 100 mg/L to about 23500 mg/L; from about 100 mg/L to about 23000 mg/L; from about 100 mg/L to about 22500 mg/L; from about 100 mg/L to about 22000 mg/L; from about 100 mg/L to about 21500 mg/L; from about 100 mg/L to about 21000 mg/L; from about 100 mg/L to about 20500 mg/L; from about 100 mg/L to about 20000 mg/L; from about 100 mg/L to about 19500 mg/L; from about 100 mg/L to about 19000 mg/L; from about 100 mg/L to about 18500 mg/L; from about 100 mg/L to about 18000 mg/L; from about 100 mg/L to about 17500 mg/L; from about 100 mg/L to about 17000 mg/L; from about 100 mg/L to about 16500 mg/L; from about 100 mg/L to about 16000 mg/L; from about 100 mg/L to about 15500 mg/L; from about 100 mg/L to about 15000 mg/L; from about 100 mg/L to about 14500 mg/L; from about 100 mg/L to about 14000 mg/L; from about 100 mg/L to about 13500 mg/L; from about 100 mg/L to about 13000 mg/L; from about 100 mg/L to about 12500 mg/L; from about 100 mg/L to about 12000 mg/L; from about 100 mg/L to about 11500 mg/L; from about 100 mg/L to about 11000 mg/L; from about 100 mg/L to about 10500 mg/L; from about 100 mg/L to about 10000 mg/L; from about 100 mg/L to about 9500 mg/L; from about 100 mg/L to about 9000 mg/L; from about 100 mg/L to about 8500 mg/L; from about 100 mg/L to about 8000 mg/L; from about 100 mg/L to about 7500 mg/L; from about 100 mg/L to about 7000 mg/L; from about 100 mg/L to about 6500 mg/L; from about 100 mg/L to about 6000 mg/L; from about 100 mg/L to about 5500 mg/L; from about 100 mg/L to about 5000 mg/L; from about 100 mg/L to about 4500 mg/L; from about 100 mg/L to about 4000 mg/L; from about 100 mg/L to about 3500 mg/L; from about 100 mg/L to about 3000 mg/L; from about 100 mg/L to about 2500 mg/L; from about 100 mg/L to about 2000 mg/L; from about 100 mg/L to about 1500 mg/L; from about 100 mg/L to about 1000 mg/L; from about 100 mg/L to about 1000 mg/L; from about 100 mg/L to about 750 mg/L; from about 100 mg/L to about 500 mg/L; from about 100 mg/L to about 250 mg/L; from about 100 mg/L to about 100 mg/L; or from about 100 mg/L to about 110 mg/L of AMP per liter of medium (supernatant of yeast fermentation broth).

In some embodiments, two expression cassettes comprising a polynucleotide operable to express an AMP can be inserted into a vector, for example a pKS022 plasmid, resulting in a yield of about 2 g/L of AMP (supernatant of yeast fermentation broth). Alternatively, in some embodiments, three expression cassettes comprising a polynucleotide operable to express an AMP can be inserted into a vector, for example a pLB103bT plasmid.

In some embodiments, multiple AMP expression cassettes can be transfected into yeast in order to enable integration of one or more copies of the optimized AMP transgene into the *K. lactis* genome. An exemplary method of introducing multiple AMP expression cassettes into a *K. lactis* genome is as follows: an AMP expression cassette DNA sequence is synthesized, comprising an intact LAC4 promoter element, a codon-optimized AMP ORF element and a pLAC4 terminator element; the intact expression cassette is ligated into the pLB103b vector between Sal I and Kpn I restriction sites, downstream of the pLAC4 terminator of pLB10V5, resulting in the double transgene AMP expression vector, pKS022; the double transgene vectors, pKS022, are then linearized using Sac II restriction endonuclease and transformed into YCT306 strain of *K. lactis* by electroporation. The resulting yeast colonies are then grown on YCB agar plate supplemented with 5 mM acetamide, which only the acetamidase-expressing cells could use efficiently as a metabolic source of nitrogen. To evaluate the yeast colonies, about 100 to 400 colonies can be picked from the pKS022 yeast plates. Inoculates from the colonies are each cultured in 2.2 mL of the defined *K. lactis* media with 2% sugar alcohol added as a carbon source. Cultures are incubated at 23.5° C., with shaking at 280 rpm, for six days, at which point cell densities in the cultures will reach their maximum levels as indicated by light absorbance at 600 nm (OD600). Cells are then removed from the cultures by centrifugation at 4,000 rpm for 10 minutes, and the resulting supernatants (conditioned media) are filtered through 0.2 μM membranes for HPLC yield analysis.

Chemically Synthesizing AMPs

Peptide synthesis or the chemical synthesis or peptides and/or polypeptides can be used to generate AMPs: these methods can be performed by those having ordinary skill in the art, and/or through the use of commercial vendors (e.g., GenScript®; Piscataway, New Jersey). For example, in some embodiments, chemical peptide synthesis can be achieved using Liquid phase peptide synthesis (LPPS), or solid phase peptide synthesis (SPPS).

In some embodiments, peptide synthesis can generally be achieved by using a strategy wherein the coupling the carboxyl group of a subsequent amino acid to the N-terminus of a preceding amino acid generates the nascent polypeptide chain—a process that is opposite to the type of polypeptide synthesis that occurs in nature.

Peptide deprotection is an important first step in the chemical synthesis of polypeptides. Peptide deprotection is the process in which the reactive groups of amino acids are blocked through the use of chemicals in order to prevent said amino acid's functional group from taking part in an unwanted or non-specific reaction or side reaction; in other words, the amino acids are "protected" from taking part in these undesirable reactions.

Prior to synthesizing the peptide chain, the amino acids must be "deprotected" to allow the chain to form (i.e., amino acids to bind). Chemicals used to protect the N-termini include 9-fluorenylmethoxycarbonyl (Fmoc), and tert-butoxycarbonyl (Boc), each of which can be removed via the use of a mild base (e.g., piperidine) and a moderately strong acid (e.g., trifluoracetic acid (TFA)), respectively.

The C-terminus protectant required is dependent on the type of chemical peptide synthesis strategy used: e.g., LPPS requires protection of the C-terminal amino acid, whereas SPPS does not owing to the solid support which acts as the protecting group. Side chain amino acids require the use of several different protecting groups that vary based on the individual peptide sequence and N-terminal protection strategy; typically, however, the protecting group used for side chain amino acids are based on the tert-butyl (tBu) or benzyl (Bzl) protecting groups.

Amino acid coupling is the next step in a peptide synthesis procedure. To effectuate amino acid coupling, the incoming amino acid's C-terminal carboxylic acid must be activated: this can be accomplished using carbodiimides such as diisopropylcarbodiimide (DIC), or dicyclohexylcarbodiimide (DCC), which react with the incoming amino acid's carboxyl group to form an O-acylisourea intermediate. The O-acylisourea intermediate is subsequently displaced via nucleophilic attack via the primary amino group on the N-terminus of the growing peptide chain. The reactive intermediate generated by carbodiimides can result in the racemization of amino acids. To avoid racemization of the amino acids, reagents such as 1-hydroxybenzotriazole (HOBt) are added in order to react with the O-acylisourea intermediate. Other couple agents that may be used include 2-(1H-benzotriazol-1-yl)-1,1,3,3-tetramethyluronium hexafluorophosphate (HBTU), and benzotriazol-1-yl-oxy-tris(dimethylamino)phosphonium hexafluorophosphate (BOP), with the additional activating bases. Finally, following amino acid deprotection and coupling, At the end of the synthesis process, removal of the protecting groups from the polypeptide must occur—a process that usually occurs through acidolysis. Determining which reagent is required for peptide cleavage is a function of the protection scheme used and overall synthesis method. For example, in some embodiments, hydrogen bromide (HBr); hydrogen fluoride (HF); or trifluoromethane sulfonic acid (TFMSA) can be used to cleave Bzl and Boc groups. Alternatively, in other embodiments, a less strong acid such as TFA can effectuate acidolysis of tBut and Fmoc groups. Finally, peptides can be purified based on the peptide's physiochemical characteristics (e.g., charge, size, hydrophobicity, etc.). Techniques that can be used to purify peptides include Purification techniques include Reverse-phase chromatography (RPC); Size-exclusion chromatography; Partition chromatography; High-performance liquid chromatography (HPLC); and Ion exchange chromatography (IEC).

Exemplary methods of peptide synthesis can be found in Anderson G. W. and McGregor A. C. (1957) T-butyloxycarbonylamino acids and their use in peptide synthesis. Journal of the American Chemical Society. 79, 6180-3; Carpino L. A. (1957) Oxidative reactions of hydrazines. Iv. Elimination of nitrogen from 1, 1-disubstituted-2-arenesulfonhydrazidesl-4. Journal of the American Chemical Society. 79, 4427-31; McKay F. C. and Albertson N. F. (1957) New amine-masking groups for peptide synthesis. Journal of the American Chemical Society. 79, 4686-90; Merrifield R. B. (1963) Solid phase peptide synthesis. I. The synthesis of a tetrapeptide. Journal of the American Chemical Society. 85, 2149-54; Carpino L. A. and Han G. Y. (1972) 9-fluorenylmethoxycarbonyl amino-protecting group. The Journal of Organic Chemistry. 37, 3404-9; and A Lloyd-Williams P. et al. (1997) Chemical approaches to the synthesis of peptides and proteins. Boca Raton: CRC Press. 278; U.S. Pat. No. 3,714,140 (filed Mar. 16, 1971); U.S. Pat. No. 4,411,994 (filed Jun. 8, 1978); U.S. Pat. No. 7,785,832 (filed Jan. 20, 2006); U.S. Pat. No. 8,314,208 (filed Feb. 10, 2006); and 10,442,834 (filed Oct., 2, 2015); and United States Patent Application 2005/0165215 (filed Dec. 23, 2004), the disclosures of which are incorporated herein by reference in their entirety.

Cell Culture and Transformation Techniques

The terms "transformation" and "transfection" both describe the process of introducing exogenous and/or heterologous polynucleotide (e.g., DNA or RNA) to a host organism. Generally, those having ordinary skill in the art sometimes reserve the term "transformation" to describe processes where exogenous and/or heterologous polynucleotide (e.g., DNA or RNA) are introduced into a bacterial cell; and reserve the term "transfection" for processes that describe the introduction of exogenous and/or heterologous polynucleotide (e.g., DNA or RNA) into eukaryotic cells. However, as used herein, the term "transformation" and "transfection" are used synonymously, regardless of whether a process describes the introduction exogenous and/or heterologous DNA or RNA into a prokaryote (e.g., bacteria) or a eukaryote (e.g., yeast, plants, or animals).

In some embodiments, a host organism can be transformed with a polynucleotide operable to encode an AMP. In some embodiments, the host organism can be an microorganism, e.g., a cell.

In some embodiments, a vector comprising an AMP expression cassette can be cloned into an expression plasmid and transformed into a host cell. In some embodiments, the host cell can be selected from any host cell described herein.

In some embodiments, a host cell can be transformed using the following methods: electroporation; cell squeezing; microinjection; impalefection; the use of hydrostatic pressure; sonoporation; optical transfection; continuous infusion; lipofection; through the use of viruses such as adenovirus, adeno-associated virus, lentivirus, herpes simplex virus, and retrovirus; the chemical phosphate method; endocytosis via DEAE-dextran or polyethylenimine (PEI); protoplast fusion; hydrodynamic deliver; magnetofection; nucleoinfection; and/or others. Exemplary methods regarding transfection and/or transformation techniques can be found in Makrides (2003), Gene Transfer and Expression in Mammalian Cells, Elvesier; Wong, TK & Neumann, E. Electric field mediated gene transfer. Biochem. Biophys. Res. Commun. 107, 584-587 (1982); Potter & Heller, Transfection by Electroporation. Curr Protoc Mol Biol. 2003 May; CHAPTER: Unit-9.3; Kim & Eberwine, Mammalian cell transfection: the present and the future. Anal Bioanal Chem. 2010 August; 397(8): 3173-3178, each of these references are incorporated herein by reference in their entireties.

Electroporation is an exemplary method for transforming host cells. Electroporation is a technique in which electricity is applied to cells causing the cell membrane to become permeable; this in turn allows exogenous DNA to be introduced into the cells. Electroporation is readily known to those having ordinary skill in the art, and the tools and devices required to achieve electroporation are commercially available (e.g., Gene Pulser Xcell™ Electroporation Systems, Bio-Rad®; Neon® Transfection System for Electroporation, Thermo-Fisher Scientific; and other tools and/or devices). Exemplary methods of electroporation are illustrated in Potter & Heller, Transfection by Electroporation. Curr Protoc Mol Biol. 2003 May; CHAPTER: Unit-9.3; Saito (2015) Electroporation Methods in Neuroscience. Springer press; Pakhomov et al., (2017) Advanced Electroporation Techniques in Biology and Medicine. Taylor & Francis; the disclosure of which is incorporated herein by reference in its entirety.

In some embodiments, electroporation can be used transform a cell with one or more vectors containing a polynucleotide operable to encode one or more AMPs or AMP-insecticidal proteins. For example, in some embodiments, electroporation can be used transform a cell with one or more vectors containing one or more AMP expression cassettes.

Exemplary Description of Yeast Transformation and Culture Methods

In some embodiments, electroporation can be used transform a yeast cell with one or more vectors containing one or more AMP expression cassettes, which can produce AMP in a yeast culture with a yield of at least 70 mg/L, at least 80 mg/L, at least 90 mg/L, at least 100 mg/L, at least 110 mg/L, at least 120 mg/L, at least 130 mg/L, at least 140 mg/L, at least 150 mg/L, at least 160 mg/L, at least 170 mg/L, at least 180 mg/L, at least 190 mg/L 200 mg/L, at least 500 mg/L, at least 750 mg/L, at least 1,000 mg/L, at least 1,250 mg/L, at least 1,500 mg/L, at least 1,750 mg/L, at least 2,000 mg/L, at least 2,500 mg/L, at least 3,000 mg/L, at least 3,500 mg/L, at least 4,000 mg/L, at least 4,500 mg/L, at least 5,000 mg/L, at least 5,500 mg/L, at least at least 6,000 mg/L, at least 6,500 mg/L, at least 7,000 mg/L, at least 7,500 mg/L, at least 8,000 mg/L, at least 8,500 mg/L, at least 9,000 mg/L, at least 9,500 mg/L, at least 10,000 mg/L, at least 11,000 mg/L, at least 12,000 mg/L, at least 12,500 mg/L, at least 13,000 mg/L, at least 14,000 mg/L, at least 15,000 mg/L, at least 16,000 mg/L, at least 17,000 mg/L, at least 17,500 mg/L, at least 18,000 mg/L, at least 19,000 mg/L, at least 20,000 mg/L, at least 25,000 mg/L, at least 30,000 mg/L, at least 40,000 mg/L, at least 50,000 mg/L, at least 60,000 mg/L, at least 70,000 mg/L, at least 80,000 mg/L, at least 90,000 mg/L, or at least 100,000 mg/L of AMP per liter of medium.

In some embodiments, electroporation can be used to introduce a vector containing a polynucleotide encoding an AMP into yeast, for example, in some embodiments, an AMP expression cassette cloned into a plasmid, and transformed into yeast cells via electroporation.

In some embodiments, an AMP expression cassette cloned into a plasmid, and transformed a host cell (e.g., a yeast cell) via electroporation can be accomplished by inoculating about 10-200 mL of yeast extract peptone dextrose (YEPD) with a suitable yeast species, for example, *Kluyveromyces lactis, Kluyveromyces marxianus, Saccharomyces cerevisiae, Pichia pastoris*, etc., and incubate on a shaker at 30° C. until the early exponential phase of yeast culture (e.g. about 0.6 to $2\times10^8$ cells/mL); harvesting the yeast in sterile centrifuge tube and centrifuging at 3000 rpm for 5 minutes at 4° C. (note: keep cells chilled during the procedure) washing cells with 40 mL of ice cold, sterile deionized water, and pelleting the cells a 23,000 rpm for 5 minutes; repeating the wash step, and the resuspending the cells in 20 mL of 1M fermentable sugar, e.g. galactose, maltose, latotriose, sucrose, fructose or glucose and/or sugar alcohol, for example, erythritol, hydrogenated starch hydrolysates, isomalt, lactitol, maltitol, mannitol, and xylitol, followed by spinning down at 3,000 rpm for 5 minutes; resuspending the cells with proper volume of ice cold 1M fermentable sugar, e.g. galactose, maltose, latotriose, sucrose, fructose or glucose and/or a sugar alcohol, for example, erythritol, hydrogenated starch hydrolysates, isomalt, lactitol, maltitol, mannitol, and xylitol to final cell density of $3\times10^9$ cell/mL; ($1.5\times10^9$ cell/mL to $6\times10^9$ cell/mL are acceptable cell densities); mixing 40 µl of the yeast suspension with about 1-4 µl (at a concentration of 100-300 ng/µl) of the vector containing a linear polynucleotide encoding an AMP (~1 µg) in a prechilled 0.2 cm electroporation cuvette (note: ensure the sample is in contact with both sides of the aluminum cuvette); providing a single pulse at 2000 V, for optimal time constant of 5 ms of the RC circuit, the cells was then let recovered in 0.5 ml YED and 0.5 mL 1M fermentable sugar, e.g. galactose, maltose, latotriose, sucrose, fructose or glucose and/or a sugar alcohol, for example, erythritol, hydrogenated starch hydrolysates, isomalt, lactitol, maltitol, mannitol, and xylitol mixture, and then spreading onto selective plates.

In some embodiments, electroporation can be used to introduce a vector containing a polynucleotide encoding an AMP into yeast, for example, an AMP cloned into a plasmid, and transformed into *K. lactis* cells via electroporation, can be accomplished by inoculating about 10-200 mL of yeast extract peptone dextrose (YEPD) incubating on a shaker at 30° C. until the early exponential phase of yeast culture (e.g. about 0.6 to $2\times10^8$ cells/mL); harvesting the yeast in sterile centrifuge tube and centrifuging at 3000 rpm for 5 minutes at 4° C. (note: keep cells chilled during the procedure) washing cells with 40 mL of ice cold, sterile deionized water, and pelleting the cells a 23,000 rpm for 5 minutes; repeating the wash step, and the resuspending the cells in 20 mL of 1M fermentable sugar, e.g. galactose, maltose, latotriose, sucrose, fructose or glucose and/or sugar alcohol, for example, erythritol, hydrogenated starch hydrolysates, isomalt, lactitol, maltitol, mannitol, and xylitol, followed by spinning down at 3,000 rpm for 5 minutes; resuspending the cells with proper volume of ice cold 1M fermentable sugar, e.g. galactose, maltose, latotriose, sucrose, fructose or glucose and/or a sugar alcohol, for example, erythritol, hydrogenated starch hydrolysates, isomalt, lactitol, maltitol, mannitol, and xylitol to final cell density of $3\times10^9$ cell/mL; mixing 40 µl of the yeast suspension with about 1-4 µl of the vector containing a linear polynucleotide encoding an AMP (~1 µg) in a prechilled 0.2 cm electroporation cuvette (note: ensure the sample is in contact with both sides of the aluminum cuvette); providing a single pulse at 2000 V, for optimal time constant of 5 ms of the RC circuit, the cells was then let recovered in 0.5 ml YED and 0.5 mL 1M fermentable sugar, e.g. galactose, maltose, latotriose, sucrose, fructose or glucose and/or a sugar alcohol, for example, erythritol, hydrogenated starch hydrolysates, isomalt, lactitol, maltitol, mannitol, and xylitol mixture, and then spreading onto selective plates.

In some embodiments, using the illustrated methods described herein, i.e., vectors of the present disclosure utilizing yeast, and methods transformation and fermentation, may result in production of AMP in amounts of: at least 70 mg/L, at least 80 mg/L, at least 90 mg/L, at least 100 mg/L, at least 110 mg/L, at least 120 mg/L, at least 130 mg/L, at least 140 mg/L, at least 150 mg/L, at least 160 mg/L, at least 170 mg/L, at least 180 mg/L, at least 190 mg/L 200 mg/L, at least 500 mg/L, at least 750 mg/L, at least 1,000 mg/L, at least 1,250 mg/L, at least 1,500 mg/L, at least 1,750 mg/L, at least 2,000 mg/L, at least 2,500 mg/L, at least 3,000 mg/L, at least 3,500 mg/L, at least 4,000 mg/L, at least 4,500 mg/L, at least 5,000 mg/L, at least 5,500 mg/L, at least at least 6,000 mg/L, at least 6,500 mg/L, at least 7,000 mg/L, at least 7,500 mg/L, at least 8,000 mg/L, at least 8,500 mg/L, at least 9,000 mg/L, at least 9,500 mg/L, at least 10,000 mg/L, at least 11,000 mg/L, at least 12,000 mg/L, at least 12,500 mg/L, at least 13,000 mg/L, at least 14,000 mg/L, at least 15,000 mg/L, at least 16,000 mg/L, at least 17,000 mg/L, at least 17,500 mg/L, at least 18,000 mg/L, at least 19,000 mg/L, at least 20,000 mg/L, at least 25,000 mg/L, at least 30,000 mg/L, at least 40,000 mg/L, at least 50,000 mg/L, at least 60,000 mg/L, at least 70,000 mg/L, at least 80,000 mg/L, at least 90,000 mg/L, or at least 100,000 mg/L of AMP per liter of medium.

In some embodiments, electroporation can be used to introduce a vector containing a polynucleotide encoding an AMP into plant protoplasts by incubating sterile plant material in a protoplast solution (e.g., around 8 mL of 10 mM 2-[N-morpholino]ethanesulfonic acid (MES), pH 5.5; 0.01% (w/v) pectylase; 1% (w/v) macerozyme; 40 mM $CaCl_2$); and 0.4 M mannitol) and adding the mixture to a rotary shaker for about 3 to 6 hours at 30° C. to produce protoplasts; removing debris via 80-µm-mesh nylon screen filtration; rinsing the screen with about 4 ml plant electroporation buffer (e.g., 5 mM $CaCl_2$); 0.4 M mannitol; and PBS); combining the protoplasts in a sterile 15 mL conical centrifuge tube, and then centrifuging at about 300×g for about 5 minutes; subsequent to centrifugation, discarding the supernatant and washing with 5 mL of plant electroporation buffer; resuspending the protoplasts in plant electroporation buffer at about $1.5\times10^6$ to $2\times10^6$ protoplasts per mL of liquid; transferring about 0.5-mL of the protoplast suspension into one or more electroporation cuvettes, set on ice, and adding the vector (note: for stable transformation, the vector should be linearized using anyone of the restriction methods described above, and about 1 to 10 g of vector may be used; for transient expression, the vector may be retained in its supercoiled state, and about 10 to 40 µg of vector may be used); mixing the vector and protoplast suspension; placing the cuvette into the electroporation apparatus, and shocking for one or more times at about 1 to 2 kV (a 3-to 25-µF capacitance may be used initially while optimizing the reaction); returning the cuvette to ice; diluting the transformed cells 20-fold in complete medium; and harvesting the protoplasts after about 48 hours.

Host Cells and Host Organisms

The methods, compositions, AMPs, and AMP-insecticidal proteins of the present disclosure may be implemented in any host organism. For example, in some embodiments, the host organism can be a cell. In some embodiments, the cell can be, e.g., a eukaryotic or prokaryotic cell.

In some embodiments, the host cell used to produce a AMP or AMP-insecticidal protein is a prokaryote. For example, in some embodiments, the host cell may be an Archaebacteria or Eubacteria, such as Gram-negative or Gram-positive organisms. Examples of useful bacteria include *Escherichia* (e.g., *E. coli*), Bacilli (e.g., *B. subtilis*), *Enterobacteria, Pseudomonas* species (e.g., *P. aeruginosa*), *Salmonella typhimurium, Serratia marcescans, Klebsiella, Proteus, Shigella, Rhizobia, Vitreoscilla*, or *Paracoccus*.

In some embodiments, the host cell used to produce a AMP or AMP-insecticidal protein may be a unicellular cell. For example, in some embodiments, the host cell may be bacterial cells such as gram positive bacteria.

In some embodiments, the host cell may be a bacteria selected from the following genera consisting of: *Candidatus Chloracidobacterium, Arthrobacter, Corynebacterium, Frankia, Micrococcus, Mycobacterium, Propionibacterium, Streptomyces, Aquifex Bacteroides, Porphyromonas, Bacteroides, Porphyromonas, Flavobacterium, Chlamydia, Prosthecobacter, Verrucomicrobium, Chloroflexus, Chroococcus, Merismopedia, Synechococcus, Anabaena, Nostoc, Spirulina, Trichodesmium, Pleurocapsa, Prochlorococcus, Prochloron, Bacillus, Listeria, Staphylococcus, Clostridium, Dehalobacter, Epulopiscium, Ruminococcus, Enterococcus, Lactobacillus, Streptococcus, Erysipelothrix, Mycoplasma, Leptospirillum, Nitrospira, Thermodesulfobacterium, Gemmata, Pirellula, Planctomyces, Caulobacter, Agrobacterium, Bradyrhizobium, Brucella, Methylobacterium,* Prosthecomicrobium, Rhizobium, Rhodopseudomonas, Sinorhizobium, Rhodobacter, *Roseobacter, Acetobacter, Rhodospirillum, Rickettsia, Rickettsia conorii, Mitochondria, Wolbachia, Erythrobacter, Erythromicrobium, Sphingomonas, Alcaligenes, Burkholderia, Leptothrix, Sphaerotilus, Thiobacillus, Neisseria, Nitrosomonas, Gallionella, Spirillum, Azoarcus, Aeromonas, Succinomonas, Succinivibrio, Ruminobacter, Nitrosococcus, Thiocapsa, Enterobacter, Escherichia, Klebsiella, Salmonella, Shigella, Wigglesworthia, Yersinia, Coxiella, Legionella, Halomonas, Pasteurella, Acinetobacter, Azotobacter, Pseudomonas, Psychrobacter, Beggiatoa, Thiomargarita, Vibrio, Xanthomonas, Bdellovibrio, Campylobacter, Helicobacter, Myxococcus, Desulfosarcina, Geobacter, Desulfuromonas, Borrelia, Leptospira, Treponema, Petrotoga, Thermotoga, Deinococcus, or Thermus.*

In some embodiments, the host cell used to produce a AMP or AMP-insecticidal protein may be selected from one of the following bacteria species: *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis, Bacillus thuringiensis, Streptomyces lividans, Streptomyces murinus, Streptomyces coelicolor, Streptomyces albicans, Streptomyces griseus, Streptomyces plicatosporus, Escherichia albertii, Escherichia blattae, Escherichia coli, Escherichia fergusonii, Escherichia hermannii, Escherichia senegalensis, Escherichia vulneris, Pseudomonas abietaniphila, Pseudomonas agarici, Pseudomonas agarolyticus, Pseudomonas alcaliphila, Pseudomonas alginovora, Pseudomonas andersonii, Pseudomonas antarctica, Pseudomonas asplenii, Pseudomonas azelaica, Pseudomonas batumici, Pseudomonas borealis, Pseudomonas brassicacearum, Pseudomonas chloritidismutans, Pseudomonas cremoricolorata, Pseudomonas diterpeniphila, Pseudomonas filiscindens, Pseudomonas frederiksbergensis, Pseudomonas gingeri, Pseudomonas graminis, Pseudomonas grimontii, Pseudomonas halodenitrificans, Pseudomonas halophila, Pseudomonas hibiscicola, Pseudomonas hydrogenovora, Pseudomonas indica, Pseudomonas japonica, Pseudomonas jessenii, Pseudomonas kilonensis, Pseudomonas koreensis, Pseudomonas lini, Pseudomonas lurida, Pseudomonas lutea, Pseudomonas marginata, Pseudomonas meridiana, Pseudomonas mesoacidophila, Pseudomonas pachastrellae, Pseudomonas palleroniana, Pseudomonas parafulva, Pseudomonas pavonanceae, Pseudomonas proteolyica, Pseudomonas psychrophila, Pseudomonas psychrotolerans, Pseudomonas pudica, Pseudomonas rathonis, Pseudomonas reactans, Pseudomonas rhizosphaerae, Pseudomonas salmononii, Pseudomonas thermaerum, Pseudomonas thermocarboxydovorans, Pseudomonas thermotolerans, Pseudomonas thivervalensis, Pseudomonas umsongensis, Pseudomonas vancouverensis, Pseudomonas wisconsinensis, Pseudomonas xanthomarina Pseudomonas xiamenensis, Pseudomonas aeruginosa, Pseudomonas alcaligenes, Pseudomonas anguilliseptica, Pseudomonas citronellolis, Pseudomonas flavescens, Pseudomonas jinjuensis, Pseudomonas mendocina, Pseudomonas nitroreducens, Pseudomonas oleovorans, Pseudomonas pseudoalcaligenes, Pseudomonas resinovorans, Pseudomonas straminae, Pseudomonas aurantiaca, Pseudomonas chlororaphis, Pseudomonas fragi, Pseudomonas lundensis, Pseudomonas taetrolens Pseudomonas azotoformans, Pseudomonas brenneri, Pseudomonas cedrina, Pseudomonas congelans, Pseudomonas corrugata, Pseudomonas costantinii, Pseudomonas extremorientalis, Pseudomonas fluorescens, Pseudomonas fulgida, Pseudomonas gessardii, Pseudomonas libanensis, Pseudomonas mandelii, Pseudomonas marginalis, Pseudomonas mediterranea, Pseudomonas migulae, Pseudomonas mucidolens, Pseudomonas orientalis, Pseudomonas poae, Pseudomonas rhodesiae, Pseudomonas synxantha, Pseudomonas tolaasii, Pseudomonas trivialis, Pseudomonas veronii Pseudomonas denitrificans, Pseudomonas pertucinogena, Pseudomonas fulva, Pseudomonas monteilii, Pseudomonas mosselii, Pseudomonas oryzihabitans, Pseudomonas plecoglossicida, Pseudomonas putida, Pseudomonas balearica, Pseudomonas luteola*, or *Pseudomonas stutzeri. Pseudomonas avellanae, Pseudomonas cannabina, Pseudomonas caricapapyae, Pseudomonas cichorii, Pseudomonas coronafaciens, Pseudomonas fuscovaginae, Pseudomonas tremae*, or *Pseudomonas viridiflava*

In some embodiments, the host cell used to produce a AMP or AMP-insecticidal protein can be eukaryote.

In some embodiments, the host cell used to produce a AMP or AMP-insecticidal protein may be a cell belonging to the clades: Opisthokonta; Viridiplantae (e.g., algae and plant); Amebozoa; Cercozoa; Alveolata; Marine flagellates; Heterokonta; Discicristata; or Excavata.

In some embodiments, the procedures and methods described herein can be accomplished using a host cell that is, e.g., a Metazoan, a Choanoflagellata, or a fungi.

In some embodiments, the procedures and methods described here can be accomplished using a host cell that is a fungi. For example, in some embodiments, the host cell may be a cell belonging to the eukaryote phyla: Ascomycota, Basidiomycota, Chytridiomycota, Microsporidia, or Zygomycota In some embodiments, the procedures and methods described here can be accomplished using a host cell that is a fungi belonging to one of the following genera: *Aspergillus, Cladosporium, Magnaporthe, Morchella, Neurospora, Penicillium, Saccharomyces, Cryptococcus*, or *Ustilago.*

In some embodiments, the procedures and methods described here can be accomplished using a host cell that is a fungi belonging to one of the following species: *Saccharomyces cerevisiae, Saccharomyces boulardi, Saccharomyces uvarum; Aspergillus flavus, A. terreus, A. awamori; Cladosporium elatum, Cladosporium Herbarum, Cladosporium Sphaerospermum*, and *Cladosporium Cladosporioides; Magnaporthe grise, Magnaporthe oryzae, Magnaporthe rhizophila; Morchella deliciosa, Morchella esculenta, Morchella conica; Neurospora crassa, Neurospora intermedia, Neurospora tetrasperma; Penicillium notatum, Penicillium chrysogenum, Penicillium roquefortii*, or *Penicillium simplicissimum.*

In some embodiments, the host cell used to produce a AMP or AMP-insecticidal protein may be a fungi belonging to one of the following genera: *Aspergillus, Cladosporium, Magnaporthe, Morchella, Neurospora, Penicillium, Saccharomyces, Cryptococcus*, or *Ustilago.*

In some embodiments, the host cell used to produce a AMP or AMP-insecticidal protein may be a member of the Saccharomycetaceae family. For example, in some embodiments, the host cell may be one of the following genera within the Saccharomycetaceae family: *Brettanomyces, Candida, Citeromyces, Cyniclomyces, Debaryomyces, Issatchenkia, Kazachstania, Kluyveromyces, Komagataella, Kuraishia, Lachancea, Lodderomyces, Nakaseomyces, Pachysolen, Pichia, Saccharomyces, Spathaspora, Tetrapisispora, Vanderwaltozyma, Torulaspora, Williopsis, Zygosaccharomyces, or Zygotorulaspora.*

In some embodiments, the host cell used to produce a AMP or AMP-insecticidal protein may be one of the following: *Aspergillus flavus, Aspergillus terreus, Aspergillus awamori, Cladosporium elatum, Cladosporium Herbarum, Cladosporium Sphaerospermum, Cladosporium cladosporioides, Magnaporthe grisea, Magnaporthe oryzae, Magnaporthe rhizophila, Morchella deliciosa, Morchella esculenta, Morchella conica, Neurospora crassa, Neurospora intermedia, Neurospora tetrasperma, Penicillium notatum, Penicillium chrysogenum, Penicillium roquefortii*, or *Penicillium simplicissimum.*

In some embodiments, the host cell used to produce a AMP or AMP-insecticidal protein may be a species within the *Candida* genus. For example, the host cell may be one of the following: *Candida albicans, Candida ascalaphidarum, Candida amphixiae, Candida antarctica, Candida argentea, Candida atlantica, Candida atmosphaerica, Candida auris, Candida blankii, Candida blattae, Candida bracarensis, Candida bromeliacearum, Candida carpophila, Candida carvajalis, Candida cerambycidarum, Candida chauliodes, Candida corydalis, Candida dosseyi, Candida dubliniensis, Candida ergatensis, Candida fructus, Candida glabrata, Candida fermentati, Candida guilliermondii, Candida haemulonii, Candida humilis, Candida insectamens, Candida insectorum, Candida intermedia, Candida jeffresii*, or *Candida kefyr.*

In some embodiments, the host cell used to produce a AMP or AMP-insecticidal protein may be any species within the genera, *Kluyveromyces.*

In some embodiments, the host cell used to produce a AMP or AMP-insecticidal protein may be a species in the genera, *Kluyveromyces*, e.g., the host cell may be one of the following: *Kluyveromyces aestuarii, Kluyveromyces dobzhanskii, Kluyveromyces lactis, Kluyveromyces marxianus, Kluyveromyces nonfermentans*, or *Kluyveromyces wickerhamii.*

In some embodiments, the host cell used to produce a AMP or AMP-insecticidal protein may be a species within the *Pichia* genus. For example, the host cell may be one of the following: *Pichia farinose, Pichia anomala, Pichia heedii, Pichia guilliermondii, Pichia kluyveri, Pichia membranifaciens, Pichia norvegensis, Pichia ohmeri, Pichia pastoris, Pichia methanolica*, or *Pichia subpelliculosa.*

In some embodiments, the host cell used to produce a AMP or AMP-insecticidal protein may be a species within the *Saccharomyces* genus. For example, the host cell may be one of the following: *Saccharomyces arboricolus, Saccharomyces bayanus, Saccharomyces bulderi, Saccharomyces cariocanus, Saccharomyces cariocus, Saccharomyces cerevisiae, Saccharomyces cerevisiae* var *boulardii, Saccharomyces chevalieri, Saccharomyces dairenensis, Saccharomyces ellipsoideus, Saccharomyces eubayanus, Saccharomyces exiguous, Saccharomyces florentinus, Saccharomyces fragilis, Saccharomyces kudriavzevii, Saccharomyces martiniae, Saccharomyces mikatae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvarum*, or *Saccharomyces zonatus.*

In some embodiments, the procedures and methods described here can be accomplished using a host cell that is a *Kluyveromyces lactis, Kluyveromyces marxianus, Saccharomyces cerevisiae, Pichia pastoris, Pichia methanolica, Schizosaccharomyces pombe*, or *Hansenula anomala.*

The use of yeast cells as a host organism to generate recombinant AMP is an exceptional method, well known to those having ordinary skill in the art. In some embodiments, the methods and compositions described herein can be performed with any species of yeast, including but not limited to any species of the genus *Saccharomyces, Pichia, Kluyveromyces, Hansenula, Yarrowia* or *Schizosaccharomyces* and the species *Saccharomyces* includes any species of *Saccharomyces*, for example *Saccharomyces cerevisiae* species selected from following strains: INVSc1, YNN27, S150-2B, W303-1B, CG25, W3124, JRY188, BJ5464, AH22, GRF18, W303-1A and BJ3505. In some embodiments, members of the *Pichia* species including any species of *Pichia*, for example the *Pichia* species, *Pichia pastoris*, for example, the *Pichia pastoris* is selected from following strains: Bg08, Y-11430, X-33, GS115, GS190, JC220, JC254, GS200, JC227, JC300, JC301, JC302, JC303, JC304, JC305, JC306, JC307, JC308, YJN165, KM71, MC100-3, SMD1163, SMD1165, SMD1168, GS241, MS105, any pep4 knock-out strain and any prb1 knock-out strain, as well as *Pichia pastoris* selected from following strains: Bg08, X-33, SMD1168 and KM71. In some embodiments, any *Kluyveromyces* species can be used to accomplish the methods described here, including any species of *Kluyveromyces*, for example, *Kluyveromyces lactis*, and we teach that the stain of *Kluyveromyces lactis* can be but is not required to be selected from following strains: GG799, YCT306, YCT284, YCT389, YCT390, YCT569, YCT598, NRRL Y-1140, MW98-8C, MS1, CBS293.91, Y721, MD2/1, PM6-7A, WM37, K6, K7, 22AR1, 22A295-1, SD11, MG1/2, MSK110, JA6, CMK5, HP101, HP108 and PM6-

3C, in addition to *Kluyveromyces lactis* species is selected from GG799, YCT306 and NRRL Y-1140.

In some embodiments, the host cell used to produce a AMP or a AMP-insecticidal protein can be an *Aspergillus oryzae*.

In some embodiments, the host cell used to produce a AMP or a AMP-insecticidal protein can be an *Aspergillus japonicas*.

In some embodiments, the host cell used to produce a AMP or a AMP-insecticidal protein can be an *Aspergillus niger*.

In some embodiments, the host cell used to produce a AMP or a AMP-insecticidal protein can be a *Bacillus licheniformis*.

In some embodiments, the host cell used to produce a AMP or a AMP-insecticidal protein can be a *Bacillus subtilis*.

In some embodiments, the host cell used to produce a AMP or a AMP-insecticidal protein can be a *Trichoderma reesei*.

In some embodiments, the procedures and methods described here can be accomplished with any species of yeast, including but not limited to any species of *Hansenula* species including any species of *Hansenula* and preferably *Hansenula polymorpha*. In some embodiments, the procedures and methods described here can be accomplished with any species of yeast, including but not limited to any species of *Yarrowia* species for example, *Yarrowia lipolytica*. In some embodiments, the procedures and methods described here can be accomplished with any species of yeast, including but not limited to any species of *Schizosaccharomyces* species including any species of *Schizosaccharomyces* and preferably *Schizosaccharomyces pombe*.

In some embodiments, yeast species such as *Kluyveromyces lactis, Saccharomyces cerevisiae, Pichia pastoris*, and others, can be used as a host organism. Yeast cell culture techniques are well known to those having ordinary skill in the art. Exemplary methods of yeast cell culture can be found in Evans, Yeast Protocols. Springer (1996); Bill, Recombinant Protein Production in Yeast. Springer (2012); Hagan et al., Fission Yeast: A Laboratory Manual, CSH Press (2016); Konishi et al., Improvement of the transformation efficiency of *Saccharomyces cerevisiae* by altering carbon sources in pre-culture. Biosci Biotechnol Biochem. 2014; 78(6):1090-3; Dymond, *Saccharomyces cerevisiae* growth media. Methods Enzymol. 2013; 533:191-204; Looke et al., Extraction of genomic DNA from yeasts for PCR-based applications. Biotechniques. 2011 May; 50(5): 325-8; and Romanos et al., Culture of yeast for the production of heterologous proteins. Curr Protoc Cell Biol. 2014 Sep. 2; 64:20.9.1-16, the disclosure of which is incorporated herein by reference in its entirety.

Recipes for yeast cell fermentation media and stocks are described herein.

Yeast Strains

The present disclosure contemplates the creation of yeast strains operable to express an AMP or an AMP-insecticidal protein. For example, in some embodiments, a host cell can be transformed with a polynucleotide operable to encode an AMP (e.g., by using any of the vectors described herein). In some embodiments, that host cell can be yeast strain.

In some embodiments, a yeast strain can be produced by preparing a vector comprising a first expression cassette comprising a polynucleotide operable to express a AMP or complementary nucleotide sequence thereof.

In some embodiments, the present disclosure comprises, consists essentially of, or consists of, a yeast strain comprising: a first expression cassette comprising a polynucleotide operable to encode an AMP, said AMP comprising an amino acid sequence that is at least 90%, 95%, 96%, 97%, 98%, 99%, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or a complementary nucleotide sequence thereof.

In some embodiments, the present disclosure comprises, consists essentially of, or consists of, a yeast strain comprising: a first expression cassette comprising a polynucleotide operable to encode an AMP, said AMP comprising an amino acid sequence that is at least 90% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; or a complementary nucleotide sequence thereof.

In some embodiments, the present disclosure comprises, consists essentially of, or consists of, a yeast strain comprising: a first expression cassette comprising a polynucleotide operable to encode an AMP, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or a complementary nucleotide sequence thereof.

In some embodiments, the present disclosure comprises, consists essentially of, or consists of, a yeast strain comprising: a first expression cassette comprising a polynucleotide operable to encode an AMP, said AMP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; or a complementary nucleotide sequence thereof.

In some embodiments, the yeast strain comprises a polynucleotide which enables the synthesis of an AMP, wherein the AMP comprises, consists essentially of, or consists of, an amino sequence that is at least 90%, 95%, 96%, 97%, 98%, 99%, or 100% as the amino acid sequence set forth in any one of SEQ ID NOs: 6, 20, 24-26, 28-36, 38-42, 48, 54, 58, 60, 62-63, 69, 108, 116, 119, and 168-169, or a complementary nucleotide sequence thereof.

In some embodiments, the yeast strain comprises a polynucleotide which enables the synthesis of an AMP, wherein the AMP comprises, consists essentially of, or consists of, an amino sequence that is at least 90%, 95%, 96%, 97%, 98%, 99%, or 100% as the amino acid sequence set forth in any one of SEQ ID NOs: 20, 24-26, 35-36, 38, and 40, or a complementary nucleotide sequence thereof.

In some embodiments, the yeast strain is operable to encode an AMP that comprises, consists essentially of, or consists of, an amino sequence as set forth in any one of SEQ ID NOs: 25, 36, 38, and 40, or a complementary nucleotide sequence thereof.

In some embodiments, the yeast strain is selected from any species belonging to the genera *Saccharomyces, Pichia, Kluyveromyces, Hansenula, Yarrowia* or *Schizosaccharomyces*.

In some embodiments, the yeast cell is selected from the group consisting of *Kluyveromyces lactis, Kluyveromyces marxianus, Saccharomyces cerevisiae*, and *Pichia pastoris*.

In some embodiments, the yeast cell is *Kluyveromyces lactis* or *Kluyveromyces marxianus*.

In some embodiments, a yeast strain can be operable to express an AMP or AMP-insecticidal protein, wherein the AMP is a homopolymer or heteropolymer of two or more AMPs, wherein the amino acid sequence of each AMP is the same or different.

In some embodiments, a yeast strain can be operable to express an AMP or AMP-insecticidal protein, wherein the AMP is a fused protein comprising two or more AMPs separated by a cleavable or non-cleavable linker, and wherein the amino acid sequence of each AMP may be the same or different.

In some embodiments, the linker is a cleavable linker.

In some embodiments, the linker has an amino acid sequence as set forth in any one of SEQ ID NOs: 184-193.

In some embodiments, the linker is cleavable inside at least one of (i) the gut or hemolymph of an insect, and (ii) cleavable inside the gut of a mammal.

In some embodiments, a yeast strain can be operable to express an AMP or AMP-insecticidal protein, wherein the vector is a plasmid comprising an alpha-MF signal.

In some embodiments, a yeast strain can be operable to express an AMP or AMP-insecticidal protein, wherein the vector is transformed into a yeast strain.

In some embodiments, a yeast strain can be operable to express an AMP or AMP-insecticidal protein, wherein the yeast strain is selected from any species of the genera *Saccharomyces, Pichia, Kluyveromyces, Hansenula, Yarrowia* or *Schizosaccharomyces*.

In some embodiments, a yeast strain can be operable to express an AMP or AMP-insecticidal protein, wherein the yeast strain is selected from the group consisting of *Kluyveromyces lactis, Kluyveromyces marxianus, Saccharomyces cerevisiae*, and *Pichia pastoris*.

In some embodiments, a yeast strain can be operable to express an AMP or AMP-insecticidal protein, wherein the yeast strain is *Kluyveromyces lactis*.

In some embodiments, a yeast strain can be operable to express an AMP or AMP-insecticidal protein, wherein expression of the AMP provides a yield of at least: 70 mg/L, 80 mg/L, 90 mg/L, 100 mg/L, 110 mg/L, 120 mg/L, 130 mg/L, 140 mg/L, 150 mg/L, 160 mg/L, 170 mg/L, 180 mg/L, 190 mg/L 200 mg/L, 500 mg/L, 750 mg/L, 1,000 mg/L, 1,250 mg/L, 1,500 mg/L, 1,750 mg/L or at least 20,000 mg/L, or more, of AMP per liter of medium.

In some embodiments, a yeast strain can be operable to express an AMP or AMP-insecticidal protein, wherein expression of the AMP provides a yield of at least 100 mg/L of AMP per liter of medium.

In some embodiments, a yeast strain can be operable to express an AMP or AMP-insecticidal protein, wherein expression of the AMP in the medium results in the expression of a single AMP in the medium.

In some embodiments, a yeast strain can be operable to express an AMP or AMP-insecticidal protein, wherein expression of the AMP in the medium results in the expression of an AMP polymer comprising two or more AMP polypeptides in the medium.

In some embodiments, a yeast strain can be operable to express an AMP or AMP-insecticidal protein, wherein the vector comprises two or three expression cassettes, each expression cassette operable to encode the AMP of the first expression cassette.

In some embodiments, a yeast strain can be operable to express an AMP or AMP-insecticidal protein, wherein the vector comprises two or three expression cassettes, each expression cassette operable to encode the AMP of the first expression cassette, or an AMP of a different expression cassette.

In some embodiments, a yeast strain can be operable to express an AMP or AMP-insecticidal protein, wherein the expression cassette is operable to encode an AMP as set forth in any one of SEQ ID NOs: 6, 20, 24-26, 28-36, 38-42, 48, 54, 58, 60, 62-63, 69, 108, 116, 119, and 168-169.

In some embodiments, a yeast strain can be operable to express an AMP or AMP-insecticidal protein, wherein the expression cassette is operable to encode an AMP as set forth in any one of SEQ ID NOs: 20, 24-26, 35-36, 38, and 40.

In some embodiments, a yeast strain can be operable to express an AMP or AMP-insecticidal protein, wherein the expression cassette is operable to encode an AMP as set forth in any one of SEQ ID NOs: 25, 36, 38, and 40.

Any of the aforementioned methods, and/or any of the methods described herein, can be used to produce one or more of the AMPs or AMP-insecticidal proteins as described herein. For example, any of the methods described herein can be used to produce one or more of the AMPs described in the present disclosure, e.g., AMPs having the amino acid sequence of SEQ ID NOs: 6, 20, 24-26, 28-36, 38-42, 48, 54, 58, 60, 62-63, 69, 108, 116, 119, and 168-169, which are likewise described herein.

Yeast Transformation, AMP Purification, and Analysis

An exemplary method of yeast transformation is as follows: first, expression vectors carrying an AMP ORF are transformed into yeast cells; the expression vectors are usually linearized by specific restriction enzyme cleavage to facilitate chromosomal integration via homologous recombination. The linear expression vector is then transformed into yeast cells by a chemical or electroporation method of transformation and integrated into the targeted locus of the yeast genome by homologous recombination. The integration can happen at the same chromosomal locus multiple times; therefore, the genome of a transformed yeast cell can contain multiple copies of AMP expression cassettes. The successfully transformed yeast cells can be identified using growth conditions that favor a selection marker engineered into the expression vector and co-integrated into yeast chromosomes with the AMP ORF; examples of such markers include, but are not limited to, acetamide prototrophy, zeocin resistance, geneticin resistance, nourseothricin resistance, and uracil prototrophy.

Selection makers are well known in the art, and any of these well-known selection markers can be implemented in the present disclosure. For example, in some embodiments, a selection marker can be a positive selection marker, or negative selection marker. Positive selection markers permit the selection for cells in which the gene product of the marker is expressed. This generally comprises contacting cells with an appropriate agent that, but for the expression of the positive selection marker, kills or otherwise selects against the cells. An exemplary method of using selection markers is disclosed in U.S. Pat. No. 5,464,764, the disclosure of which is incorporated herein by reference in its entirety. Additional exemplary descriptions and methods concerning selection markers are provided in Wigler et al., Cell 11:223 (1977); Szybalska & Szybalski, Proc. Natl. Acad. Sci. USA 48:202 (1992); Lowy et al., Cell 22:817 (1980); Wigler et al., Natl. Acad. Sci. USA 77:357 (1980); O'Hare et al., Proc. Natl. Acad. Sci. USA 78:1527 (1981); Mulligan & Berg, Proc. Natl. Acad. Sci. USA 78:2072 (1981); Wu and Wu, Biotherapy 3:87-95 (1991); Tolstoshev, Ann. Rev. Pharmacol. Toxicol. 32:573-596 (1993); Mulligan, Science 260:926-932 (1993); Morgan and Anderson, Ann. Rev. Biochem. 62:191-217 (1993); Santerre et al., Gene 30:147 (1984); Ausubel et al. (eds.), Current Protocols in Molecular Biology, John Wiley & Sons, N Y (1993); Kriegler, Gene Transfer and Expression, A Laboratory Manual, Stockton Press, N Y (1990); in Chapters 12 and 13, Dracopoli et al. (eds), Current Protocols in Human Genetics, John Wiley & Sons, N Y (1994); Colberre-Garapin et al., J. Mol. Biol. 150:1 (1981); U.S. Pat. No. 6,548,285 (filed Apr. 3, 1997); U.S. Pat. No. 6,165,715 (filed Jun. 22, 1998); and 6,110,707 (filed Jan. 17, 1997), the disclosures of which are incorporated by reference herein in their entireties.

Due to the influence of unpredictable and variable factors—such as epigenetic modification of genes and networks of genes, and variation in the number of integration events that occur in individual cells in a population undergoing a transformation procedure—individual yeast colonies of a given transformation process will differ in their capacities to produce an AMP ORF. Therefore, transgenic yeast colonies carrying the AMP transgenes should be screened for high yield strains. Two effective methods for such screening—each dependent on growth of small-scale cultures of the transgenic yeast to provide conditioned media samples for subsequent analysis—use reverse-phase HPLC or housefly injection procedures to analyze conditioned media samples from the positive transgenic yeast colonies.

The transgenic yeast cultures can be obtained, e.g., using 14 mL round bottom polypropylene culture tubes with 5 to 10 mL defined medium added to each tube, or in 48-well deep well culture plates with 2.2 mL defined medium added to each well. The defined medium, not containing crude proteinaceous extracts or by-products such as yeast extract or peptone, is used for the cultures to reduce the protein background in the conditioned media harvested for the later screening steps. The cultures are performed at the optimal temperature, for example, 23.5° C. for *K. lactis*, for about 5-6 days, until the maximum cell density is reached. AMPs will now be produced by the transformed yeast cells and secreted out of cells to the growth medium. To prepare samples for the screening, cells are removed from the cultures by centrifugation and the supernatants are collected as the conditioned media, which are then cleaned by filtration through 0.22 μm filter membrane and then made ready for strain screening.

In some embodiments, positive yeast colonies transformed with AMP can be screened via reverse-phase HPLC (rpHPLC) screening of putative yeast colonies. In this screening method, an HPLC analytic column with bonded phase of C18 can be used. Acetonitrile and water are used as mobile phase solvents, and a UV absorbance detector set at 220 nm is used for the peptide detection. Appropriate amounts of the conditioned medium samples are loaded into the rpHPLC system and eluted with a linear gradient of mobile phase solvents. The corresponding peak area of the insecticidal peptide in the HPLC chromatograph is used to quantify the AMP concentrations in the conditioned media. Known amounts of pure AMP are run through the same rpHPLC column with the same HPLC protocol to confirm the retention time of the peptide and to produce a standard peptide HPLC curve for the quantification.

An exemplary reverse-phase HPLC screening process of positive *K. lactis* cells is as follows: an AMP ORF can be inserted into the expression vector, pKLAC1, and transformed into the *K. lactis* strain, YCT306, from New England Biolabs, Ipswich, MA, USA. pKLAC1 vector is an integrative expression vector. Once the AMP transgenes were cloned into pKLAC1 and transformed into YCT306, their expression was controlled by the LAC4 promoter. The resulting transformed colonies produced pre-propeptides comprising an α-mating factor signal peptide, a Kex2 cleavage site and mature AMPs. The α-Mating factor signal peptide guides the pre-propeptides to enter the endogenous secretion pathway, and mature AMPs are released into the growth media.

In some embodiments, codon optimization for AMP expression can be performed in two rounds, for example, in the first round, based on some common features of high expression DNA sequences, multiple variants of the AMP ORF, expressing an α-Mating factor signal peptide, a Kex2 cleavage site and the AMP, are designed and their expression levels are evaluated in the YCT306 strain of *K. lactis*, resulting in an initial *K. lactis* expression algorithm; in a second round of optimization, additional variant AMP ORFs can be designed based on the initial *K. lactis* expression algorithm to further fine-tuned the *K. lactis* expression algorithm, and identify the best ORF for AMP expression in *K. lactis*. In some embodiments, the resulting DNA sequence from the foregoing optimization can have an open reading frame encoding an α-MF signal peptide, a Kex2 cleavage site and an AMP, which can be cloned into the pKLAC1 vector using Hind III and Not I restriction sites, resulting in AMP expression vectors.

In some embodiments, the yeast, *Pichia pastoris*, can be transformed with an AMP expression cassette. An exemplary method for transforming *P. pastoris* is as follows: yeast vectors can be used to transform an AMP expression cassette into *P. pastoris*. The vectors can be obtained from commercial vendors known to those having ordinary skill in the art. In some embodiments, the vectors can be integrative vectors, and may use the uracil phosphoribosyltransferase promoter (pUPP) to enhance the heterologous transgene expression. In some embodiments, the vectors may offer different selection strategies; e.g., in some embodiments, the only difference between the vectors can be that one vector may provide G418 resistance to the host yeast, while the other vector may provide Zeocin resistance. In some embodiments, pairs of complementary oligonucleotides, encoding the AMP may be designed and synthesized for subcloning into the two yeast expression vectors. Hybridization reactions can be performed by mixing the corresponding complementary oligonucleotides to a final concentration of 20 μM in 30 mM NaCl, 10 mM Tris-Cl (all final concentrations), pH 8, and then incubating at 95° C. for 20 min, followed by a 9-hour incubation starting at 92° C. and ending at 17° C., with 3° C. drops in temperature every 20 min. The hybridization reactions will result in DNA fragments encoding AMP. The two *P. pastoris* vectors can be digested with BsaI-HF restriction enzymes, and the double stranded DNA products of the reactions are then subcloned into the linearized *P. pastoris* vectors using standard procedures. Following verification of the sequences of the subclones, plasmid aliquots can be transfected by electroporation into a *P. pastoris* strain (e.g., Bg08). The resulting transformed yeast, can be selected based on resistance (e.g., in this example, to Zeocin or G418) conferred by elements engineered into the vectors.

Methods of protein purification are well-known in the art, and any known method can be employed to purify and/or recover AMPs of the present disclosure. For example, in some embodiments, the following procedures are exemplary of suitable purification procedures: fractionation on immunoaffinity or ion-exchange columns; ethanol precipitation; reverse phase HPLC; chromatography on silica, or on a cation-exchange resin such as DEAE; chromatofocusing; SDS-PAGE; ammonium sulfate precipitation; gel filtration using, for example, Sephadex G-75; and the like. In some embodiments, proteins of the present disclosure can be purified using one of the following; affinity chromatography; ion exchange chromatography; filtration; electrophoresis; hydrophobic interaction chromatography; gel filtration chromatography; reverse phase chromatography; concanavalin A chromatography; and differential solubilization.

Exemplary methods of protein purification are provided in: U.S. Pat. Nos. 6,339,142; 7,585,955; 8,946,395; 9,067,990; 10,246,484; and Marshak et al., "Strategies for Protein Purification and Characterization-A Laboratory Course Manual" CSHL Press (1996); the disclosures of which are incorporated herein by reference in their entireties.

Peptide Yield Screening and Evaluation

Peptide yield can be determined by any of the methods known to those of skill in the art (e.g., capillary gel electrophoresis (CGE), Western blot analysis, and the like). Activity assays, as described herein and known in the art, can also provide information regarding peptide yield. In some embodiments, these or any other methods known in the art can be used to evaluate peptide yield.

Quantification Assays

In some embodiments, and without limitation, AMP peptide yield can be measured using: HPLC; Mass spectrometry (MS) and related techniques; LC/MS/MS; reverse phase protein arrays (RPPA); immunohistochemistry; ELISA; suspension bead array, mass spectrometry; dot blot; SDS-PAGE; capillary gel electrophoresis (CGE); Western blot analysis; Bradford assay; measuring UV absorption at 260 nm; Lowry assay; Smith copper/bicinchoninic assay; a secretion assay; Pierce protein assay; Biuret reaction; and the like. Exemplary methods of protein quantification are provided in Stoscheck, C. 1990 "Quantification of Protein" *Methods in Enzymology,* 182:50-68; Lowry, O. Rosebrough, A., Farr, A. and Randall, R. 1951 *J. Biol. Chem.* 193:265; Smith, P. et al., (1985) Anal. Biochem. 150:76-85; Bradford, M. 1976 "A Rapid and Sensitive Method for the Quantitation of Microgram Quantities of Protein Utilizing the Principle of Protein-Dye Binding" Anal. Biochem. 72:248-254; Cabib, E. and Polacheck, I. 1984 "Protein assay for dilute solutions." Methods in Enzymology, 104:318-328; Turcanu, Victor; Williams, Neil A. (2001). "Cell identification and isolation on the basis of cytokine secretion: A novel tool for investigating immune responses." Nature Medicine. 7 (3): 373-376; U.S. Pat. No. 6,391,649; the disclosures of which are incorporated herein by reference in their entireties.

In other embodiments, AMP peptide yield can be quantified and/or assessed using methods that include, without limitation: recombinant protein mass per volume of culture (e.g., gram or milligrams protein per liter culture); percent or fraction of recombinant protein insoluble precipitate obtained after cell lysis determined in (e.g., recombinant protein extracted supernatant in an amount/amount of protein in the insoluble components); percentage or fraction of active protein (e.g., an amount/analysis of the active protein for use in protein amount); total cell protein (tcp) percentage or fraction; and/or the amount of protein/cell and the dry biomass of a percentage or ratio.

In some embodiments, wherein yield is expressed in terms of culture volume, the culture cell density may be taken into account, particularly when yields between different cultures are being compared.

In some embodiments, the present disclosure provides a method of producing a heterologous polypeptide that is at least about 5%, at least about 10%, about 15%, about 20%, about 25%, about 30%, about 40%, about 45%, about 50%, about 55%, about 60%, about 65%, about 70%, about 75%, or greater of total cell protein (tcp). "Percent total cell protein" is the amount of heterologous polypeptide in the host cell as a percentage of aggregate cellular protein. The determination of the percent total cell protein is well known in the art.

"Total cell protein (tcp)" or "Percent total cell protein (% tcp)" is the amount of protein or polypeptide in the host cell as a percentage of aggregate cellular protein. Methods for the determination of the percent total cell protein are well known in the art.

In some embodiments, HPLC can be used to quantify peptide yield. For example, in some embodiments, peptide yield can be quantified using an Agilent 1100 HPLC system equipped with an Onyx monolithic 4.5×100 mm, C18 reverse-phase analytical HPLC column and an auto-injector. An illustrative use of the Agilent 1100 HPLC system equipped with an Onyx monolithic 4.5×100 mm, C18 reverse-phase analytical HPLC column and an auto-injector is as follows: filtered conditioned media samples from transformed *K. lactis* cells are analyzed using Agilent 1100 HPLC system equipped with an Onyx monolithic 4.5×100 mm, C18 reverse-phase analytical HPLC column and an auto-injector by analyzing HPLC grade water and acetonitrile containing 0.1% trifluoroacetic acid, constituting the two mobile phase solvents used for the HPLC analyses; the peak areas of both the AMP or AMP-insecticidal protein are analyzed using HPLC chromatographs, and then used to calculate the peptide concentration in the conditioned media, which can be further normalized to the corresponding final cell densities (as determined by OD600 measurements) as normalized peptide yield.

Activity Assays

In some embodiments, positive yeast colonies transformed with AMP or AMP-insecticidal protein can be screened using a housefly injection assay. AMP or AMP-insecticidal protein can paralyze/kill houseflies when injected in measured doses through the body wall of the dorsal thorax. The efficacy of the AMP or AMP-insecticidal protein can be defined by the median paralysis/lethal dose of the peptide ($PD_{50}/LD_{50}$), which causes 50% knock-down ratio or mortality of the injected houseflies respectively. The pure AMP or AMP-insecticidal protein is normally used in the housefly injection assay to generate a standard dose-response curve, from which a $PD_{50}/LD_{50}$ value can be determined. Using a $PD_{50}/LD_{50}$ value from the analysis of a standard dose-response curve of the pure AMP or AMP-insecticidal protein, quantification of the AMP or AMP-insecticidal protein produced by the transformed yeast can be achieved using a housefly injection assay performed with serial dilutions of the corresponding conditioned media.

An exemplary housefly injection bioassay is as follows: conditioned media is serially diluted to generate full dose-response curves from the housefly injection bioassay. Before injection, adult houseflies (*Musca domestica*) are immobilized with $CO_2$, and 12-18 mg houseflies are selected for injection. A microapplicator, loaded with a 1 cc syringe and 30-gauge needle, is used to inject 0.5 μL per fly, doses of serially diluted conditioned media samples into houseflies through the body wall of the dorsal thorax. The injected houseflies are placed into closed containers with moist filter paper and breathing holes on the lids, and they are examined by knock-down ratio or by mortality scoring at 24 hours post-injection. Normalized yields are calculated. Peptide yield means the peptide concentration in the conditioned media in units of mg/L. However, peptide yields are not always sufficient to accurately compare the strain production rate. Individual strains may have different growth rates, hence when a culture is harvested, different cultures may vary in cell density. A culture with a high cell density may produce a higher concentration of the peptide in the media, even though the peptide production rate of the strain is lower than another strain which has a higher production rate. Accordingly, the term "normalized yield" is created by dividing the peptide yield with the cell density in the corresponding culture and this allows a better comparison of the peptide production rate between strains. The cell density is represented by the light absorbance at 600 nm with a unit of "A" (Absorbance unit).

Screening yeast colonies that have undergone a transformation with a polynucleotide operable to encode an AMP or AMP-insecticidal protein can identify the high yield yeast strains from hundreds of potential colonies. These strains can be fermented in bioreactor to achieve at least up to 4 g/L or at least up to 3 g/L or at least up to 2 g/L yield of the AMP or AMP-insecticidal protein when using optimized fermentation media and fermentation conditions described herein. The higher rates of production (expressed in mg/L) can be anywhere from about 100 mg/L to about 100,000 mg/L; or from about 100 mg/L to about 90,000 mg/L; or from about 100 mg/L to about 80,000 mg/L; or from about 100 mg/L to about 70,000 mg/L; or from about 100 mg/L to about 60,000 mg/L; or from about 100 mg/L to about 50,000 mg/L; or from about 100 mg/L to about 40,000 mg/L; or from about 100 mg/L to about 30,000 mg/L; or from about 100 mg/L to about 20,000 mg/L; or from about 100 mg/L to about 17,500 mg/L; or from about 100 mg/L to about 15,000 mg/L; or from about 100 mg/L to about 12,500 mg/L; or from about 100 mg/L to about 10,000 mg/L; or from about 100 mg/L to about 9,000 mg/L; or from about 100 mg/L to about 8,000 mg/L; or from about 100 mg/L to about 7,000 mg/L; or from about 100 mg/L to about 6,000 mg/L; or from about 100 mg/L to about 5,000 mg/L; or from about 100 mg/L to about 3,000 mg/L; or from about 100 mg/L to 2,000 mg/L; or from about 100 mg/L to 1,500 mg/L; or from about 100 mg/L to 1,000 mg/L; or from about 100 mg/L to 750 mg/L; or from about 100 mg/L to 500 mg/L; or from about 150 mg/L to 100,000 mg/L; or from about 200 mg/L to 100,000 mg/L; or from about 300 mg/L to 100,000 mg/L; or from about 400 mg/L to 100,000 mg/L; or from about 500 mg/L to 100,000 mg/L; or from about 750 mg/L to 100,000 mg/L; or from about 1,000 mg/L to 100,000 mg/L; or from about 1,250 mg/L to 100,000 mg/L; or from about 1,500 mg/L to 100,000 mg/L; or from about 2,000 mg/L to 100,000 mg/L; or from about 2,500 mg/L to 100,000 mg/L; or from about 3,000 mg/L to 100,000 mg/L; or from about 3,500 mg/L to 100,000 mg/L; or from about 4,000 mg/L to 100,000 mg/L; or from about 4,500 mg/L to 100,000 mg/L; or from about 5,000 mg/L to 100,000 mg/L; or from about 6,000 mg/L to 100,000 mg/L; or from about 7,000 mg/L to 100,000 mg/L; or from about 8,000 mg/L to 100,000 mg/L; or from about 9,000 mg/L to 100,000 mg/L; or from about 10,000 mg/L to 100,000 mg/L; or from about 12,500 mg/L to 100,000 mg/L; or from about 15,000 mg/L to 100,000 mg/L; or from about 17,500 mg/L to 100,000 mg/L; or from about 20,000 mg/L to 100,000 mg/L; or from about 30,000 mg/L to 100,000 mg/L; or from about 40,000 mg/L to 100,000 mg/L; or from about 50,000 mg/L to 100,000 mg/L; or from about 60,000 mg/L to 100,000 mg/L; or from about 70,000 mg/L to 100,000 mg/L; or from about 80,000 mg/L to 100,000 mg/L; or from about 90,000 mg/L to 100,000 mg/L; or any range of any value provided or even greater yields than can be achieved with a peptide before conversion, using the same or similar production methods that were used to produce the peptide before conversion.

Culture and Fermentation Conditions

Cell culture techniques are well-known in the art. In some embodiments, the culture method and/or materials will necessarily require adaption based on the host cell selected; and, such adaptions (e.g., modifying pH, temperature, medium contents, and the like) are well known to those having ordinary skill in the art. In some embodiments, any known culture technique may be employed to produce an AMP or AMP-insecticidal protein of the present disclosure.

Exemplary culture methods are provided in U.S. Pat. Nos. 3,933,590; 3,946,780; 4,988,623; 5,153,131; 5,153,133; 5,155,034; 5,316,905; 5,330,908; 6,159,724; 7,419,801; 9,320,816; 9,714,408; and 10,563,169; the disclosures of which are incorporated herein by reference in their entireties.

Yeast Culture

Yeast cell culture techniques are well known to those having ordinary skill in the art. Exemplary methods of yeast cell culture can be found in Evans, Yeast Protocols. Springer (1996); Bill, Recombinant Protein Production in Yeast. Springer (2012); Hagan et al., Fission Yeast: A Laboratory Manual, CSH Press (2016); Konishi et al., Improvement of the transformation efficiency of *Saccharomyces cerevisiae* by altering carbon sources in pre-culture. Biosci Biotechnol Biochem. 2014; 78(6):1090-3; Dymond, *Saccharomyces cerevisiae* growth media. Methods Enzymol. 2013; 533:191-204; Looke et al., Extraction of genomic DNA from yeasts for PCR-based applications. Biotechniques. 2011 May; 50(5):325-8; and Romanos et al., Culture of yeast for the production of heterologous proteins. Curr Protoc Cell Biol. 2014 Sep. 2; 64:20.9.1-16, the disclosure of which is incorporated herein by reference in its entirety.

Yeast can be cultured in a variety of media, e.g., in some embodiments, yeast can be cultured in minimal medium; YPD medium; yeast synthetic drop-out medium; Yeast Nitrogen Base (YNB with or without amino acids); YEPD medium; ADE D medium; ADE DS" medium; LEU D medium; HIS D medium; or Mineral salts medium.

In some embodiments, yeast can be cultured in minimal medium. In some embodiments, minimal medium ingredients can comprise: 2% Sugar; Phosphate Buffer, pH 6.0; Magnesium Sulfate; Calcium Chloride; Ammonium Sulfate; Sodium Chloride; Potassium Chloride; Copper Sulfate; Manganese Sulfate; Zinc Chloride; Potassium Iodide; Cobalt Chloride; Sodium Molybdate; Boric Acid; Iron Chloride; Biotin; Calcium pantothenate; Thiamine; Myo-inositol; Nicotinic Acid; and Pyridoxine.

In some embodiments, yeast can be cultured in YPD medium. YPD medium comprises a bacteriological peptone, yeast extract, and glucose.

In some embodiments, yeast can be cultured in yeast synthetic drop-out medium, which can be used to differentiate auxotrophic mutant strains that cannot grow without a specific medium component transformed with a plasmid that allows said transformant to grow on a medium lacking the required component.

In some embodiments, yeast can be cultured using Yeast Nitrogen Base (YNB with or without amino acids), which comprises nitrogen, vitamins, trace elements, and salts.

In some embodiments, the medium can be YEPD medium, e.g., a medium comprising 2% D-glucose, 2% BACTO Peptone (Difco Laboratories, Detroit, MI), 1% BACTO yeast extract (Difco), 0.004% adenine, and 0.006% L-leucine; or, a variation thereof, wherein the carbon source is a sugar alcohol, e.g., glycerol or sorbitol In some embodiments, the medium can be ADE D medium, e.g., a medium comprising 0.056%-Ade-Trp-Thr powder, 0.67% yeast nitrogen base without amino acids, 2% D-glucose, and 0.5% 200×tryptophan, threonine solution; or, a variation thereof, wherein the carbon source is a sugar alcohol, e.g., glycerol or sorbitol In some embodiments, the medium can be ADE DS" medium, e.g., a medium comprising 0.056%-Ade-Trp-Thr powder, 0.67% yeast nitrogen base without amino acids, 2% D-glucose, 0.5% 200×tryptophan, threonine solution, and 18.22% D-sorbitol; or, a variation thereof, wherein the carbon source is entirely a sugar alcohol, e.g., glycerol or sorbitol In some embodiments, the medium can be LEU D medium e.g., a medium comprising 0.052%-Leu-Trp-Thr powder, 0.67% yeast nitrogen base without amino acids, 2% D-glucose, and 0.5% 200×tryptophan, threonine solution; or, a variation thereof, wherein the carbon source is a sugar alcohol, e.g., glycerol or sorbitol.

In some embodiments, the medium can be HIS D medium, e.g., a medium comprising 0.052%-His-Trp-Thr powder, 0.67% yeast nitrogen base without amino acids, 2% D-glucose, and 0.5% 200×tryptophan, threonine solution; or, a variation thereof, wherein the carbon source is a sugar alcohol, e.g., glycerol or sorbitol.

In some embodiments, a mineral salts medium can be used. Mineral salts media consists of mineral salts and a carbon source such as, e.g., glucose, sucrose, or glycerol. Examples of mineral salts media include, e.g., M9 medium, *Pseudomonas* medium (ATCC 179), and Davis and Mingioli medium. See, Davis & Mingioli (1950) J. Bact. 60:17-28. The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source.

In comparison to mineral salts media, minimal media can also contain mineral salts and a carbon source, but can be supplemented with, e.g., low levels of amino acids, vitamins, peptones, or other ingredients, though these are added at very minimal levels. Media can be prepared using the methods described in the art, e.g., in U.S. Pat. App. Pub. No. 2006/0040352, the disclosure of which is incorporated herein by reference in its entirety. Details of cultivation procedures and mineral salts media useful in the methods of the present disclosure are described by Riesenberg, D et al., 1991, "High cell density cultivation of *Escherichia coli* at controlled specific growth rate," J. Biotechnol. 20 (1):17-27.

In some embodiments, *Kluyveromyces lactis* are grown in minimal media supplemented with 2% glucose, galactose, sorbitol, or glycerol as the sole carbon source. Cultures are incubated at 30° C. until mid-log phase (24-48 hours) for β-galactosidase measurements, or for 6 days at 23.5° C. for heterologous protein expression.

In some embodiments, yeast cells can be cultured in 48-well Deep-well plates, sealed after inoculation with sterile, air-permeable cover. Colonies of yeast, for example, *K. lactis* cultured on plates can be picked and inoculated the deep-well plates with 2.2 mL media per well, composed of DMS or. Inoculated deep-well plates can be grown for 6 days at 23.5° C. with 280 rpm shaking in a refrigerated incubator-shaker. On day 6 post-inoculation, conditioned media should be harvested by centrifugation at 4000 rpm for 10 minutes, followed by filtration using filter plate with 0.22 μM membrane, with filtered media are subject to HPLC analyses.

In some embodiments, yeast species such as *Kluyveromyces lactis, Saccharomyces cerevisiae, Pichia pastoris*, and others, can be used as a host organism, and/or the yeast to be modified using the methods described herein.

Temperature and pH conditions will vary depending on the stage of culture and the host cell species selected. Variables such as temperature and pH in cell culture are readily known to those having ordinary skill in the art.

The pH level is important in the culturing of yeast. One of skill in the art will appreciate that the culturing process includes not only the start of the yeast culture but the maintenance of the culture as well. The yeast culture may be started at any pH level, however, since the media of a yeast culture tends to become more acidic (i.e., lowering the pH) over time, care must be taken to monitor the pH level during the culturing process.

In some embodiments of the invention, the yeast is grown in a medium at a pH level that is dictated based on the species of yeast used, the stage of culture, and/or the temperature. Thus, in some embodiments, the pH level can fall within a range from about 2 to about 10. Those having ordinary skill in the art will recognize that the optimum pH for most microorganisms is near the neutral point (pH 7.0). However, in some embodiments, some fungal species prefer an acidic environment: accordingly, in some embodiments, the pH can range from 2 to 6.5. In some embodiments, the pH can range from about 4 to about 4.5. Some fungal species (e.g., molds) can grow can grow in a pH of from about 2 to about 8.5, but favor an acid pH. See Mountney & Gould, Practical food microbiology and technology. 1988. Ed. 3; and Pena et al., Effects of high medium pH on growth, metabolism and transport in *Saccharomyces cerevisiae*. FEMS Yeast Res. 2015 March;15(2):fou005.

In other embodiments, the pH is about 5.7 to 5.9, 5.8 to 6.0, 5.9 to 6.1, 6.0 to 6.2, 6.1 to 6.3, 6.2 to 6.5, 6.4 to 6.7, 6.5 to 6.8, 6.6 to 6.9, 6.7 to 7.0, 6.8 to 7.1, 6.9 to 7.2, 7.0 to 7.3, 7.1 to 7.4, 7.2 to 7.5, 7.3 to 7.6, 7.4 to 7.7, 7.5 to 7.8, 7.6 to 7.9, 7.7 to 8.0, 7.8 to 8.1, 7.9 to 8.2, 8.0 to 8.3, 8.1 to 8.4, 8.2 to 8.5, 8.3 to 8.6, 8.4 to 8.7, or 8.5 to 8.8.

In some embodiments, the pH of the medium can be at least 5.5. In other aspects, the medium can have a pH level of about 5.5. In other aspects, the medium can have a pH level of between 4 and 8. In some cases, the culture is maintained at a pH level of between 5.5 and 8. In other aspects, the medium has a pH level of between 6 and 8. In some cases, medium has a pH level that is maintained at a pH level of between 6 and 8. In some embodiments, the yeast is grown and/or maintained at a pH level of between 6.1 and 8.1. In some embodiments, the yeast is grown and/or maintained at a pH level of between 6.2 and 8.2. In some embodiments, the yeast is grown and/or maintained at a pH level of between 6.3 and 8.3. In some embodiments, the yeast is grown and/or maintained at a pH level of between 6.4 and 8.4. In some embodiments, the yeast is grown and/or maintained at a pH level of between 5.5 and 8.5. In some embodiments, the yeast is grown and/or maintained at a pH level of between 6.5 and 8.5. In some embodiments, the yeast is grown at a pH level of about 5.6, 5.7, 5.8 or 5.9. In some embodiments, the yeast is grown at a pH level of about 6. In some embodiments, the yeast is grown at a pH level of about 6.5. In some embodiments, the yeast is grown at a pH level of about 6, 6.1, 6.2, 6.3, 6.4, 6.5, 6.6, 6.7, 6.8, 6.9 or 7.0. In some embodiments, the yeast is grown at a pH level of about 7, 7.1, 7.2, 7.3, 7.4, 7.5, 7.6, 7.7, 7.8, 7.9, or 8.0. In some embodiments, the yeast is grown at a level of above 8.

In some embodiments, the pH of the medium can range from a pH of 2 to 8.5. In certain embodiments, the pH is about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8.

Exemplary methods of yeast culture can be found in U.S. Pat. No. 5,436,136, entitled "Repressible yeast promoters" (filed Dec. 20, 1991; assignee Ciba-Geigy Corporation); U.S. Pat. No. 6,645,739, entitled "Yeast expression systems, methods of producing polypeptides in yeast, and compositions relating to same" (filed Jul. 26, 2001; assignee Phoenix Pharmacologies, Inc., Lexington, KY); and U.S. Pat. No. 10,023,836, entitled "Medium for yeasts" (filed Aug. 23, 2013; assignee Yamaguchi University); the disclosures of which are incorporated herein by reference in their entirety.

Fermentation

The present disclosure contemplates the culture of host organisms in any fermentation format. For example, batch, fed-batch, semi-continuous, and continuous fermentation modes may be employed herein.

Fermentation may be performed at any scale. The methods and techniques contemplated according to the present disclosure are useful for recombinant protein expression at any scale. Thus, in some embodiments, e.g., microliter-scale, milliliter scale, centiliter scale, and deciliter scale fermentation volumes may be used, and 1 Liter scale and larger fermentation volumes can be used.

In some embodiments, the fermentation volume is at or above about 1 Liter. For example, in some embodiments, the fermentation volume is about 1 liter to about 100 liters. In some embodiments, the fermentation volume is about 1 liter, about 2 liters, about 3 liters, about 4 liters, about 5 liters, about 6 liters, about 7 liters, about 8 liters, about 9 liters, or about 10 liters. In some embodiments, the fermentation volume is about 1 liter to about 5 liters, about 1 liter to about 10 liters, about 1 liter to about 25 liters, about 1 liter to about 50 liters, about 1 liter to about 75 liters, about 10 liters to about 25 liters, about 25 liters to about 50 liters, or about 50 liters to about 100 liters In other embodiments, the fermentation volume is at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters, or 50,000 Liters.

In some embodiments, the fermentation medium can be a nutrient solution used for growing and or maintaining cells. Without limitation, this solution ordinarily provides at least one component from one or more of the following categories: (1) an energy source, usually in the form of a carbon source, e.g., glucose; (2) all essential amino acids, and usually the basic set of twenty amino acids; (3) vitamins and/or other organic compounds required at low concentrations; (4) free fatty acids or lipids, for example linoleic acid; and (5) trace elements, where trace elements are defined as inorganic compounds or naturally occurring elements that are typically required at very low concentrations, usually in the micromolar range.

In some embodiments, the fermentation medium can be the same as the cell culture medium or any other media described herein. In some embodiments, the fermentation medium can be different from the cell culture medium. In some embodiments, the fermentation medium can be modified in order to accommodate the large-scale production of proteins.

In some embodiments, the fermentation medium can be supplemented electively with one or more components from any of the following categories: (1) hormones and other growth factors such as, serum, insulin, transferrin, and the like; (2) salts, for example, magnesium, calcium, and phosphate; (3) buffers, such as HEPES; (4) nucleosides and bases such as, adenosine, thymidine, etc.; (5) protein and tissue hydrolysates, for example peptone or peptone mixtures which can be obtained from purified gelatin, plant material, or animal byproducts; (6) antibiotics, such as gentamycin; and (7) cell protective agents, for example pluronic polyol.

In some embodiments, the pH of the fermentation medium can be maintained using pH buffers and methods known to those of skill in the art. Control of pH during fermentation can also can be achieved using aqueous ammonia. In some embodiments, the pH of the fermentation medium will be selected based on the preferred pH of the organism used. Thus, in some embodiments, and depending on the host cell and temperature, the pH can range from about to 1 to about 10.

In some embodiments, the pH of the fermentation medium can range from a pH of 2 to 8.5. In certain embodiments, the pH is about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8.

In other embodiments, the pH is about 5.7 to 5.9, 5.8 to 6.0, 5.9 to 6.1, 6.0 to 6.2, 6.1 to 6.3, 6.2 to 6.5, 6.4 to 6.7, 6.5 to 6.8, 6.6 to 6.9, 6.7 to 7.0, 6.8 to 7.1, 6.9 to 7.2, 7.0 to 7.3, 7.1 to 7.4, 7.2 to 7.5, 7.3 to 7.6, 7.4 to 7.7, 7.5 to 7.8, 7.6 to 7.9, 7.7 to 8.0, 7.8 to 8.1, 7.9 to 8.2, 8.0 to 8.3, 8.1 to 8.4, 8.2 to 8.5, 8.3 to 8.6, 8.4 to 8.7, or 8.5 to 8.8

In some embodiments, e.g., where *Escherichia coli* (*E. coli*) is used, the optimal pH range is between 6.5 and 7.5, depending on the temperature.

In other embodiments, e.g., where a yeast strain is used, the pH can range from about 4.0 to 8.0.

In some embodiments, neutral pH, i.e., a pH of about 7.0 can be used.

Those having ordinary skill in the art will recognize that during fermentation, the pH levels may drift as result of conversion and production of substrates and metabolic compounds.

In some embodiments, the fermentation medium can be supplemented with a buffer or other chemical in order to avoid changes to the pH. For example, in some embodiments, the addition of $Ca(OH)_2$, $CaCO_3$, NaOH, or $NH_4OH$ can be added to the fermentation medium to neutralize the production of acidic compounds that occur, e.g., in some yeast species during industrial processes.

Temperature is another important consideration in the fermentation process; and, like pH considerations, temperature will depend on the type of host cell selected.

In some embodiments, the fermentation temperature is maintained at about 4° C. to about 42° C. In certain embodiments, the fermentation temperature is about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C.

In other embodiments, the fermentation temperature is maintained at about 25° C. to about 27° C., about 25° C. to about 28° C., about 25° C. to about 29° C., about 25° C. to about 30° C., about 25° C. to about 31° C., about 25° C. to about 32° C., about 25° C. to about 33° C., about 26° C. to about 28° C., about 26° C. to about 29° C., about 26° C. to about 30° C., about 26° C. to about 31° C., about 26° C. to about 32° C., about 27° C. to about 29° C., about 27° C. to about 30° C., about 27° C. to about 31° C., about 27° C. to about 32° C., about 26° C. to about 33° C., about 28° C. to about 30° C., about 28° C. to about 31° C., about 28° C. to about 32° C., about 29° C. to about 31° C., about 29° C. to about 32° C., about 29° C. to about 33° C., about 30° C. to about 32° C., about 30° C. to about 33° C., about 31° C. to about 33° C., about 31° C. to about 32° C., about 30° C. to about 33° C., or about 32° C. to about 33° C.

In other embodiments, the temperature is changed during fermentation, e.g., depending on the stage of fermentation.

Fermentation can be achieved with a variety of microorganisms known to those having ordinary skill in the art. Suitable microorganisms for up-scaled production of an AMP or AMP-insecticidal protein include any microorganism listed herein. In some embodiments, non-limiting examples of microorganisms include strains of the genus *Saccharomyces* spp. (including, but not limited to, *S. cerevisiae* (baker's yeast), *S. distaticus, S. uvarum*), the genus *Kluyveromyces*, (including, but not limited to, *K. marxianus, K. fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii*. Other suitable microorganisms include, for example, *Zymomonas mobilis, Clostridium* spp. (including, but not limited to, *C. thermocellum*; C. saccharobutylacetonicum, *C. saccharobutylicum*, C. *Puniceum*, C. beijernckii, and *C. acetobutylicum*), Moniliella pollinis, Moniliella megachiliensis, *Lactobacillus* spp. *Yarrowia lipolytica, Aureobasidium* sp., Trichosporonoides sp., Trigonopsis *variabilis, Trichosporon* sp., Moniliellaacetoabutans sp., Typhula *variabilis, Candida* magnolias, Ustilaginomycetes sp., Pseudozyma tsukubaensis, yeast species of genera *Zygosaccharomyces, Debaryomyces, Hansenula* and *Pichia*, and fungi of the dematioid genus Torula. See, e.g., Philippidis, G. P., 1996, Cellulose bioconversion technology, in Handbook on Bioethanol: Production and Utilization, Wyman, C. E., ed., Taylor & Francis, Washington, D.C., 179-212.

Fermentation medium may be selected depending on the host cell and/or needs of the end-user. Any necessary supplements besides, e.g., carbon, may also be included at appropriate concentrations introduced alone or as a mixture with another supplement or medium such as a complex nitrogen source.

Yeast Fermentation

Fermentation methods using yeast are well known to those having ordinary skill in the art. In some embodiments, batch fermentation can be used according to the methods provided herein; in other embodiments, continuous fermentation procedures can be used.

In some embodiments, the batch method of fermentation can be used to produce AMPs of the present disclosure. Briefly, the batch method of fermentation refers to a type of fermentation that is performed with a closed system, wherein the composition of the medium is determined at the beginning of the fermentation and is not subject to artificial alterations during the fermentation (i.e., the medium is inoculated with one or more yeast cells at the start of fermentation, and fermentation is allowed to proceed, uninterrupted by the user). Typically, in batch fermentation systems, the metabolite and biomass compositions of the system change constantly up to the time the fermentation is stopped. Within batch cultures, yeast cells pass through a static lag phase to a high growth log phase, and, finally, to a stationary phase, in which the growth rate is diminished or stopped. If untreated, yeast cells in the stationary phase will eventually die. In a batch method, yeast cells in log phase generally are responsible for the bulk of synthesis of end product.

In some embodiments, fed-batch fermentation can be used to produce AMPs of the present disclosure. Briefly, fed-batch fermentation is similar to typical batch method (described above), however, the substrate in the fed-batch method is added in increments as the fermentation progresses. Fed-batch fermentation is useful when catabolite repression may inhibit yeast cell metabolism, and when it is desirable to have limited amounts of substrate in the medium. Generally, the measurement of the substrate concentration in a fed-batch system is estimated on the basis of the changes of measurable factors reflecting metabolism, such as pH, dissolved oxygen, the partial pressure of waste gases (e.g., $CO_2$), and the like.

In some embodiments, the fed-batch fermentation procedure can be used to produce AMPs as follows: culturing a production organism (e.g., a modified yeast cell) in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial first and second carbon source concentration of 20 g/L. As the modified yeast cells grow and utilize the carbon sources, additional 70% carbon source mixture is then fed into the bioreactor at a rate approximately balancing carbon source consumption. The temperature of the bioreactor is generally maintained at 30° C. Growth continues for approximately 24 hours or more, and the heterologous peptides reach a desired concentration, e.g., with the cell density being between about 5 and 10 g/L. Upon completion of the cultivation period, the fermenter contents can be passed through a cell separation unit such as a centrifuge to remove cells and cell debris, and the fermentation broth can be transferred to a product separations unit. Isolation of the heterologous peptides can take place by standard separations procedures well known in the art.

In some embodiments, continuous fermentation can be used to produce AMPs of the present disclosure. Briefly, continuous fermentation refers to fermentation with an open system, wherein a fermentation medium is added continuously to a bioreactor, and an approximately equal amount of conditioned medium is removed simultaneously for processing. Continuous fermentation generally maintains the cultures at a high density, in which yeast cells are primarily in log phase growth. Typically, continuous fermentation methods are performed to maintain steady state growth conditions, and yeast cell loss, due to medium withdrawal, should be balanced against the cell growth rate in the fermentation.

In some embodiments, the continuous fermentation method can be used to produce AMPs as follows: a modified yeast strain can be cultured using a bioreactor apparatus and a medium composition, albeit where the initial first and second carbon source is about, e.g., 30-50 g/L. When the carbon source is exhausted, feed medium of the same composition is supplied continuously at a rate of between about 0.5 L/hr and 1 L/hr, and liquid is withdrawn at the same rate. The heterologous peptide concentration in the bioreactor generally remains constant along with the cell density. Temperature is generally maintained at 30° C., and the pH is generally maintained at about 4.5 using concentrated NaOH and HCl, as required.

In some embodiments, when producing AMPs, the bioreactor can be operated continuously, for example, for about one month, with samples taken every day or as needed to assure consistency of the target chemical compound concentration. In continuous mode, fermenter contents are constantly removed as new feed medium is supplied. The exit stream, containing cells, medium, and heterologous peptides, can then be subjected to a continuous product separations procedure, with or without removing cells and cell debris, and can be performed by continuous separations methods well known in the art to separate organic products from peptides of interest.

In some embodiments, a yeast cell operable to express an AMP or AMP-insecticidal protein can be grown, e.g., using a fed batch process in aerobic bioreactor. Briefly, reactors are filled to about 20% to about 70% capacity with medium comprising a carbon source and other reagents. Temperature and pH is maintained using one or more chemicals as described herein. Oxygen level is maintained by sparging air intermittently in concert with agitation.

For example, in some embodiments, the present disclosure provides a method of using a fed batch process in aerobic bioreactor, wherein the reactor is filled to about 20%; 21%; 22%; 23%; 24%; 25%; 26%; 27%; 28%; 29%; 30%; 31%; 32%; 33%; 34%; 35%; 36%; 37%; 38%; 39%; 40%; 41%; 42%; 43%; 44%; 45%; 46%; 47%; 48%; 49%; 50%; 51%; 52%; 53%; 54%; 55%; 56%; 57%; 58%; 59%; 60%; 61%; 62%; 63%; 64%; 65%; 66%; 67%; 68%; 69%; or 70% capacity.

In some embodiments, the present disclosure provides a fed batch fermentation method using an aerobic bioreactor to produce AMPs, wherein the medium is a rich culture medium. For example, in some embodiments, the carbon source can be glucose, sorbitol, or lactose.

In some embodiments, the amount of glucose can be about 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; or 30 g/L of the medium.

In some embodiments, the amount of sorbitol can be about 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; or 30 g/L of the medium.

In some embodiments, the amount of lactose can be about 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; or 30 g/L of the medium.

In some embodiments, the present disclosure provides a fed batch fermentation method using an aerobic bioreactor, wherein the medium is supplemented with one or more of phosphoric acid, calcium sulfate, potassium sulfate, magnesium sulfate heptahydrate, potassium hydroxide, and/or corn steep liquor.

In some embodiments, the medium can be supplemented with phosphoric acid in an amount of about 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; or 30 g/L to the medium.

In some embodiments, the medium can be supplemented with calcium sulfate in an amount of about 0.05 g/L; 0.15 g/L; 0.25 g/L; 0.35 g/L; 0.45 g/L; 0.55 g/L; 0.65 g/L; 0.75 g/L; 0.85 g/L; 0.95 g/L; 1.05 g/L; 1.15 g/L; 1.25 g/L; 1.35 g/L; 1.45 g/L; 1.55 g/L; 1.65 g/L; 1.75 g/L; 1.85 g/L; 1.95 g/L; 2.05 g/L; 2.15 g/L; 2.25 g/L; 2.35 g/L; 2.45 g/L; 2.55 g/L; 2.65 g/L; 2.75 g/L; 2.85 g/L; or 2.95 g/L to the medium.

In some embodiments, the medium can be supplemented with potassium sulfate in an amount of about 2 g/L; 2.5 g/L; 3 g/L; 3.5 g/L; 4 g/L; 4.5 g/L; 5 g/L; 5.5 g/L; 6 g/L; 6.5 g/L; 7 g/L; 7.5 g/L; 8 g/L; 8.5 g/L; 9 g/L; 9.5 g/L; 10 g/L; 10.5 g/L; 11 g/L; 11.5 g/L; 12 g/L; 12.5 g/L; 13 g/L; 13.5 g/L; 14 g/L; 14.5 g/L; 15 g/L; 15.5 g/L; 16 g/L; 16.5 g/L; 17 g/L; 17.5 g/L; 18 g/L; 18.5 g/L; 19 g/L; 19.5 g/L; or 20 g/L to the medium.

In some embodiments, the medium can be supplemented with magnesium sulfate heptahydrate in an amount of about 0.25 g/L; 0.5 g/L; 0.75 g/L; 1 g/L; 1.25 g/L; 1.5 g/L; 1.75 g/L; 2 g/L; 2.25 g/L; 2.5 g/L; 2.75 g/L; 3 g/L; 3.25 g/L; 3.5 g/L; 3.75 g/L; 4 g/L; 4.25 g/L; 4.5 g/L; 4.75 g/L; 5 g/L; 5.25 g/L; 5.5 g/L; 5.75 g/L; 6 g/L; 6.25 g/L; 6.5 g/L; 6.75 g/L; 7 g/L; 7.25 g/L; 7.5 g/L; 7.75 g/L; 8 g/L; 8.25 g/L; 8.5 g/L; 8.75 g/L; 9 g/L; 9.25 g/L; 9.5 g/L; 9.75 g/L; 10 g/L; 10.25 g/L; 10.5 g/L; 10.75 g/L; 11 g/L; 11.25 g/L; 11.5 g/L; 11.75 g/L; 12 g/L; 12.25 g/L; 12.5 g/L; 12.75 g/L; 13 g/L; 13.25 g/L; 13.5 g/L; 13.75 g/L; 14 g/L; 14.25 g/L; 14.5 g/L; 14.75 g/L; or 15 g/L to the medium.

In some embodiments, the medium can be supplemented with potassium hydroxide in an amount of about 0.25 g/L; 0.5 g/L; 0.75 g/L; 1 g/L; 1.25 g/L; 1.5 g/L; 1.75 g/L; 2 g/L; 2.25 g/L; 2.5 g/L; 2.75 g/L; 3 g/L; 3.25 g/L; 3.5 g/L; 3.75 g/L; 4 g/L; 4.25 g/L; 4.5 g/L; 4.75 g/L; 5 g/L; 5.25 g/L; 5.5 g/L; 5.75 g/L; 6 g/L; 6.25 g/L; 6.5 g/L; 6.75 g/L; or 7 g/L to the medium.

In some embodiments, the medium can be supplemented with corn steep liquor in an amount of about 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; 30 g/L; 31 g/L; 32 g/L; 33 g/L; 34 g/L; 35 g/L; 36 g/L; 37 g/L; 38 g/L; 39 g/L; 40 g/L; 41 g/L; 42 g/L; 43 g/L; 44 g/L; 45 g/L; 46 g/L; 47 g/L; 48 g/L; 49 g/L; 50 g/L; 51 g/L; 52 g/L; 53 g/L; 54 g/L; 55 g/L; 56 g/L; 57 g/L; 58 g/L; 59 g/L; 60 g/L; 61 g/L; 62 g/L; 63 g/L; 64 g/L; 65 g/L; 66 g/L; 67 g/L; 68 g/L; 69 g/L; or 70 g/L to the medium.

In some embodiments, the temperature of the reactor can be maintained between about 15° C. and about 45° C. In some embodiments, the reactor can have a temperature of about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C.

In some embodiments, the pH can have a level of about 3 to about 6. In some embodiments, the pH can be 3.0, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, or 6.0.

In some embodiments, the pH can be maintained at a constant level via the addition of one or more chemicals. For example, in some embodiments, ammonium hydroxide can be added to maintain pH. In some embodiments, ammonium hydroxide can be added to a level of ammonium hydroxide in the medium that is about 5%, 6%, 7%, 8%, 9%, 10%, 11%, 12%, 13%, 14%, 15%, 16%, 17%, 18%, 19%, or 20%, of ammonium hydroxide In some embodiments, oxygen levels can be maintained by sparging. For example, in some embodiments, dissolved oxygen can be maintained at a constant level by sparging air between 0.5-1.5 volume/volume/min and by increasing agitation to maintain a set point of 10-30%.

In some embodiments, inoculation of the reactor can be accomplished based on an overnight seed culture comprising from about 2.5 g/L to about 50 g/L of a carbon source, e.g., glucose, sorbitol, or lactose. In some embodiments, the overnight seed culture can comprise corn steep liquor, e.g., from about 2.5 g/L to about 50 g/L of corn steep liquor.

In some embodiments, the inoculation percentage can range from about 5-20% of initial fill volume. Following inoculation, the reactor can be fed with from about a 50% to about an 80% solution of the selected carbon source up until the reactor is filled and/or the desired supernatant peptide concentration is achieved. In some embodiments, the time required to fill the reactor can range from about 86 hours to about 160 hours. In some embodiments, the quantity required to reach the desired peptide concentration can range from about 0.8 g/L to about 1.2 g/L. Upon completion of the fermentation, the contents can be passed through a cell separation unit and optionally concentrated, depending on intended use of the material.

Additional recipes for yeast fermentation media are provided herein.

Recipes for yeast cell fermentation media and stocks are described as follows: (1) MSM media recipe: 2 g/L sodium citrate dihydrate; 1 g/L calcium sulfate dihydrate (0.79 g/L anhydrous calcium sulfate); 42.9 g/L potassium phosphate monobasic; 5.17 g/L ammonium sulfate; 14.33 g/L potassium sulfate; 11.7 g/L magnesium sulfate heptahydrate; 2 mL/L PTM1trace salt solution; 0.4 ppm biotin (from 500×, 200 ppm stock); 1-2% pure glycerol or other carbon source. (2) PTM1 trace salts solution: Cupric sulfate-5H2O 6.0 g; Sodium iodide 0.08 g; Manganese sulfate-H2O 3.0 g; Sodium molybdate-2H2O 0.2 g; Boric Acid 0.02 g; Cobalt chloride 0.5 g; Zinc chloride 20.0 g; Ferrous sulfate-7H2O 65.0 g; Biotin 0.2 g; Sulfuric Acid 5.0 ml; add Water to a final volume of 1 liter. An illustrative composition for *K. lactis* defined medium (DMSor) is as follows: 11.83 g/L $KH_2PO_4$, 2.299 g/L $K_2HPO_4$, 20 g/L of a fermentable sugar, e.g., galactose, maltose, latotriose, sucrose, fructose or glucose and/or a sugar alcohol, for example, erythritol, hydrogenated starch hydrolysates, isomalt, lactitol, maltitol, mannitol, and xylitol, 1 g/L $MgSO_4 \cdot 7H_2O$, 10 g/L $(NH_4)SO_4$, 0.33 g/L $CaCl_2 \cdot 2H_2O$, 1 g/L NaCl, 1 g/L KCl, 5 mg/L $CuSO_4 \cdot 5H_2O$, 30 mg/L $MnSO_4 \cdot H_2O$, 10 mg/L, $ZnCl_2$, 1 mg/L KI, 2 mg/L $CoCl_2 \cdot 6H_2O$, 8 mg/L $Na_2MoO_4 \cdot 2H_2O$, 0.4 mg/L $H_3BO_3 \cdot 15$ mg/L $FeCl_3 \cdot 6H_2O$, 0.8 mg/L biotin, 20 mg/L Ca-pantothenate, 15 mg/L thiamine, 16 mg/L myoinositol, 10 mg/L nicotinic acid, and 4 mg/L pyridoxine.

Peptide Degradation

Proteins, polypeptides, and peptides degrade in both biological samples and in solution (e.g., cell culture and/or during fermentation).

Methods of detecting AMP peptide degradation are well known in the art. Any of the well-known methods of detecting peptide degradation (e.g., during fermentation) may be employed here.

In some embodiments, peptide degradation can be detected using isotope labeling techniques; liquid chromatography/mass spectrometry (LC/MS); HPLC; radioactive amino acid incorporation and subsequent detection, e.g., via scintillation counting; the use of a reporter protein, e.g., a protein that can be detected (e.g., by fluorescence, spectroscopy, luminometry, etc.); fluorescent intensity of one or more bioluminescent proteins and/or fluorescent proteins and/or fusions thereof, pulse-chase analysis (e.g., pulse-labeling a cell with radioactive amino acids and following the decay of the labeled protein while chasing with unlabeled precursor, and arresting protein synthesis and measuring the decay of total protein levels with time); cycloheximide-chase assays;

In some embodiments, an assay can be used to detect peptide degradation, wherein a sample is contacted with a non-fluorescent compound that is operable to react with free primary amine in said sample produced via the degradation of a peptide, and which then produces a fluorescent signal that can be quantified and compared to a standard. Examples of non-fluorescent compounds that can be utilized as fluorescent tags for free amines according to the present disclosure are 3-(4-carboxybenzoyl) quinoline-2-carboxaldehyde (CBQCA), fluorescamine, and o-phthaldialdehyde.

In some embodiments, the method to determine the readout signal from the reporter protein depends from the nature of the reporter protein. For example, for fluorescent reporter proteins, the readout signal corresponds to the intensity of the fluorescent signal. The readout signal may be measured using spectroscopy-, fluorometry-, photometry-, and/or luminometry-based methods and detection systems, for example. Such methods and detection systems are well known in the art.

In some embodiments, standard immunological procedures known to those having ordinary skill in the art can be used to detect peptide degradation. For example, in some embodiments, peptide degradation can be detected in a sample using immunoassays that employ a detectable antibody. Such immunoassays include, for example, agglutination assays, ELISA, Pandex microfluorimetric assay, flow cytometry, serum diagnostic assays, and immunohistochemical staining procedures, all of which are well-known in the art. In some embodiments, the levels (e.g., of fluorescence) in one sample can be compared to a standard. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Exemplary methods of detecting peptide degradation is provided in U.S. Pat. Nos. 5,766,927; 7,504,253; 9,201,073; 9,429,566; United States Patent Application 20120028286; Eldeeb et al., A molecular toolbox for studying protein degradation in mammalian cells. J Neurochem. 2019 November; 151(4):520-533; and Buchanan et al., Cycloheximide Chase Analysis of Protein Degradation in *Saccharomyces cerevisiae*. J Vis Exp. 2016; (110): 53975, the disclosures of which are incorporated herein by reference in their entireties.

Agriculturally Acceptable Salts

As used herein, the term "pharmaceutically acceptable salt" and "agriculturally acceptable salt" are synonymous.

In some embodiments, agriculturally acceptable salts, hydrates, solvates, crystal forms and individual isomers, enantiomers, tautomers, diastereomers and prodrugs of the AMP described herein can be utilized.

In some embodiments, an agriculturally acceptable salt of the present disclosure possesses the desired pharmacological activity of the parent compound. Such salts include: acid addition salts, formed with inorganic acids; acid addition salts formed with organic acids; or salts formed when an acidic proton present in the parent compound is replaced by a metal ion, e.g., an alkali metal ion, aluminum ion; or coordinates with an organic base such as ethanolamine, and the like.

In some embodiments, agriculturally acceptable salts include conventional toxic or non-toxic salts. For example, in some embodiments, convention non-toxic salts include those such as fumarate, phosphate, citrate, chlorydrate, and the like. In some embodiments, the agriculturally acceptable salts of the present disclosure can be synthesized from a parent compound by conventional chemical methods. In some embodiments, such salts can be prepared by reacting the free acid or base forms of these compounds with a stoichiometric amount of the appropriate base or acid in water or in an organic solvent, or in a mixture of the two. In some embodiments, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is incorporated herein by reference in its entirety.

In some embodiments, an agriculturally acceptable salt can be one of the following: hydrochloride; sodium; sulfate; acetate; phosphate or diphosphate; chloride; potassium; maleate; calcium; citrate; mesylate; nitrate; tartrate; aluminum; or gluconate.

In some embodiments, a list of agriculturally acceptable acids that can be used to form salts can be: glycolic acid; hippuric acid; hydrobromic acid; hydrochloric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; nitric acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); undecylenic acid; a 1-hydroxy-2-naphthoic acid; 2,2-dichloroacetic acid; 2-hydroxyethanesulfonic acid; 2-oxo-glutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; or glycerophosphoric acid.

In some embodiments, agriculturally acceptable salt can be any organic or inorganic addition salt.

In some embodiments, the salt may use an inorganic acid and an organic acid as a free acid. The inorganic acid may be hydrochloric acid, bromic acid, nitric acid, sulfuric acid, perchloric acid, phosphoric acid, etc. The organic acid may be citric acid, acetic acid, lactic acid, maleic acid, fumaric acid, gluconic acid, methane sulfonic acid, gluconic acid, succinic acid, tartaric acid, galacturonic acid, embonic acid, glutamic acid, aspartic acid, oxalic acid, (D) or (L) malic acid, maleic acid, methane sulfonic acid, ethane sulfonic acid, 4-toluene sulfonic acid, salicylic acid, citric acid, benzoic acid, malonic acid, etc.

In some embodiments, the salts include alkali metal salts (sodium salts, potassium salts, etc.) and alkaline earth metal salts (calcium salts, magnesium salts, etc.). For example, the acid addition salt may include acetate, aspartate, benzoate, besylate, bicarbonate/carbonate, bisulfate/sulfate, borate, camsylate, citrate, edisilate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthalate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, zinc salt, etc., and among them, hydrochloride or trifluoroacetate may be used.

In yet other embodiments, the agriculturally acceptable salt can be a salt with an acid such as acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, p-toluenesulfonic acid, laurylsulfuric acid, malic acid, aspartic acid, glutaminic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, polyacrylate or carboxyvinyl polymer.

In some embodiments, the agriculturally acceptable salt can be prepared from either inorganic or organic bases. Salts derived from inorganic bases include, but are not limited to, the sodium, potassium, lithium, ammonium, calcium, magnesium, ferrous, zinc, copper, manganous, aluminum, ferric, manganic salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline.

In some embodiments, agriculturally acceptable salt refers to those salts which are, within the scope of sound medical judgment, suitable for use in contact with the tissues of humans and lower animals without undue toxicity, irritation, allergic response and the like, and are commensurate with a reasonable benefit/risk ratio. Agriculturally acceptable salts are well known in the art. For example, S. M. Berge, et al. describe agriculturally acceptable salts in detail in J. Pharmaceutical Sciences, 66: 1-19 (1977), the disclosure of which is incorporated herein by reference in its entirety.

In some embodiments, the salts of the present disclosure can be prepared in situ during the final isolation and purification of the compounds of the invention, or separately by reacting the free base function with a suitable organic acid. Examples of agriculturally acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other agriculturally acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further agriculturally acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Exemplary descriptions of pharmaceutically acceptable salts is provided in P. H. Stahl and C. G. Wermuth, (editors), *Handbook of Pharmaceutical Salts: Properties, Selection and Use*, John Wiley & Sons, Aug. 23, (2002), the disclosure of which is incorporated herein by reference in its entirety.

AMP Incorporation into Plants or Parts Thereof

The AMPs described herein, and/or an insecticidal protein comprising at least one AMP as described herein, can be incorporated into plants, plant tissues, plant cells, plant seeds, and/or plant parts thereof, for either the stable, or transient expression of an AMP or an AMP-insecticidal protein, and/or a polynucleotide sequence encoding the same.

In some embodiments, the AMP or AMP-insecticidal protein can be incorporated into a plant using recombinant techniques known in the art. In some embodiments, the AMP or AMP-insecticidal protein may be in the form of an insecticidal protein which may comprise one or more AMP monomers.

As used herein, with respect to transgenic plants, plant tissues, plant cells, and plant seeds, the term "AMP" also encompasses an AMP-insecticidal protein, and a "AMP polynucleotide" is similarly also used to encompass a polynucleotide or group of polynucleotides operable to express and/or encode an insecticidal protein comprising one or more AMPs.

The goal of incorporating an AMP into plants is to deliver AMPs and/or AMP-insecticidal proteins to the pest via the insect's consumption of the transgenic AMP expressed in a plant tissue consumed by the insect. Upon the consumption of the AMP by the insect from its food (e.g., via an insect feeding upon a transgenic plant transformed with an AMP), the consumed AMP may have the ability to inhibit the growth, impair the movement, or even kill an insect. Accordingly, transgenic plants expressing an AMP polynucleotide and/or an AMP polypeptide may express said AMP polynucleotide/polypeptide in a variety of plant tissues, including but not limited to: the epidermis (e.g., mesophyll); periderm; phloem; xylem; parenchyma; collenchyma; sclerenchyma; and primary and secondary meristematic tissues. For example, in some embodiments, a polynucleotide sequence encoding an AMP can be operably linked to a regulatory region containing a phosphoenolpyruvate carboxylase promoter, resulting in the expression of an AMP in a plant's mesophyll tissue.

Transgenic plants expressing an AMP and/or a polynucleotide operable to express AMP can be generated by any one of the various methods and protocols well known to those having ordinary skill in the art; such methods of the invention do not require that a particular method for introducing a nucleotide construct to a plant be used, only that the nucleotide construct gains access to the interior of at least one cell of the plant. Methods for introducing nucleotide constructs into plants are known in the art including, but not limited to, stable transformation methods, transient transformation methods, and virus-mediated methods. "Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. Typically, a construct that expresses an exogenous or heterologous peptide or polypeptide of interest (e.g., an AMP), would contain a promoter to drive transcription of the gene, as well as a 3' untranslated region to allow transcription termination and polyadenylation. The design and organization of such constructs is well known in the art. In some embodiments, a gene can be engineered such that the resulting peptide is secreted, or otherwise targeted within the plant cell to a specific region and/or organelle. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically, a plant expression cassette can be inserted into a plant transformation vector. This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the AMP are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) Trends in Plant Science 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) The Plant Journal 6:271-282; Ishida et al. (1996) Nature Biotechnology 14:745-750). Explants are typically transferred to a fresh supply of the same medium and cultured routinely. A general description of the techniques and methods for generating transgenic plants are found in Ayres and Park (1994) Critical Reviews in Plant Science 13:219-239 and Bommineni and Jauhar (1997) Maydica 42:107-120. Because the transformed material contains many cells, both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation, Lec transformation, and various other non-particle direct-mediated methods to transfer DNA. Exemplary transformation protocols are disclosed in U.S. Published Application No. 20010026941; U.S. Pat. No. 4,945,050; International Publication No. WO 91/00915; and U.S. Published Application No. 2002015066, the disclosures of which are incorporated herein by reference in their entireties.

Chloroplasts can also be readily transformed, and methods concerning the transformation of chloroplasts are known in the art. See, for example, Svab et al. (1990) Proc. Natl. Acad. Sci. USA 87:8526-8530; Svab and Maliga (1993) Proc. Natl. Acad. Sci. USA 90:913-917; Svab and Maliga (1993) EMBO J. 12:601-606, the disclosure of which is incorporated herein by reference in its entirety. The method of chloroplast transformation relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

Following integration of heterologous foreign DNA into plant cells, one having ordinary skill may then apply a maximum threshold level of appropriate selection chemical/reagent (e.g., an antibiotic) in the medium to kill the untransformed cells, and separate and grow the putatively transformed cells that survive from this selection treatment by transferring said surviving cells regularly to a fresh medium. By continuous passage and challenge with appropriate selection, an artisan identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional methods known to those having ordinary skill in the art. See, for example, McCormick et al. (1986) Plant Cell Reports 5:81-84, the disclosure of which is incorporated herein by reference in its entirety. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a nucleotide construct of the invention, for example, an expression cassette of the invention, stably incorporated into their genome.

In various embodiments, the present disclosure provides an AMP-insecticidal protein, that act as substrates for insect proteinases, proteases and peptidases (collectively referred to herein as "proteases") as described above.

In some embodiments, transgenic plants or parts thereof, that may be receptive to the expression of AMPs can include: alfalfa, banana, barley, bean, broccoli, cabbage, canola, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and a wheat plant.

In some embodiments the transgenic plant may be grown from cells that were initially transformed with the DNA constructs described herein. In other embodiments, the transgenic plant may express the encoded AMP in a specific tissue, or plant part, for example, a leaf, a stem a flower, a sepal, a fruit, a root, a seed, or combinations thereof.

In some embodiments, the plant, plant tissue, plant cell, plant seed, or part thereof, can be transformed with an AMP or a polynucleotide encoding the same, wherein the AMP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or a complementary nucleotide sequence thereof.

In some embodiments, the plant, plant tissue, plant cell, plant seed, or part thereof, can be transformed with an AMP or a polynucleotide encoding the same, wherein the AMP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; or a complementary nucleotide sequence thereof.

In some embodiments, the present disclosure comprises, consists essentially of, or consists of, a plant, plant tissue, plant cell, plant seed, or part thereof, comprising, consisting essentially of, or consisting of, one or more AMPs, or a polynucleotide encoding the same, said AMP comprising an amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-X-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent.

In some embodiments, the present disclosure comprises, consists essentially of, or consists of, a plant, plant tissue, plant cell, plant seed, or part thereof, comprising, consisting essentially of, or consisting of, one or more AMPs, or a polynucleotide encoding the same, said AMP comprising an amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent.

In some embodiments, the plant, plant tissue, plant cell, or plant seed can be transformed with an AMP that comprises, consists essentially of, or consists of, an amino sequence as set forth in any one of SEQ ID NOs: 6, 20, 24-26, 28-36, 38-42, 48, 54, 58, 60, 62-63, 69, 108, 116, 119, and 168-169.

In some embodiments, the plant, plant tissue, plant cell, or plant seed can be transformed with an AMP that comprises, consists essentially of, or consists of, an amino sequence as set forth in any one of SEQ ID NOs: 20, 24-26, 35-36, 38, and 40.

In some embodiments, the plant, plant tissue, plant cell, or plant seed can be transformed with an AMP that comprises, consists essentially of, or consists of, an amino sequence as set forth in any one of SEQ ID NOs: 25, 36, 38, and 40.

In some embodiments, the plant, plant tissue, plant cell, plant seed, or part thereof, can be transformed with an AMP or a polynucleotide encoding the same, wherein the AMP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQDCYPDGCDGPK" (SEQ ID NO: 20).

In some embodiments, the plant, plant tissue, plant cell, plant seed, or part thereof, can be transformed with an AMP or a polynucleotide encoding the same, wherein the AMP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPNGCSGPK" (SEQ ID NO: 24).

In some embodiments, the plant, plant tissue, plant cell, plant seed, or part thereof, can be transformed with an AMP or a polynucleotide encoding the same, wherein the AMP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCDGPK" (SEQ ID NO: 25).

In some embodiments, the plant, plant tissue, plant cell, plant seed, or part thereof, can be transformed with an AMP or a polynucleotide encoding the same, wherein the AMP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWPGCPWGQNCYPEGCSGPK" (SEQ ID NO: 26).

In some embodiments, the plant, plant tissue, plant cell, plant seed, or part thereof, can be transformed with an AMP or a polynucleotide encoding the same, wherein the AMP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWPGCPWGQNCYPEGCRGPD" (SEQ ID NO: 35).

In some embodiments, the plant, plant tissue, plant cell, plant seed, or part thereof, can be transformed with an AMP or a polynucleotide encoding the same, wherein the AMP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCSGPG" (SEQ ID NO: 36).

In some embodiments, the plant, plant tissue, plant cell, plant seed, or part thereof, can be transformed with an AMP or a polynucleotide encoding the same, wherein the AMP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCGGPG" (SEQ ID NO: 38).

In some embodiments, the plant, plant tissue, plant cell, plant seed, or part thereof, can be transformed with an AMP or a polynucleotide encoding the same, wherein the AMP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCSGPKVG" (SEQ ID NO: 40).

In some embodiments, the plant, plant tissue, plant cell, plant seed, or part thereof, can be transformed with an AMP or a polynucleotide encoding the same, wherein the polynucleotide is operable to encode a homopolymer or heteropolymer of two or more AMPs, wherein the amino acid sequence of each AMP is the same or different.

In some embodiments, the plant, plant tissue, plant cell, plant seed, or part thereof, can be transformed with an AMP or a polynucleotide encoding the same, wherein the polynucleotide is operable to encode an AMP that is a fused protein comprising two or more AMPs separated by a cleavable or non-cleavable linker, and wherein the amino acid sequence of each AMP may be the same or different.

In some embodiments, the linker is a cleavable linker.

In some embodiments, the linker has an amino acid sequence as set forth in any one of SEQ ID NOs: 184-193.

In some embodiments, the linker is cleavable inside at least one of (i) the gut or hemolymph of an insect, and (ii) cleavable inside the gut of a mammal.

In some embodiments, the plant, plant tissue, plant cell, or plant seed can be transformed with an AMP wherein the AMP has an amino acid sequence of any of the aforementioned AMPs (e.g., one or more the AMPs enumerated in Table 1 or Table 2), or a polynucleotide encoding the same.

In some embodiments, the plant, plant tissue, plant cell, or plant seed can be transformed with an AMP having an amino acid sequence selected from the group consisting of SEQ NOs: 6, 20, 24-26, 28-36, 38-42, 48, 54, 58, 60, 62-63, 69, 108, 116, 119, and 168-169, or a polynucleotide encoding the same.

In some embodiments, the plant, plant tissue, plant cell, or plant seed can be transformed with an AMP having an amino acid sequence selected from the group consisting of SEQ NOs: 20, 24-26, 35-36, 38, and 40, or a polynucleotide encoding the same.

In some embodiments, the plant, plant tissue, plant cell, or plant seed can be transformed with an AMP having an amino acid sequence selected from the group consisting of SEQ NOs: 25, 36, 38, and 40, or a polynucleotide encoding the same.

In some embodiments, the plant, plant tissue, plant cell, or plant seed can be transformed with an AMP wherein the AMP is a homopolymer or heteropolymer of two or more AMP polypeptides, wherein the amino acid sequence of each AMP is the same or different, or a polynucleotide encoding the same.

Any of the aforementioned methods, and/or any of the methods described herein, can be used to incorporate one or more of the AMPs or AMP-insecticidal proteins as described herein, into plants or plant parts thereof. For example, any of the methods described herein can be used to incorporate into plants one or more of the AMPs described in the present disclosure, e.g., AMPs having the amino acid sequence of SEQ ID NOs: 6, 20, 24-26, 28-36, 38-42, 48, 54, 58, 60, 62-63, 69, 108, 116, 119, and 168-169, which are likewise described herein.

Polynucleotide Incorporation into Plants, the Proteins Expressed Therefrom

A challenge regarding the expression of heterogeneous polypeptides in transgenic plants is maintaining the desired effect (e.g., insecticidal activity) of the introduced polypeptide upon expression in the host organism; one way to maintain such an effect is to increase the chance of proper protein folding through the use of an operably linked Endoplasmic Reticulum Signal Peptide (ERSP). Another method to maintain the effect of a transgenic protein is to incorporate a Translational Stabilizing Protein (STA).

Plants can be transiently or stably transfected with the DNA sequence that encodes an AMP or an AMP-insecticidal protein comprising one or more AMPs, using any of the transfection methods described above. Alternatively, plants can be transfected with a polynucleotide that encodes an AMP, wherein said AMP is operably linked to a polynucleotide operable to encode an Endoplasmic Reticulum Signal Peptide (ERSP); linker, Translational Stabilizing Protein (STA); or combination thereof. For example, in some embodiments, a transgenic plant or plant genome can be transformed with a polynucleotide sequence that encodes the Endoplasmic Reticulum Signal Peptide (ERSP); AMP; and/or intervening linker peptide (LINKER or L), thus causing mRNA transcribed from the heterogeneous DNA to be expressed in the transformed plant, and subsequently, said mRNA to be translated into a peptide.

Endoplasmic Reticulum Signal Peptide (ERSP)

The subcellular targeting of a recombinant protein to the ER can be achieved through the use of an ERSP operably linked to said recombinant protein; this allows for the correct assembly and/or folding of such proteins, and the high level accumulation of these recombinant proteins in plants. Exemplary methods concerning the compartmentalization of host proteins into intracellular storage are disclosed in McCormick et al., Proc. Natl. Acad. Sci. USA 96(2):703-708, 1999; Staub et al., Nature Biotechnology 18:333-338, 2000; Conrad et al., Plant Mol. Biol. 38:101-109, 1998; and Stoger et al., Plant Mol. Biol. 42:583-590, 2000, the disclosures of which are incorporated herein by reference in their entireties. Accordingly, one way to achieve the correct assembly and/or folding of recombinant proteins, is to operably link an endoplasmic reticulum signal peptide (ERSP) to the recombinant protein of interest.

In some embodiments, a peptide comprising an Endoplasmic Reticulum Signal Peptide (ERSP) can be operably linked to an AMP (designated as ERSP-AMP), wherein said ERSP is the N-terminal of said peptide. In some embodiments, the ERSP peptide is between 3 to 60 amino acids in length, between 5 to 50 amino acids in length, between 20 to 30 amino acids in length.

In some embodiments, AMP ORF starts with an ersp at its 5'-end. For the AMP to be properly folded and functional when it is expressed from a transgenic plant, it must have an ersp nucleotide fused in frame with the polynucleotide encoding an AMP. During the cellular translation process, translated ERSP can direct the AMP being translated to insert into the Endoplasmic Reticulum (ER) of the plant cell by binding with a cellular component called a signal-recognition particle. Within the ER the ERSP peptide is cleaved by signal peptidase and the AMP is released into the ER, where the AMP is properly folded during the post-translation modification process, for example, the formation of disulfide bonds. Without any additional retention protein signals, the protein is transported through the ER to the Golgi apparatus, where it is finally secreted outside the plasma membrane and into the apoplastic space. AMP can accumulate at apoplastic space efficiently to reach the insecticidal dose in plants.

The ERSP peptide is at the N-terminal region of the plant-translated AMP complex and the ERSP portion is composed of about 3 to 60 amino acids. In some embodiments it is 5 to 50 amino acids. In some embodiments it is 10 to 40 amino acids but most often is composed of 15 to 20; 20 to 25; or 25 to 30 amino acids. The ERSP is a signal peptide so called because it directs the transportation of a protein. Signal peptides may also be called targeting signals, signal sequences, transit peptides, or localization signals. The signal peptides for ER trafficking are often 15 to 30 amino acid residues in length and have a tripartite organization, comprised of a core of hydrophobic residues flanked by a positively charged amino terminal and a polar, but uncharged carboxyterminal region. (Zimmermann, et al, "Protein translocation across the ER membrane," Biochimica et Biohysica Δcta, 2011, 1808: 912-924).

Many ERSPs are known. It is NOT required that the ERSP be derived from a plant ERSP, non-plant ERSPs will work with the procedures described herein. Many plant ERSPs are however well known and we describe some plant derived ERSPs here. For example, ins some embodiments, the ERSP can be a barley alpha-amylase signal peptide (BAAS), which is derived from the plant, *Hordeum vulgare*, and has an amino acid sequence as follows: "MANKHLSLSLFLVLLGLSASLASG" (SEQ ID NO:173)

Plant ERSPs, which are selected from the genomic sequence for proteins that are known to be expressed and released into the apoplastic space of plants, include examples such as BAAS, carrot extensin, and tobacco PR1. The following references provide further descriptions, and are incorporated by reference herein in their entirety: De Loose, M. et al. "The extensin signal peptide allows secretion of a heterologous protein from protoplasts" Gene, 99 (1991) 95-100; De Loose, M. et al. described the structural analysis of an extension-encoding gene from *Nicotiana plumbaginifolia*, the sequence of which contains a typical signal peptide for translocation of the protein to the endoplasmic reticulum; Chen, M. H. et al. "Signal peptide-dependent targeting of a rice alpha-amylase and cargo proteins to plastids and extracellular compartments of plant cells" Plant Physiology, 2004 July; 135(3): 1367-77. Epub 2004 Jul. 2. Chen, M. H. et al. studied the subcellular localization of α-amylases in plant cells by analyzing the expression of α-amylase, with and without its signal peptide, in transgenic tobacco. These references and others teach and disclose the signal peptide that can be used in the methods, procedures and peptide, protein and nucleotide complexes and constructs described herein.

In some embodiments, the ERSP can include, but is not limited to, one of the following: a BAAS; a tobacco extensin signal peptide; a modified tobacco extensin signal peptide; or a Jun a 3 signal peptide from *Juniperus ashei*. For example, in some embodiments, a plant can be transformed with a nucleotide that encodes any of the peptides that are described herein as Endoplasmic Reticulum Signal Peptides (ERSP), and an AMP.

The tobacco extensin signal peptide motif is another exemplary type of ERSP. See Memelink et al, the Plant Journal, 1993, V4: 1011-1022; Pogue G P et al, Plant Biotechnology Journal, 2010, V8: 638-654, the disclosures of which are incorporated herein by reference in their entireties.

In some embodiments, an AMP ORF can have a nucleotide sequence operable to encode a tobacco extensin signal peptide motif. In one embodiment, the AMP ORF can encode an extensin motif according to SEQ ID NO:174. In another embodiment, the AMP ORF can encode an extensin motif according to SEQ ID NO:175.

An illustrative example of how to generate an embodiment with an extensin signal motif is as follows: A DNA sequence encoding an extensin motif is designed (for example, the DNA sequence shown in SEQ ID NO: 176 or SEQ ID NO:177) using oligo extension PCR with four synthetic DNA primers; ends sites such as a restriction site, for example, a Pac I restriction site at the 5'-end, and a 5'-end of a GFP sequence at the 3'-end, can be added using PCR with the extensin DNA sequence serving as a template, and resulting in a fragment; the fragment is used as the forward PCR primer to amplify the DNA sequence encoding an AMP ORF, for example "gfp-l-amp" contained in a pFECT vector, thus producing an AMP ORF encoding (from N' to C' terminal) "ERSP-GFP-L-AMP" wherein the ERSP is extensin. The resulting DNA sequence can then be cloned into Pac I and Avr II restriction sites of a FECT vector to generate the pFECT-AMP vector for transient plant expression of GFP fused AMP.

In some embodiments, an illustrative expression system can include the FECT expression vectors containing AMP ORF is transformed into *Agrobacterium*, GV3101, and the transformed GV3101 is injected into tobacco leaves for transient expression of AMP ORF.

Translational Stabilizing Protein (STA)

A Translational stabilizing protein (STA) can increase the amount of AMP in plant tissues. One of the AMP ORFs, i.e., ERSP-AMP, may be sufficient to express a properly folded AMP in the transfected plant; however, in some embodiments, effective protection of a plant from pest damage may require that the plant expressed AMP accumulate. With transfection of a properly constructed AMP ORF, a transgenic plant can express and accumulate greater amounts of the correctly folded AMP. When a plant accumulates greater amounts of properly folded AMP, it can more easily resist, inhibit, and/or kill the pests that attack and eat the plants. One method of increasing the accumulation of a polypeptide in transgenic tissues is through the use of a translational stabilizing protein (STA). The translational stabilizing protein can be used to significantly increase the accumulation of AMP in plant tissue, and thus increase the efficacy of a plant transfected with AMP with regard to pest resistance. The translational stabilizing protein is a protein with sufficient tertiary structure that it can accumulate in a cell without being targeted by the cellular process of protein degradation.

In some embodiments, the translational stabilizing protein can be a domain of another protein, or it can comprise an entire protein sequence. In some embodiments, the translational stabilizing protein can be between 5 and 50 amino acids, 50 to 250 amino acids (e.g., GNA), 250 to 750 amino acids (e.g., chitinase) and 750 to 1500 amino acids (e.g., enhancin).

One embodiment of the translational stabilizing protein can be a polymer of fusion proteins comprising at least one AMP. A specific example of a translational stabilizing protein is provided here to illustrate the use of a translational stabilizing protein. The example is not intended to limit the disclosure or claims in any way. Useful translational stabilizing proteins are well known in the art, and any proteins of this type could be used as disclosed herein. Procedures for evaluating and testing production of peptides are both known in the art and described herein. One example of one translational stabilizing protein is Green-Fluorescent Protein (GFP) (SEQ ID NO:178; NCBI Accession No. P42212.1).

In some embodiments, a protein comprising an Endoplasmic Reticulum Signal Peptide (ERSP) can be operably linked to an AMP, which is in turn operably linked to a Translational Stabilizing Protein (STA). Here, this configuration is designated as ERSP-STA-AMP or ERSP-AMP-STA, wherein said ERSP is the N-terminal of said protein and said STA may be either on the N-terminal side (upstream) of the AMP, or of the C-terminal side (downstream) of the AMP. In some embodiments, a protein designated as ERSP-STA-AMP or ERSP-AMP-STA, comprising any of the ERSPs or AMPs described herein, can be operably linked to a STA, for example, any of the translational stabilizing proteins described, or taught by this document including GFP (Green Fluorescent Protein; SEQ ID NO: 178; NCBI Accession No. P42212), or Jun a 3, (*Juniperus ashei*; SEQ ID NO: 179; NCBI Accession No. P81295.1).

Additional examples of translational stabilizing proteins can be found in the following references, the disclosures of which are incorporated herein by reference in their entirety: Kramer, K. J. et al. "Sequence of a cDNA and expression of the gene encoding epidermal and gut chitinases of *Manduca sexta*" Insect Biochemistry and Molecular Biology, Vol. 23, Issue 6, September 1993, pp. 691-701. Kramer, K. J. et al. isolated and sequenced a chitinase-encoding cDNA from the tobacco homworm, *Manduca sexta*. Hashimoto, Y. et al. "Location and nucleotide sequence of the gene encoding the viral enhancing factor of the *Trichoplusia ni granulosis* virus" Journal of General Virology, (1991), 72, 2645-2651. These references and others teach and disclose translational stabilizing proteins that can be used in the methods, procedures and peptide, protein and nucleotide complexes and constructs described herein.

In some embodiments, an AMP ORF can be transformed into a plant, for example, in the tobacco plant, *Nicotiana benthamiana*, using an AMP ORF that contains a STA. For example, in some embodiments, the STA can be Jun a 3. The mature Jun a 3 is a ~30 kDa plant defending protein that is also an allergen for some people. Jun a 3 is produced by *Juniperus ashei* trees and can be used in some embodiments as a translational stabilizing protein (STA). In some embodiments, the Jun a 3 amino acid sequence can be the sequence shown in SEQ ID NO:179. In other embodiments, the Jun a 3 amino acid sequence can be the sequence shown in SEQ ID NO:180.

Linkers

Linker proteins assist in the proper folding of the different motifs composing an AMP ORF. The AMP ORF described in this invention also incorporates polynucleotide sequences encoding intervening linker peptides between the polynucleotide sequences encoding the AMP (amp) and the translational stabilizing protein (sta), or between polynucleotide sequence encoding multiple polynucleotide sequences encoding AMP, i.e., $(\text{l-amp})_N$ or $(\text{amp-l})_N$, if the expression ORF involves multiple AMP domain expression. The intervening linker peptides (LINKERS or L or LN) separate the different parts of the expressed AMP construct, and help proper folding of the different parts of the complex during the expression process. In the expressed AMP construct, different intervening linker peptides can be involved to separate different functional domains. In some embodiments, the LINKER is attached to an AMP and this bivalent group can be repeated up to 10 (N=1-10) and possibly even more than 10 times (e.g., N=200) in order to facilitate the accumulation of properly folded AMP in the plant that is to be protected.

In some embodiments the intervening linker peptide can be between 1 and 30 amino acids in length. However, it is not necessarily an essential component in the expressed AMP in plants.

In some embodiments, the AMP-insecticidal protein comprises at least one AMP operably linked to a cleavable peptide. In other embodiments, the AMP-insecticidal protein comprises at least one AMP operably linked to a non-cleavable peptide.

A cleavable linker peptide can be designed to the AMP ORF to release the properly AMP from the expressed AMP complex in the transformed plant to improve the protection the AMP affords the plant with regard to pest damage. One type of the intervening linker peptide is the plant cleavable linker peptide. This type of linker peptides can be completely removed from the expressed AMP ORF complex during plant post-translational modification. Therefore, in some embodiments, the properly folded AMP linked by this type of intervening linker peptides can be released in the plant cells from the expressed AMP ORF complex during post-translational modification in the plant.

Another type of the cleavable intervening linker peptide is not cleavable during the expression process in plants. However, it has a protease cleavage site specific to serine, threonine, cysteine, aspartate proteases or metalloproteases. The type of cleavable linker peptide can be digested by proteases found in the insect and lepidopteran gut environment and/or the insect hemolymph and lepidopteran hemolymph environment to release the AMP in the insect gut or hemolymph. Using the information taught by this disclosure it should be a matter of routine for one skilled in the art to make or find other examples of LINKERS that will be useful in this invention.

In some embodiments, the AMP ORF can contain a cleavable type of intervening linker, for example, the type listed in SEQ ID NO:181, having the amino acid code of "IGER" (SEQ ID NO:181). The molecular weight of this intervening linker or LINKER is 473.53 Daltons. In other embodiments, the intervening linker peptide (LINKER) can also be one without any type of protease cleavage site, i.e., an uncleavable intervening linker peptide, for example, the linker "EEKKN" (SEQ ID NO: 182) or "ETMFKHGL" (SEQ ID NO:183).

In some embodiments, the AMP-insecticidal protein can have two or more cleavable peptides, wherein the insecticidal protein comprises an insect cleavable linker (L), the insect cleavable linker being fused in frame with a construct comprising $(\text{AMP-L})_n$, wherein "n" is an integer ranging from 1 to 200, or from 1 to 100, or from 1 to 10. In another embodiment, the AMP-insecticidal protein, and described herein, comprises an endoplasmic reticulum signal peptide (ERSP) operably linked with an AMP, which is operably linked with an insect cleavable linker (L) and/or a repeat construct $(\text{L-AMP})_n$ or $(\text{AMP-L})_n$, wherein n is an integer ranging from 1 to 200, or from 1 to 100, or from 1 to 10.

In some embodiments, a protein comprising an Endoplasmic Reticulum Signal Peptide (ERSP) can be operably linked to an AMP and an intervening linker peptide (L or Linker); such a construct is designated as ERSP-L-AMP, or ERSP-AMP-L, wherein said ERSP is the N-terminal of said protein, and said L or Linker may be either on the N-terminal side (upstream) of the AMP, or the C-terminal side (downstream) of the AMP. A protein designated as ERSP-L-AMP, or ERSP-AMP-L, comprising any of the ERSPs or AMPs described herein, can have a Linker "L" that can be an uncleavable linker peptide, or a cleavable linker peptide, and which may be cleavable in a plant cells during protein expression process, or may be cleavable in an insect gut environment and/or hemolymph environment.

In some embodiments, an AMP-insecticidal protein can comprise any of the intervening linker peptides (LINKER or L) described herein, or taught by this document, including but not limited to following sequences: IGER (SEQ ID NO:181), EEKKN, (SEQ ID NO:182), and ETMFKHGL (SEQ ID NO:183), or combinations thereof.

In some embodiments, the linker can be one or more of the following: ALKFLV (SEQ ID NO: 184), ALKLFV (SEQ ID NO: 185), IFVRLR (SEQ ID NO: 186), LFAAPF (SEQ ID NO: 187), ALKFLVGS (SEQ ID NO: 188), ALKLFVGS (SEQ ID NO: 189), IFVRLRGS (SEQ ID NO: 190), LFAAPFGS (SEQ ID NO: 191), LFVRLRGS (SEQ ID NO: 192), and/or LGERGS (SEQ ID NO: 193).

In various embodiments, an exemplary insecticidal protein can include a protein construct comprising: (ERSP)-(AMP-L)$_n$; (ERSP)-(L)-(AMP-L)$_n$; (ERSP)-(L-AMP)$_n$; (ERSP)-(L-AMP)$_n$-(L); wherein n is an integer ranging from 1 to 200 or from 1 to 100, or from 1 to 10. In various related embodiments described above, an AMP is the Av3b mutant peptide, L is a non-cleavable or cleavable peptide, and n is an integer ranging from 1 to 200, preferably an integer ranging from 1 to 100, and more preferably an integer ranging from 1 to 10. In some embodiments, the AMP-insecticidal protein may contain AMP peptides that are the same or different, and insect cleavable peptides that are the same or different. In some embodiments, the C-terminal AMP is operably linked at its C-terminus with a cleavable peptide that is operable to be cleaved in an insect gut environment. In some embodiments, the N-terminal AMP is operably linked at its N-terminus with a cleavable peptide that is operable to be cleaved in an insect gut environment.

Some of the available proteases and peptidases found in the insect gut environment are dependent on the life-stage of the insect, as these enzymes are often spatially and temporally expressed. The digestive system of the insect is composed of the alimentary canal and associated glands. Food enters the mouth and is mixed with secretions that may or may not contain digestive proteases and peptidases. The foregut and the hind gut are ectodermal in origin. The foregut serves generally as a storage depot for raw food. From the foregut, discrete boluses of food pass into the midgut (mesenteron or ventriculus). The midgut is the site of digestion and absorption of food nutrients. Generally, the presence of certain proteases and peptidases in the midgut follow the pH of the gut. Certain proteases and peptidases in the human gastrointestinal system may include: pepsin, trypsin, chymotrypsin, elastase, carboxypeptidase, aminopeptidase, and dipeptidase.

The insect gut environment includes the regions of the digestive system in the herbivore species where peptides and proteins are degraded during digestion. Some of the available proteases and peptidases found in insect gut environments may include: (1) serine proteases; (2) cysteine proteases; (3) aspartic proteases, and (4) metalloproteases.

The two predominant protease classes in the digestive systems of phytophagous insects are the serine and cysteine proteases. Murdock et al. (1987) carried out an elaborate study of the midgut enzymes of various pests belonging to Coleoptera, while Srinivasan et al. (2008) have reported on the midgut enzymes of various pests belonging to Lepidoptera. Serine proteases are known to dominate the larval gut environment and contribute to about 95% of the total digestive activity in Lepidoptera, whereas the Coleopteran species have a wider range of dominant gut proteases, including cysteine proteases.

The papain family contains peptidases with a wide variety of activities, including endopeptidases with broad specificity (such as papain), endopeptidases with very narrow specificity (such as glycyl endopeptidases), aminopeptidases, dipeptidyl-peptidase, and peptidases with both endopeptidase and exopeptidase activities (such as cathepsins B and H). Other exemplary proteinases found in the midgut of various insects include trypsin-like enzymes, e.g. trypsin and chymotrypsin, pepsin, carboxypeptidase-B and aminotripeptidases.

Serine proteases are widely distributed in nearly all animals and microorganisms (Joanitti et al., 2006). In higher organisms, nearly 2% of genes code for these enzymes (Barrette-Ng et al., 2003). Being essentially indispensable to the maintenance and survival of their host organism, serine proteases play key roles in many biological processes.

Serine proteases are classically categorized by their substrate specificity, notably by whether the residue at P1: trypsin-like (Lys/Arg preferred at P1), chymotrypsin-like (large hydrophobic residues such as Phe/Tyr/Leu at P1), or elastase-like (small hydrophobic residues such as Ala/Val at P1) (revised by Tyndall et. al., 2005). Serine proteases are a class of proteolytic enzymes whose central catalytic machinery is composed of three invariant residues, an aspartic acid, a histidine and a uniquely reactive serine, the latter giving rise to their name, the "catalytic triad". The Asp-His-Ser triad can be found in at least four different structural contexts (Hedstrom, 2002). These four clans of serine proteases are typified by chymotrypsin, subtilisin, carboxypeptidase Y, and Clp protease. The three serine proteases of the chymotrypsin-like clan that have been studied in greatest detail are chymotrypsin, trypsin, and elastase. More recently, serine proteases with novel catalytic triads and dyads have been discovered for their roles in digestion, including Ser-His-Glu, Ser-Lys/His, His-Ser-His, and N-terminal Ser.

One class of well-studied digestive enzymes found in the gut environment of insects is the class of cysteine proteases. The term "cysteine protease" is intended to describe a protease that possesses a highly reactive thiol group of a cysteine residue at the catalytic site of the enzyme. There is evidence that many phytophagous insects and plant parasitic nematodes rely, at least in part, on midgut cysteine proteases for protein digestion. These include but are not limited to Hemiptera, especially squash bugs (*Anasa tristis*); green stink bug (*Acrosternum hilare*); *Riptortus clavatus*; and almost all Coleoptera examined to date, especially, Colorado potato beetle (*Leptinotarsa deaemlineata*); three-lined potato beetle (*Lema trilineata*); asparagus beetle (*Crioceris asparagi*); Mexican bean beetle (*Epilachna varivestis*); red flour beetle (*Triolium castaneum*); confused flour beetle (*Tribolium confusum*); the flea beetles (*Chaetocnema* spp., *Haltica* spp., and *Epitrix* spp.); corn rootworm (*Diabrotica* Spp.); cowpea weevil (*Callosobruchus aculatue*); boll weevil (*Antonomus grandis*); rice weevil (*Sitophilus oryza*); maize weevil (*Sitophilus zeamais*); granary weevil (*Sitophilus granarius*); Egyptian alfalfa weevil (*Hypera postica*); bean weevil (*Acanthoseelides obtectus*); lesser grain borer (*Rhyzopertha dominica*); yellow meal worm (*Tenebrio molitor*); *Thysanoptera*, especially, western flower *thrips* (*Franklini ella occidentalis*); Diptera, especially, leafminer spp. (*Liriomyza trifolii*); plant parasitic nematodes especially the potato cyst nematodes (*Globodera* spp.), the beet cyst nematode (*Heterodera schachtii*) and root knot nematodes (*Meloidogyne* spp.).

Another class of digestive enzymes is the aspartic proteases. The term "aspartic protease" is intended to describe a protease that possesses two highly reactive aspartic acid residues at the catalytic site of the enzyme and which is most often characterized by its specific inhibition with pepstatin, a low molecular weight inhibitor of nearly all known aspartic proteases. There is evidence that many phytophagous insects rely, in part, on midgut aspartic proteases for protein digestion most often in conjunction with cysteine proteases. These include but are not limited to Hemiptera especially (*Rhodnius prolixus*) and bedbug (*Cimex* spp.) and members of the families Phymatidae, Pentatomidae, Lygaeidae and Belostomatidae; Coleoptera, in the families of the Meloidae, Chrysomelidae, Coccinelidae and Bruchidae all belonging to the series Cucujiformia, especially, Colorado potato beetle (*Leptinotarsa decemlineata*) three-lined potato beetle (*Lematri lineata*); southern and western corn rootworm (*Diabrotica undecimpunctata* and *D. virgifera*), boll weevil (*Anthonomus grandis*), squash bug (*Anasatristis*); flea beetle (*Phyllotreta crucifera*), bruchid beetle (*Callosobruchus maculatus*), Mexican bean beetle (*Epilachna varivestis*), soybean leafminer (*Odontota horni*), margined blister beetle (*Epicauta pestifera*) and the red flour beetle (*Triolium castaneum*); Diptera, especially housefly (*Musca domestica*). See Terra and Ferreira (1994) Comn. Biochem. Physiol. 109B: 1-62; Wolfson and Murdock (1990) J. Chem. Ecol. 16: 1089-1102.

Other examples of intervening linker peptides can be found in the following references, which are incorporated by reference herein in their entirety: a plant expressed serine proteinase inhibitor precursor was found to contain five homogeneous protein inhibitors separated by six same linker peptides, as disclosed in Heath et al. "Characterization of the protease processing sites in a multidomain proteinase inhibitor precursor from *Nicotiana alata*" European Journal of Biochemistry, 1995; 230: 250-257. A comparison of the folding behavior of green fluorescent proteins through six different linkers is explored in Chang, H. C. et al. "De novo folding of GFP fusion proteins: high efficiency in eukaryotes but not in bacteria" Journal of Molecular Biology, 2005 Oct. 21; 353(2): 397-409. An isoform of the human GalNAc-Ts family, GalNAc-T2, was shown to retain its localization and functionality upon expression in *N. benthamiana* plants by Daskalova, S. M. et al. "Engineering of *N. benthamiana* L. plants for production of N-acetylgalactosamine-glycosylated proteins" BMC Biotechnology, 2010 Aug. 24; 10: 62. The ability of endogenous plastid proteins to travel through stromules was shown in Kwok, E. Y. et al. "GFP-labelled Rubisco and aspartate aminotransferase are present in plastid stromules and traffic between plastids" Journal of Experimental Botany, 2004 March; 55(397): 595-604. Epub 2004 Jan. 30. A report on the engineering of the surface of the tobacco mosaic virus (TMV), virion, with a mosquito decapeptide hormone, trypsin-modulating oostatic factor (TMOF) was made by Borovsky, D. et al. "Expression of *Aedes* trypsin-modulating oostatic factor on the virion of TMV: A potential larvicide" Proc Natl Acad Sci, 2006 Dec. 12; 103(50): 18963-18968. These references and others teach and disclose the intervening linkers that can be used in the methods, procedures and peptide, protein and nucleotide complexes and constructs described herein.

The AMP ORF and AMP Constructs

"AMP ORF" refers to a nucleotide encoding an AMP, and/or one or more stabilizing proteins, secretory signals, or target directing signals, for example, ERSP or STA, and is defined as the nucleotides in the ORF that has the ability to be translated. Thus, a "AMP ORF diagram" refers to the composition of one or more AMP ORFs, as written out in diagram or equation form. For example, a "AMP ORF diagram" can be written out as using acronyms or short-hand references to the DNA segments contained within the expression ORF. Accordingly, in one example, a "AMP ORF diagram" may describe the polynucleotide segments encoding the ERSP, LINKER, STA, and AMP, by diagramming in equation form the DNA segments as "ersp" (i.e., the polynucleotide sequence that encodes the ERSP polypeptide); "linker" or "L" (i.e., the polynucleotide sequence that encodes the LINKER polypeptide); "sta" (i.e., the polynucleotide sequence that encodes the STA polypeptide), and "amp" (i.e., the polynucleotide sequence encoding an AMP), respectively. An example of an AMP ORF diagram is "ersp-sta-(linker$_i$-amp$_j$)$_N$," or "ersp-(amp$_j$-linker$_i$)$_N$-sta" and/or any combination of the DNA segments thereof.

The following equations describe two examples of an AMP ORF that encodes an ERSP, a STA, a linker, and an AMP:

ersp-sta-l-amp or ersp-amp-l-sta

In some embodiments, the AMP open reading frame (ORF) described herein is a polynucleotide sequence that will enable the plant to express mRNA, which in turn will be translated into peptides that will folded properly, and/or accumulated to such an extent that said proteins provide a dose sufficient to inhibit and/or kill one or more pests. In one embodiment, an example of a protein AMP ORF can be a Av3b mutant polynucleotide (amp), an "ersp" (i.e., the polynucleotide sequence that encodes the ERSP polypeptide) a "linker" (i.e., the polynucleotide sequence that encodes the LINKER polypeptide), a "sta" (i.e., the polynucleotide sequence that encodes the STA polypeptide), or any combination thereof, and can be described in the following equation format:

ersp-sta-(linker$_i$-amp$_j$)$_n$, or ersp-(amp$_j$-linker$_i$)$_n$-sta

The foregoing illustrative embodiment of a polynucleotide equation would result in the following protein complex being expressed: ERSP-STA-(LINKER$_I$-AMP$_J$)$_N$, containing four possible peptide components with dash signs to separate each component. The nucleotide component of ersp is a polynucleotide segment encoding a plant endoplasmic reticulum trafficking signal peptide (ERSP). The component of sta is a polynucleotide segment encoding a translation stabilizing protein (STA), which helps the accumulation of the AMP expressed in plants, however, in some embodiments, the inclusion of sta may not be necessary in the AMP ORF. The component of linker$_i$ is a polynucleotide segment encoding an intervening linker peptide (L OR LINKER) to separate the AMP from other components contained in ORF, and from the translation stabilizing protein. The subscript letter "i" indicates that in some embodiments, different types of linker peptides can be used in the AMP ORF. The component "amp" indicates the polynucleotide segment encoding the AMP. The subscript "j" indicates different polynucleotides may be included in the AMP ORF. For example, in some embodiments, the polynucleotide sequence can encode an AMP with a different amino acid substitution. The subscript "n" as shown in "(linker$_i$-amp$_j$)$_n$" indicates that the structure of the nucleotide encoding an intervening linker peptide and an AMP can be repeated "n" times in the same open reading frame in the same AMP ORF, where "n" can be any integrate number from 1 to 10; "n" can be from 1 to 10, specifically "n" can be 1, 2, 3, 4, or 5, and in some embodiments "n" is 6, 7, 8, 9 or 10. The repeats may contain polynucleotide segments encoding different intervening linkers (LINKER) and different AMPs. The different polynucleotide segments including the repeats within the same AMP ORF are all within the same translation frame. In some embodiments, the inclusion of a sta polynucleotide in the AMP ORF may not be required. For example, an ersp polynucleotide sequence can be directly be linked to the polynucleotide encoding an AMP variant polynucleotide without a linker.

In the foregoing exemplary equation, the polynucleotide "amp" encoding the polypeptide "AMP" can be the polynucleotide sequence that encodes any AMP as described herein, e.g., an AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or a complementary nucleotide sequence thereof.

In the foregoing exemplary equation, the polynucleotide "amp" encoding the polypeptide "AMP" can be the polynucleotide sequence that encodes any AMP as described herein, e.g., an AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; or a complementary nucleotide sequence thereof.

In some embodiments, the amp polynucleotide, or polynucleotide operable to encode an AMP, can encode an AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or a complementary nucleotide sequence thereof.

In some embodiments, the amp polynucleotide, or polynucleotide operable to encode an AMP, can encode an AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; or a complementary nucleotide sequence thereof.

In some embodiments, the amp polynucleotide, or polynucleotide operable to encode an AMP, can encode an AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence set forth in any one of SEQ ID NOs: 6, 20, 24-26, 28-36, 38-42, 48, 54, 58, 60, 62-63, 69, 108, 116, 119, and 168-169.

In some embodiments, a polynucleotide is operable to encode an AMP-insecticidal protein having the following AMP construct orientation and/or arrangement: ERSP-AMP; ERSP-$(AMP)_N$; ERSP-AMP-L; ERSP-$(AMP)_N$-L; ERSP-$(AMP\text{-}L)_N$; ERSP-L-AMP; ERSP-L-$(AMP)_N$; ERSP-$(L\text{-}AMP)_N$; ERSP-STA-AMP; ERSP-STA-$(AMP)_N$; ERSP-AMP-STA; ERSP-$(AMP)_N$-STA; ERSP-$(STA\text{-}AMP)_N$; ERSP-$(AMP\text{-}STA)_N$; ERSP-L-AMP-STA; ERSP-L-STA-AMP; ERSP-L-$(AMP\text{-}STA)_N$; ERSP-L-$(STA\text{-}AMP)_N$; ERSP-L-$(AMP)_N$-STA; ERSP-$(L\text{-}AMP)_N$-STA; ERSP-$(L\text{-}STA\text{-}AMP)_N$; ERSP-$(L\text{-}AMP\text{-}STA)_N$; ERSP-(L-

STA)$_N$-AMP; ERSP-(L-AMP)$_N$-STA; ERSP-STA-L-AMP; ERSP-STA-AMP-L; ERSP-STA-L-(AMP)$_N$; ERSP-(STA-L)$_N$-AMP; ERSP-STA-(L-AMP)$_N$; ERSP-(STA-L-AMP)$_N$; ERSP-STA-(AMP)$_N$-L; ERSP-STA-(AMP-L)$_N$; ERSP-(STA-AMP)$_N$-L; ERSP-(STA-AMP-L)$_N$; ERSP-AMP-L-STA; ERSP-AMP-STA-L; ERSP-(AMP)$_N$-STA-L ERSP-(AMP-L)$_N$-STA; ERSP-(AMP-STA)$_N$-L; ERSP-(AMP-L-STA)$_N$; or ERSP-(AMP-STA-L)$_N$;

wherein N is an integer ranging from 1 to 200.

Any of the aforementioned methods, and/or any of the methods described herein, can be used to incorporate into a plant or a plant part thereof, one or more polynucleotides operable to express any one or more of the AMPs or AMP-insecticidal proteins as described herein; e.g., one or more AMPs or AMP-insecticidal protein having the amino acid sequence of SEQ ID NOs: 6, 20, 24-26, 28-36, 38-42, 48, 54, 58, 60, 62-63, 69, 108, 116, 119, and 168-169, which are likewise described herein.

The present disclosure may be used for transformation of any plant species, including, but not limited to, monocots and dicots. Crops for which a transgenic approach or PEP would be an especially useful approach include, but are not limited to: alfalfa, cotton, tomato, maize, wheat, corn, sweet corn, luceme, soybean, sorghum, field pea, linseed, safflower, rapeseed, oil seed rape, rice, soybean, barley, sunflower, trees (including coniferous and deciduous), flowers (including those grown commercially and in greenhouses), field lupins, switchgrass, sugarcane, potatoes, tomatoes, tobacco, crucifers, peppers, sugarbeet, barley, and oilseed rape, *Brassica* sp., rye, millet, peanuts, sweet potato, cassaya, coffee, coconut, pineapple, citrus trees, cocoa, tea, banana, avocado, fig, guava, mango, olive, papaya, cashew, macadamia, almond, oats, vegetables, ornamentals, and conifers.

Transforming Plants with Polynucleotides

In some embodiments, the AMP ORFs and AMP constructs described above and herein can be cloned into any plant expression vector for AMP to be expressed in plants, either transiently or stably.

Transient plant expression systems can be used to promptly optimize the structure of the AMP ORF for some specific AMP expression in plants, including the necessity of some components, codon optimization of some components, optimization of the order of each component, etc. A transient plant expression vector is often derived from a plant virus genome. Plant virus vectors provide advantages in quick and high level of foreign gene expression in plant due to the infection nature of plant viruses. The full length of the plant viral genome can be used as a vector, but often a viral component is deleted, for example the coat protein, and transgenic ORFs are subcloned in that place. The AMP ORF can be subcloned into such a site to create a viral vector. These viral vectors can be introduced into plant mechanically since they are infectious themselves, for example through plant wound, spray-on etc. They can also be transfected into plants via agroinfection, by cloning the virus vector into the T-DNA of the crown gall bacterium, *Agrobacterium tumefaciens*, or the hairy root bacterium, *Agrobacterium rhizogenes*. The expression of the AMP in this vector is controlled by the replication of the RNA virus, and the virus translation to mRNA for replication is controlled by a strong viral promoter, for example, 35S promoter from Cauliflower mosaic virus. Viral vectors with AMP ORF are usually cloned into T-DNA region in a binary vector that can replicate itself in both *E. coli* strains and *Agrobacterium* strains. The transient transfection of a plant can be done by infiltration of the plant leaves with the *Agrobacterium* cells which contain the viral vector for AMP expression. In the transient transformed plant, it is common for the foreign protein expression to be ceased in a short period of time due to the post-transcriptional gene silencing (PTGS). Sometimes a PTGS suppressing protein gene is necessary to be co-transformed into the plant transiently with the same type of viral vector that drives the expression of with the AMP ORF. This improves and extends the expression of the AMP in the plant. The most commonly used PTGS suppressing protein is P19 protein discovered from tomato bushy stunt virus (TBSV).

In some embodiments, transient transfection of plants can be achieved by recombining a polynucleotide encoding a AMP with any one of the readily available vectors (see above and described herein), and confirmed, using a marker or signal (e.g., GFP emission). In some embodiments, a transiently transfected plant can be created by recombining a polynucleotide encoding a AMP with a DNA encoding a GFP-Hybrid fusion protein in a vector, and transfection said vector into a plant (e.g., tobacco) using different FECT vectors designed for targeted expression. In some embodiments, a polynucleotide encoding a AMP can be recombined with a pFECT vector for APO (apoplast localization) accumulation; a pFECT vector for CYTO (cytoplasm localization) accumulation; or pFECT with ersp vector for ER (endoplasm reticulum localization) accumulation.

An exemplary transient plant transformation strategy is agroinfection using a plant viral vector due to its high efficiency, ease, and low cost. In some embodiments, a tobacco mosaic virus overexpression system can be used to transiently transform plants with AMP. See TRBO, Lindbo J A, Plant Physiology, 2007, V145: 1232-1240, the disclosure of which is incorporated herein by reference in its entirety.

The TRBO DNA vector has a T-DNA region for agroinfection, which contains a CaMV 35S promoter that drives expression of the tobacco mosaic virus RNA without the gene encoding the viral coating protein. Moreover, this system uses the "disarmed" virus genome, therefore viral plant to plant transmission can be effectively prevented.

In another embodiment, the FECT viral transient plant expression system can be used to transiently transform plants with AMP. See Liu Z & Kearney C M, BMC Biotechnology, 2010, 10:88, the disclosure of which is incorporated herein by reference in its entirety. The FECT vector contains a T-DNA region for agroinfection, which contains a CaMV 35S promoter that drives the expression of the foxtail mosaic virus RNA without the genes encoding the viral coating protein and the triple gene block. Moreover, this system uses the "disarmed" virus genome, therefore viral plant to plant transmission can be effectively prevented. To efficiently express the introduced heterologous gene, the FECT expression system additionally needs to co-express P19, a RNA silencing suppressor protein from tomato bushy stunt virus, to prevent the post-transcriptional gene silencing (PTGS) of the introduced T-DNA (the TRBO expression system does not need co-expression of P19).

In some embodiments, the AMP ORF can be designed to encode a series of translationally fused structural motifs that can be described as follows: N'-ERSP-STA-L-AMP-C' wherein the "N'" and "C'" indicating the N-terminal and C-terminal amino acids, respectively, and the ERSP motif can be the Barley Alpha-Amylase Signal peptide (BAAS) (SEQ ID NO:173); the stabilizing protein (STA) can be GFP (SEQ ID NO:178); the linker peptide "L" can be IGER (SEQ ID NO:81) In some embodiments, the ersp-sta-l-amp ORF can chemically synthesized to include restrictions sites, for example a Pac I restriction site at its 5'-end, and an Avr II restriction site at its 3'-end. In some embodiments, the AMP ORF can be cloned into the Pac I and Avr II restriction sites of a FECT expression vector (pFECT) to create an AMP expression vector for the FECT transient plant expression system (pFECT-AMP). To maximize expression in the FECT expression system, some embodiments may have a FECT vector expressing the RNA silencing suppressor protein P19 (pFECT-P19) generated for co-transformation.

In some embodiments, a vector can be recombined for use in a TRBO transient plant expression system, for example, by performing a routine PCR procedure and adding a Not I restriction site to the 3'-end of the AMP ORF described above, and then cloning the AMP ORF into Pac I and Not I restriction sites of the TRBO expression vector (pTRBO-AMP).

In some embodiments, an *Agrobacterium tumefaciens* strain, for example, commercially available GV3101 cells, can be used for the transient expression of a AMP ORF in a plant tissue (e.g., tobacco leaves) using one or more transient expression systems, for example, the FECT and TRBO expression systems. An exemplary illustration of such a transient transfection protocol includes the following: an overnight culture of GV3101 can be used to inoculate 200 mL Luria-Bertani (LB) medium; the cells can be allowed to grow to log phase with OD600 between 0.5 and 0.8; the cells can then be pelleted by centrifugation at 5000 rpm for 10 minutes at 4° C.; cells can then be washed once with 10 mL prechilled TE buffer (Tris-HCl 10 mM, EDTA 1 mM, pH8.0), and then resuspended into 20 mL LB medium; GV3101 cell resuspension can then be aliquoted in 250 μL fractions into 1.5 mL microtubes; aliquots can then be snap-frozen in liquid nitrogen and stored at −80° C. freezer for future transformation. The pFECT-AMP and pTRBO-AMP vectors can then transformed into the competent GV3101 cells using a freeze-thaw method as follows: the stored competent GV3101 cells are thawed on ice and mixed with 1 to 5 μg pure DNA (pFECT-AMP or pTRBO-AMP vector). The cell-DNA mixture is kept on ice for 5 minutes, transferred to −80° C. for 5 minutes, and incubated in a 37° C. water bath for 5 minutes. The freeze-thaw treated cells are then diluted into 1 mL LB medium and shaken on a rocking table for 2 to 4 hours at room temperature. A 200 μL aliquot of the cell-DNA mixture is then spread onto LB agar plates with the appropriate antibiotics (10 μg/mL rifampicin, 25 μg/mL gentamycin, and 50 μg/mL kanamycin can be used for both pFECT-AMP transformation and pTRBO-AMP transformation) and incubated at 28° C. for two days. Resulting transformed colonies are then picked and cultured in 6 mL aliquots of LB medium with the appropriate antibiotics for transformed DNA analysis and making glycerol stocks of the transformed GV3101 cells.

In some embodiments, the transient transformation of plant tissues, for example, tobacco leaves, can be performed using leaf injection with a 3-mL syringe without needle. In one illustrative example, the transformed GV3101 cells are streaked onto an LB plate with the appropriate antibiotics (as described above) and incubated at 28° C. for two days. A colony of transformed GV3101 cells are inoculated to 5 ml of LB-MESA medium (LB media supplemented with 10 mM MES, and 20 μM acetosyringone) and the same antibiotics described above, and grown overnight at 28° C. The cells of the overnight culture are collected by centrifugation at 5000 rpm for 10 minutes and resuspended in the induction medium (10 mM MES, 10 mM $MgCl_2$, 100 μM acetosyringone) at a final OD600 of 1.0. The cells are then incubated in the induction medium for 2 hours to overnight at room temperature and are then ready for transient transformation of tobacco leaves. The treated cells can be infiltrated into the underside of attached leaves of *Nicotiana benthamiana* plants by injection, using a 3-mL syringe without a needle attached.

In some embodiments, the transient transformation can be accomplished by transfecting one population of GV3101 cells with pFECT-AMP or pTRBO-AMP and another population with pFECT-P19, mixing the two cell populations together in equal amounts for infiltration of tobacco leaves by injection with a 3-mL syringe.

Stable integration of polynucleotide operable to encode AMP is also possible with the present disclosure, for example, the AMP ORF can also be integrated into plant genome using stable plant transformation technology, and therefore AMPs can be stably expressed in plants and protect the transformed plants from generation to generation. For the stable transformation of plants, the AMP expression vector can be circular or linear. The AMP ORF, the AMP expression cassette, and/or the vector with polynucleotide encoding an AMP for stable plant transformation should be carefully designed for optimal expression in plants based on what is known to those having ordinary skill in the art, and/or by using predictive vector design tools such as Gene Designer 2.0 (Atum Bio); VectorBuilder (Cyagen); SnapGene® viewer; GeneArt™ Plasmid Construction Service (Thermo-Fisher Scientific); and/or other commercially available plasmid design services. See Tolmachov, Designing plasmid vectors. Methods Mol Biol. 2009; 542:117-29. The expression of AMP is usually controlled by a promoter that promotes transcription in some, or all the cells of the transgenic plant. The promoter can be a strong plant viral promoter, for example, the constitutive 35S promoter from Cauliflower Mosaic Virus (CaMV); it also can be a strong plant promoter, for example, the hydroperoxide lyase promoter (pHPL) from *Arabidopsis thaliana*; the *Glycine max* polyubiquitin (Gmubi) promoter from soybean; the ubiquitin promoters from different plant species (rice, corn, potato, etc.), etc. A plant transcriptional terminator often occurs after the stop codon of the ORF to halt the RNA polymerase and transcription of the mRNA. To evaluate the AMPs expression, a reporter gene can be included in the AMP expression vector, for example, beta-glucuronidase gene (GUS) for GUS straining assay, green fluorescent protein (GFP) gene for green fluorescence detection under UV light, etc. For selection of transformed plants, a selection marker gene is usually included in the AMP expression vector. In some embodiments, the marker gene expression product can provide the transformed plant with resistance to specific antibiotics, for example, kanamycin, hygromycin, etc., or specific herbicide, for example, glyphosate etc. If agroinfection technology is adopted for plant transformation, T-DNA left border and right border sequences are also included in the AMP expression vector to transport the T-DNA portion into the plant.

The constructed AMP expression vector can be transfected into plant cells or tissues using many transfection technologies. Agroinfection is a very popular way to transform a plant using an *Agrobacterium tumefaciens* strain or an *Agrobacterium rhizogenes* strain. Particle bombardment (also called Gene Gun, or Biolistics) technology is also very common method of plant transfection. Other less common transfection methods include tissue electroporation, silicon carbide whiskers, direct injection of DNA, etc. After transfection, the transfected plant cells or tissues placed on plant regeneration media to regenerate successfully transfected plant cells or tissues into transgenic plants.

Evaluation of a transformed plant can be accomplished at the DNA level, RNA level and protein level. A stably transformed plant can be evaluated at all of these levels and a transiently transformed plant is usually only evaluated at protein level. To ensure that the AMP ORF integrates into the genome of a stably transformed plant, the genomic DNA can be extracted from the stably transformed plant tissues for and analyzed using PCR or Southern blot. The expression of the AMP in the stably transformed plant can be evaluated at the RNA level, for example, by analyzing total mRNA extracted from the transformed plant tissues using northern blot or RT-PCR. The expression of the AMP in the transformed plant can also be evaluated in protein level directly. There are many ways to evaluate expression of AMP in a transformed plant. If a reporter gene included in the AMP ORF, a reporter gene assay can be performed, for example, in some embodiments a GUS straining assay for GUS reporter gene expression, a green fluorescence detection assay for GFP reporter gene expression, a luciferase assay for luciferase reporter gene expression, and/or other reporter techniques may be employed.

In some embodiments total protein can be extracted from the transformed plant tissues for the direct evaluation of the expression of the AMP using a Bradford assay to evaluate the total protein level in the sample.

In some embodiments, analytical HPLC chromatography technology, Western blot technique, or iELISA assay can be adopted to qualitatively or quantitatively evaluate the AMP in the extracted total protein sample from the transformed plant tissues. AMP expression can also be evaluated by using the extracted total protein sample from the transformed plant tissues in an insect bioassay, for example, in some embodiments, the transformed plant tissue or the whole transformed plant itself can be used in insect bioassays to evaluate AMP expression and its ability to provide protection for the plant.

In some embodiments, a plant, plant tissue, plant cell, plant seed, or part thereof of the present disclosure, can comprise one or more AMPs, or a polynucleotide encoding the same, said AMP comprising an amino acid sequence that is at least Confirming Successful Transformation Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) Molecular Cloning: A Laboratory Manual. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformed plant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformed plant, fractionated in a formaldehyde agarose gel, and blotted onto a nylon filter according to standard procedures that are routinely used in the art (Sambrook and Russell, 2001, supra).

Expression of RNA encoded by the polynucleotide encoding a AMP is then tested by hybridizing the filter to a radioactive probe derived from a AMP, by methods known in the art (Sambrook and Russell, 2001, supra).

Western blot, biochemical assays and the like may be carried out on the transgenic plants to confirm the presence of protein encoded by the AMP gene by standard procedures (Sambrook and Russell, 2001, supra) using antibodies that bind to one or more epitopes present on the AMP.

A number of markers have been developed to determine the success of plant transformation, for example, resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) J. Biol. Chem. 263:6310-6314 (bromoxynil resistance nitrilase gene); and Sathasivan et al. (1990) Nucl. Acids Res. 18:2188 (AHAS imidazolinone resistance gene). Additionally, the genes disclosed herein are useful as markers to assess transformation of bacterial, yeast, or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a AMP and/or a polynucleotide encoding the same may be tested for pesticidal activity, and the plants showing optimal activity selected for further breeding. Methods are available in the art to assay for pest activity. Generally, the protein is mixed and used in feeding assays. See, for example Marrone et al. (1985) J. of Economic Entomology 78:290-293.

In some embodiments, evaluating the success of a transient transfection procedure can be determined based on the expression of a reporter gene, for example, GFP. In some embodiments, GFP can be detected under UV light in tobacco leaves transformed with the FECT and/or TRBO vectors.

In some embodiments, AMP expression can be quantitatively evaluated in a plant (e.g., tobacco). An exemplary procedure that illustrates AMP quantification in a tobacco plant is as follows: 100 mg disks of transformed leaf tissue is collected by punching leaves with the large opening of a 1000 μL pipette tip. The collected leaf tissue is place into a 2 mL microtube with 5/32" diameter stainless steel grinding balls, and frozen in −80° C. for 1 hour, and then homogenized using a Troemner-Talboys High Throughput Homogenizer. Next, 750 μL ice-cold TSP-SE1 extraction solutions (sodium phosphate solution 50 mM, 1:100 diluted protease inhibitor cocktail, EDTA 1 mM, DIECA 10 mM, PVPP 8%, pH 7.0) is added into the tube and vortexed. The microtube is then left still at room temperature for 15 minutes and then centrifuged at 16,000 g for 15 minutes at 4° C.; 100 μL of the resulting supernatant is taken and loaded into pre-Sephadex G-50-packed column in 0.45 μm Millipore MultiScreen filter microtiter plate with empty receiving Costar microtiter plate on bottom. The microtiter plates are then centrifuged at 800 g for 2 minutes at 4° C. The resulting filtrate solution, herein called total soluble protein extract (TSP extract) of the tobacco leaves, is then ready for the quantitative analysis.

In some embodiments, the total soluble protein concentration of the TSP extract can be estimated using Pierce Coomassie Plus protein assay. BSA protein standards with known concentrations can be used to generate a protein quantification standard curve. For example, 2 μL of each TSP extract can be mixed into 200 μL of the chromogenic reagent (CPPA reagent) of the Coomassie Plus protein assay kits and incubated for 10 minutes. The chromogenic reaction can then be evaluated by reading OD595 using a SpectroMax-M2 plate reader using SoftMax Pro as control software. The concentrations of total soluble proteins can be about 0.788±0.20 μg/μL or about 0.533±0.03 μg/μL in the TSP extract from plants transformed via FECT and TRBO, respectively, and the results can be used to calculate the percentage of the expressed AMP in the TSP (% TSP) for the iELISA assay In some embodiments, an indirect ELISA (iELISA) assay can be used to quantitatively evaluate the AMP content in the tobacco leaves transiently transformed with the FECT and/or TRBO expression systems. An illustrative example of using iELISA to quantify AMP is as follows: 5 μL of the leaf TSP extract is diluted with 95 μL of CB2 solution (Immunochemistry Technologies) in the well of an Immulon 2HD 96-well plate, with serial dilutions performed as necessary; leaf proteins obtained from extract samples are then allowed to coat the well walls for 3 hours in the dark, at room temperature, and the CB2 solution is then subsequently removed; each well is washed twice with 200 μL PBS (Gibco); 150 μL blocking solution (Block BSA in PBS with 5% non-fat dry milk) is added into each well and incubated for 1 hour, in the dark, at room temperature; after the removal of the blocking solution, a PBS wash of the wells, 100 μL of primary antibodies directed against AMP (custom antibodies are commercially available from ProMab Biotechnologies, Inc.; GenScript®; or raised using the knowledge readily available to those having ordinary skill in the art); the antibodies diluted at 1: 250 dilution in blocking solution are added to each well and incubated for 1 hour in the dark at room temperature; the primary antibody is removed and each well is washed with PBS 4 times;100 μL of HRP-conjugated secondary antibody (i.e., antibody directed against host species used to generate primary antibody, used at 1:1000 dilution in the blocking solution) is added into each well and incubated for 1 hour in the dark at room temperature.; the secondary antibody is removed and the wells are washed with PBS, 100 μL; substrate solution (a 1:1 mixture of ABTS peroxidase substrate solution A and solution B, KPL) is added to each well, and the chromogenic reaction proceeds until sufficient color development is apparent; 100 μL of peroxidase stop solution is added to each well to stop the reaction; light absorbance of each reaction mixture in the plate is read at 405 nm using a SpectroMax-M2 plate reader, with SoftMax Pro used as control software; serially diluted known concentrations of pure AMPs samples can be treated in the same manner as described above in the iELISA assay to generate a mass-absorbance standard curve for quantities analysis. The expressed AMP can be detected by iELISA at about 3.09±1.83 ng/μL in the leaf TSP extracts from the FECT transformed tobacco; and about 3.56±0.74 ng/μL in the leaf TSP extract from the TRBO transformed tobacco. Alternatively, the expressed AMP can be about 0.40% total soluble protein (% TSP) for FECT transformed plants and about 0.67% TSP in TRBO transformed plants.

In some embodiments, the present disclosure provides a plant, plant tissue, plant cell, plant seed, or part thereof, comprising, consisting essentially of, or consisting of, one or more AMPs, or a polynucleotide encoding the same, said AMP comprising an amino acid sequence that is at least 90% identical to the amino acid sequence according to Formula (I): $X_1$-S-C-C-P-C-Y-W-$X_2$-$X_3$-C-P-W-G-Q-$X_4$-C-Y-P-X-G-C-$X_6$-G-$X_7$-X-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent.

In some embodiments, the present disclosure provides a plant, plant tissue, plant cell, plant seed, or part thereof, comprising, consisting essentially of, or consisting of, one or more AMPs, or a polynucleotide encoding the same, said AMP comprising an amino acid sequence that is at least 90% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent.

In some embodiments, the plant, plant tissue, plant cell, plant seed, or part thereof has an AMP wherein the AMP comprises, consists essentially of, or consists of, an amino sequence as set forth in any one of SEQ ID NOs: 6, 20, 24-26, 28-36, 38-42, 48, 54, 58, 60, 62-63, 69, 108, 116, 119, and 168-169.

In some embodiments, the plant, plant tissue, plant cell, plant seed, or part thereof has an AMP, wherein the AMP comprises, consists essentially of, or consists of, an amino sequence as set forth in any one of SEQ ID NOs: 20, 24-26, 35-36, 38, and 40.

In some embodiments, the plant, plant tissue, plant cell, plant seed, or part thereof has an AMP, wherein the AMP comprises, consists essentially of, or consists of, an amino sequence as set forth in any one of SEQ ID NOs: 25, 36, 38, and 40.

In some embodiments, the plant, plant tissue, plant cell, plant seed, or part thereof has an AMP, wherein the AMP further comprises a homopolymer or heteropolymer of two or more AMPs, wherein the amino acid sequence of each AMP is the same or different.

In some embodiments, The plant, plant tissue, plant cell, plant seed, or part thereof has an AMP, wherein the AMP is a fused protein comprising two or more AMPs separated by a cleavable or non-cleavable linker, and wherein the amino acid sequence of each AMP may be the same or different.

In some embodiments, the plant, plant tissue, plant cell, plant seed, or part thereof has an AMP, wherein the linker is cleavable inside the gut or hemolymph of an insect, or the gut of a mammal.

Any of the linkers described herein can be used in the foregoing plants, plant tissues, plant cells, plant seeds, or plant parts thereof.

Mixtures, Compositions, and Formulations

As used herein, "v/v" or "% v/v" or "volume per volume" refers to the volume concentration of a solution ("v/v" stands for volume per volume). Here, v/v can be used when both components of a solution are liquids. For example, when 50 mL of ingredient X is diluted with 50 mL of water, there will be 50 mL of ingredient X in a total volume of 100 mL; therefore, this can be expressed as "ingredient X 50% v/v." Percent volume per volume (% v/v) is calculated as follows: (volume of solute (mL)/volume of solution (100 mL)); e.g., % v/v=mL of solute/100 mL of solution.

As used herein, "w/w" or "% w/w" or "weight per weight" refers to the weight concentration of a solution, i.e., percent weight in weight ("w/w" stands for weight per weight). Here, w/w expresses the number of grams (g) of a constituent in 100 g of solution or mixture. For example, a mixture consisting of 30 g of ingredient X, and 70 g of water would be expressed as "ingredient X 30% w/w." Percent weight per weight (% w/w) is calculated as follows: (weight of solute (g)/weight of solution (g))×100; or (mass of solute (g)/mass of solution (g))×100.

As used herein, "w/v" or "% w/v" or "weight per volume" refers to the mass concentration of a solution, i.e., percent weight in volume ("w/v" stands for weight per volume). Here, w/v expresses the number of grams (g) of a constituent in 100 mL of solution. For example, if 1 g of ingredient X is used to make up a total volume of 100 mL, then a "1% w/v solution of ingredient X" has been made. Percent weight per volume (% w/v) is calculated as follows: (Mass of solute (g)/Volume of solution (mL))×100.

Any of the AMPs or AMP-insecticidal proteins described herein (e.g., an AMP having an amino acid sequence as set forth in SEQ ID NOs: 6, 20, 24-26, 28-36, 38-42, 48, 54, 58, 60, 62-63, 69, 108, 116, 119, and 168-169, or an agriculturally acceptable salt thereof) can be used to create a mixture and/or composition, wherein said mixture and/or composition consists of at least one AMP.

In some embodiments, the present disclosure comprises, consists essentially of, or consists of, a combination, a mixture, or a composition comprising, consisting essentially of, or consisting of, one or more AMPs, one or more AMP-insecticidal proteins, and/or combinations thereof.

In some embodiments, the invention contemplates a mixture of one or more AMPs, one or more AMP-insecticidal proteins, and/or combinations thereof. For example, in some embodiments, one or more AMPs, one or more AMP-insecticidal proteins, and/or combinations thereof, can be blended together in in varying proportions.

In some embodiments, the invention contemplates a combination of one or more AMPs, one or more AMP-insecticidal proteins, and/or combinations thereof. For example, in some embodiments, one or more AMPs, one or more AMP-insecticidal proteins, and/or combinations thereof, can be provided as a combination, e.g., in the same container, or in different containers.

In some embodiments, the invention contemplates a composition of one or more AMPs, one or more AMP-insecticidal proteins, and/or combinations thereof. For example, in some embodiments, one or more AMPs, one or more AMP-insecticidal proteins, and/or combinations thereof, can be provided as a composition further comprising an excipient.

In some embodiments, the combination, mixture, or composition comprises, consists essentially of, or consists of, an Av3 mutant polypeptide (AMP) having insecticidal activity against one or more insect species, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences provided in Table 1.

In some embodiments, the combination, mixture, or composition comprises, consists essentially of, or consists of, an Av3 mutant polypeptide (AMP) having insecticidal activity against one or more insect species, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences provided in Table 2.

In some embodiments, the combination, mixture, or composition comprises, consists essentially of, or consists of, an AMP having insecticidal activity against one or more insect species, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or an agriculturally acceptable salt thereof.

In some embodiments, the combination, mixture, or composition comprises, consists essentially of, or consists of, an AMP having insecticidal activity against one or more insect species, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-

G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; or an agriculturally acceptable salt thereof.

In some embodiments, the combination, mixture, or composition comprises, consists essentially of, or consists of, an AMP having an amino sequence as set forth in any one of SEQ ID NOs: 6, 20, 24-26, 28-36, 38-42, 48, 54, 58, 60, 62-63, 69, 108, 116, 119, and 168-169, or an agriculturally acceptable salt thereof.

In some embodiments, the combination, mixture, or composition comprises, consists essentially of, or consists of, an AMP having an amino sequence as set forth in any one of SEQ ID NOs: 20, 24-26, 35-36, 38, and 40, or an agriculturally acceptable salt thereof.

In some embodiments, the combination, mixture, or composition comprises, consists essentially of, or consists of, an AMP having an amino sequence as set forth in any one of SEQ ID NOs: 25, 36, 38, and 40, or an agriculturally acceptable salt thereof.

In some embodiments, a combination, mixture, or composition of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQDCYPDGCDGPK" (SEQ ID NO: 20), or an agriculturally acceptable salt thereof.

In some embodiments, a combination, mixture, or composition of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQDCYPDGCDGPK" (SEQ ID NO: 20), or an agriculturally acceptable salt thereof.

In some embodiments, a combination, mixture, or composition of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPNGCSGPK" (SEQ ID NO: 24), or an agriculturally acceptable salt thereof.

In some embodiments, a combination, mixture, or composition of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCDGPK" (SEQ ID NO: 25), or an agriculturally acceptable salt thereof.

In some embodiments, a combination, mixture, or composition of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWPGCPWGQNCYPEGCSGPK" (SEQ ID NO: 26), or an agriculturally acceptable salt thereof.

In some embodiments, a combination, mixture, or composition of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWPGCPWGQNCYPEGCRGPD" (SEQ ID NO: 35), or an agriculturally acceptable salt thereof.

In some embodiments, a combination, mixture, or composition of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCSGPG" (SEQ ID NO: 36), or an agriculturally acceptable salt thereof.

In some embodiments, a combination, mixture, or composition of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCGGPG" (SEQ ID NO: 38), or an agriculturally acceptable salt thereof.

In some embodiments, a combination, mixture, or composition of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KSCCPCYWGGCPWGQNCYPEGCSGPKVG" (SEQ ID NO: 40), or an agriculturally acceptable salt thereof.

In some embodiments, a combination, mixture, or composition of the present disclosure can comprise, consist essentially of, or consist of, an AMP, wherein said AMP homopolymer or heteropolymer of two or more AMPs, wherein the amino acid sequence of each AMP is the same or different.

In some embodiments, a combination, mixture, or composition of the present disclosure can comprise, consist essentially of, or consist of, an AMP that is a fused protein comprising two or more AMPs separated by a cleavable or non-cleavable linker, and wherein the amino acid sequence of each AMP may be the same or different.

In some embodiments, a combination, mixture, or composition of the present disclosure can comprise, consist essentially of, or consist of, an AMP having a linker, wherein the linker is a cleavable linker.

In some embodiments, a combination, mixture, or composition of the present disclosure can comprise, consist essentially of, or consist of, an AMP having a linker, wherein the linker has an amino acid sequence as set forth in any one of SEQ ID NOs: 184-193.

In some embodiments, a combination, mixture, or composition of the present disclosure can comprise, consist essentially of, or consist of, an AMP having a linker, wherein the linker is cleavable inside at least one of (i) the gut or hemolymph of an insect, and (ii) cleavable inside the gut of a mammal.

Any of the compositions, products, proteins, polypeptides, peptides, and/or plants transformed with polynucleotides operable to express an AMP, and described herein, can be used to control pests, their growth, and/or the damage caused by their actions, especially their damage to plants.

Compositions comprising an AMP, an AMP-insecticidal protein, or an agriculturally acceptable salt thereof, for example, agrochemical compositions, can include, but are not limited to, aerosols and/or aerosolized products, e.g., sprays, fumigants, powders, dusts, and/or gases; seed dressings; oral preparations (e.g., insect food, etc.); transgenic organisms expressing and/or producing an AMP, an AMP-insecticidal protein, and/or an AMP ORF (either transiently and/or stably), e.g., a plant or an animal.

The composition may be formulated as a powder, dust, pellet, granule, spray, emulsion, colloid, solution, or such like, and may be prepared by such conventional means as desiccation, lyophilization, homogenization, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

In some embodiments, the pesticide compositions described herein may be made by formulating either the AMP, AMP-insecticidal protein, or agriculturally acceptable salt thereof, with the desired agriculturally-acceptable carrier. The compositions may be formulated prior to administration in an appropriate means such as lyophilized, freeze-dried, desiccated, or in an aqueous carrier, medium or suitable diluent, such as saline and/or other buffer. In some embodiments, the formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. In some embodiments, the formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, the disclosure of which is incorporated by reference herein in its entirety.

In some embodiments, a composition can comprise, consist essentially of, or consist of, an AMP and an excipient.

In some embodiments, a composition can comprise, consist essentially of, or consist of, an AMP-insecticidal protein and an excipient.

In some embodiments, a composition can comprise, consist essentially of, or consist of, an AMP, an AMP-insecticidal protein, or an agriculturally acceptable salt thereof, and an excipient.

In some embodiments, a composition of the present disclosure can comprise: an AMP, an AMP-insecticidal protein, or an agriculturally acceptable salt thereof, and an excipient; wherein the AMP, AMP-insecticidal protein, or agriculturally acceptable salt thereof is in an amount ranging from about 0.000001% w/w to about 99.9% w/w of the total composition, or from about 0.010% to about 99.9%; from about 0.02% to about 99.9%; from about 0.03% to about 99.9%; from about 0.04% to about 99.9%; from about 0.05% to about 99.9%; from about 0.06% to about 99.9%; from about 0.07% to about 99.9%; from about 0.08% to about 99.9%; from about 0.09% to about 99.9%; from about 0.1% to about 99.9%; from about 0.2% to about 99.9%; from about 0.3% to about 99.9%; from about 0.4% to about 99.9%; from about 0.5% to about 99.9%; from about 0.6% to about 99.9%; from about 0.7% to about 99.9%; from about 0.8% to about 99.9%; from about 0.9% to about 99.9%; from about 1% to about 99.9%; from about 2% to about 99.9%; from about 3% to about 99.9%; from about 4% to about 99.9%; from about 5% to about 99.9%; from about 6% to about 99.9%; from about 7% to about 99.9%; from about 8% to about 99.9%; from about 9% to about 99.9%; from about 10% to about 99.9%; from about 11% to about 99.9%; from about 12% to about 99.9%; from about 13% to about 99.9%; from about 14% to about 99.9%; from about 15% to about 99.9%; from about 16% to about 99.9%; from about 17% to about 99.9%; from about 18% to about 99.9%; from about 19% to about 99.9%; from about 20% to about 99.9%; from about 21% to about 99.9%; from about 22% to about 99.9%; from about 23% to about 99.9%; from about 24% to about 99.9%; from about 25% to about 99.9%; from about 26% to about 99.9%; from about 27% to about 99.9%; from about 28% to about 99.9%; from about 29% to about 99.9%; from about 30% to about 99.9%; from about 31% to about 99.9%; from about 32% to about 99.9%; from about 33% to about 99.9%; from about 34% to about 99.9%; from about 35% to about 99.9%; from about 36% to about 99.9%; from about 37% to about 99.9%; from about 38% to about 99.9%; from about 39% to about 99.9%; from about 40% to about 99.9%; from about 41% to about 99.9%; from about 42% to about 99.9%; from about 43% to about 99.9%; from about 44% to about 99.9%; from about 45% to about 99.9%; from about 46% to about 99.9%; from about 47% to about 99.9%; from about 48% to about 99.9%; from about 49% to about 99.9%; from about 50% to about 99.9%; from about 51% to about 99.9%; from about 52% to about 99.9%; from about 53% to about 99.9%; from about 54% to about 99.9%; from about 55% to about 99.9%; from about 56% to about 99.9%; from about 57% to about 99.9%; from about 58% to about 99.9%; from about 59% to about 99.9%; from about 60% to about 99.9%; from about 61% to about 99.9%; from about 62% to about 99.9%; from about 63% to about 99.9%; from about 64% to about 99.9%; from about 65% to about 99.9%; from about 66% to about 99.9%; from about 67% to about 99.9%; from about 68% to about 99.9%; from about 69% to about 99.9%; from about 70% to about 99.9%; from about 71% to about 99.9%; from about 72% to about 99.9%; from about 73% to about 99.9%; from about 74% to about 99.9%; from about 75% to about 99.9%; from about 76% to about 99.9%; from about 77% to about 99.9%; from about 78% to about 99.9%; from about 79% to about 99.9%; from about 80% to about 99.9%; from about 81% to about 99.9%; from about 82% to about 99.9%; from about 83% to about 99.9%; from about 84% to about 99.9%; from about 85% to about 99.9%; from about 86% to about 99.9%; from about 87% to about 99.9%; from about 88% to about 99.9%; from about 89% to about 99.9%; from about 90% to about 99.9%; from about 91% to about 99.9%; from about 92% to about 99.9%; from about 93% to about 99.9%; from about 94% to about 99.9%; from about 95% to about 99.9%; from about 96% to about 99.9%; from about 97% to about 99.9%; from about 98% to about 99.9%; or from about 99% to about 99.9%, w/w of the total composition.

In some embodiments, a composition of the present disclosure comprises: an AMP, an AMP-insecticidal protein, or an agriculturally acceptable salt thereof, and an excipient, wherein the concentration of the AMP, AMP-insecticidal protein, or agriculturally acceptable salt thereof ranges from about 0.1% to about 99.9%; from about 1% to about 99.9%; from about 2% to about 99.9%; from about 3% to about 99.9%; from about 4% to about 99.9%; from about 5% to about 99.9%; from about 6% to about 99.9%; from about 7% to about 99.9%; from about 8% to about 99.9%; from about 9% to about 99.9%; from about 10% to about 99.9%; from about 11% to about 99.9%; from about 12% to about 99.9%; from about 13% to about 99.9%; from about 14% to about 99.9%; from about 15% to about 99.9%; from about 16% to about 99.9%; from about 17% to about 99.9%; from about 18% to about 99.9%; from about 19% to about 99.9%; from about 20% to about 99.9%; from about 21% to about 99.9%; from about 22% to about 99.9%; from about 23% to about 99.9%; from about 24% to about 99.9%; from about 25% to about 99.9%; from about 26% to about 99.9%; from about 27% to about 99.9%; from about 28% to about 99.9%; from about 29% to about 99.9%; from about 30% to about 99.9%; from about 31% to about 99.9%; from about 32% to about 99.9%; from about 33% to about 99.9%; from about 34% to about 99.9%; from about 35% to about 99.9%; from about 36% to about 99.9%; from about 37% to about 99.9%; from about 38% to about 99.9%; from about 39% to about 99.9%; from about 40% to about 99.9%; from about 41% to about 99.9%; from about 42% to about 99.9%; from about 43% to about 99.9%; from about 44% to about 99.9%; from about 45% to about 99.9%; from about 46% to about 99.9%; from about 47% to about 99.9%; from about 48% to about 99.9%; from about 49% to about 99.9%; from about 50% to about 99.9%; from about 51% to about 99.9%; from about 52% to about 99.9%; from about 53% to about 99.9%; from about 54% to about 99.9%; from about 55% to about 99.9%; from about 56% to about 99.9%; from about 57% to about 99.9%; from about 58% to about 99.9%; from about 59% to about 99.9%; from about 60% to about 99.9%; from about 61% to about 99.9%; from about 62% to about 99.9%; from about 63% to about 99.9%; from about 64% to about 99.9%; from about 65% to about 99.9%; from about 66% to about 99.9%; from about 67% to about 99.9%; from about 68% to about 99.9%; from about 69% to about 99.9%; from about 70% to about 99.9%; from about 71% to about 99.9%; from about 72% to about 99.9%; from about 73% to about 99.9%; from about 74% to about 99.9%; from about 75% to about 99.9%; from about 76% to about 99.9%; from about 77% to about 99.9%; from about 78% to about 99.9%; from about 79% to about 99.9%; from about 80% to about 99.9%; from about 81% to about 99.9%; from about 82% to about 99.9%; from about 83% to about 99.9%; from about 84% to about 99.9%;

from about 85% to about 99.9%; from about 86% to about 99.9%; from about 87% to about 99.9%; from about 88% to about 99.9%; from about 89% to about 99.9%; from about 90% to about 99.9%; from about 91% to about 99.9%; from about 92% to about 99.9%; from about 93% to about 99.9%; from about 94% to about 99.9%; from about 95% to about 99.9%; from about 96% to about 99.9%; from about 97% to about 99.9%; from about 98% to about 99.9%; or from about 99% to about 99.9%, wt/wt of the total combination or composition.

In some embodiments, a composition of the present disclosure comprises: an AMP, an AMP-insecticidal protein, or an agriculturally acceptable salt thereof, and an excipient, wherein the concentration of the AMP, AMP-insecticidal protein, or agriculturally acceptable salt thereof ranges from about 0.1% to about 99%; from about 0.1% to about 98%; from about 0.1% to about 97%; from about 0.1% to about 96%; from about 0.1% to about 95%; from about 0.1% to about 94%; from about 0.1% to about 93%; from about 0.1% to about 92%; from about 0.1% to about 91%; from about 0.1% to about 90%; from about 0.1% to about 89%; from about 0.1% to about 88%; from about 0.1% to about 87%; from about 0.1% to about 86%; from about 0.1% to about 85%; from about 0.1% to about 84%; from about 0.1% to about 83%; from about 0.1% to about 82%; from about 0.1% to about 81%; from about 0.1% to about 80%; from about 0.1% to about 79%; from about 0.1% to about 78%; from about 0.1% to about 77%; from about 0.1% to about 76%; from about 0.1% to about 75%; from about 0.1% to about 74%; from about 0.1% to about 73%; from about 0.1% to about 72%; from about 0.1% to about 71%; from about 0.1% to about 70%; from about 0.1% to about 69%; from about 0.1% to about 68%; from about 0.1% to about 67%; from about 0.1% to about 66%; from about 0.1% to about 65%; from about 0.1% to about 64%; from about 0.1% to about 63%; from about 0.1% to about 62%; from about 0.1% to about 61%; from about 0.1% to about 60%; from about 0.1% to about 59%; from about 0.1% to about 58%; from about 0.1% to about 57%; from about 0.1% to about 56%; from about 0.1% to about 55%; from about 0.1% to about 54%; from about 0.1% to about 53%; from about 0.1% to about 52%; from about 0.1% to about 510%; from about 0.1% to about 50%; from about 0.1% to about 49%; from about 0.1% to about 48%; from about 0.1% to about 47%; from about 0.1% to about 46%; from about 0.1% to about 45%; from about 0.1% to about 44%; from about 0.1% to about 43%; from about 0.1% to about 42%; from about 0.1% to about 41%; from about 0.1% to about 40%; from about 0.1% to about 39%; from about 0.1% to about 38%; from about 0.1% to about 37%; from about 0.1% to about 36%; from about 0.1% to about 35%; from about 0.1% to about 34%; from about 0.1% to about 33%; from about 0.1% to about 32%; from about 0.1% to about 31%; from about 0.1% to about 30%; from about 0.1% to about 29%; from about 0.1% to about 28%; from about 0.1% to about 27%; from about 0.1% to about 26%; from about 0.1% to about 25%; from about 0.1% to about 24%; from about 0.1% to about 23%; from about 0.1% to about 22%; from about 0.1% to about 21%; from about 0.1% to about 20%; from about 0.1% to about 19%; from about 0.1% to about 18%; from about 0.1% to about 17%; from about 0.1% to about 16%; from about 0.1% to about 15%; from about 0.1% to about 14%; from about 0.1% to about 13%; from about 0.1% to about 12%; from about 0.1% to about 11%; from about 0.1% to about 10%; from about 0.1% to about 9%; from about 0.1% to about 8%; from about 0.1% to about 7%; from about 0.1% to about 6%; from about 0.1% to about 5%; from about 0.1% to about 4%; from about 0.1% to about 3%; from about 0.1% to about 2%; from about 0.1% to about 1%; or from about 0.1% to about 0.5%, wt/wt of the total composition.

In some embodiments, a composition of the present disclosure comprises: an AMP, an AMP-insecticidal protein, or an agriculturally acceptable salt thereof, and an excipient, wherein the concentration of the AMP, AMP-insecticidal protein, or agriculturally acceptable salt thereof ranges from about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10, 1%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, %57% 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% by weight of the total composition.

In some embodiments, a composition of the present disclosure can comprise: an AMP, an AMP-insecticidal protein, or an agriculturally acceptable salt thereof, and an excipient; wherein the excipient is in an amount ranging from about 0.000001% w/w to about 99.9% w/w of the total composition, or from about 0.01% to about 99.9%; from about 0.02% to about 99.9%; from about 0.03% to about 99.9%; from about 0.04% to about 99.9%; from about 0.05% to about 99.9%; from about 0.06% to about 99.9%; from about 0.07% to about 99.9%; from about 0.08% to about 99.9%; from about 0.09% to about 99.9%; from about 0.1% to about 99.9%; from about 0.2% to about 99.9%; from about 0.3% to about 99.9%; from about 0.4% to about 99.9%; from about 0.5% to about 99.9%; from about 0.6% to about 99.9%; from about 0.7% to about 99.9%; from about 0.8% to about 99.9%; from about 0.9% to about 99.9%; from about 1% to about 99.9%; from about 2% to about 99.9%; from about 3% to about 99.9%; from about 4% to about 99.9%; from about 5% to about 99.9%; from about 6% to about 99.9%; from about 7% to about 99.9%; from about 8% to about 99.9%; from about 9% to about 99.9%; from about 10% to about 99.9%; from about 110% to about 99.9%; from about 12% to about 99.9%; from about 13% to about 99.9%; from about 14% to about 99.9%; from about 15% to about 99.9%; from about 16% to about 99.9%; from about 17% to about 99.9%; from about 18% to about 99.9%; from about 19% to about 99.9%; from about 20% to about 99.9%; from about 21% to about 99.9%; from about 22% to about 99.9%; from about 23% to about 99.9%; from about 24% to about 99.9%; from about 25% to about 99.9%; from about 26% to about 99.9%; from about 27% to about 99.9%; from about 28% to about 99.9%; from about 29% to about 99.9%; from about 30% to about 99.9%; from about 31% to about 99.9%; from about 32% to about 99.9%; from about 33% to about 99.9%; from about 34% to about 99.9%; from about 35% to about 99.9%; from about 36% to about 99.9%; from about 37% to about 99.9%; from about 38% to about 99.9%; from about 39% to about 99.9%; from about 40% to about 99.9%; from about 41% to about 99.9%; from about 42% to about 99.9%; from about 43% to about 99.9%; from about 44% to about 99.9%; from about 45% to about 99.9%; from about 46% to about 99.9%; from about 47% to about 99.9%; from about 48% to about 99.9%; from about 49% to about 99.9%; from about 50% to about 99.9%; from about 51% to about 99.9%; from about 52% to about 99.9%; from about 53% to about 99.9%; from about 54% to about 99.9%; from about 55% to about 99.9%; from about 56% to about 99.9%; from about 57% to about 99.9%; from about 58% to about 99.9%; from about 59% to about 99.9%; from about 60% to about 99.9%; from about 61% to about 99.9%; from about 62% to about 99.9%; from about 63% to about 99.9%; from about 64% to about 99.9%; from about 65% to about 99.9%; from about 66% to about 99.9%; from about 67% to about 99.9%; from about 68% to about 99.9%; from about 69% to about 99.9%; from about 70% to about 99.9%; from about 71% to about 99.9%; from about 72% to about 99.9%; from about 73% to about 99.9%; from about 74% to about 99.9%; from about 75% to about 99.9%; from about 76% to about 99.9%; from about 77% to about 99.9%; from about 78% to about 99.9%; from about 79% to about 99.9%; from about 80% to about 99.9%; from about 81% to about 99.9%; from about 82% to about 99.9%; from about 83% to about 99.9%; from about 84% to about 99.9%; from about 85% to about 99.9%; from about 86% to about 99.9%; from about 87% to about 99.9%; from about 88% to about 99.9%; from about 89% to about 99.9%; from about 90% to about 99.9%; from about 91% to about 99.9%; from about 92% to about 99.9%; from about 93% to about 99.9%; from about 94% to about 99.9%; from about 95% to about 99.9%; from about 96% to about 99.9%; from about 97% to about 99.9%; from about 98% to about 99.9%; or from about 99% to about 99.9%, w/w of the total composition.

In some embodiments, a composition of the present disclosure comprises: an AMP, an AMP-insecticidal protein, or an agriculturally acceptable salt thereof, and an excipient, wherein the concentration of the excipient ranges from about 0.10% to about 99.9%; from about 1% to about 99.9%; from about 2% to about 99.9%; from about 3% to about 99.9%; from about 4% to about 99.9%; from about 5% to about 99.9%; from about 6% to about 99.9%; from about 7% to about 99.9%; from about 8% to about 99.9%; from about 9% to about 99.9%; from about 10% to about 99.9%; from about 11% to about 99.9%; from about 12% to about 99.9%; from about 13% to about 99.9%; from about 14% to about 99.9%; from about 15% to about 99.9%; from about 16% to about 99.9%; from about 17% to about 99.9%; from about 18% to about 99.9%; from about 19% to about 99.9%; from about 20% to about 99.9%; from about 21% to about 99.9%; from about 22% to about 99.9%; from about 23% to about 99.9%; from about 24% to about 99.9%; from about 25% to about 99.9%; from about 26% to about 99.9%; from about 27% to about 99.9%; from about 28% to about 99.9%; from about 29% to about 99.9%; from about 30% to about 99.9%; from about 31% to about 99.9%; from about 32% to about 99.9%; from about 33% to about 99.9%; from about 34% to about 99.9%; from about 35% to about 99.9%; from about 36% to about 99.9%; from about 37% to about 99.9%; from about 38% to about 99.9%; from about 39% to about 99.9%; from about 40% to about 99.9%; from about 41% to about 99.9%; from about 42% to about 99.9%; from about 43% to about 99.9%; from about 44% to about 99.9%; from about 45% to about 99.9%; from about 46% to about 99.9%; from about 47% to about 99.9%; from about 48% to about 99.9%; from about 49% to about 99.9%; from about 50% to about 99.9%; from about 51% to about 99.9%; from about 52% to about 99.9%; from about 53% to about 99.9%; from about 54% to about 99.9%; from about 55% to about 99.9%; from about 56% to about 99.9%; from about 57% to about 99.9%; from about 58% to about 99.9%; from about 59% to about 99.9%; from about 60% to about 99.9%; from about 61% to about 99.9%; from about 62% to about 99.9%; from about 63% to about 99.9%; from about 64% to about 99.9%; from about 65% to about 99.9%; from about 66% to about 99.9%; from about 67% to about 99.9%; from about 68% to about 99.9%; from about 69% to about 99.9%; from about 70% to about 99.9%; from about 71% to about 99.9%; from about 72% to about 99.9%; from about 73% to about 99.9%; from about 74% to about 99.9%; from about 75% to about 99.9%; from about 76% to about 99.9%; from about 77% to about 99.9%; from about 78% to about 99.9%; from about 79% to about 99.9%; from about 80% to about 99.9%; from about 81% to about 99.9%; from about 82% to about 99.9%; from about 83% to about 99.9%; from about 84% to about 99.9%; from about 85% to about 99.9%; from about 86% to about 99.9%; from about 87% to about 99.9%; from about 88% to about 99.9%; from about 89% to about 99.9%; from about 90% to about 99.9%; from about 91% to about 99.9%; from about 92% to about 99.9%; from about 93% to about 99.9%; from about 94% to about 99.9%; from about 95% to about 99.9%; from about 96% to about 99.9%; from about 97% to about 99.9%; from about 98% to about 99.9%; or from about 99% to about 99.9%, wt/wt of the total combination or composition.

In some embodiments, a composition of the present disclosure comprises: an AMP, an AMP-insecticidal protein, or an agriculturally acceptable salt thereof, and an excipient, wherein the concentration of the excipient ranges from about 0.10% to about 99%; from about 0.1% to about 98%; from about 0.1% to about 97%; from about 0.1% to about 96%; from about 0.1% to about 95%; from about 0.1% to about 94%; from about 0.1% to about 930%; from about 0.10% to about 92%; from about 0.10% to about 910%; from about 0.10% to about 90%; from about 0.10% to about 89%; from about 0.10% to about 88%; from about 0.1% to about 87%; from about 0.1% to about 86%; from about 0.1% to about 85%; from about 0.10% to about 84%; from about 0.10% to about 83%; from about 0.10% to about 82%; from about 0.1% to about 81%; from about 0.1% to about 80%; from about 0.1% to about 79%; from about 0.1% to about 78%; from about 0.1% to about 77%; from about 0.1% to about 76%; from about 0.1% to about 75%; from about 0.1% to about 74%; from about 0.1% to about 73%; from about 0.10% to about 72%; from about 0.10% to about 71%; from about 0.1% to about 70%; from about 0.1% to about 69%; from about 0.1% to about 68%; from about 0.10% to about 67%; from about 0.10% to about 66%; from about 0.10% to about 65%; from about 0.1% to about 64%; from about 0.1% to about 63%; from about 0.1% to about 62%; from about 0.1% to about 61%; from about 0.1% to about 60%; from about 0.1% to about 59%; from about 0.1% to about 58%; from about 0.1% to about 57%; from about 0.1% to about 56%; from about 0.1% to about 55%; from about 0.1% to about 54%; from about 0.1% to about 53%; from about 0.1% to about 52%; from about 0.1% to about 51%; from about 0.1% to about 50%; from about 0.1% to about 49%; from about 0.1% to about 48%; from about 0.1% to about 47%; from about 0.1% to about 46%; from about 0.1% to about 45%; from about 0.1% to about 44%; from about 0.1% to about 43%; from about 0.1% to about 42%; from about 0.1% to about 41%; from about 0.1% to about 40%; from about 0.1% to about 39%; from about 0.1% to about 38%; from about 0.1% to about 37%; from about 0.1% to about 36%; from about 0.1% to about 35%; from about 0.1% to about 34%; from about 0.1% to about 33%; from about 0.1% to about 32%; from about 0.1% to about 31%; from about 0.1% to about 30%; from about 0.1% to about 29%; from about 0.1% to about 28%; from about 0.1% to about 27%; from about 0.1% to about 26%; from about 0.1% to about 25%; from about 0.1% to about 24%; from about 0.1% to about 23%; from about 0.1% to about 22%; from about 0.1% to about 21%; from about 0.1% to about 20%; from about 0.1% to about 19%; from about 0.1% to about 18%; from about 0.1% to about 17%; from about 0.1% to about 16%; from about 0.1% to about 15%; from about 0.1% to about 14%; from about 0.1% to about 13%; from about 0.1% to about 12%; from about 0.1% to about 11%; from about 0.1% to about 10%; from about 0.1% to about 9%; from about 0.1% to about 8%; from about 0.1% to about 7%; from about 0.1% to about 6%; from about 0.1% to about 5%; from about 0.1% to about 4%; from about 0.1% to about 3%; from about 0.1% to about 2%; from about 0.1% to about 10%; or from about 0.1% to about 0.5%, wt/wt of the total composition.

In some embodiments, a composition of the present disclosure comprises: an AMP, an AMP-insecticidal protein, or an agriculturally acceptable salt thereof, and an excipient, wherein the concentration of the excipient ranges from about 0.010%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52, 53% 54%, 55%, 56%, %57% 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% by weight of the total composition.

Sprayable Compositions

Examples of spray products of the present disclosure can include field sprayable formulations for agricultural usage and indoor sprays for use in interior spaces in a residential or commercial space. In some embodiments, residual sprays or space sprays comprising an AMP, an AMP-insecticidal protein, or an agriculturally acceptable salt thereof can be used to reduce or eliminate insect pests in an interior space.

Surface spraying indoors (SSI) is the technique of applying a variable volume sprayable volume of an insecticide onto indoor surfaces where vectors rest, such as on walls, windows, floors and ceilings. The primary goal of variable volume sprayable volume is to reduce the lifespan of the insect pest, (for example, a fly, a flea, a tick, or a mosquito vector) and thereby reduce or interrupt disease transmission. The secondary impact is to reduce the density of insect pests within the treatment area. SSI can be used as a method for the control of insect pest vector diseases, such as Lyme disease, *Salmonella*, Chikungunya virus, Zika virus, and malaria, and can also be used in the management of parasites carried by insect vectors, such as Leishmaniasis and Chagas disease. Many mosquito vectors that harbor Zika virus, Chikungunya virus, and malaria include endophilic mosquito vectors, resting inside houses after taking a blood meal. These mosquitoes are particularly susceptible to control through surface spraying indoors (SSI) with a sprayable composition comprising an AMP, an AMP-insecticidal protein, or an agriculturally acceptable salt thereof, and an excipient. As its name implies, SSI involves applying the composition onto the walls and other surfaces of a house with a residual insecticide.

In one embodiment, the composition comprising an AMP, an AMP-insecticidal protein, or an agriculturally acceptable salt thereof, and an excipient will knock down insect pests that come in contact with these surfaces. SSI does not directly prevent people from being bitten by mosquitoes. Rather, it usually controls insect pests after they have blood fed, if they come to rest on the sprayed surface. SSI thus prevents transmission of infection to other persons. To be effective, SSI must be applied to a very high proportion of households in an area (usually greater than 40-80 percent). Therefore, sprays in accordance with the invention having good residual efficacy and acceptable odor are particularly suited as a component of integrated insect pest vector management or control solutions.

In contrast to SSI, which requires that the active AMP or AMP-insecticidal protein be bound to surfaces of dwellings, such as walls or ceilings, as with a paint, for example, space spray products of the invention rely on the production of a large number of small insecticidal droplets intended to be distributed through a volume of air over a given period of time. When these droplets impact on a target insect pest, they deliver a knockdown effective dose of the AMP or AMP-insecticidal protein effective to control the insect pest. The traditional methods for generating a space-spray include thermal fogging (whereby a dense cloud of a composition comprising an AMP, an AMP-insecticidal protein, or an agriculturally acceptable salt thereof is produced giving the appearance of a thick fog) and Ultra Low Volume (ULV), whereby droplets are produced by a cold, mechanical aerosol-generating machine. Ready-to-use aerosols such as aerosol cans may also be used.

Because large areas can be treated at any one time, the foregoing method is a very effective way to rapidly reduce the population of flying insect pests in a specific area. And, because there is very limited residual activity from the application, it must be repeated at intervals of 5-7 days in order to be fully effective. This method can be particularly effective in epidemic situations where rapid reduction in insect pest numbers is required. As such, it can be used in urban dengue control campaigns.

Effective space-spraying is generally dependent upon the following specific principles. Target insects are usually flying through the spray cloud (or are sometimes impacted whilst resting on exposed surfaces). The efficiency of contact between the spray droplets and target insects is therefore crucial. This is achieved by ensuring that spray droplets remain airborne for the optimum period of time and that they contain the right dose of insecticide. These two issues are largely addressed through optimizing the droplet size. If droplets are too big they drop to the ground too quickly and don't penetrate vegetation or other obstacles encountered during application (limiting the effective area of application). If one of these big droplets impacts an individual insect then it is also "overkill," because a high dose will be delivered per individual insect. If droplets are too small then they may either not deposit on a target insect (no impaction) due to aerodynamics or they can be carried upwards into the atmosphere by convection currents. The optimum size of droplets for space-spray application are droplets with a Volume Median Diameter (VMD) of 10-25 microns.

In some embodiments, a sprayable composition may contain an amount of an AMP, or an agriculturally acceptable salt thereof, ranging from about 0.005 wt % to about 99 wt %.

In some embodiments, a sprayable composition may contain an amount of an AMP-insecticidal protein, or an agriculturally acceptable salt thereof, ranging from about 0.005 wt % to about 99 wt %.

Foams

The active compositions of the present disclosure comprising an AMP, an AMP-insecticidal protein, or an agriculturally acceptable salt thereof, and an excipient, may be made available in a spray product as an aerosol-based application, including aerosolized foam applications. Pressurized cans are the typical vehicle for the formation of aerosols. An aerosol propellant that is compatible with the AMP or AMP-insecticidal protein used. Preferably, a liquefied-gas type propellant is used.

Suitable propellants include compressed air, carbon dioxide, butane and nitrogen. The concentration of the propellant in the active compound composition is from about 5 percent to about 40 percent by weight of the pyridine composition, preferably from about 15 percent to about 30 percent by weight of the comprising an AMP, an AMP-insecticidal protein, or an agriculturally acceptable salt thereof, and an excipient.

In one embodiment, formulations comprising an AMP, an AMP-insecticidal protein, or an agriculturally acceptable salt thereof can also include one or more foaming agents. Foaming agents that can be used include sodium laureth sulfate, cocamide DEA, and cocamidopropyl betaine. Preferably, the sodium laureth sulfate, cocamide DEA and cocamidopropyl are used in combination. The concentration of the foaming agent(s) in the active compound composition is from about 10 percent to about 25 percent by weight, more preferably 15 percent to 20 percent by weight of the composition.

When such formulations are used in an aerosol application not containing foaming agents, the active compositions of the present disclosure can be used without the need for mixing directly prior to use. However, aerosol formulations containing the foaming agents do require mixing (i.e., shaking) immediately prior to use. In addition, if the formulations containing foaming agents are used for an extended time, they may require additional mixing at periodic intervals during use.

In some embodiments, an aerosolized foam may contain an amount of an AMP, or an agriculturally acceptable salt thereof, ranging from about 0.005 wt % to about 99 Wt %.

In some embodiments, an aerosolized foam may contain an amount of an AMP-insecticidal protein, or an agriculturally acceptable salt thereof, ranging from about 0.005 wt % to about 99 wt %.

Burning Formulations

In some embodiments, a dwelling area may also be treated with an active AMP or AMP-insecticidal protein composition by using a burning formulation, such as a candle, a smoke coil or a piece of incense containing the composition. For example, the composition may be formulated into household products such as "heated" air fresheners in which insecticidal compositions are released upon heating, e.g., electrically, or by burning. The active compound compositions of the present disclosure comprising an AMP, an AMP-insecticidal protein, or an agriculturally acceptable salt thereof may be made available in a spray product as an aerosol, a mosquito coil, and/or a vaporizer or fogger.

In some embodiments, a burning formulation may contain an amount of an AMP, or an agriculturally acceptable salt thereof, ranging from about 0.005 wt % to about 99 Wt %.

In some embodiments, a burning formulation may contain an amount of an AMP-insecticidal protein, or an agriculturally acceptable salt thereof, ranging from about 0.005 wt % to about 99 wt %.

Fabric Treatments

In some embodiments, fabrics and garments may be made containing a pesticidal effective composition comprising an AMP, an AMP-insecticidal protein, or an agriculturally acceptable salt thereof, and an excipient. In some embodiments, the concentration of the AMP or AMP-insecticidal protein in the polymeric material, fiber, yarn, weave, net, or substrate described herein, can be varied within a relatively wide concentration range from, for example, 0.05 to 15 percent by weight, preferably 0.2 to 10 percent by weight, more preferably 0.4 to 8 percent by weight, especially 0.5 to 5, such as 1 to 3, percent by weight.

Similarly, the concentration of the composition comprising an AMP, an AMP-insecticidal protein, or an agriculturally acceptable salt thereof, and an excipient (whether for treating surfaces or for coating a fiber, yarn, net, weave) can be varied within a relatively wide concentration range from, for example 0.1 to 70 percent by weight, such as 0.5 to 50 percent by weight, preferably 1 to 40 percent by weight, more preferably 5 to 30 percent by weight, especially 10 to 20 percent by weight.

The concentration of the AMP or AMP-insecticidal protein may be chosen according to the field of application such that the requirements concerning knockdown efficacy, durability and toxicity are met. Adapting the properties of the material can also be accomplished and so custom-tailored textile fabrics are obtainable in this way.

Accordingly, an effective amount of an AMP, an AMP-insecticidal protein, or an agriculturally acceptable salt thereof can depend on the specific use pattern, the insect pest against which control is most desired and the environment in which the AMP or AMP-insecticidal protein will be used. Therefore, an effective amount of an AMP, an AMP-insecticidal protein, or an agriculturally acceptable salt thereof is sufficient that control of an insect pest is achieved.

In some embodiments, a fabric treatment may contain an amount of an AMP, or an agriculturally acceptable salt thereof, ranging from about 0.005 wt % to about 99 wt %.

In some embodiments, a fabric treatment may contain an amount of an AMP-insecticidal protein, or an agriculturally acceptable salt thereof, ranging from about 0.005 wt % to about 99 wt %.

Surface-Treatment Compositions

In some embodiments, the present disclosure provides compositions or formulations comprising an AMP and an excipient, or comprising an AMP-insecticidal protein and an excipient, for coating walls, floors and ceilings inside of buildings, and for coating a substrate or non-living material. The inventive compositions comprising an AMP, an AMP-insecticidal protein, or an agriculturally acceptable salt thereof, and an excipient, can be prepared using known techniques for the purpose in mind. Preparations of compositions comprising an AMP-insecticidal protein and an excipient, could be so formulated to also contain a binder to facilitate the binding of the compound to the surface or other substrate. Agents useful for binding are known in the art and tend to be polymeric in form. The type of binder suitable for a compositions to be applied to a wall surface having particular porosities and/or binding characteristics would be different compared to a fiber, yam, weave or net—thus, a skilled person, based on known teachings, would select a suitable binder based on the desired surface and/or substrate.

Typical binders are poly vinyl alcohol, modified starch, poly vinyl acrylate, polyacrylic, polyvinyl acetate co polymer, polyurethane, and modified vegetable oils. Suitable binders can include latex dispersions derived from a wide variety of polymers and co-polymers and combinations thereof. Suitable latexes for use as binders in the inventive compositions comprise polymers and copolymers of styrene, alkyl styrenes, isoprene, butadiene, acrylonitrile lower alkyl acrylates, vinyl chloride, vinylidene chloride, vinyl esters of lower carboxylic acids and alpha, beta-ethylenically unsaturated carboxylic acids, including polymers containing three or more different monomer species copolymerized therein, as well as post-dispersed suspensions of silicones or polyurethanes. Also suitable may be a polytetrafluoroethylene (PTFE) polymer for binding the active ingredient to other surfaces.

In some embodiments, a surface-treatment composition may contain an amount of an AMP, or an agriculturally acceptable salt thereof, ranging from about 0.005 wt % to about 99 wt %.

In some embodiments, a surface-treatment composition may contain an amount of an AMP-insecticidal protein, or an agriculturally acceptable salt thereof, ranging from about 0.005 wt % to about 99 wt %.

Dispersants

In some exemplary embodiments, an insecticidal formulation according to the present disclosure may consist of an AMP, an AMP-insecticidal protein, or an agriculturally acceptable salt thereof, and an excipient, diluent or carrier (e.g., such as water), a polymeric binder, and/or additional components such as a dispersing agent, a polymerizing agent, an emulsifying agent, a thickener, an alcohol, a fragrance, or any other inert excipients used in the preparation of sprayable insecticides known in the art.

In some embodiments, a composition comprising an AMP, an AMP-insecticidal protein, or an agriculturally acceptable salt thereof, and an excipient, can be prepared in a number of different forms or formulation types, such as suspensions or capsules suspensions. And a person skilled in the art can prepare the relevant composition based on the properties of the particular AMP or AMP-insecticidal protein, its uses, and also its application type. For example, the AMP or AMP-insecticidal protein used in the methods, embodiments, and other aspects of the present disclosure, may be encapsulated in a suspension or capsule suspension formulation. An encapsulated AMP or AMP-insecticidal protein can provide improved wash-fastness, and also a longer period of activity. The formulation can be organic based or aqueous based, preferably aqueous based.

In some embodiments, a dispersant may contain an amount of an AMP, or an agriculturally acceptable salt thereof, ranging from about 0.005 wt % to about 99 wt %.

In some embodiments, a dispersant may contain an amount of an AMP-insecticidal protein, or an agriculturally acceptable salt thereof, ranging from about 0.005 wt % to about 99 wt %.

Microencapsulation

Microencapsulated AMP or AMP-insecticidal protein suitable for use in the compositions and methods according to the present disclosure may be prepared with any suitable technique known in the art. For example, various processes for microencapsulating material have been previously developed. These processes can be divided into three categories: physical methods, phase separation, and interfacial reaction. In the physical methods category, microcapsule wall material and core particles are physically brought together and the wall material flows around the core particle to form the microcapsule. In the phase separation category, microcapsules are formed by emulsifying or dispersing the core material in an immiscible continuous phase in which the wall material is dissolved and caused to physically separate from the continuous phase, such as by coacervation, and deposit around the core particles. In the interfacial reaction category, microcapsules are formed by emulsifying or dispersing the core material in an immiscible continuous phase and then an interfacial polymerization reaction is caused to take place at the surface of the core particles. The concentration of the AMP or AMP-insecticidal protein present in the microcapsules can vary from 0.1 to 60% by weight of the microcapsule.

In some embodiments, a microencapsulation may contain an amount of an AMP, or an agriculturally acceptable salt thereof, ranging from about 0.005 wt % to about 99 Wt %.

In some embodiments, a microencapsulation may contain an amount of an AMP-insecticidal protein, or an agriculturally acceptable salt thereof, ranging from about 0.005 wt % to about 99 wt %.

Formulations, Dispersants, Kits, and the Ingredients Thereof

The formulation used in the compositions (comprising an AMP, an AMP-insecticidal protein, or an agriculturally acceptable salt thereof, and an excipient), methods, embodiments and other aspects according to the present disclosure, may be formed by mixing all ingredients together with water, and optionally using suitable mixing and/or dispersing aggregates. In general, such a formulation is formed at a temperature of from 10 to 70° C., preferably 15 to 50° C., more preferably 20 to 40° C. Generally, a formulation comprising one or more of (A), (B), (C), and/or (D) is possible, wherein it is possible to use: an AMP, an AMP-insecticidal protein, or an agriculturally acceptable salt thereof (as pesticide) (A); solid polymer (B); optional additional additives (D); and to disperse them in the aqueous component (C). If a binder is present in a composition of the present disclosure (comprising an AMP, an AMP-insecticidal protein, or an agriculturally acceptable salt thereof, and an excipient), it is preferred to use dispersions of the polymeric binder (B) in water as well as aqueous formulations of the AMP or AMP-insecticidal protein (A) in water which have been separately prepared before. Such separate formulations may contain additional additives for stabilizing (A) and/or (B) in the respective formulations and are commercially available. In a second process step, such raw formulations and optionally additional water (component (C)) are added. Also, combinations of the abovementioned ingredients based on the foregoing scheme are likewise possible, e.g., using a pre-formed dispersion of (A) and/or (B) and mixing it with solid (A) and/or (B). A dispersion of the polymeric binder (B) may be a pre-manufactured dispersion already made by a chemicals manufacturer.

Moreover, it is also within the scope of the present disclosure to use "hand-made" dispersions, i.e., dispersions made in small-scale by an end-user. Such dispersions may be made by providing a mixture of about 20 percent of the binder (B) in water, heating the mixture to temperature of 90° C. to 100° C. and intensively stirring the mixture for several hours. It is possible to manufacture the formulation as a final product so that it can be readily used by the end-user for the process according to the present disclosure. And, it is of course similarly possible to manufacture a concentrate, which may be diluted by the end-user with additional water (C) to the desired concentration for use.

In an embodiment, a composition (comprising an AMP, an AMP-insecticidal protein, or an agriculturally acceptable salt thereof, and an excipient) suitable for SSI application or a coating formulation (comprising an AMP, an AMP-insecticidal protein, or an agriculturally acceptable salt thereof, and an excipient), contains the active ingredient and a carrier, such as water, and may also one or more co-formulants selected from a dispersant, a wetter, an anti-freeze, a thickener, a preservative, an emulsifier and a binder or sticker.

In some embodiments, an exemplary solid formulation of an AMP, an AMP-insecticidal protein, or an agriculturally acceptable salt thereof, is generally milled to a desired particle size, such as the particle size distribution d(0.5) is generally from 3 to 20, preferably 5 to 15, especially 7 to 12, μm.

Furthermore, it may be possible to ship the formulation to the end-user as a kit comprising at least a first component comprising an AMP, an AMP-insecticidal protein, or an agriculturally acceptable salt thereof (A); and a second component comprising at least one polymeric binder (B). Further additives (D) may be a third separate component of the kit, or may be already mixed with components (A) and/or (B). The end-user may prepare the formulation for use by just adding water (C) to the components of the kit and mixing. The components of the kit may also be formulations in water. Of course it is possible to combine an aqueous formulation of one of the components with a dry formulation of the other component(s). As an example, the kit can consist of one formulation of an AMP, an AMP-insecticidal protein, or an agriculturally acceptable salt thereof (A) and optionally water (C); and a second, separate formulation of at least one polymeric binder (B), water as component (C) and optionally components (D).

The concentrations of the components (A), (B), (C) and optionally (D) will be selected by the skilled artisan depending of the technique to be used for coating/treating. In general, the amount of an AMP, an AMP-insecticidal protein, or an agriculturally acceptable salt thereof (A) may be up to 50, preferably 1 to 50, such as 10 to 40, especially 15 to 30, percent by weight, based on weight of the composition. The amount of polymeric binder (B) may be in the range of 0.01 to 30, preferably 0.5 to 15, more preferably 1 to 10, especially 1 to 5, percent by weight, based on weight of the composition. If present, in general the amount of additional components (D) is from 0.1 to 20, preferably 0.5 to 15, percent by weight, based on weight of the composition. If present, suitable amounts of pigments and/or dyestuffs and/or fragrances are in general 0.01 to 5, preferably 0.1 to 3, more preferably 0.2 to 2, percent by weight, based on weight of the composition. A typical formulation ready for use comprises 0.1 to 40, preferably 1 to 30, percent of components (A), (B), and optionally (D), the residual amount being water (C). A typical concentration of a concentrate to be diluted by the end-user may comprise 5 to 70, preferably 10 to 60, percent of components (A), (B), and optionally (D), the residual amount being water (C).

Illustrative Mixtures, Compositions, Products, And Transgenic Organisms

The present disclosure contemplates mixtures, compositions, products, and transgenic organisms that contain—or, in the case of transgenic organisms, express or otherwise produce—one or more AMPs, or one or more AMP-insecticidal proteins.

In some embodiments, the illustrative mixtures consists of: (1) an AMP, an AMP-insecticidal proteins, or an agriculturally acceptable salt thereof, and (2) an excipient (e.g., any of the excipients described herein).

In some embodiments, the mixtures of the present disclosure consist of: (1) one or more AMPs, one or more AMP-insecticidal proteins, or an agriculturally acceptable salt thereof; and (2) one or more excipients (e.g., any of the excipients described herein).

In some embodiments, the mixtures of the present disclosure consist of: (1) one or more AMPs, one or more AMP-insecticidal proteins, or an agriculturally acceptable salt thereof; and (2) one or more excipients (e.g., any of the excipients described herein); wherein either of the foregoing (1) or (2) can be used concomitantly, or sequentially.

Any of the combinations, mixtures, products, polypeptides and/or plants utilizing an AMP, or an AMP-insecticidal protein (as described herein), can be used to control pests, their growth, and/or the damage caused by their actions, especially their damage to plants.

Compositions comprising an AMP or an AMP-insecticidal protein, or an agriculturally acceptable salt thereof, and an excipient, can include agrochemical compositions. For example, in some embodiments, agrochemical compositions can include, but is not limited to, aerosols and/or aerosolized products (e.g., sprays, fumigants, powders, dusts, and/or gases); seed dressings; oral preparations (e.g., insect food, etc.); or a transgenic organisms (e.g., a cell, a plant, or an animal) expressing and/or producing an AMP or an AMP-insecticidal protein, either transiently and/or stably.

In some embodiments, the active ingredients of the present disclosure can be applied in the form of compositions and can be applied to the crop area or plant to be treated, simultaneously or in succession, with other non-active compounds. These compounds can be fertilizers, weed killers, cryoprotectants, surfactants, detergents, soaps, dormant oils, polymers, and/or time-release or biodegradable carrier formulations that permit long-term dosing of a target area following a single application of the formulation. One or more of these non-active compounds can be prepared, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise, the formulations may be prepared into edible "baits" or fashioned into pest "traps" to permit feeding or ingestion by a target pest of the pesticidal formulation.

Methods of applying an active ingredient of the present disclosure or an agrochemical composition of the present disclosure that consists of an AMP or AMP-insecticidal protein or an agriculturally acceptable salt thereof, and an excipient, as produced by the methods described herein of the present disclosure, include leaf application, seed coating and soil application. In some embodiments, the number of applications and the rate of application depend on the intensity of infestation by the corresponding pest.

The composition comprising an AMP or an AMP-insecticidal protein or an agriculturally acceptable salt thereof and an excipient may be formulated as a powder, dust, pellet, granule, spray, emulsion, colloid, solution, or such like, and may be prepared by such conventional means as desiccation, lyophilization, homogenization, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

In some embodiments, compositions containing AMPs or AMP-insecticidal proteins (or an agriculturally acceptable salt thereof) may be prophylactically applied to an environmental area to prevent infestation by a susceptible pest, for example, a lepidopteran and/or coleopteran pest, which may be killed or reduced in numbers in a given area by the methods of the invention. In some embodiments, the pest ingests, or comes into contact with, a pesticidally-effective amount of the polypeptide.

In some embodiments, the pesticide compositions described herein may be made by formulating either the AMP or AMP-insecticidal-protein or an agriculturally acceptable salt thereof transformed bacterial, yeast, or other cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline and/or other buffer. In some embodiments, the formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. In some embodiments, the formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, the disclosure of which is incorporated herein by reference in its entirety.

METHODS OF USING THE PRESENT DISCLOSURE

Any of the methods of using the present disclosure, e.g., methods of protecting plants, plant parts, and seeds; or methods of using mixtures and compositions; can be implemented using any one or more of the AMPs or AMP-insecticidal proteins as described herein. For example, any of the methods of using the present disclosure as described herein can be implemented using, e.g., one or more AMP having the amino acid sequence selected from any one of SEQ ID NOs: 6, 20, 24-26, 28-36, 38-42, 48, 54, 58, 60, 62-63, 69, 108, 116, 119, and 168-169, which are likewise described herein.

Methods for Protecting Plants, Plant Parts, and Seeds

In some embodiments, the present disclosure provides a method for controlling an invertebrate pest in agronomic and/or nonagronomic applications, comprising contacting the invertebrate pest or its environment, a solid surface, including a plant surface, or part thereof, with a pesticidally effective amount of one or more of the AMPs of the invention, one or more AMP-insecticidal proteins, or an agriculturally acceptable salt thereof.

In some embodiments, the present disclosure provides a method for controlling an invertebrate pest in agronomic and/or nonagronomic applications, comprising contacting the invertebrate pest or its environment, a solid surface, including a plant surface or part thereof, with a pesticidally effective amount of a composition comprising at least one AMP of the invention and an excipient.

In some embodiments, the present disclosure provides a method for controlling an invertebrate pest in agronomic and/or nonagronomic applications, comprising contacting the invertebrate pest or its environment, a solid surface, including a plant surface or part thereof, with a pesticidally effective amount of a composition comprising at least one AMP-insecticidal protein of the invention and an excipient.

Examples of suitable compositions comprising: (1) at least one AMP of the invention; two or more of the AMPs of the present disclosure; an AMP-insecticidal protein; two or more AMP-insecticidal proteins; or an agriculturally acceptable salt thereof; and (2) an excipient; include said compositions formulated win inactive ingredients to be delivered in the form of: a liquid solution, an emulsion, a powder, a granule, a nanoparticle, a microparticle, or a combination thereof.

In some embodiments, to achieve contact with a compound, mixture, or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising an AMP, an AMP-insecticidal protein, or an agriculturally acceptable salt thereof, and an excipient, can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present disclosure in the form of a soil drench liquid formulation. Also of note is a method for controlling an invertebrate pest comprising contacting the invertebrate pest or its environment with a biologically effective amount of an AMP or AMP-insecticidal protein. Of further note, in some illustrative embodiments, the illustrative method contemplates a soil environment, wherein the composition is applied to the soil as a soil drench formulation. Of further note is that an AMP, an AMP-insecticidal protein, or an agriculturally acceptable salt thereof, is also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compounds of this invention can also be impregnated into materials for fabricating invertebrate control devices (e.g., insect netting, application onto clothing, application into candle formulations and the like).

In some embodiments, an AMP, an AMP-insecticidal protein, or an agriculturally acceptable salt thereof, is also useful in seed treatments for protecting seeds from invertebrate pests. In the context of the present disclosure and claims, treating a seed means contacting the seed with a biologically effective amount of an AMP, an AMP-insecticidal protein, or an agriculturally acceptable salt thereof, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the AMP or AMP-insecticidal protein within the developing plant. Seed treatments can be applied to all types of seeds, including those from which plants genetically transformed to express specialized traits will germinate. In addition, an AMP or an AMP-insecticidal protein can be transformed into a plant or part thereof, for example a plant cell, or plant seed, that is already transformed, e.g., those expressing herbicide resistance such as glyphosate acetyltransferase, which provides resistance to glyphosate.

One method of seed treatment is by spraying or dusting the seed with an AMP, an AMP-insecticidal protein, or an agriculturally acceptable salt thereof, (i.e. as a formulated composition or a mixture comprising an AMP, an AMP-insecticidal protein, or an agriculturally acceptable salt thereof and an excipient) before sowing the seeds. Compositions formulated for seed treatment generally consist of an AMP, an AMP-insecticidal protein, or an agriculturally acceptable salt thereof, and a film former or adhesive agent. Therefore, typically, a seed coating composition of the present disclosure consists of a biologically effective amount of an AMP, an AMP-insecticidal protein, or an agriculturally acceptable salt thereof, and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., Seed Treatment: Progress and Prospects, 1994 BCPC Monograph No. 57, and references listed therein, the disclosures of which are incorporated herein by reference in their entireties.

The treated seed typically comprises an AMP, an AMP-insecticidal protein, or an agriculturally acceptable salt thereof, in an amount ranging from about 0.01 g to 1 kg per 100 kg of seed (i.e. from about 0.00001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

In some embodiments, the invention provides a method for controlling insects comprising, providing to said insect a transgenic plant that comprises in its genome a stably incorporated expression cassette, wherein said stably incorporated expression cassette comprises a polynucleotide operable to encode an AMP.

In some embodiments, the present disclosure provides a method for controlling insects and/or for protecting against a pest, wherein the pest is selected from the group consisting of: group consisting of: Achema Sphinx Moth (Hornworm) (*Eumorpha achemon*); Alfalfa Caterpillar (*Colias eurytheme*); Almond Moth (*Caudra cautella*); Amorbia Moth (*Amorbia humerosana*); Armyworm (*Spodoptera* spp., e.g. *exigua, frugiperda, littoralis, Pseudaletia unipuncta*); Artichoke Plume Moth (*Platyptilia carduidactyla*); Azalea Caterpillar (*Datana major*); Bagworm (*Thyridopteryx*); ephemeraeformis); Banana Moth (*Hypercompe scribonia*); Banana Skipper (*Erionota thrax*); Blackheaded Budworm (*Acleris gloverana*); California Oakworm (*Phryganidia californica*); Spring Cankerworm (*Paleacrita merriccata*); Cherry Fruitworm (*Grapholita packardi*); China Mark Moth (*Nymphula stagnata*); Citrus Cutworm (*Xylomyges curialis*); Codling Moth (*Cydia pomonella*); Cranberry Fruitworm (*Acrobasis vaccinii*); Cross-striped Cabbageworm (*Evergestis rimosalis*); Cutworm (*Noctuid* species, *Agrotis ipsilon*); Douglas Fir Tussock Moth (*Orgyia pseudotsugata*); Ello Moth (Homworm) (*Erinnyis ello*); Elm Spanworm (*Ennomos subsignaria*); European Grapevine Moth (*Lobesia botrana*); European Skipper (*Thymelicus lineola*); Essex Skipper; Fall Webworm (*Melissopus latiferreanus*)); Filbert Leafroller (*Archips rosanus*)); Fruittree Leafroller (*Archips argyrospilia*)); Grape Berry Moth (*Paralobesia viteana*)); Grape Leafroller (*Platynota stultana*)); Grapeleaf Skeletonizer (*Harrisina americana*); Green Cloverworm (*Plathypena scabra*)); Greenstriped Mapleworm (*Dryocampa rubicunda*)); Gummosos-*Batrachedra comosae* (Hodges); Gypsy Moth (*Lymantria dispar*); Hemlock Looper (*Lambdina fiscellaria*); Hornworm (*Manduca* spp.); Imported Cabbageworm (*Pieris rapae*); Io Moth (*Automeris io*); Jack Pine Budworm (*Choristoneura pinus*); Light Brown Apple Moth (*Epiphyas postvittana*); Melonworm (*Diaphania hyalinata*); *Mimosa* Webworm (*Homadaula anisocentra*); Obliquebanded Leafroller (*Choristoneura rosaceana*); *Oleander* Moth (*Syntomeida epilais*); Omnivorous Leafroller (*Playnota stultana*); Omnivorous Looper (*Sabulodes aegrotata*); Orangedog (*Papilio cresphontes*); Orange *Tortrix* (*Argyrotaenia citrana*); Oriental Fruit Moth (*Grapholita molesta*); Peach Twig Borer (*Anarsia lineatella*); Pine Butterfly (*Neophasia menapia*); Podworm; Redbanded Leafroller (*Argyrotaenia velutinana*); Redhumped Caterpillar (*Schizura concinna*); Rindworm Complex (Various Leps.); Saddleback Caterpillar (*Sibine stimulea*); Saddle Prominent Caterpillar *Heterocampa guttivitta*); Saltmarsh Caterpillar (*Estigmene acrea*); Sod Webworm (*Crambus* spp.); Spanworm (*Ennomos subsignaria*); Fall Cankerworm (*Alsophila pometaria*); Spruce Budworm (*Choristoneura fumiferana*); Tent Caterpillar (Various *Lasiocampidae*); Thecla-*Thecla Basilides* (Geyr) (*Thecla basilides*); Tobacco Hornworm (*Manduca sexta*); Tobacco Moth (*Ephestia elutella*); Tufted Apple Budmoth (*Platynota idaeusalis*); Twig Borer (*Anarsialineatella*); Variegated Cutworm (*Peridroma saucia*); Variegated Leafroller (*Platynota flavedana*); Velvetbean Caterpillar (*Anticarsia gemmatalis*); Walnut Caterpillar (*Datana integerrima*); Webworm (*Hyphantria cunea*); Western Tussock Moth (*Orgyia vetusta*); Southern Cornstalk Borer (*Diatraea crambidoides*); Corn Earworm; Sweet potato weevil; Pepper weevil; Citrus root weevil; Strawberry root weevil; Pecan weevil); Filbert weevil; Ricewater weevil; Alfalfa weevil; Clover weevil; Tea shot-hole borer; Root weevil; Sugarcane beetle; Coffee berry borer; Annual blue grass weevil (*Listronotus maculicollis*); Asiatic garden beetle (*Maladera castanea*); European chafer (*Rhizotroqus majalis*); Green June beetle (*Cotinis nitida*); Japanese beetle (*Popillia japonica*); May or June beetle (*Phyllophaga* sp.); Northern masked chafer (*Cyclocephala borealis*); Oriental beetle (*Anomala orientalis*); Southern masked chafer (*Cyclocephala lurida*); Billbug (*Curculionoidea*); *Aedes aegypti; Busseola fusca; Chilo suppressalis; Culex pipiens; Culex quinquefasciatus; Diabrotica virgifera; Diatraea saccharalis; Helicoverpa armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni*; and *Xanthogaleruca luteola.*

Methods of Using Mixtures and Compositions

In some embodiments, the invention provides a method of combating, controlling, or inhibiting a pest comprising, applying a pesticidally effective amount of the combination, mixture, or composition comprising, consisting essentially of, or consisting of an AMP, an AMP-insecticidal protein, and/or combinations thereof, to (i) the pest, a locus of the pest, a food supply of the pest, a habitat of the pest, or a breeding ground of the pest; (ii) a plant, a seed, a plant part, a locus of a plant, or an environment of a plant that is susceptible to an attack by the pest; (iii) an animal, a locus of an animal, or an environment of an animal susceptible to an attack by the pest; or (iv) a combination of any one of (i)-(iii).

In some embodiments, the present disclosure provides a method of using a mixture comprising: (1) an AMP, an AMP-insecticidal protein, or an agriculturally acceptable salt thereof, and (2) an excipient; to control insects, wherein the AMP is selected from one or any combination of the AMPs described herein, e.g., an AMP having insecticidal activity against one or more insect species, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or an agriculturally acceptable salt thereof, and wherein said method comprises, preparing the mixture and then applying said mixture to (i) the insect, a locus of the insect, a food supply of the insect, a habitat of the insect, or a breeding ground of the insect; (ii) a plant, a seed, a plant part, a locus of a plant, or an environment of a plant that is susceptible to an attack by the insect; (iii) an animal, a locus of an animal, or an environment of an animal susceptible to an attack by the insect; or (iv) a combination of any one of (i)-(iii) . . . .

In some embodiments, the present disclosure provides a method of using a mixture comprising: (1) an AMP, an AMP-insecticidal protein, or an agriculturally acceptable salt thereof, and (2) an excipient; to control insects, wherein the AMP is selected from one or any combination of the AMPs described herein, e.g., an AMP having insecticidal activity against one or more insect species, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; or an agriculturally acceptable salt thereof, and wherein said method comprises, preparing the mixture and then applying said mixture to the (i) the pest, a locus of the pest, a food supply of the pest, a habitat of the pest, or a breeding ground of the pest; (ii) a plant, a seed, a plant part, a locus of a plant, or an environment of a plant that is susceptible to an attack by the pest; (iii) an animal, a locus of an animal, or an environment of an animal susceptible to an attack by the pest; or (iv) a combination of any one of (i)-(iii).

In some embodiments, the present disclosure provides a method of using a mixture comprising: (1) an AMP, an AMP-insecticidal protein, or an agriculturally acceptable salt thereof, and (2) an excipient; to control insects, wherein the AMP is selected from one or any combination of the AMPs described herein, e.g., an AMP having insecticidal activity against one or more insect species, said AMP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence set forth in any one of SEQ ID NOs: 6, 20, 24-26, 28-36, 38-42, 48, 54, 58, 60, 62-63, 69, 108, 116, 119, and 168-169; or an agriculturally acceptable salt thereof; and wherein said method comprises, preparing the mixture and then applying said mixture to the locus of an insect.

In some embodiments, the present disclosure provides a method of using a mixture to control insects, said mixture comprising: (1) an AMP, an AMP-insecticidal protein, or an agriculturally acceptable salt thereof, and (2) an excipient; wherein the insects are selected from the group consisting of: Achema Sphinx Moth (Hornworm) (*Eumorpha achemon*); Alfalfa Caterpillar (*Colias eurytheme*); Almond Moth (*Caudra cautella*); Amorbia Moth (*Amorbia humerosana*); Armyworm (*Spodoptera* spp., e.g. *exigua, frugiperda, littoralis, Pseudaletia unipuncta*); Artichoke Plume Moth (*Platyptilia carduidactyla*); Azalea Caterpillar (*Datana major*); Bagworm (*Thyridopteryx*); *ephemeraeformis*); Banana Moth (*Hypercompe scribonia*); Banana Skipper (*Erionota thrax*); Blackheaded Budworm (*Acleris gloverana*); California Oakworm (*Phryganidia californica*); Spring Cankerworm (*Paleacrita merriccata*); Cherry Fruitworm (*Grapholita packardi*); China Mark Moth (*Nymphula stagnata*); Citrus Cutworm (*Xylomyges curialis*); Codling Moth (*Cydia pomonella*); Cranberry Fruitworm (*Acrobasis vaccinii*); Cross-striped Cabbageworm (*Evergestis rimosalis*); Cutworm (*Noctuid* species, *Agrotis ipsilon*); Douglas Fir Tussock Moth (*Orgyia pseudotsugata*); Ello Moth (Homworm) (*Erinnyis ello*); Elm Spanworm (*Ennomos subsignaria*); European Grapevine Moth (*Lobesia botrana*); European Skipper (*Thymelicus lineola*; Essex Skipper; Fall Webworm (*Melissopus latiferreanus*)); Filbert Leafroller (*Archips rosanus*)); Fruittree Leafroller (*Archips argyrospilia*)); Grape Berry Moth (*Paralobesia viteana*)); Grape Leafroller (*Platynota stultana*)); Grapeleaf Skeletonizer (*Harrisina americana*) (ground only); Green Cloverworm (*Plathypena scabra*)); Greenstriped Mapleworm (*Dryocampa rubicunda*)); Gummosos-*Batrachedra comosae* (Hodges); Gypsy Moth (*Lymantria dispar*); Hemlock Looper (*Lambdina fiscellaria*); Hornworm (*Manduca* spp.); Imported Cabbageworm (*Pieris rapae*); Io Moth (*Automeris io*); Jack Pine Budworm (*Choristoneura pinus*); Light Brown Apple Moth (*Epiphyas postvittana*); Melonworm (*Diaphania hyalinata*); MimosaWebworm (*Homadaula anisocentra*); Obliquebanded Leafroller (*Choristoneura rosaceana*); *Oleander* Moth (*Syntomeida epilais*); Omnivorous Leafroller (*Playnota stultana*); Omnivorous Looper (*Sabulodes aegrotata*); Orangedog (*Papilio cresphontes*); Orange Tortrix (*Argyrotaenia citrana*); Oriental Fruit Moth (*Grapholita molesta*); Peach Twig Borer (*Anarsia lineatella*); Pine Butterfly (*Neophasia menapia*); Podworm; Redbanded Leafroller (*Argyrotaenia velutinana*); Redhumped Caterpillar (*Schizura concinna*); Rindworm Complex; Saddleback Caterpillar (*Sibine stimulea*); Saddle Prominent Caterpillar (*Heterocampa guttivitta*); Saltmarsh Caterpillar (*Estigmene acrea*); Sod Webworm (*Crambus* spp.); Spanworm (*Ennomos subsignaria*); Fall Cankerworm (*Alsophila pometaria*); Spruce Budworm (*Choristoneura fumiferana*); Tent Caterpillar (Various *Lasiocampidae*); Thecla-Thecla Basilides (Geyr) (*Thecla basilides*); Tobacco Hornworm (*Manduca sexta*); Tobacco Moth (*Ephestia elutella*); Tufted Apple Budmoth (*Platynota idaeusalis*); Twig Borer (*Anarsia lineatella*); Variegated Cutworm (*Peridroma saucia*); Variegated Leafroller (*Platynota flavedana*); Velvetbean Caterpillar (*Anticarsia gemmatalis*); Walnut Caterpillar (*Datana integerrima*); Webworm (*Hyphantria cunea*); Western Tussock Moth (*Orgyia vetusta*); Southern Cornstalk Borer (*Diatraea crambidoides*); Corn Earworm; Sweet potato weevil; Pepper weevil; Citrus root weevil; Strawberry root weevil; Pecan weevil); Filbert weevil; Ricewater weevil; Alfalfa weevil; Clover weevil; Tea shot-hole borer; Root weevil; Sugarcane beetle; Coffee berry borer; Annual blue grass weevil (*Listronotus maculicollis*); Asiatic garden beetle (*Maladera castanea*); European chafer (*Rhizotroqus majalis*); Green June beetle (*Cotinis nitida*); Japanese beetle (*Popillia japonica*); May or June beetle (*Phyllophaga* sp.); Northern masked chafer (*Cyclocephala borealis*); Oriental beetle (*Anomala orientalis*); Southern masked chafer (*Cyclocephala lurida*); Billbug (*Curculionoidea*); *Aedes aegypti; Busseola fusca; Chilo suppressalis; Culex pipiens; Culex quinquefasciatus; Diabrotica virgifera; Diatraea saccharalis; Helicoverpa armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni*; and/or *Xanthogaleruca luteola.*

In some embodiments, the present disclosure provides a method of protecting a plant from insects comprising, providing a plant which expresses one or more AMPs, one or more AMP-insecticidal proteins, or polynucleotides encoding the same.

In some embodiments, the present disclosure provides a method of protecting a plant from insects comprising, providing a plant that expresses an AMP, or polynucleotide encoding the same, wherein said AMP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-S-C-C-P-C-Y-W-$X_2$-$X_3$-C-P-W-G-Q-$X_4$-C-Y-P-$X_5$-G-C-$X_6$-G-$X_7$-$X_8$-$X_9$-$X_{10}$; wherein the polypeptide comprises at least one amino acid substitution relative to the mutant Av3 amino acid sequence set forth in SEQ ID NO: 1; wherein $X_1$ is K, H, Q, T, S, N, E, I, L, or V; $X_2$ is G, P, or A; $X_3$ is G, or N; $X_4$ is N or D; $X_5$ is E, D, or N; $X_6$ is S, D, G, T, V, or R; $X_7$ is P or absent; $X_8$ is K, H, A, R, G, T, D, or absent; $X_9$ is G, V, or absent; $X_{10}$ is G, I, or absent; or an agriculturally acceptable salt thereof.

In some embodiments, the present disclosure provides a method of protecting a plant from insects comprising, providing a plant that expresses an AMP, or polynucleotide encoding the same, wherein said AMP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): K-S-C-C-P-C-Y-W-G-G-C-P-W-G-Q-$X_1$-C-Y-P-$X_2$-G-C-$X_3$-G-P-$X_4$-$X_5$-$X_6$; wherein the polypeptide comprises at least one amino acid substitution relative to the mutant Av3 amino acid sequence set forth in SEQ ID NO: 1; $X_1$ is N or D; $X_2$ is E, D, or N; $X_3$ is S, D, R, or G; $X_4$ is K, G, or D; $X_5$ is V or absent; or an agriculturally acceptable salt thereof.

In some embodiments, the present disclosure provides a method of protecting a plant from insects comprising, providing a plant that expresses an AMP, or polynucleotide encoding the same, wherein the AMP has an amino acid sequence as set forth in any one of SEQ ID NOs: 6, 20, 24-26, 28-36, 38-42, 48, 54, 58, 60, 62-63, 69, 108, 116, 119, and 168-169, or an agriculturally acceptable salt thereof.

In some embodiments, the present disclosure provides a method of protecting a plant from insects comprising, providing a plant that expresses an AMP, or polynucleotide encoding the same, wherein the AMP has an amino acid sequence as set forth in any one of SEQ ID NOs: 20, 24-26, 35-36, 38, and 40, or an agriculturally acceptable salt thereof.

In some embodiments, the present disclosure provides a method of protecting a plant from insects comprising, providing a plant that expresses an AMP, or polynucleotide encoding the same, wherein the AMP has an amino acid sequence as set forth in any one of SEQ ID NOs: 25, 36, 38, and 40, or an agriculturally acceptable salt thereof.

In some embodiments, the present disclosure provides a method of protecting a plant from insects comprising, providing a plant that expresses an AMP, or polynucleotide encoding the same, wherein the polynucleotide encodes an AMP having an amino acid sequence as set forth in any one of SEQ ID NOs: 6, 20, 24-26, 28-36, 38-42, 48, 54, 58, 60, 62-63, 69, 108, 116, 119, and 168-169, or a complementary nucleotide sequence thereof.

In some embodiments, the present disclosure provides a method of protecting a plant from insects comprising, providing a plant that expresses an AMP, or polynucleotide encoding the same, wherein the polynucleotide encodes an AMP having an amino acid sequence as set forth in any one of SEQ ID NOs: 20, 24-26, 35-36, 38, and 40, or a complementary nucleotide sequence thereof.

In some embodiments, the present disclosure provides a method of protecting a plant from insects comprising, providing a plant that expresses an AMP, or polynucleotide encoding the same, wherein the polynucleotide encodes an AMP having an amino acid sequence as set forth in any one of SEQ ID NOs: 25, 36, 38, and 40, or a complementary nucleotide sequence thereof.

In some embodiments, the present disclosure provides a method of protecting a plant from insects comprising, providing a plant that expresses an AMP, or polynucleotide encoding the same, wherein the AMP further comprises a homopolymer or heteropolymer of two or more AMPs, wherein the amino acid sequence of each AMP is the same or different.

In some embodiments, the present disclosure provides a method of protecting a plant from insects comprising, providing a plant that expresses an AMP, or polynucleotide encoding the same, wherein the AMP is a fused protein comprising two or more AMPs separated by a cleavable or non-cleavable linker, and wherein the amino acid sequence of each AMP may be the same or different.

In some embodiments, the present disclosure provides a method of protecting a plant from insects comprising, providing a plant that expresses an AMP, or polynucleotide encoding the same, wherein the AMP is a fused protein comprising two or more AMPs separated by a cleavable linker. In some embodiments, the linker has an amino acid sequence as set forth in any one of SEQ ID NOs: 184-193.

In some embodiments, the present disclosure provides a method of protecting a plant from insects comprising, providing a plant that expresses an AMP, or polynucleotide encoding the same, wherein the AMP is a fused protein comprising two or more AMPs separated by a linker, wherein the linker is cleavable inside at least one of (i) the gut or hemolymph of an insect, and (ii) cleavable inside the gut of a mammal.

In some embodiments, the present disclosure provides a method for controlling insects comprising, providing to said insect a transgenic plant that comprises in its genome a stably incorporated expression cassette, wherein said stably incorporated expression cassette comprises polynucleotide operable to encode an AMP.

In some embodiments, the present disclosure provides a method of combating, controlling, or inhibiting a pest comprising, applying a pesticidally effective amount of a mixture comprising: (1) an AMP, an AMP-insecticidal protein, or an agriculturally acceptable salt thereof, and (2) an excipient; wherein the AMP is selected from one or any combination of the AMPs described herein, e.g., an AMP having an amino acid sequence set forth in in SEQ ID NOs: 6, 20, 24-26, 28-36, 38-42, 48, 54, 58, 60, 62-63, 69, 108, 116, 119, and 168-169, or an agriculturally acceptable salt thereof, wherein the mixture is applied to (i) the pest, a locus of the pest, a food supply of the pest, a habitat of the pest, or a breeding ground of the pest; (ii) a plant, a seed, a plant part, a locus of a plant, or an environment of a plant that is susceptible to an attack by the pest; (iii) an animal, a locus of an animal, or an environment of an animal susceptible to an attack by the pest; or (iv) a combination of any one of (i)-(iii).

In some embodiments, the present disclosure provides a method of combating, controlling, or inhibiting a pest comprising, applying a pesticidally effective amount of a mixture comprising: (1) an AMP, an AMP-insecticidal protein, or an agriculturally acceptable salt thereof, and (2) an excipient; to (i) the pest, a locus of the pest, a food supply of the pest, a habitat of the pest, or a breeding ground of the pest; (ii) a plant, a seed, a plant part, a locus of a plant, or an environment of a plant that is susceptible to an attack by the pest; (iii) an animal, a locus of an animal, or an environment of an animal susceptible to an attack by the pest; or (iv) a combination of any one of (i)-(iii), wherein the pest is selected from the group consisting of: Achema Sphinx Moth (Hornworm) (*Eumorpha achemon*); Alfalfa Caterpillar (*Colias eurytheme*); Almond Moth (*Caudra cautella*); Amorbia Moth (*Amorbia humerosana*); Armyworm (*Spodoptera* spp., e.g. *exigua, frugiperda, littoralis, Pseudaletia unipuncta*); Artichoke Plume Moth (*Platyptilia carduidactyla*); Azalea Caterpillar (*Datana major*); Bagworm (*Thyridopteryx*); ephemeraeformis); Banana Moth (*Hypercompe scribonia*); Banana Skipper (*Erionota thrax*); Blackheaded Budworm (*Acleris gloverana*); California Oakworm (*Phryganidia californica*); Spring Cankerworm (*Paleacrita merriccata*); Cherry Fruitworm (*Grapholita packardi*); China Mark Moth (*Nymphula stagnata*); Citrus Cutworm (*Xylomyges curialis*); Codling Moth (*Cydia pomonella*); Cranberry Fruitworm (*Acrobasis vaccinii*); Cross-striped Cabbageworm (*Evergestis rimosalis*); Cutworm (*Noctuid* species, *Agrotis ipsilon*); Douglas Fir Tussock Moth (*Orgyia pseudotsugata*); Ello Moth (Homworm) (*Erinnyis ello*); Elm Spanworm (*Ennomos subsignaria*); European Grapevine Moth (*Lobesia botrana*); European Skipper (*Thymelicus lineola*; Essex Skipper; Fall Webworm (*Melissopus latiferreanus*)); Filbert Leafroller (*Archips rosanus*)); Fruittree Leafroller (*Archips argyrospilia*)); Grape Berry Moth (*Paralobesia viteana*)); Grape Leafroller (*Platynota stultana*)); Grapeleaf Skeletonizer (*Harrisina americana*) (ground only); Green Cloverworm (*Plathypena scabra*)); Green-striped Mapleworm (*Dryocampa rubicunda*)); Gummosos-*Batrachedra comosae* (Hodges); Gypsy Moth (*Lymantria dispar*); Hemlock Looper (*Lambdina fiscellaria*); Hornworm (*Manduca* spp.); Imported Cabbageworm (*Pieris rapae*); Io Moth (*Automeris io*); Jack Pine Budworm (*Choristoneura pinus*); Light Brown Apple Moth (*Epiphyas postvittana*); Melonworm (*Diaphania hyalinata*); Mimosa Webworm (*Homadaula anisocentra*); Obliquebanded Leafroller (*Choristoneura rosaceana*); *Oleander* Moth (*Syntomeida epilais*); Omnivorous Leafroller (*Playnota stultana*); Omnivorous Looper (*Sabulodes aegrotata*); Orangedog (*Papilio cresphontes*); Orange Tortrix (*Argyrotaenia citrana*); Oriental Fruit Moth (*Grapholita molesta*); Peach Twig Borer (*Anarsia lineatella*); Pine Butterfly (*Neophasia menapia*); Podworm; Redbanded Leafroller (*Argyrotaenia velutinana*); Redhumped Caterpillar (*Schizura concinna*); Rindworm Complex; Saddleback Caterpillar (*Sibine stimulea*); Saddle Prominent Caterpillar (*Heterocampa guttivitta*); Saltmarsh Caterpillar (*Estigmene acrea*); Sod Webworm (*Crambus* spp.); Spanworm (*Ennomos subsignaria*); Fall Cankerworm (*Alsophila pometaria*); Spruce Budworm (*Choristoneura fumiferana*); Tent Caterpillar (Various *Lasiocampidae*); Thecla-Thecla Basilides (Geyr) (*Thecla basilides*); Tobacco Hornworm (*Manduca sexta*); Tobacco Moth (*Ephestia elutella*); Tufted Apple Budmoth (*Platynota idaeusalis*); Twig Borer (*Anarsia lineatella*); Variegated Cutworm (*Peridroma saucia*); Variegated Leafroller (*Platynota flavedana*); Velvetbean Caterpillar (*Anticarsia gemmatalis*); Walnut Caterpillar (*Datana integerrima*); Webworm (*Hyphantria cunea*); Western Tussock Moth (*Orgyiavetusta*); Southern Cornstalk Borer (*Diatraea crambi-

*doides*); Corn Earworm; Sweet potato weevil; Pepper weevil; Citrus root weevil; Strawberry root weevil; Pecan weevil); Filbert weevil; Ricewater weevil; Alfalfa weevil; Clover weevil; Tea shot-hole borer; Root weevil; Sugarcane beetle; Coffee berry borer; Annual blue grass weevil (*Listronotus maculicollis*); Asiatic garden beetle (*Maladera castanea*); European chafer (*Rhizotroqus majalis*); Green June beetle (*Cotinis nitida*); Japanese beetle (*Popillia japonica*); May or June beetle (*Phyllophaga* sp.); Northern masked chafer (*Cyclocephala borealis*); Oriental beetle (*Anomala orientalis*); Southern masked chafer (*Cyclocephala lurida*); Billbug (*Curculionoidea*); *Aedes aegypti; Busseola fusca; Chilo suppressalis; Culex pipiens; Culex quinquefasciatus; Diabrotica virgifera; Diatraeasaccharalis; Helicoverpa armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni*; and/or *Xanthogaleruca luteola.*

Crops and Pests

Specific crop pests and insects that may be controlled by these methods include the following: *Dictyoptera* (cockroaches); *Isoptera* (termites); *Orthoptera* (locusts, grasshoppers and crickets); *Diptera* (house flies, mosquito, tsetse fly, crane-flies and fruit flies); *Hymenoptera* (ants, wasps, bees, saw-flies, ichneumon flies and gall-wasps); *Anoplura* (biting and sucking lice); *Siphonaptera* (fleas); and *Hemiptera* (bugs and aphids), as well as arachnids such as *Acari* (ticks and mites), and the parasites that each of these organisms harbor.

"Pest" includes, but is not limited to: insects, fungi, bacteria, nematodes, mites, ticks, and the like.

Insect pests include, but are not limited to, insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, and the like. More particularly, insect pests include Coleoptera, Lepidoptera, and Diptera.

Insects of suitable agricultural, household and/or medical/veterinary importance for treatment with the insecticidal peptides described herein include, but are not limited to, members of the following classes and orders:

The order Coleoptera includes the suborders Adephaga and Polyphaga. Suborder Adephaga includes the superfamilies Caraboidea and Gyrinoidea. Suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

Examples of Coleoptera include, but are not limited to: the American bean weevil *Acanthoscelides obtectus*, the leaf beetle *Agelastica alni*, click beetles (*Agriotes lineatus, Agriotes obscurus, Agriotes* bicolor), the grain beetle A*hasverus advena*, the summer schafer *Amphimallon solstitialis*, the furniture beetle *Anobium punctatum, Anthonomus* spp. (weevils), the Pygmy mangold beetle *Atomaria linearis*, carpet beetles (*Anthrenus* spp., *Attagenus* spp.), the cowpea weevil C*allosobruchus maculates*, the fried fruit beetle *Carpophilus hemipterus*, the cabbage seedpod weevil *Ceutorhynchus assimilis*, the rape winter stem weevil *Ceutorhynchus picitarsis*, the wireworms *Conoderus vespertinus* and *Conoderus falli*, the banana weevil *Cosmopolites sordidus*, the New Zealand grass grub *Costelytra zealandica*, the June beetle *Cotinis nitida*, the sunflower stem weevil *Cylindrocopturus adspersus*, the larder beetle *Dermestes lardarius*, the corn rootworms *Diabrotica virgifera, Diabrotica virgifera virgifera*, and *Diabrotica barberi*, the Mexican bean beetle *Epilachna varivestis*, the old house borer *Hylotropes bajulus*, the luceme weevil *Hypera postica*, the shiny spider beetle *Gibbium psylloides*, the cigarette beetle *Lasioderma serricorne*, the Colorado potato beetle *Leptinotarsa decemlineata*, Lyctus beetles (*Lyctus* spp.), the pollen beetle *Meligethes aeneus*, the common cockshafer *Melolontha melolontha*, the American spider beetle *Mezium americanum*, the golden spider beetle *Niptus hololeucus*, the grain beetles *Oryzaephilus surinamensis* and *Oryzaephilus mercator*, the black vine weevil *Otiorhynchus sulcatus*, the mustard beetle *Phaedon cochleariae*, the crucifer flea beetle *Phyllotreta cruciferae*, the striped flea beetle *Phyllotreta striolata*, the cabbage steam flea beetle *Psylliodes chrysocephala, Ptinus* spp. (spider beetles), the lesser grain borer *Rhizopertha dominica*, the pea and been weevil *Sitona lineatus*, the rice and granary beetles *Sitophilus oryzae* and *Sitophilus granaries*, the red sunflower seed weevil *Smicronyx fulvus*, the drugstore beetle *Stegobium paniceum*, the yellow mealworm beetle *Tenebrio molitor*, the flour beetles *Tribolium castaneum* and *Tribolium confusum*, warehouse and cabinet beetles (*Trogoderma* spp.), and the sunflower beetle *Zygogramma exclamationis.*

Examples of Dermaptera (earwigs) include, but are not limited to: the European earwig, *Forficula auricularia*, and the striped earwig, *Labidura riparia.*

Examples of Dictvontera include, but are not limited to: the oriental cockroach, *Blatta orientalis*, the German cockroach, *Blatella germanica*, the Madeira cockroach, *Leucophaea maderae*, the American cockroach, *Periplaneta americana*, and the smokybrown cockroach *Periplaneta fuiginosa.*

Examples of Diplonoda include, but are not limited to: the spotted snake millipede *Blaniulus guttulatus*, the flat-back millipede *Brachydesmus superus*, and the greenhouse millipede *Oxidus gracilis.*

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae.

Section Calyptratae includes the families Hippoboscidae, Oestridae, Tachinidae, Anthomyiidae, Muscidae, Calliphoridae, and Sarcophagidae.

Examples of Diptera include, but are not limited to: the house fly (*Musca domestica*), the African tumbu fly (*Cordylobia anthropophaga*), biting midges (*Culicoides* spp.), bee louse (*Braula* spp.), the beet fly *Pegomyia betae*, blackflies (*Cnephia* spp., *Eusimulium* spp., *Simulium* spp.), bot flies (*Cuterebra* spp., *Gastrophilus* spp., *Oestrus* spp.), craneflies (*Tipula* spp.), eye gnats (*Hippelates* spp.), filth-breeding flies (*Calliphora* spp., *Fannia* spp., *Hermetia* spp., *Lucilia* spp., *Musca* spp., *Muscina* spp., *Phaenicia* spp., *Phormia* spp.), flesh flies (*Sarcophaga* spp., *Wohlfahrtia* spp.); the flit fly *Oscinella frit*, fruitflies (*Dacus* spp., *Drosophila* spp.), head and canon flies (*Hydrotea* spp.), the hessian fly *Mayetiola destructor*, hom and buffalo flies (*Haematobia* spp.), horse and deer flies (*Chrysops* spp., *Haematopota* spp., *Tabanus* spp.), louse flies (*Lipoptena* spp., *Lynchia* spp., and *Pseudolynchia* spp.), medflies (*Ceratitus* spp.), mosquitoes (*Aedes* spp., *Anopheles* spp., *Culex* spp., *Psorophora* spp.), sandflies (*Phlebotomus* spp., *Lutzomyia* spp.), screw-worm flies (*Chtysomya bezziana* and *Cochliomyia hominivorax*), sheep keds (*Melophagus* spp.); stable flies (*Stomoxys* spp.), tsetse flies (*Glossina* spp.), and warble flies (*Hypoderma* spp.).

Examples of Isontera (termites) include, but are not limited to: species from the familes Hodotennitidae, Kalotermitidae, Mastotermitidae, Rhinotennitidae, Seritermitidae, Termitidae, and Termopsidae.

Examples of Heteroptera include, but are not limited to: the bed bug *Cimex lectularius*, the cotton stainer *Dysdercus intermedius*, the Sunn pest *Eurygaster integriceps*, the tamished plant bug *Lygus lineolaris*, the green stink bug *Nezara antennata*, the southern green stink bug *Nezara viridula*, and the triatomid bugs *Panstrogylus megistus, Rhodnius ecuadoriensis, Rhodnius pallescans, Rhodnius prolixus, Rhodnius robustus, Triatoma dimidiata, Triatoma infestans*, and *Triatoma sordida.*

Examples of Homoptera include, but are not limited to: the California red scale *Aonidiella aurantii*, the black bean aphid *Aphis fabae*, the cotton or melon aphid *Aphis gossypii*, the green apple aphid *Aphis pomi*, the citrus spiny whitefly *Aleurocanthus spiniferus*, the oleander scale *Aspidiotus hederae*, the sweet potato whitefly *Bemesia tabaci*, the cabbage aphid *Brevicoryne brassicae*, the pear psylla *Cacopsylla pyricola*, the currant aphid *Cryptomyzus ribis*, the grape phylloxera *Daktulosphaira vitifoliae*, the citrus psylla *Diaphorina citri*, the potato leafhopper *Empoasca fabae*, the bean leafhopper *Empoasca solana*, the vine leafhopper *Empoasca vitis*, the woolly aphid *Eriosoma lanigerum*, the European fruit scale *Eulecanium corni*, the mealy plum aphid *Hyalopterus arundinis*, the small brown planthopper *Laodelphax striatellus*, the potato aphid *Macrosiphum euphorbiae*, the green peach aphid *Myzus persicae*, the green rice leafhopper *Nephotettix cinticeps*, the brown planthopper *Nilaparvata lugens*, gall-forming aphids (Pemphigus spp.), the hop aphid *Phorodon humuli*, the bird-cherry aphid *Rhopalosiphum padi*, the black scale *Saissetia oleae*, the greenbug *Schizaphis graminum*, the grain aphid *Sitobion avenae*, and the greenhouse whitefly *Trialeurodes vaporariorum.*

Examples of Isopoda include, but are not limited to: the common pillbug *Armadillidium vulgare* and the common woodlouse Oniscus asellus.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Examples of Lepidoptera include, but are not limited to: *Adoxophyes orana* (summer fruit tortrix moth), *Agrotis ipsolon* (black cutworm), *Archips podana* (fruit tree tortrix moth), *Bucculatrix pyrivorella* (pear leafiiner), *Bucculatrix thurberiella* (cotton leaf perforator), *Bupalus piniarius* (pine looper), *Carpocapsa pomonella* (codling moth), *Chilo suppressalis* (striped rice borer), *Choristoneura fumiferana* (eastern spruce budworm), *Cochylis hospes* (banded sunflower moth), *Diatraea grandiosella* (southwestern corn borer), *Earls insulana* (Egyptian bollworm), *Euphestia kuehniella* (Mediterranean flour moth), *Eupoecilia ambiguella* (European grape berry moth), *Euproctis chrysorrhoea* (brown-tail moth), *Euproctis subflava* (oriental tussock moth), *Galleria mellonella* (greater wax moth), *Helicoverpa armigera* (cotton bollworm), *Helicoverpa zea* (cotton bollworm), *Heliothis virescens* (tobacco budworm), *Hofnannophila pseudopretella* (brown house moth), *Homeosoma electellum* (sunflower moth), *Homona magnanima* (oriental tea tree tortrix moth), *Lithocolletis blancardella* (spotted tentiform leafminer), *Lymantria dispar* (gypsy moth), *Malacosoma neustria* (tent caterpillar), *Mamestra brassicae* (cabbage armyworm), *Mamestra confgurata* (Bertha armyworm), the homworms *Manduca sexta* and *Manuduca quinquemaculata, Operophtera brumata* (winter moth), *Ostrinia nubilalis* (European corn borer), *Panolis flammea* (pine beauty moth), *Pectinophora gossypiella* (pink bollworm), *Phyllocnistis citrella* (citrus leafminer), *Pieris brassicae* (cabbage white butterfly), *Plutella xylostella* (diamondback moth), *Rachiplusia ni* (soybean looper), *Spilosoma virginica* (yellow bear moth), *Spodoptera exigua* (beet armyworm), *Spodoptera frugiperda* (fall armyworm), *Spodoptera littoralis* (cotton leafworin), *Spodoptera litura* (common cutworm), *Spodoptera praefica* (yellowstriped armyworm), *Sylepta derogata* (cotton leaf roller), *Tineola bisselliella* (webbing clothes moth), *Tineola pellionella* (case-making clothes moth), *Tortrix viridana* (European oak leafroller), *Trichoplusia ni* (cabbage looper), and *Yponomeuta padella* (small ermine moth).

Examples of Orthoptera include, but are not limited to: the common cricket *Acheta domesticus*, tree locusts (*Anacridium* spp.), the migratory locust *Locusta migratoria*, the twostriped grasshopper *Melanoplus bivittatus*, the differential grasshopper *Melanoplus dfferentialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria.*

Examples of Phthiraptera include, but are not limited to: the cattle biting louse *Bovicola bovis*, biting lice (*Damalinia* spp.), the cat louse *Felicola subrostrata*, the shortnosed cattle louse *Haematopinus eloysternus*, the tail-switch louse *Haematopinus quadriperiussus*, the hog louse *Haematopinus suis*, the face louse *Linognathus ovillus*, the foot louse *Linognathus pedalis*, the dog sucking louse *Linognathus setosus*, the long-nosed cattle louse *Linognathus vituli*, the chicken body louse *Menacanthus stramineus*, the poultry shaft louse *Menopon gallinae*, the human body louse *Pediculus humanus*, the pubic louse *Phthirus pubis*, the little blue cattle louse *Solenopotes capillatus*, and the dog biting louse *Trichodectes canis.*

Examples of Psocoptera include, but are not limited to: the booklice *Liposcelis bostrychophila, Liposcelis decolor, Liposcelis entomophila*, and *Trogium pulsatorium*. Examples of Siphonaptera include, but are not limited to: the bird flea *Ceratophyllus gallinae*, the dog flea *Ctenocephalides canis*, the cat flea *Ctenocephalides fells*, the humanflea *Pulex irritans*, and the oriental rat flea *Xenopsylla cheopis*.

Examples of Symphvla include, but are not limited to: the garden symphylan Scutigerella immaculate.

Examples of Thysanura include, but are not limited to: the gray silverfish *Ctenolepisma longicaudata*, the four-lined silverfish *Ctenolepisma quadriseriata*, the common silverfnsh *Lepisma saccharina*, and the flrebrat *Thennobia domestica;*

Examples of Thysanoptera include, but are not limited to: the tobacco thrips *Frankliniella fusca*, the flower thrips *Frankliniella intonsa*, the western flower thrips *Frankliniella occidentalis*, the cotton bud thrips *Frankliniella schultzei*, the banded greenhouse thrips *Hercinothrips femoralis*, the soybean thrips *Neohydatothrips variabilis*, Kelly's citrus thrips *Pezothrips kellyanus*, the avocado thrips *Scirtothrips perseae*, the melon thrips, *Thrips palmi*, and the onion thrips, *Thrips tabaci*.

Examples of Nematodes include, but are not limited to: parasitic nematodes such as root-knot, cyst, and lesion nematodes, including *Heterodera* spp., *Meloidogyne* spp., and *Globodera* spp.; particularly members of the cyst nematodes, including, but not limited to: *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include, but are not limited to: *Pratylenchus* spp.

Other insect species susceptible to the present disclosure include: athropod pests that cause public and animal health concerns, for example, mosquitos for example, mosquitoes from the genera *Aedes, Anopheles* and *Culex*, from ticks, flea, and flies etc.

In one embodiment, an AMP, an AMP-insecticidal protein, or an agriculturally acceptable salt thereof can be employed to treat ectoparasites. Ectoparasites include, but are not limited to: fleas, ticks, mange, mites, mosquitoes, nuisance and biting flies, lice, and combinations comprising one or more of the foregoing ectoparasites. The term "fleas" includes the usual or accidental species of parasitic flea of the order Siphonaptera, and in particular the species *Ctenocephalides*, in particular *C. fells* and *C. cams*, rat fleas (*Xenopsylla cheopis*) and human fleas (*Pulex irritans*).

The present disclosure may be used to control, inhibit, and/or kill insect pests of major crops, e.g., in some embodiments, the major crops and corresponding insect pest include, but are not limited to: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; *Sorghum: Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*, corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, banded winged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus*, chinch bug; *Acrosternum hilare*, green stink bug; Soybean: *Pseudoplusia includens*, soybean looper; *Anticarsia gemmatalis*, velvet bean caterpillar; *Plathypena scabra*, green clover worm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

In some embodiments, an AMP, an AMP-insecticidal protein, or an agriculturally acceptable salt thereof can be employed to treat any one or more of the foregoing insects, or any of the insects described herein.

The insects that are susceptible to present disclosure include but are not limited to the following: familes such as: Blattaria, Coleoptera, Collembola, Diptera, Echinostomida, Hemiptera, Hymenoptera, Isoptera, Lepidoptera, Neuroptera, Orthoptera, Rhabditida, Siphonoptera, and Thysanoptera. Genus Species are indicated as follows: *Actebia fennica, Agrotis ipsilon, A. segetum, Anticarsia gemmatalis, Argyrotaenia citrana, Artogeia rapae, Bombyx mori, Busseola fusca, Cacyreus marshall, Chilo suppressalis, Christoneura fumiferana, C. occidentalis, C. pinus pinus, C. rosacena, Cnaphalocrocis medinalis, Conopomorpha cramerella, Ctenopsuestis obliquana, Cydia pomonella, Danaus plexippus, Diatraea saccharallis, D. grandiosella, Earias vittella, Elasmolpalpus lignoselius, Eldana saccharina, Ephestia kuehniella, Epinotia aporema, Epiphyas postvittana, Galleria mellonella*, Genus-Species, *Helicoverpa zea, H. punctigera, H. armigera, Heliothis virescens, Hyphantria cunea, Lambdina fiscellaria, Leguminivora glycinivorella, Lobesia botrana, Lymantria dispar, Malacosoma disstria, Mamestra brassicae, M configurata, Manduca sexta, Marasmia patnalis, Maruca vitrata, Orgyia leucostigma, Ostrinia nubilalis, O. furnacalis, Pandemis pyrusana, Pectinophora gossypiella, Perileucoptera coffeella, Phthorimaea opercullela, Pianotortrix octo, Piatynota stultana, Pieris brassicae, Plodia interpunctala, Plutella xylostella, Pseudoplusia includens, Rachiplusia nu, Sciropophaga incertulas, Sesamia calamistis, Spilosoma virginica, Spodoptera exigua, Spodoptera frugiperda, Spodoptera littoralis, Spodoptera exempta, Spodoptera litura, Tecia solanivora, Thaumetopoea pityocampa, Trichoplusia ni, Wiseana cervinata, Wiseana copularis, Wiseana jocosa, Blattaria blattella, Collembola xenylla, Collembola folsomia, Folsomia candida, Echinostomida fasciola, Hemiptera oncopeltrus, Hemiptera bemisia, Hemiptera macrosiphum, Hemiptera rhopalosiphum, Hemiptera myzus, Hymenoptera diprion, Hymenoptera apis, Hymenoptera Macrocentrus, Hymenoptera Meteorus, Hymenoptera Nasonia, Hymenoptera Solenopsis, Isopoda porcellio, Isoptera reticulitermes, Orthoptera Achta, Prostigmata tetranychus, Rhabitida acrobeloides, Rhabitida caenorhabditis, Rhabitida distolabrellus, Rhabitida panagrellus, Rhabitida pristionchus, Rhabitida pratylenchus, Rhabitida ancylostoma, Rhabitida nippostrongylus, Rhabitida panagrellus, Rhabitida haemonchus, Rhabitida meloidogyne*, and *Siphonaptera ctenocephalides*.

The present disclosure provides methods for plant transformation, which may be used for transformation of any plant species, including, but not limited to, monocots and dicots. Crops for which a transgenic approach would be an especially useful approach include, but are not limited to: alfalfa, cotton, tomato, maize, wheat, corn, sweet corn, lucerne, soybean, sorghum, field pea, linseed, safflower, rapeseed, oil seed rape, rice, soybean, barley, sunflower, trees (including coniferous and deciduous), flowers (including those grown commercially and in greenhouses), field lupins, switchgrass, sugarcane, potatoes, tomatoes, tobacco, crucifers, peppers, sugarbeet, barley, and oilseed rape, *Brassica* sp., rye, millet, peanuts, sweet potato, cassaya, coffee, coconut, pineapple, citrus trees, cocoa, tea, banana, avocado, fig, guava, mango, olive, papaya, cashew, macadamia, almond, oats, vegetables, ornamentals, and conifers.

The present disclosure provides methods for plant transformation, which may be used for transformation of any plant species, including, but not limited to, monocots and dicots. Crops for which a transgenic approach or plaint incorporated protectants (PIP) would be an especially useful approach include, but are not limited to: alfalfa, cotton, tomato, maize, wheat, corn, sweet corn, lucerne, soybean, sorghum, field pea, linseed, safflower, rapeseed, oil seed rape, rice, soybean, barley, sunflower, trees (including coniferous and deciduous), flowers (including those grown commercially and in greenhouses), field lupins, switchgrass, sugarcane, potatoes, tomatoes, tobacco, crucifers, peppers, sugarbeet, barley, and oilseed rape, *Brassica* sp., rye, millet, peanuts, sweet potato, cassaya, coffee, coconut, pineapple, citrus trees, cocoa, tea, banana, avocado, fig, guava, mango, olive, papaya, cashew, macadamia, almond, oats, vegetables, omamentals, and conifers.

In some embodiments, the compositions, mixtures, and/or methods of the present disclosure can be applied to the locus of an insect and/or pest selected from the group consisting of Loopers; Omnivorous Leafroller; Hornworms; Imported Cabbageworm; Diamondback Moth; Green Cloverworm; Webworm; Saltmarsh Caterpillar; Armyworms; Cutworms; Cross-Striped Cabbageworm; Podworms; Velvetbean Caterpillar; Soybean Looper; Tomato Fruitworm; Variegated Cutworm; Melonworms; Rindworm complex; Fruittree Leafroller; Citrus Cutworm; *Heliothis*; Orangedog; Citrus Cutworm; Redhumped Caterpillar; Tent Caterpillars; Fall Webworm; Walnut Caterpillar; Cankerworms; Gypsy Moth; Variegated Leafroller; Redbanded Leafroller; Tufted Apple Budmoth; Oriental Fruit Moth); Filbert Leafroller; Obliquebanded Leafroller; Codling Moth; Twig Borer; Grapeleaf Skeletonizer; Grape Leafroller; Achema Sphinx Moth (Hornworm); Orange Tortrix; Tobacco Budworm); Grape Berry Moth; Spanworm; Alfalfa Caterpillar; Cotton Bollworm; Head Moth; Amorbia Moth; Omnivorous Looper; Ello Moth (Hornworm); Io Moth; Oleander Moth; Azalea Caterpillar; Hornworm; Leafrollers; Banana Skipper; *Batrachedra comosae* (Hodges); Thecla Moth; Artichoke Plume Moth; Thistle Butterfly; Bagworm; Spring & Fall Cankerworm; Elm Spanworm; California Oakworm; Pine Butterfly; Spruce Budworms; Saddle Prominent Caterpillar; Douglas Fir Tussock Moth; Western Tussock Moth; Blackheaded Budworm; Mimosa Webworm; Jack Pine Budworm; Saddleback Caterpillar; Greenstriped Mapleworm; or Hemlock Looper.

In some embodiments, the peptides, proteins, compositions, mixtures, and/or methods of the present disclosure can be applied to the locus of an insect and/or pest selected from the group consisting of. Achema Sphinx Moth (Hornworm) (*Eumorpha achemon*); Alfalfa Caterpillar (*Colias eurytheme*); Almond Moth (*Caudra cautella*); Amorbia Moth (*Amorbia humerosana*); Armyworm (*Spodoptera* spp., e.g. *exigua, frugiperda, littoralis, Pseudaletia unipuncta*); Artichoke Plume Moth (*Platyptilia carduidactyla*); Azalea Caterpillar (*Datana major*); Bagworm (*Thyridopteryx*); ephemeraeformis); Banana Moth (*Hypercompe scribonia*); Banana Skipper (*Erionota thrax*); Blackheaded Budworm (*Acleris gloverana*); California Oakworm (*Phryganidia californica*); Spring Cankerworm (*Paleacrita merriccata*); Cherry Fruitworm (*Grapholita packardi*); China Mark Moth (*Nymphula*

*stagnata*); Citrus Cutworm (*Xylomyges curialis*); Codling Moth (*Cydia pomonella*); Cranberry Fruitworm (*Acrobasis vaccinii*); Cross-striped Cabbageworm (*Evergestis rimosalis*); Cutworm (*Noctuid* species, *Agrotis ipsilon*); Douglas Fir Tussock Moth (*Orgyia pseudotsugata*); Ello Moth (Homworm) (*Erinnyis ello*); Elm Spanworm (*Ennomos subsignaria*); European Grapevine Moth (*Lobesia botrana*); European Skipper (*Thymelicus lineola*) (Essex Skipper); Fall Webworm (*Melissopus latiferreanus*); Filbert Leafroller (*Archips rosanus*); Fruittree Leafroller (*Archips argyrospilia*); Grape Berry Moth (*Paralobesia viteana*); Grape Leafroller (*Platynota stultana*); Grapeleaf Skeletonizer (*Harrisina americana*) (ground only); Green Cloverworm (*Plathypena scabra*); Greenstriped Mapleworm (*Dryocampa rubicunda*); Gummosos-*Batrachedra Comosae* (Hodges); Gypsy Moth (*Lymantria dispar*); Hemlock Looper (*Lambdina fiscellaria*); Hornworm (*Manduca* spp.); Imported Cabbageworm (*Pieris rapae*); Io Moth (*Automeris io*); Jack Pine Budworm (*Choristoneura pinus*); Light Brown Apple Moth (*Epiphyas postvittana*); Melonworm (*Diaphania hyalinata*); Mimosa Webworm (*Homadaula anisocentra*); Obliquebanded Leafroller (*Choristoneura rosaceana*); *Oleander* Moth (*Syntomeida epilais*); Omnivorous Leafroller (*Playnota stultana*); Omnivorous Looper (*Sabulodes aegrotata*); Orangedog (*Papilio cresphontes*); Orange Tortrix (*Argyrotaenia citrana*); Oriental Fruit Moth (*Grapholita molesta*); Peach Twig Borer (*Anarsia lineatella*); Pine Butterfly (*Neophasia menapia*); Redbanded Leafroller (*Argyrotaenia velutinana*); Redhumped Caterpillar (*Schizura concinna*); Rindworm Complex (Various Leps.); Saddleback Caterpillar (*Sibine stimulea*); Saddle Prominent Caterpillar (*Heterocampa guttivitta*); Saltmarsh Caterpillar (*Estigmene acrea*); Sod Webworm (*Crambus* spp.); Spanworm (*Ennomos subsignaria*); Fall Cankerworm (*Alsophila pometaria*); Spruce Budworm (*Choristoneura fumiferana*); Tent Caterpillar (Various *Lasiocampidae*); Thecla-Thecla Basilides (Geyr) (*Thecla basilides*); Tobacco Hornworm (*Manduca sexta*); Tobacco Moth (*Ephestia elutella*); Tufted Apple Budmoth (*Platynota idaeusalis*); Twig Borer (*Anarsia lineatella*); Variegated Cutworm (*Peridroma saucia*); Variegated Leafroller (*Platynotaf lavedana*); Velvetbean Caterpillar (*Anticarsia gemmatalis*); Walnut Caterpillar (*Datana integerrima*); Webworm (*Hyphantria cunea*); Western Tussock Moth (*Orgyia vetusta*); Southern Cornstalk Borer (*Diatraea crambidoides*); Corn Earworm; Sweet potato weevil; Pepper weevil; Citrus root weevil; Strawberry root weevil; Pecan weevil); Filbert weevil; Ricewater weevil; Alfalfa weevil; Clover weevil; Tea shot-hole borer; Root weevil; Sugarcane beetle; Coffee berry borer; Annual blue grass weevil (*Listronotus maculicollis*); Asiatic garden beetle (*Maladera castanea*); European chafer (*Rhizotroqus majalis*); Green June beetle (*Cotinis nitida*); Japanese beetle (*Popillia japonica*); May or June beetle (*Phyllophaga* sp.); Northern masked chafer (*Cyclocephala borealis*); Oriental beetle (*Anomala orientalis*); Southern masked chafer (*Cyclocephala lurida*); Billbug (*Curculionoidea*); *Aedes aegypti; Busseola fusca; Chilo suppressalis; Culex pipiens; Culex quinquefasciatus; Diabrotica virgifera; Diatraea saccharalis; Helicoverpa armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni*; and/or *Xanthogaleruca luteola.*

In some embodiments, the peptides, proteins, compositions, mixtures, and/or methods of the present disclosure can be applied to the locus of an adult beetle selected from the group consisting of: Asiatic garden beetle (*Maladera castanea*); Gold spotted oak borer (*Agrilus coxalis auroguttatus*); Green June beetle (*Cotinis nitida*); Japanese beetle (*Popillia japonica*); May or June beetle (*Phyllophaga* sp.); Oriental beetle (*Anomala orientalis*); and/or Soap berry-borer (*Agrilus prionurus*).

In some embodiments, the compositions, mixtures, and/or methods of the present disclosure can be applied to the locus of an insect and/or pest that is a larvae (annual white grub) selected from the group consisting of: Annual blue grass weevil (*Listronotus maculicollis*); Asiatic garden beetle (*Maladera castanea*); European chafer (*Rhizotroqus majalis*); Green June beetle (*Cotinis nitida*); Japanese beetle (*Popillia japonica*); May or June beetle (*Phyllophaga* sp.); Northern masked chafer (*Cyclocephala borealis*); Oriental beetle (*Anomala orientalis*); Southern masked chafer (*Cyclocephala lurida*); and Billbug (*Curculionoidea*).

EXAMPLES

The Examples in this specification are not intended to, and should not be used to, limit the invention; they are provided only to illustrate the invention.

Example 1. Av3b

Av3 is a type III sea anemone toxin produced by *Anemonia viridis* (otherwise known by its common name, the Snakelocks anemone). An exemplary Av3 polypeptide is from *Anemonia viridis* is provided having the amino acid sequence "RSCCPCYWGGCPWGQNCYPEGCSGPKV" (SEQ ID NO: 172) (NCBI Accession No. P01535.1). Wild-type Av3 can be mutated, e.g., in some embodiments, an Wild-type Av3 can have an N-terminal mutation and a C-terminal mutation, wherein the N-terminal mutation results in an amino acid substitution of RIK relative to SEQ ID NO:172, and the C-terminal mutation results in an amino acid deletion relative to SEQ ID NO:172; thus, the wild-type Av3 peptide amino acid sequence is changed from "RSCCPCYWGGCPWGQNCYPEGCSGPKV" (SEQ ID NO: 172), to the amino acid sequence: "KSCCPCYWGGCPWGQNCYPEGCSGPK" (SEQ ID NO: 1). The term "Av3b" refers to those embodiments that have the foregoing mutations.

An exemplary method of obtaining Av3b is disclosed in PCT Application No. PCT/US2019/051093, the disclosure of which is incorporated herein by reference in its entirety.

While Av3b exhibits superior properties relative to wild-type Av3 (see PCT/US2019/051093), the industrial production of recombinant proteins still poses several challenges. Indeed, the scale-up of manufacturing processes related to the production of desirable recombinant proteins can be expensive and complicated, with a plethora of issues to consider. For example, common challenges in the production of recombinant proteins include, e.g., failure of the recombinant protein to bind columns during purification; poor lysis of the host protein (e.g., in bacterial expression systems); poor secretion of the protein (e.g., in yeast expression systems); degradation of the protein; co-purification of unwanted endogenous proteins; precipitation of the recombinant protein and/or unwanted aggregation; improper folding; low stability; poor expression; reduced activity; undesirable post-translational modifications; and others that are known to those having ordinary skill in the art. See, e.g., S. Rudge and M. Ladisch, Industrial Challenges of Recombinant Proteins. Adv Biochem Eng Biotechnol. 2020; 171:1-22; and Palomares et al., Production of recombinant proteins: challenges and solutions. Methods Mol Biol. 2004; 267:15-52. Accordingly, in light of the foregoing challenges (and the failure of others to present solutions), there remains a long-felt need in the industry.

Single Mutant Energy State (ΔΔG) Analysis

In order to identify Av3b mutants that possessed desirable properties and overcame the challenges presented in protein production, a single mutant energy state (ΔΔG) analysis was performed using an online Rosetta protein modeling program provided by Cyrus Biotechnology.

In the analysis, every residue in the Av3b primary sequence except the six cysteine residues was mutated to 19 possible amino acids except itself individually in silicone using Rosetta ΔΔG algorithm. The Gibbs free energy change difference (ΔΔG) between the folded Av3b peptide and the folded single mutant peptide was calculated for each mutation. The ΔΔG from all possible mutations composes a ΔΔG map for Av3b peptide, which can provide guidance for following protein engineering.

The "ΔΔG" or "Delta Delta G" or "DDG" is a useful metric for predicting how point mutations influence protein stability. Here, ΔΔG represents the change in the change in Gibbs free energy, i.e., it is a measure of the change in energy between the folded and unfolded states (ΔG folding), and the change in said ΔG folding when a point mutation is present. The Gibbs free energy is the thermodynamic quantity minimized for spontaneous reactions occurring at constant pressure; Gibbs free energy can be represented by the following equation: (G)=Enthalpy (H)−Temperature (T)× Entropy (S). See Atkins and de Paula, Physical Chemistry, 7th Edition (2002), the disclosure of which is incorporated herein by reference in its entirety. Thus, the change in Gibbs free energy during a chemical process (i.e., ΔG) is a function of a reaction enthalpy change AH, the reaction entropy change ΔS, and the reaction temperature T: ΔG=AH−TAS.

The mutant energy analysis revealed several amino acid residues and positions that might influence stability. See table below.

TABLE 3

Results of single mutant energy state (ΔΔG) analysis.

| No. | Org. | A | R | N | D | C | E | Q | G | H | I |
|---|---|---|---|---|---|---|---|---|---|---|---|
| 1 | K | −0.2 | −0.4 | −0.6 | −0.7 | 0.59 | −0.7 | −0.4 | −0.2 | 0.08 | −0.3 |
| 2 | S | 2.69 | 2.21 | 1.65 | 2.68 | 2.58 | 2.57 | 2.76 | 2.76 | 3.31 | 2.73 |
| 3 | C | | | | | | | | | | |
| 4 | C | | | | | | | | | | |
| 5 | P | 1.71 | 2.21 | 0.28 | 0.99 | 2.27 | 0.57 | 2.02 | 3.25 | 3.29 | 0.86 |
| 6 | C | | | | | | | | | | |
| 7 | Y | 0.26 | 0.41 | −0 | 0.67 | 1.71 | −0.3 | 0.07 | 2.35 | 0.12 | 0.99 |
| 8 | W | −0.8 | −0.9 | −2.1 | −0.6 | 0.18 | −1.1 | −1.4 | 1.26 | −2.3 | −2 |
| 9 | G | −2.3 | −0.7 | −0.7 | −0.1 | 0.1 | −0.3 | −2.3 | | −0.5 | 3.83 |
| 10 | G | −0.9 | −1 | **−3.5** | **−3.5** | −0.4 | −2.5 | −1.5 | | −2 | −1 |
| 11 | C | | | | | | | | | | |
| 12 | P | **−3.2** | **−3.6** | **−4** | **−3** | −1.6 | −1.7 | **−4** | −2.4 | 1.58 | −2.2 |
| 13 | W | 0.19 | 0.14 | −1.3 | −0.8 | 1.33 | −1.7 | −0.9 | 1.24 | −1 | 0.17 |
| 14 | G | 0.68 | 15 | 19.1 | 25 | 13.8 | 19.8 | 17 | | 21.4 | 31.3 |
| 15 | Q | −0.3 | −0.3 | −1 | −0.7 | 1.06 | −0.6 | | 1 | −0.4 | 2.37 |
| 16 | N | 2.21 | 1.75 | | 0.16 | 2.95 | 2.13 | 1.77 | 4.49 | 0.56 | 2.28 |
| 17 | C | | | | | | | | | | |
| 18 | Y | 6.23 | 7.17 | 6.08 | 12.4 | 4.87 | 11.1 | 7.08 | 16.1 | 3.59 | 9.63 |
| 19 | P | 4.24 | 4.52 | 4.26 | 2.61 | 5.82 | 3.94 | 0.96 | 5.3 | 4.97 | 4.74 |
| 20 | E | 1.59 | 1.09 | 0.54 | 0.59 | 2.57 | | 0.46 | 2.24 | 0.6 | 3.18 |
| 21 | G | 5.65 | 10.1 | 5.58 | 5.6 | 10.1 | 9.55 | 6.3 | | 8.69 | 13.7 |
| 22 | C | | | | | | | | | | |
| 23 | S | 0.75 | −0.9 | −0.2 | −0.1 | 1.86 | −0.1 | 0.43 | 0.78 | 0.51 | 1.26 |
| 24 | G | 5.5 | 18 | 28.6 | 22.4 | 21.6 | 23.2 | 45.3 | | 31.4 | 36.1 |
| 25 | P | 3.72 | −1.8 | 3.88 | 2.36 | 5.57 | 1.4 | 3.77 | −0.2 | 3.54 | 5.68 |
| 26 | K | −0.4 | −0.3 | −2 | 0.87 | 0.29 | −0.6 | −1 | 0.49 | −1.6 | 0.3 |

| No. | Org. | L | K | M | F | P | S | T | W | Y | V |
|---|---|---|---|---|---|---|---|---|---|---|---|
| 1 | K | 0.06 | | −2.3 | 1.12 | **−7.3** | −0.9 | −0.3 | 1.41 | 0.72 | 0.08 |
| 2 | S | 3.04 | 2.35 | 2.13 | 2.45 | **−8.6** | | −0.9 | 2.42 | 2.17 | 2.71 |
| 3 | C | | | | | | | | | | |
| 4 | C | | | | | | | | | | |
| 5 | P | 0.02 | 2.14 | 1.28 | −0.1 | | 2.48 | 1.22 | 3.81 | −0.5 | 0.85 |
| 6 | C | | | | | | | | | | |
| 7 | Y | −0.4 | −0.4 | 0.62 | −0.2 | 0.69 | 0.49 | 0.64 | −0.1 | | 0.67 |
| 8 | W | −1.9 | −1.2 | −1.4 | −1.9 | −0.3 | −0.6 | −1.2 | | −2.2 | −1.9 |
| 9 | G | 3.85 | −0.3 | −1.8 | −0.5 | **−8.4** | −0.7 | 3.53 | −1.3 | −1.2 | 2.83 |
| 10 | G | −2.1 | −1.7 | −1.2 | −1.9 | **−7.2** | −1.6 | −1.9 | −1.5 | −2.1 | −1.2 |
| 11 | C | | | | | | | | | | |
| 12 | P | −2.3 | −1.8 | **−4.5** | 2.13 | | 0.63 | 1.68 | −0.8 | 1.2 | −1.7 |
| 13 | W | −0.8 | −0.6 | 0.5 | −0.8 | 10.2 | 0.01 | −0.1 | | −1.1 | 0.26 |
| 14 | G | 27.9 | 12.1 | 13.3 | 19 | 16.1 | 11.2 | 19.6 | 22.7 | 19.4 | 23.9 |
| 15 | Q | −0.7 | −0.4 | 0.63 | 0.45 | 3.79 | −0.2 | −0.1 | 1.28 | 0.06 | 0.6 |
| 16 | N | 0.85 | 1.68 | 1.51 | 0.15 | 0.64 | 2.13 | 1.49 | 0.79 | −0 | 2.2 |
| 17 | C | | | | | | | | | | |
| 18 | Y | 5.66 | 10.5 | 5.45 | −0.9 | 21.1 | 7.38 | 5.24 | 1.28 | | 6.21 |
| 19 | P | 3.83 | 3.59 | 1.58 | 3.67 | | 3.59 | 4.11 | 4.37 | 4.3 | 3.71 |
| 20 | E | 0.41 | 0.23 | 0.95 | 0.24 | 9.97 | 1.39 | 1.29 | 1.46 | −0.3 | 1.48 |
| 21 | G | 9.33 | 6.26 | 11.2 | 9.88 | 6.34 | 3.14 | 8.82 | 9.93 | 7.86 | 13.8 |
| 22 | C | | | | | | | | | | |

TABLE 3-continued

Results of single mutant energy state (ΔΔG) analysis.

| | | | | | | | | | | | |
|---|---|---|---|---|---|---|---|---|---|---|---|
| 23 | S | 0.5 | −0.5 | 0.82 | 0.63 | 3.25 | | 0.42 | 1.51 | 0.24 | 0.92 |
| 24 | G | 43.6 | 20.2 | 21.8 | 26.1 | 5.44 | 9.82 | 24.5 | 32.1 | 30.8 | 31.3 |
| 25 | P | 3.98 | 1.47 | 2.64 | 4.27 | | 2.45 | 2.74 | 3.53 | 3.95 | 3.75 |
| 26 | K | −0.2 | | −0.1 | −1.4 | 0.2 | −0.8 | −1.2 | −0.2 | −0.1 | −0.6 |

No. = position number; Org. = original amino acid residue.
ΔΔG < −3 indicates amino acid substitutions that may stabilize the protein.
ΔΔG between −3 to 3 indicates amino acid substitutions having an average low energy state.
ΔΔG > indicates amino acid substitutions that are unstable.
Cells in bold show a DDG < −3.

Example 2. Generation of Mutant Candidates: First Round

To engineer new Av3b mutant peptides (AMPs), the non-essential residues of Av3b were selected for mutation targets and the ΔΔG map of Av3b was used as guidance for mutation selections for all selected target residues based on multiple different engineering strategies, then Rosetta Relax algorithm provided by Cyrus Biotechnology was applied to all possible mutations, resulting Av3b mutants with different stability measured by the ΔΔG. The top most stable mutants were selected for the tests to determine the effect on peptide yield. Additional mutational strategies were also pursued; e.g., mutations that targeted residues involved in disulfide bond formation A list of all the mutants evaluated in the first round of mutations can be found in the table below.

Generation of the Av3b mutant peptides was performed as follows: First, an expression *Kluyveromyces lactis* yeast strain was created operable to express a given Av3b mutant peptides amino acid sequence. Next, the DNA codons for each mutant construct were optimized for *K. lactis* expression. Finally a peptide expression vector was generated based on the pLB103b2T4 yeast expression vector, in which the Av3b mutant peptides were expressed as a secretion peptide and a Kanamycin-resistance gene provides the expression strain with Geneticin (G418) resistance.

The expression vector was linearized by the digestion with the restriction enzyme SacII; the resulting linear plasmid was then transformed into *K. lactis* cell by electroporation. At least 16 of resulting positive transformation colonies were picked for yield analysis. The picked transformants were used to inoculate the culture wells of a 48-well deep-well culture plate with each well containing 2.2 mL culture medium (DMSor): 2 g/L Solulys 095K, 11.83 g/L $KH_2PO_4$, 2.299 g/L $K_2HPO_4$, 40 g/L sorbitol, 1 g/L $MgSO_4{\cdot}7H_2O$, 10 g/L $(NH_4)SO_4$, 0.33 g/L $CaCl_2){\cdot}2H_2O$, 1 g/L NaCl, 1 g/L KCl, 5 mg/L $CuSO_4{\cdot}5H_2O$, 30 mg/L $MnSO_4{\cdot}H_2O$, 10 mg/L $ZnCl_2$, 1 mg/L KI, 2 mg/L $CoCl_2{\cdot}6H_2O$, 8 mg/L $Na_2MoO_4{\cdot}2H_2O$, 0.4 mg/L $H_3BO_3$, 15 mg/L $FeCl_3{\cdot}6H_2O$, 0.8 mg/L biotin, 20 mg/L Ca-pantothenate, 15 mg/L thiamine, 16 mg/L myo-inositol, 10 mg/L nicotinic acid, and 4 mg/L pyridoxine.

The deep-well culture plate was sealed with a sterile breathable seal and culture at 23.5° C., 250 rpm for 6 days. After six days culture, the deep-well culture plate was spun at 4000 rpm for 10 minute to collect the cell pallets and supernatants, the cell pallets were resuspended into 1 mL of 20% glycerol for long-term storage of the strain at −80° C. freezer. The supermatants contain the expressed Av3b mutant peptides, and were subsequently subjected to rpHPLC evaluation to determine peptide yield. 009771 To run rpHPLC, the supernatants were filtered through 0.2 cm filter membrane; then, 300 μL of filtered supernatant was then transferred to a 500 μL 96-well plate for rpHPLC analysis using Ultramate 3000 HPLC system (ThermoFisher®) controlled by Chromeleon 7 software. The rpHPLC was performed using monolithic C18 columns using water with 0.100 Trifloroacetic acid, and acetonitrile as the mobile phase. An elution protocol using 23-37% acetonitrile was used for peptide purification, in which the peptides were eluted between a range of M32135% acetonitrile. The corresponding Av3b mutant peak area from the HPLC chromatograph was used to calculate the peptide yield.

The peaks observed in the HPLC analysis were purified by rpHPLC and subjected to LC/MS identification using a Waters/Micromass ESI-TOF mass spectrometer on-line with an Agilent HPLC system. The LC/MS results confirmed the new mutant amino acid sequences.

TABLE 4

First round list of mutants. Mutations are show relative to wild-type Av3. Increased yield is relative to Av3b expression: Y = Yes; N = No.

| Name | Amino acid sequence | Mutations | Increased Yield |
|---|---|---|---|
| Av3b | KSCCPCYWGGCPWGQNCYPEGCSGPK (SEQ ID NO: 1) | R1K, Δ C-terminal | NA |
| Av3bM1 | KSACPCYWGGAPWGQNCYPEGCSGPK (SEQ ID NO: 2) | C3A, C11A | N |
| Av3bM2 | KSPCPCYWGGAPWGQNCYPEGCSGPK (SEQ ID NO: 3) | C3P, C11A | N |
| Av3bM3 | KSNCPCYWGGTPWGQNCYPEGCSGPK (SEQ ID NO: 4) | C3N, C11T | N |
| Av3bM4 | PSCCPCYWPNCPWGQNCYPEGCSGPK (SEQ ID NO: 5) | K1P, G9P, G10N | N |

TABLE 4-continued

First round list of mutants. Mutations are show relative to wild-type Av3. Increased yield is relative to Av3b expression: Y = Yes; N = No.

| Name | Amino acid sequence | Mutations | Increased Yield |
|---|---|---|---|
| Av3bM5 | KSCCPCYWPNCPWGQNCYPEGCSGPK (SEQ ID NO: 6) | G9P, G10N | Y |
| Av3bM6 | TSCCPCYWPYCPWGQNCYPEGCSGPT (SEQ ID NO: 7) | K1T, G9P, G10Y, K26T | N |
| Av3bM7 | TSCCPCYWPYCPWGQNCYPEGCSGPR (SEQ ID NO: 8) | K1T, G9P, G19Y, K26R | N |
| Av3bM8 | TSCCPCYWGGCPWGQNCYPEGCSGPT (SEQ ID NO: 9) | K1T, K26R | N |
| Av3bM9 | TSCCPCYWGGCPWGTTCYPNGCDGPT (SEQ ID NO: 10) | K1T, Q15T, N16T, E20N, S23D, K26T | N |
| Av3bM10 | TSCCPCYWGGCPWGQTCYPNGCDGPT (SEQ ID NO: 11) | K1T, N16T, E20N, S23D, K26T | N |
| Av3bM11 | TSCCPCYWGGCPWGQTCYPNGCDGPR (SEQ ID NO: 12) | K1T, N16T, E20N, S23D, K26R | N |
| Av3bM12 | TSCCPCYWGGCPWGTTCYPNGCDGST (SEQ ID NO: 13) | K1T, Q15T, N16T, E20N, S23D, P25S, K26T | N |
| Av3bM13 | TSCCPCYWGGCPWGQTCYPNGCDGST (SEQ ID NO: 14) | K1T, N16T, E20N, S23D, P25S, K26T | N |
| Av3bM14 | TSCCPCYWGGCPWGQTCYPNGCDGSE (SEQ ID NO: 15) | K1T, N16T, E20N, S23D, P25S, K26E | N |
| Av3bM15 | TSCCPCYWGGCPWGTTCYPNGCDGSR (SEQ ID NO: 16) | K1T, Q15T, N16T, E20N, S23D, P25S, K26R | N |
| Av3bM16 | TSCCPCYWGGCPWGQTCYPNGCDGSR (SEQ ID NO: 17) | K1T, N16T, E20N, S23D, P25S, K26R | N |
| Av3bM17 | KSCAPCYWGGAPWGQNCYPEGCSGPK (SEQ ID NO: 18) | C4A, C11A | N |
| Av3bM18 | KSACPCYWGGCPWGQNAYPEGCSGPK (SEQ ID NO: 19) | C3A, C17A | N |

As shown above, and in FIG. 1, a lead mutant candidate, Av3bM5, was identified. Av3bM5 has the amino acid sequence "KSCCPCYWPNCPWGQNCYPEGCSGPK" (SEQ ID NO: 6), and has G9P, G10N mutations relative to the wild-type sequence. FIG. 1.

Accordingly, as the Av3bM5 mutant resulted in increased yield relative to Av3b, this mutant was used as a starting point for other mutations in a second round of mutations aiming to further increase yield and/or insecticidal activity.

Example 3. Generation of Mutant Candidates: Second Round

Following the outcome of the first round of mutations above, additional mutation strategies were pursued. These mutation strategies include: mutations to non-crucial locations of the peptide; mutations focusing on positions G9, G10; and mutations at the N-and C-termini. Each mutation strategy is discussed in turn, below.

Non-Crucial Mutations

The Av3b sequence is "KSCCPCYWGGCPWGQNCY-PEGCSGPK" (SEQ ID NO: 1). Av3b has a hydrophobic nicotinic acetylcholine (NaCh) binding surface that involves residues at positions P5, Y7, W8, P12 and W13. The Av3b pharmacophore differs from other NaCh site III toxins, which utilize charged amino acid for binding. Based on identity of binding residues, and those residues identified in the DDG analysis as medium energy state mutations, six non-crucial residues were identified for further analysis: S2, Q15, $N_{16}$, E20, S23, and P25. These non-crucial residues were examined, in mutants Av3bM19 to Av3bM24, for mutations that might be responsible for yield improvement.

G9-G10 Mutants

During the initial single mutant energy state (ΔΔG) analysis, mutations G9P, G10N (Av3bM5) showed improved yield. To further examine this location of the peptide, a Rosetta relax design was performed with a focus on G9 and G10, resulting 3 mutants, Av3bM25 to Av3bM27.

Under the Rosetta relax design, the Rosetta program interface was used to select candidate residues and the desired mutated amino acids; the program was then instructed to run a "relax design" in which the program will perform simple all-atom refinement of structures for all different combinations of mutations after folding based on Av3b structure. The program will give the ΔΔG value for each mutant peptide, thus giving an indication as to the mutant's stability. If a mutant is not stable (as indicated by its high ΔΔG value), it would be unlikely that such a mutant will result in high yield in yeast. Therefore, the most stable mutants indicated under the relax design were selected for further investigation high yield candidate mutants.

Terminal Mutants

The N-terminal and/or C-terminal lysine has been suggested as a target point for Av3b degradation. Accordingly, these amino acids were evaluated to determine how K1 or K26 mutants might withstand degradation. Here, the Rosetta relax design was performed for terminal mutations, resulting in six mutants, Av3bM28 to Av3bM33.

The new mutants identified via the aforementioned mutation strategies are provided in the table below.

TABLE 5

Second round list of mutants.

| Name | Amino acid sequence | Mutations | Strategy |
|---|---|---|---|
| Av3bM19 | KSCCPCYWGGCPWGQDCYPDGCDGPK (SEQ ID NO: 20) | N16D, E20D, S23D | Non-crucial |
| Av3bM20 | KSCCPCYWGGCPWGTTCYPNGCDGPK (SEQ ID NO: 21) | Q15T, N16T, E20N, S23D | |
| Av3bM21 | KSCCPCYWGGCPWGTNCYPEGCSGPK (SEQ ID NO: 22) | Q15T | |
| Av3bM22 | KSCCPCYWGGCPWGQTCYPEGCSGPK (SEQ ID NO: 23) | N16T | |
| Av3bM23 | KSCCPCYWGGCPWGQNCYPNGCSGPK (SEQ ID NO: 24) | E20N | |
| Av3bM24 | KSCCPCYWGGCPWGQNCYPEGCDGPK (SEQ ID NO: 25) | S23D | |
| Av3bM25 | KSCCPCYWPGCPWGQNCYPEGCSGPK (SEQ ID NO: 26) | G9P | G9-G10 |
| Av3bM26 | KSCCPCYWPPCPWGQNCYPEGCSGPK (SEQ ID NO: 27) | G9P, G10P | |
| Av3bM27 | KSCCPCYWAGCPWGQNCYPEGCSGPK (SEQ ID NO: 28) | G9A | |
| Av3bM28 | HSCCPCYWGGCPWGQNCYPEGCSGPK (SEQ ID NO: 29) | K1H | Terminal mutants |
| Av3bM29 | QSCCPCYWGGCPWGQNCYPEGCSGPK (SEQ ID NO: 30) | K1Q | |
| Av3bM30 | QSCCPCYWGGCPWGQNCYPEGCSGPH (SEQ ID NO: 31) | K1Q, K26H | |
| Av3bM31 | TSCCPCYWGGCPWGQNCYPEGCSGPK (SEQ ID NO: 32) | K1T | |
| Av3bM32 | SSCCPCYWGGCPWGQNCYPEGCSGPK (SEQ ID NO: 33) | K1S | |
| Av3bM33 | SSCCPCYWGGCPWGQNCYPEGCSGPT (SEQ ID NO: 34) | K1S, K26T | |

Example 4. Yield of New Mutants

The expression vectors of the target mutants were linearized by the digestion with the restriction enzyme SacII; the resulting linear plasmids were then transformed into *K. lactis* cell by electroporation; at least 16 of resulting positive transformation colonies were picked for yield analysis. The picked transformants were then used to inoculate the culture wells in a 48-well deep-well culture plate with each well containing 2.2 mL culture medium (DMSor): 2 g/L Solulys 095K, 11.83 g/L $KH_2PO_4$, 2.299 g/L $K_2HPO_4$, 40 g/L sorbitol, 1 g/L $MgSO_4·7H_2O$, 10 g/L $(NH_4)SO_4$, 0.33 g/L $CaCl_2)·2H_2O$, 1 g/L NaCl, 1 g/L KCl, 5 mg/L $CuSO_4·5H_2O$, 30 mg/L $MnSO_4·H_2O$, 10 mg/L $ZnCl_2$, 1 mg/L KI, 2 mg/L $CoCl_2·6H_2O$, 8 mg/L $Na_2MoO_4·2H_2O$, 0.4 mg/L $H_3BO_3$, 15 mg/L $FeCl_3·6H_2O$, 0.8 mg/L biotin, 20 mg/L Ca-pantothenate, 15 mg/L thiamine, 16 mg/L myo-inositol, and 10 mg/L nicotinic acid, and 4 mg/L pyridoxine.

The deep-well culture plate was sealed with a sterile breathable seal and incubated at 23.5° C., 250 rpm for 6 days. After six days culture, the deep-well culture plate was spun at 4000 rpm for 10 minute to collect the cell pallets and supernatants, the cell pallets were resuspended into 1 mL of 20% glycerol for long-term storage of the strain at −80° C. freezer. The supernatant containing the expressed mutant peptide were then subjected to rpHPLC evaluation to determine the peptide yield.

To run the rpHPLC, the supernatants were filtered through 0.2 μm filter membrane. Next, 300 μL of the filtered supernatants were transferred to a 500 μL 96-well plate for rpHPLC analysis using Ultramate 3000 HPLC system (ThermoFisher), controlled by Chromeleon 7 software. The rpHPLC was performed via monolithic C18 columns using water with 0.10% Trifloroacetic acid, and acetonitrile as the mobile phase. An elution protocol using 23-37% acetonitrile was used for peptide purification, in which the peptides were eluted between a range of 32-35% acetonitrile.

To calculate the mutant peptide yield, previously generated Av3b peptide mass and its HPLC peak area relationship was used to calculate the yield based on the corresponding Av3b mutant peak area from the HPLC chromatograph.

Figure 2:
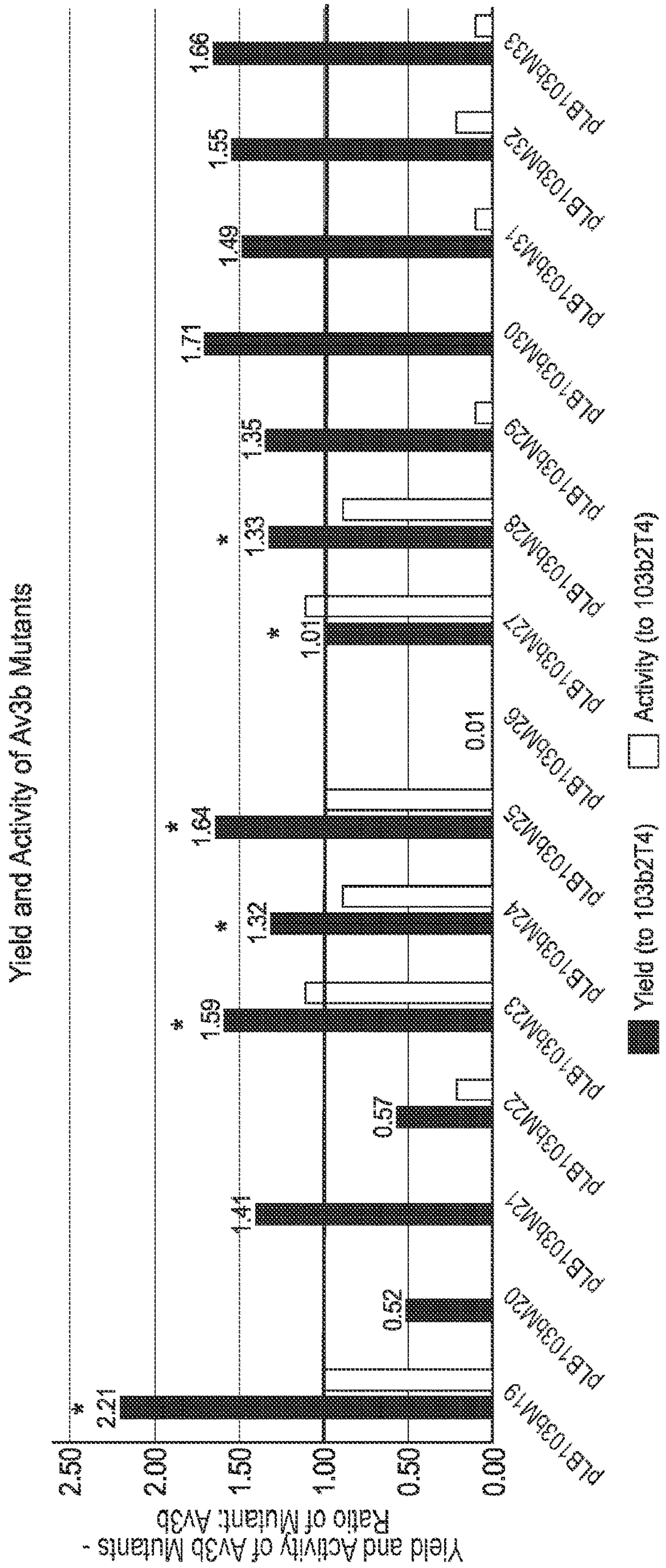
FIG. 2 depicts the yield and activity of the Av3b mutants, Av3bM19-Av3bM33. Mutant peptides were expressed in a *K. lactis* expression system. The yield and activity of a given mutant was normalized to that of an Av3b expression strain, with the ratio shown in the bars.

The yield and activity of the new mutants was evaluated. Mutant peptides were expressed in a *K. lactis* expression system. The yield of the new mutants were then normalized to an Av3b expression strain. FIG. 2. Here, the average yield of a given new mutant strain was normalized to the average yield of the Av3b production strain, with the ratio shown (blue bars in FIG. 2).

Here, all the new mutants generated in the second round of mutations exhibited an increased yield, with the exception of Av3bM20, Av3bM22, and Av3bM26.

Example 5. Housefly Assay

A housefly injection assay was performed to determine the activity of the new mutants. Adult houseflies were immobilized with C02 for 10 minutes, and then transferred to a C02 pan to keep immobilized. Flies with weight between 12-20 mg were picked for injection. The new mutants and Av3b control were diluted in water to proper doses for injection. Next, a 0.5 μL peptide solution was injected into each housefly at the dorsal thorax using a hand-microapplicator with 1 cc all-glass syringe with 30 gauge straight needle. The injected flies were then transferred to a 2 oz. transparent portion container with a wet #4 filter paper. Fly knock-down was assessed at 5-hours post-injection. The activity of a given new mutant was then normalized to the activity of the Av3b production strain (control), using the fly knock-down score at 5 hours. The ratio of knock-down scores (new mutant KD/Av3b KD) is presented in FIG. 2 (red bars).

The results of the housefly assay show that Av3bM19, Av3bM23, Av3bM24, Av3bM25 and Av3bM28 possessed improved yield, albeit without a concomitant reduction in housefly knock-down activity. In addition, Av3bM27 behaved like Av3b. FIG. 2.

TABLE 6

Yield and activity for second round mutants. Mutants highlighted bold exhibited both increased yield relative to Av3b while maintaining insecticidal activity.

| Name | Amino acid sequence | Mutations | Yield | Activity |
|---|---|---|---|---|
| Av3bM19 | KSCCPCYWGGCPWGQDCYPDGCDGPK (SEQ ID NO: 20) | N16D, E20D, S23D | Yes | Yes |
| Av3bM20 | KSCCPCYWGGCPWGTTCYPNGCDGPK (SEQ ID NO: 21) | Q15T, N16T, E20N, S23D | No | No |
| Av3bM21 | KSCCPCYWGGCPWGTNCYPEGCSGPK (SEQ ID NO: 22) | Q15T | Yes | No |
| Av3bM22 | KSCCPCYWGGCPWGQTCYPEGCSGPK (SEQ ID NO: 23) | N16T | No | No |
| Av3bM23 | KSCCPCYWGGCPWGQNCYPNGCSGPK (SEQ ID NO: 24) | E20N | Yes | Yes |
| Av3bM24 | KSCCPCYWGGCPWGQNCYPEGCDGPK (SEQ ID NO: 25) | S23D | Yes | Yes |
| Av3bM25 | KSCCPCYWPGCPWGQNCYPEGCSGPK (SEQ ID NO: 26) | G9P | Yes | Yes |
| Av3bM26 | KSCCPCYWPPCPWGQNCYPEGCSGPK (SEQ ID NO: 27) | G9P, G10P | No | No |
| Av3bM27 | KSCCPCYWAGCPWGQNCYPEGCSGPK (SEQ ID NO: 28) | G9A | Yes | Yes |
| Av3bM28 | HSCCPCYWGGCPWGQNCYPEGCSGPK (SEQ ID NO: 29) | K1H | Yes | Yes |
| Av3bM29 | QSCCPCYWGGCPWGQNCYPEGCSGPK (SEQ ID NO: 30) | K1Q | Yes | Nc |
| Av3bM30 | QSCCPCYWGGCPWGQNCYPEGCSGPH (SEQ ID NO: 31) | K1Q, K26H | Yes | No |
| Av3bM31 | TSCCPCYWGGCPWGQNCYPEGCSGPK (SEQ ID NO: 32) | K1T | Yes | No |
| Av3bM32 | SSCCPCYWGGCPWGQNCYPEGCSGPK (SEQ ID NO: 33) | K1S | Yes | No |
| Av3bM33 | SSCCPCYWGGCPWGQNCYPEGCSGPT (SEQ ID NO: 34) | K1S, K26T | Yes | No |

In the second round of mutations, the mutants Av3bM19, Av3bM23, Av3bM24, Av3bM25, and Av3bM28 were shown to have increased yield relative to Av3b, and insecticidal activity. The new mutant Av3bM27 had yields and insecticidal activity comparable to Av3b. FIG. 2.

Figure 10:
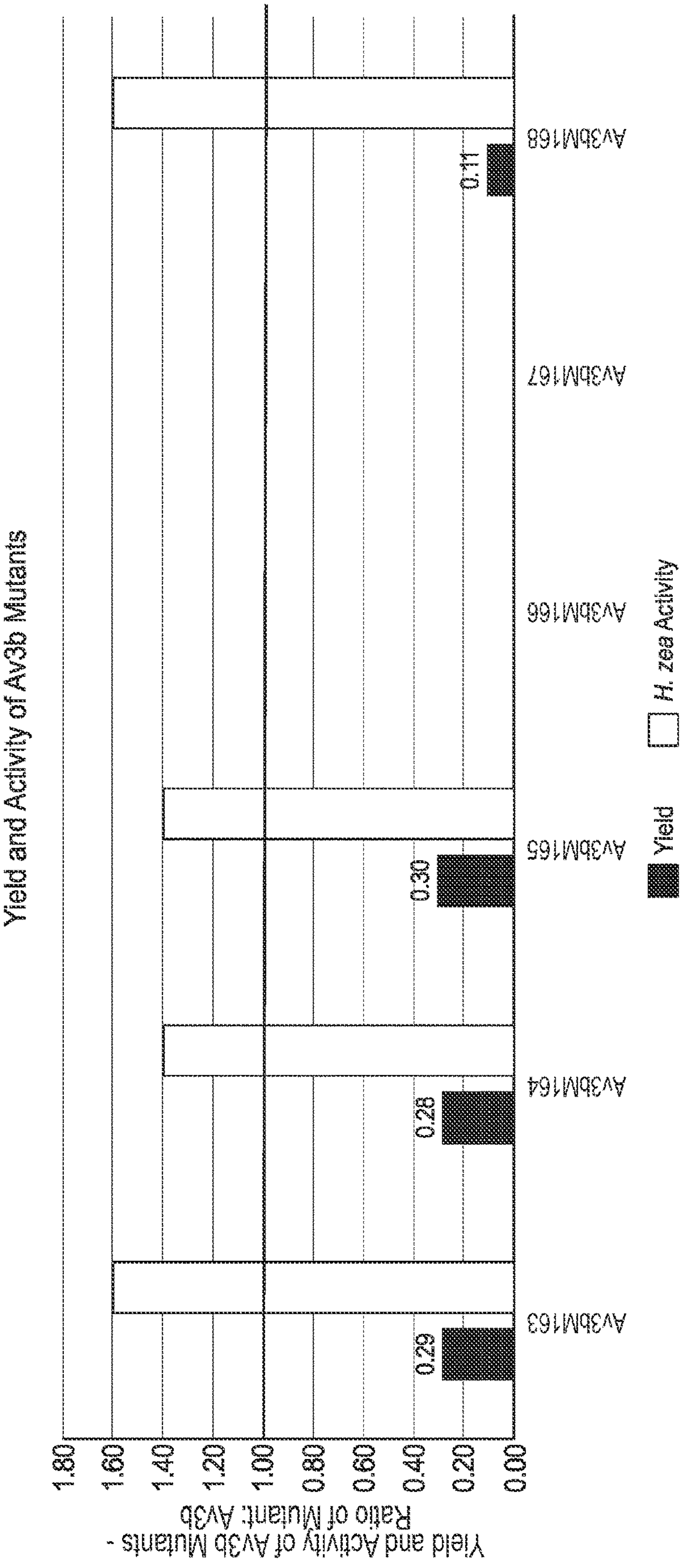
FIG. 10 shows the yield and activity for Av3 mutants Av3bM163-Av3bM168. Mutant peptides were expressed in a *K. lactis* expression system. The yield and activity of a given mutant was normalized to that of an Av3b expression strain, with the ratio shown in the bars. Here, activity was assessed in a *Helicoverpa zea* (corn earworm or "CEW") injection assay.
Figure 11:
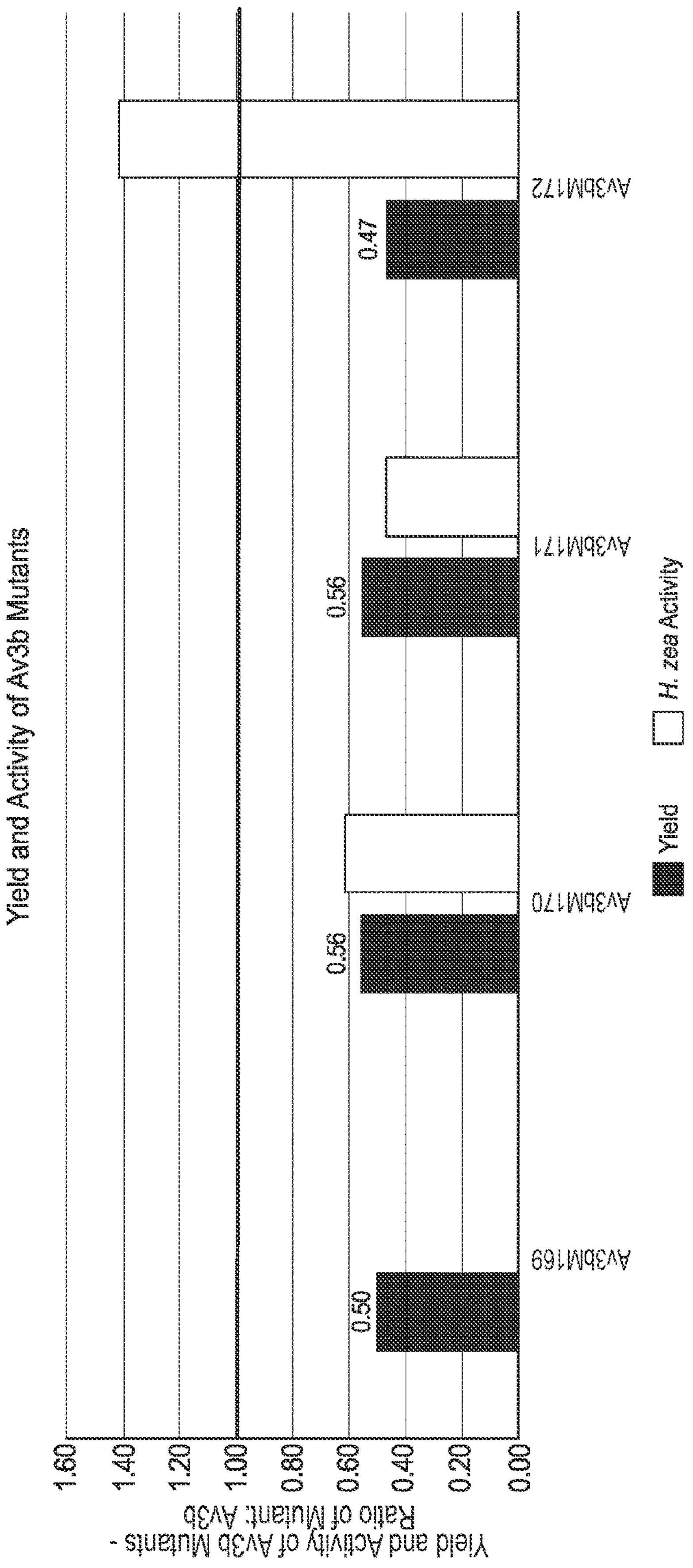
FIG. 11 shows the yield and activity for Av3 mutants Av3bM169-Av3bM172. Mutant peptides were expressed in a *K. lactis* expression system. The yield and activity of a given mutant was normalized to that of an Av3b expression strain, with the ratio shown in the bars. Here, activity was assessed in a *Helicoverpa zea* (corn earworm or "CEW") injection assay.

The complete yield and housefly injection assay activity results for the Av3b mutants tested herein are provided in FIGS. 3-9. Yield and *Helicoverpa zea* (corn earworm or "CEW") injection assay results are presented in FIGS. 10-11. The *Helicoverpa zea* injection assay methods are described below.

Example 6. Av3b Mutant Stability During Fermentation

The use of yeast strains to produce recombinant peptides is a common technique in the biotech industry, with methods that are well known in the art. However, one of the challenges associated with the production of recombinant proteins is the prevention of their unintended proteolytic degradation. See, e.g., Fricke, J. et al. Designing a fully automated multi-bioreactor plant for fast DoE optimization of pharmaceutical protein production. Biotechnol. J. 8, 738-747. Accordingly, the prevention of such proteolytic degradation is an important goal and long-felt need that remains to be met by the industry.

To test the stability of Av3b during production, a stability fermentation assay was performed using fermentation conditions as described herein.

Figure 3:
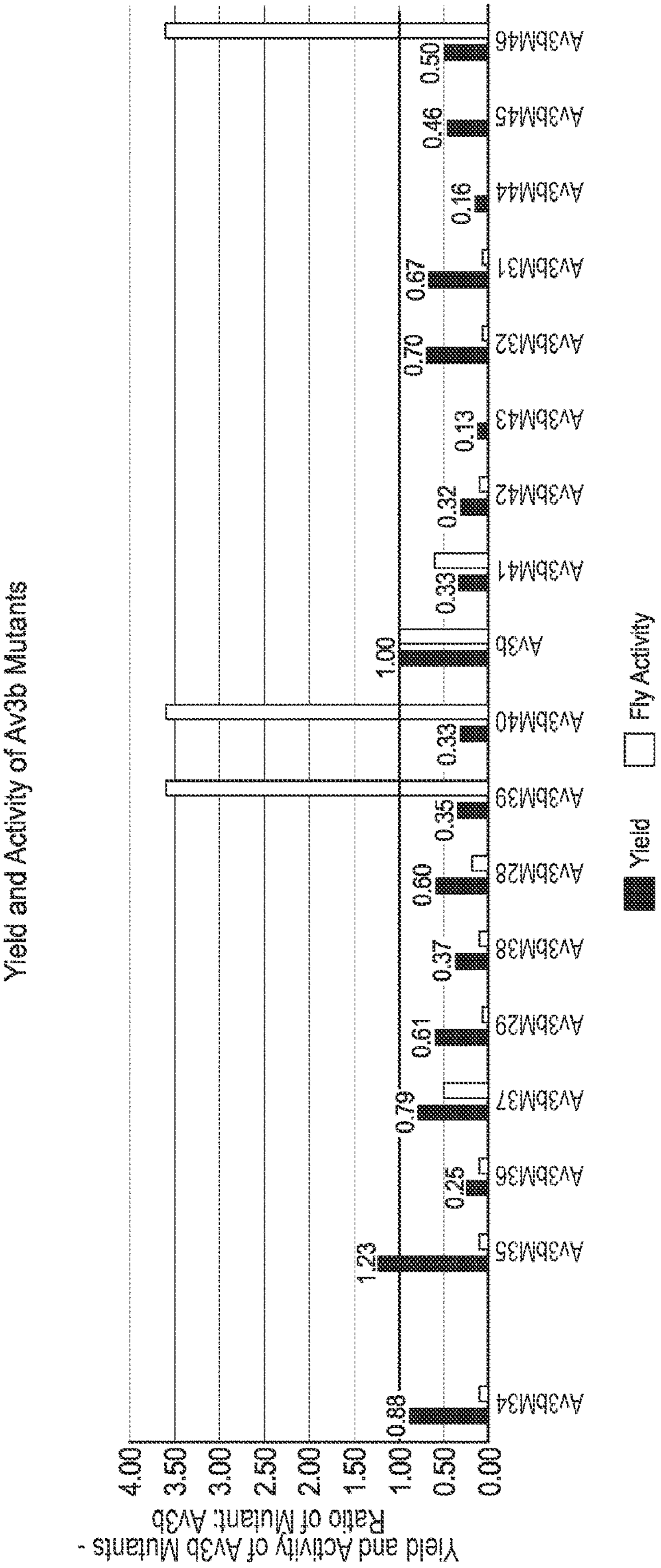
FIG. 3 shows the yield and activity for Av3 mutants Av3bM34-Av3bM46. Mutant peptides were expressed in a *K. lactis* expression system. The yield and activity of a given mutant was normalized to that of an Av3b expression strain, with the ratio shown in the bars. Activity was assessed in a housefly injection assay.
Figure 4:
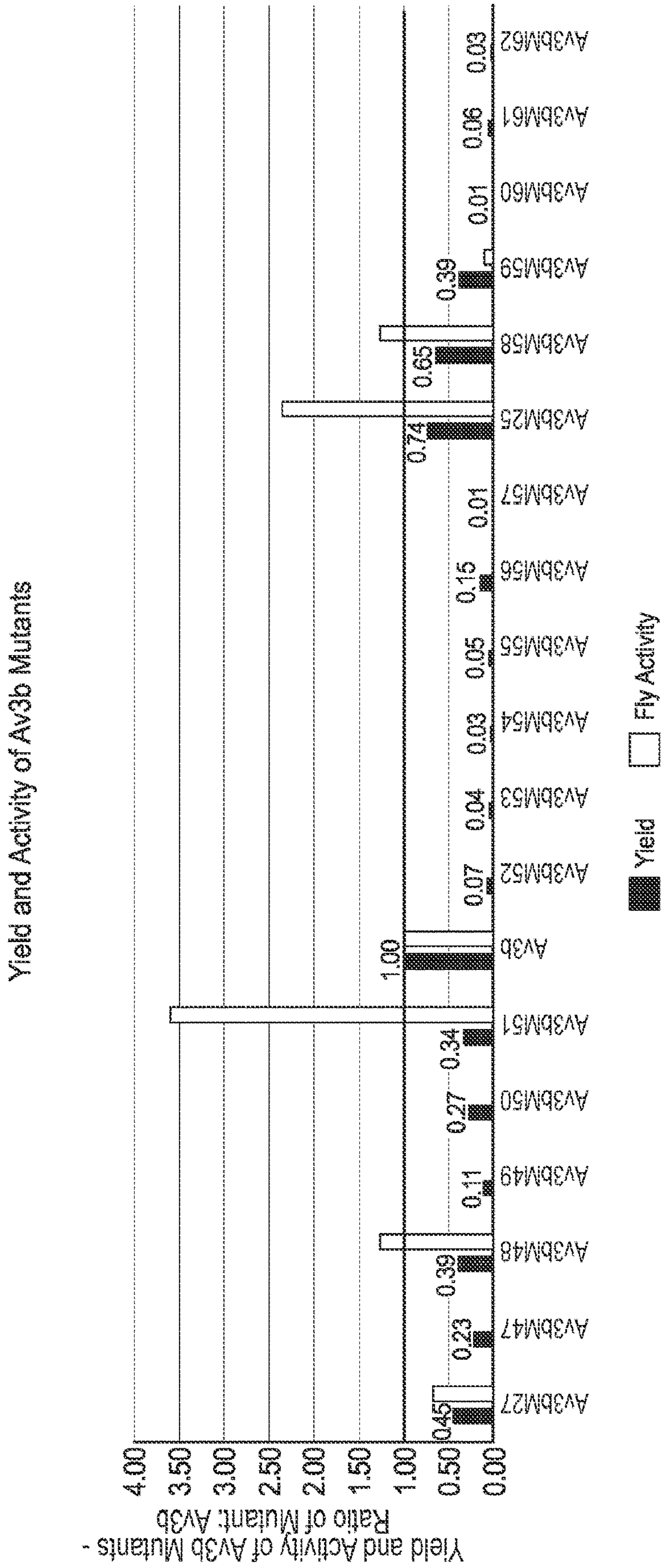
FIG. 4 shows the yield and activity for Av3 mutants Av3bM47-Av3bM62. Mutant peptides were expressed in a *K. lactis* expression system. The yield and activity of a given mutant was normalized to that of an Av3b expression strain, with the ratio shown in the bars. Activity was assessed in a housefly injection assay.
Figure 5:
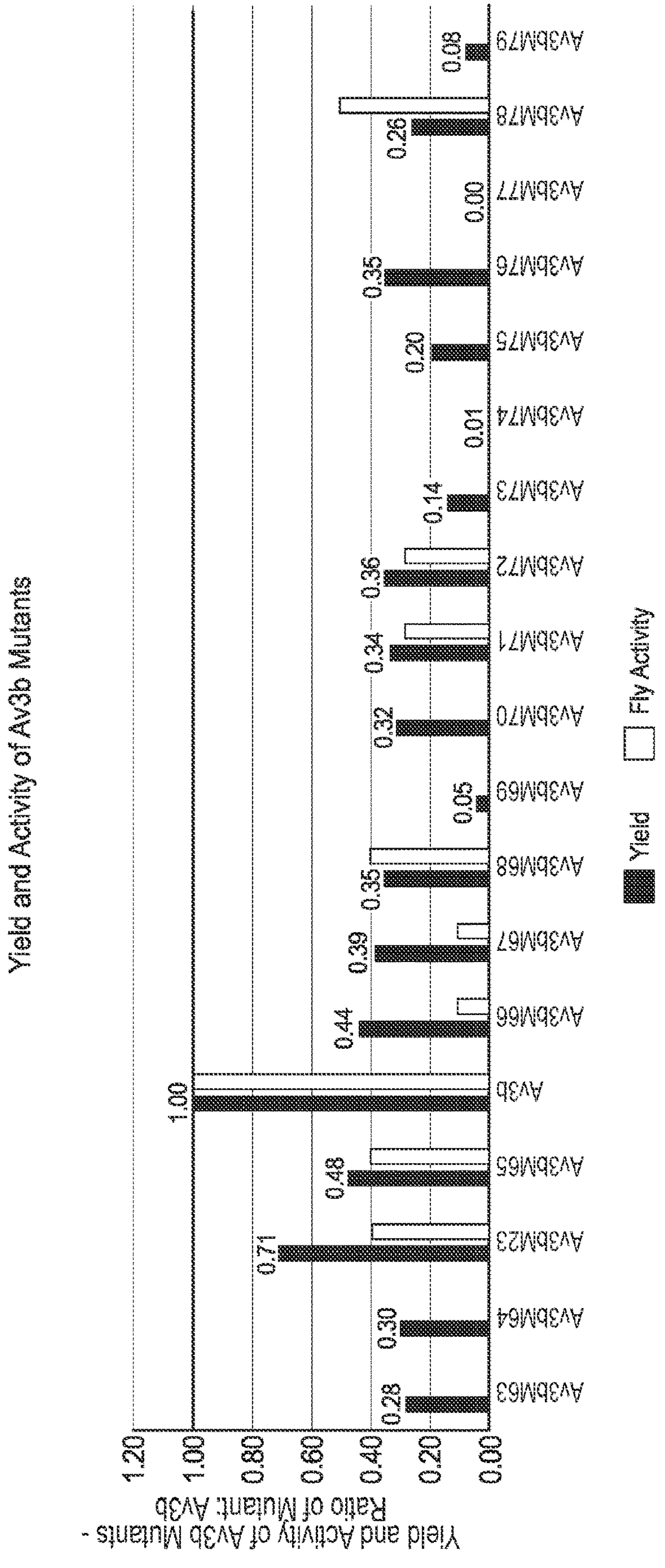
FIG. 5 shows the yield and activity for Av3 mutants Av3bM63-Av3bM79. Mutant peptides were expressed in a *K. lactis* expression system. The yield and activity of a given mutant was normalized to that of an Av3b expression strain, with the ratio shown in the bars. Activity was assessed in a housefly injection assay.
Figure 6:
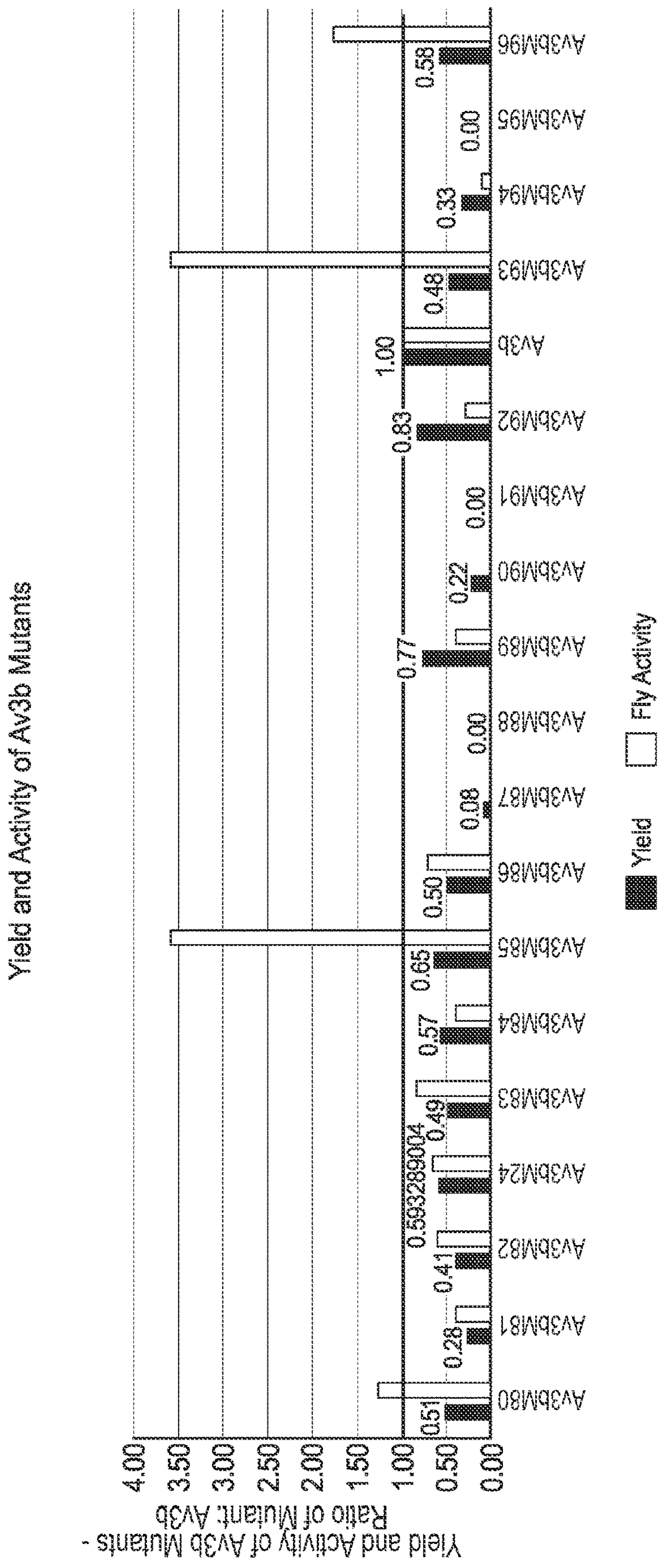
FIG. 6 shows the yield and activity for Av3 mutants Av3bM80-Av3bM96. Mutant peptides were expressed in a *K. lactis* expression system. The yield and activity of a given mutant was normalized to that of an Av3b expression strain, with the ratio shown in the bars. Activity was assessed in a housefly injection assay.
Figure 7:
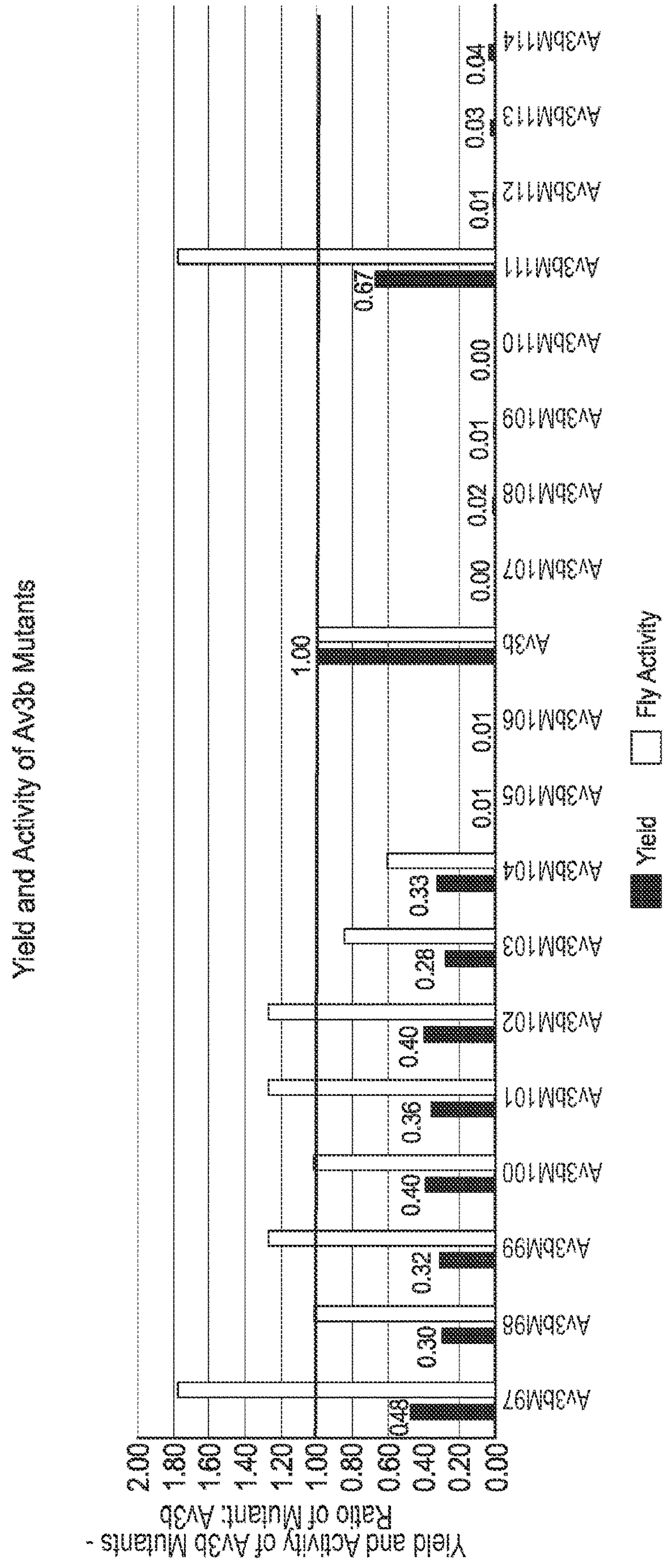
FIG. 7 shows the yield and activity for Av3 mutants Av3bM97-Av3bM114. Mutant peptides were expressed in a *K. lactis* expression system. The yield and activity of a given mutant was normalized to that of an Av3b expression strain, with the ratio shown in the bars. Activity was assessed in a housefly injection assay.
Figure 8:
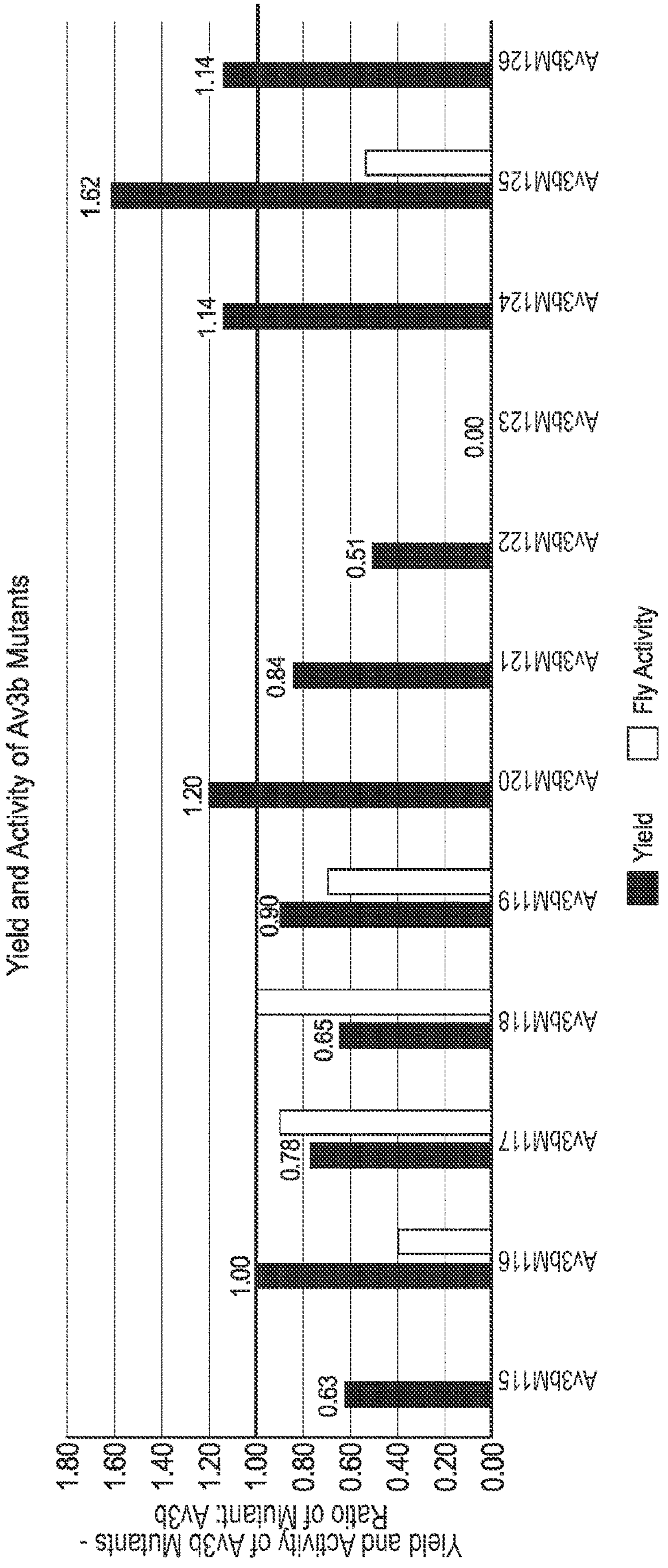
FIG. 8 shows the yield and activity for Av3 mutants Av3bM115-Av3bM126. Mutant peptides were expressed in a *K. lactis* expression system. The yield and activity of a given mutant was normalized to that of an Av3b expression strain, with the ratio shown in the bars. Activity was assessed in a housefly injection assay.
Figure 9:
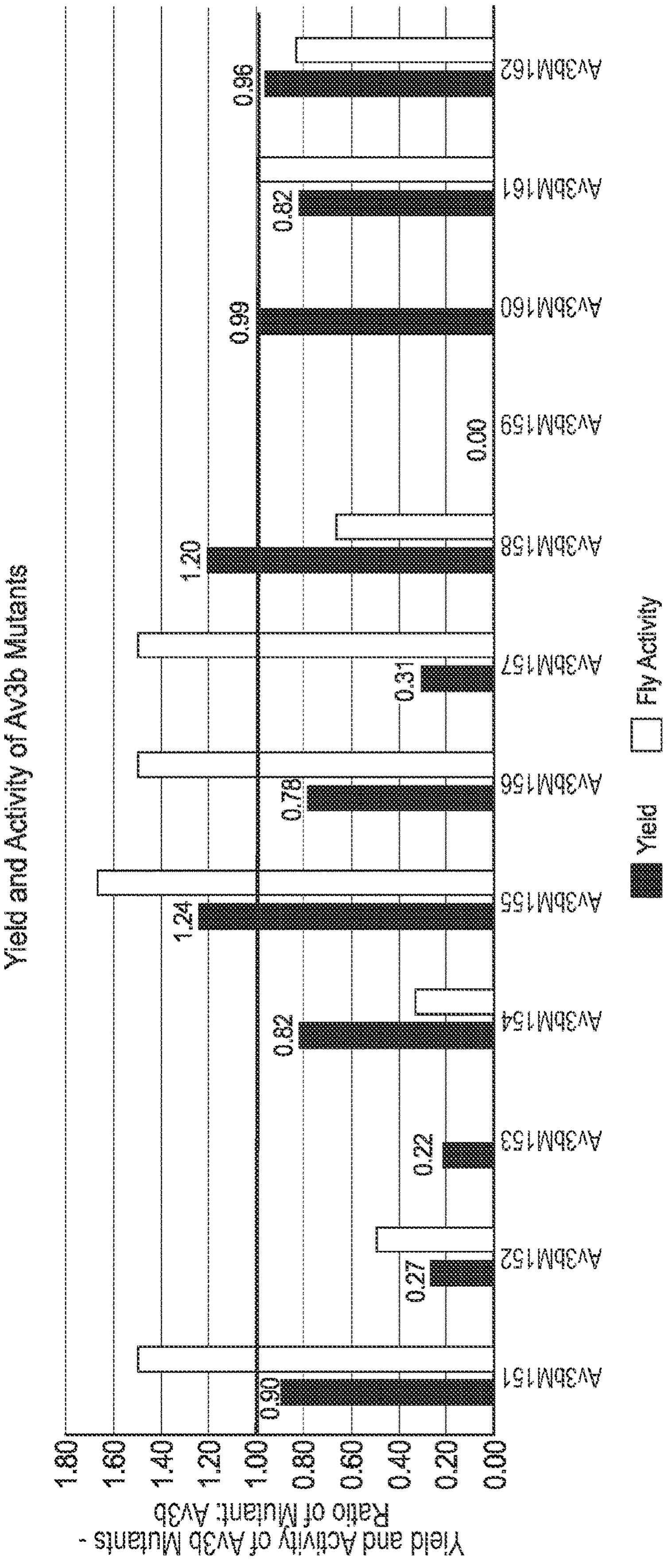
FIG. 9 shows the yield and activity for Av3 mutants Av3bM151-Av3bM162. Mutant peptides were expressed in a *K. lactis* expression system. The yield and activity of a given mutant was normalized to that of an Av3b expression strain, with the ratio shown in the bars. Activity was assessed in a housefly injection assay.

The fermentation beer that is generated during the large-scale production of Av3b peptides contains proteolytic enzymes that degrade Av3b. It was observed that degradation of Av3b occurred at pH 6.5, however, degradation occurred much slower at pH 4.5. Moreover, Av3b was shown to be stable when contained in buffer solutions having a pH of 4.5 or a pH of 6.5. In addition, autoclaving fermentation beer eliminated the degradation of Av3b; and, the addition of EDTA likewise reduced the amount of Av3b degradation in the fermentation beer. Accordingly, these observations indicated that some proteases, which may be produced from the yeast cells during the fermentation process, may be responsible for the degradation of Av3b. FIG. 3.

Figure 12:
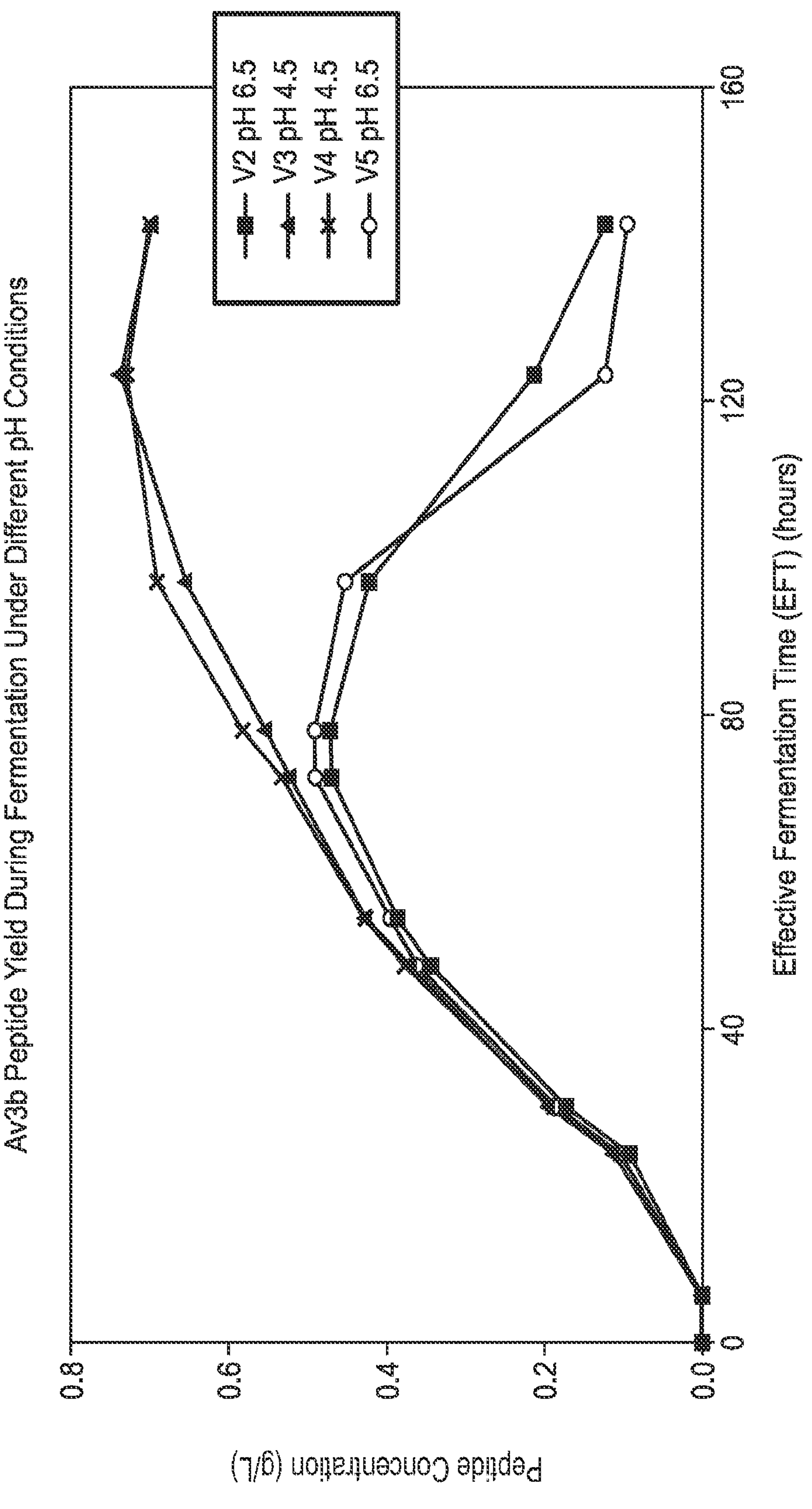
FIG. 12 depicts a graph showing Av3b peptide yield during fermentation under different pH conditions. The Y-axis represents the Av3b peptide concentration in the fermentation beer supernatant as g/L. The X-axis represents the fermentation time (EFT: Effective Fermentation Time). Four fermentations were performed simultaneously using the same conditions, with the exception of pH. The pH conditions were: pH control, pH4.5, and pH6.5. Each pH condition had two replication fermentations. V2=pH 6.5 (light blue line); V3=pH 4.5 (purple line); V4=pH 4.5 (brown line); V5=pH 6.5 (dark blue line).

As shown in FIG. 12, during the Av3b fermentation process, the yeast strain not only produces Av3b, but also likely secretes some proteases that have the ability to cleave Av3b, as indicated by the reduction in Av3b production after 80 hours. However, the lower pH could alternatively either inhibit the protease activity, or reduce the protease secretion from the cell.

One method of preventing proteolytic degradation of desirable recombinant proteins is to design yeast comprising a knock-out of the offending protease. Another method is to design peptides resistant to degradation, and/or that reduce protease access to potential cleavage sites. Thus, the following two strategies were pursued: first, the identification and knock-out the responsible proteases from the yeast cells; and second, to re-engineer the Av3 peptide to avoid protease access.

Example 7. Identification of Av3b Degradation Products

Figure 13:
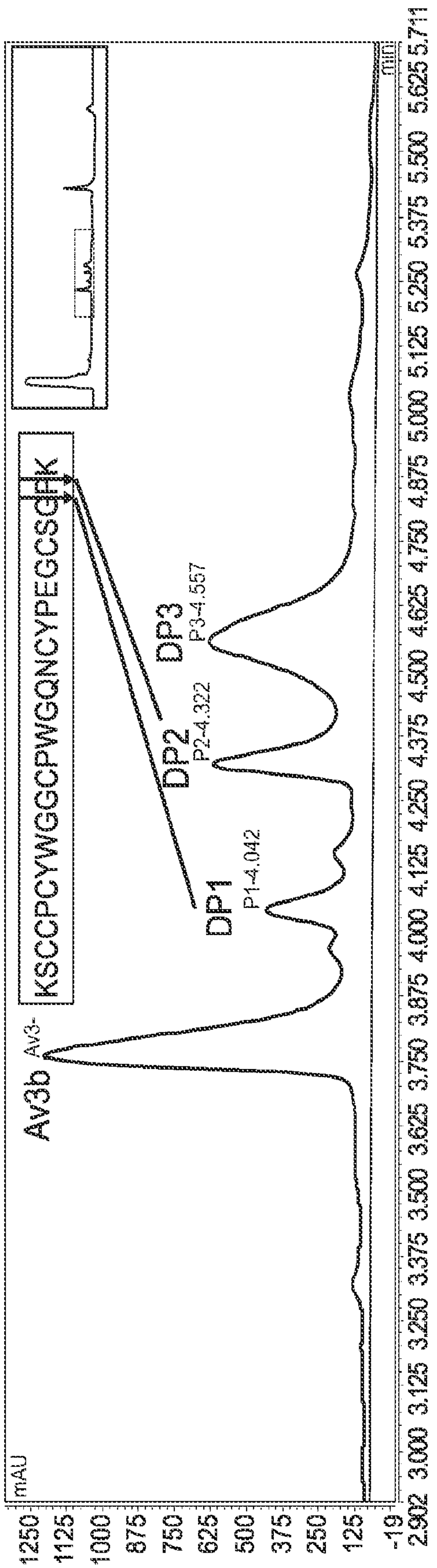
FIG. 13 depicts a rpHPLC chromatogram identifying the Av3b degradation products during fermentation. Samples were analyzed at the end of fermentation, with fermentation lasting around 120 hours. There are 3 extra peaks following the major Av3b peak (identified as DP1, DP2 and DP3). DP1 was a mixture of two C-terminal truncation products of Av3b: ΔK26 and ΔP25-ΔK26, with latter being the major species present. DP2 was identified as a K26 truncation product. DP3 was not identified by LC/MS. These data indicated a carboxyl-peptidases were likely responsible for the Av3b degradation during fermentation.

To identify the Av3b degradation products, a reversed phase HPLC (rpHPLC) was performed. Chromatographs of the Av3b fermentation beer indicated that there are 3 extra peaks following the major Av3b peak (identified as DP1, DP2 and DP3). FIG. 13.

The peaks were collected and analyzed by Liquid chromatography/mass spectrometry (LC/MS). The LC/MS analysis indicated that DP1 was a mixture of two C-terminal truncation products of Av3b: ΔK26 and ΔP25-ΔK26, with latter being the major species present. DP2 was identified as a K26 truncation product. And, DP3 was not identified by LC/MS. These data indicated a carboxyl-peptidases were likely responsible for the Av3b degradation during fermentation. FIG. 13.

Example 8. Identification of Proteases in Av3b Fermentation Beer

The fermentation beer from the Av3b production strain was fractionated by using an AKTA Pure 25 fast protein liquid chromatography (FPLC) system (Product No. 29018226 Cytiva, Global Life Sciences Solutions USA LLC, 100 Results Way, Marlborough, MA 01752, USA), and using a pre-packed Superdex Increase 200GL size-exclusion column (Product No. 28990944; Cytiva, Global Life Sciences Solutions USA LLC, 100 Results Way, Marlborough, MA 01752, USA).

Briefly, a GE AKTA Pure 25 FPLC system was used to collect the Av3b beer fraction. The column used was a pre-packed size-exclusion column (GE, Superdex Increase 200GL, size: 10×300 mm, bed volume 24 mL; Separate protein size: 10,000 to 600,000 Daltons. Max load volume: 0.5 mL). The calibration and elution buffers were as follows:: MES buffer: 2-(N-morpholino)ethanesulfonic acid (MES) 50 mM, NaCl 150 mM, pH 6.0.

A sample of the fermentation beer batch of the yeast strain "pKS022-YCT-38-14" (an Av3b production strain) strain cultured at 27° C., pH 6.5 was obtained. Degradation started at 72 hours during fermentation process, and the final amount of Av3b in the fermentation beer was 0 g/L at the end of the fermentation process.

Figure 14:
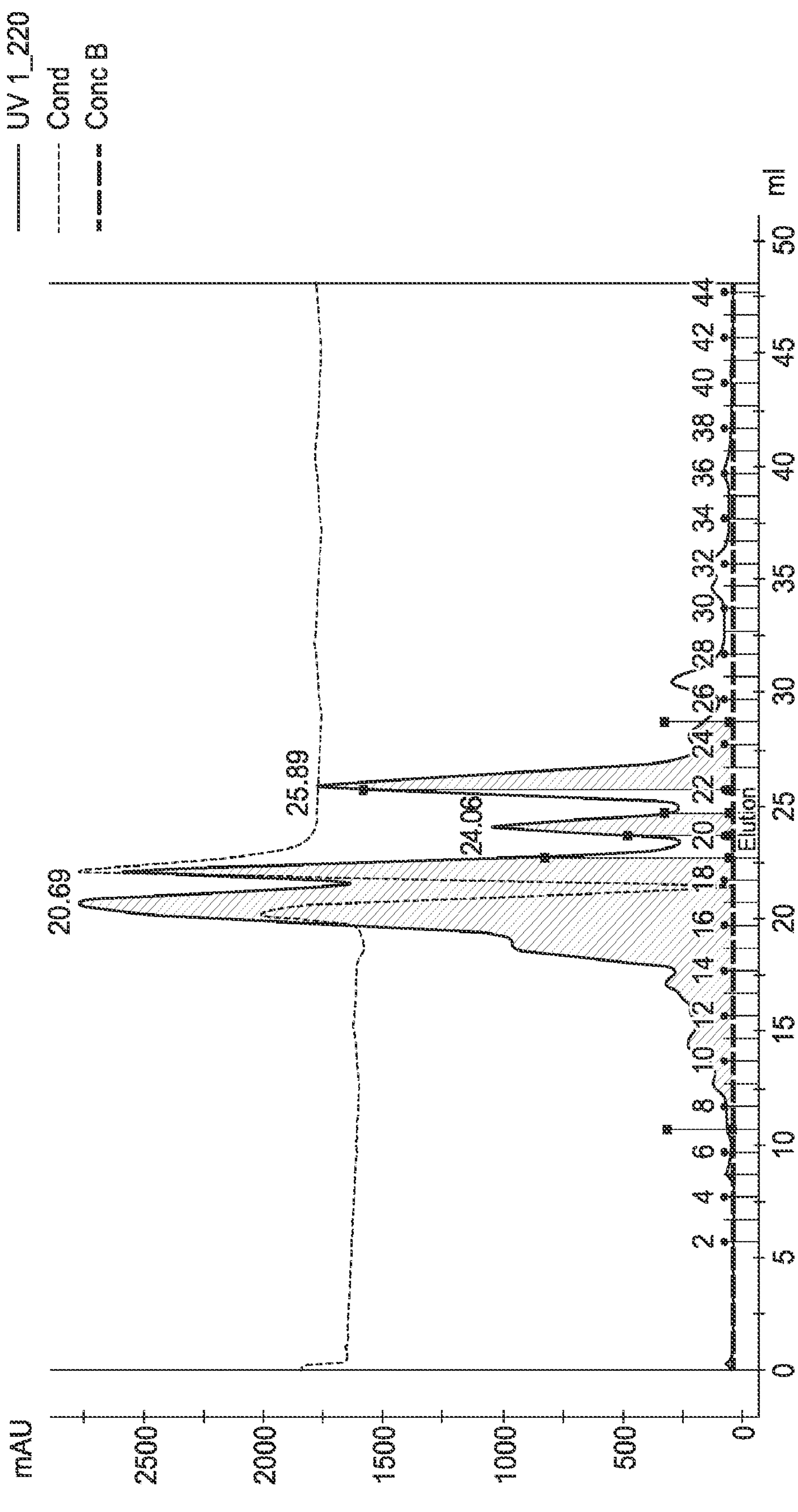
FIG. 14 depicts FPLC size-exclusion chromatograph of fractions of fermentation beer collected from an Av3b fermentation beer sample. Fractions were collected using a GE AKTA Pure 25 system with Superdex Increase 200GL column.

Elution was performed using MES buffer at pH 6.0, for fraction collection; 200 μL of all the collected fractions were spiked with HPLC purified Av3b (10 μg) to final 0.05 μg/μL, and were incubated at 37° C. for 40 hour prior to HPLC evaluation of Av3b degradation. FIG. 14.

Figure 15:
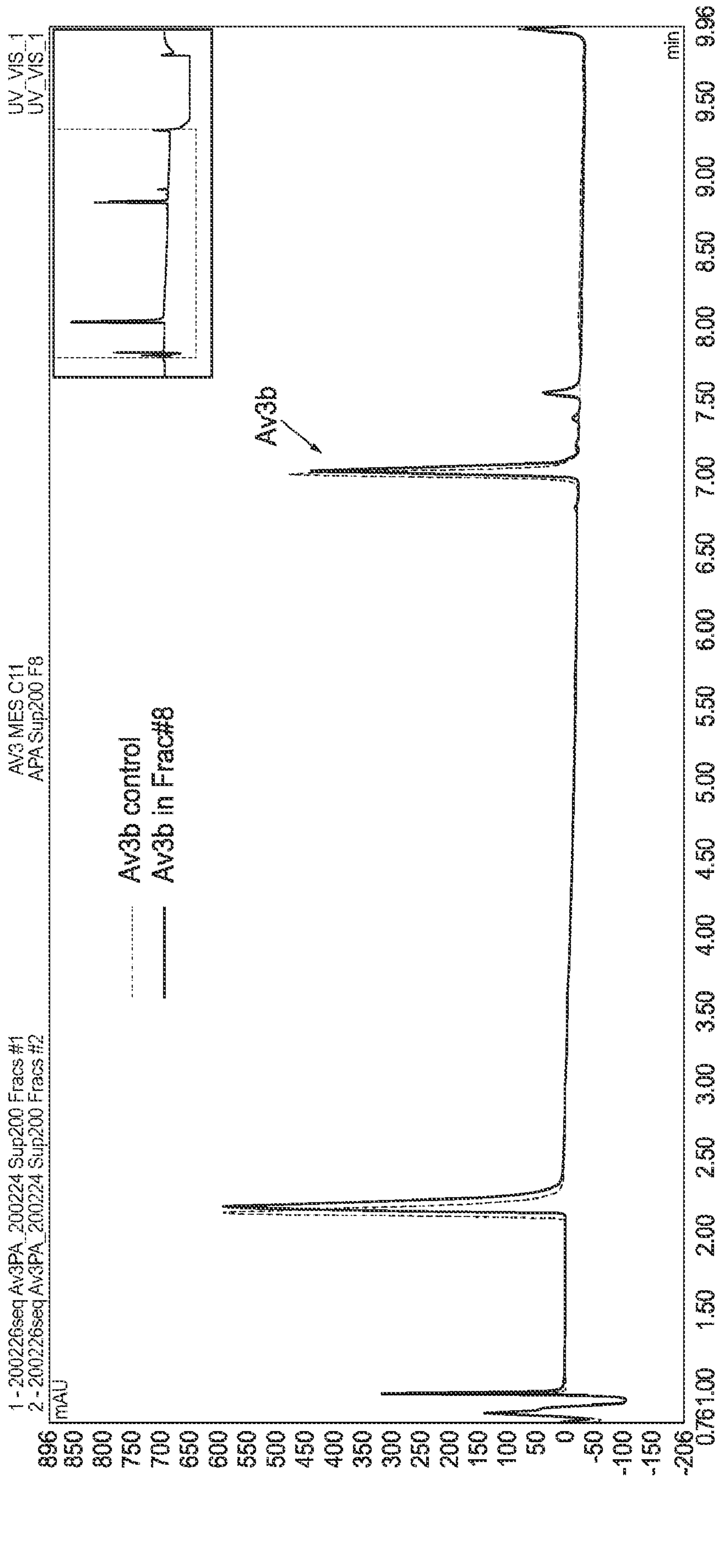
FIG. 15 depicts a chromatograph showing protease activity of fraction #8 shown in FIG. 14. Here, fraction #8 was spiked with Av3b peptide. Fraction #8 showed weak protease activity, which showed some level of Av3b degradation and release of degradation peaks.

Four fractions showed protease activity: Fractions #8, #9, #12 and #13. The HPLC chromatograph after Av3b incubation with 200 μL of fraction #8 is shown in FIG. 15. As shown in FIG. 15, some level of degradation occurred, thus resulting in the release of some degraded peak.

Figure 16:
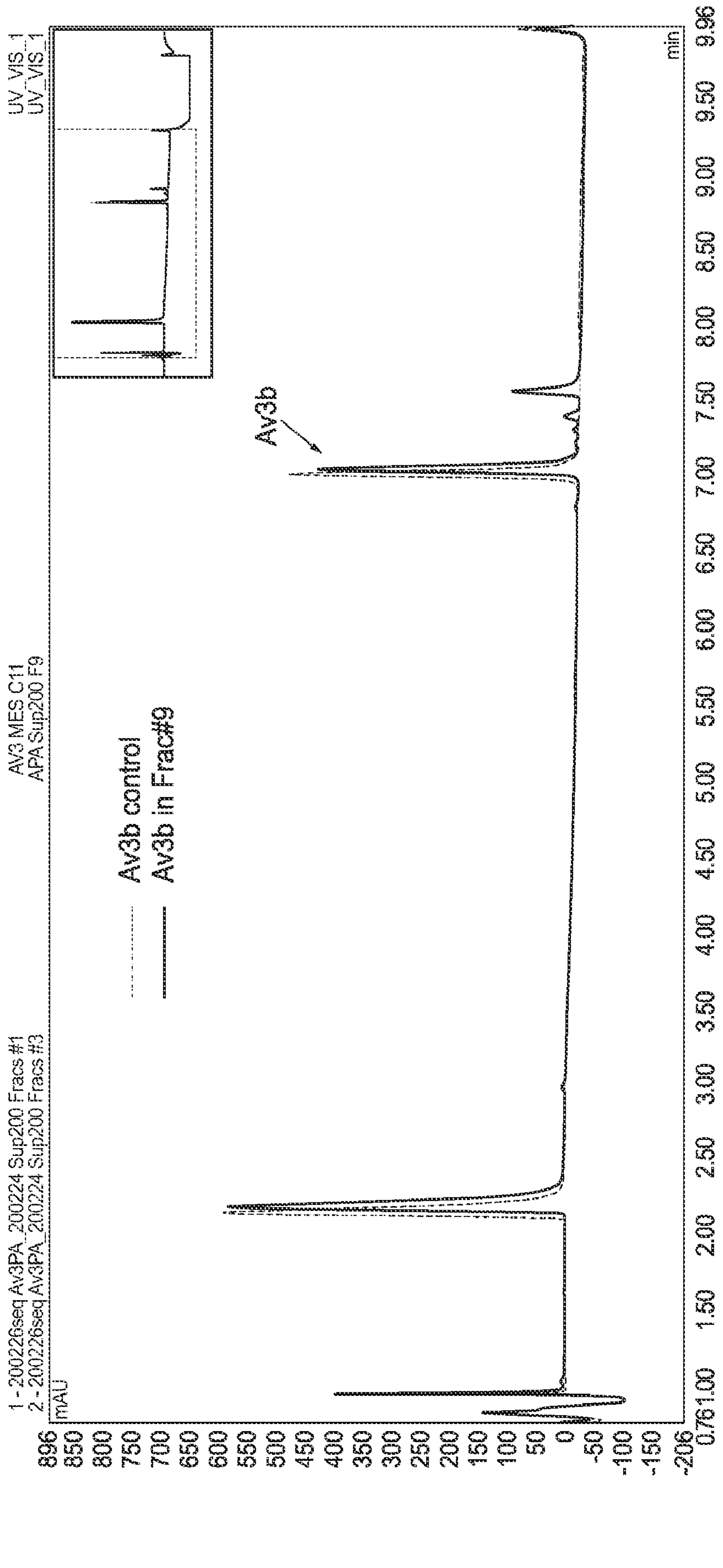
FIG. 16 depicts a chromatograph showing protease activity of fraction #9 shown in FIG. 14. Here, fraction #9 was spiked with Av3b peptide. Fraction #9 showed stronger protease activity than Fraction #8, causing Av3b degradation and release of degradation peaks.

The HPLC chromatograph after Av3b incubation with 200 μL of fraction #9 is shown in FIG. 16. As shown in FIG. 16, a higher ratio of degradation occurred compared to fraction #8, and similarly there was a release of some degraded peak.

Figure 17:
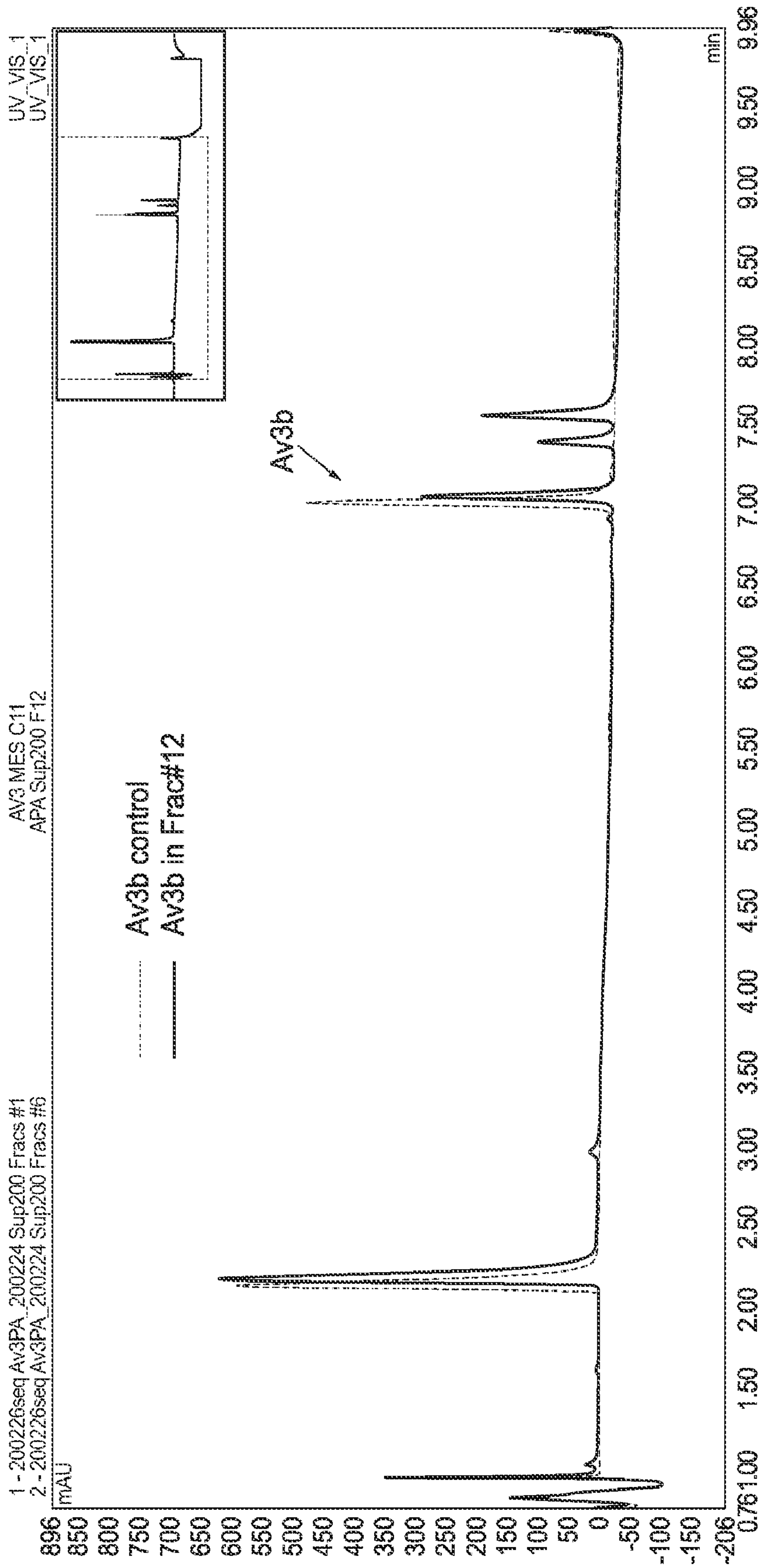
FIG. 17 depicts a chromatograph showing protease activity of the fraction #12 shown in FIG. 14. Here, fraction #12 was spiked with Av3b peptide. Fraction #12 had the highest ratio of degradation out of the four active fractions, as indicated by the Av3b peak reduction and release of degradation peaks.

The HPLC chromatograph after Av3b incubation with 200 μL of fraction #12 is shown in FIG. 17. As shown in FIG. 17, the highest ratio of degradation was observed in fraction #12 out of the four active fractions; similarly here, there was a release of some degraded peak.

Figure 18:
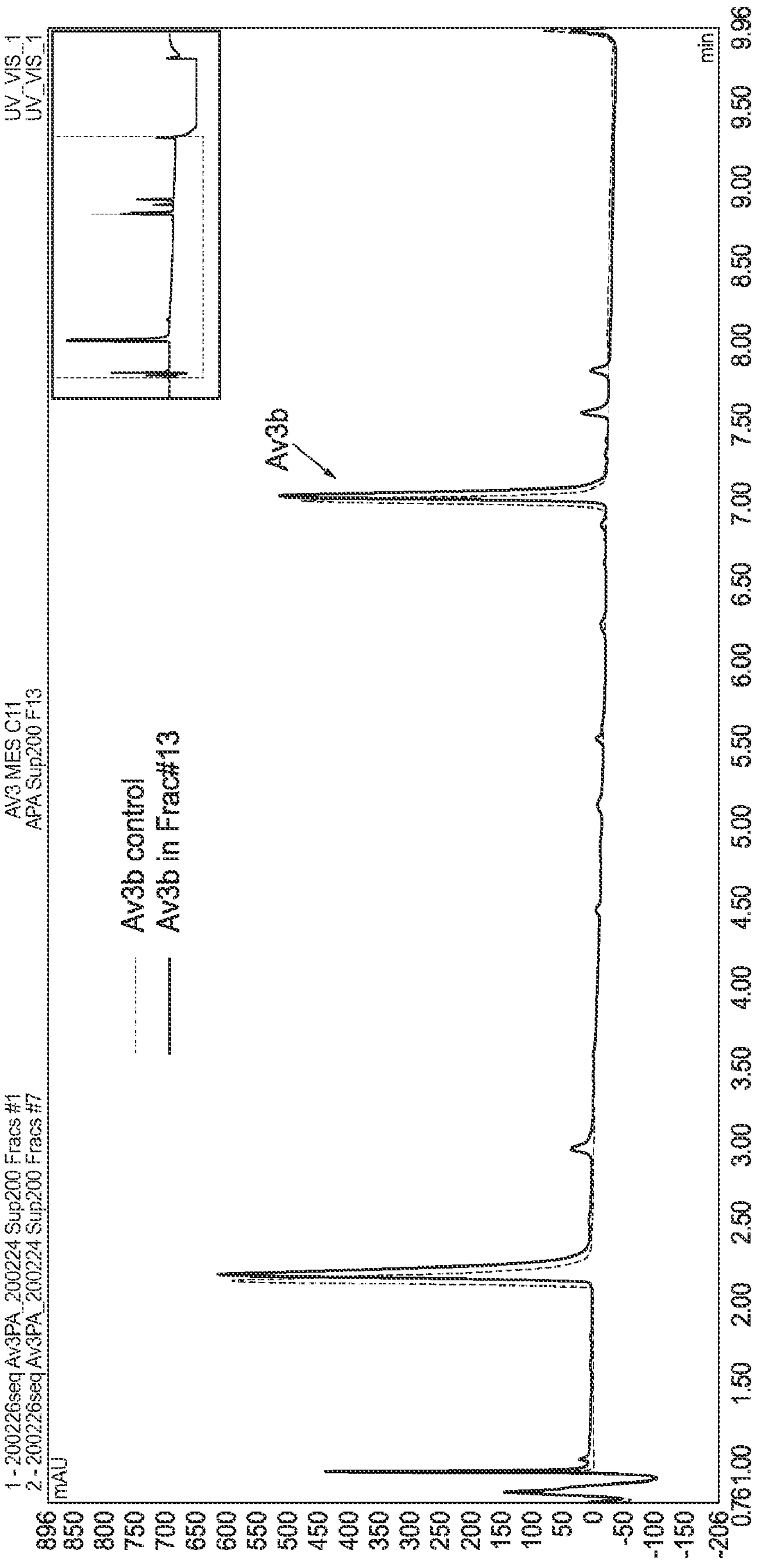
FIG. 18 depicts a chromatograph showing protease activity of the fraction #13 shown in FIG. 14. Here, fraction #13 was spiked with Av3b peptide. Fraction #13 showed that some level of degradation occurred, resulting in the release of some degraded peak, albeit with a peak profile that was slightly different relative to the rest of the fractions

The HPLC chromatograph after Av3b incubation with 200 μL of fraction #13 is shown in FIG. 18. As shown in FIG. 18, some level of degradation occurred, resulting in the release of some degraded peak, albeit with a peak profile that was slightly different relative to the rest of the fractions.

Fractions #8 and #9, which contain proteins with a size of around 150 kD, were combined for MS/MS analysis. Fractions #12 and #13 had proteins with sizes between 17 kD and 45 kD, and were likewise combined for MS/MS analysis To more precisely separate the proteases from the Av3b fermentation beer, the Av3b fermentation beer went through DEAE anion Exchange followed by Size-exclusion chromatography (SEC) Fast Protein Liquid Chromatography (FPLC). Here, 25 mL of Av3b fermentation beer, which had complete Av3b degradation during fermentation process and had been pH adjusted to pH 6.0, were loaded onto chromatograph column containing 2 mL of DEAE (anion exchange resin); the column was eluted with 1M NaCl/100 mM Tris HCl pH 6, followed by collection of the fractions. The protease activity of the fractions were evaluated by spiking Av3b peptide and incubating for 16 hours at 30° C., pH 6.0. The active fractions (5 mL each) were pooled and concentrated using a 10K MWCO membrane to 0.56 mL.

Figure 19:
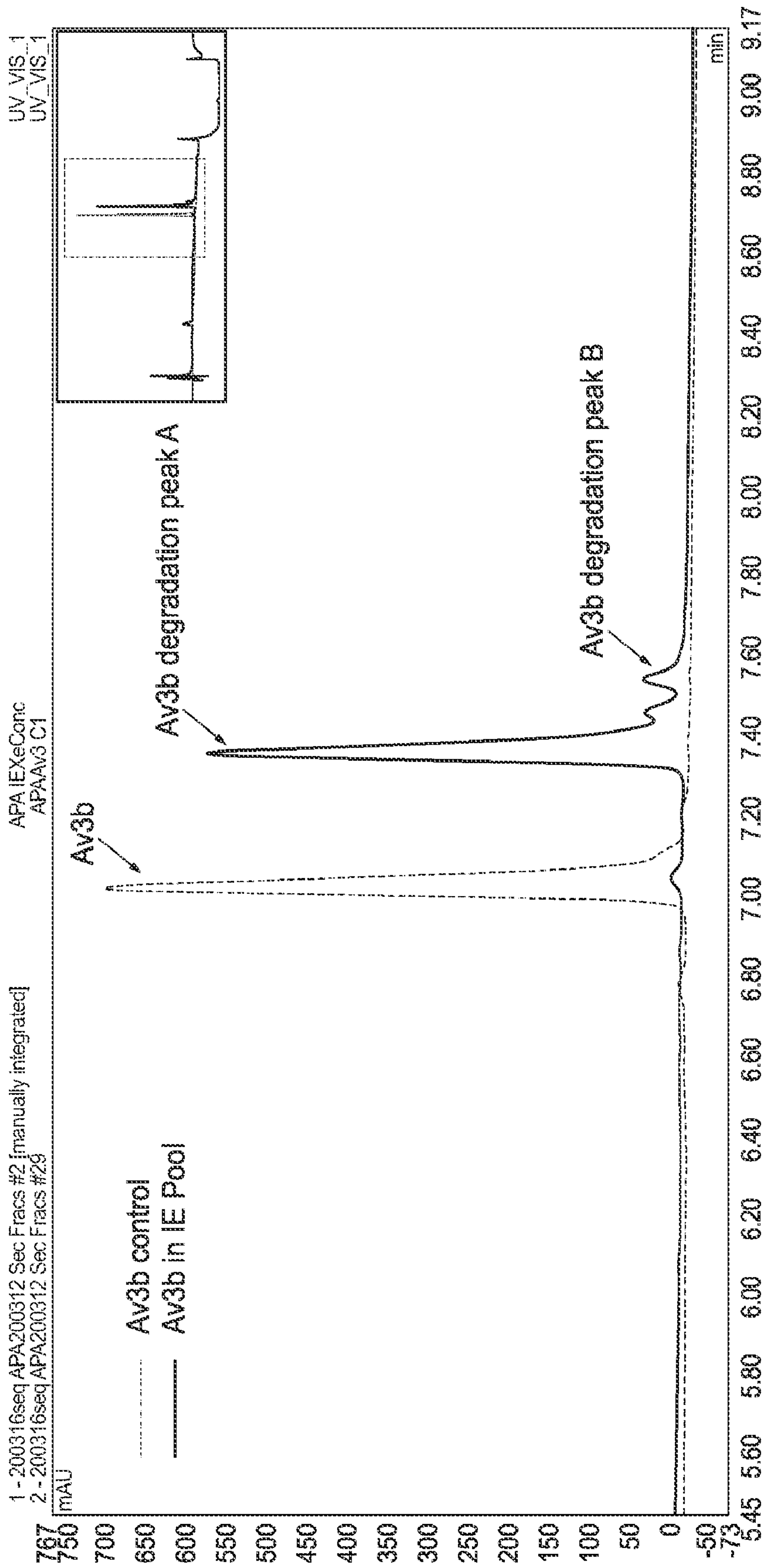
FIG. 19 depicts a chromatograph showing protease activity of the elution fraction pool, which combined all the protease-active fractions collected from the elution of DEAE anion-exchange (IE) chromatography of Av3b fermentation beer. As shown in the graph, Av3b was completely converted to degradation Peak A (Av3b Deg PkA) and Peak B (Av3b Deg PkB) after incubation in the fraction pool, over-night at room temperature.

Anion exchange pooled fractions spiked with Av3b were to evaluate degradation was then performed. Here, after pooling all the active fractions from anion exchange and concentration, purified Av3b was spiked into the concentrated pool and incubated at room temperature overnight. Av3b completely disappeared after overnight incubation, and was replaced with the following: (1) PK-A (Av3b with C-Lys cleaved, Av3b-1), the major peak; and (2) PK-B (Av3b with C-Pro-Lys cleaved, Av3b-2), the minor peak. FIG. 19.

Figure 20:
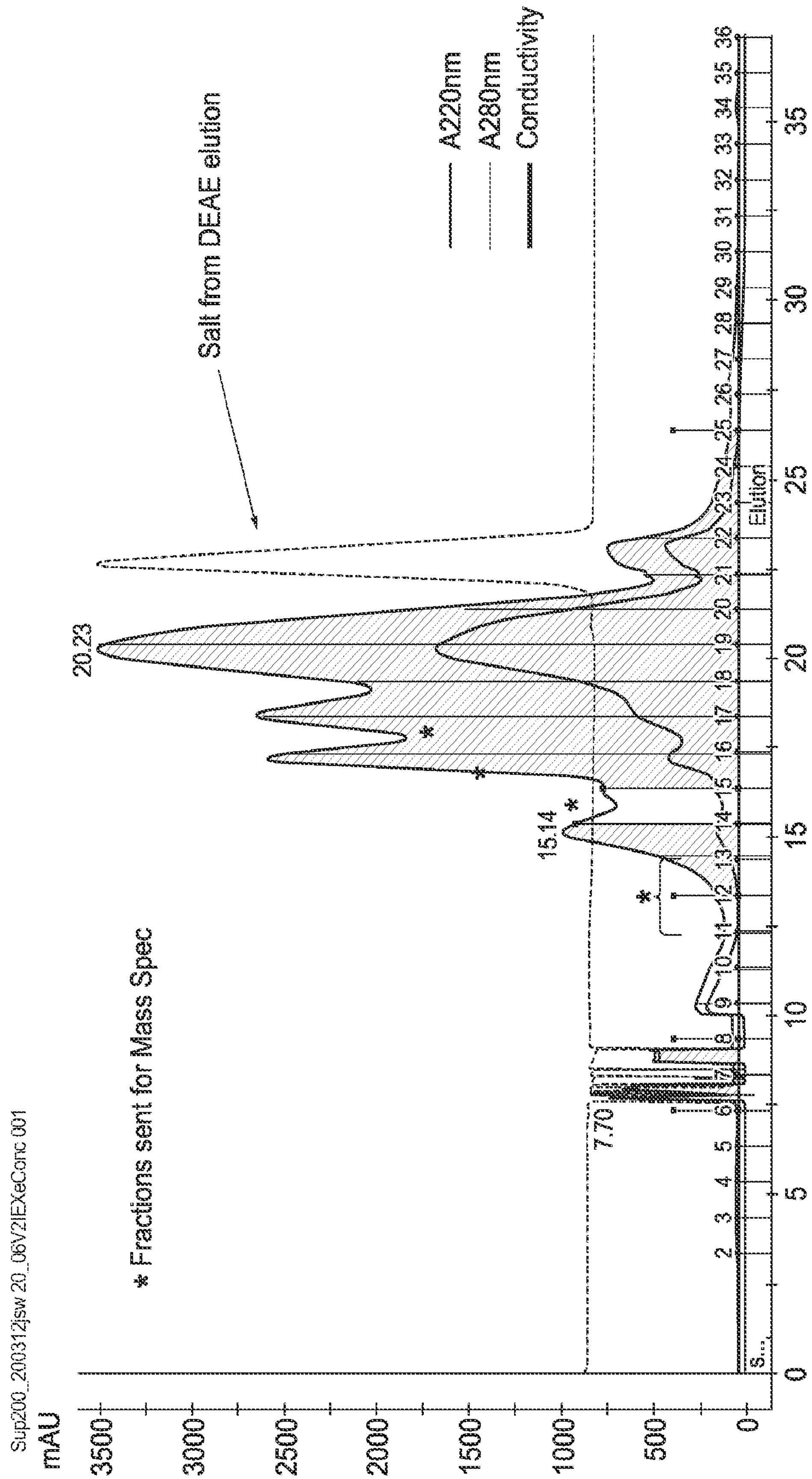
FIG. 20 depicts a FPLC size-exclusion chromatograph with fraction collection of the protease-active fraction pool collected from the elution of DEAE anion-exchange chromatography of Av3b fermentation beer, using GE AKTA Pure 25 system with Superdex Increase 200GL column.

Size-Exclusion Chromatograph using AKTA FPLC system was then performed to further fractionate the active pool from anion exchange chromatography. The concentrated active pool from DEAE chromatograph was further fractionated using Size-Exclusion Chromatograph by AKTA FPLC system with MES buffer as mobile phase, following the procedure described above. Four fractions were found active in spiked Av3b degradation assay. FIG. 20.

Figure 21:
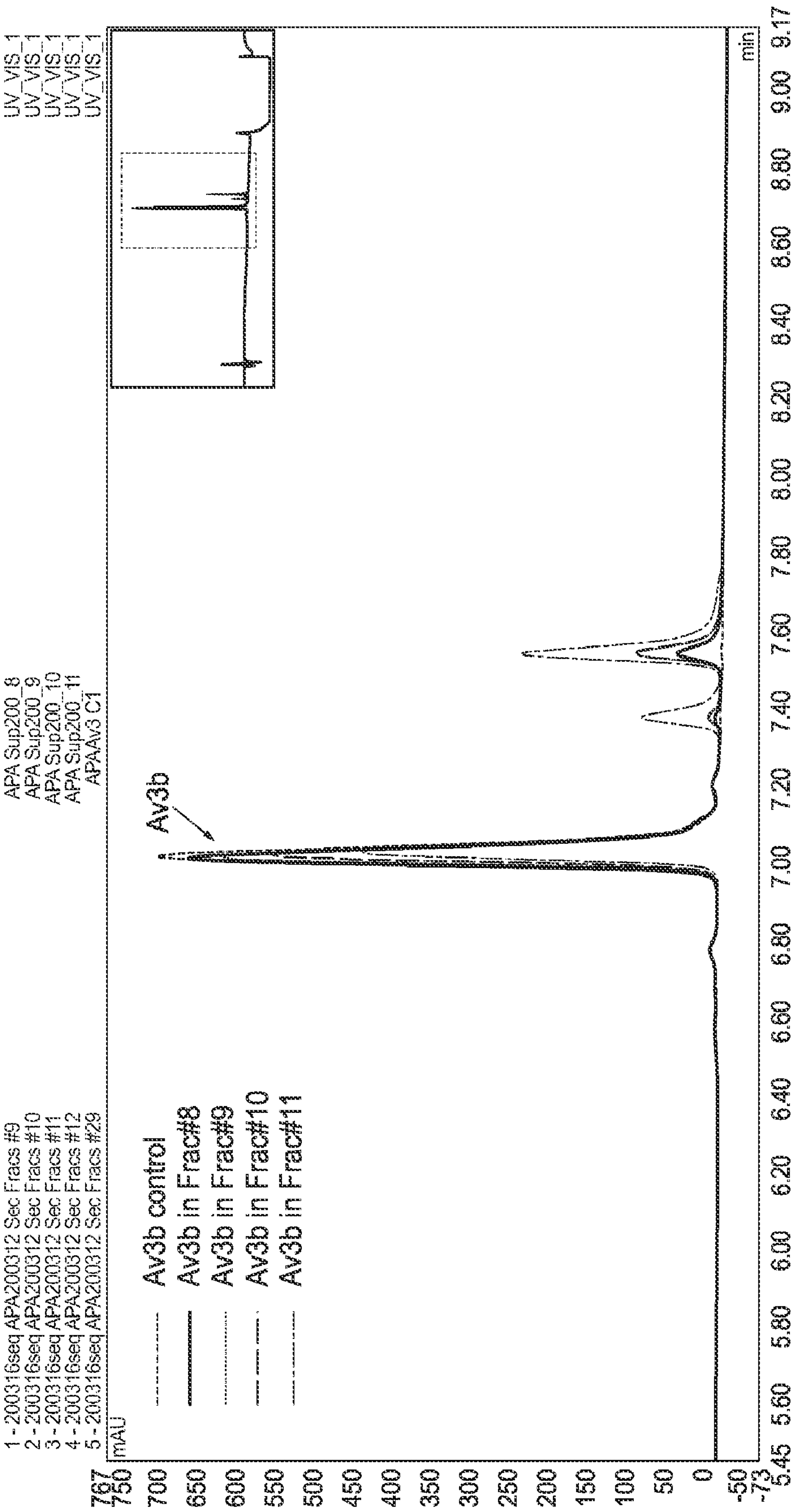
FIG. 21 depicts a chromatograph showing protease activity of the fraction pool from fraction #8 to #11 as shown in FIG. 20, after spiking the fractions Av3b peptide. Peaks indicate the degradation of Av3b peak, and release of degradation peaks. "Frac" means fraction.
Figure 22:
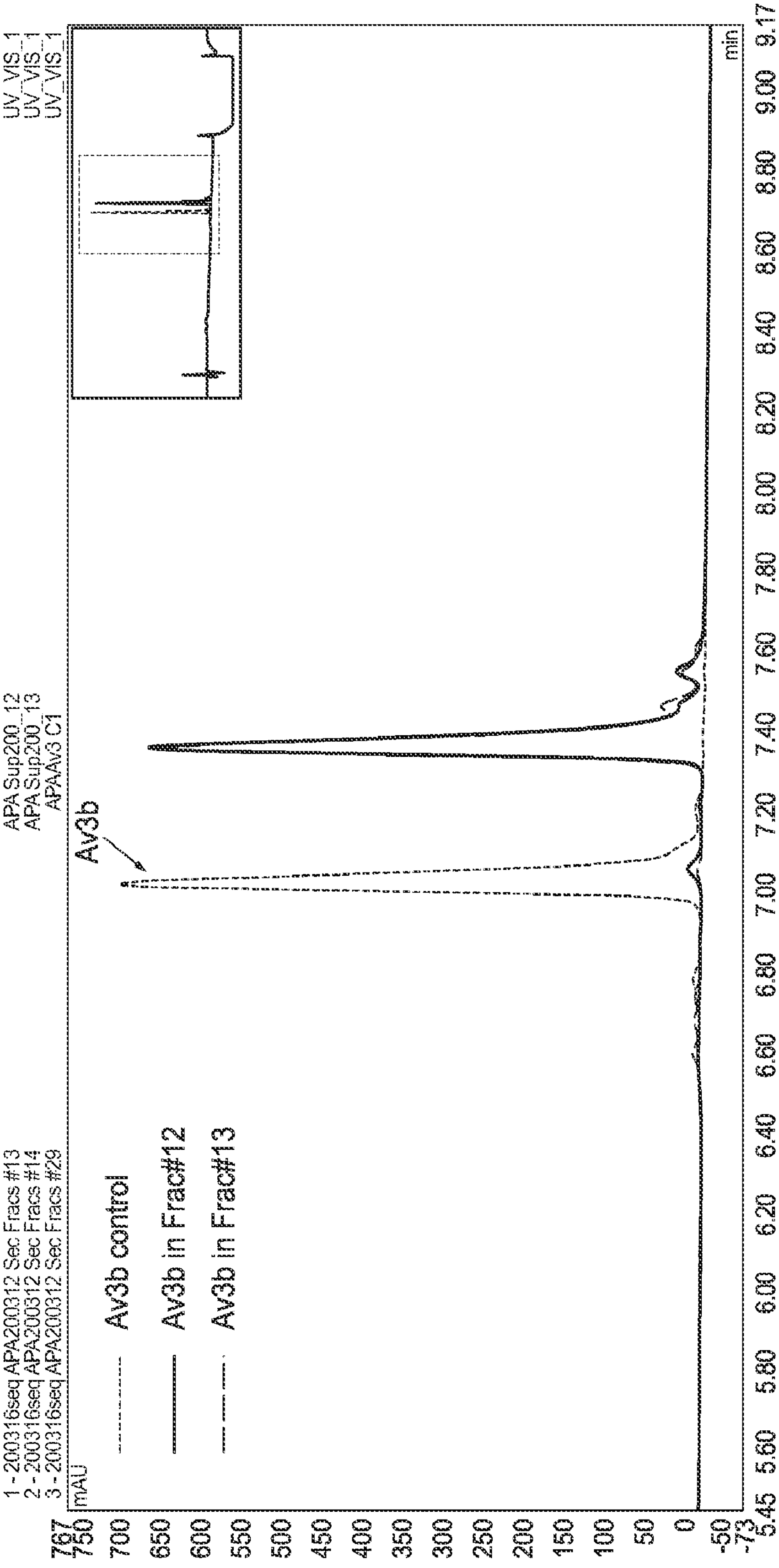
FIG. 22 depicts a chromatograph showing protease activity of the fraction pool from fraction #12 to #13 as shown in FIG. 20, after spiking the fractions with Av3b peptide. Here the peaks indicate the Av3b peptide peak complete converts to degradation Peaks.
Figure 23:
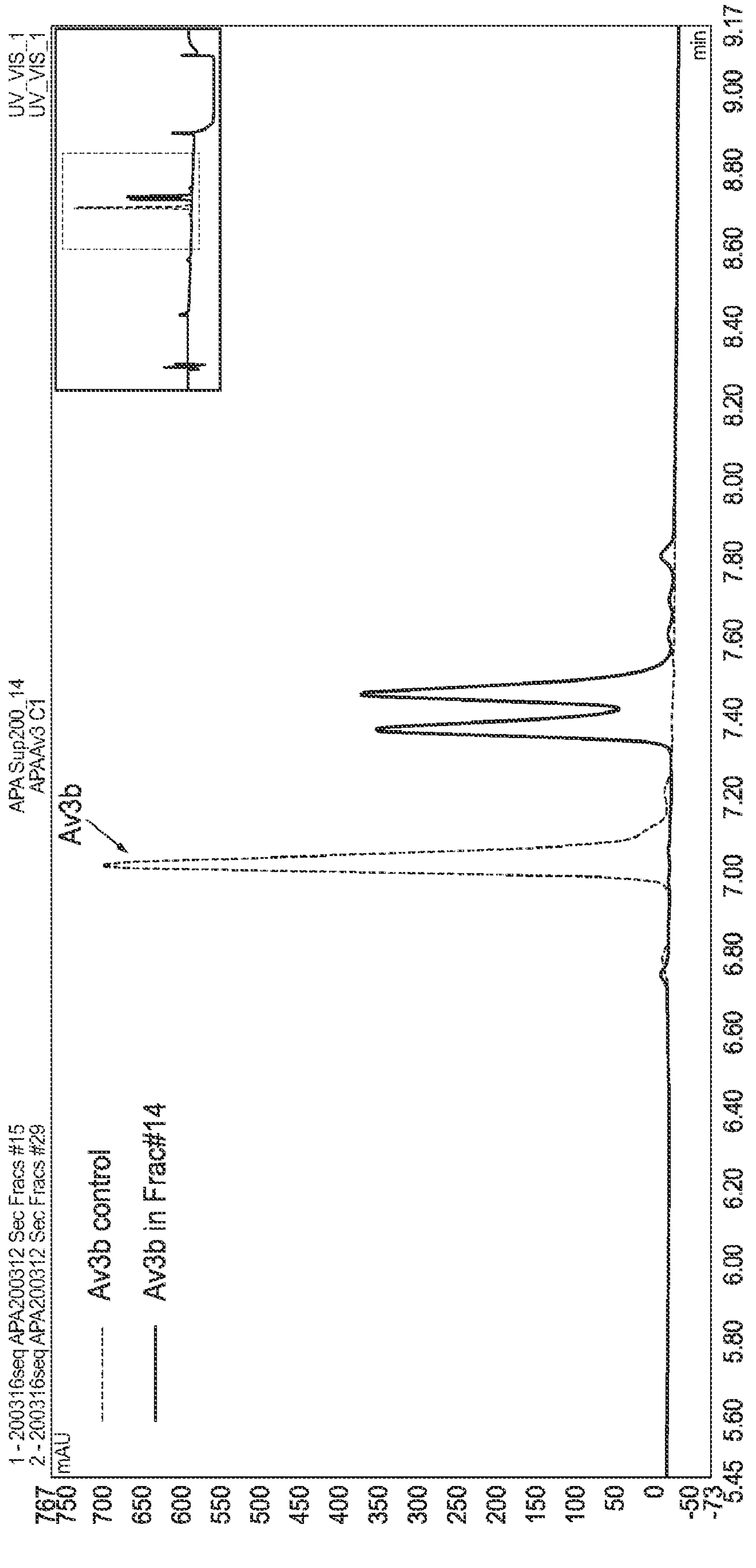
FIG. 23 depicts a chromatograph showing protease activity of the fraction #14 as shown in FIG. 20, after spiking with Av3b peptide. Here the peaks indicate the Av3b peptide peak complete converts to degradation Peaks.
Figure 24:
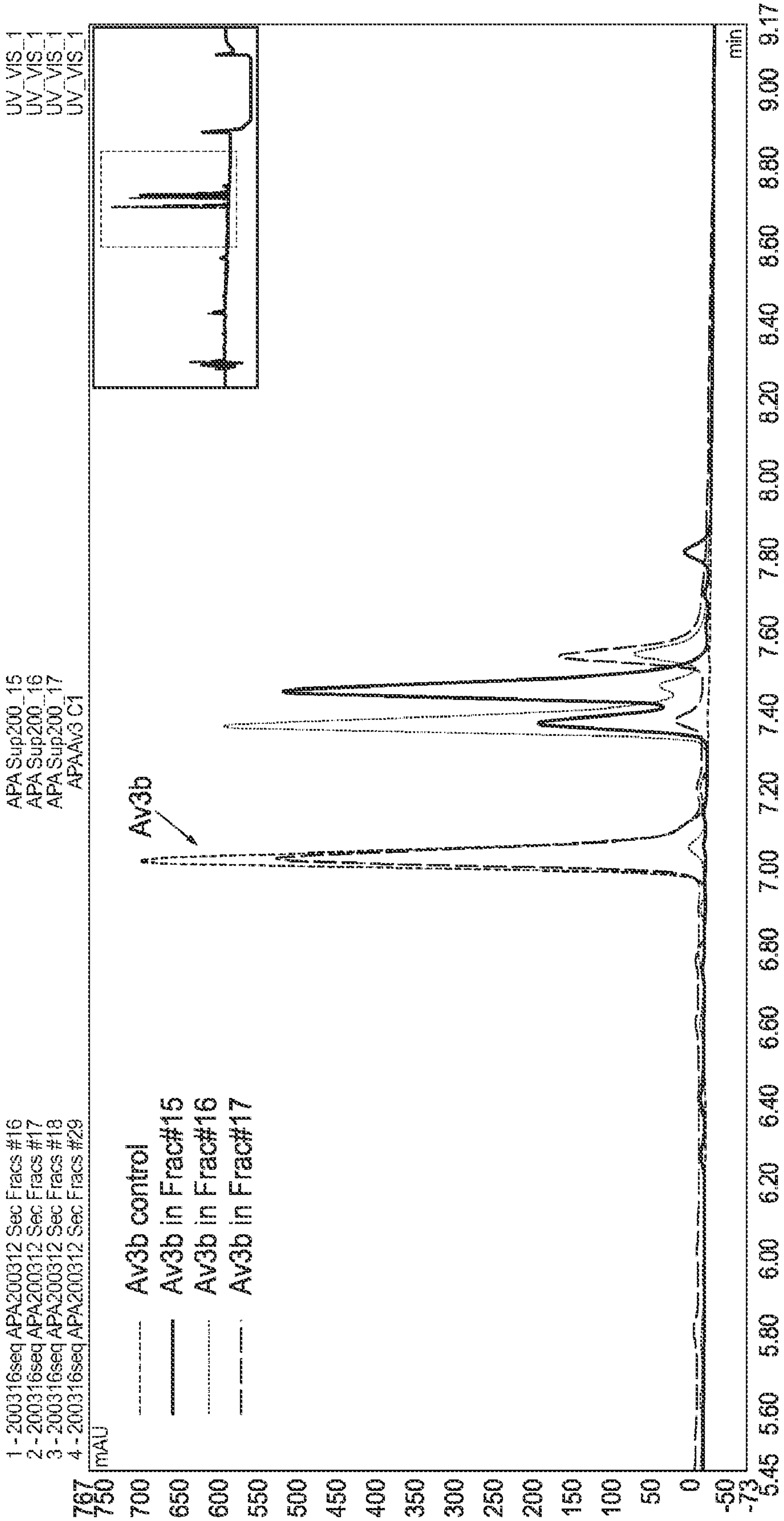
FIG. 24 depicts a chromatograph showing protease activity of the fraction #15, #16, and #17, respectively, as shown in FIG. 20, after spiking with the Av3b peptide. Peaks indicated the Av3b peak conversion to degradation Peaks.

SEC Fractions 8-11 had partial Av3b degradation after 18 hour incubation at 37° C. (FIG. 21); SEC Fractions 12-13 had complete Av3b degradation after 18 hour incubation at 37° C. (FIG. 22); SEC Fractions 14 had complete Av3b degradation after 18 hour incubation at 37° C. (FIG. 23); and SEC Fractions 15-17 had complete Av3b degradation after 18 hour incubation at 37° C. (FIG. 24). Four collections used for MS/MS were as follows: fractions pool of #12 & #13, #15, #16 and #17. Though fraction #14 showed strong protease activity, from the FPLC chromatograph it was part of the peak in fraction #15. Therefore, it was not included in the sample for MS/MS analysis.

Next, the fractions isolated from FPLC, which actively cleaved spiked Av3b, were analyzed by tandem mass spectrometry (MS/MS).

Tandem mass spectrometry (MS/MS) is the name given to a group of mass spectrometric methods wherein "parent or precursor" ions generated from a sample are fragmented to yield one or more "fragment or product" ions, which are subsequently mass analyzed by a second MS procedure. MS/MS methods are useful for the analysis of complex mixtures, especially biological samples, in part because the selectivity of MS/MS can minimize the need for extensive sample clean-up prior to analysis. In an example of an MS/MS method, precursor ions are generated from a sample and passed through a first mass filter to select those ions having a particular mass-to-charge ratio. These ions are then fragmented, typically by collisions with neutral gas molecules in a suitable ion containment device, to yield product (fragment) ions, the mass spectrum of which is recorded by an electron multiplier detector. The product ion spectra so produced are indicative of the structure of the precursor ion, and the two stages of mass filtering can eliminate ions from interfering species present in the conventional mass spectrum of a complex mixture.

An exemplary description of tandem mass spectrometry (MS/MS) is provided in U.S. Pat. Nos. 6,107,623; and 9,091,695, the disclosures of which are incorporated herein by reference in their entireties.

The six FPLC samples from FPLC elution fractions of direct Av3b beer chromatography and FPLC elution fractions of DEAE anion exchange fraction pool, as described above, were evaluated using MS/MS for proteases, especially those from *K. lactis*. A total of 201 proteins were discovered from the 6 samples. Among them, 8 were *K. lactis* related proteases, which are summarized in the table below.

Example 9. Knock-Out of Proteases

Based on the MS/MS results, three carboxy-proteases were discovered in the fraction: prb1, prc1 and atg42.

To evaluate the role that proteases play on degradation of Av3b, the proteases prb1 and prc1 were each knocked-out as follows: first, a pKLAC1 plasmid was obtained from New England Biolabs® Inc., (item no. (NEB #E1000). The pKLAC1 plasmid is designed to accomplish high-level expression of recombinant protein in the yeast species, *Kluyveromyces lactis*, by integrating into pLAC4 locus of the chromosome B in *K. lactis* cells.

Figure 26:
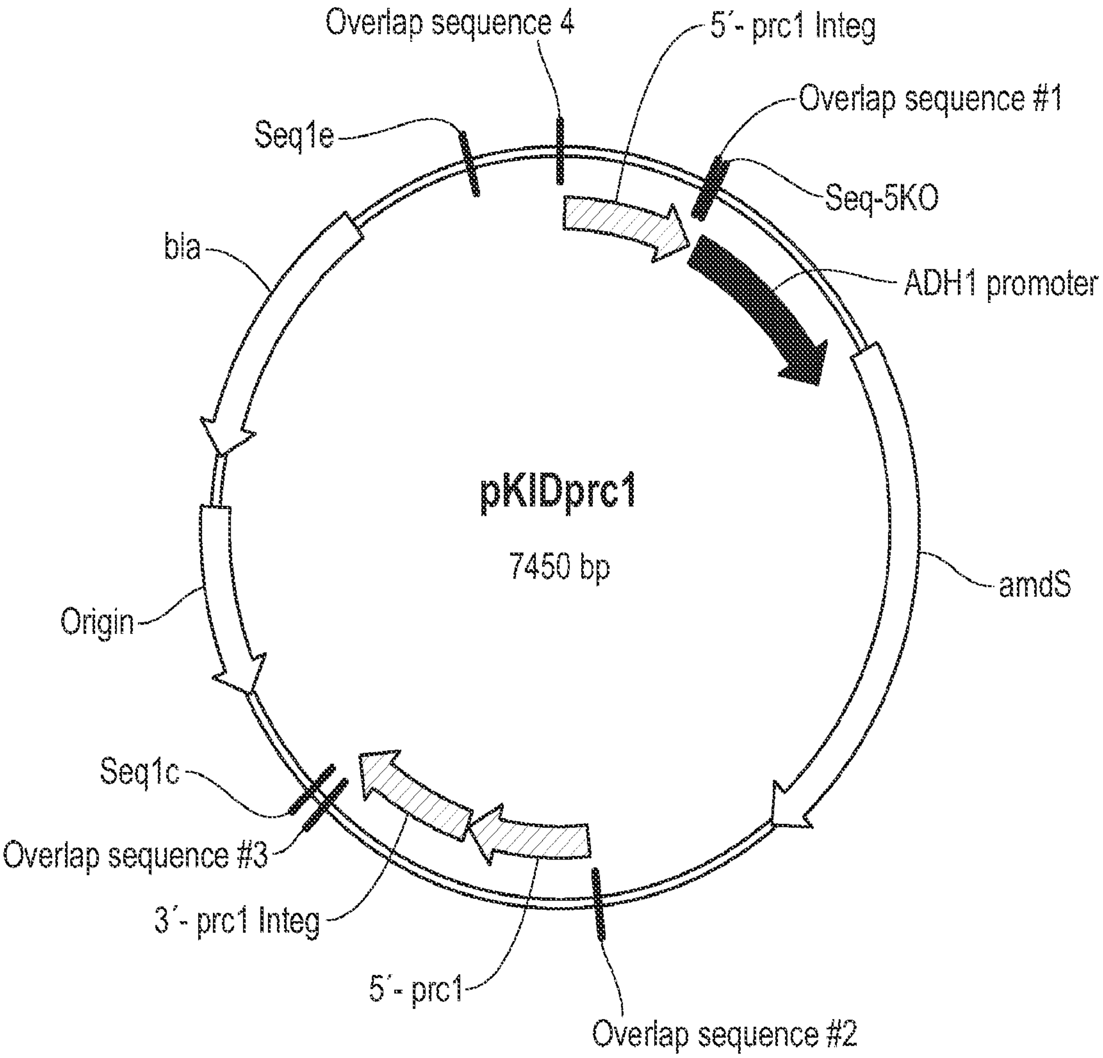
FIG. 26 shows a plasmid map of the pK1prc1 plasmid.

Using the pKLAC1 plasmid as a starting vector, a *K. lactis* (K1) prc1 knock-out integration vector, "pK1Dprc1," was designed as shown in FIG. 26, by replacing 3'- and 5'-pLAC4 homologous recombination sequences with 3'- and 5'-prc1 homologous recombination sequences for pcr1 knock-out. The vector was designed for Acetamide (amdS) selection marker self-out-recombination by attaching an extra 5'-prc1 homologous sequence to the 3'-prc1 homologous sequence. The pK1Dprc1 vector was linearized by SacII digestion and then transformed into the YCT306 strain of *K. lactis*. Acetamide (amdS) was used as a positive selection marker, integrating into the yeast genome prc1 locus and replacing partial prc1 (knock-out) with a selection marker of AmdS, resulting in the strain, "VSTLB9a." The strain VSTLB9a contains the heterologous AmdS cassette, which was designed for self out-recombination during cell growth by flanking with two homologous perl 5'-fragment in the pK1prc1 vector. AmdS out-recombination from the VSTLB9a strain was counter-selected with fluoroacetamide, which is toxic to VSTLB9a strain with AmdS expression.

TABLE 7

Results of MS/MS analysis. The information contained in this table was taken from KEGG, Uniprot, and MEROPS.

| Protease type | Protease name | Gene name | Protein size | Genome locus | Cellular location | Cleavage site (P1) | Optimal pH |
|---|---|---|---|---|---|---|---|
| Metallo-protease | Ape2 aminopeptidase | Ape2/ YKL157W | 859 AA or 94 kD | KLLA0_C11033g | Mitochondrion cell wall secreted | N-Leu and N-Lys | ~7.2 |
| | Ape3, or Aminopeptidase Y | Ape3/ YBR286W | 525 AA, or 58 kD | KLLA0_D06424g | vacuole | N-AA (preferential), release of N-terminal lysine. K(A, R, N, C, Q, L, M, F, P, S, Y) | vacuole 6.2 |
| | mername-AA063 peptidase, aminopeptidase, or Peptide hydrolase | N/A (LAP1?) | 373 AA, or 41 kD | KLLA0_A02013g | un-identified protein in K. lactis (sequence is homologous to LAP1 of *S. cerevisiae*) | Leucine aminopeptidase? K (A, C, E, G, H, I, L, R, M, F, P, V) | unknown |
| Serine protease | Cathepsin A or Carboxypeptidase C, or carboxypeptidase Y | PRC1/ YMR297W | 535 AA, or 59 kD | KLLA0_A09977g | vacuole, extracellular region or secreted | C-terminal AA, A (I, L, M, F, V, G) | vacuole 6.2 |
| | Carboxypeptidase | Atg42/ YBR139W | 491 AA or 54 kD | KLLA0_E17821g | vacuole | C-terminal AA | vacuole 6.2 |
| | cerevisin or proteinase B | PRB1/ YEL060C | 561 AA or 62 kD | KLLA0_D00979g | vacuole | K(R, Y, L, F, Q) | vacuole 6.2 |
| Aspartyl protease | Saccharopepsin or PEP4 | PEP4/ YPL154C | 409 AA, or 45 kD | KLLA0_D05929g | vacuole | K (N, T, W, Q, L, F, Y, E) | vacuole 6.2 |
| Unknown | unknown | unknown | 248 AA, or 27 kD | KLLA0_A03377g | unknown | unknown | unknown |

Figure 25:
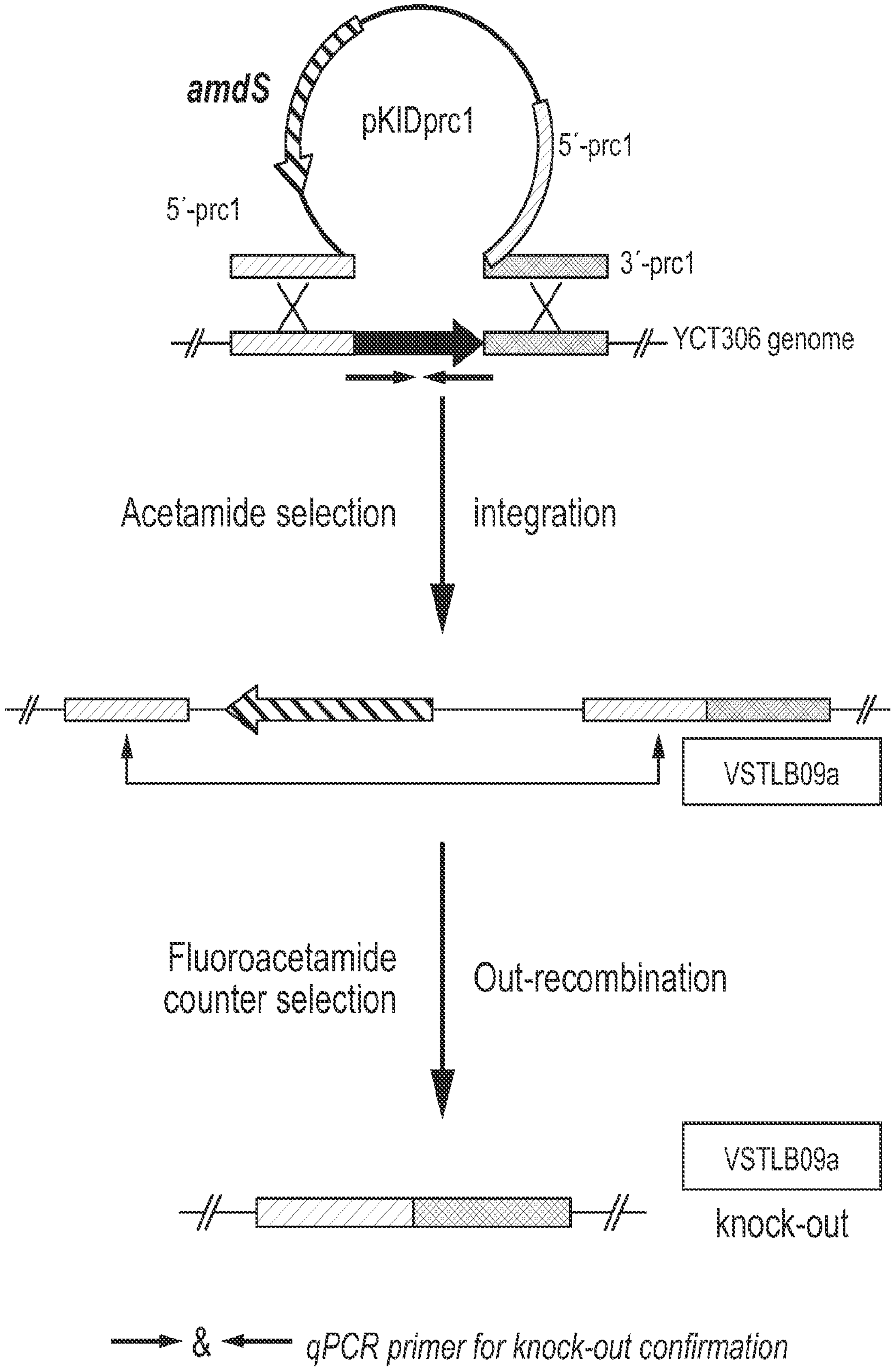
FIG. 25 depicts the knock-out strategy for the carboxy-protease, prc1. "VSTLB09" refers to the positive yeast strain. To knock-out prc1, a counter-selection homologous recombination strategy was used. The designed knock-out vector integrated into the yeast genome prc1 locus and replaced partial prc1 (knock-out) with a selection marker of AmdS. The heterologous AmdS cassette was designed for self out-recombination by flanking with two homologous pcr1 5'-fragment. These two step strain modification process resulted in "VSTLB09", referring to the positive pcr1 knock-out yeast strain without any heterologous gene.

These two step strain modification processes resulted in strain of "VSTLB09," which had pcr1 gene knocked-out without any heterologous gene in the genome. FIG. 25 depicts the knockout design strategy. FIG. 26 shows a map of the pK1prc1 plasmid.

The *K. lactis* prc1 gene encodes a protease, Cathepsin A, Carboxypeptidase C, or Carboxypeptidase Y. See, e.g., NCBI Gene ID: 2896412; NCBI Protein ID: XP_451436; UniProt ID: Q6CXA3. The *K. lactis* prc1 gene is located between positions 876594-878201 bp, in Chromosome A of the *K. lactis* genome (in the 5' to 3' orientation), with an assigned genome entry (locus entry) of KLLA0_A09977g (total 1608 bp). An example of a *K. lactis* prc1 gene is provided in SEQ ID NO: 199.

Upstream of the *K. lactis* prc1 gene (5'-Upstream) is a serine palmitoyltransferase gene, with a 1239 bp non-transcriptional region in between it and prc1. Downstream of *K. lactis* prc1 (3'-downstream), is an uncharacterized gene, with a 362 bp non-transcriptional region in between it and prc1 (including both terminator for prc1 and promoter for the unknown gene).

Figure 27:
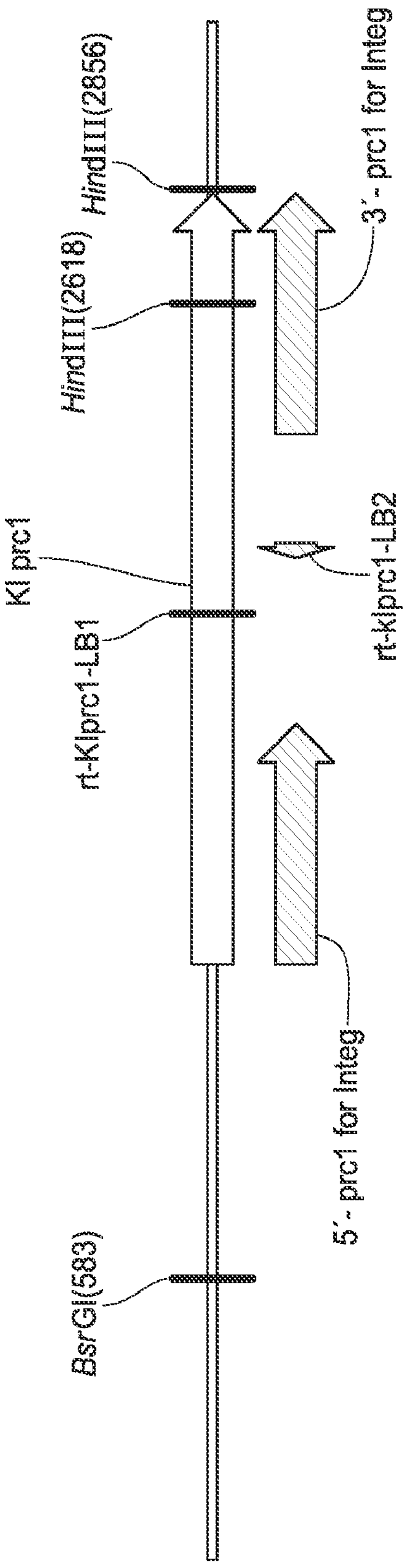
FIG. 27 depicts the 5'- and 3'-homology arms of the pK1Dprc1 plasmid, and the integration strategy. Here, rt-K1prc1-LB1 refers to qPCR forward primer for prc1 knock-out evaluation; K1 prc1 refers to *K. lactis* prc1; and rt-k1prc1-LB2 refers to qPCR reverse primer for prc1 knock-out evaluation.

To knock-out the *K. lactis* prc1 gene without affecting the adjacent genes, the 5' integration segment of the pK1Dprc1 plasmid included a 500 bp segment of 5'-prc1; and, the 3' integration segment had a 500 bp of 3'-prc1. FIG. 27.

To generate a prc1 knock-out strain, *K. lactis* cells were transformed with the knock-out vector described above, and then grown in yeast carbon based (YCB)+acetamide medium, with selection for VSTLB9a strains. Glycerol stocks were made from positive colonies, and gDNA was extracted for qPCR analysis.

The qPCR primers for the prc1 gene are as follows:

```
rt-Klprc1-LB1:
                                    (SEQ ID NO: 194)
GTACGCATCGGGCCAAGATTTCC

rt-Klprc1-LB2:
                                    (SEQ ID NO: 195)
CGGTTAGACCGTTACCGATAAGAACAGAAG.
```

Figure 28:
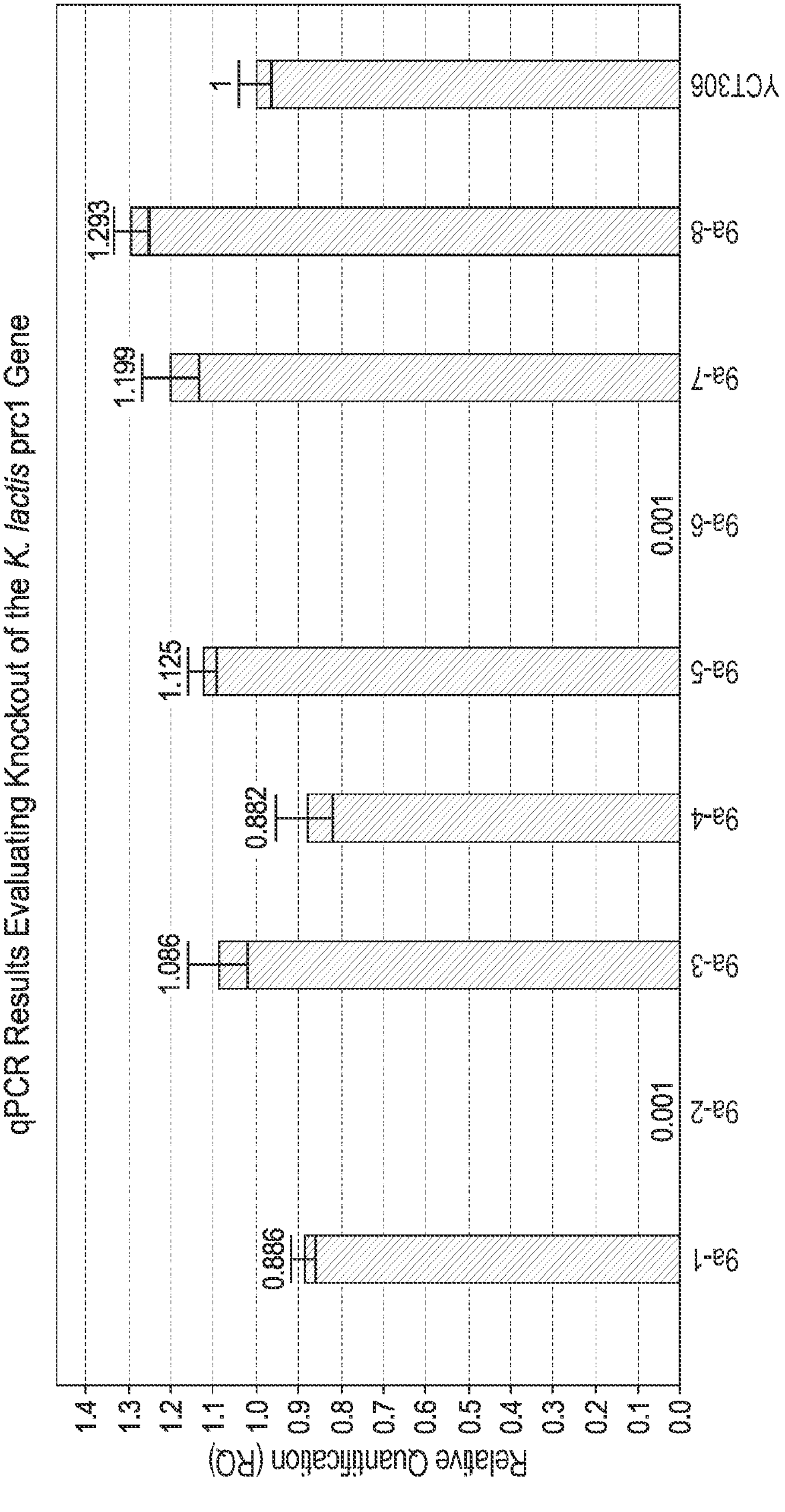
FIG. 28 depicts the qPCR results evaluating knockout of the *K. lactis* prc1 gene. Here, YCT306 is used as a calibration strain, showing the presence of one copy of the prc1 gene. Strains VSTLB9a-2 and 6 show successful knock-out of the prc1 gene.

Positive clones were identified and purified by plating the yeast onto YCB+Acetamide plates. Eight colonies were identified as being positive for pcr1 knock-out based on acetamide selection; these eight clones were picked (designated as VSTLB09a-1 to 8) and cultured in 5 mL of DMSor medium. Of the 8 positive strains, VSTLB09a-2 and VSTLB09a-6 were identified by qPCR as having a successful knock-out of prc1. FIG. 28. The strains VSTLB09a-2 and 6 were plated onto YCT-Amd agar plates for strain puriication.

Figure 29:
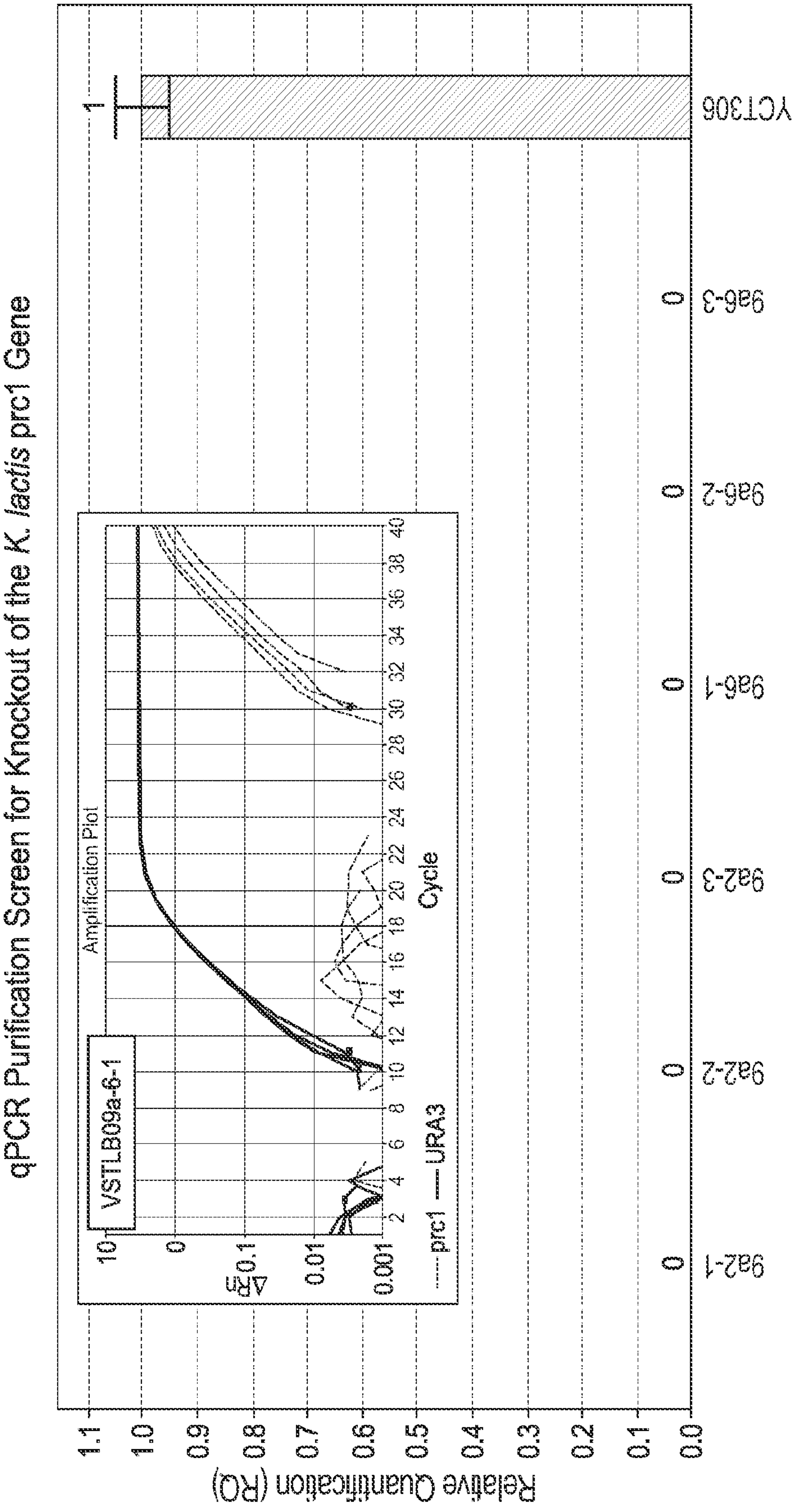
FIG. 29 a depicts the results of the qPCR purification screen for knockout of the *K. lactis* prc1 gene. The Y-axis shows relative quantification ("RQ"), or $2^{-\Delta\Delta ct}$ Here, YCT306 is used as a calibration strain, showing the presence of one copy of the prc1 gene. URA3 is used as a reference gene. The insert shows the amplification plot for clone VSTLB09a-6-1 and YCT306.

Three colonies from each of the strains were picked, and cultured in DMSor for qPCR screening. Glycerol stocks were made from the culture, and gDNA was extracted. A qPCR purification screen was performed, indicating all 6 colonies contained desired pcr1 knock-out. FIG. 29. Out of the 6 colonies, VSTLB09a-6-1 was chosen for out-recombination of heterologous AmdS gene cassette.

FIG. 29 depicts the results of the qPCR purification screen for knockout of the *K. lactis* prc1 gene. The Y-axis shows relative quantification ("RQ"), or $2^{-\Delta\Delta ct}$ Here, YCT306 is used as a calibration strain, showing the presence of one copy of the prc1 gene. URA3 is used as a reference gene. The insert shows the amplification plot for clone VSTLB09a-6-1 and YCT306. The Primers for URA3 are as follows:

```
rt-URA3c-LB1: forward primer,
                                    (SEQ ID NO: 196)
TTCCAAGGGTTCTCTAGCACACGG

rt-URA3c-LB2: reverse primer,
                                    (SEQ ID NO: 197)
CCTACACCTGGGGTCATGATTAGCC.

Here, the reference gene used was URA3, with
primers described above. The AmdS qPCR primers
were as follows:
rt-AmdS-LB1: forward,
                                    (SEQ ID NO: 198)
AAGGGAACTCGATGAATACTACGCAAAGC;
and

rt-AmdS-LB2: reverse,
                                    (SEQ ID NO: 199)
CGTACTTGTTTAGCCATGAGATGTAGCCC.
```

VSTLB09a-6-1 was then cultured in non-selective DMSor for out-recombination to remove the amdS marker. After 4 days, a VSTLB09a-6-1 culture was plated onto YPGly+100 ppm Famd plates for selection of out-recombination cells (at 1000, or 5000 cells per plate). After another 4 days, small colonies had formed.

A total of 10 colonies were picked and cultured in DMSor for a primary screen of the "VSTLB09" strain, for screen of amdS out-recombination from the strain of VSTLB09a-6-1. Three days later, glycerol stocks were made from all of the strains, and gDNA was extracted for qPCR analysis.

Next, a qPCR primary screen for the VSTLB09 strains was performed according to the methods described above, with two references: a YCT306 reference to demonstrate prc1 knock-out; and a VSTLB09a-6-1 gDNA reference for amdS out-recombination.

Figure 30:
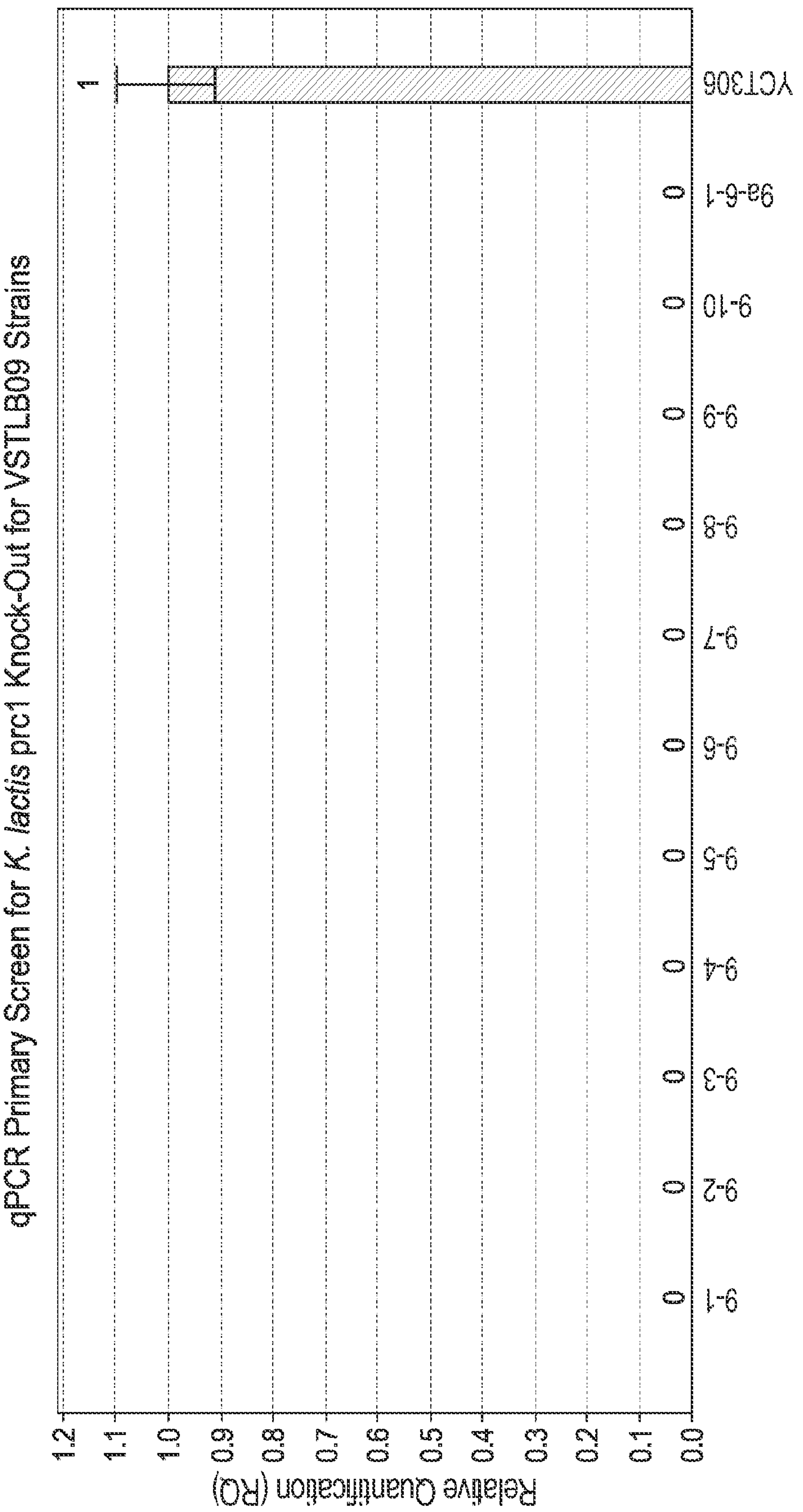
FIG. 30 shows the results of a qPCR primary screen for *K. lactis* prc1 knock-out for VSTLB09 strains. The Y-axis shows relative quantification ("RQ"), or $2^{-\Delta\Delta ct}$ The yeast strain YCT306 is used as a reference.
Figure 31:
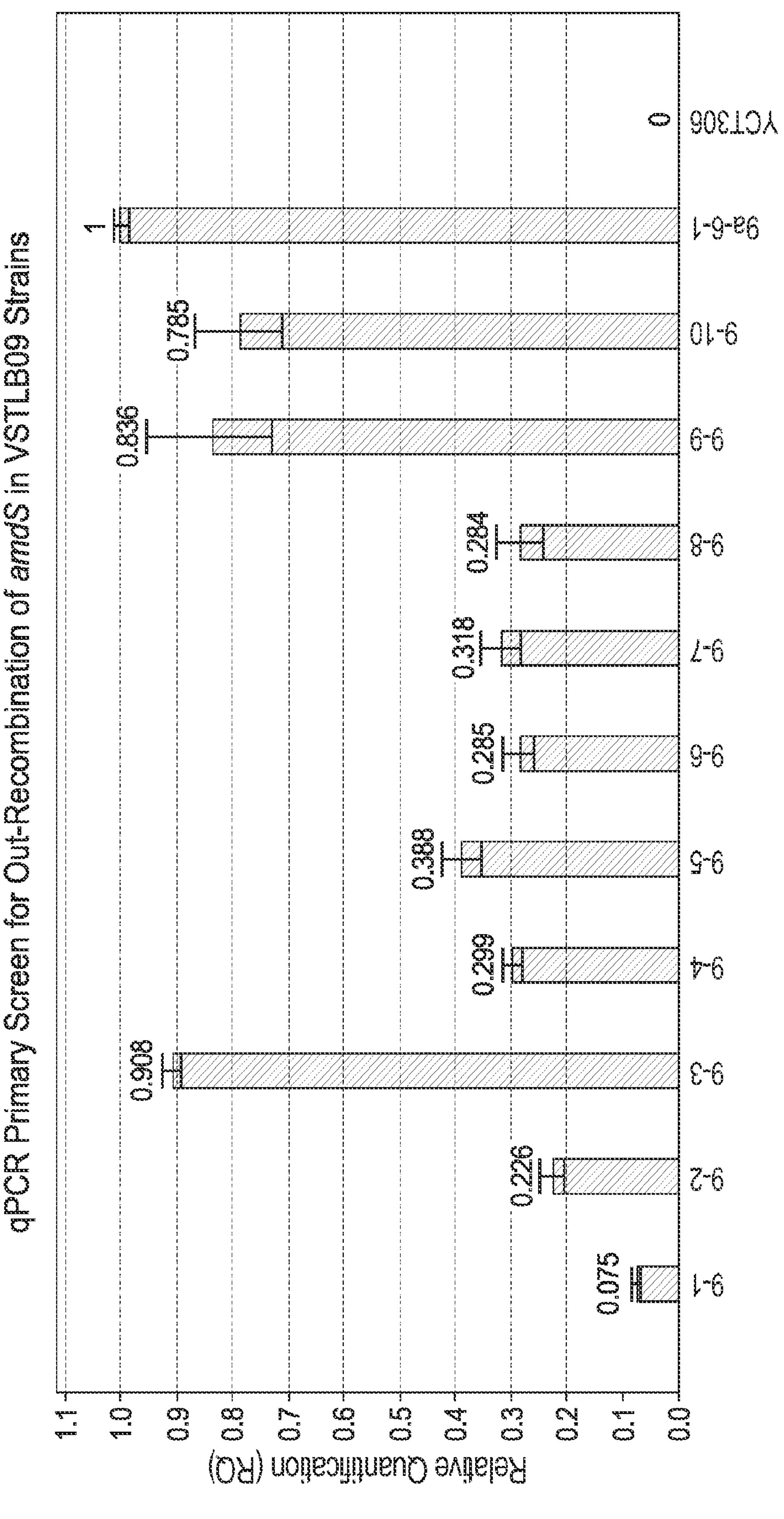
FIG. 31 shows the results of a qPCR primary screen for out-recombination of amdS in VSTLB09 strains The Y-axis shows relative quantification ("RQ"), or $2^{-\Delta\Delta Ct}$ The yeast strain YCT306 is used as a reference.

As shown in FIG. 30, all of the 10 "VSTLB09" colonies had the prc1 gene knock-out. And, as shown in FIG. 31, VSTLB09-1, -2, -4, -5, -6, -7, and-8 colonies had low amdS signal, indicating a mixture of out-recombined and non-out-recombined strains. VSTLB09-3, -9, and-10 had high amdS signal, indicating non-out-recombination. FIG. 31. VSTLB09-1 had lowest signal of amdS, and was stored and processed for purification.

The same strategy employed above was used to knock out prb1, resulting in a prb1/prc1 double knockout strain. The *K. lactis* prb1 gene encodes a protease, Proteinase B, which is homologous to the *S. cerevisiae* protease, cerevisin. See, e.g., NCBI Gene ID: 2892752; NCBI Protein ID: XP 453114; UniProt ID: A0A3G9K$_{911}$. The *K. lactis* prb1 gene is located between positions 86703-88388 bp, in Chromosome D of the *K. lactis* genome (in the 5' to 3' orientation), with an assigned genome entry (locus entry) of KLLA0_D00979g (total 1686 bp). An exemplary *K. lactis* prb1 gene is provided in SEQ ID NO: 201.

To transform the prc1/prb1 knockout strain with the Av3b transgene, an Av3b expression vector, pKS022, was transformed into prb1/prc1 double knock-out strain; this resulted in the creation of anew Av3b expression strain without prb1 nor prc1 expression.

Briefly, an exemplary method of introducing an Av3b transgene into a *K. lactis* genome is as follows: a Av3b expression cassette DNA sequence is synthesized, comprising an intact LAC4 promoter element, a codon-optimized AV3B ORF element and a pLAC4 terminator element; the intact expression cassette is ligated into the pLB103b vector between Sal I and Kpn I restriction sites, downstream of the pLAC4 terminator, resulting in the Av3b expression vector, pKS022. The pKS022 vector is then linearized using Sac II restriction endonuclease and transformed into YCT306 strain of *K. lactis* by electroporation. The resulting yeast colonies are then grown on YCB agar plate supplemented with 5 mM acetamide, which only the acetamidase-expressing cells can use efficiently as a metabolic source of nitrogen. To evaluate the yeast colonies, about 100 colonies can be picked from the pKS022 yeast plates. Inoculates from the colonies are each cultured in 2.2 mL of the defined *K. lactis* media with 2% sugar alcohol added as a carbon source. Cultures are incubated at 23.5° C., with shaking at 280 rpm, for six days, at which point cell densities in the cultures will reach their maximum levels as indicated by light absorbance at 600 nm (OD600). Cells are then removed from the cultures by centrifugation at 4,000 rpm for 10 minutes, and the resulting supernatants (conditioned media) are filtered through 0.2 μM membranes for HPLC yield analysis.

Figure 32:
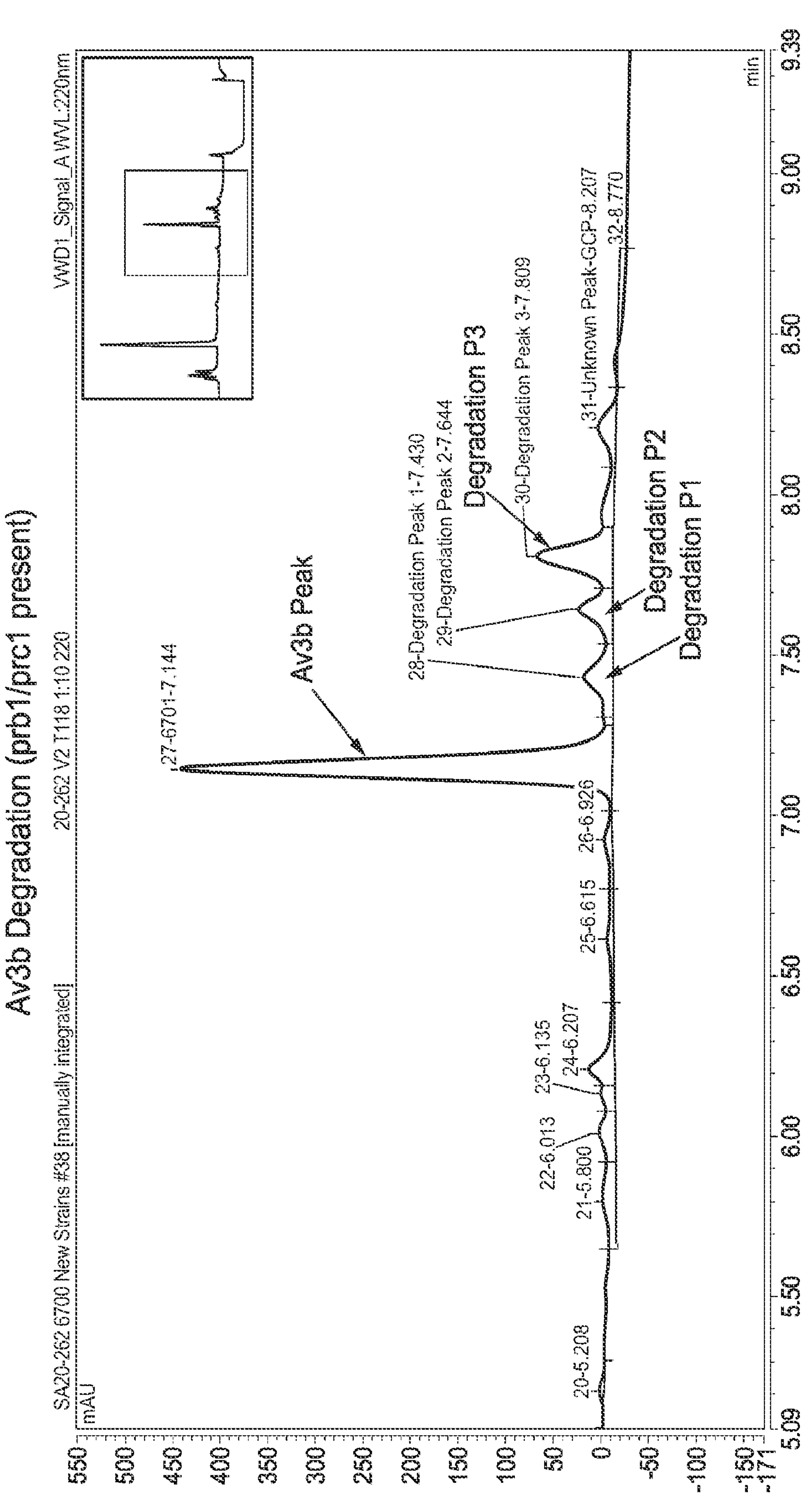
FIG. 32 shows an HPLC chromatogram for the Av3b expression strain fermentation beer sampled at 118 hours during fermentation process. There are 3 extra peaks following the major Av3b peak (identified as Degradation P1, P2 and P3).
Figure 33:
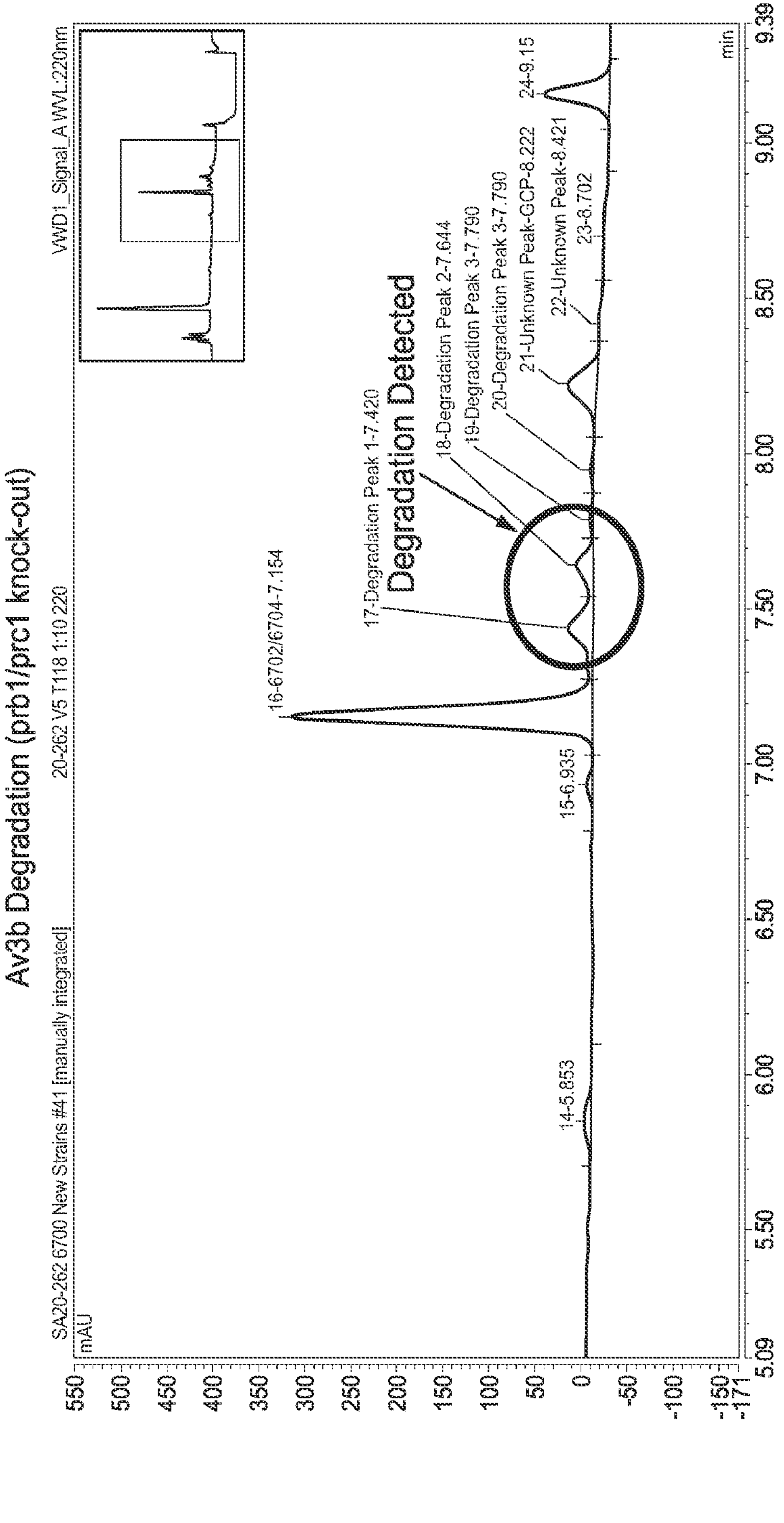
FIG. 33 shows an HPLC chromatogram for the prb1/prc1 Av3b knockout strain fermentation beer sampled at 118 hours during fermentation process. Here, the degradation is reduced relative to the Av3b expression strain, however, there is still some degradation—as indicated by the peaks in the circle.

Knocking-out prb1 and prc1 resulted in a decrease in Av3b degradation. FIG. 32 shows the degradation profile of Av3b when prc1 and prb1 are present. As shown in FIG. 33, the prb1/prc1 knock-out strain resulted in less degradation of Av3b. Accordingly, fermentation with the prb1/prc1 knock-out Av3b expression strain resulted in a reduction of degradation of Av3b, however, degradation was not totally prevented. These results indicate that besides prb1 and prc1, other un-identified carboxylproteases may also be involved.

Example 10. Av3b Mutant Stability

Based on the mutants Av3bM19, Av3bM23, Av3bM24, Av3bM25, and Av3bM28 having increased yield relative to Av3b, and insecticidal activity (as shown above), these mutants were selected for subsequent stability studies. Methods for making the mutants Av3bM19, Av3bM23, Av3bM24, Av3bM25, and Av3bM28 are described in Example 2. A summary of the these mutants, and their mutations, is presented in the table below.

TABLE 8

Summary of mutants evaluated in stability studies. The mutants Av3bM19, Av3bM23, Av3bM24, Av3bM25, and Av3bM28 were evaluated. Residues underlined and in bold show the location of mutations. Mutants with names in bold are those exhibiting increased stability in fermentation beer based on initial amount of peptide and amount remaining. See also FIG. 34.

| Name | Sequence | Mutation(s) | SEQ ID NO. |
|---|---|---|---|
| Av3bM19 | KSCCPCYWGGCPWGQ**D**CYP**D**GC**D**GPK | N16D, E20D, S23D | 20 |
| Av3bM23 | KSCCPCYWGGCPWGQNCYP**N**GCSGPK | E20N | 24 |
| Av3bM24 | KSCCPCYWGGCPWGQNCYPEGC**D**GPK | S23D | 25 |
| Av3bM25 | KSCCPCYW**P**GCPWGQNCYPEGCSGPK | G9P | 26 |
| Av3bM28 | **H**SCCPCYWGGCPWGQNCYPEGCSGPK | K1H | 29 |

To determine the stability of the new mutants, Av3bM19, Av3bM23, Av3bM24, Av3bM25, Av3bM27, and Av3bM28 were purified and incubated in Av3b fermentation beer. The mutants were purified by cation-exchange chromatography using a GE SP-Sephadex C-25 column. The column was first calibrated with 30 mM sodium citrate buffer at pH 3.0. Then, the culture supernatant containing the secreted mutant peptide was loaded into the column to let the mutant peptide bind to the resin. The column was then washed with 30 mM sodium citrate buffer, pH 3.0, followed by washing with 30 mM sodium acetate, pH 4.0. Next, the bound mutant peptide was eluted by 1 M or 2 M NaCl with 30 mM sodium acetate, pH 4.0. The elution was then concentrated and buffer-exchanged to 30 mM sodium acetate, pH 4.0 using a 1 kD cutoff spin concentrator.

After purification, each of the mutants, Av3bM19, Av3bM23, Av3bM24, Av3bM25, Av3bM27, and Av3bM28, were evaluated for stability by spiking them into Av3b strain fermentation beer at pH 6.5. As a negative control, Av3b was evaluated in a pH 4.0 buffer. As a positive control, purified Av3b was evaluated by spiking into the same Av3b fermentation beer at pH 6.5. All stability experiments were performed at room temperature. Samples were taken from the treatments described above, at the following incubation times: 0, 15, 39, 62.5 and 144 hours; the samples were evaluated via rpHPLC to determine the peptide peak area change that occurred during the process. The amount of peptide remaining relative to the beginning was determined by normalizing the peak area at different time to the one at 0 hour for each treatment. The degradation trend is visualized by the bar graph of the relative remaining peptide amount trend.

Figure 34:
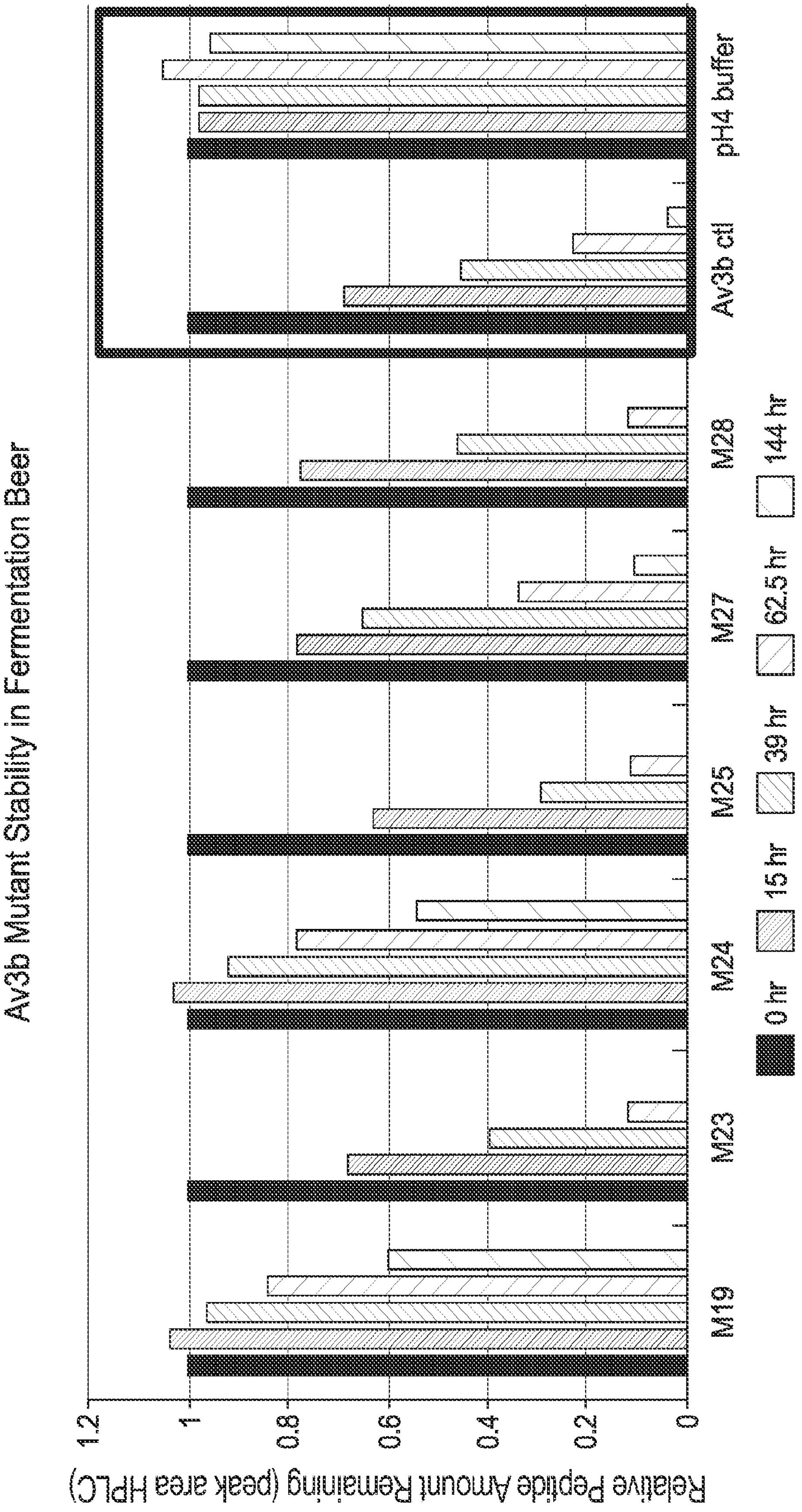
FIG. 34 depicts a graph showing peptide stability for a given mutant, i.e., Av3bM19 ("M19"); Av3bM23 ("M23"); Av3bM24 ("M24"); Av3bM25 ("M25"); Av3bM27 ("M27"); Av3bM28 ("M28"); Av3b peptide control, spiking into the Av3b fermentation beer at pH 6.5; and Av3b spiking in pH 4 buffer. The Y-axis is the relative peptide amount (as peptide peak area in the HPLC) compared to the starting amount of peptide in each group. Peptide amount is represented by the HPLC peak area. Each bar represents the peptide amount relative to Av3b, of a given mutant at the corresponding time point, i.e., at 0-, 15-, 39-, 62.5-, and 144-hours. The box indicates positive (Av3b) and negative (pH 4 buffer) controls. For example, the "pH4 buffer" group is Av3b peptide incubated in pH4 buffer. All the bars in this control group had similar height, indicating Av3b peptide had no degradation during the whole incubation period. In the group of "Av3b ctl," Av3b was spiked into Av3b fermentation beer; as the incubation time increased, the relative amount of Av3b peptide decreased, indicating Av3b peptide loss or degradation in the beer.

As shown in FIG. 34, Av3bM19 and Av3bM24 showed greater resistance to yeast fermentation beer protease cleavage compared to the control Av3b. All other mutants showed a similar degradation profile to Av3b. Here, each group of the bar represents a specific peptide/treatment. Each bar represents the relative amount of peptide compared to the starting amount of peptide in each group.

Here, when incubated in a pH 4 buffer, Av3b showed no loss of the peptide (indicating the stability of the Av3b control). In the group of "Av3b ctl," Av3b was spiked into Av3b fermentation beer, which contains secreted proteases that in turn cause degradation or loss of Av3b peptide. As the incubation time increased, the relative amount of Av3b peptide decreased, indicating Av3b peptide loss or degradation in the fermentation beer. A similar result was observed for the other groups. The Y-axis of FIG. 34 shows the relative peptide amount (as peptide peak area in the HPLC) compared to the start amount in each group. Peptide amount is represented by the HPLC peak area; therefore, the relative number is derived from the normalization of Peak area at different time to the start time (0 hours).

Figure 35:
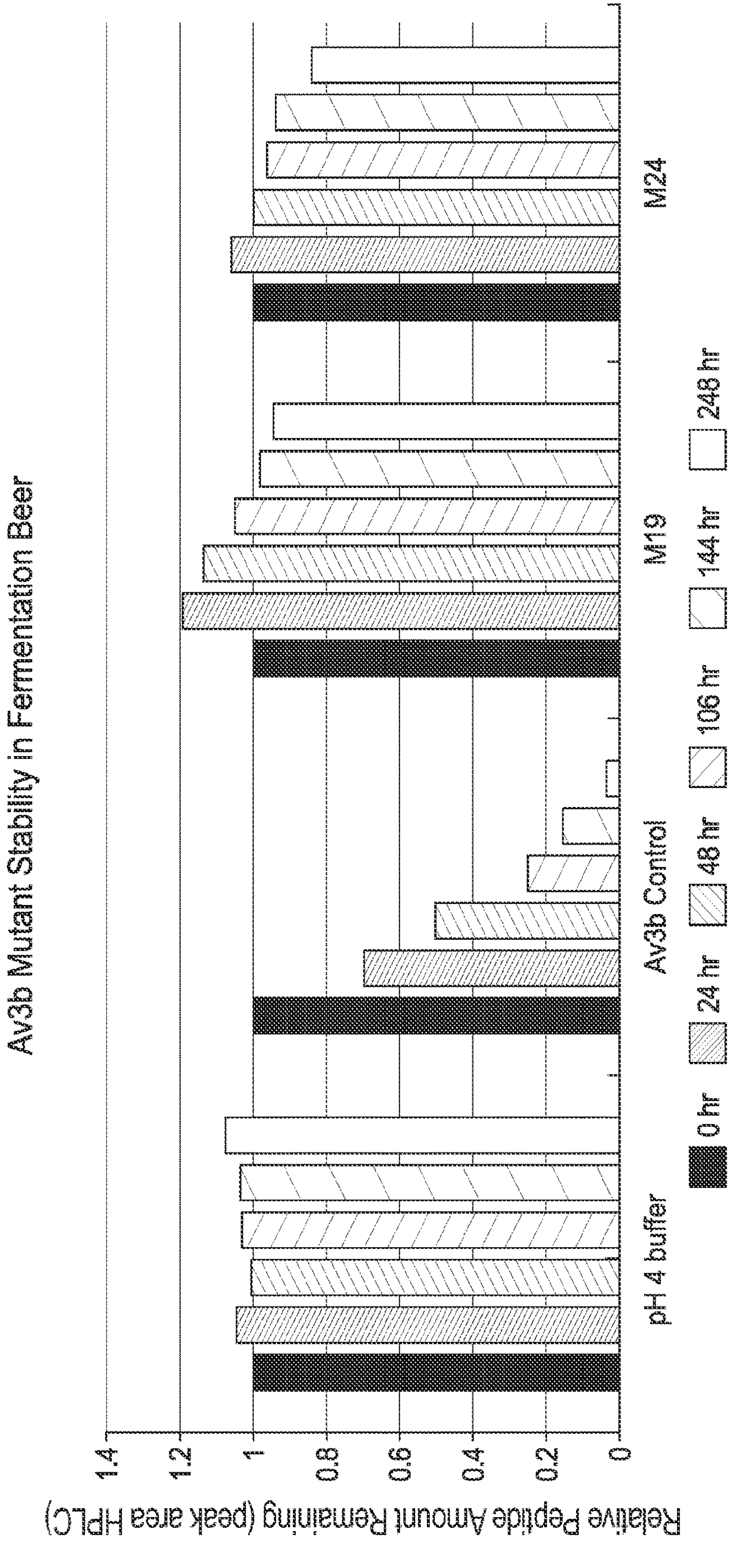
FIG. 35 depicts a graph showing peptide stability of a given mutant spiked into the Av3b fermentation beer at pH6.5. Grouped left to right are: (1) Av3b spiked in the pH 4 buffer; (2) the Av3b control; (3) Av3bM19 ("M19"); and (4) Av3bM24 ("M24"). Each bar represents the peptide amount relative to its starting amount, and at the time points: 0-, 24-, 48-, 106-, 144-, and 248-hours. Here, the "pH4 buffer" group is Av3b peptide incubated in pH4 buffer. The Y-axis is the relative peptide amount (as peptide peak area in the HPLC) compared to the starting amount of peptide in each group. Peptide amount is represented by the HPLC peak
Figure 36:
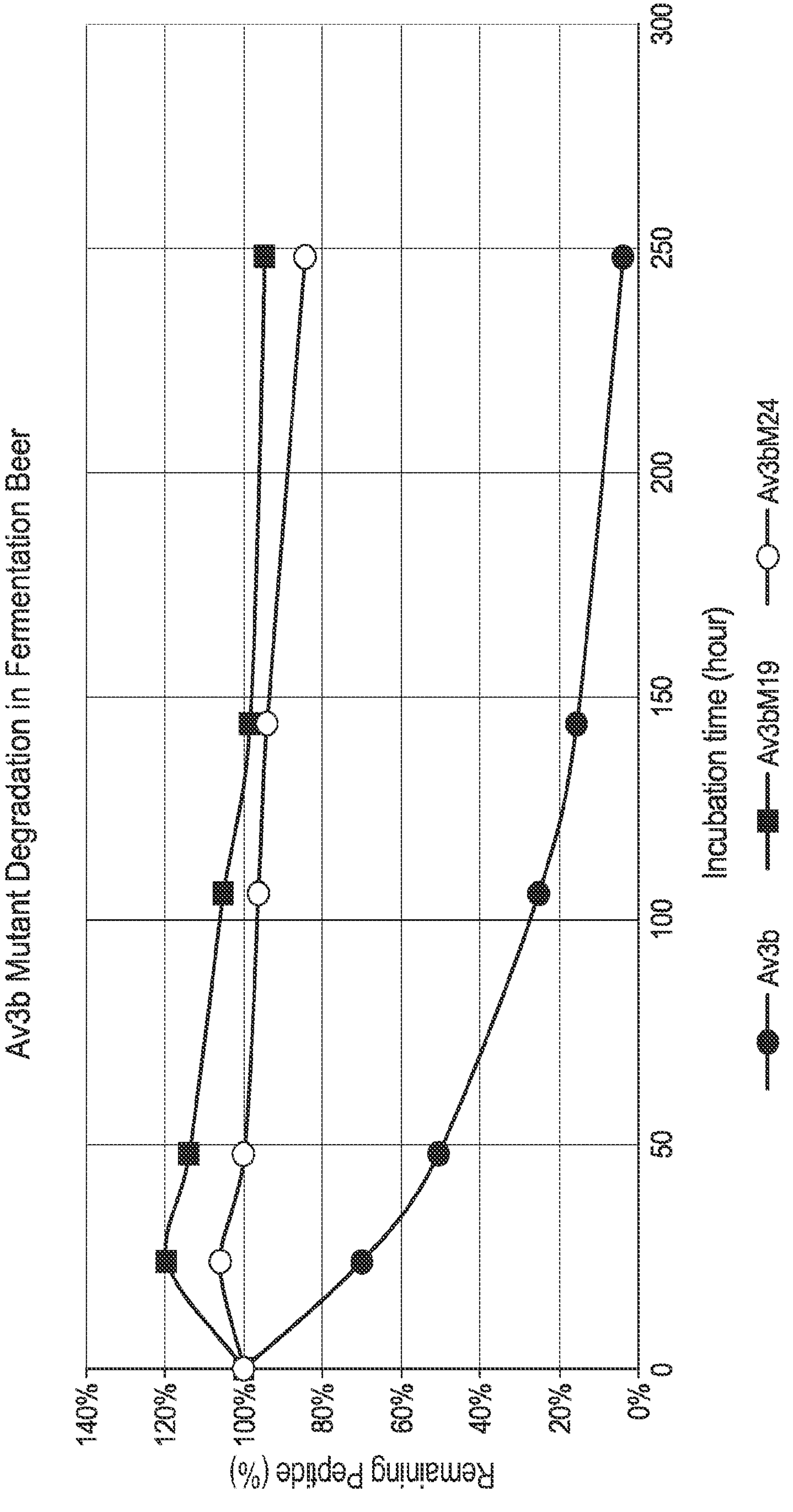
FIG. 36 shows the degradation of Av3bM19 and Av3bM24 in fermentation beer over time. The Y-axis is the relative peptide amount (as peptide peak area in the HPLC) compared to the starting amount of peptide. As shown here, at 248 hours, there is 95% of the Av3bM19 peptide remaining, and 84% of the Av3bM24 peptide remaining. There is 3.8% of Av3b remaining after 248 hours.

A subsequent round of stability assessment was performed focusing on Av3bM19 and Av3bM24; this round of experiments confirmed that Av3bM19 and Av3bM24 had improved resistance to fermentation beer cleavage. FIG. 35. Here, the stability analysis was performed as previously described, however, peptide amounts were evaluated at 0-, 24-, 48-, 106-, 144-, and 248-hours. FIG. 36 shows the results of this stability analysis as a function of remaining peptide over time.

Example 11. Resistance of Av3b Mutants to Proteolysis in Fermentation Beer

The mutants Av3bM19 and M24 are resistant to degradation when incubated in fermentation beer. Av3bM19 and M24 were selected because they showed possible higher yield than Av3b. As shown in FIG. 34, only M19 and M24 showed improved stability; thus, they were chosen for more detailed study here.

After spiking into pKS022-YCT-38-14 (an Av3b production strain) fermentation beer with pH 6.5, Av3b was found to be degraded and ultimately disappeared after 10 days of incubation in the Av3b fermentation beer—with a half-degradation time of 46 hours. Surprisingly, two mutants, Av3bM19 (mutations $N_{16}D$, E20D, S23D relative to Av3b) and Av3bM24 (mutation S23D relative to Av3b), were found to resist the degradation in Av3b fermentation beer.

Figure 37:
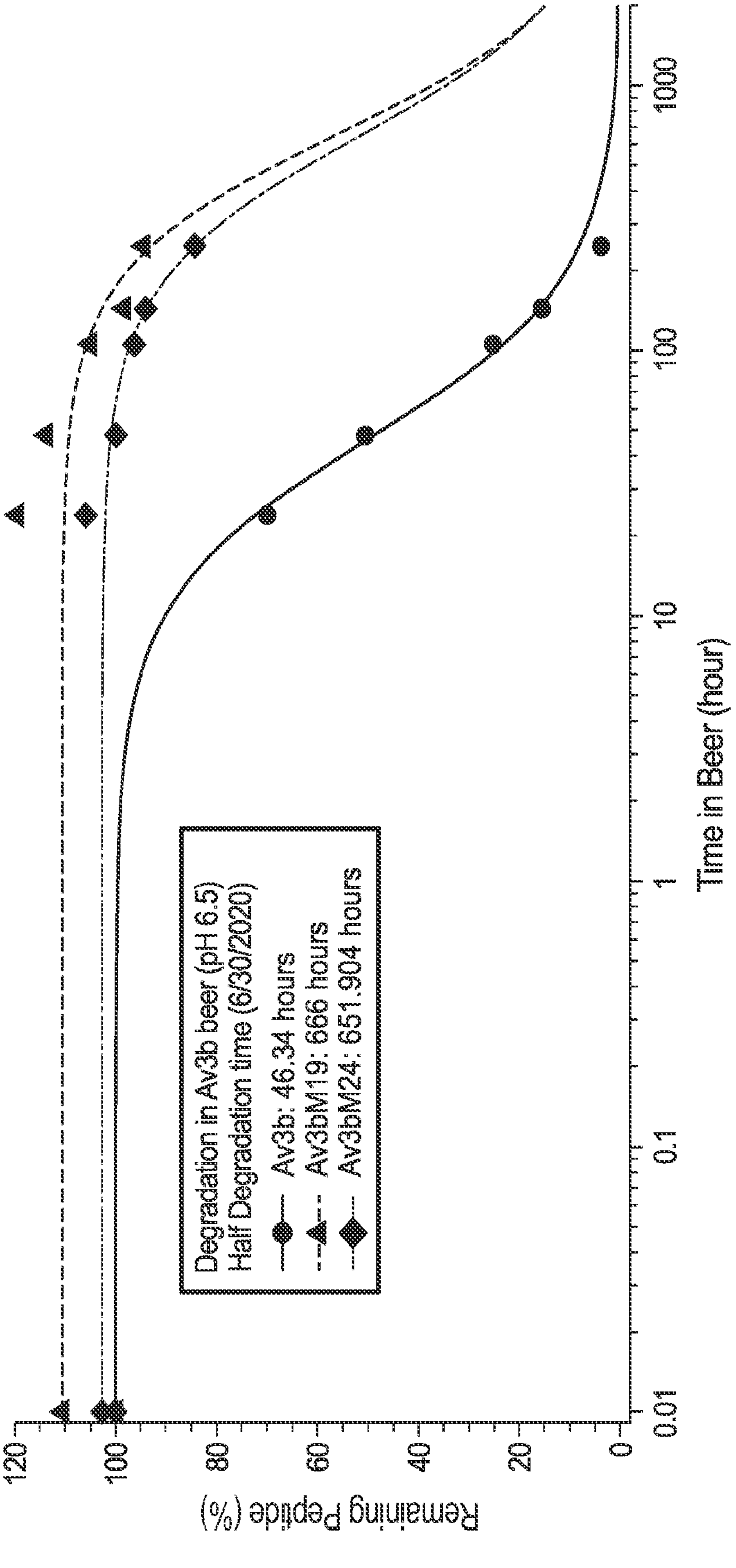
FIG. 37 shows a graph depicting degradation of Av3b mutants in Av3b production fermentation beer. Av3b has a half-degradation time of 46.34 hours. The mutant, Av3bM19, has a much longer degradation time, with a half degradation time of 666 hours. Likewise, the mutant Av3bM24 has a half-degradation time of 652 hours.

FIG. 37 shows a graph depicting degradation of Av3b mutants in Av3b production fermentation beer. Here, Av3b was shown to have a half-degradation time of 46.34 hours. By contrast, the mutant, Av3bM19 (KSCCPCYWGGCPWGQDCYPDGCDGPK; SEQ ID NO: 20), has a much longer degradation time: 666 hours. Likewise, the mutant Av3bM24 (KSCCPCYWGGCPWGQN-CYPEGCDGPK; SEQ ID NO: 25) has a half-degradation time of 652 hours. These results show that the mutants Av3bM19 and Av3bM24 dramatically slow the degradation of the respective Av3b mutants in fermentation beer.

Figure 38:
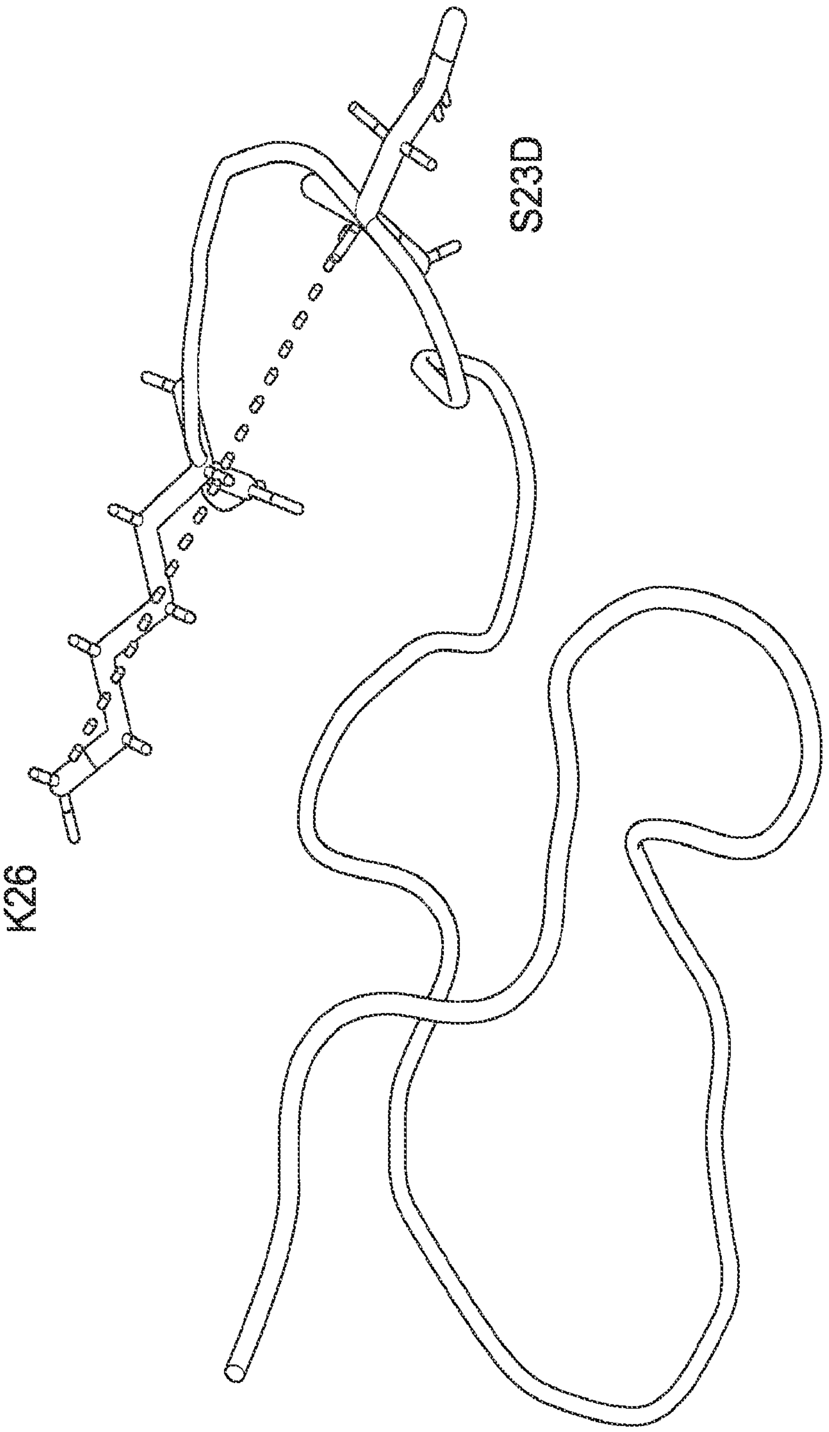
FIG. 38 shows a computational Av3bM24 3-D-structure created using Rosetta protein modeling program and PyMol.

Both Av3bM19 and Av3bM24 contain the S23D mutation; accordingly, perhaps the negatively-charged S23D mutation might protect positively-charged C-terminal lysine from cleavage via static electro-interaction. However, these two residues are located far away from each other (16.5 A) based on the Av3b NMR structure; thus, unless there is some conformational change allowing a closer proximity between the residues that results from the mutation, the electro-interaction is unexpected. FIG. 38.

Example 12. Static Electro-Interactions Between Positions 23 and 26

To confirm whether the hypothesis that S23D (negatively-charged) and K26 (positively-charged) might form a static electro-interaction, another mutant was designed, Av3bM125, having the amino acid sequence: KSCCPCYWPGCPWGQNCYPEGCRGPE (SEQ ID NO: 35). Av3bM125 has the residue charge swapped between the two positions, i.e., with S23R (positively-charged instead of negatively) and K26D (negatively-charged instead of positively).

Figure 39:
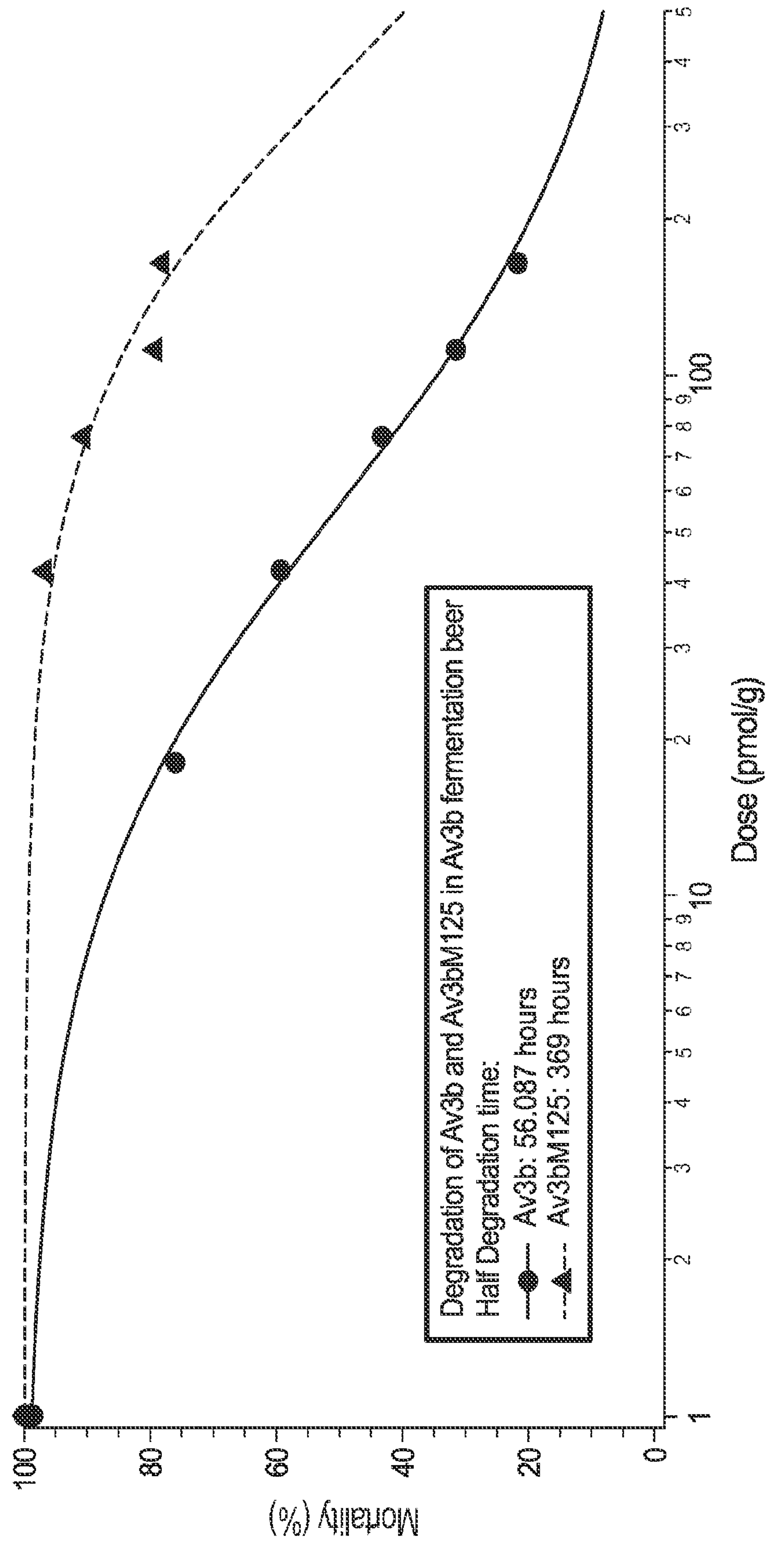
FIG. 39 shows a graph depicting degradation of Av3b mutants in Av3b production fermentation beer. Av3b has a half-degradation time of 56.087 hours. The mutant, Av3bM125, has a much longer degradation time, with a half degradation time of 369 hours.

Av3bM125 was spiked into the fermentation beer at pH 6.5, and its stability in the fermentation beer was evaluated with the Av3b peptide as a control. AV3bM125 showed dramatically improved resistance to degradation comparted to Av3b peptide. Here, Av3bM125 had a half-degradation time of 369 hours compared to the 56-hour half-degradation time for Av3b in the same treatment. FIG. 39.

Figure 40:
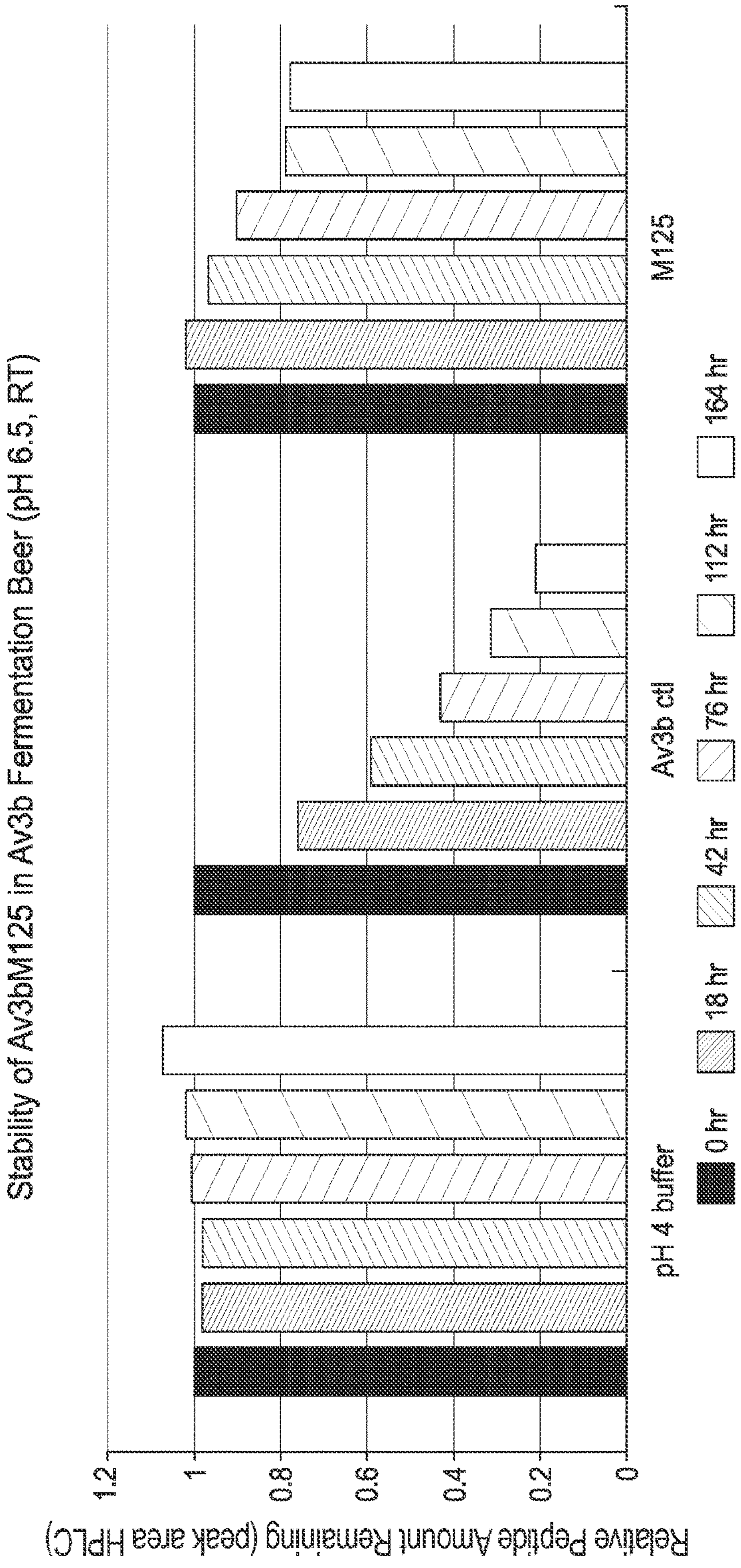
FIG. 40 depicts a graph showing the stability of Av3bM125 in Av3b fermentation beer, at room temperature and pH 6.5. Y-axis shows the amount of peptide relative to its start amount. The first set of bar graphs shows the stability of Av3bM125 in pH 4 buffer. The second set of bar graphs show the Av3b degradation in the fermentation beer at pH 6.5. The third set of bar graphs show Av3bM125. Each bar corresponds to a time, from left to right, 0-, 18-, 42-, 76-, 112-, and 164-hours.
Figure 41:
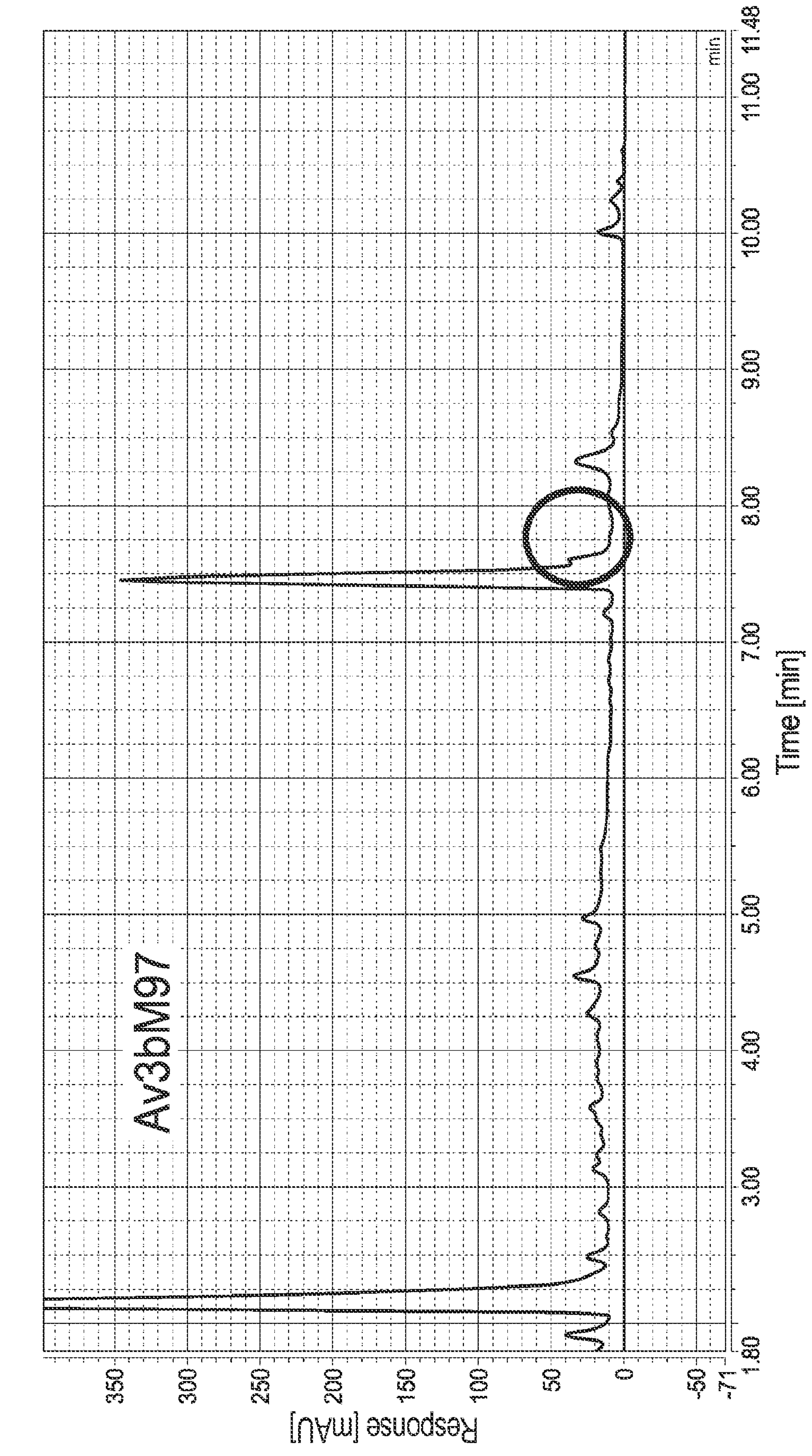
FIG. 41 shows an HPLC chromatogram for the Av3b mutant, Av3bM97, from the mutant strain fermentation sample obtained at 119.5 hours during the fermentation process. The circle indicates degradation product.
Figure 42:
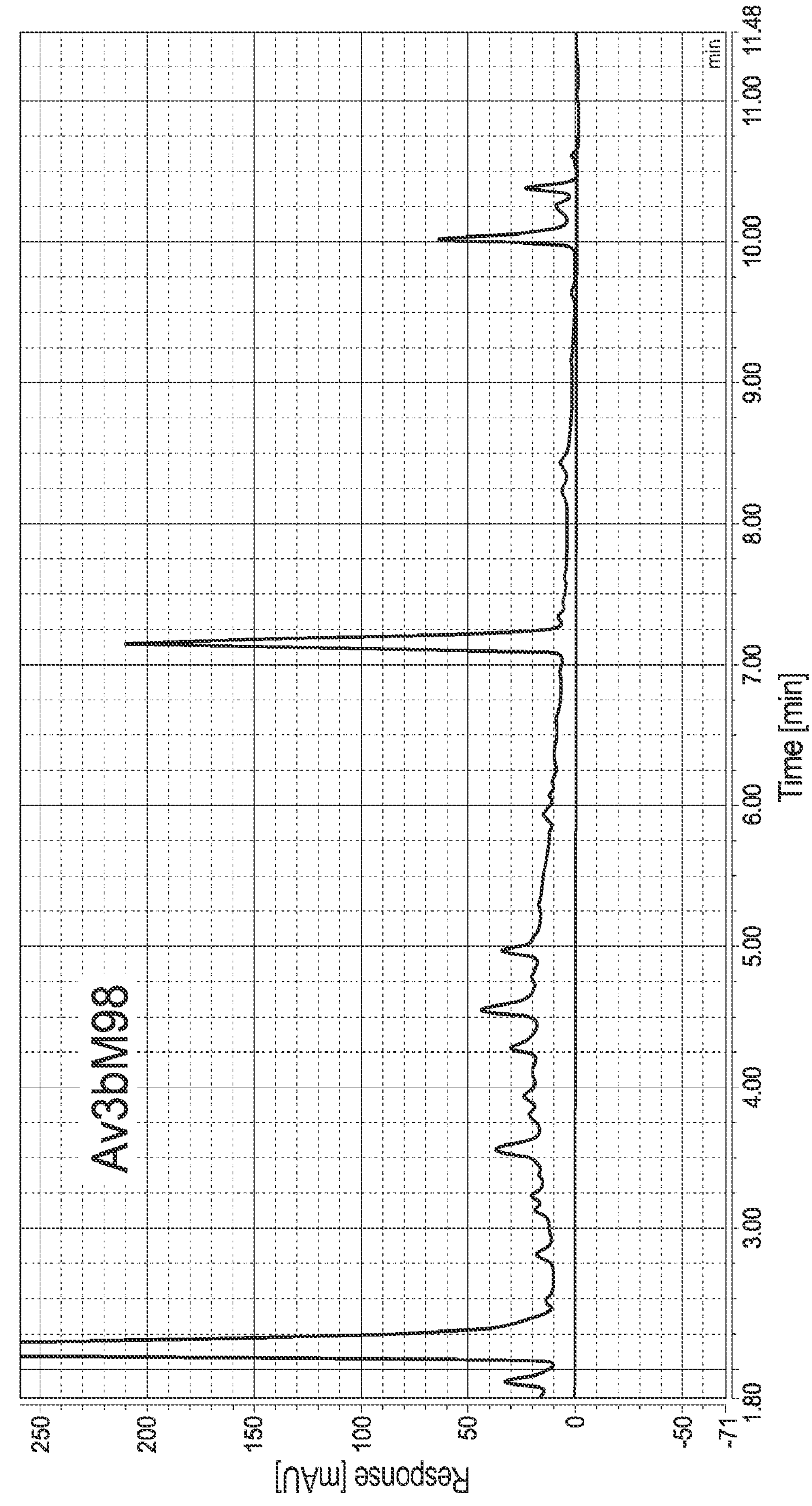
FIG. 42 shows an HPLC chromatogram for the Av3b mutant, Av3bM98, from the mutant strain fermentation sample taken at 119.5 hours during the fermentation process. Here, there is no degradation product.
Figure 43:
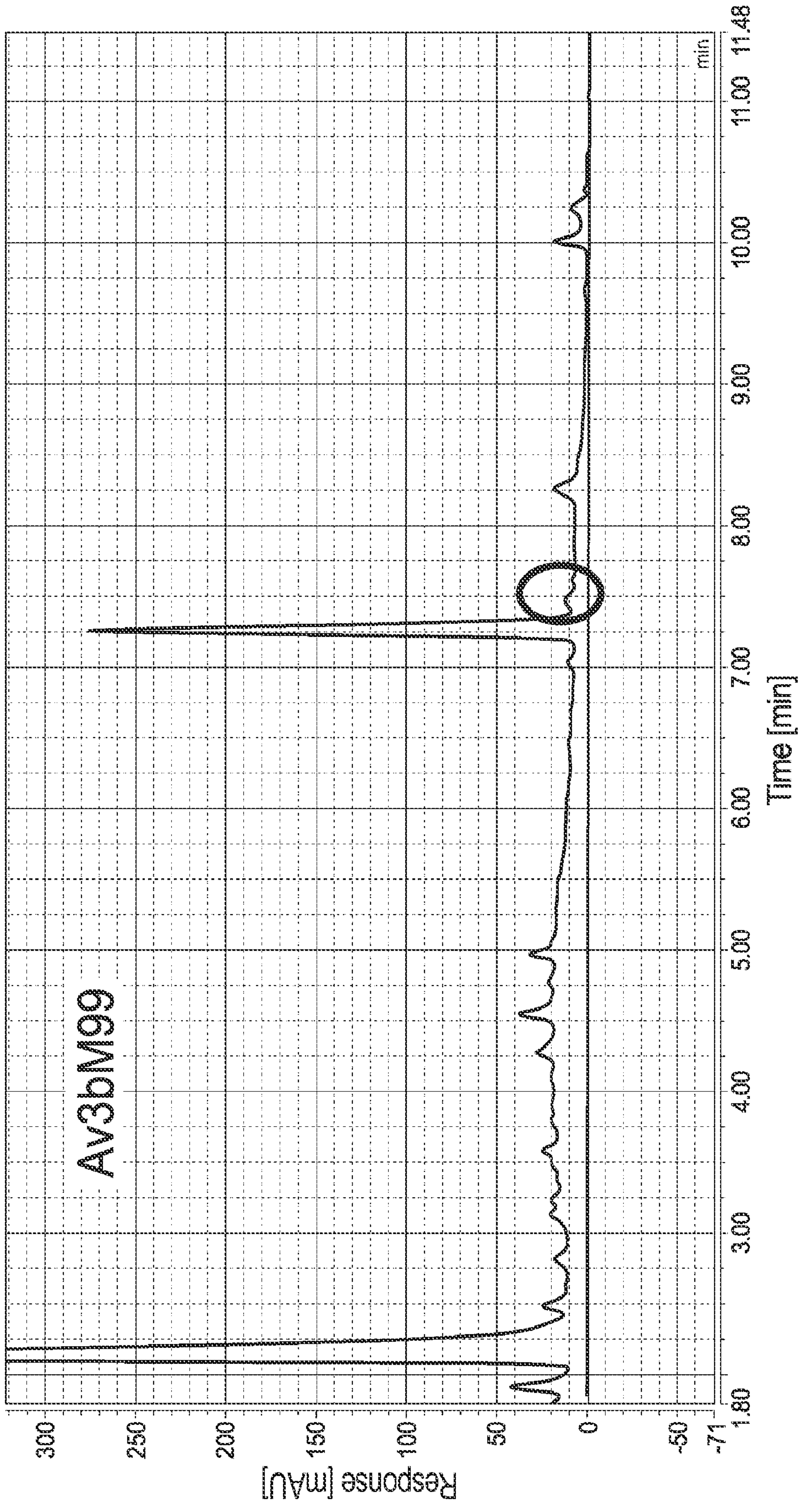
FIG. 43 shows an HPLC chromatogram for the Av3b mutant, Av3bM99, from the mutant strain fermentation sample taken at 119.5 hours during the fermentation process. The circle indicates degradation product.
Figure 44:
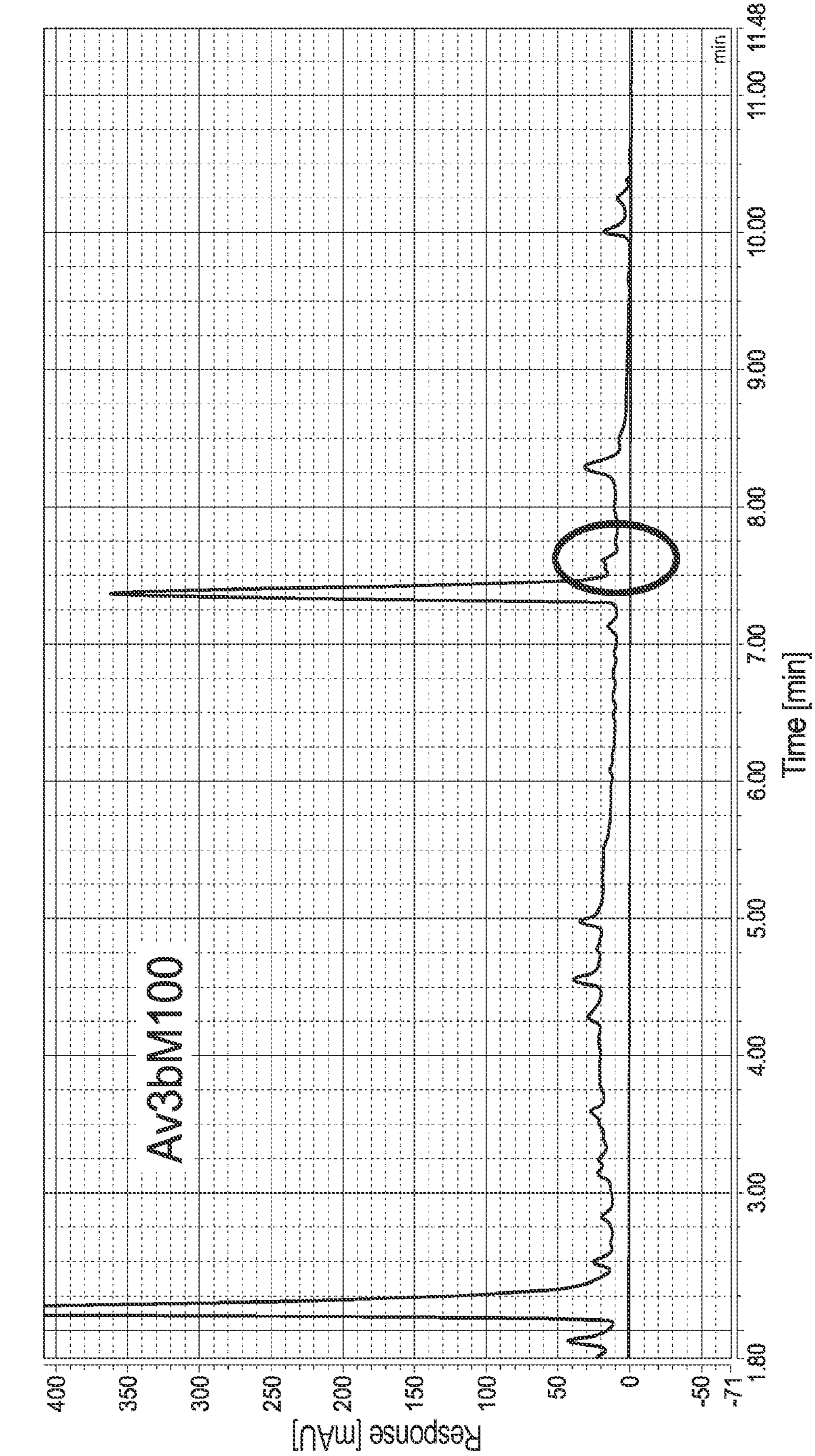
FIG. 44 shows an HPLC chromatogram for the Av3b mutant, Av3bM100, from the mutant strain fermentation sample taken at 119.5 hours during the fermentation process. The circle indicates degradation product.
Figure 45:
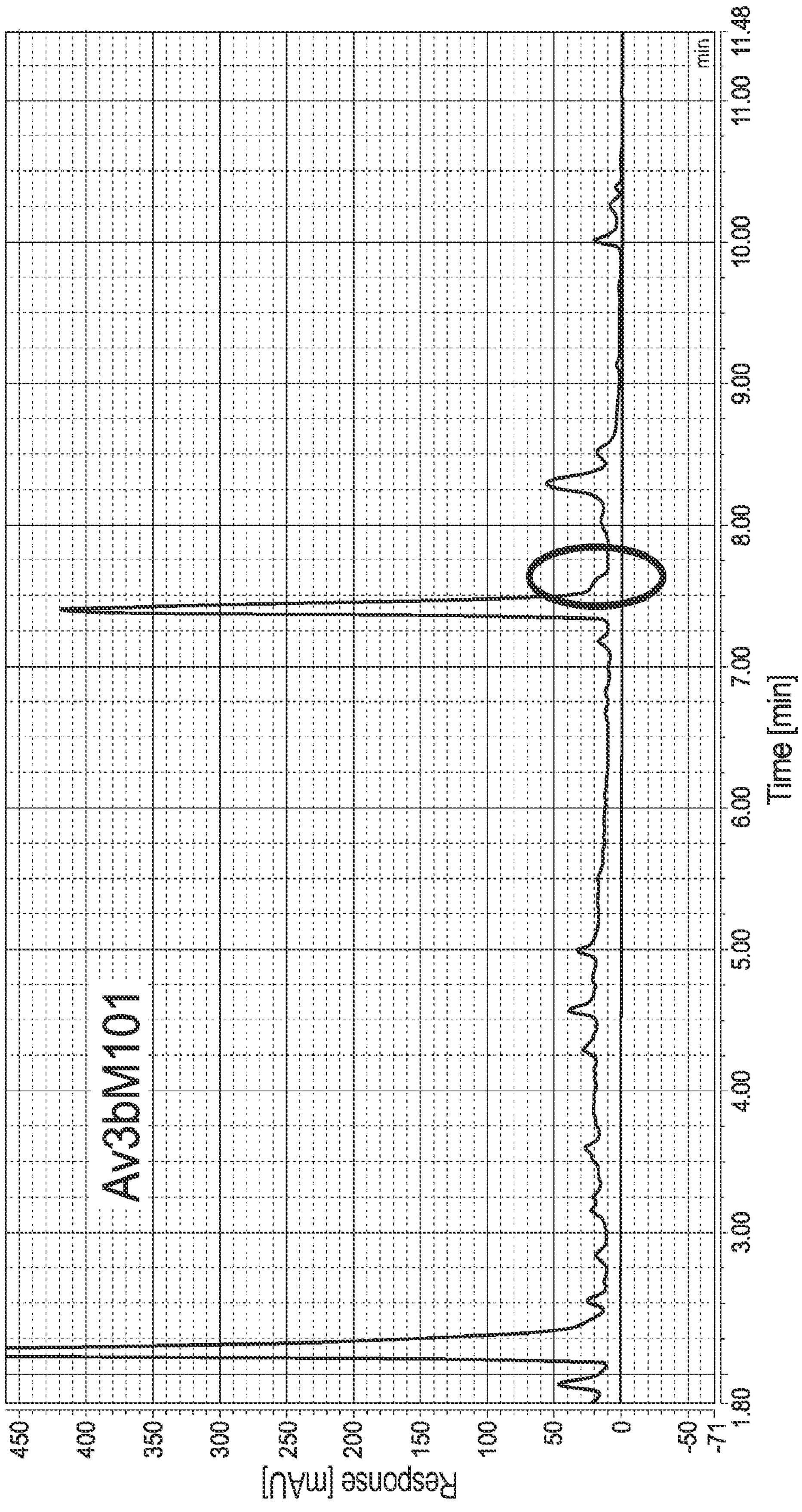
FIG. 45 shows an HPLC chromatogram for the Av3b mutant, Av3bM101, from the mutant strain fermentation sample taken at 119.5 hours during the fermentation process. The circle indicates degradation product.
Figure 46:
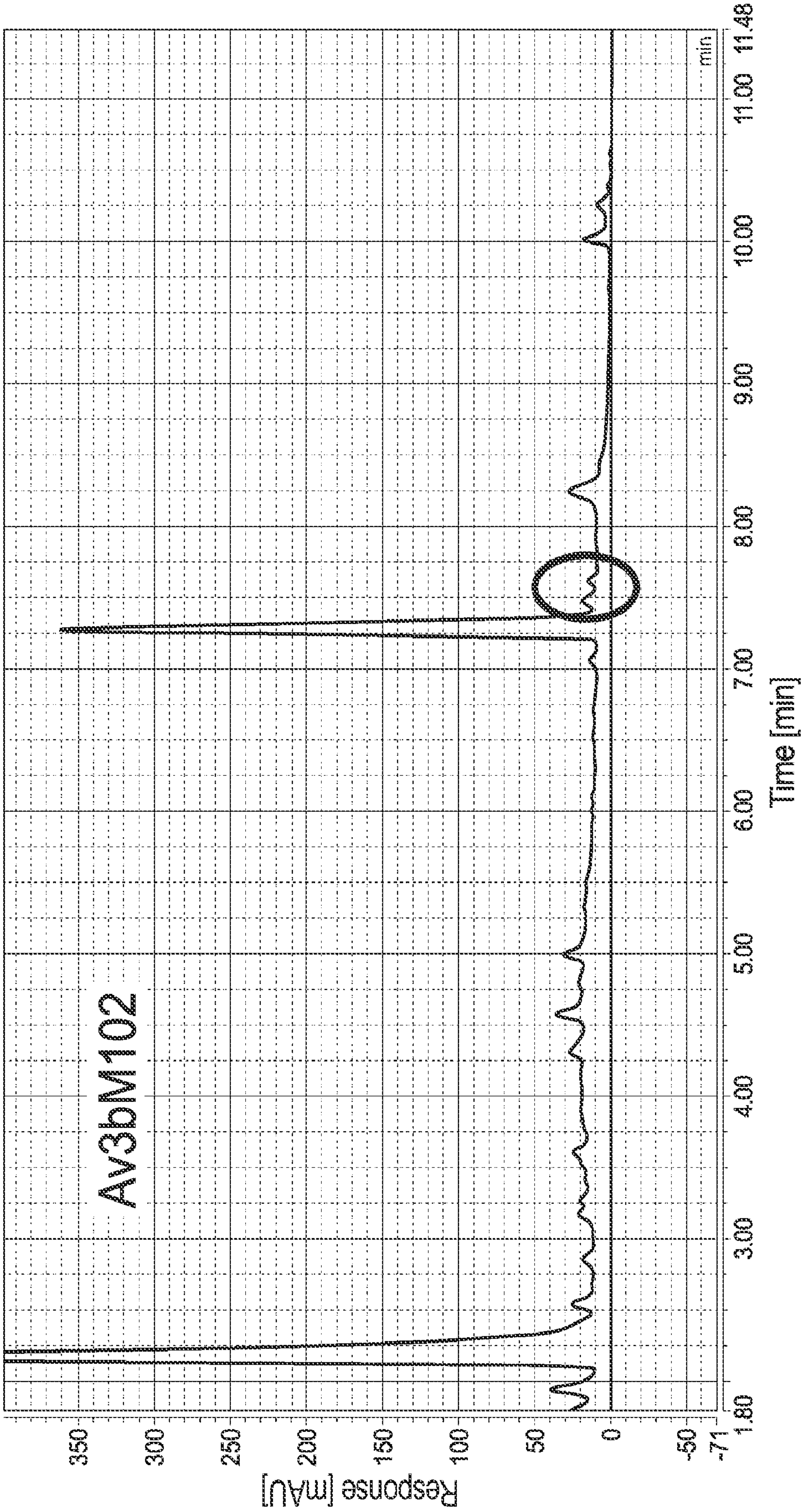
FIG. 46 shows an HPLC chromatogram for the Av3b mutant, Av3bM102, from the mutant strain fermentation sample taken at 119.5 hours during the fermentation process. The circle indicates degradation product.
Figure 47:
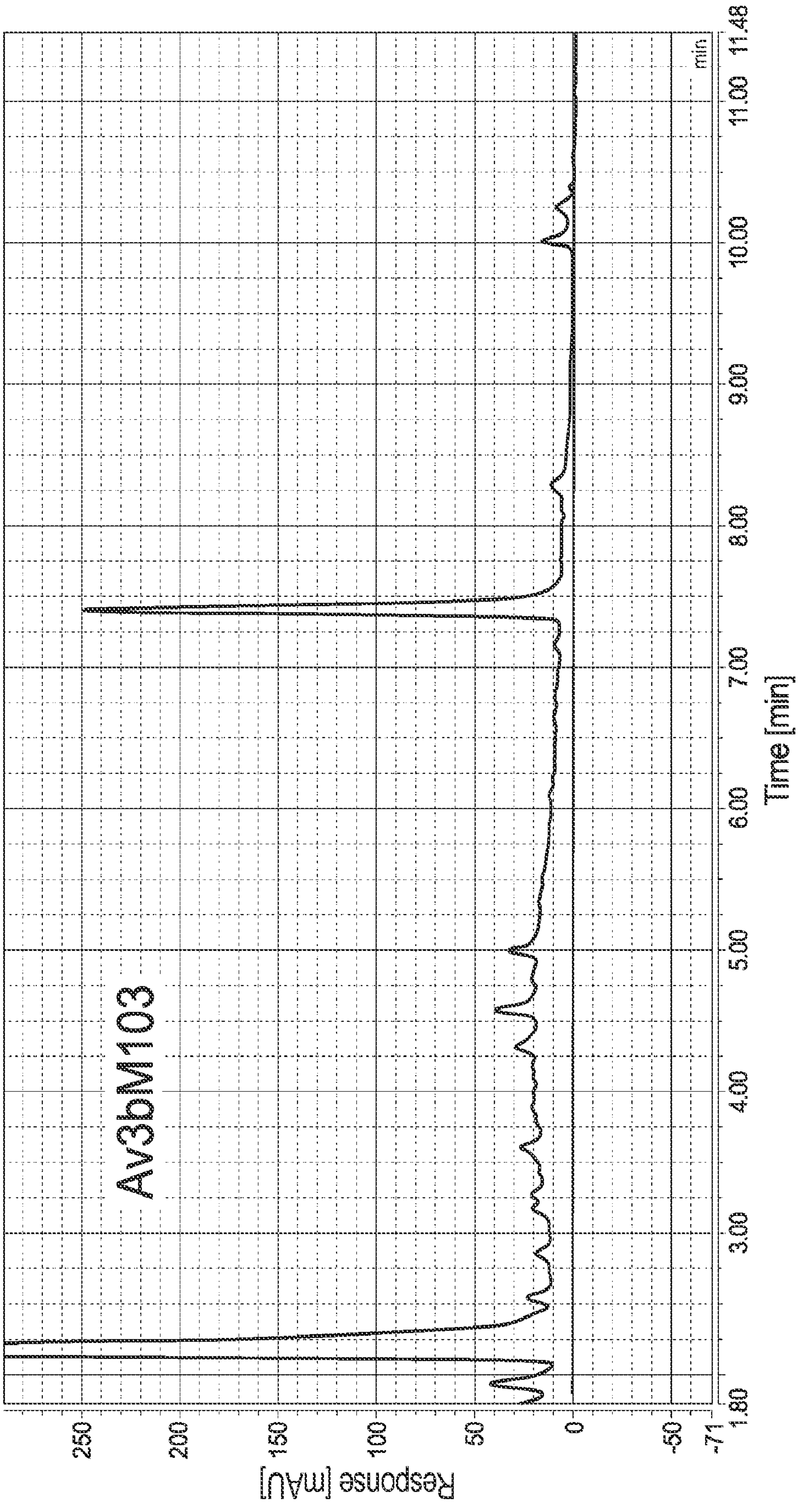
FIG. 47 shows an HPLC chromatogram for the Av3b mutant, Av3bM103, from the mutant strain fermentation sample taken at 119.5 hours during the fermentation process.
Figure 48:
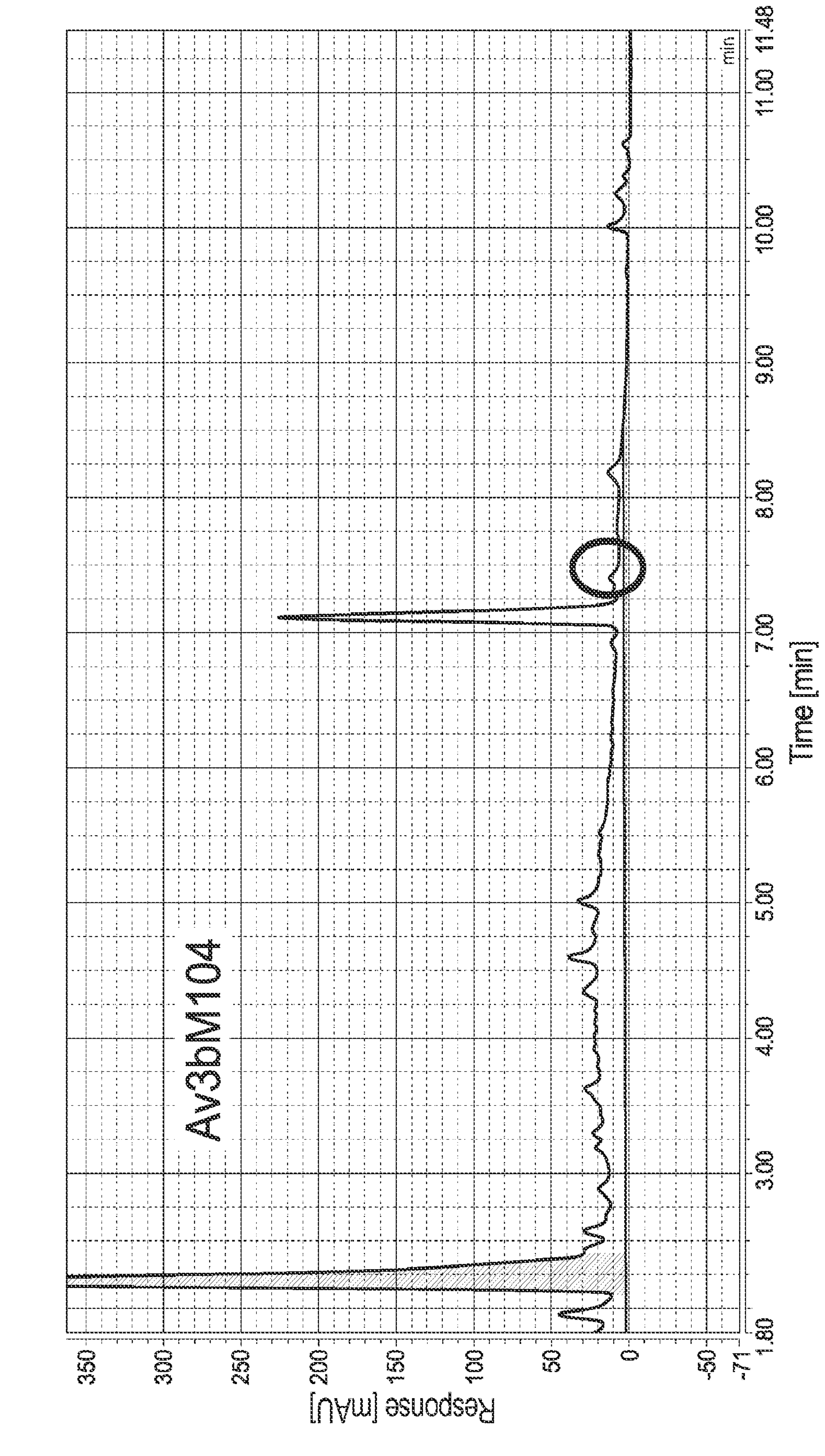
FIG. 48 shows an HPLC chromatogram for the Av3b mutant, Av3bM104, from the mutant strain fermentation sample taken at 119.5 hours during the fermentation process. The circle indicates degradation product.
Figure 49:
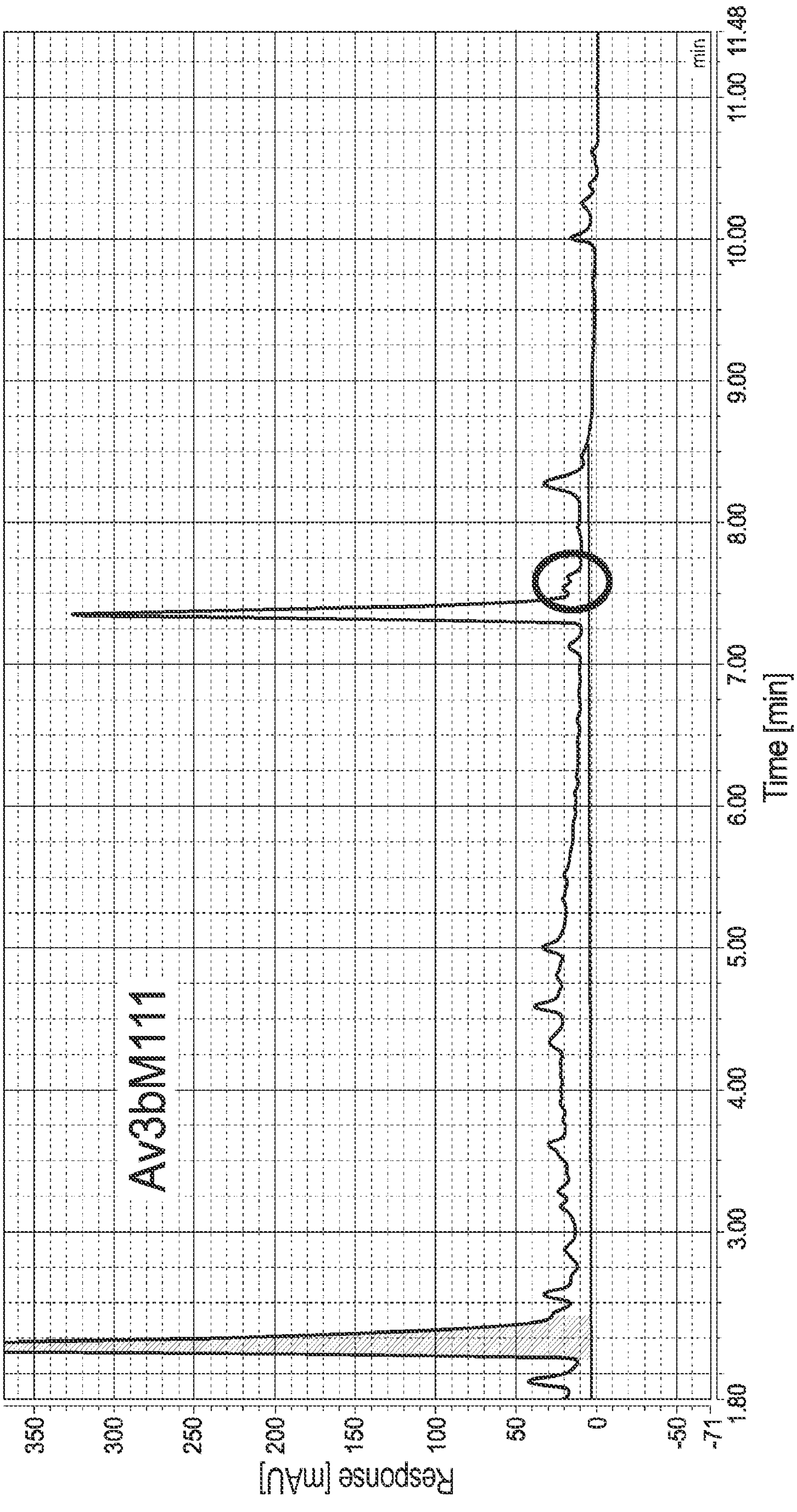
FIG. 49 shows an HPLC chromatogram for the Av3b mutant, Av3bM111, from the mutant strain fermentation sample taken at 119.5 hours during the fermentation process. The circle indicates degradation product.
Figure 50:
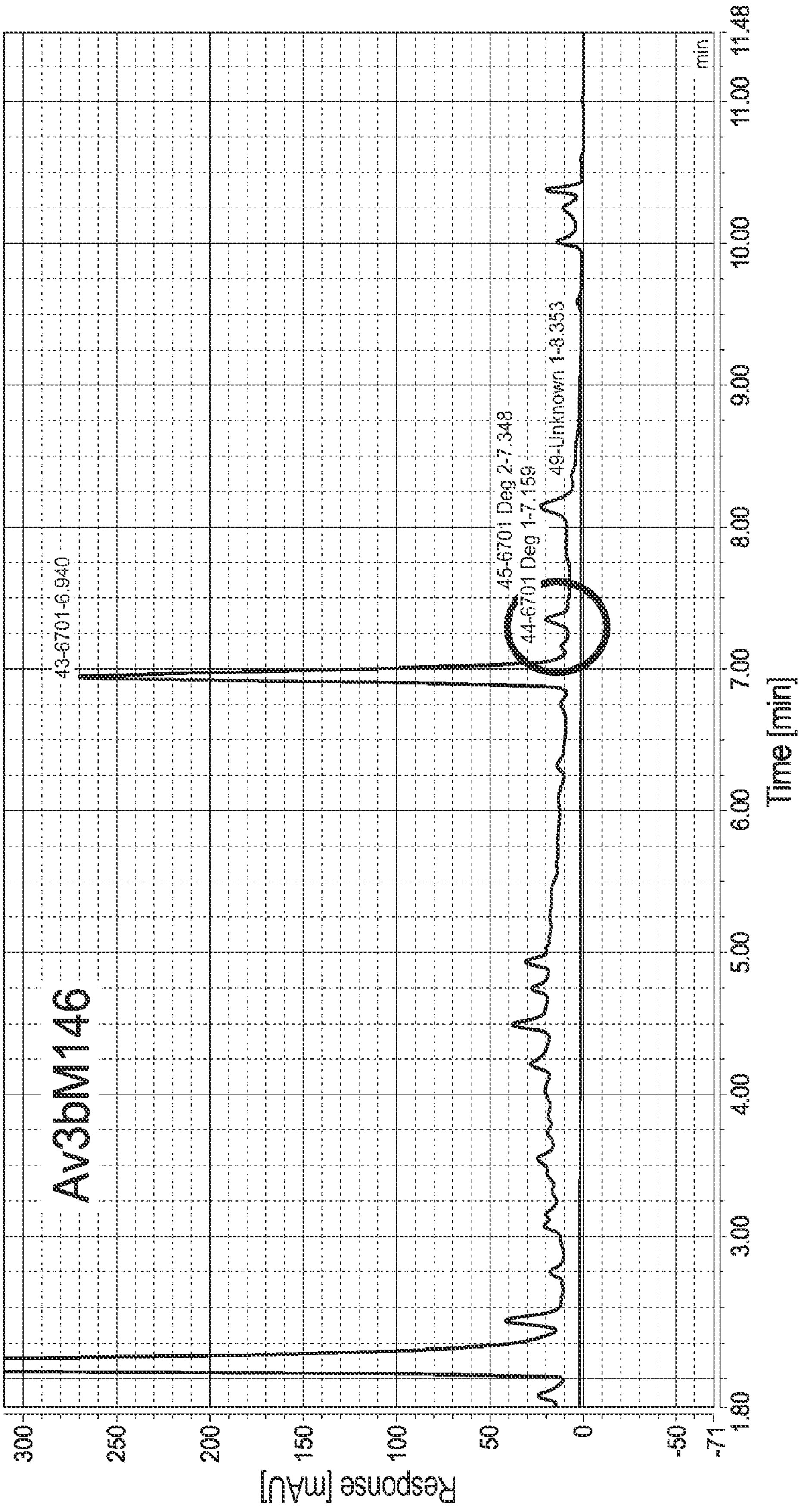
FIG. 50 shows an HPLC chromatogram for the Av3b mutant, Av3bM146, from the mutant strain fermentation sample taken at 119.5 hours during the fermentation process. The circle indicates degradation product.
Figure 51:
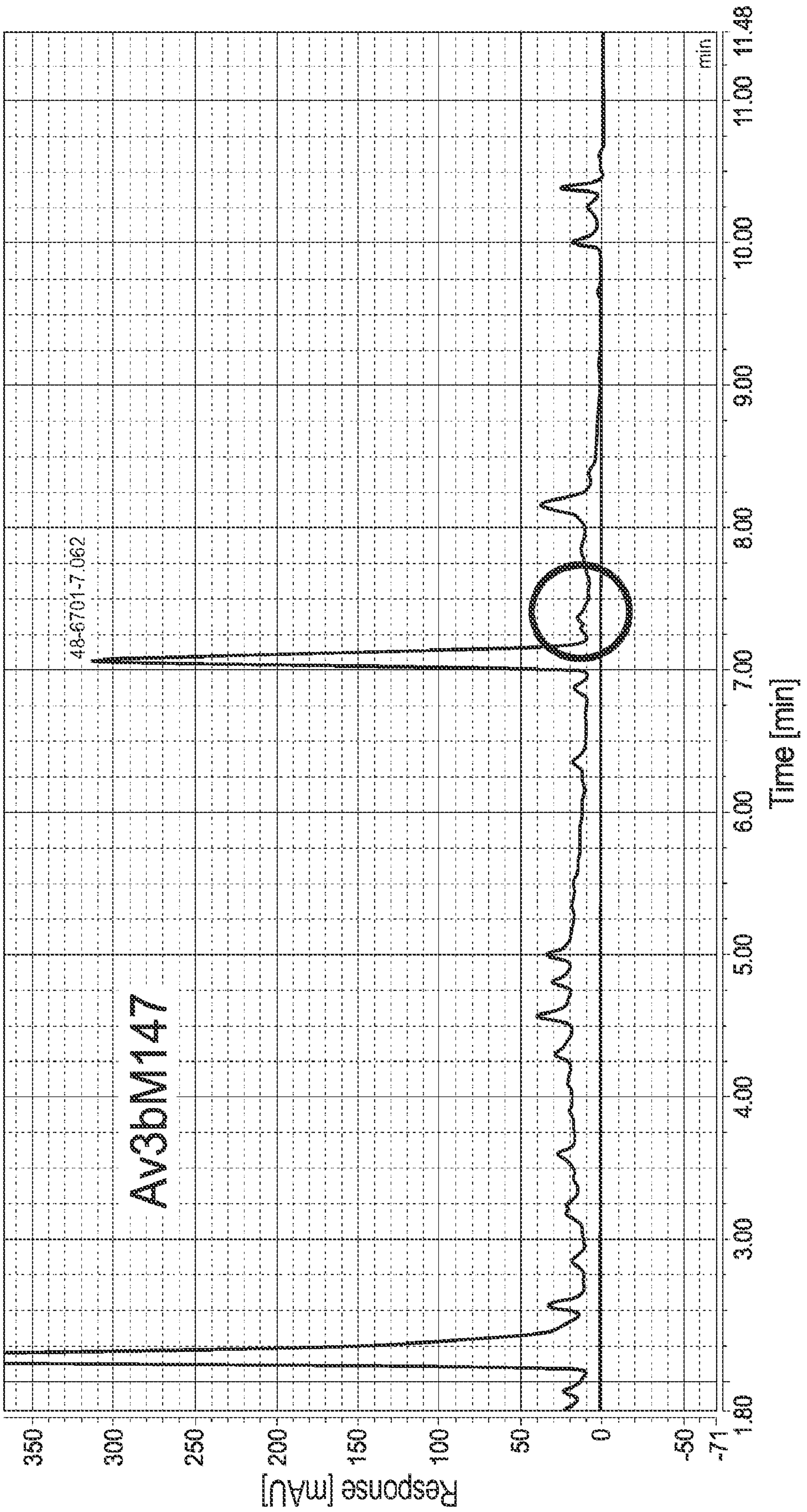
FIG. 51 shows an HPLC chromatogram for the Av3b mutant, Av3bM147, from the mutant strain fermentation sample taken at 119.5 hours during the fermentation process. The circle indicates degradation product.
Figure 52:
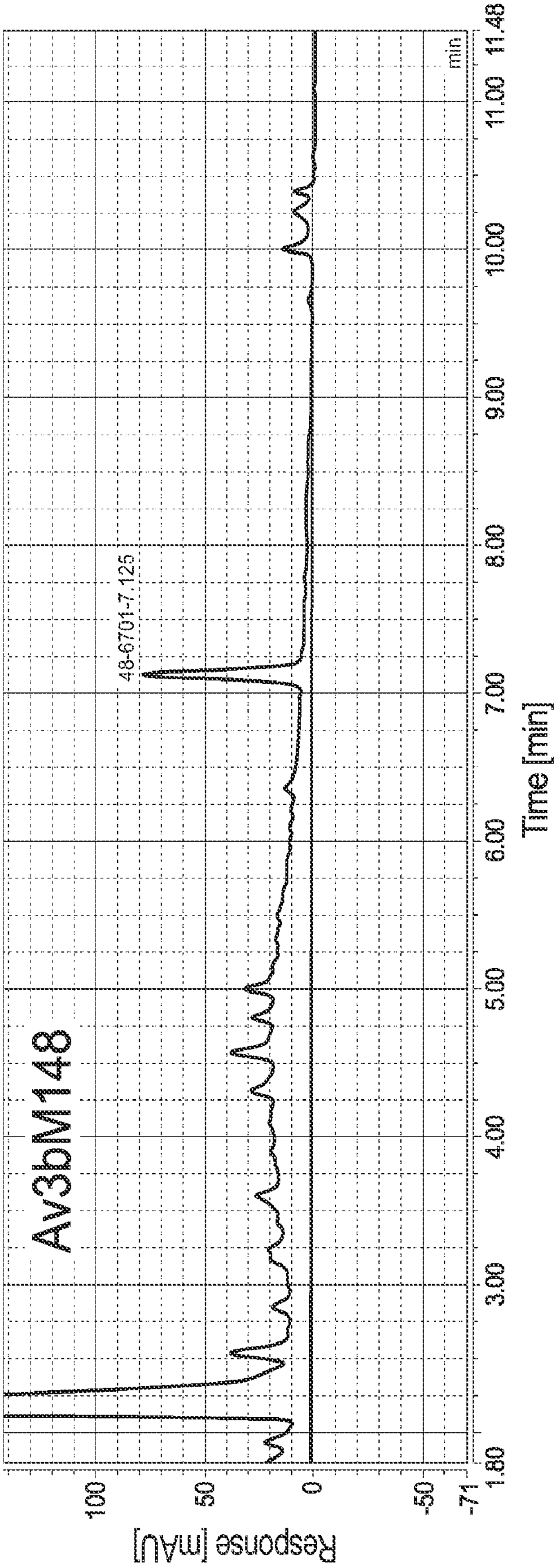
FIG. 52 shows an HPLC chromatogram for the Av3b mutant, Av3bM148, from the mutant strain fermentation sample taken at 119.5 hours during the fermentation process.
Figure 53:
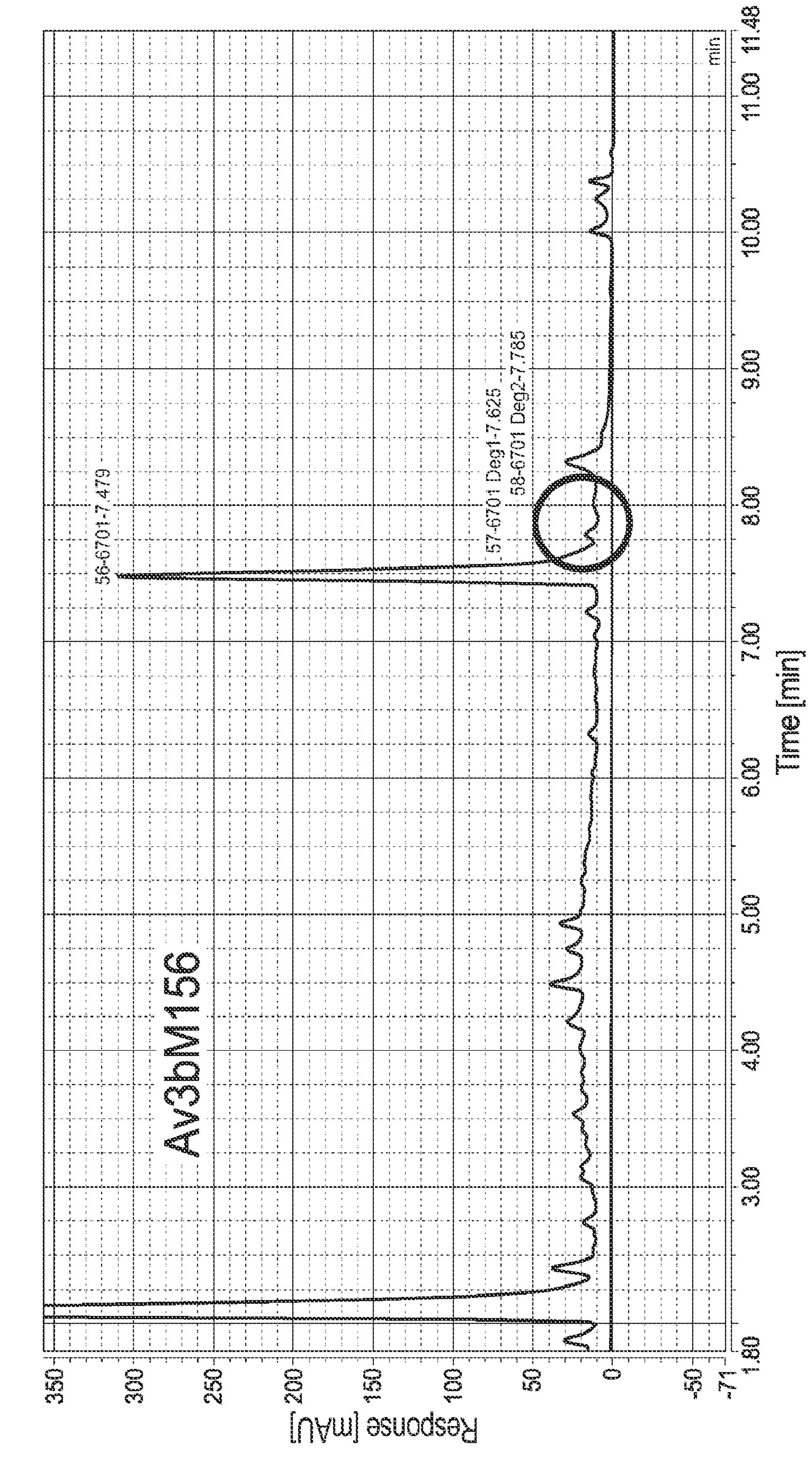
FIG. 53 shows an HPLC chromatogram for the Av3b mutant, Av3bM156, from the mutant strain fermentation sample taken at 119.5 hours during the fermentation process. The circle indicates degradation product.
Figure 54:
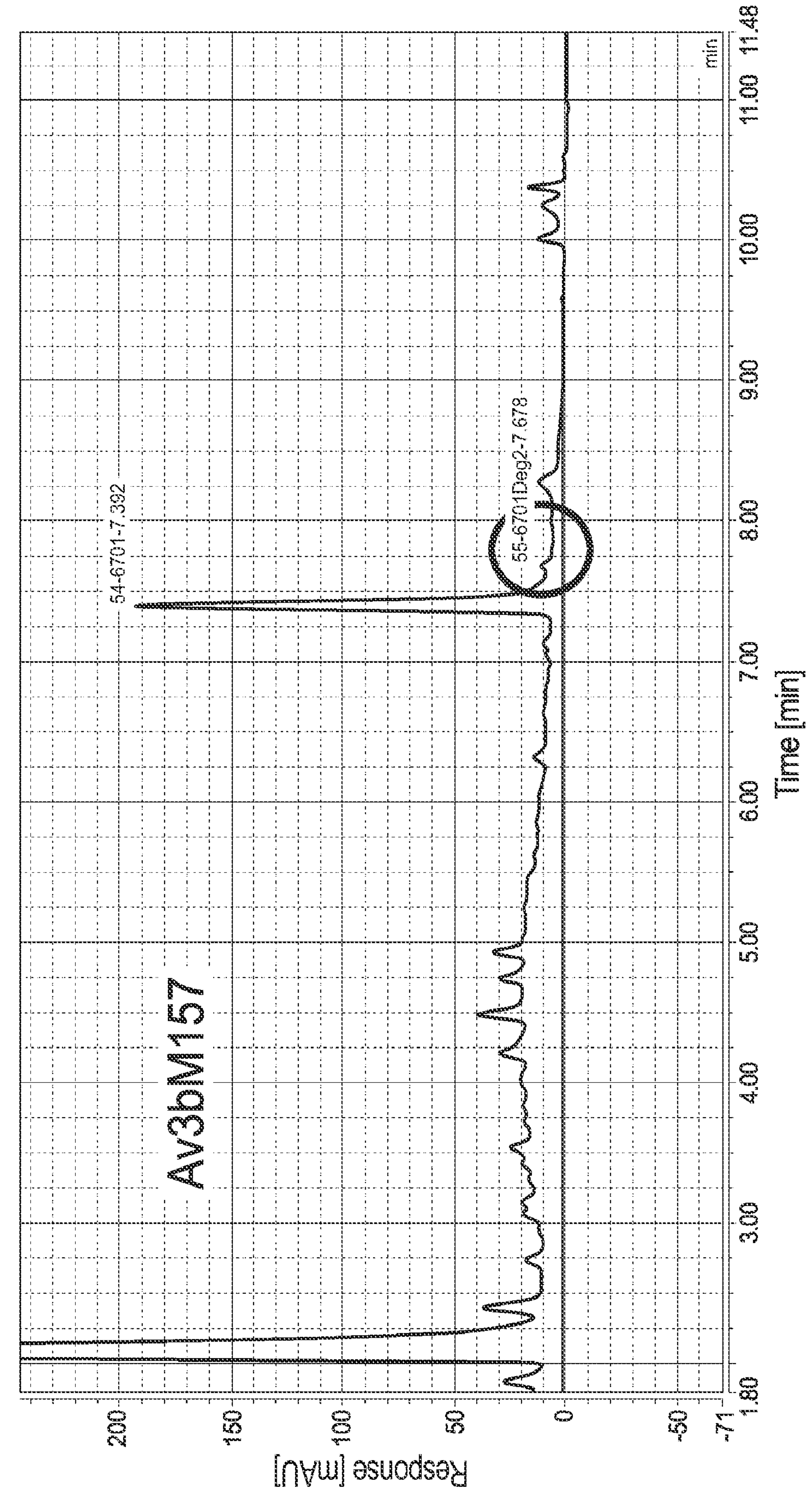
FIG. 54 shows an HPLC chromatogram for the Av3b mutant, Av3bM157, from the mutant strain fermentation sample taken at 119.5 hours during the fermentation process. The circle indicates degradation product.
Figure 55:
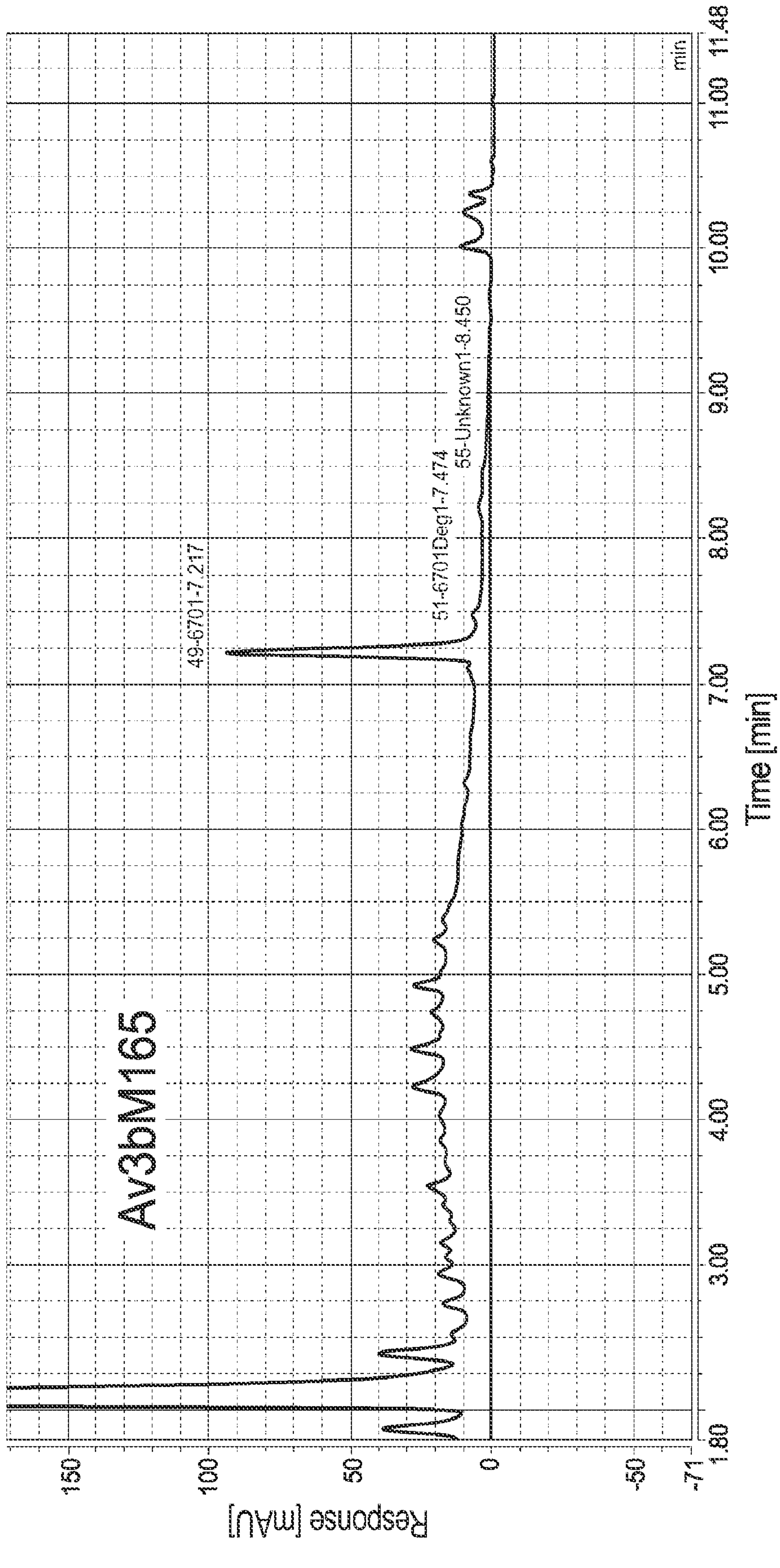
FIG. 55 shows an HPLC chromatogram for the Av3b mutant, Av3bM165, from the mutant strain fermentation sample taken at 119.5 hours during the fermentation process.
Figure 56:
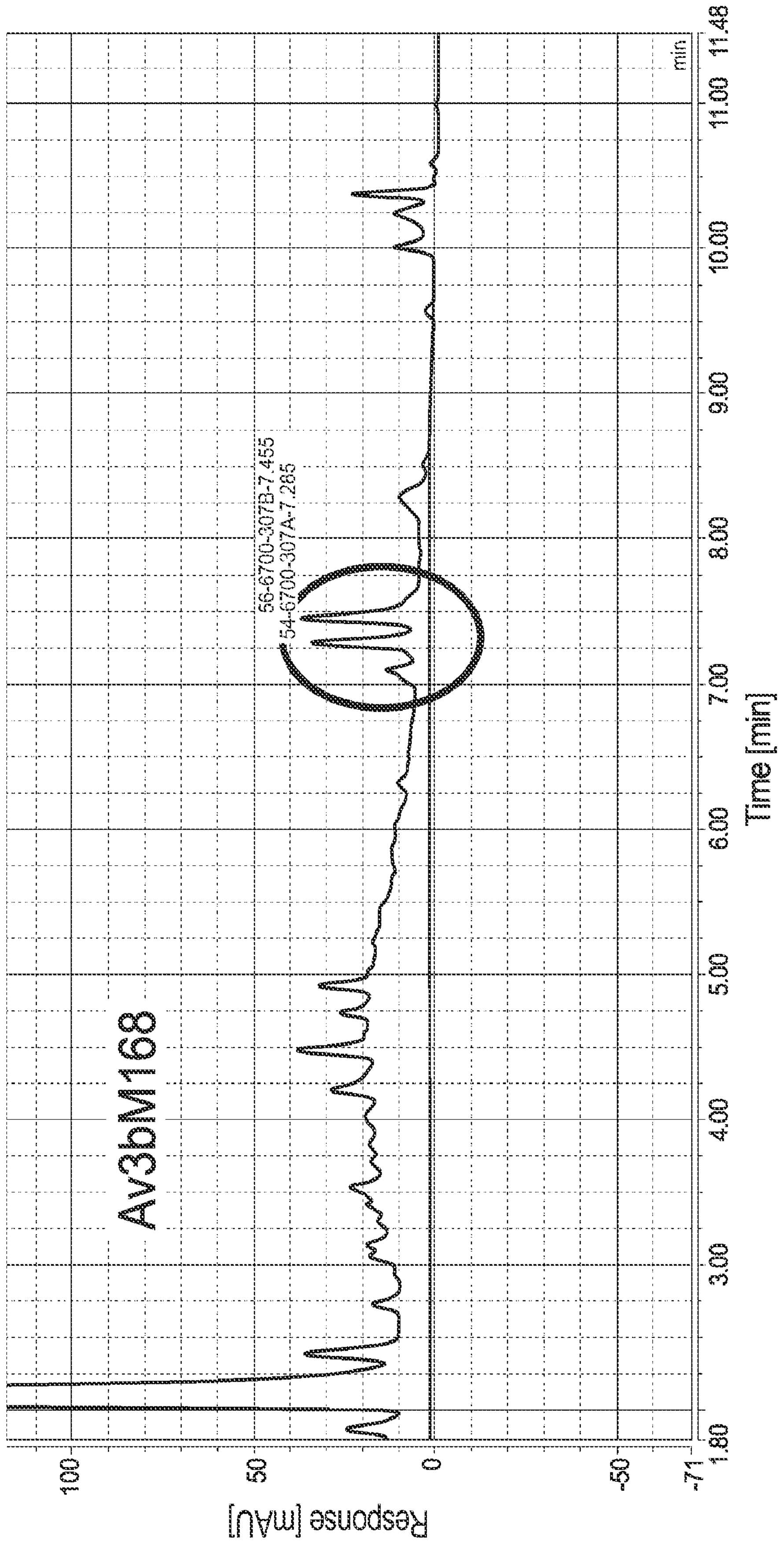
FIG. 56 shows an HPLC chromatogram for the Av3b mutant, Av3bM168, from the mutant strain fermentation sample taken at 119.5 hours during the fermentation process. The circle indicates degradation product.
Figure 57:
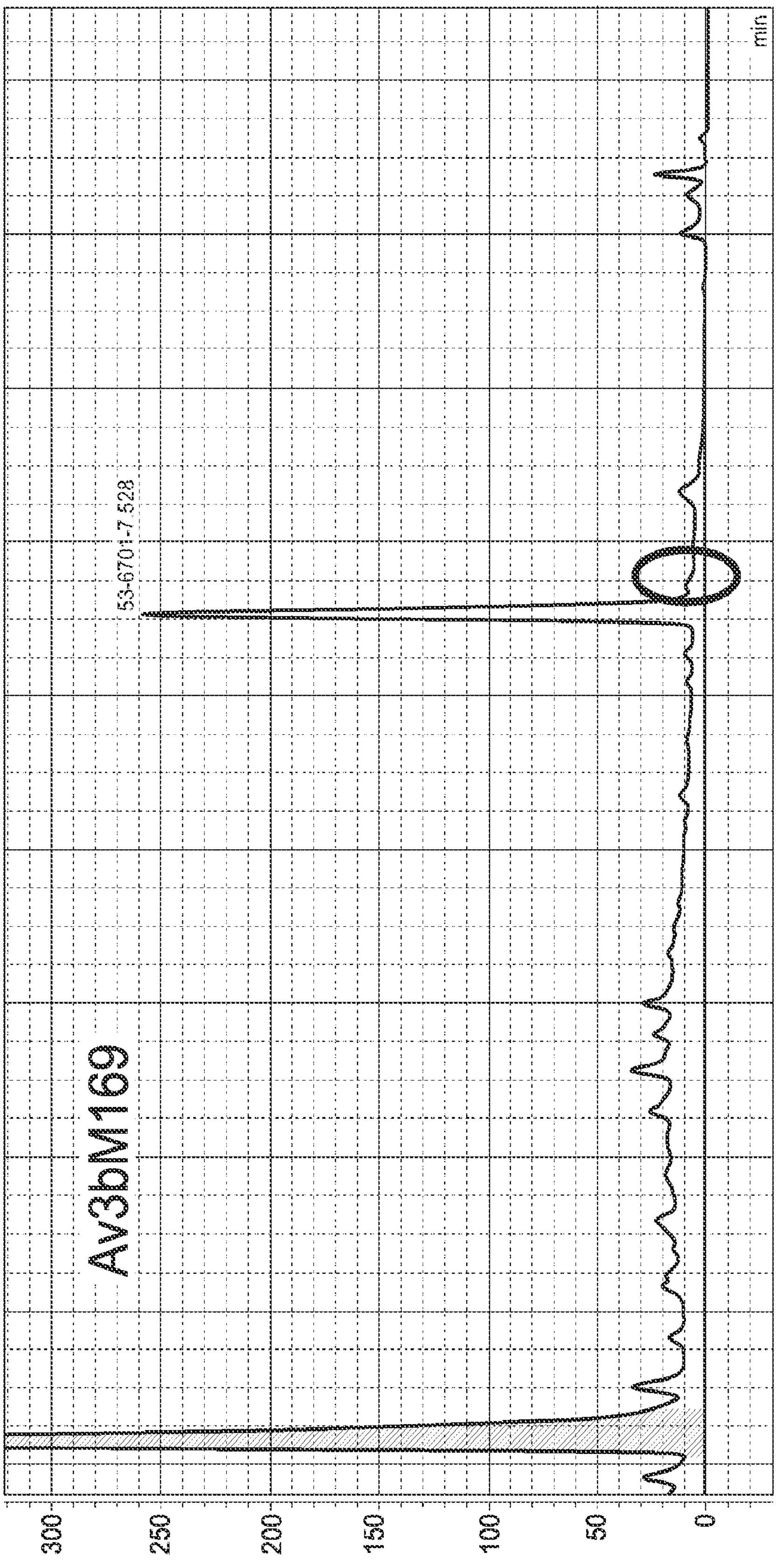
FIG. 57 shows an HPLC chromatogram for the Av3b mutant, Av3bM169, from the mutant strain fermentation sample taken at 119.5 hours during the fermentation process. The circle indicates degradation product.
Figure 58:
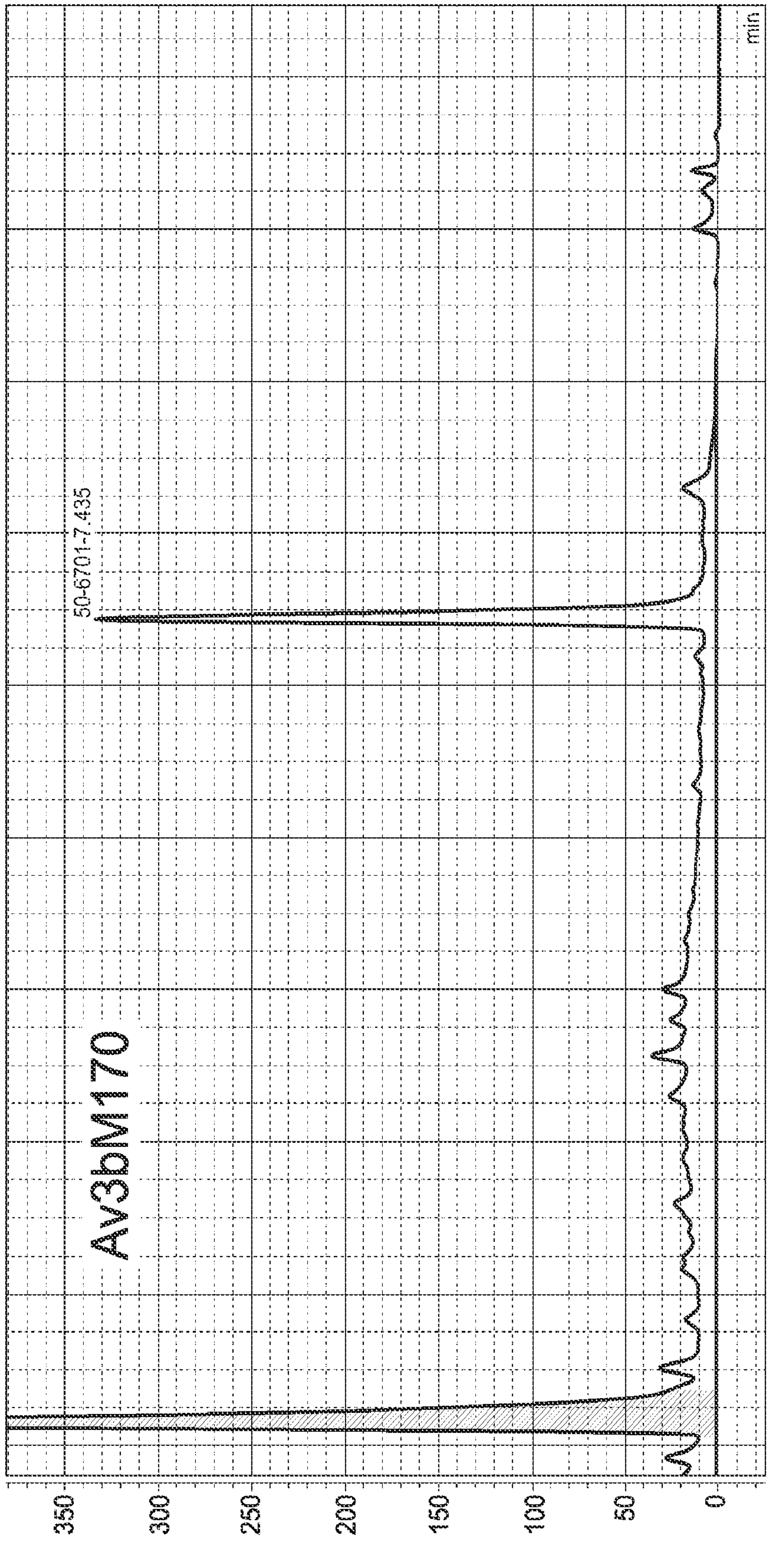
FIG. 58 shows an HPLC chromatogram for the Av3b mutant, Av3bM170, from the mutant strain fermentation sample taken at 119.5 hours during the fermentation process.
Figure 59:
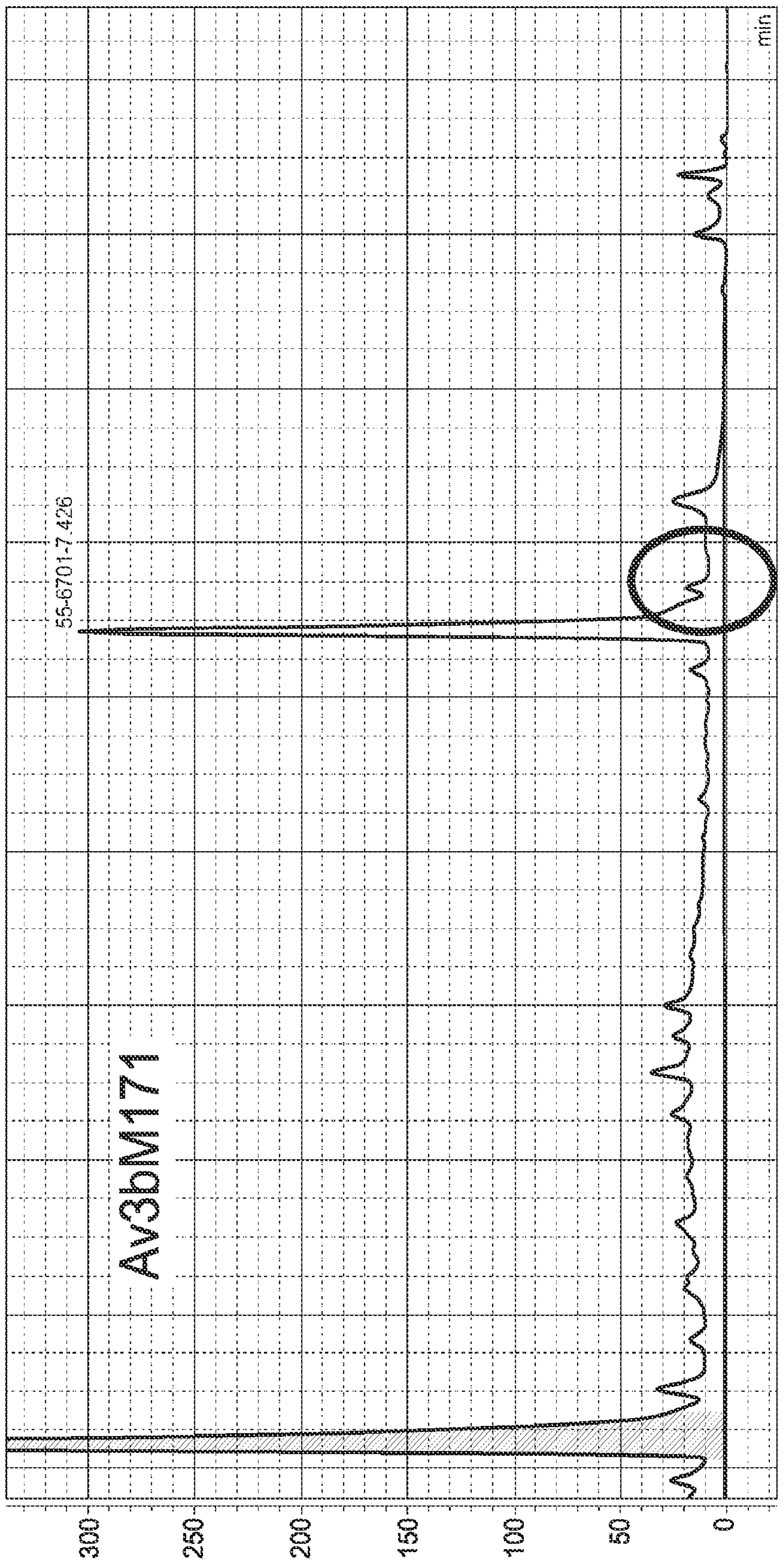
FIG. 59 shows an HPLC chromatogram for the Av3b mutant, Av3bM171, from the mutant strain fermentation sample taken at 119.5 hours during the fermentation process. The circle indicates degradation product.
Figure 60:
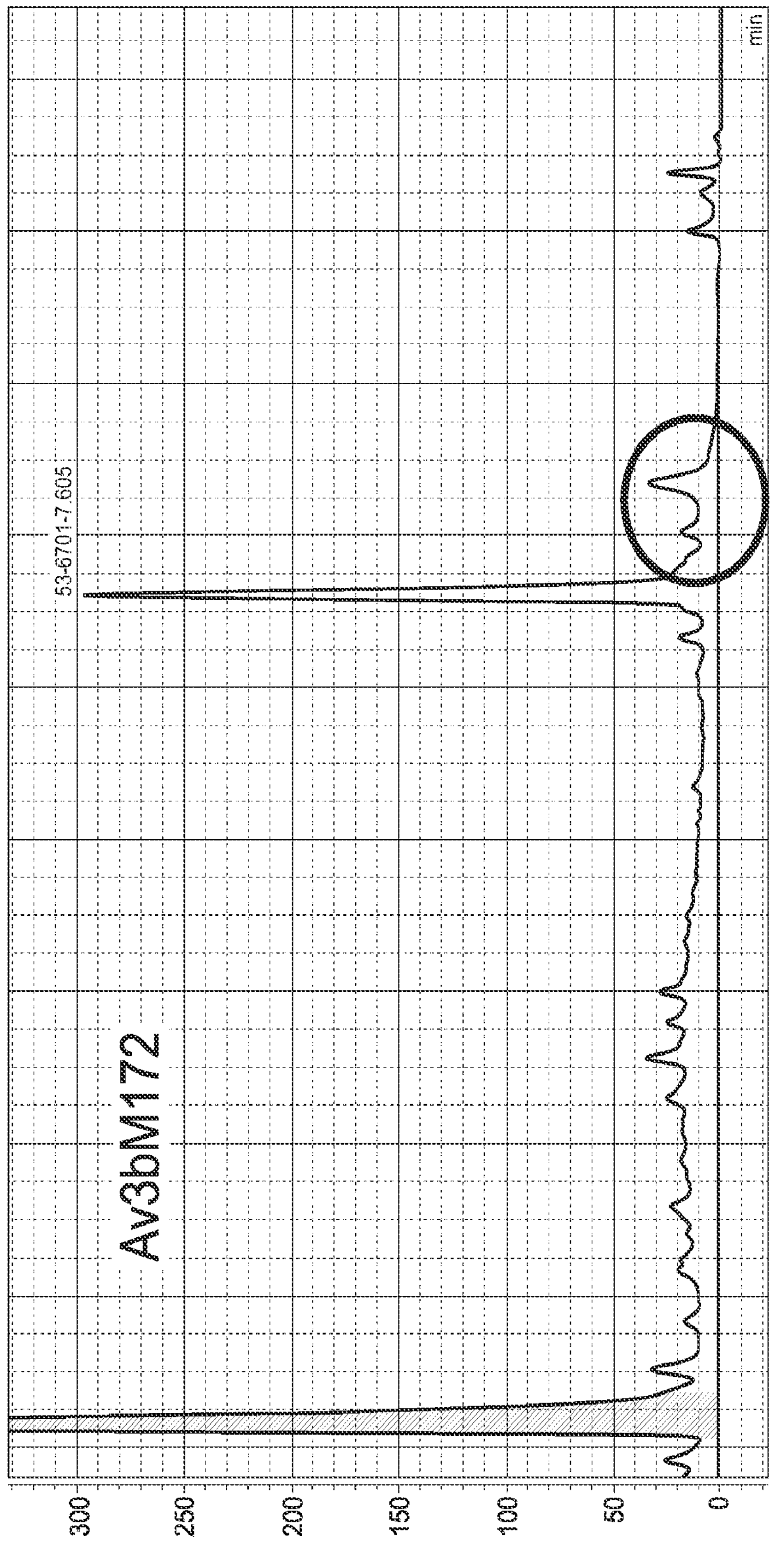
FIG. 60 shows an HPLC chromatogram for the Av3b mutant, Av3bM172, from the mutant strain fermentation sample taken at 119.5 hours during the fermentation process. The circle indicates degradation product.

FIG. 40 shows a graph showing the stability of Av3bM125 in Av3b fermentation beer, at room temperature and pH 6.5. The first set of bar graphs shows that Av3b was stable in pH 4 buffer. The second set of bar graphs show the Av3b control. The third set of bar graphs show Av3bM125. Each bar corresponds to a time, from left to right, 0-, 18-, 42-, 76-, 112-, and 164-hours.

The results shown in the foregoing figures indicates that there is a possible static-electrical interaction between position 23 and 26 in the Av3b sequence.

Example 13. Proteolytic Resistance of Av3b Mutants in Fermentation Conditions Based upon the MS/MS data obtained from the Av3b strain fermentation beer (shown above), prb1 and prc1 were identified as the likely carboxylproteases responsible for the degradation of Av3b peptide secreted from the cells. Therefore, a Av3b expression strain with prb1/prc1 knock-out background was generated to prevent the Av3b degradation during fermentation. However, as shown above, fermentation with the prb1/prc1 knock-out Av3b expression strain revealed that degradation of Av3b was reduced but not totally prevented, indicating that in addition to prb1 and prc1, other unidentified carboxylproteases may also be involved.

And, while the mutations in Av3bM19 and Av3bM24 both dramatically slowed their degradation in fermentation beer, degradation did occur eventually; accordingly, additional mutations were implemented to determine if resistance to degradation could be further improved upon.

The mutants in the table below were evaluated for stability in fermentation beer. Fermentation conditions and HPLC analysis were performed as described above. The mutant production strains were generated using YCT306 *K. lactis* strain. The production of mutants was performed as described in Example 2; fermentation conditions were performed using the same fermentation process described above regarding the Av3b production strain, with pH control at pH 6.5. In the fermentation conditions described here, Av3b peptide showed degradation during fermentation, resulting in extra HPLC peaks after the anticipated Av3b peak. See FIGS. 12 and 13. To identify the mutant with proteolytic resistance, the mutant strains were grown under the same fermentation conditions as Av3b, and samples were taken throughout the fermentation process. The samples taken at 140 hour of fermentation process were analyzed in rpHPLC.

TABLE 9

Av3b mutants evaluated in fermentation beer stability study. Av3b mutants with names shown in bold did not show degradation after incubation in Av3b fermentation beer following incubation for 140 hours.

| Name | Sequence | SEQ ID NO | Degradation? |
|---|---|---|---|
| Av3bM97 | KSCCPCYWGGCPWGQNCYPEGCSGPA | 41 | Yes |
| Av3bM98 | KSCCPCYWGGCPWGQNCYPEGCSGPR | 42 | No |
| Av3bM99 | KSCCPCYWGGCPWGQNCYPEGCSGPN | 43 | Yes |
| Av3bM100 | KSCCPCYWGGCPWGQNCYPEGCSGPD | 44 | Yes |
| Av3bM101 | KSCCPCYWGGCPWGQNCYPEGCSGPE | 45 | Yes |
| Av3bM102 | KSCCPCYWGGCPWGQNCYPEGCSGPQ | 46 | Yes |
| Av3bM103 | KSCCPCYWGGCPWGQNCYPEGCSGPG | 36 | No |
| Av3bM104 | KSCCPCYWGGCPWGQNCYPEGCSGPH | 47 | Yes |
| Av3bM111 | KSCCPCYWGGCPWGQNCYPEGCSGPT | 48 | Yes |
| Av3bM146 | KSCCPCYWGGCPWGQNCYPEGCSGGV | 49 | Yes |
| Av3bM147 | KSCCPCYWGGCPWGQNCYPEGCSGRV | 50 | Yes |
| Av3bM148 | KSCCPCYWGGCPWGQNCYPEGCSGPKG | 51 | No |
| Av3bM156 | KSCCPCYWGGCPWGQNCYPEGCDGPA | 52 | Yes |
| Av3bM157 | KSCCPCYWGGCPWGQNCYPEGCDGPT | 53 | Yes |
| Av3bM165 | KSCCPCYWGGCPWGQNCYPEGCSGPKVG | 40 | No |
| Av3bM168 | KSCCPCYWGGCPWGQNCYPEGCSGPKVI | 54 | Yes |
| Av3bM169 | KSCCPCYWGGCPWGQNCYPEGCTGPG | 37 | Yes |
| Av3bM170 | KSCCPCYWGGCPWGQNCYPEGCGGPG | 38 | No |

TABLE 9-continued

Av3b mutants evaluated in fermentation beer stability study. Av3b mutants with names shown in bold did not show degradation after incubation in Av3b fermentation beer following incubation for 140 hours.

| Name | Sequence | SEQ ID NO | Degradation? |
|---|---|---|---|
| Av3bM171 | KSCCPCYWGGCPWGQNCYPEGCDGPG | 55 | Yes |
| Av3bM172 | KSCCPCYWGGCPWGQNCYPEGCDGP | 56 | Yes |

The HPLC chromatograms showing the results of the fermentation stability for the mutants listed in the table above are shown in FIGS. 41-60. As shown in the foregoing figures, the mutants Av3bM98, Av3bM103, Av3bM148, Av3bM165, and Av3bM170 did not show any degradation product.

Example 14. C-Terminal Glycine Mutants Protect from Degradation

Mutation of the C-terminal residue to Glycine of Av3b was found to provide protection from C-terminal cleavage during fermentation. The three Av3b mutants with C-terminal mutations of K26G were found to prevent degradation, i.e., Av3bM103, having the amino acid sequence: KSCCPCYWGGCPWGQNCYPEGCSGPG (SEQ ID NO: 36);

Av3bM169, having the amino acid sequence:

(SEQ ID NO: 37)
KSCCPCYWGGCPWGQNCYPEGCTGPG

Av3bM170, having the amino acid sequence:

(SEQ ID NO: 38)
KSCCPCYWGGCPWGQNCYPEGCGGPG

In addition, the mutant Av3bM148, with a V27G mutation, and having an amino acid sequence of: KSCCPCYWGGCPWGQNCYPEGCSGPKG (SEQ ID NO: 39), along with mutant Av3bM165, which has an addition of glycine to the C-terminus, and having an amino acid sequence of: KSCCPCYWGGCPWGQNCY-PEGCSGPKVG (SEQ ID NO: 40), also were shown to have HPLC peaks without apparent degradation products. See FIGS. 47, 55, 57, and 58.

Example 15. Strain Yield Comparison

The foregoing experiments led to four candidate Av3b mutant peptides: Av3bM24; Av3bM165; Av3bM103; and Av3bM170. A deep-well plate culture was performed as described below, to compare and rank the yield of the abovementioned candidates. The deep-well plate culture was performed as follows: a sterile 48-well 5 mL conical bottom deep-well plate was prepared in a biosafety hood. Next, 2.2 mL of culture medium was pipetted into every well of culture plate. A single colony from a yeast strain agar plate was picked using a 200 µL pipette tip and inoculated into the medium in one well of the plate until all wells are inoculated. Then the inoculated plate was sealed with a breathable seal and placed into a shaker at 250 rpm at 23.5° C. for 6 days, or 27° C. for 4 days, for peptide yield evaluation.

The results of the deep-well culture are presented in the table below.

TABLE 10

Deep-well culture comparing yields of Av3b mutants. The fermentation yield is the predicted yield in fermentation conditions based on the results from the glycerol stock yield.

| Name | Glycerol Stock Yield | Fermentation yield (g/L) | 12-gene copy yield (g/L) |
|---|---|---|---|
| Av3b | 100% | 1.2 | 1.2 |
| Av3bM24 | 109% | 1.3 | 1.2 |
| Av3bM165 | 24% | 0.3 | 0.395 |
| Av3bM103 | 84% | 1.0 | 0.476 |
| Av3bM170 | 95% | 1.14 | 0.938 |

Figure 61:
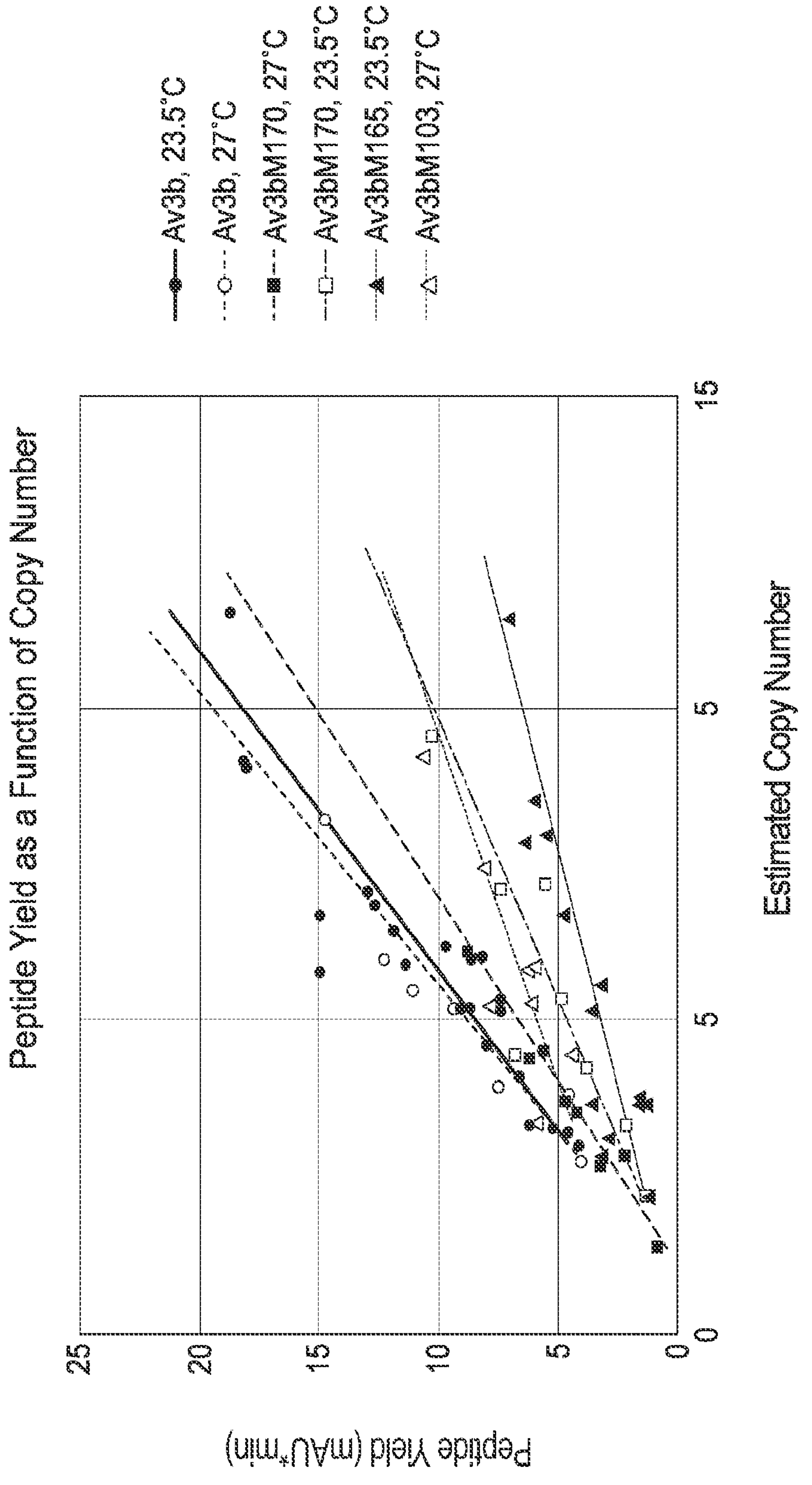
FIG. 61 shows a graph illustrating the peptide yield as it relates to copy number of the Av3b peptide transgene integrated into the expression strain genome at two different temperatures, 23.5° C. and 27° C., which can better predict the yield from new peptide strain by yield per integrated peptide gene. The yield was calculated by making a linear fitting curve, and extending the fitting curve to the point of 12 integrated gene copies.

FIG. 61 shows a graph illustrating the peptide yield as it relates to copy number of the Av3b peptide transgene integrated into the expression strain genome from the 48-well deep well plate cultures at two different temperatures, 23.5° C. and 27° C., which may better predict the yield from new peptide strain by yield per integrated peptide gene. The yield was calculated by making a linear fitting curve, and extending the fitting curve to the point of 12 integrated gene copies, as indicated in Table 10.

Regarding the 12-gene copy yield results, multiple transformant colonies from each strain were analyzed for yield and integrated gene copy. Because different colonies from the same transformation plate contain different number of integrated Av3 mutant gene copy, a relation between the yield and gene copy could be generated. A linear relationship between the yield and integrated gene copy number was observed in the range of integrated gene copy number from 1 to 12, such that the more gene copies integrated into the cell genome, the more yield could be observed. Thus, the linear relation of each strain can be extended to 12 integration gene copy, which is the integrated Av3b gene copy number in our current Av3b production strain and can be achieved for the mutants strains by colony screening, in order to find out what the theoretic yield is when the mutant production strains have 12 integrated gene copy in the genome; here, all mutant strain yields were normalized to the Av3b strain yield to produce a yield ratio of Av3b mutant over Av3b. In fermentation, the routine average yield for the Av3b strain was 1.2 g/L: therefore the mutant strain yield was estimated using the 1.2 g/L yield ratio.

As shown here, with the exception of Av3bM165, the yields of the Av3b mutants had comparable yields to the original Av3b strain.

Example 16. DASbox Fermentation

DASbox® is a parallel bioreactor system (Eppendorf, 175 Freshwater Blvd, Enfield, CT 06082, USA). The DASbox system used here contains 8 fermentation vessels with 250 mL volume capacity, allowing 8 small scale fermentation runs simultaneously. The DASbox fermentation runs were performed according to the manufacturer's instructions, and using the fermentation conditions described herein.

The screening of the Av3b mutants was conducted using a fed batch process in aerobic bioreactor. Reactors were initially filled to ~45% capacity with a rich culture media containing 5-20 g/L of a carbon source such as glucose, sorbitol, or lactose, 5-20 g/L phosphoric acid, 0.1-1.5 g/L Calcium sulfate, 5-15 g/L Potassium sulfate, 0.5-10 g/L Magnesium sulfate heptahydrate, 1-5 g/L potassium hydroxide, and 10-60 g/L of corn steep liquor. The temperature of the reactor was maintained between 25-35° C. for the duration of the fermentation. The pH was held constant between 4-5.5 with the addition of 15% ammonium hydroxide. Dissolved oxygen was held constant by sparging air between 0.5-1.5 volume/volume/min and by increasing agitation to maintain a set point of 10-30%.

Inoculation of the reactor was from an overnight seed culture containing 5-40 g/L of a carbon source such as glucose, sorbitol, or lactose, and 5-40 g/L of corn steep liquor. Inoculation percentage ranged from 5-20% of initial fill volume. Once inoculated, the reactor was fed with a 70% solution of the selected carbon source until the reactor was filled and/or desired supernatant peptide concentration was achieved, approximately 96-140 hours and 0.8-1.2 g/L, respectively.

Figure 62:
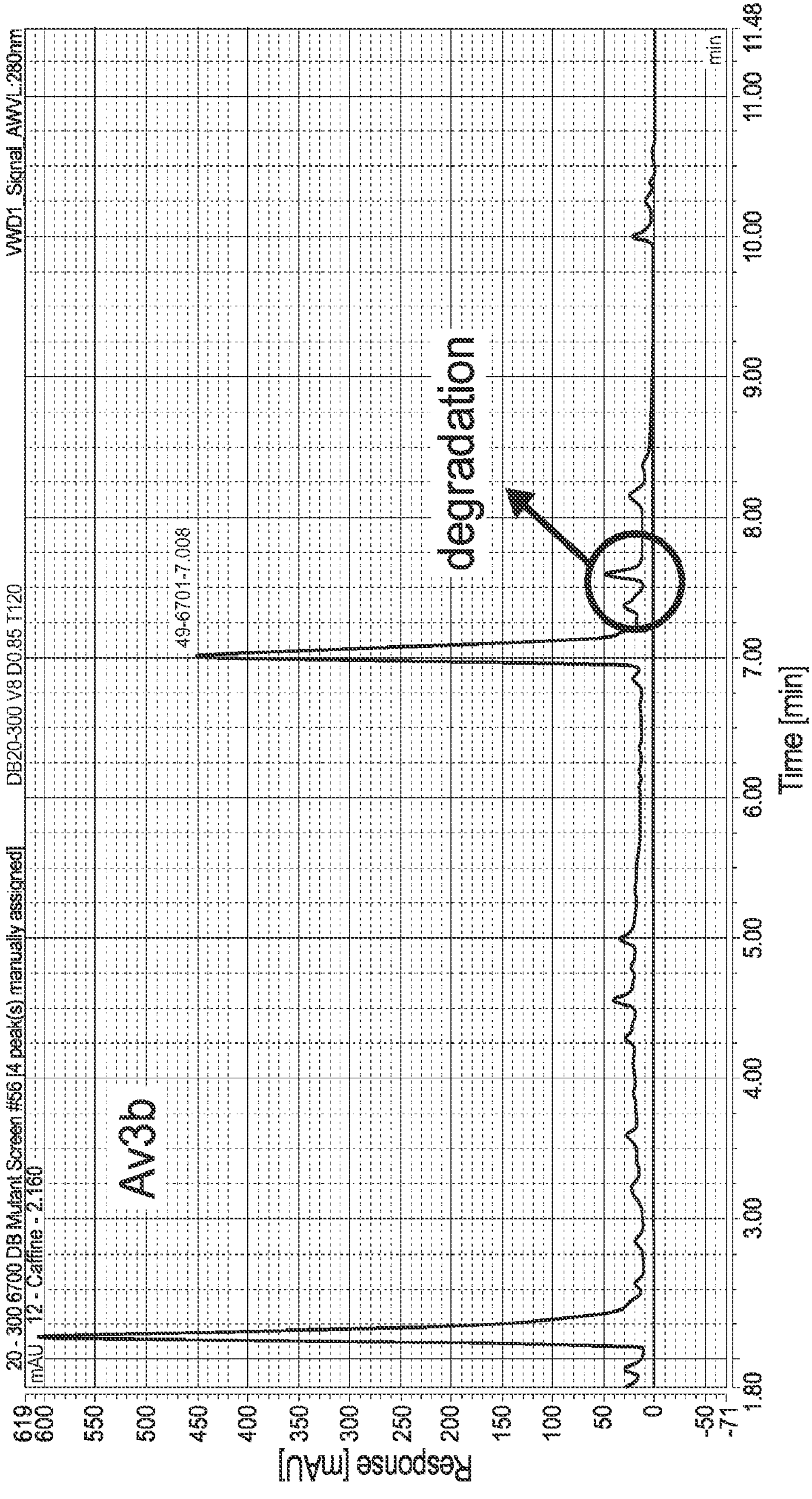
FIG. 62 shows an HPLC chromatogram for the Av3b expression strain, pKS022-YCT-38-14. incubated in a small-scale fermentation run.
Figure 63:
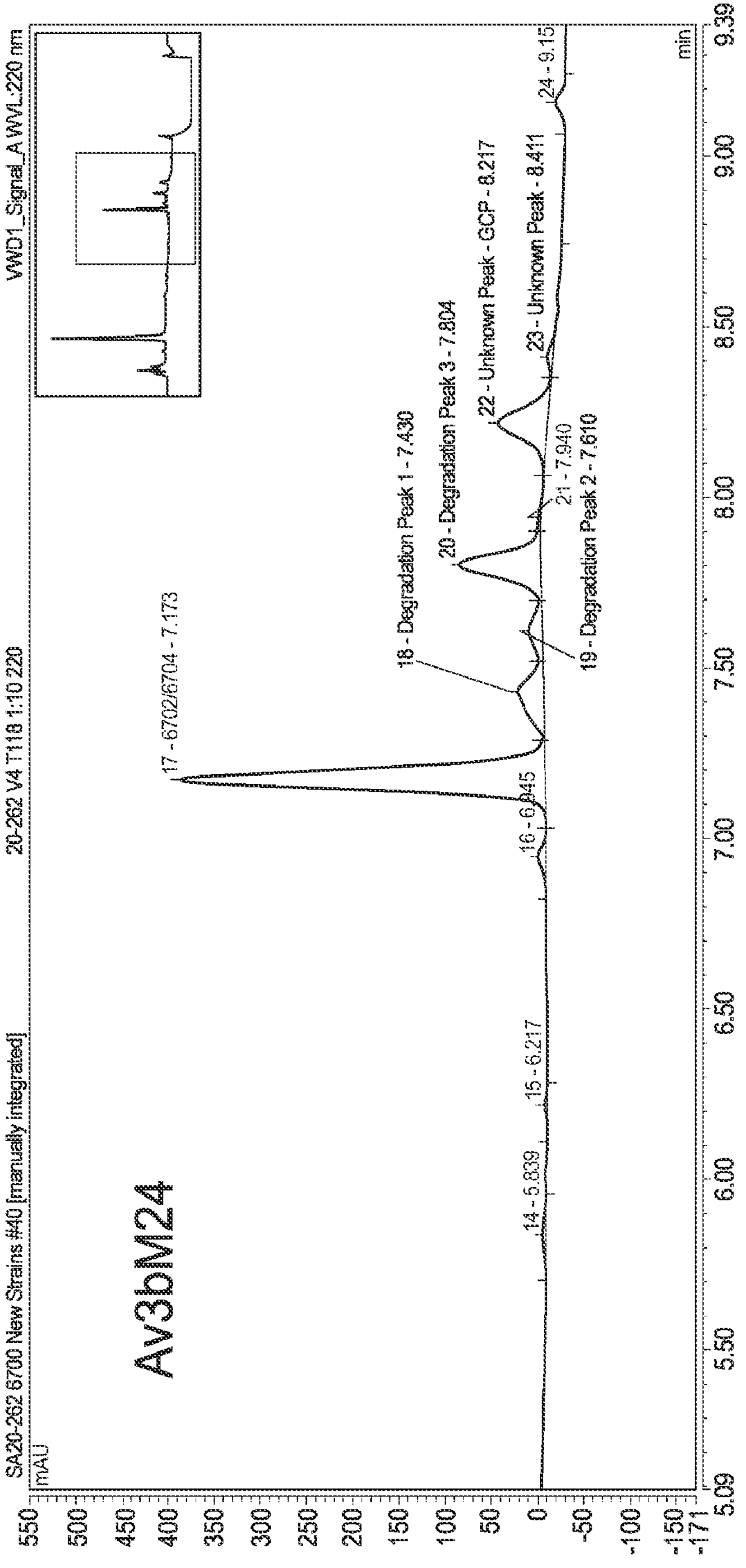
FIG. 63 shows an HPLC chromatogram for the Av3bM24 mutant strain incubated in a small-scale fermentation run.

Following the fermentation runs, degradation was detected in the Av3b and Av3bM24 strains via HPLC and LC/MS. FIGS. 62-63.

Figure 64:
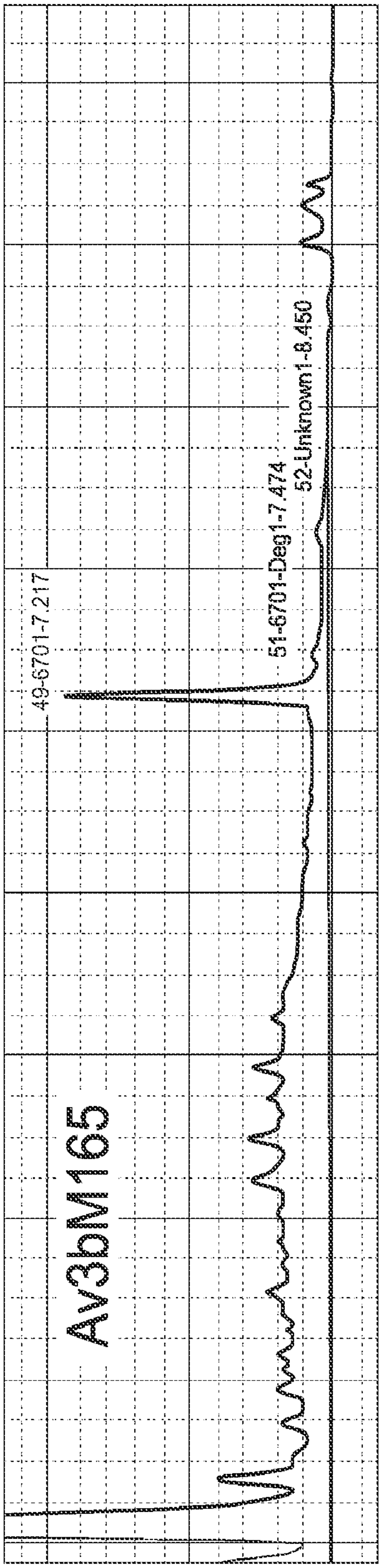
FIG. 64 shows an HPLC chromatogram for the Av3bM165 mutant strain incubated in a small-scale fermentation run.
Figure 65:
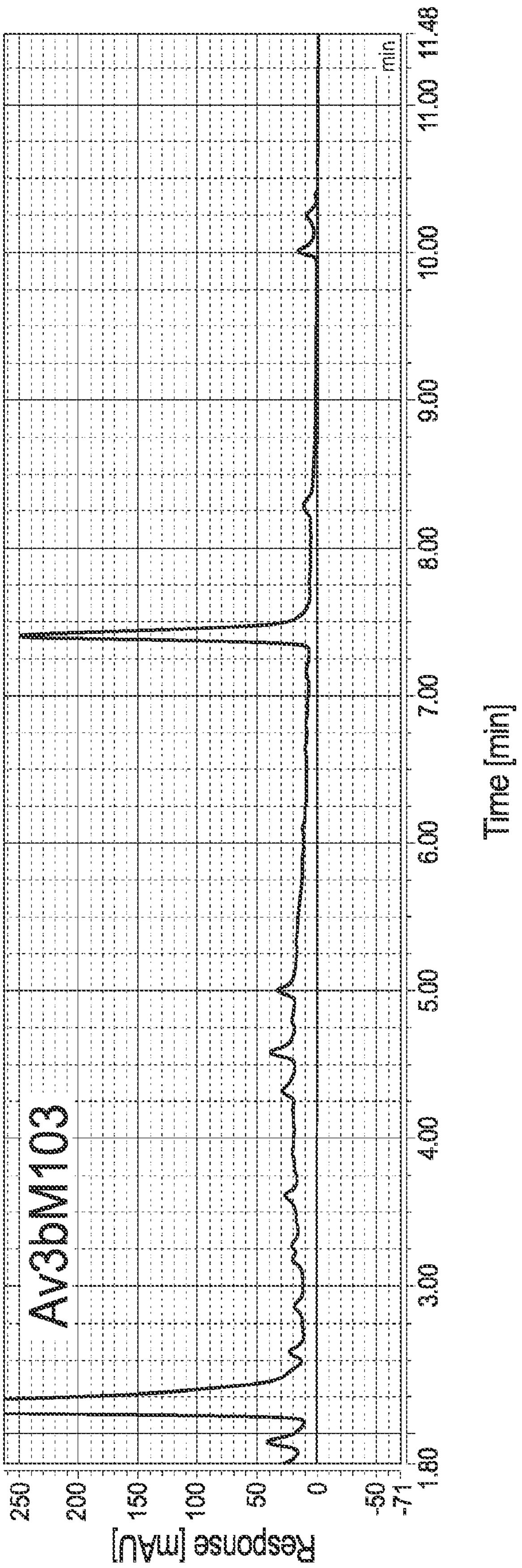
FIG. 65 shows an HPLC chromatogram for the Av3bM103 mutant strain incubated in a small-scale fermentation run.
Figure 66:
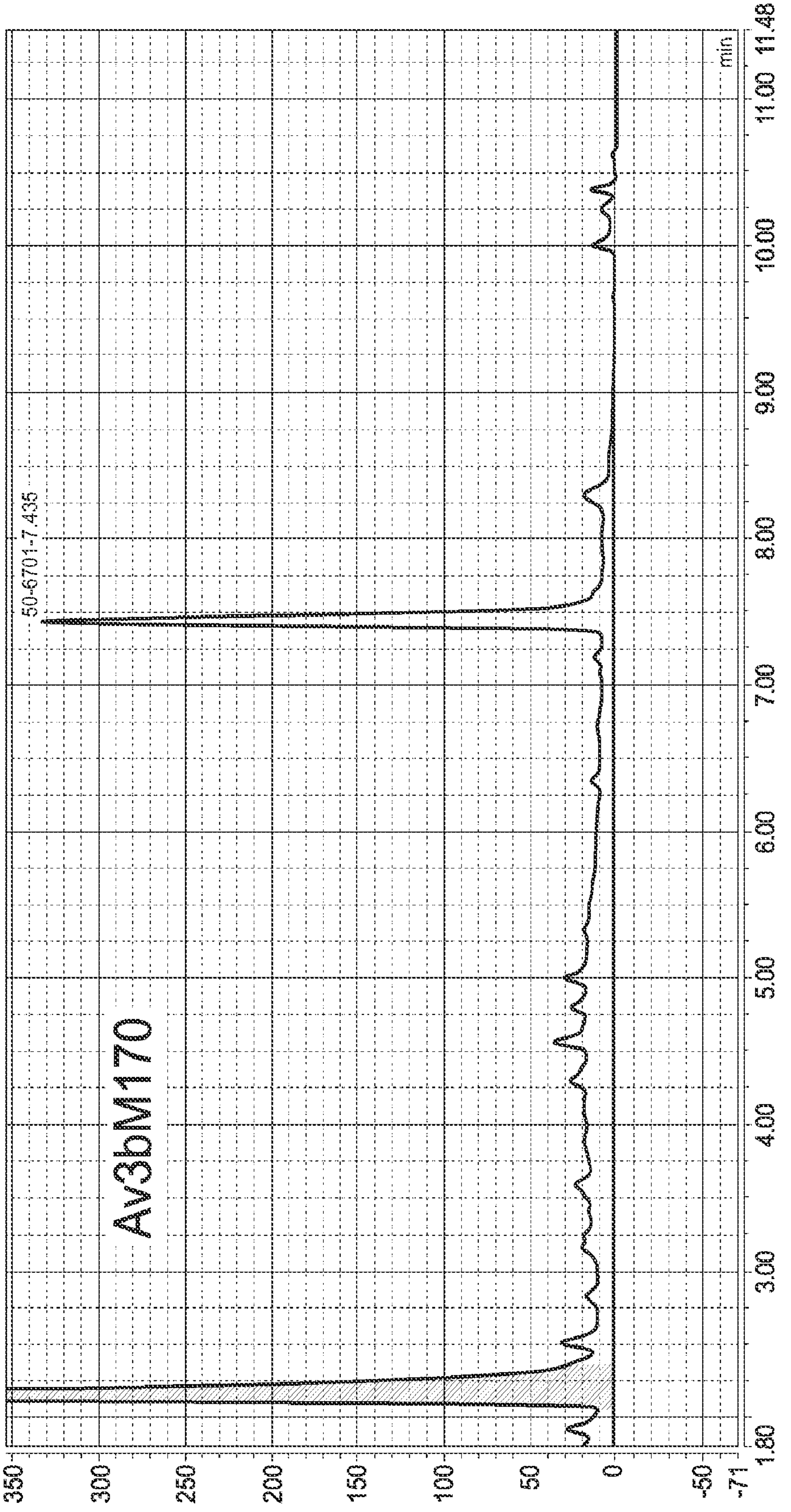
FIG. 66 shows an HPLC chromatogram for the Av3bM170 mutant strain incubated in a small-scale fermentation run.

However, degradation was not detected in the Av3bM165, Av3bM103 and Av3bM170 strains via HPLC and LC/MS. FIGS. 64-66.

Example 17. Lepidoptera Injection Assay

An injection assay was performed on *Helicoverpa zea* (corn earworm or "CEW") and *Spodoptera frugiperda* (fall armyworm or "FAW"). Injections comprised a given Av3b mutant peptide combined with water to arrive at the planned dose. The Av3b mutants included Av3bM24; Av3bM165; Av3bM103; and Av3bM170. Av3b was used as a control.

Dose calculations were made using the following formula:

$$\frac{\text{pmol}}{\text{g}} = \frac{(\text{peptide solution, ppm})(\text{injection volume, }\mu\text{L})}{(\text{insect mass, mg})(\text{peptide mol weight})} \times 10^6 \quad \text{Formula (IV)}$$

Insects were reared on an artificial diet prepared from General Purpose Lepidoptera diet (Frontier Scientific, Newark, DE 19713, product No. F9772) according to the manufacturer's instructions. To perform the insect injection bioassay, 5 mL of hot diet was dispensed into the well of a rearing tray (Bio-Service Inc., Bio-RT-32), with 8 wells per injection treatment. The hot diet was then allowed to cool and solidify. Next, third instar larva were incubated on ice in order to immobilize them. Injections were prepared on a hand-microapplicator with injection solution (>100 μL) in 1-cc all-glass syringe having a 30 gauge straight needle. Air bubbles were removed from the syringe, and the syringe was set it up on the microapplicator. Injection volume was adjusted in the microapplicator at 2 μL.

To inject the larva, the insects were picked up and positioned close to the injection needle. The needle was allowed to penetrate the cuticle of the third pro-leg of the larva. The injection knob of the microapplicator was then rotated to inject a 2 μL solution into hemolymph from the third pro-leg. After injection the larva maintained on the needle for a few seconds to make sure the injected solution was absorbed. Then, the larva were gently removed from the needle and placed into the wells of prepared tray, along with 5 mL of solidified diet per well. Finally, the tray was sealed with vent covers.

Injected larva were incubated at 28° C. in an insect incubator, and scored at 24-hours post-injection based on their condition. Insect conditions were categorized as follows: alive (walking, eating, normal behavior); affected (showing toxic symptoms, such as tremors, writhing, unbalanced gait, or a combination thereof), knockdown (paralyzed albeit able to move with gentle poke); and dead (unmoving, discoloration, or a combination thereof). The $KD_{50}$ results of the injection assay are provided in the table below.

TABLE 11

Results of lepidopteran injection assay.

| Name | $KD_{50}$ in pmol/g CEW | $KD_{50}$ in pmol/g FAW |
|---|---|---|
| Av3b | 367 ± 166 (N = 6) | 883 ± 25 (N = 2) |
| Av3bM24 | 428 ± 131 (N = 4) | 949 |
| Av3bM165 | 389 | 578 |
| Av3bM103 | 518 ± 390 (N = 2) | 879 |
| Av3bM170 | 104 | 495 ± 148 (N = 2) |

As shown by the $KD_{50}$ results in the table above, Av3bM24; Av3bM165; and Av3bM103 had comparable knock-down effects to Av3b. However, Av3bM170 required a much lower dose of 104 μmol/g and 495±148 μmol/g in CEW and FAW, respectively.

Example 18. Circular Dichroism Assay

Circular Dichroism (CD) is an absorption spectroscopy method. CD employs the differential absorption of left and right circularly polarized light. The spectrum obtained due to this phenomenon is called CD spectrum in which the CD signal is represented in terms of millidegrees (mdeg).

An optically active chiral molecule will absorb one direction of the circularly polarized light in a preferential manner; and, the difference in this absorption—i.e., of the left or right circularly polarized light—can be measured and quantified. Ultraviolet (UV) CD can be used to determine aspects of protein secondary structures, e.g., alpha-helix, beta-sheet, random coil, etc. For example, one of the most widely used applications of CD is to evaluate whether a protein is folded correctly, and/or whether a given mutation affects that protein's stability or conformation. See N. Greenfield, Using circular dichroism spectra to estimate protein secondary structure, Nat Protoc. 2006; 1(6): 2876-2890.

A JASCO J-1500 CD spectrometer (JASCO, 28600 Mary's Court, Easton, MD 21601 USA) was used to measure the CD spectrum and the secondary structure information of the Av3bM24, Av3bM165, Av3bM103, and Av3bM170 peptides (with Av3b as a comparator). The peptides were prepared in 10 mM $Na_3PO_4$ solution, pH 5.9, and loaded into the cuvette for CD spectrum measurement. Measurements were processed with a light wavelength scan ranging from 180 nm to 250 nm, with a 1 nm interval; the temperature graduate changed from 20° C. to 98° C., with 2° C. interval.

Figure 67:
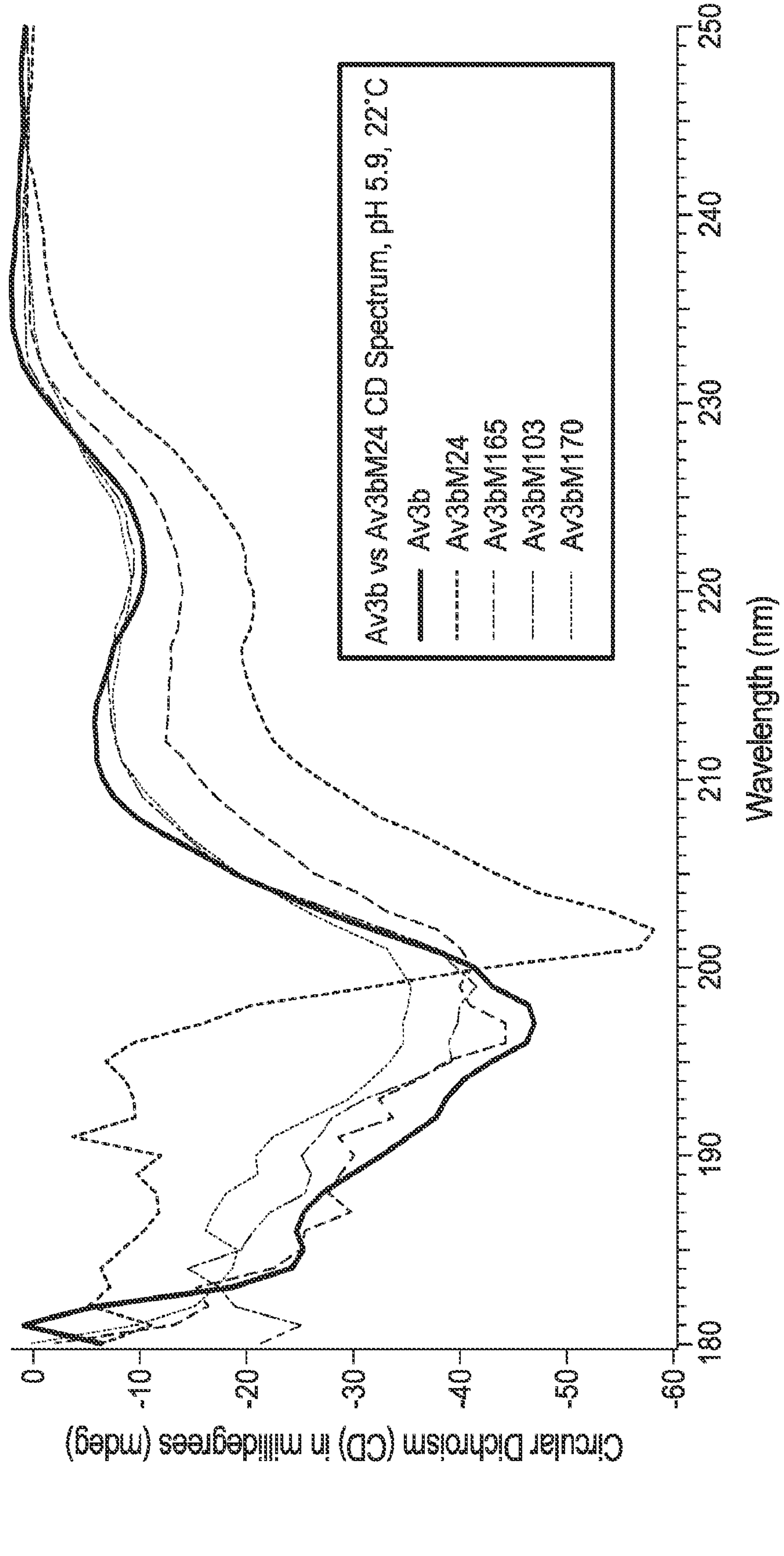
FIG. 67 depicts the results of a Circular Dichroism (CD) analysis. CD spectrum, in which the CD signal is represented, is shown in millidegrees (mdeg) on the Y-axis, which was scanned with UV light with wavelength from 180 nm to 250 nm, as shown in the X-axis.

The majority secondary structure detected for all the peptides was a random coil structure, i.e., the peptides exhibited a secondary structure with no well-known specific secondary fold pattern. FIG. 67.

All candidate peptides showed Random Coil Structure: Av3b, Av3bM165, Av3bM103 and Av3bM170 all possessed this similar random coil structure. Av3b, Av3bM165, Av3bM103 and Av3bM170 had major (−) ellipticity of around 198 nm, whereas Av3bM24 had a major (−) ellipticity around 202 nm and was narrower. FIG. 67.

The results of the CD analysis indicates that the peptides had similar folding structure. Av3bM24 also had a random coil structure, however, its structure was different from others-indicating Av3bM24 folding may occur in a slightly different from other peptides analyzed. Accordingly, the different random coil structure of Av3bM24 may explain why it is less thermostable than Av3b, Av3bM165, Av3bM103 and Av3bM170.

The CD Melting temperature of the peptides were as follows: Av3b=69.3° C.; Av3bM24=80° C.; Av3bM165=80° C.; Av3bM103=82° C.; and Av3bM170=70° C. In general, protein is not stable at higher CD melting temperature. With an increase in temperature, the interactions holding the protein structure together eventually break, causing the protein to denature. Denatured and/or proteins that are unfolded have a very different CD signal compared to the folded protein. This CD melting temperature shown here indicates the threshold temperature at which the proteins are expected to unfold. Thus, a higher CD melting temperature indicates a more thermostable protein from a structural standpoint.

Example 19. Thermo-Stability at 54° C.

Figure 68:
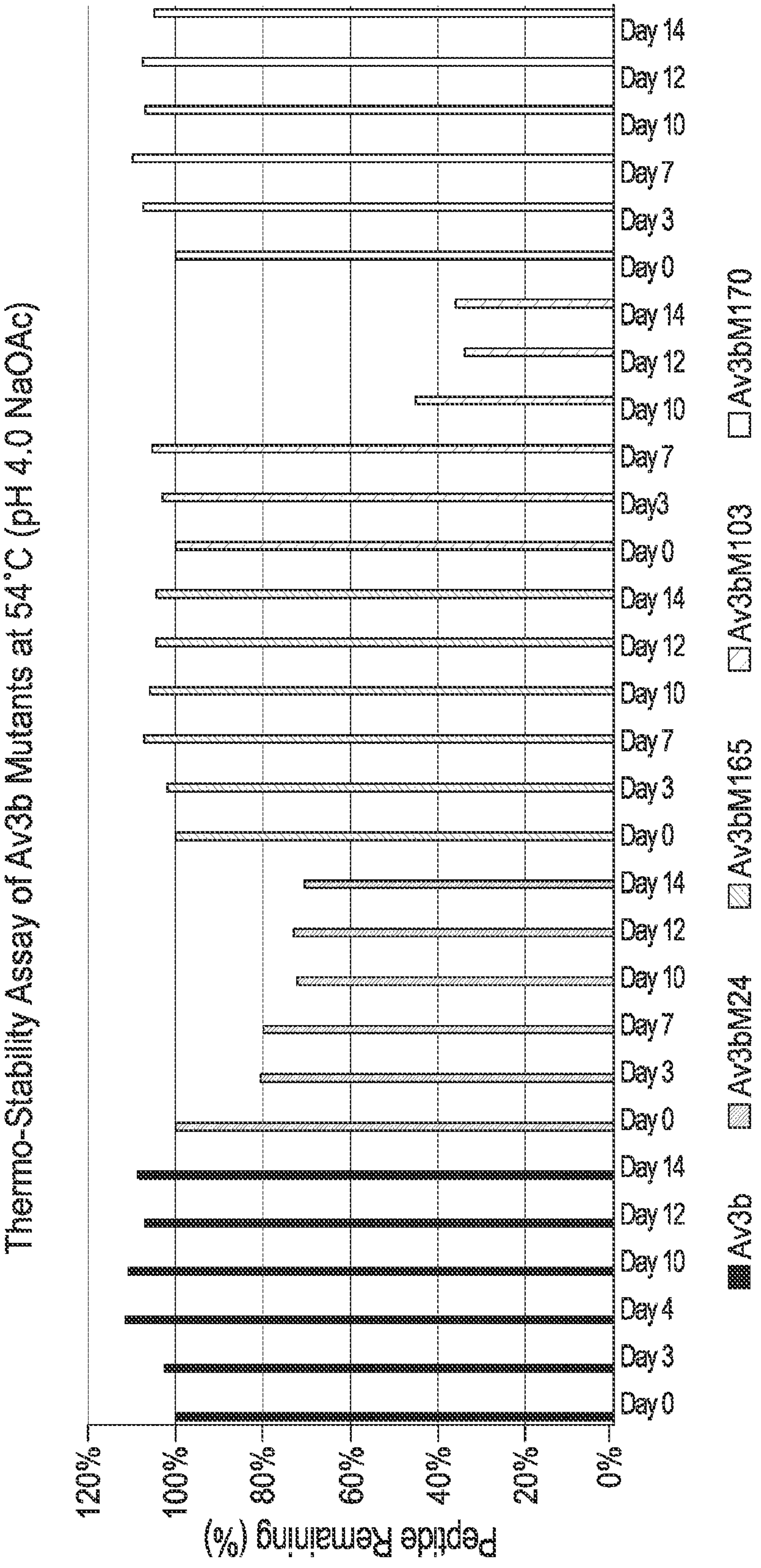
FIG. 68 depicts the results of a thermo-stability assay at 54° C. performed for Av3b, Av3bM24, Av3bM165, Av3bM103, and Av3bM170 in a pH 4.0 sodium acetate (NaOAc) buffer solution for 0, 3, 7, 10, 12, and 14 days, with a caffeine internal control to cancel variation from evaporation. Percent (%) Av3bM remaining shows the amount of peptide remaining at a given day relative to the initial amount, as measured by HPLC peak area.
Figure 69:
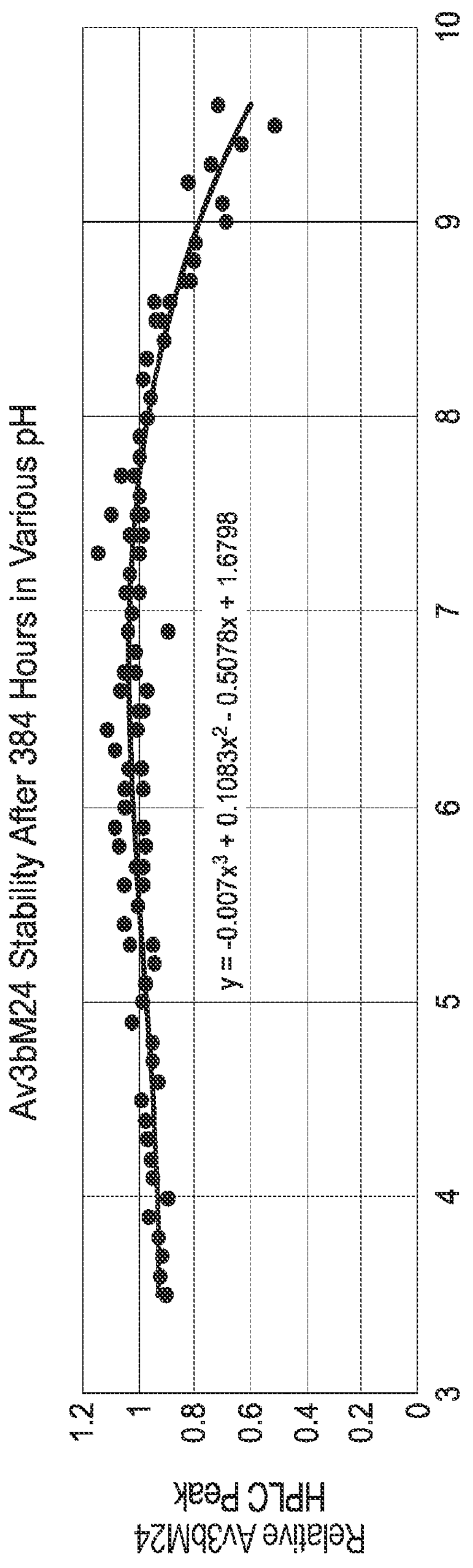
FIG. 69 shows the stability of Av3bM24 in a pH range of 3.1 to pH 9.6 after 384 hours. Here, relative peak refers to the peak area at a different time point relative to the start HPLC peak area.
Figure 70:
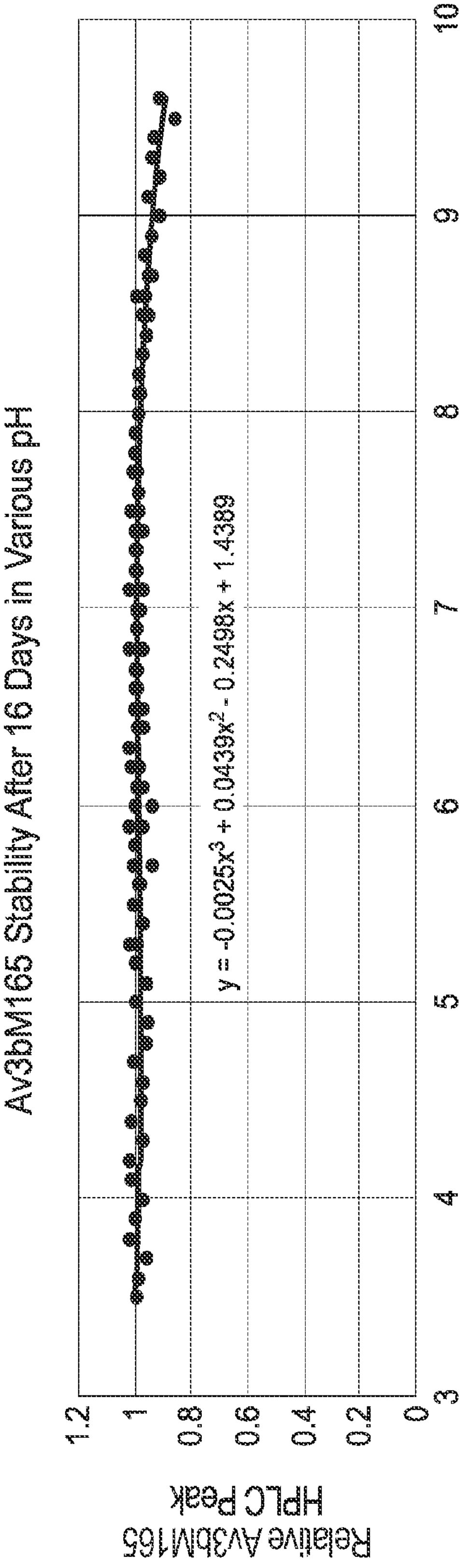
FIG. 70 shows the stability of Av3bM165 in a pH range of 3.1 to pH 9.6 after 16 days.
Figure 71:
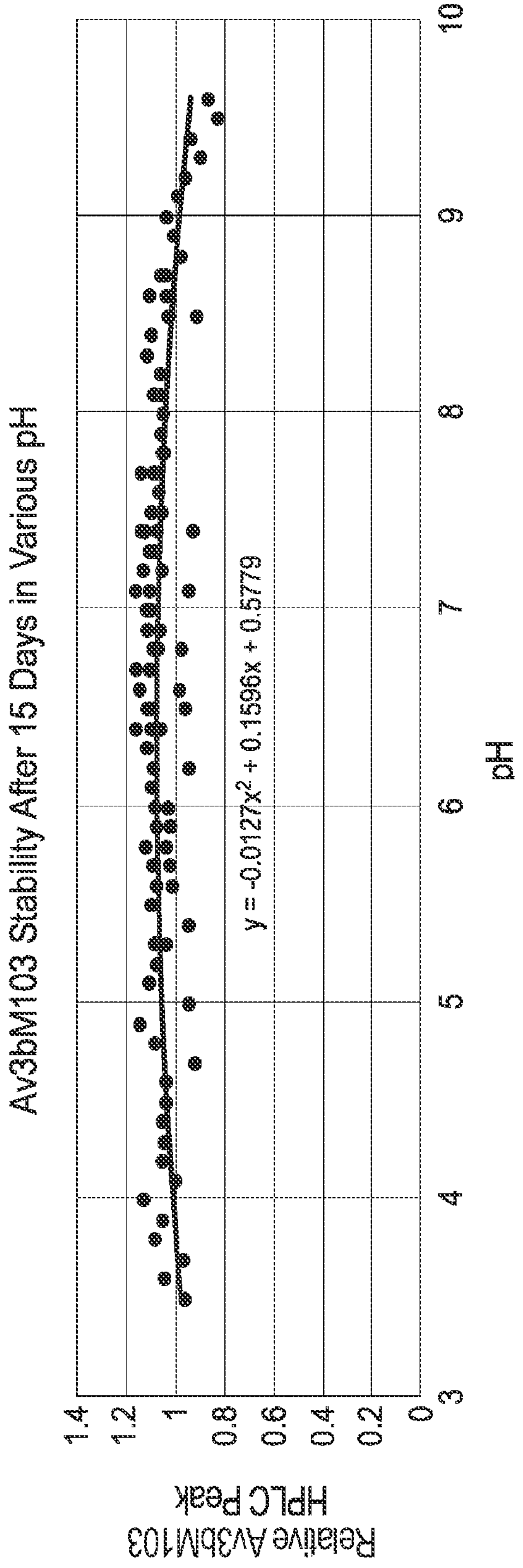
FIG. 71 shows the stability of Av3bM165 in a pH range of 3.1 to pH 9.6 after 15 days.
Figure 72:
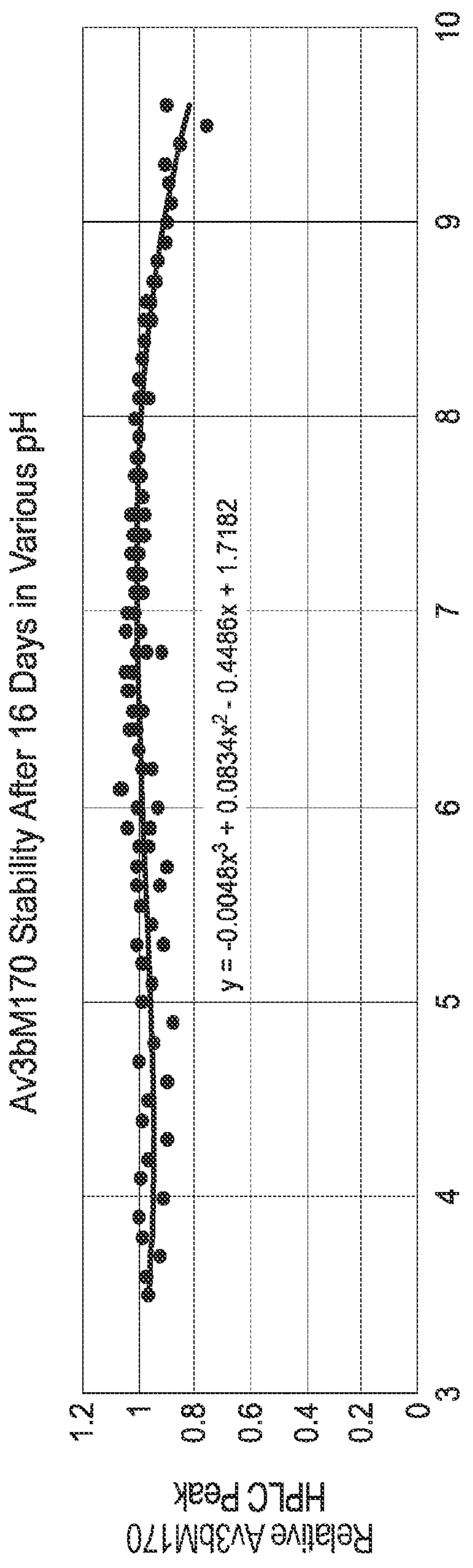
FIG. 72 shows the stability of Av3bM170 in a pH range of 3.1 to pH 9.6 after 16 days.

A thermo-stability study was performed for Av3b, Av3bM24, Av3bM165, Av3bM103, and Av3bM170 in a pH 4.0 solution at 54° C. for 0, 3, 7, 10, 12, and 14 days, with a caffeine internal control to cancel variation from evaporation. Samples of 1 mL were prepared in 1.5 mL microtube with sodium acetate buffer (NaOAc) at pH 4.0, containing 0.1 μg/μL of peptide, and 0.025 μg/μL of caffeine. The samples were incubated at 54° C. in a dry mixer. At 0, 3, 7, 10, 12, and 14 days, 20 μL of each sample was analyzed via analytic rpHPLC system to evaluate peptide loss. Each sample contained a fixed amount caffeine, which was used to compensate the peptide HPLC UV absorbance peak change due to volume change by evaporation. FIG. 68.

As shown in FIG. 68, Av3b, Av3bM165 and Av3bM170 were stable for at least 14 days in solution (pH 4) at 54° C. However, Av3bM24 was not stable, as its degradation was observed by day 3, but the degradation dramatically slowed after day 3. Surprisingly, Av3bM103 was also found to degrade in this experiment. Here, Av3bM103 was very stable at 54° C. for 7 days, at which point it suddenly degraded. FIG. 68.

The peptide change on day 14 for the peptides were as follows: Av3b=+8.3%; Av3bM24=−29.5%; Av3bM165=+4.2%; Av3bM103=−64.1%; and Av3bM170=+4.6%.

Here, peptide change on day 14 refers to the peptide mass change indicated by HPLC after 54° C. heat treatment. The peptide mass is represented by the HPLC peak area, and is calculated according to the following equation:

$$\text{Peptide change} = \frac{\text{day 14 peak area} - \text{day 0 peak area}}{\text{day 0 peak area}} \qquad \text{Formula (V)}$$

Therefore, a "+" means a mass increase (likely an artifact due to evaporation), and a "−" mean a mass loss.

The results shown here demonstrate that at 54° C. Av3b, Av3bM165 and Av3b M170 are thermo-stable, while Av3bM24 and Av3bM103 are not thermo-stable. Thus, when taken in concert with the examples provided above, these results indicate that Av3bM24 may not be stable with regard to temperature, but it is more stable to protease cleavage.

Example 20. Stability of Av3b Mutants in pH Conditions

Samples of Av3bM24, Av3bM165, Av3bM103, and Av3bM170 were prepared in 96 well plate, each well containing 300 μL of a solution comprising 0.1 μg/μL of peptide and 0.025 μg/μL of caffeine (to control for evaporation) and buffers ranging from pH 3.1 to pH 9.6.

The plate was placed at room temperature. At ~16 days, 20 μL of each sample was analyzed with an analytic rpHPLC system to determine peptide loss. Each sample contains a fixed amount caffeine, which was used to compensate the peptide HPLC UV absorbance peak change due to volume change by evaporation.

As shown in FIGS. 69-72, Av3bM24, Av3bM165, Av3bM103, and Av3bM170 are stable over a wide range of pH conditions, and for at least 16 days.

Example 21. Stability of Av3b Mutants in Insect Gut Extract

To test the stability of the Av3b mutants in the gut enzymes of a lepidopteran pest, the gut extract were prepared from *Helicoverpa zea* (Corn Earworm or "CEW"). Corn Earworm insects were obtained commercially from Benzon Research (Carlisle, PA) as eggs. Hatched larvae were raised on artificial diet until $4/5^{th}$ instar (20 mm long) before guts were isolated. Before gut extraction, larvae were anesthetized using $CO_2$. The larva was then pinned on the dissection plate at both the head and the tail. Using dissection scissors, the cuticle was nicked. The dissection scissors were then inserted into the nick and the cuticle was lengthwise along the insect. The cuticle was then carefully pulled back and pinned open to reveal the digestive track. Using DI water, the insect was thoroughly rinsed to remove hemolymph.

After the insect guts were extracted from the larva, they were spun at 15000 rpm for 5 minutes. The resulting supernatant is the "insect gut extract" that was used to determine peptide stability. Av3b mutant peptide was mixed with the gut extract to final volume of 2 μg/μL, and incubated at room temperature. At time points between 0-100 hours, 6 μL of a given sample was mixed with 93 μL dH2O followed by the addition of 1 μL of a 2% trifluoracetic acid solution to stop the reaction. The sample was then analyzed by rpHPLC to determine the peptide loss during the gut extract treatment.

Figure 73:
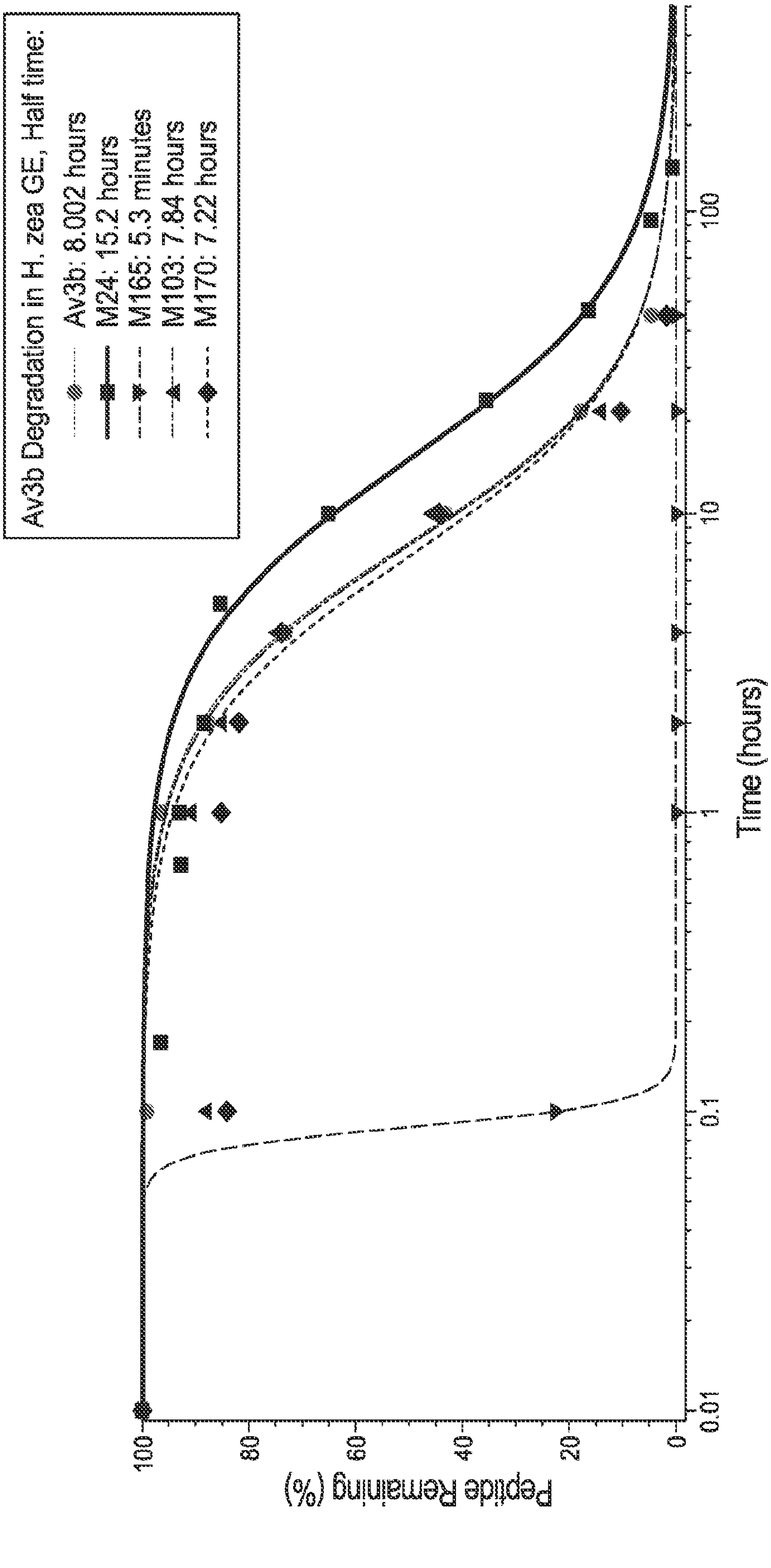
FIG. 73 depicts the degradation of Av3b mutants in *Helicoverpa zea* gut extract (GE). The mutants tested were Av3bM24; Av3bM165; Av3bM103; Av3bM170, and Av3b as a comparator.

The results of the insect gut extract assay are shown in FIG. 73. As shown here, Av3bM24 was the most resistant to degradation during the *H. zea* gut extract digestion. Av3b, Av3bM103 and Av3bM170 were also all resistant to degradation in *H. zea* gut extract, with a degradation half time between 7 and 8 hours. During the incubation, Av3bM165 quickly converted to Av3b peptide in *H. zea* gut extract, with half conversion time of 5.3 minutes. FIG. 73.

Example 22. Summary of Mutants Evaluated

The Table below provides a summary of the mutants evaluated herein.

TABLE 12

Summary of Av3b mutants evaluated. Mutants with names shown in bold were those Av3b mutant peptides possessing one or more desirable properties relative to Av3b. The properties include: Y = yield; A = activity; E = expression; S = general stability; D = resistance to proteolytic degradation in fermentation beer; F = similar protein folding relative to Av3b (as determined via circular dichroism); T = thermostable at 54° C.; P = stable under diverse pH conditions; G = stable in insect gut extract. Here, yield and activity are scored when a given peptide's yield or activity comparable to, or better than, the yield or activity of Av3b under the same conditions.

| Name | SEQ ID NO. | Sequence | Desirable Property |
|---|---|---|---|
| Av3b | 1 | KSCCPCYWGGCPWGQNCYPEGCSGPK | — |
| Av3bM1 | 2 | KSACPCYWGGAPWGQNCYPEGCSGPK | — |
| Av3bM2 | 3 | KSPCPCYWGGAPWGQNCYPEGCSGPK | — |
| Av3bM3 | 4 | KSNCPCYWGGTPWGQNCYPEGCSGPK | — |
| Av3bM4 | 5 | PSCCPCYWPNCPWGQNCYPEGCSGPK | — |
| Av3bM5 | 6 | KSCCPCYWPNCPWGQNCYPEGCSGPK | Y |
| Av3bM6 | 7 | TSCCPCYWPYCPWGQNCYPEGCSGPT | — |
| Av3bM7 | 8 | TSCCPCYWPYCPWGQNCYPEGCSGPR | — |
| Av3bM8 | 9 | TSCCPCYWGGCPWGQNCYPEGCSGPT | — |
| Av3bM9 | 10 | TSCCPCYWGGCPWGTTCYPNGCDGPT | — |
| Av3bM10 | 11 | TSCCPCYWGGCPWGQTCYPNGCDGPT | — |
| Av3bM11 | 12 | TSCCPCYWGGCPWGQTCYPNGCDGPR | — |
| Av3bM12 | 13 | TSCCPCYWGGCPWGTTCYPNGCDGST | — |
| Av3bM13 | 14 | TSCCPCYWGGCPWGQTCYPNGCDGST | — |
| Av3bM14 | 15 | TSCCPCYWGGCPWGQTCYPNGCDGSE | — |
| Av3bM15 | 16 | TSCCPCYWGGCPWGTTCYPNGCDGSR | — |
| Av3bM16 | 17 | TSCCPCYWGGCPWGQTCYPNGCDGSR | — |
| Av3bM17 | 18 | KSCAPCYWGGAPWGQNCYPEGCSGPK | — |
| Av3bM18 | 19 | KSACPCYWGGCPWGQNAYPEGCSGPK | — |
| Av3bM19 | 20 | KSCCPCYWGGCPWGQDCYPDGCDGPK | Y, A, S, D |
| Av3bM20 | 21 | KSCCPCYWGGCPWGTTCYPNGCDGPK | — |
| Av3bM21 | 22 | KSCCPCYWGGCPWGTNCYPEGCSGPK | — |
| Av3bM22 | 23 | KSCCPCYWGGCPWGQTCYPEGCSGPK | — |
| Av3bM23 | 24 | KSCCPCYWGGCPWGQNCYPNGCSGPK | Y, A |
| Av3bM24 | 25 | KSCCPCYWGGCPWGQNCYPEGCDGPK | Y, A, S, D,G |
| Av3bM25 | 26 | KSCCPCYWPGCPWGQNCYPEGCSGPK | Y, A |
| Av3bM26 | 27 | KSCCPCYWPPCPWGQNCYPEGCSGPK | — |
| Av3bM27 | 28 | KSCCPCYWAGCPWGQNCYPEGCSGPK | A |

TABLE 12-continued

Summary of Av3b mutants evaluated. Mutants with names shown in bold were those Av3b mutant peptides possessing one or more desirable properties relative to Av3b. The properties include: Y = yield; A = activity; E = expression; S = general stability; D = resistance to proteolytic degradation in fermentation beer; F = similar protein folding relative to Av3b (as determined via circular dichroism); T = thermostable at 54° C.; P = stable under diverse pH conditions; G = stable in insect gut extract. Here, yield and activity are scored when a given peptide's yield or activity comparable to, or better than, the yield or activity of Av3b under the same conditions.

| Name | SEQ ID NO. | Sequence | Desirable Property |
|---|---|---|---|
| Av3bM28 | 29 | HSCCPCYWGGCPWGQNCYPEGCSGPK | Y |
| Av3bM29 | 30 | QSCCPCYWGGCPWGQNCYPEGCSGPK | Y |
| Av3bM30 | 31 | QSCCPCYWGGCPWGQNCYPEGCSGPH | Y |
| Av3bM31 | 32 | TSCCPCYWGGCPWGQNCYPEGCSGPK | Y |
| Av3bM32 | 33 | SSCCPCYWGGCPWGQNCYPEGCSGPK | Y |
| Av3bM33 | 34 | SSCCPCYWGGCPWGQNCYPEGCSGPT | Y |
| Av3bM34 | 57 | ASCCPCYWGGCPWGQNCYPEGCSGPK | — |
| Av3bM35 | 58 | NSCCPCYWGGCPWGQNCYPEGCSGPK | Y |
| Av3bM36 | 59 | DSCCPCYWGGCPWGQNCYPEGCSGPK | — |
| Av3bM37 | 60 | ESCCPCYWGGCPWGQNCYPEGCSGPK | Y |
| Av3bM38 | 61 | GSCCPCYWGGCPWGQNCYPEGCSGPK | — |
| Av3bM39 | 62 | ISCCPCYWGGCPWGQNCYPEGCSGPK | A |
| Av3bM40 | 63 | LSCCPCYWGGCPWGQNCYPEGCSGPK | A |
| Av3bM41 | 64 | MSCCPCYWGGCPWGQNCYPEGCSGPK | — |
| Av3bM42 | 65 | FSCCPCYWGGCPWGQNCYPEGCSGPK | — |
| Av3bM43 | 66 | PSCCPCYWGGCPWGQNCYPEGCSGPK | — |
| Av3bM44 | 67 | WSCCPCYWGGCPWGQNCYPEGCSGPK | — |
| Av3bM45 | 68 | YSCCPCYWGGCPWGQNCYPEGCSGPK | — |
| Av3bM46 | 69 | VSCCPCYWGGCPWGQNCYPEGCSGPK | A |
| Av3bM47 | 70 | KSCCPCYWRGCPWGQNCYPEGCSGPK | — |
| Av3bM48 | 71 | KSCCPCYWNGCPWGQNCYPEGCSGPK | — |
| Av3bM49 | 72 | KSCCPCYWDGCPWGQNCYPEGCSGPK | — |
| Av3bM50 | 73 | KSCCPCYWEGCPWGQNCYPEGCSGPK | — |
| Av3bM51 | 74 | KSCCPCYWQGCPWGQNCYPEGCSGPK | — |
| Av3bM52 | 75 | KSCCPCYWHGCPWGQNCYPEGCSGPK | — |
| Av3bM53 | 76 | KSCCPCYWIGCPWGQNCYPEGCSGPK | — |
| Av3bM54 | 77 | KSCCPCYWLGCPWGQNCYPEGCSGPK | — |
| Av3bM55 | 78 | KSCCPCYWKGCPWGQNCYPEGCSGPK | — |
| Av3bM56 | 79 | KSCCPCYWMGCPWGQNCYPEGCSGPK | — |
| Av3bM57 | 80 | KSCCPCYWFGCPWGQNCYPEGCSGPK | — |
| Av3bM58 | 81 | KSCCPCYWSGCPWGQNCYPEGCSGPK | — |

TABLE 12-continued

Summary of Av3b mutants evaluated. Mutants with names shown in bold were those Av3b mutant peptides possessing one or more desirable properties relative to Av3b. The properties include: Y = yield; A = activity; E = expression; S = general stability; D = resistance to proteolytic degradation in fermentation beer; F = similar protein folding relative to Av3b (as determined via circular dichroism); T = thermostable at 54° C.; P = stable under diverse pH conditions; G = stable in insect gut extract. Here, yield and activity are scored when a given peptide's yield or activity comparable to, or better than, the yield or activity of Av3b under the same conditions.

| Name | SEQ ID NO. | Sequence | Desirable Property |
|---|---|---|---|
| Av3bM59 | 82 | KSCCPCYWTGCPWGQNCYPEGCSGPK | — |
| Av3bM60 | 83 | KSCCPCYWWGCPWGQNCYPEGCSGPK | — |
| Av3bM61 | 84 | KSCCPCYWYGCPWGQNCYPEGCSGPK | — |
| Av3bM62 | 85 | KSCCPCYWVGCPWGQNCYPEGCSGPK | — |
| Av3bM63 | 86 | KSCCPCYWGGCPWGQNCYPAGCSGPK | — |
| Av3bM64 | 87 | KSCCPCYWGGCPWGQNCYPRGCSGPK | — |
| Av3bM65 | 88 | KSCCPCYWGGCPWGQNCYPDGCSGPK | — |
| Av3bM66 | 89 | KSCCPCYWGGCPWGQNCYPQGCSGPK | — |
| Av3bM67 | 90 | KSCCPCYWGGCPWGQNCYPGGCSGPK | — |
| Av3bM68 | 91 | KSCCPCYWGGCPWGQNCYPHGCSGPK | — |
| Av3bM69 | 92 | KSCCPCYWGGCPWGQNCYPIGCSGPK | — |
| Av3bM70 | 93 | KSCCPCYWGGCPWGQNCYPLGCSGPK | — |
| Av3bM71 | 94 | KSCCPCYWGGCPWGQNCYPKGCSGPK | — |
| Av3bM72 | 95 | KSCCPCYWGGCPWGQNCYPMGCSGPK | — |
| Av3bM73 | 96 | KSCCPCYWGGCPWGQNCYPFGCSGPK | — |
| Av3bM74 | 97 | KSCCPCYWGGCPWGQNCYPPGCSGPK | — |
| Av3bM75 | 98 | KSCCPCYWGGCPWGQNCYPSGCSGPK | — |
| Av3bM76 | 99 | KSCCPCYWGGCPWGQNCYPTGCSGPK | — |
| Av3bM77 | 100 | KSCCPCYWGGCPWGQNCYPWGCSGPK | — |
| Av3bM78 | 101 | KSCCPCYWGGCPWGQNCYPYGCSGPK | — |
| Av3bM79 | 102 | KSCCPCYWGGCPWGQNCYPVGCSGPK | — |
| Av3bM80 | 103 | KSCCPCYWGGCPWGQNCYPEGCAGPK | — |
| Av3bM81 | 104 | KSCCPCYWGGCPWGQNCYPEGCRGPK | — |
| Av3bM82 | 105 | KSCCPCYWGGCPWGQNCYPEGCNGPK | — |
| Av3bM83 | 106 | KSCCPCYWGGCPWGQNCYPEGCEGPK | — |
| Av3bM84 | 107 | KSCCPCYWGGCPWGQNCYPEGCQGPK | — |
| Av3bM85 | 108 | KSCCPCYWGGCPWGQNCYPEGCGGPK | A |
| Av3bM86 | 109 | KSCCPCYWGGCPWGQNCYPEGCHGPK | — |
| Av3bM87 | 110 | KSCCPCYWGGCPWGQNCYPEGCIGPK | — |
| Av3bM88 | 111 | KSCCPCYWGGCPWGQNCYPEGCLGPK | — |
| Av3bM89 | 112 | KSCCPCYWGGCPWGQNCYPEGCKGPK | — |

TABLE 12-continued

Summary of Av3b mutants evaluated. Mutants with names shown in bold were those Av3b mutant peptides possessing one or more desirable properties relative to Av3b. The properties include: Y = yield; A = activity; E = expression; S = general stability; D = resistance to proteolytic degradation in fermentation beer; F = similar protein folding relative to Av3b (as determined via circular dichroism); T = thermostable at 54° C.; P = stable under diverse pH conditions; G = stable in insect gut extract. Here, yield and activity are scored when a given peptide's yield or activity comparable to, or better than, the yield or activity of Av3b under the same conditions.

| Name | SEQ ID NO. | Sequence | Desirable Property |
|---|---|---|---|
| Av3bM90 | 113 | KSCCPCYWGGCPWGQNCYPEGCMGPK | — |
| Av3bM91 | 114 | KSCCPCYWGGCPWGQNCYPEGCFGPK | — |
| Av3bM92 | 115 | KSCCPCYWGGCPWGQNCYPEGCPGPK | — |
| Av3bM93 | 116 | KSCCPCYWGGCPWGQNCYPEGCTGPK | A |
| Av3bM94 | 117 | KSCCPCYWGGCPWGQNCYPEGCWGPK | — |
| Av3bM95 | 118 | KSCCPCYWGGCPWGQNCYPEGCYGPK | — |
| Av3bM96 | 119 | KSCCPCYWGGCPWGQNCYPEGCVGPK | A |
| Av3bM97 | 41 | KSCCPCYWGGCPWGQNCYPEGCSGPA | A |
| Av3bM98 | 42 | KSCCPCYWGGCPWGQNCYPEGCSGPR | D |
| Av3bM99 | 43 | KSCCPCYWGGCPWGQNCYPEGCSGPN | — |
| Av3bM100 | 44 | KSCCPCYWGGCPWGQNCYPEGCSGPD | — |
| Av3bM101 | 45 | KSCCPCYWGGCPWGQNCYPEGCSGPE | — |
| Av3bM102 | 46 | KSCCPCYWGGCPWGQNCYPEGCSGPQ | — |
| Av3bM103 | 36 | KSCCPCYWGGCPWGQNCYPEGCSGPG | D, F, T, P, G |
| Av3bM104 | 47 | KSCCPCYWGGCPWGQNCYPEGCSGPH | — |
| Av3bM105 | 120 | KSCCPCYWGGCPWGQNCYPEGCSGPI | — |
| Av3bM106 | 121 | KSCCPCYWGGCPWGQNCYPEGCSGPL | — |
| Av3bM107 | 122 | KSCCPCYWGGCPWGQNCYPEGCSGPM | — |
| Av3bM108 | 123 | KSCCPCYWGGCPWGQNCYPEGCSGPF | — |
| Av3bM109 | 124 | KSCCPCYWGGCPWGQNCYPEGCSGPP | — |
| Av3bM110 | 125 | KSCCPCYWGGCPWGQNCYPEGCSGPS | — |
| Av3bM111 | 48 | KSCCPCYWGGCPWGQNCYPEGCSGPT | A |
| Av3bM112 | 126 | KSCCPCYWGGCPWGQNCYPEGCSGPW | — |
| Av3bM113 | 127 | KSCCPCYWGGCPWGQNCYPEGCSGPY | — |
| Av3bM114 | 128 | KSCCPCYWGGCPWGQNCYPEGCSGPV | — |
| Av3bM115 | 129 | HSCCPCYWPGCPWGQNCYPDGCDGPK | — |
| Av3bM116 | 130 | KSCCPCYWPGCPWGQNCYPNGCDGPR | — |
| Av3bM117 | 131 | KSCCPCYWPGCPWGQNCYPDGCDGPR | — |
| Av3bM118 | 132 | KSCCPCYWPGCPWGQNCYPNGCDGPT | — |
| Av3bM119 | 133 | KSCCPCYWPGCPWGQNCYPNGCRGPT | — |
| Av3bM120 | 134 | KSCCPCYWPGCPWGQNCYPNGCRGPR | — |

TABLE 12-continued

Summary of Av3b mutants evaluated. Mutants with names shown in bold were those Av3b mutant peptides possessing one or more desirable properties relative to Av3b. The properties include: Y = yield; A = activity; E = expression; S = general stability; D = resistance to proteolytic degradation in fermentation beer; F = similar protein folding relative to Av3b (as determined via circular dichroism); T = thermostable at 54° C.; P = stable under diverse pH conditions; G = stable in insect gut extract. Here, yield and activity are scored when a given peptide's yield or activity comparable to, or better than, the yield or activity of Av3b under the same conditions.

| Name | SEQ ID NO. | Sequence | Desirable Property |
|---|---|---|---|
| Av3bM121 | 135 | KSCCPCYWGGCPWGQNCYPEGCSGPD | — |
| Av3bM122 | 136 | KSCCPCYWGGCPWGQNCYPEGCSGPE | — |
| Av3bM123 | 137 | KSCCPCYWPGCPWGQNCYPEGCSGPD | — |
| Av3bM124 | 138 | KSCCPCYWPGCPWGQNCYPEGCSGPE | — |
| Av3bM125 | 35 | KSCCPCYWPGCPWGQNCYPEGCRGPD | Y, D |
| Av3bM126 | 140 | KSCCPCYWPGCPWGQNCYPEGCRGPE | — |
| Av3bM127 | 141 | GSCCPCGDGGCQTGQRCFPEGCDGPKV | — |
| Av3bM128 | 142 | GSCCPCGDGGCQTGQRCFPEGCDGPK | — |
| Av3bM129 | 143 | GSCCPCHDGGCWSGQRCYPEGCDGPK | — |
| Av3bM130 | 144 | GSCCPCGGGGCPHGQRCYPEGCDGPK | — |
| Av3bM131 | 145 | GSCCPCGDGGCQWGQRCYPEGCDGPK | — |
| Av3bM132 | 146 | HSCCPCWWGGCIWGQRCYPEGCSGPK | — |
| Av3bM133 | 147 | HSCCPCGDGGCPNGQRCYPEGCDGPK | — |
| Av3bM134 | 148 | HSCCPCFDGGCPFGQRCFPEGCDGPK | — |
| Av3bM135 | 149 | HSCCPCGAGGCPVGQRCYPEGCDGPK | — |
| Av3bM136 | 150 | QSCCPCYWGGCHHGQDCGPEGCSGPK | — |
| Av3bM137 | 151 | KSCCPCWWGGCDWGQDCGPEGCSGPK | — |
| Av3bM138 | 152 | KSCCPCYWGGCHTGQDCGPEGCSGPK | — |
| Av3bM143 | 153 | HSCCPCYWGGCPWGQNCYPEGCDGPK | — |
| Av3bM144 | 154 | KPCCPCYWGGCPWGQNCYPEGCSGPKV | — |
| Av3bM145 | 155 | KSCCPCYWGGCPWGQNCYPEGCSGMKV | — |
| Av3bM146 | 49 | KSCCPCYWGGCPWGQNCYPEGCSGGV | — |
| Av3bM147 | 50 | KSCCPCYWGGCPWGQNCYPEGCSGRV | — |
| Av3bM148 | 39 | KSCCPCYWGGCPWGQNCYPEGCSGPKG | D |
| Av3bM149 | 156 | KSCCPCYWGGCPWGQNCYPEGCSGPKF | — |
| Av3bM150 | 157 | KSCCPCYWGGCPWGQNCYPEGCSGPKI | — |
| Av3bM151 | 158 | VSCCPCYWGGCPWGQNCYPEGCDGPK | — |
| Av3bM152 | 159 | ISCCPCYWGGCPWGQNCYPEGCDGPK | — |
| Av3bM153 | 160 | LSCCPCYWGGCPWGQNCYPEGCDGPK | — |
| Av3bM154 | 161 | KSCCPCYWQGCPWGQNCYPEGCDGPK | — |
| Av3bM155 | 162 | KSCCPCYWPGCPWGQNCYPEGCDGPK | — |

TABLE 12-continued

Summary of Av3b mutants evaluated. Mutants with names shown in bold were those Av3b mutant peptides possessing one or more desirable properties relative to Av3b. The properties include: Y = yield; A = activity; E = expression; S = general stability; D = resistance to proteolytic degradation in fermentation beer; F = similar protein folding relative to Av3b (as determined via circular dichroism); T = thermostable at 54° C.; P = stable under diverse pH conditions; G = stable in insect gut extract. Here, yield and activity are scored when a given peptide's yield or activity comparable to, or better than, the yield or activity of Av3b under the same conditions.

| Name | SEQ ID NO. | Sequence | Desirable Property |
|---|---|---|---|
| Av3bM156 | 52 | KSCCPCYWGGCPWGQNCYPEGCDGPA | — |
| Av3bM157 | 53 | KSCCPCYWGGCPWGQNCYPEGCDGPT | — |
| Av3bM158 | 163 | VSCCPCYWPGCPWGQNCYPEGCRGPD | — |
| Av3bM159 | 164 | ISCCPCYWPGCPWGQNCYPEGCRGPD | — |
| Av3bM160 | 165 | LSCCPCYWPGCPWGQNCYPEGCRGPD | — |
| Av3bM161 | 166 | VSCCPCYWPGCPWGQNCYPEGCTGPT | — |
| Av3bM162 | 167 | VSCCPCYWPGCPWGQNCYPEGCTGPK | — |
| Av3bM163 | 168 | KSCCPCYWGGCPWGQNCYPEGCSGP | A |
| Av3bM164 | 169 | KSCCPCYWGGCPWGQNCYPEGCSG | A |
| Av3bM165 | 40 | KSCCPCYWGGCPWGQNCYPEGCSGPKVG | A, D, F, T, P |
| Av3bM166 | 170 | KSCCPCYWGGCPWGQNCYPEGCSGPKVQ | — |
| Av3bM167 | 171 | KSCCPCYWGGCPWGQNCYPEGCSGPKVD | — |
| Av3bM168 | 54 | KSCCPCYWGGCPWGQNCYPEGCSGPKVI | A |
| Av3bM169 | 37 | KSCCPCYWGGCPWGQNCYPEGCTGPG | — |
| Av3bM170 | 38 | KSCCPCYWGGCPWGQNCYPEGCGGPG | A, D, F, T, P, G |
| Av3bM171 | 55 | KSCCPCYWGGCPWGQNCYPEGCDGPG | — |
| Av3bM172 | 56 | KSCCPCYWGGCPWGQNCYPEGCDGP | — |

As shown above, the present disclosure provides numerous examples of Av3 mutant polypeptides, along with which mutations provide unexpected properties, and which mutations do not.

The invention claimed is:

1. An Av3 mutant polypeptide (AMP) comprising or consisting of an amino acid sequence as set forth in any one of SEQ ID NOs: 25, 36, 38, and 40, or an agriculturally acceptable salt thereof.

2. The AMP of claim 1, wherein the AMP is a fused protein comprising two or more AMPs separated by a cleavable or non-cleavable linker, and wherein the amino acid sequence of each AMP may be the same or different.

3. A combination or mixture, comprising, or consisting of, two or more AMPs of any one of claims 1 or 2.

4. A composition comprising, consisting essentially of, or consisting of, one or more AMPs of any one of claims 1 or 2, and an excipient.

5. A polynucleotide capable of encoding an AMP comprising or consisting of an amino acid sequence as set forth in any one of SEQ ID NOs: 25, 36, 38, and 40.

6. A method of producing an AMP, the method comprising:

(a) preparing a vector comprising a first expression cassette comprising, or consisting of, a polynucleotide encoding an AMP, said AMP comprising an amino acid sequence of any one of SEQ ID NOs: 25, 36, 38, and 40;

(b) introducing the vector into a host cell; and (c) growing the host cell in a growth medium under conditions allowing expression of the AMP and secretion into the growth medium.

7. The method of claim 6, wherein the vector is a plasmid comprising an alpha-MF signal.

8. The method of claim 6, wherein the host cell is a yeast strain selected from *Kluyveromyces lactis, Kluyveromyces marxianus, Saccharomyces cerevisiae*, and *Pichia pastoris.*

9. The method of claim 6, wherein the AMP is secreted into the growth medium.

10. A method for protecting a plant from insects, the method comprising: providing a plant that expresses an AMP of claim 1, or a polynucleotide encoding the same.

11. The method of claim 10, wherein the insects are selected from the group consisting of: *Eumorpha achemon; Colias eurytheme; Caudra cautella; Amorbia humerosana; Pseudaletia unipuncta; Platyptilia carduidactyla; Datana major; Thyridopteryx ephemeraeformis; Hypercompe scribonia; Erionota thrax; Acleris gloverana; Phryganidia californica; Paleacrita merriccata; Grapholita packardi; Nymphula stagnata; Xylomyges curialis; Cydia pomonella; Acrobasis vaccinii; Evergestis rimosalis; Noctuid* species; *Agrotis ipsilon; Orgyia pseudotsugata; Erinnyis ello; Ennomos subsignaria; Lobesia botrana; Thymelicus lineola; Melissopus latiferreanus; Archips rosanus; Archips argyrospilia; Paralobesia viteana*); *Platynota stultana; Harrisina americana; Plathypena scabra; Dryocampa rubicunda; Batrachedra comosae; Lymantria dispar; Lambdina fiscellaria; Manduca quinquemaculata; Manduca sexta; Pieris rapae; Automeris io; Choristoneura pinus; Epiphyas postvittana; Diaphania hyalinata; Homadaula anisocentra; Choristoneura rosaceana; Syntomeida epilais; Playnota stultana; Sabulodes aegrotata; Papilio cresphontes; Argyrotaenia citrana; Grapholita molesta; Anarsia lineatella; Neophasia menapia; Argyrotaenia velutinana; Schizura concinna; Sibine stimulea; Heterocampa guttivitta; Estigmene acrea; Crambus* sp.; *Ennomos subsignaria; Alsophila pometaria; Choristoneura fumiferana; Lasiocampidae* sp.; *Thecla basilides; Ephestia elutella; Platynota idaeusalis; Anarsia lineatella; Peridroma saucia; Platynota flavedana; Anticarsia gemmatalis; Datana integerrima; Hyphantria cunea; Orgyia vetusta*; Southern *Diatraea crambidoides; Cylas formicarius; Anthonomus eugenii; Diaprepes abbreviatus; Otiorhynchus ovatus; Curculio caryae; Curculio occidentis; Lissorhoptrus oryzophilus; Hypera postica; Hypera zoilus; Euwallacea fornicatus; Euetheola humilis; Hypothenemus hampei; Listronotus maculicollis; Maladera castanea; Rhizotroqus majalis; Cotinis nitida; Popilia japonica; Phyllophaga* sp.; *Cyclocephala borealis; Anomala orientalis; Cyclocephala lurida; Sphenophorus parvulus; Sphenophorus apicalis; Sphenophorus cariosus; Sphenophorus inaequalis; Sphenophorus minimus; Aedes aegypti; Busseola fusca; Chilo suppressalis; Culex pipiens; Culex quinquefasciatus; Diabrotica virgifera; Diatraea saccharalis; Helicoverpa armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni*; and *Xanthogaleruca luteola.*

12. The method of claim 11, wherein the insects are selected from the group consisting of: *Aedes aegypti; Busseola fusca; Chilo suppressalis; Culex pipiens; Culex quinquefasciatus; Diabrotica virgifera; Diatraea saccharalis; Helicoverpa armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni*; and *Xanthogaleruca luteola.*

13. A method for controlling insects comprising, providing to said insect a transgenic plant that comprises in its genome a stably incorporated expression cassette, wherein said stably incorporated expression cassette comprises a polynucleotide encoding an AMP of claim 1.

14. A method of combating, controlling, or inhibiting a pest comprising, applying a pesticidally effective amount of: (1) an Av3 mutant polypeptide (AMP) comprising or consisting of an amino acid sequence set forth in any one of SEQ ID NOs: 25, 36, 38, and 40, or an agriculturally acceptable salt thereof; (2) a combination or mixture comprising two or more AMPs, each AMP comprising or consisting of an amino acid sequence set forth in any one of SEQ ID NOs: 25, 36, 38, and 40, or an agriculturally acceptable salt thereof, wherein the two or more AMPs are the same or different; or (3) a composition comprising one or more AMPs comprising or consisting of an amino acid sequence set forth in any one of SEQ ID NOs: 25, 36, 38, and 40, or an agriculturally acceptable salt thereof, to: the pest, a locus of the pest, a food supply of the pest, a habitat of the pest, or a breeding ground of the pest; a plant, a seed, a plant part, a locus of a plant, or an environment of a plant that is susceptible to an attack by the pest; an animal, a locus of an animal, or an environment of an animal susceptible to an attack by the pest; or a combination thereof.

15. The method of claim 14, wherein the pest is selected from the group consisting of: group consisting of: *Eumorpha achemon; Colias eurytheme; Caudra cautella; Amorbia humerosana; Pseudaletia unipuncta; Platyptilia carduidactyla; Datana major; Thyridopteryx ephemeraeformis; Hypercompe scribonia; Erionota thrax; Acleris gloverana; Phryganidia calfornica; Paleacrita merriccata; Grapholita packardi; Nymphula stagnata; Xylomyges curialis; Cydia pomonella; Acrobasis vaccinii; Evergestis rimosalis; Noctuid* species; *Agrotis ipsilon; Orgyia pseudotsugata; Erinnyis ello; Ennomos subsignaria; Lobesia botrana; Thymelicus lineola; Melissopus latiferreanus; Archips rosanus; Archips argyrospilia; Paralobesia viteana*); *Platynota stultana; Harrisina americana; Plathypena scabra; Dryocampa rubicunda; Batrachedra comosae; Lymantria dispar; Lambdina fiscellaria; Manduca quinquemaculata; Manduca sexta; Pieris rapae; Automeris io; Choristoneura pinus; Epiphyas postvittana; Diaphania hyalinata; Homadaula anisocentra; Choristoneura rosaceana; Syntomeida epilais; Playnota stultana; Sabulodes aegrotata; Papilio cresphontes; Argyrotaenia citrana; Grapholita molesta; Anarsia lineatella; Neophasia menapia; Argyrotaenia velutinana; Schizura concinna; Sibine stimulea; Heterocampa guttivitta; Estigmene acrea; Crambus* sp.; *Ennomos subsignaria; Alsophila pometaria; Choristoneura fumiferana; Lasiocampidae* sp.; *Thecla basilides; Ephestia elutella; Platynota idaeusalis; Anarsia lineatella; Peridroma saucia; Platynota fla-*

*vedana; Anticarsia gemmatalis; Datana integerrima; Hyphantria cunea; Orgyia vetusta*; Southern *Diatraea crambidoides; Cylas formicarius; Anthonomus eugenii; Diaprepes abbreviatus; Otiorhynchus ovatus; Curculio caryae; Curculio occidentis; Lissorhoptrus oryzophilus; Hypera postica; Hypera zoilus; Euwallacea fornicatus; Euetheola humilis; Hypothenemus hampei; Listronotus maculicollis; Maladera castanea; Rhizotroqus majalis; Cotinis nitida; Popilia japonica; Phyllophaga* sp.; *Cyclocephala borealis; Anomala orientalis; Cyclocephala lurida; Sphenophorus parvulus; Sphenophorus apicalis; Sphenophorus cariosus; Sphenophorus inaequalis; Sphenophorus minimus; Aedes aegypti; Busseola fusca; Chilo suppressalis; Culex pipiens; Culex quinquefasciatus; Diabrotica virgifera; Diatraea saccharalis; Helicoverpa armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni*; and *Xanthogaleruca luteola.*

16. The method of claim 15, wherein the pest is selected from the group consisting of: *Aedes aegypti; Busseola fusca; Chilo suppressalis; Culex pipiens; Culex quinquefasciatus; Diabrotica virgifera; Diatraea saccharalis; Helicoverpa armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni*; and *Xanthogaleruca luteola.*

17. A vector comprising a polynucleotide encoding an AMP having an amino acid sequence set forth in any one of SEQ ID NOs: 25, 36, 38, and 40.

18. A yeast strain comprising: a first expression cassette comprising a polynucleotide encoding an AMP, said AMP comprising an amino acid sequence as set forth in any one of SEQ ID NOs: 25, 36, 38, and 40.

19. The yeast strain of claim 18, wherein the yeast cell is selected from the group consisting of *Kluyveromyces lactis, Kluyveromyces marxianus, Saccharomyces cerevisiae*, and *Pichia pastoris.*

20. An Av3 mutant polypeptide (AMP) having insecticidal activity against one or more insect species, said AMP comprising, consisting essentially of, or consisting of, an amino acid sequence set forth in any one of SEQ ID NOs: 25, 36, 38, and 40.

21. The Av3 mutant polypeptide (AMP) of claim 1, wherein the AMP comprises an amino acid sequence as set forth in SEQ ID NO: 25.

22. The Av3 mutant polypeptide (AMP) of claim 1, wherein the AMP comprises an amino acid sequence as set forth in SEQ ID NO: 36.

23. The Av3 mutant polypeptide (AMP) of claim 1, wherein the AMP comprises an amino acid sequence as set forth in SEQ ID NO: 38.

24. The Av3 mutant polypeptide (AMP) of claim 1, wherein the AMP comprises an amino acid sequence as set forth in SEQ ID NO: 40.

* * * * *

SEQUENCE LISTING

<160> NUMBER OF SEQ ID NOS: 201

<210> SEQ ID NO 1
<211> LENGTH: 26
<212> TYPE: PRT
<213> ORGANISM: Artificial Sequence
<220> FEATURE:
<223> OTHER INFORMATION: Av3b
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 1

```
Lys Ser Cys Cys Pro Cys Tyr Trp Gly Gly Cys Pro Trp Gly Gln Asn
1               5                   10                  15

Cys Tyr Pro Glu Gly Cys Ser Gly Pro Lys
            20                  25


<210> SEQ ID NO 2
<211> LENGTH: 26
<212> TYPE: PRT
<213> ORGANISM: Artificial Sequence
<220> FEATURE:
<223> OTHER INFORMATION: Av3bM1
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 2

Lys Ser Ala Cys Pro Cys Tyr Trp Gly Gly Ala Pro Trp Gly Gln Asn
1               5                   10                  15

Cys Tyr Pro Glu Gly Cys Ser Gly Pro Lys
            20                  25


<210> SEQ ID NO 3
<211> LENGTH: 26
<212> TYPE: PRT
<213> ORGANISM: Artificial Sequence
<220> FEATURE:
<223> OTHER INFORMATION: Av3bM2
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 3

Lys Ser Pro Cys Pro Cys Tyr Trp Gly Gly Ala Pro Trp Gly Gln Asn
1               5                   10                  15

Cys Tyr Pro Glu Gly Cys Ser Gly Pro Lys
            20                  25


<210> SEQ ID NO 4
<211> LENGTH: 26
<212> TYPE: PRT
<213> ORGANISM: Artificial Sequence
<220> FEATURE:
<223> OTHER INFORMATION: Av3bM3
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 4

Lys Ser Asn Cys Pro Cys Tyr Trp Gly Gly Thr Pro Trp Gly Gln Asn
1               5                   10                  15

Cys Tyr Pro Glu Gly Cys Ser Gly Pro Lys
            20                  25


<210> SEQ ID NO 5
<211> LENGTH: 26
<212> TYPE: PRT
<213> ORGANISM: Artificial Sequence
<220> FEATURE:
<223> OTHER INFORMATION: Av3bM4
<220> FEATURE:
<221> NAME/KEY: VARIANT
<222> LOCATION: (1)..(26)
```

<223> OTHER INFORMATION: Recombinant variant of Anemonia viridis Av3
      peptide

<400> SEQUENCE: 5

Pro Ser Cys Cys Pro Cys Tyr Trp Pro Asn Cys Pro Trp Gly Gln Asn
1               5                   10                  15

Cys Tyr Pro Glu Gly Cys Ser Gly Pro Lys
            20                  25

<210> SEQ ID NO 6
<211> LENGTH: 26
<212> TYPE: PRT
<213> ORGANISM: Artificial Sequence
<220> FEATURE:
<223> OTHER INFORMATION: Av3bM5
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 6

Lys Ser Cys Cys Pro Cys Tyr Trp Pro Asn Cys Pro Trp Gly Gln Asn
1               5                   10                  15

Cys Tyr Pro Glu Gly Cys Ser Gly Pro Lys
            20                  25

<210> SEQ ID NO 7
<211> LENGTH: 26
<212> TYPE: PRT
<213> ORGANISM: Artificial Sequence
<220> FEATURE:
<223> OTHER INFORMATION: Av3bM6
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 7

Thr Ser Cys Cys Pro Cys Tyr Trp Pro Tyr Cys Pro Trp Gly Gln Asn
1               5                   10                  15

Cys Tyr Pro Glu Gly Cys Ser Gly Pro Thr
            20                  25

<210> SEQ ID NO 8
<211> LENGTH: 26
<212> TYPE: PRT
<213> ORGANISM: Artificial Sequence
<220> FEATURE:
<223> OTHER INFORMATION: Av3bM7
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 8

Thr Ser Cys Cys Pro Cys Tyr Trp Pro Tyr Cys Pro Trp Gly Gln Asn
1               5                   10                  15

Cys Tyr Pro Glu Gly Cys Ser Gly Pro Arg
            20                  25

<210> SEQ ID NO 9
<211> LENGTH: 26
<212> TYPE: PRT
<213> ORGANISM: Artificial Sequence
<220> FEATURE:
<223> OTHER INFORMATION: Av3bM8
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 9

Thr Ser Cys Cys Pro Cys Tyr Trp Gly Gly Cys Pro Trp Gly Gln Asn
1 5 10 15

Cys Tyr Pro Glu Gly Cys Ser Gly Pro Thr
20 25

<210> SEQ ID NO 10
<211> LENGTH: 26
<212> TYPE: PRT
<213> ORGANISM: Artificial Sequence
<220> FEATURE:
<223> OTHER INFORMATION: Av3bM9
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 10

Thr Ser Cys Cys Pro Cys Tyr Trp Gly Gly Cys Pro Trp Gly Thr Thr
1 5 10 15

Cys Tyr Pro Asn Gly Cys Asp Gly Pro Thr
20 25

<210> SEQ ID NO 11
<211> LENGTH: 26
<212> TYPE: PRT
<213> ORGANISM: Artificial Sequence
<220> FEATURE:
<223> OTHER INFORMATION: Av3bM10
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 11

Thr Ser Cys Cys Pro Cys Tyr Trp Gly Gly Cys Pro Trp Gly Gln Thr
1 5 10 15

Cys Tyr Pro Asn Gly Cys Asp Gly Pro Thr
20 25

<210> SEQ ID NO 12
<211> LENGTH: 26
<212> TYPE: PRT
<213> ORGANISM: Artificial Sequence
<220> FEATURE:
<223> OTHER INFORMATION: Av3bM11
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 12

Thr Ser Cys Cys Pro Cys Tyr Trp Gly Gly Cys Pro Trp Gly Gln Thr
1 5 10 15

Cys Tyr Pro Asn Gly Cys Asp Gly Pro Arg
20 25

<210> SEQ ID NO 13
<211> LENGTH: 26
<212> TYPE: PRT
<213> ORGANISM: Artificial Sequence
<220> FEATURE:
<223> OTHER INFORMATION: Av3bM12
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 13

Thr Ser Cys Cys Pro Cys Tyr Trp Gly Gly Cys Pro Trp Gly Thr Thr
1               5                   10                  15

Cys Tyr Pro Asn Gly Cys Asp Gly Ser Thr
            20                  25

<210> SEQ ID NO 14
<211> LENGTH: 26
<212> TYPE: PRT
<213> ORGANISM: Artificial Sequence
<220> FEATURE:
<223> OTHER INFORMATION: Av3bM13
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 14

Thr Ser Cys Cys Pro Cys Tyr Trp Gly Gly Cys Pro Trp Gly Gln Thr
1               5                   10                  15

Cys Tyr Pro Asn Gly Cys Asp Gly Ser Thr
            20                  25

<210> SEQ ID NO 15
<211> LENGTH: 26
<212> TYPE: PRT
<213> ORGANISM: Artificial Sequence
<220> FEATURE:
<223> OTHER INFORMATION: Av3bM14
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 15

Thr Ser Cys Cys Pro Cys Tyr Trp Gly Gly Cys Pro Trp Gly Gln Thr
1               5                   10                  15

Cys Tyr Pro Asn Gly Cys Asp Gly Ser Glu
            20                  25

<210> SEQ ID NO 16
<211> LENGTH: 26
<212> TYPE: PRT
<213> ORGANISM: Artificial Sequence
<220> FEATURE:
<223> OTHER INFORMATION: Av3bM15
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 16

Thr Ser Cys Cys Pro Cys Tyr Trp Gly Gly Cys Pro Trp Gly Thr Thr

```
1               5                   10                  15

Cys Tyr Pro Asn Gly Cys Asp Gly Ser Arg
            20                  25


<210> SEQ ID NO 17
<211> LENGTH: 26
<212> TYPE: PRT
<213> ORGANISM: Artificial Sequence
<220> FEATURE:
<223> OTHER INFORMATION: Av3bM16
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 17

Thr Ser Cys Cys Pro Cys Tyr Trp Gly Gly Cys Pro Trp Gly Gln Thr
1               5                   10                  15

Cys Tyr Pro Asn Gly Cys Asp Gly Ser Arg
            20                  25


<210> SEQ ID NO 18
<211> LENGTH: 26
<212> TYPE: PRT
<213> ORGANISM: Artificial Sequence
<220> FEATURE:
<223> OTHER INFORMATION: Av3bM17
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 18

Lys Ser Cys Ala Pro Cys Tyr Trp Gly Gly Ala Pro Trp Gly Gln Asn
1               5                   10                  15

Cys Tyr Pro Glu Gly Cys Ser Gly Pro Lys
            20                  25


<210> SEQ ID NO 19
<211> LENGTH: 26
<212> TYPE: PRT
<213> ORGANISM: Artificial Sequence
<220> FEATURE:
<223> OTHER INFORMATION: Av3bM18
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 19

Lys Ser Ala Cys Pro Cys Tyr Trp Gly Gly Cys Pro Trp Gly Gln Asn
1               5                   10                  15

Ala Tyr Pro Glu Gly Cys Ser Gly Pro Lys
            20                  25


<210> SEQ ID NO 20
<211> LENGTH: 26
<212> TYPE: PRT
<213> ORGANISM: Artificial Sequence
<220> FEATURE:
<223> OTHER INFORMATION: Av3bM19
<220> FEATURE:
<221> NAME/KEY: VARIANT
<222> LOCATION: (1)..(26)
<223> OTHER INFORMATION: Recombinant variant of Anemonia viridis Av3
```

peptide

<400> SEQUENCE: 20

Lys Ser Cys Cys Pro Cys Tyr Trp Gly Gly Cys Pro Trp Gly Gln Asp
1               5                   10                  15

Cys Tyr Pro Asp Gly Cys Asp Gly Pro Lys
            20                  25

<210> SEQ ID NO 21
<211> LENGTH: 26
<212> TYPE: PRT
<213> ORGANISM: Artificial Sequence
<220> FEATURE:
<223> OTHER INFORMATION: Av3bM20
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 21

Lys Ser Cys Cys Pro Cys Tyr Trp Gly Gly Cys Pro Trp Gly Thr Thr
1               5                   10                  15

Cys Tyr Pro Asn Gly Cys Asp Gly Pro Lys
            20                  25

<210> SEQ ID NO 22
<211> LENGTH: 26
<212> TYPE: PRT
<213> ORGANISM: Artificial Sequence
<220> FEATURE:
<223> OTHER INFORMATION: Av3bM21
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 22

Lys Ser Cys Cys Pro Cys Tyr Trp Gly Gly Cys Pro Trp Gly Thr Asn
1               5                   10                  15

Cys Tyr Pro Glu Gly Cys Ser Gly Pro Lys
            20                  25

<210> SEQ ID NO 23
<211> LENGTH: 26
<212> TYPE: PRT
<213> ORGANISM: Artificial Sequence
<220> FEATURE:
<223> OTHER INFORMATION: Av3bM22
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 23

Lys Ser Cys Cys Pro Cys Tyr Trp Gly Gly Cys Pro Trp Gly Gln Thr
1               5                   10                  15

Cys Tyr Pro Glu Gly Cys Ser Gly Pro Lys
            20                  25

<210> SEQ ID NO 24
<211> LENGTH: 26
<212> TYPE: PRT
<213> ORGANISM: Artificial Sequence
<220> FEATURE:

<223> OTHER INFORMATION: Av3bM23
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 24

Lys Ser Cys Cys Pro Cys Tyr Trp Gly Gly Cys Pro Trp Gly Gln Asn
1               5                   10                  15

Cys Tyr Pro Asn Gly Cys Ser Gly Pro Lys
            20                  25

<210> SEQ ID NO 25
<211> LENGTH: 26
<212> TYPE: PRT
<213> ORGANISM: Artificial Sequence
<220> FEATURE:
<223> OTHER INFORMATION: Av3bM24
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 25

Lys Ser Cys Cys Pro Cys Tyr Trp Gly Gly Cys Pro Trp Gly Gln Asn
1               5                   10                  15

Cys Tyr Pro Glu Gly Cys Asp Gly Pro Lys
            20                  25

<210> SEQ ID NO 26
<211> LENGTH: 26
<212> TYPE: PRT
<213> ORGANISM: Artificial Sequence
<220> FEATURE:
<223> OTHER INFORMATION: Av3bM25
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 26

Lys Ser Cys Cys Pro Cys Tyr Trp Pro Gly Cys Pro Trp Gly Gln Asn
1               5                   10                  15

Cys Tyr Pro Glu Gly Cys Ser Gly Pro Lys
            20                  25

<210> SEQ ID NO 27
<211> LENGTH: 26
<212> TYPE: PRT
<213> ORGANISM: Artificial Sequence
<220> FEATURE:
<223> OTHER INFORMATION: Av3bM26
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 27

Lys Ser Cys Cys Pro Cys Tyr Trp Pro Pro Cys Pro Trp Gly Gln Asn
1               5                   10                  15

Cys Tyr Pro Glu Gly Cys Ser Gly Pro Lys
            20                  25

<210> SEQ ID NO 28
<211> LENGTH: 26
<212> TYPE: PRT
<213> ORGANISM: Artificial Sequence
<220> FEATURE:
<223> OTHER INFORMATION: Av3bM27
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 28

```
Lys Ser Cys Cys Pro Cys Tyr Trp Ala Gly Cys Pro Trp Gly Gln Asn
1               5                   10                  15

Cys Tyr Pro Glu Gly Cys Ser Gly Pro Lys
            20                  25
```

<210> SEQ ID NO 29
<211> LENGTH: 26
<212> TYPE: PRT
<213> ORGANISM: Artificial Sequence
<220> FEATURE:
<223> OTHER INFORMATION: Av3bM28
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 29

```
His Ser Cys Cys Pro Cys Tyr Trp Gly Gly Cys Pro Trp Gly Gln Asn
1               5                   10                  15

Cys Tyr Pro Glu Gly Cys Ser Gly Pro Lys
            20                  25
```

<210> SEQ ID NO 30
<211> LENGTH: 26
<212> TYPE: PRT
<213> ORGANISM: Artificial Sequence
<220> FEATURE:
<223> OTHER INFORMATION: Av3bM29
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 30

```
Gln Ser Cys Cys Pro Cys Tyr Trp Gly Gly Cys Pro Trp Gly Gln Asn
1               5                   10                  15

Cys Tyr Pro Glu Gly Cys Ser Gly Pro Lys
            20                  25
```

<210> SEQ ID NO 31
<211> LENGTH: 26
<212> TYPE: PRT
<213> ORGANISM: Artificial Sequence
<220> FEATURE:
<223> OTHER INFORMATION: Av3bM30
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 31

```
Gln Ser Cys Cys Pro Cys Tyr Trp Gly Gly Cys Pro Trp Gly Gln Asn
1               5                   10                  15
```

Cys Tyr Pro Glu Gly Cys Ser Gly Pro His
20 25

<210> SEQ ID NO 32
<211> LENGTH: 26
<212> TYPE: PRT
<213> ORGANISM: Artificial Sequence
<220> FEATURE:
<223> OTHER INFORMATION: Av3bM31
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 32

Thr Ser Cys Cys Pro Cys Tyr Trp Gly Gly Cys Pro Trp Gly Gln Asn
1 5 10 15

Cys Tyr Pro Glu Gly Cys Ser Gly Pro Lys
20 25

<210> SEQ ID NO 33
<211> LENGTH: 26
<212> TYPE: PRT
<213> ORGANISM: Artificial Sequence
<220> FEATURE:
<223> OTHER INFORMATION: Av3bM32
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 33

Ser Ser Cys Cys Pro Cys Tyr Trp Gly Gly Cys Pro Trp Gly Gln Asn
1 5 10 15

Cys Tyr Pro Glu Gly Cys Ser Gly Pro Lys
20 25

<210> SEQ ID NO 34
<211> LENGTH: 26
<212> TYPE: PRT
<213> ORGANISM: Artificial Sequence
<220> FEATURE:
<223> OTHER INFORMATION: Av3bM33
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 34

Ser Ser Cys Cys Pro Cys Tyr Trp Gly Gly Cys Pro Trp Gly Gln Asn
1 5 10 15

Cys Tyr Pro Glu Gly Cys Ser Gly Pro Thr
20 25

<210> SEQ ID NO 35
<211> LENGTH: 26
<212> TYPE: PRT
<213> ORGANISM: Artificial Sequence
<220> FEATURE:
<223> OTHER INFORMATION: M125
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 35

Lys Ser Cys Cys Pro Cys Tyr Trp Pro Gly Cys Pro Trp Gly Gln Asn
1               5                   10                  15

Cys Tyr Pro Glu Gly Cys Arg Gly Pro Asp
            20                  25

<210> SEQ ID NO 36
<211> LENGTH: 26
<212> TYPE: PRT
<213> ORGANISM: Artificial Sequence
<220> FEATURE:
<223> OTHER INFORMATION: M103
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 36

Lys Ser Cys Cys Pro Cys Tyr Trp Gly Gly Cys Pro Trp Gly Gln Asn
1               5                   10                  15

Cys Tyr Pro Glu Gly Cys Ser Gly Pro Gly
            20                  25

<210> SEQ ID NO 37
<211> LENGTH: 26
<212> TYPE: PRT
<213> ORGANISM: Artificial Sequence
<220> FEATURE:
<223> OTHER INFORMATION: M169
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 37

Lys Ser Cys Cys Pro Cys Tyr Trp Gly Gly Cys Pro Trp Gly Gln Asn
1               5                   10                  15

Cys Tyr Pro Glu Gly Cys Thr Gly Pro Gly
            20                  25

<210> SEQ ID NO 38
<211> LENGTH: 26
<212> TYPE: PRT
<213> ORGANISM: Artificial Sequence
<220> FEATURE:
<223> OTHER INFORMATION: M170
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 38

Lys Ser Cys Cys Pro Cys Tyr Trp Gly Gly Cys Pro Trp Gly Gln Asn
1               5                   10                  15

Cys Tyr Pro Glu Gly Cys Gly Gly Pro Gly
            20                  25

<210> SEQ ID NO 39
<211> LENGTH: 27
<212> TYPE: PRT
<213> ORGANISM: Artificial Sequence
<220> FEATURE:
<223> OTHER INFORMATION: M148

<220> FEATURE:
<221> NAME/KEY: VARIANT
<222> LOCATION: (1)..(27)
<223> OTHER INFORMATION: Recombinant variant of Anemonia viridis Av3 peptide

<400> SEQUENCE: 39

```
Lys Ser Cys Cys Pro Cys Tyr Trp Gly Gly Cys Pro Trp Gly Gln Asn
1               5                   10                  15

Cys Tyr Pro Glu Gly Cys Ser Gly Pro Lys Gly
            20                  25
```

<210> SEQ ID NO 40
<211> LENGTH: 28
<212> TYPE: PRT
<213> ORGANISM: Artificial Sequence
<220> FEATURE:
<223> OTHER INFORMATION: M165
<220> FEATURE:
<221> NAME/KEY: VARIANT
<222> LOCATION: (1)..(28)
<223> OTHER INFORMATION: Recombinant variant of Anemonia viridis Av3 peptide

<400> SEQUENCE: 40

```
Lys Ser Cys Cys Pro Cys Tyr Trp Gly Gly Cys Pro Trp Gly Gln Asn
1               5                   10                  15

Cys Tyr Pro Glu Gly Cys Ser Gly Pro Lys Val Gly
            20                  25
```

<210> SEQ ID NO 41
<211> LENGTH: 26
<212> TYPE: PRT
<213> ORGANISM: Artificial Sequence
<220> FEATURE:
<223> OTHER INFORMATION: Av3bM97
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 41

```
Lys Ser Cys Cys Pro Cys Tyr Trp Gly Gly Cys Pro Trp Gly Gln Asn
1               5                   10                  15

Cys Tyr Pro Glu Gly Cys Ser Gly Pro Ala
            20                  25
```

<210> SEQ ID NO 42
<211> LENGTH: 26
<212> TYPE: PRT
<213> ORGANISM: Artificial Sequence
<220> FEATURE:
<223> OTHER INFORMATION: Av3bM98
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 42

```
Lys Ser Cys Cys Pro Cys Tyr Trp Gly Gly Cys Pro Trp Gly Gln Asn
1               5                   10                  15

Cys Tyr Pro Glu Gly Cys Ser Gly Pro Arg
            20                  25
```

<210> SEQ ID NO 43

<211> LENGTH: 26
<212> TYPE: PRT
<213> ORGANISM: Artificial Sequence
<220> FEATURE:
<223> OTHER INFORMATION: Av3bM99
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 43

Lys Ser Cys Cys Pro Cys Tyr Trp Gly Gly Cys Pro Trp Gly Gln Asn
1 5 10 15

Cys Tyr Pro Glu Gly Cys Ser Gly Pro Asn
20 25

<210> SEQ ID NO 44
<211> LENGTH: 26
<212> TYPE: PRT
<213> ORGANISM: Artificial Sequence
<220> FEATURE:
<223> OTHER INFORMATION: Av3bM100
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 44

Lys Ser Cys Cys Pro Cys Tyr Trp Gly Gly Cys Pro Trp Gly Gln Asn
1 5 10 15

Cys Tyr Pro Glu Gly Cys Ser Gly Pro Asp
20 25

<210> SEQ ID NO 45
<211> LENGTH: 26
<212> TYPE: PRT
<213> ORGANISM: Artificial Sequence
<220> FEATURE:
<223> OTHER INFORMATION: Av3bM101
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 45

Lys Ser Cys Cys Pro Cys Tyr Trp Gly Gly Cys Pro Trp Gly Gln Asn
1 5 10 15

Cys Tyr Pro Glu Gly Cys Ser Gly Pro Glu
20 25

<210> SEQ ID NO 46
<211> LENGTH: 26
<212> TYPE: PRT
<213> ORGANISM: Artificial Sequence
<220> FEATURE:
<223> OTHER INFORMATION: Av3bM102
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 46

Lys Ser Cys Cys Pro Cys Tyr Trp Gly Gly Cys Pro Trp Gly Gln Asn
1 5 10 15

```
Cys Tyr Pro Glu Gly Cys Ser Gly Pro Gln
            20                  25


<210> SEQ ID NO 47
<211> LENGTH: 26
<212> TYPE: PRT
<213> ORGANISM: Artificial Sequence
<220> FEATURE:
<223> OTHER INFORMATION: Av3bM104
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 47

Lys Ser Cys Cys Pro Cys Tyr Trp Gly Gly Cys Pro Trp Gly Gln Asn
1               5                   10                  15

Cys Tyr Pro Glu Gly Cys Ser Gly Pro His
            20                  25


<210> SEQ ID NO 48
<211> LENGTH: 26
<212> TYPE: PRT
<213> ORGANISM: Artificial Sequence
<220> FEATURE:
<223> OTHER INFORMATION: Av3bM111
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 48

Lys Ser Cys Cys Pro Cys Tyr Trp Gly Gly Cys Pro Trp Gly Gln Asn
1               5                   10                  15

Cys Tyr Pro Glu Gly Cys Ser Gly Pro Thr
            20                  25


<210> SEQ ID NO 49
<211> LENGTH: 26
<212> TYPE: PRT
<213> ORGANISM: Artificial Sequence
<220> FEATURE:
<223> OTHER INFORMATION: Av3bM146
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 49

Lys Ser Cys Cys Pro Cys Tyr Trp Gly Gly Cys Pro Trp Gly Gln Asn
1               5                   10                  15

Cys Tyr Pro Glu Gly Cys Ser Gly Gly Val
            20                  25


<210> SEQ ID NO 50
<211> LENGTH: 26
<212> TYPE: PRT
<213> ORGANISM: Artificial Sequence
<220> FEATURE:
<223> OTHER INFORMATION: Av3bM147
<220> FEATURE:
<221> NAME/KEY: VARIANT
<222> LOCATION: (1)..(26)
<223> OTHER INFORMATION: Recombinant variant of Anemonia viridis Av3
      peptide
```

<400> SEQUENCE: 50

Lys Ser Cys Cys Pro Cys Tyr Trp Gly Gly Cys Pro Trp Gly Gln Asn
1 5 10 15

Cys Tyr Pro Glu Gly Cys Ser Gly Arg Val
20 25

<210> SEQ ID NO 51
<211> LENGTH: 27
<212> TYPE: PRT
<213> ORGANISM: Artificial Sequence
<220> FEATURE:
<223> OTHER INFORMATION: Av3bM148
<220> FEATURE:
<221> NAME/KEY: VARIANT
<222> LOCATION: (1)..(27)
<223> OTHER INFORMATION: Recombinant variant of Anemonia viridis Av3 peptide

<400> SEQUENCE: 51

Lys Ser Cys Cys Pro Cys Tyr Trp Gly Gly Cys Pro Trp Gly Gln Asn
1 5 10 15

Cys Tyr Pro Glu Gly Cys Ser Gly Pro Lys Gly
20 25

<210> SEQ ID NO 52
<211> LENGTH: 26
<212> TYPE: PRT
<213> ORGANISM: Artificial Sequence
<220> FEATURE:
<223> OTHER INFORMATION: Av3bM156
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 52

Lys Ser Cys Cys Pro Cys Tyr Trp Gly Gly Cys Pro Trp Gly Gln Asn
1 5 10 15

Cys Tyr Pro Glu Gly Cys Asp Gly Pro Ala
20 25

<210> SEQ ID NO 53
<211> LENGTH: 26
<212> TYPE: PRT
<213> ORGANISM: Artificial Sequence
<220> FEATURE:
<223> OTHER INFORMATION: Av3bM157
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 53

Lys Ser Cys Cys Pro Cys Tyr Trp Gly Gly Cys Pro Trp Gly Gln Asn
1 5 10 15

Cys Tyr Pro Glu Gly Cys Asp Gly Pro Thr
20 25

<210> SEQ ID NO 54
<211> LENGTH: 28
<212> TYPE: PRT
<213> ORGANISM: Artificial Sequence
<220> FEATURE:
<223> OTHER INFORMATION: Av3bM168
<220> FEATURE:

```
<221> NAME/KEY: VARIANT
<222> LOCATION: (1)..(28)
<223> OTHER INFORMATION: Recombinant variant of Anemonia viridis Av3
      peptide

<400> SEQUENCE: 54

Lys Ser Cys Cys Pro Cys Tyr Trp Gly Gly Cys Pro Trp Gly Gln Asn
1               5                   10                  15

Cys Tyr Pro Glu Gly Cys Ser Gly Pro Lys Val Ile
            20                  25


<210> SEQ ID NO 55
<211> LENGTH: 26
<212> TYPE: PRT
<213> ORGANISM: Artificial Sequence
<220> FEATURE:
<223> OTHER INFORMATION: Av3bM171
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 55

Lys Ser Cys Cys Pro Cys Tyr Trp Gly Gly Cys Pro Trp Gly Gln Asn
1               5                   10                  15

Cys Tyr Pro Glu Gly Cys Asp Gly Pro Gly
            20                  25


<210> SEQ ID NO 56
<211> LENGTH: 25
<212> TYPE: PRT
<213> ORGANISM: Artificial Sequence
<220> FEATURE:
<223> OTHER INFORMATION: Av3bM172
<220> FEATURE:
<221> NAME/KEY: VARIANT
<222> LOCATION: (1)..(25)
<223> OTHER INFORMATION: Recombinant variant of Anemonia viridis Av3
      peptide

<400> SEQUENCE: 56

Lys Ser Cys Cys Pro Cys Tyr Trp Gly Gly Cys Pro Trp Gly Gln Asn
1               5                   10                  15

Cys Tyr Pro Glu Gly Cys Asp Gly Pro
            20                  25


<210> SEQ ID NO 57
<211> LENGTH: 26
<212> TYPE: PRT
<213> ORGANISM: Artificial Sequence
<220> FEATURE:
<223> OTHER INFORMATION: Av3bM34
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 57

Ala Ser Cys Cys Pro Cys Tyr Trp Gly Gly Cys Pro Trp Gly Gln Asn
1               5                   10                  15

Cys Tyr Pro Glu Gly Cys Ser Gly Pro Lys
            20                  25


<210> SEQ ID NO 58
<211> LENGTH: 26
```

<212> TYPE: PRT
<213> ORGANISM: Artificial Sequence
<220> FEATURE:
<223> OTHER INFORMATION: Av3bM35
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 58

Asn Ser Cys Cys Pro Cys Tyr Trp Gly Gly Cys Pro Trp Gly Gln Asn
1 5 10 15

Cys Tyr Pro Glu Gly Cys Ser Gly Pro Lys
20 25

<210> SEQ ID NO 59
<211> LENGTH: 26
<212> TYPE: PRT
<213> ORGANISM: Artificial Sequence
<220> FEATURE:
<223> OTHER INFORMATION: Av3bM36
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 59

Asp Ser Cys Cys Pro Cys Tyr Trp Gly Gly Cys Pro Trp Gly Gln Asn
1 5 10 15

Cys Tyr Pro Glu Gly Cys Ser Gly Pro Lys
20 25

<210> SEQ ID NO 60
<211> LENGTH: 26
<212> TYPE: PRT
<213> ORGANISM: Artificial Sequence
<220> FEATURE:
<223> OTHER INFORMATION: Av3bM37
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 60

Glu Ser Cys Cys Pro Cys Tyr Trp Gly Gly Cys Pro Trp Gly Gln Asn
1 5 10 15

Cys Tyr Pro Glu Gly Cys Ser Gly Pro Lys
20 25

<210> SEQ ID NO 61
<211> LENGTH: 26
<212> TYPE: PRT
<213> ORGANISM: Artificial Sequence
<220> FEATURE:
<223> OTHER INFORMATION: Av3bM38
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 61

Gly Ser Cys Cys Pro Cys Tyr Trp Gly Gly Cys Pro Trp Gly Gln Asn
1 5 10 15

Cys Tyr Pro Glu Gly Cys Ser Gly Pro Lys 20 25

<210> SEQ ID NO 62
<211> LENGTH: 26
<212> TYPE: PRT
<213> ORGANISM: Artificial Sequence
<220> FEATURE:
<223> OTHER INFORMATION: Av3bM39
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 62

Ile Ser Cys Cys Pro Cys Tyr Trp Gly Gly Cys Pro Trp Gly Gln Asn
1 5 10 15

Cys Tyr Pro Glu Gly Cys Ser Gly Pro Lys
20 25

<210> SEQ ID NO 63
<211> LENGTH: 26
<212> TYPE: PRT
<213> ORGANISM: Artificial Sequence
<220> FEATURE:
<223> OTHER INFORMATION: Av3bM40
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 63

Leu Ser Cys Cys Pro Cys Tyr Trp Gly Gly Cys Pro Trp Gly Gln Asn
1 5 10 15

Cys Tyr Pro Glu Gly Cys Ser Gly Pro Lys
20 25

<210> SEQ ID NO 64
<211> LENGTH: 26
<212> TYPE: PRT
<213> ORGANISM: Artificial Sequence
<220> FEATURE:
<223> OTHER INFORMATION: Av3bM41
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 64

Met Ser Cys Cys Pro Cys Tyr Trp Gly Gly Cys Pro Trp Gly Gln Asn
1 5 10 15

Cys Tyr Pro Glu Gly Cys Ser Gly Pro Lys
20 25

<210> SEQ ID NO 65
<211> LENGTH: 26
<212> TYPE: PRT
<213> ORGANISM: Artificial Sequence
<220> FEATURE:
<223> OTHER INFORMATION: Av3bM42
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 65

Phe Ser Cys Cys Pro Cys Tyr Trp Gly Gly Cys Pro Trp Gly Gln Asn
1               5                   10                  15

Cys Tyr Pro Glu Gly Cys Ser Gly Pro Lys
            20                  25

<210> SEQ ID NO 66
<211> LENGTH: 26
<212> TYPE: PRT
<213> ORGANISM: Artificial Sequence
<220> FEATURE:
<223> OTHER INFORMATION: Av3bM43
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 66

Pro Ser Cys Cys Pro Cys Tyr Trp Gly Gly Cys Pro Trp Gly Gln Asn
1               5                   10                  15

Cys Tyr Pro Glu Gly Cys Ser Gly Pro Lys
            20                  25

<210> SEQ ID NO 67
<211> LENGTH: 26
<212> TYPE: PRT
<213> ORGANISM: Artificial Sequence
<220> FEATURE:
<223> OTHER INFORMATION: Av3bM44
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 67

Trp Ser Cys Cys Pro Cys Tyr Trp Gly Gly Cys Pro Trp Gly Gln Asn
1               5                   10                  15

Cys Tyr Pro Glu Gly Cys Ser Gly Pro Lys
            20                  25

<210> SEQ ID NO 68
<211> LENGTH: 26
<212> TYPE: PRT
<213> ORGANISM: Artificial Sequence
<220> FEATURE:
<223> OTHER INFORMATION: Av3bM45
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 68

Tyr Ser Cys Cys Pro Cys Tyr Trp Gly Gly Cys Pro Trp Gly Gln Asn
1               5                   10                  15

Cys Tyr Pro Glu Gly Cys Ser Gly Pro Lys
            20                  25

<210> SEQ ID NO 69
<211> LENGTH: 26
<212> TYPE: PRT
<213> ORGANISM: Artificial Sequence
<220> FEATURE:
<223> OTHER INFORMATION: Av3bM46
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 69

Val Ser Cys Cys Pro Cys Tyr Trp Gly Gly Cys Pro Trp Gly Gln Asn
1               5                   10                  15

Cys Tyr Pro Glu Gly Cys Ser Gly Pro Lys
            20                  25

<210> SEQ ID NO 70
<211> LENGTH: 26
<212> TYPE: PRT
<213> ORGANISM: Artificial Sequence
<220> FEATURE:
<223> OTHER INFORMATION: Av3bM47
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 70

Lys Ser Cys Cys Pro Cys Tyr Trp Arg Gly Cys Pro Trp Gly Gln Asn
1               5                   10                  15

Cys Tyr Pro Glu Gly Cys Ser Gly Pro Lys
            20                  25

<210> SEQ ID NO 71
<211> LENGTH: 26
<212> TYPE: PRT
<213> ORGANISM: Artificial Sequence
<220> FEATURE:
<223> OTHER INFORMATION: Av3bM48
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 71

Lys Ser Cys Cys Pro Cys Tyr Trp Asn Gly Cys Pro Trp Gly Gln Asn
1               5                   10                  15

Cys Tyr Pro Glu Gly Cys Ser Gly Pro Lys
            20                  25

<210> SEQ ID NO 72
<211> LENGTH: 26
<212> TYPE: PRT
<213> ORGANISM: Artificial Sequence
<220> FEATURE:
<223> OTHER INFORMATION: Av3bM49
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 72

Lys Ser Cys Cys Pro Cys Tyr Trp Asp Gly Cys Pro Trp Gly Gln Asn
1               5                   10                  15

Cys Tyr Pro Glu Gly Cys Ser Gly Pro Lys
            20                  25

<210> SEQ ID NO 73
<211> LENGTH: 26
<212> TYPE: PRT

<213> ORGANISM: Artificial Sequence
<220> FEATURE:
<223> OTHER INFORMATION: Av3bM50
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 73

Lys Ser Cys Cys Pro Cys Tyr Trp Glu Gly Cys Pro Trp Gly Gln Asn
1 5 10 15

Cys Tyr Pro Glu Gly Cys Ser Gly Pro Lys
20 25

<210> SEQ ID NO 74
<211> LENGTH: 26
<212> TYPE: PRT
<213> ORGANISM: Artificial Sequence
<220> FEATURE:
<223> OTHER INFORMATION: Av3bM51
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 74

Lys Ser Cys Cys Pro Cys Tyr Trp Gln Gly Cys Pro Trp Gly Gln Asn
1 5 10 15

Cys Tyr Pro Glu Gly Cys Ser Gly Pro Lys
20 25

<210> SEQ ID NO 75
<211> LENGTH: 26
<212> TYPE: PRT
<213> ORGANISM: Artificial Sequence
<220> FEATURE:
<223> OTHER INFORMATION: Av3bM52
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 75

Lys Ser Cys Cys Pro Cys Tyr Trp His Gly Cys Pro Trp Gly Gln Asn
1 5 10 15

Cys Tyr Pro Glu Gly Cys Ser Gly Pro Lys
20 25

<210> SEQ ID NO 76
<211> LENGTH: 26
<212> TYPE: PRT
<213> ORGANISM: Artificial Sequence
<220> FEATURE:
<223> OTHER INFORMATION: Av3bM53
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 76

Lys Ser Cys Cys Pro Cys Tyr Trp Ile Gly Cys Pro Trp Gly Gln Asn
1 5 10 15

Cys Tyr Pro Glu Gly Cys Ser Gly Pro Lys
20 25

<210> SEQ ID NO 77
<211> LENGTH: 26
<212> TYPE: PRT
<213> ORGANISM: Artificial Sequence
<220> FEATURE:
<223> OTHER INFORMATION: Av3bM54
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 77

Lys Ser Cys Cys Pro Cys Tyr Trp Leu Gly Cys Pro Trp Gly Gln Asn
1 5 10 15

Cys Tyr Pro Glu Gly Cys Ser Gly Pro Lys
20 25

<210> SEQ ID NO 78
<211> LENGTH: 26
<212> TYPE: PRT
<213> ORGANISM: Artificial Sequence
<220> FEATURE:
<223> OTHER INFORMATION: Av3bM55
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 78

Lys Ser Cys Cys Pro Cys Tyr Trp Lys Gly Cys Pro Trp Gly Gln Asn
1 5 10 15

Cys Tyr Pro Glu Gly Cys Ser Gly Pro Lys
20 25

<210> SEQ ID NO 79
<211> LENGTH: 26
<212> TYPE: PRT
<213> ORGANISM: Artificial Sequence
<220> FEATURE:
<223> OTHER INFORMATION: Av3bM56
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 79

Lys Ser Cys Cys Pro Cys Tyr Trp Met Gly Cys Pro Trp Gly Gln Asn
1 5 10 15

Cys Tyr Pro Glu Gly Cys Ser Gly Pro Lys
20 25

<210> SEQ ID NO 80
<211> LENGTH: 26
<212> TYPE: PRT
<213> ORGANISM: Artificial Sequence
<220> FEATURE:
<223> OTHER INFORMATION: Av3bM57
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 80

Lys Ser Cys Cys Pro Cys Tyr Trp Phe Gly Cys Pro Trp Gly Gln Asn
1 5 10 15

Cys Tyr Pro Glu Gly Cys Ser Gly Pro Lys
20 25

<210> SEQ ID NO 81
<211> LENGTH: 26
<212> TYPE: PRT
<213> ORGANISM: Artificial Sequence
<220> FEATURE:
<223> OTHER INFORMATION: Av3bM58
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 81

Lys Ser Cys Cys Pro Cys Tyr Trp Ser Gly Cys Pro Trp Gly Gln Asn
1 5 10 15

Cys Tyr Pro Glu Gly Cys Ser Gly Pro Lys
20 25

<210> SEQ ID NO 82
<211> LENGTH: 26
<212> TYPE: PRT
<213> ORGANISM: Artificial Sequence
<220> FEATURE:
<223> OTHER INFORMATION: Av3bM59
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 82

Lys Ser Cys Cys Pro Cys Tyr Trp Thr Gly Cys Pro Trp Gly Gln Asn
1 5 10 15

Cys Tyr Pro Glu Gly Cys Ser Gly Pro Lys
20 25

<210> SEQ ID NO 83
<211> LENGTH: 26
<212> TYPE: PRT
<213> ORGANISM: Artificial Sequence
<220> FEATURE:
<223> OTHER INFORMATION: Av3bM60
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 83

Lys Ser Cys Cys Pro Cys Tyr Trp Trp Gly Cys Pro Trp Gly Gln Asn
1 5 10 15

Cys Tyr Pro Glu Gly Cys Ser Gly Pro Lys
20 25

<210> SEQ ID NO 84
<211> LENGTH: 26
<212> TYPE: PRT
<213> ORGANISM: Artificial Sequence
<220> FEATURE:
<223> OTHER INFORMATION: Av3bM61
<220> FEATURE:
<221> NAME/KEY: VARIANT
<222> LOCATION: (1)..(26)

<223> OTHER INFORMATION: Recombinant variant of Anemonia viridis Av3
peptide

<400> SEQUENCE: 84

Lys Ser Cys Cys Pro Cys Tyr Trp Tyr Gly Cys Pro Trp Gly Gln Asn
1 5 10 15

Cys Tyr Pro Glu Gly Cys Ser Gly Pro Lys
20 25

<210> SEQ ID NO 85
<211> LENGTH: 26
<212> TYPE: PRT
<213> ORGANISM: Artificial Sequence
<220> FEATURE:
<223> OTHER INFORMATION: Av3bM62
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 85

Lys Ser Cys Cys Pro Cys Tyr Trp Val Gly Cys Pro Trp Gly Gln Asn
1 5 10 15

Cys Tyr Pro Glu Gly Cys Ser Gly Pro Lys
20 25

<210> SEQ ID NO 86
<211> LENGTH: 26
<212> TYPE: PRT
<213> ORGANISM: Artificial Sequence
<220> FEATURE:
<223> OTHER INFORMATION: Av3bM63
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 86

Lys Ser Cys Cys Pro Cys Tyr Trp Gly Gly Cys Pro Trp Gly Gln Asn
1 5 10 15

Cys Tyr Pro Ala Gly Cys Ser Gly Pro Lys
20 25

<210> SEQ ID NO 87
<211> LENGTH: 26
<212> TYPE: PRT
<213> ORGANISM: Artificial Sequence
<220> FEATURE:
<223> OTHER INFORMATION: Av3bM64
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 87

Lys Ser Cys Cys Pro Cys Tyr Trp Gly Gly Cys Pro Trp Gly Gln Asn
1 5 10 15

Cys Tyr Pro Arg Gly Cys Ser Gly Pro Lys
20 25

<210> SEQ ID NO 88
<211> LENGTH: 26
<212> TYPE: PRT
<213> ORGANISM: Artificial Sequence
<220> FEATURE:
<223> OTHER INFORMATION: Av3bM65
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 88

Lys Ser Cys Cys Pro Cys Tyr Trp Gly Gly Cys Pro Trp Gly Gln Asn
1               5                   10                  15

Cys Tyr Pro Asp Gly Cys Ser Gly Pro Lys
            20                  25

<210> SEQ ID NO 89
<211> LENGTH: 26
<212> TYPE: PRT
<213> ORGANISM: Artificial Sequence
<220> FEATURE:
<223> OTHER INFORMATION: Av3bM66
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 89

Lys Ser Cys Cys Pro Cys Tyr Trp Gly Gly Cys Pro Trp Gly Gln Asn
1               5                   10                  15

Cys Tyr Pro Gln Gly Cys Ser Gly Pro Lys
            20                  25

<210> SEQ ID NO 90
<211> LENGTH: 26
<212> TYPE: PRT
<213> ORGANISM: Artificial Sequence
<220> FEATURE:
<223> OTHER INFORMATION: Av3bM67
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 90

Lys Ser Cys Cys Pro Cys Tyr Trp Gly Gly Cys Pro Trp Gly Gln Asn
1               5                   10                  15

Cys Tyr Pro Gly Gly Cys Ser Gly Pro Lys
            20                  25

<210> SEQ ID NO 91
<211> LENGTH: 26
<212> TYPE: PRT
<213> ORGANISM: Artificial Sequence
<220> FEATURE:
<223> OTHER INFORMATION: Av3bM68
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 91

Lys Ser Cys Cys Pro Cys Tyr Trp Gly Gly Cys Pro Trp Gly Gln Asn
1               5                   10                  15

Cys Tyr Pro His Gly Cys Ser Gly Pro Lys
            20                  25

<210> SEQ ID NO 92
<211> LENGTH: 26
<212> TYPE: PRT
<213> ORGANISM: Artificial Sequence
<220> FEATURE:
<223> OTHER INFORMATION: Av3bM69
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 92

```
Lys Ser Cys Cys Pro Cys Tyr Trp Gly Gly Cys Pro Trp Gly Gln Asn
1               5                   10                  15

Cys Tyr Pro Ile Gly Cys Ser Gly Pro Lys
            20                  25
```

<210> SEQ ID NO 93
<211> LENGTH: 26
<212> TYPE: PRT
<213> ORGANISM: Artificial Sequence
<220> FEATURE:
<223> OTHER INFORMATION: Av3bM70
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 93

```
Lys Ser Cys Cys Pro Cys Tyr Trp Gly Gly Cys Pro Trp Gly Gln Asn
1               5                   10                  15

Cys Tyr Pro Leu Gly Cys Ser Gly Pro Lys
            20                  25
```

<210> SEQ ID NO 94
<211> LENGTH: 26
<212> TYPE: PRT
<213> ORGANISM: Artificial Sequence
<220> FEATURE:
<223> OTHER INFORMATION: Av3bM71
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 94

```
Lys Ser Cys Cys Pro Cys Tyr Trp Gly Gly Cys Pro Trp Gly Gln Asn
1               5                   10                  15

Cys Tyr Pro Lys Gly Cys Ser Gly Pro Lys
            20                  25
```

<210> SEQ ID NO 95
<211> LENGTH: 26
<212> TYPE: PRT
<213> ORGANISM: Artificial Sequence
<220> FEATURE:
<223> OTHER INFORMATION: Av3bM72
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 95

```
Lys Ser Cys Cys Pro Cys Tyr Trp Gly Gly Cys Pro Trp Gly Gln Asn
```

```
1               5                   10                  15

Cys Tyr Pro Met Gly Cys Ser Gly Pro Lys
            20                  25


<210> SEQ ID NO 96
<211> LENGTH: 26
<212> TYPE: PRT
<213> ORGANISM: Artificial Sequence
<220> FEATURE:
<223> OTHER INFORMATION: Av3bM73
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 96

Lys Ser Cys Cys Pro Cys Tyr Trp Gly Gly Cys Pro Trp Gly Gln Asn
1               5                   10                  15

Cys Tyr Pro Phe Gly Cys Ser Gly Pro Lys
            20                  25


<210> SEQ ID NO 97
<211> LENGTH: 26
<212> TYPE: PRT
<213> ORGANISM: Artificial Sequence
<220> FEATURE:
<223> OTHER INFORMATION: Av3bM74
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 97

Lys Ser Cys Cys Pro Cys Tyr Trp Gly Gly Cys Pro Trp Gly Gln Asn
1               5                   10                  15

Cys Tyr Pro Pro Gly Cys Ser Gly Pro Lys
            20                  25


<210> SEQ ID NO 98
<211> LENGTH: 26
<212> TYPE: PRT
<213> ORGANISM: Artificial Sequence
<220> FEATURE:
<223> OTHER INFORMATION: Av3bM75
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 98

Lys Ser Cys Cys Pro Cys Tyr Trp Gly Gly Cys Pro Trp Gly Gln Asn
1               5                   10                  15

Cys Tyr Pro Ser Gly Cys Ser Gly Pro Lys
            20                  25


<210> SEQ ID NO 99
<211> LENGTH: 26
<212> TYPE: PRT
<213> ORGANISM: Artificial Sequence
<220> FEATURE:
<223> OTHER INFORMATION: Av3bM76
<220> FEATURE:
<221> NAME/KEY: VARIANT
<222> LOCATION: (1)..(26)
<223> OTHER INFORMATION: Recombinant variant of Anemonia viridis Av3
```

peptide

<400> SEQUENCE: 99

Lys Ser Cys Cys Pro Cys Tyr Trp Gly Gly Cys Pro Trp Gly Gln Asn
1 5 10 15

Cys Tyr Pro Thr Gly Cys Ser Gly Pro Lys
20 25

<210> SEQ ID NO 100
<211> LENGTH: 26
<212> TYPE: PRT
<213> ORGANISM: Artificial Sequence
<220> FEATURE:
<223> OTHER INFORMATION: Av3bM77
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 100

Lys Ser Cys Cys Pro Cys Tyr Trp Gly Gly Cys Pro Trp Gly Gln Asn
1 5 10 15

Cys Tyr Pro Trp Gly Cys Ser Gly Pro Lys
20 25

<210> SEQ ID NO 101
<211> LENGTH: 26
<212> TYPE: PRT
<213> ORGANISM: Artificial Sequence
<220> FEATURE:
<223> OTHER INFORMATION: Av3bM78
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 101

Lys Ser Cys Cys Pro Cys Tyr Trp Gly Gly Cys Pro Trp Gly Gln Asn
1 5 10 15

Cys Tyr Pro Tyr Gly Cys Ser Gly Pro Lys
20 25

<210> SEQ ID NO 102
<211> LENGTH: 26
<212> TYPE: PRT
<213> ORGANISM: Artificial Sequence
<220> FEATURE:
<223> OTHER INFORMATION: Av3bM79
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 102

Lys Ser Cys Cys Pro Cys Tyr Trp Gly Gly Cys Pro Trp Gly Gln Asn
1 5 10 15

Cys Tyr Pro Val Gly Cys Ser Gly Pro Lys
20 25

<210> SEQ ID NO 103
<211> LENGTH: 26
<212> TYPE: PRT
<213> ORGANISM: Artificial Sequence
<220> FEATURE:

```
<223> OTHER INFORMATION: Av3bM80
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 103

Lys Ser Cys Cys Pro Cys Tyr Trp Gly Gly Cys Pro Trp Gly Gln Asn
1               5                   10                  15

Cys Tyr Pro Glu Gly Cys Ala Gly Pro Lys
            20                  25


<210> SEQ ID NO 104
<211> LENGTH: 26
<212> TYPE: PRT
<213> ORGANISM: Artificial Sequence
<220> FEATURE:
<223> OTHER INFORMATION: Av3bM81
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 104

Lys Ser Cys Cys Pro Cys Tyr Trp Gly Gly Cys Pro Trp Gly Gln Asn
1               5                   10                  15

Cys Tyr Pro Glu Gly Cys Arg Gly Pro Lys
            20                  25


<210> SEQ ID NO 105
<211> LENGTH: 26
<212> TYPE: PRT
<213> ORGANISM: Artificial Sequence
<220> FEATURE:
<223> OTHER INFORMATION: Av3bM82
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 105

Lys Ser Cys Cys Pro Cys Tyr Trp Gly Gly Cys Pro Trp Gly Gln Asn
1               5                   10                  15

Cys Tyr Pro Glu Gly Cys Asn Gly Pro Lys
            20                  25


<210> SEQ ID NO 106
<211> LENGTH: 26
<212> TYPE: PRT
<213> ORGANISM: Artificial Sequence
<220> FEATURE:
<223> OTHER INFORMATION: Av3bM83
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 106

Lys Ser Cys Cys Pro Cys Tyr Trp Gly Gly Cys Pro Trp Gly Gln Asn
1               5                   10                  15

Cys Tyr Pro Glu Gly Cys Glu Gly Pro Lys
            20                  25
```

<210> SEQ ID NO 107
<211> LENGTH: 26
<212> TYPE: PRT
<213> ORGANISM: Artificial Sequence
<220> FEATURE:
<223> OTHER INFORMATION: Av3bM84
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 107

Lys Ser Cys Cys Pro Cys Tyr Trp Gly Gly Cys Pro Trp Gly Gln Asn
1 5 10 15

Cys Tyr Pro Glu Gly Cys Gln Gly Pro Lys
20 25

<210> SEQ ID NO 108
<211> LENGTH: 26
<212> TYPE: PRT
<213> ORGANISM: Artificial Sequence
<220> FEATURE:
<223> OTHER INFORMATION: Av3bM85
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 108

Lys Ser Cys Cys Pro Cys Tyr Trp Gly Gly Cys Pro Trp Gly Gln Asn
1 5 10 15

Cys Tyr Pro Glu Gly Cys Gly Gly Pro Lys
20 25

<210> SEQ ID NO 109
<211> LENGTH: 26
<212> TYPE: PRT
<213> ORGANISM: Artificial Sequence
<220> FEATURE:
<223> OTHER INFORMATION: Av3bM86
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 109

Lys Ser Cys Cys Pro Cys Tyr Trp Gly Gly Cys Pro Trp Gly Gln Asn
1 5 10 15

Cys Tyr Pro Glu Gly Cys His Gly Pro Lys
20 25

<210> SEQ ID NO 110
<211> LENGTH: 26
<212> TYPE: PRT
<213> ORGANISM: Artificial Sequence
<220> FEATURE:
<223> OTHER INFORMATION: Av3bM87
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 110

Lys Ser Cys Cys Pro Cys Tyr Trp Gly Gly Cys Pro Trp Gly Gln Asn
1 5 10 15

```
Cys Tyr Pro Glu Gly Cys Ile Gly Pro Lys
            20                  25


<210> SEQ ID NO 111
<211> LENGTH: 26
<212> TYPE: PRT
<213> ORGANISM: Artificial Sequence
<220> FEATURE:
<223> OTHER INFORMATION: Av3bM88
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 111

Lys Ser Cys Cys Pro Cys Tyr Trp Gly Gly Cys Pro Trp Gly Gln Asn
1               5                   10                  15

Cys Tyr Pro Glu Gly Cys Leu Gly Pro Lys
            20                  25


<210> SEQ ID NO 112
<211> LENGTH: 26
<212> TYPE: PRT
<213> ORGANISM: Artificial Sequence
<220> FEATURE:
<223> OTHER INFORMATION: Av3bM89
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 112

Lys Ser Cys Cys Pro Cys Tyr Trp Gly Gly Cys Pro Trp Gly Gln Asn
1               5                   10                  15

Cys Tyr Pro Glu Gly Cys Lys Gly Pro Lys
            20                  25


<210> SEQ ID NO 113
<211> LENGTH: 26
<212> TYPE: PRT
<213> ORGANISM: Artificial Sequence
<220> FEATURE:
<223> OTHER INFORMATION: Av3bM90
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 113

Lys Ser Cys Cys Pro Cys Tyr Trp Gly Gly Cys Pro Trp Gly Gln Asn
1               5                   10                  15

Cys Tyr Pro Glu Gly Cys Met Gly Pro Lys
            20                  25


<210> SEQ ID NO 114
<211> LENGTH: 26
<212> TYPE: PRT
<213> ORGANISM: Artificial Sequence
<220> FEATURE:
<223> OTHER INFORMATION: Av3bM91
<220> FEATURE:
<221> NAME/KEY: VARIANT
<222> LOCATION: (1)..(26)
<223> OTHER INFORMATION: Recombinant variant of Anemonia viridis Av3
      peptide
```

<400> SEQUENCE: 114

```
Lys Ser Cys Cys Pro Cys Tyr Trp Gly Gly Cys Pro Trp Gly Gln Asn
1               5                   10                  15

Cys Tyr Pro Glu Gly Cys Phe Gly Pro Lys
            20                  25
```

<210> SEQ ID NO 115
<211> LENGTH: 26
<212> TYPE: PRT
<213> ORGANISM: Artificial Sequence
<220> FEATURE:
<223> OTHER INFORMATION: Av3bM92
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 115

```
Lys Ser Cys Cys Pro Cys Tyr Trp Gly Gly Cys Pro Trp Gly Gln Asn
1               5                   10                  15

Cys Tyr Pro Glu Gly Cys Pro Gly Pro Lys
            20                  25
```

<210> SEQ ID NO 116
<211> LENGTH: 26
<212> TYPE: PRT
<213> ORGANISM: Artificial Sequence
<220> FEATURE:
<223> OTHER INFORMATION: Av3bM93
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 116

```
Lys Ser Cys Cys Pro Cys Tyr Trp Gly Gly Cys Pro Trp Gly Gln Asn
1               5                   10                  15

Cys Tyr Pro Glu Gly Cys Thr Gly Pro Lys
            20                  25
```

<210> SEQ ID NO 117
<211> LENGTH: 26
<212> TYPE: PRT
<213> ORGANISM: Artificial Sequence
<220> FEATURE:
<223> OTHER INFORMATION: Av3bM94
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 117

```
Lys Ser Cys Cys Pro Cys Tyr Trp Gly Gly Cys Pro Trp Gly Gln Asn
1               5                   10                  15

Cys Tyr Pro Glu Gly Cys Trp Gly Pro Lys
            20                  25
```

<210> SEQ ID NO 118
<211> LENGTH: 26
<212> TYPE: PRT
<213> ORGANISM: Artificial Sequence
<220> FEATURE:
<223> OTHER INFORMATION: Av3bM95

<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 118

Lys Ser Cys Cys Pro Cys Tyr Trp Gly Gly Cys Pro Trp Gly Gln Asn
1 5 10 15

Cys Tyr Pro Glu Gly Cys Tyr Gly Pro Lys
20 25

<210> SEQ ID NO 119
<211> LENGTH: 26
<212> TYPE: PRT
<213> ORGANISM: Artificial Sequence
<220> FEATURE:
<223> OTHER INFORMATION: Av3bM96
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 119

Lys Ser Cys Cys Pro Cys Tyr Trp Gly Gly Cys Pro Trp Gly Gln Asn
1 5 10 15

Cys Tyr Pro Glu Gly Cys Val Gly Pro Lys
20 25

<210> SEQ ID NO 120
<211> LENGTH: 26
<212> TYPE: PRT
<213> ORGANISM: Artificial Sequence
<220> FEATURE:
<223> OTHER INFORMATION: Av3bM105
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 120

Lys Ser Cys Cys Pro Cys Tyr Trp Gly Gly Cys Pro Trp Gly Gln Asn
1 5 10 15

Cys Tyr Pro Glu Gly Cys Ser Gly Pro Ile
20 25

<210> SEQ ID NO 121
<211> LENGTH: 26
<212> TYPE: PRT
<213> ORGANISM: Artificial Sequence
<220> FEATURE:
<223> OTHER INFORMATION: Av3bM106
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 121

Lys Ser Cys Cys Pro Cys Tyr Trp Gly Gly Cys Pro Trp Gly Gln Asn
1 5 10 15

Cys Tyr Pro Glu Gly Cys Ser Gly Pro Leu
20 25

<210> SEQ ID NO 122

```
<211> LENGTH: 26
<212> TYPE: PRT
<213> ORGANISM: Artificial Sequence
<220> FEATURE:
<223> OTHER INFORMATION: Av3bM107
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 122

Lys Ser Cys Cys Pro Cys Tyr Trp Gly Gly Cys Pro Trp Gly Gln Asn
1               5                   10                  15

Cys Tyr Pro Glu Gly Cys Ser Gly Pro Met
            20                  25


<210> SEQ ID NO 123
<211> LENGTH: 26
<212> TYPE: PRT
<213> ORGANISM: Artificial Sequence
<220> FEATURE:
<223> OTHER INFORMATION: Av3bM108
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 123

Lys Ser Cys Cys Pro Cys Tyr Trp Gly Gly Cys Pro Trp Gly Gln Asn
1               5                   10                  15

Cys Tyr Pro Glu Gly Cys Ser Gly Pro Phe
            20                  25


<210> SEQ ID NO 124
<211> LENGTH: 26
<212> TYPE: PRT
<213> ORGANISM: Artificial Sequence
<220> FEATURE:
<223> OTHER INFORMATION: Av3bM109
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 124

Lys Ser Cys Cys Pro Cys Tyr Trp Gly Gly Cys Pro Trp Gly Gln Asn
1               5                   10                  15

Cys Tyr Pro Glu Gly Cys Ser Gly Pro Pro
            20                  25


<210> SEQ ID NO 125
<211> LENGTH: 26
<212> TYPE: PRT
<213> ORGANISM: Artificial Sequence
<220> FEATURE:
<223> OTHER INFORMATION: Av3bM110
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 125

Lys Ser Cys Cys Pro Cys Tyr Trp Gly Gly Cys Pro Trp Gly Gln Asn
1               5                   10                  15
```

```
Cys Tyr Pro Glu Gly Cys Ser Gly Pro Ser
            20                  25


<210> SEQ ID NO 126
<211> LENGTH: 26
<212> TYPE: PRT
<213> ORGANISM: Artificial Sequence
<220> FEATURE:
<223> OTHER INFORMATION: Av3bM112
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 126

Lys Ser Cys Cys Pro Cys Tyr Trp Gly Gly Cys Pro Trp Gly Gln Asn
1               5                   10                  15

Cys Tyr Pro Glu Gly Cys Ser Gly Pro Trp
            20                  25


<210> SEQ ID NO 127
<211> LENGTH: 26
<212> TYPE: PRT
<213> ORGANISM: Artificial Sequence
<220> FEATURE:
<223> OTHER INFORMATION: Av3bM113
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 127

Lys Ser Cys Cys Pro Cys Tyr Trp Gly Gly Cys Pro Trp Gly Gln Asn
1               5                   10                  15

Cys Tyr Pro Glu Gly Cys Ser Gly Pro Tyr
            20                  25


<210> SEQ ID NO 128
<211> LENGTH: 26
<212> TYPE: PRT
<213> ORGANISM: Artificial Sequence
<220> FEATURE:
<223> OTHER INFORMATION: Av3bM114
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 128

Lys Ser Cys Cys Pro Cys Tyr Trp Gly Gly Cys Pro Trp Gly Gln Asn
1               5                   10                  15

Cys Tyr Pro Glu Gly Cys Ser Gly Pro Val
            20                  25


<210> SEQ ID NO 129
<211> LENGTH: 26
<212> TYPE: PRT
<213> ORGANISM: Artificial Sequence
<220> FEATURE:
<223> OTHER INFORMATION: Av3bM115
<220> FEATURE:
<221> NAME/KEY: VARIANT
<222> LOCATION: (1)..(26)
<223> OTHER INFORMATION: Recombinant variant of Anemonia viridis Av3
      peptide
```

<400> SEQUENCE: 129

His Ser Cys Cys Pro Cys Tyr Trp Pro Gly Cys Pro Trp Gly Gln Asn
1               5                   10                  15

Cys Tyr Pro Asp Gly Cys Asp Gly Pro Lys
            20                  25

<210> SEQ ID NO 130
<211> LENGTH: 26
<212> TYPE: PRT
<213> ORGANISM: Artificial Sequence
<220> FEATURE:
<223> OTHER INFORMATION: Av3bM116
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 130

Lys Ser Cys Cys Pro Cys Tyr Trp Pro Gly Cys Pro Trp Gly Gln Asn
1               5                   10                  15

Cys Tyr Pro Asn Gly Cys Asp Gly Pro Arg
            20                  25

<210> SEQ ID NO 131
<211> LENGTH: 26
<212> TYPE: PRT
<213> ORGANISM: Artificial Sequence
<220> FEATURE:
<223> OTHER INFORMATION: Av3bM117
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 131

Lys Ser Cys Cys Pro Cys Tyr Trp Pro Gly Cys Pro Trp Gly Gln Asn
1               5                   10                  15

Cys Tyr Pro Asp Gly Cys Asp Gly Pro Arg
            20                  25

<210> SEQ ID NO 132
<211> LENGTH: 26
<212> TYPE: PRT
<213> ORGANISM: Artificial Sequence
<220> FEATURE:
<223> OTHER INFORMATION: Av3bM118
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 132

Lys Ser Cys Cys Pro Cys Tyr Trp Pro Gly Cys Pro Trp Gly Gln Asn
1               5                   10                  15

Cys Tyr Pro Asn Gly Cys Asp Gly Pro Thr
            20                  25

<210> SEQ ID NO 133
<211> LENGTH: 26
<212> TYPE: PRT
<213> ORGANISM: Artificial Sequence
<220> FEATURE:
<223> OTHER INFORMATION: Av3bM119
<220> FEATURE:

```
<221> NAME/KEY: VARIANT
<222> LOCATION: (1)..(26)
<223> OTHER INFORMATION: Recombinant variant of Anemonia viridis Av3
      peptide

<400> SEQUENCE: 133

Lys Ser Cys Cys Pro Cys Tyr Trp Pro Gly Cys Pro Trp Gly Gln Asn
1               5                   10                  15

Cys Tyr Pro Asn Gly Cys Arg Gly Pro Thr
            20                  25


<210> SEQ ID NO 134
<211> LENGTH: 26
<212> TYPE: PRT
<213> ORGANISM: Artificial Sequence
<220> FEATURE:
<223> OTHER INFORMATION: Av3bM120
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 134

Lys Ser Cys Cys Pro Cys Tyr Trp Pro Gly Cys Pro Trp Gly Gln Asn
1               5                   10                  15

Cys Tyr Pro Asn Gly Cys Arg Gly Pro Arg
            20                  25


<210> SEQ ID NO 135
<211> LENGTH: 26
<212> TYPE: PRT
<213> ORGANISM: Artificial Sequence
<220> FEATURE:
<223> OTHER INFORMATION: Av3bM121
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 135

Lys Ser Cys Cys Pro Cys Tyr Trp Gly Gly Cys Pro Trp Gly Gln Asn
1               5                   10                  15

Cys Tyr Pro Glu Gly Cys Ser Gly Pro Asp
            20                  25


<210> SEQ ID NO 136
<211> LENGTH: 26
<212> TYPE: PRT
<213> ORGANISM: Artificial Sequence
<220> FEATURE:
<223> OTHER INFORMATION: Av3bM122
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 136

Lys Ser Cys Cys Pro Cys Tyr Trp Gly Gly Cys Pro Trp Gly Gln Asn
1               5                   10                  15

Cys Tyr Pro Glu Gly Cys Ser Gly Pro Glu
            20                  25


<210> SEQ ID NO 137
<211> LENGTH: 26
```

<212> TYPE: PRT
<213> ORGANISM: Artificial Sequence
<220> FEATURE:
<223> OTHER INFORMATION: Av3bM123
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 137

Lys Ser Cys Cys Pro Cys Tyr Trp Pro Gly Cys Pro Trp Gly Gln Asn
1 5 10 15

Cys Tyr Pro Glu Gly Cys Ser Gly Pro Asp
20 25

<210> SEQ ID NO 138
<211> LENGTH: 26
<212> TYPE: PRT
<213> ORGANISM: Artificial Sequence
<220> FEATURE:
<223> OTHER INFORMATION: Av3bM124
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 138

Lys Ser Cys Cys Pro Cys Tyr Trp Pro Gly Cys Pro Trp Gly Gln Asn
1 5 10 15

Cys Tyr Pro Glu Gly Cys Ser Gly Pro Glu
20 25

<210> SEQ ID NO 139
<211> LENGTH: 26
<212> TYPE: PRT
<213> ORGANISM: Artificial Sequence
<220> FEATURE:
<223> OTHER INFORMATION: Av3bM125
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 139

Lys Ser Cys Cys Pro Cys Tyr Trp Pro Gly Cys Pro Trp Gly Gln Asn
1 5 10 15

Cys Tyr Pro Glu Gly Cys Arg Gly Pro Asp
20 25

<210> SEQ ID NO 140
<211> LENGTH: 26
<212> TYPE: PRT
<213> ORGANISM: Artificial Sequence
<220> FEATURE:
<223> OTHER INFORMATION: Av3bM126
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 140

Lys Ser Cys Cys Pro Cys Tyr Trp Pro Gly Cys Pro Trp Gly Gln Asn
1 5 10 15

Cys Tyr Pro Glu Gly Cys Arg Gly Pro Glu 20 25

<210> SEQ ID NO 141
<211> LENGTH: 27
<212> TYPE: PRT
<213> ORGANISM: Artificial Sequence
<220> FEATURE:
<223> OTHER INFORMATION: Av3bM127
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 141

Gly Ser Cys Cys Pro Cys Gly Asp Gly Gly Cys Gln Thr Gly Gln Arg
1 5 10 15

Cys Phe Pro Glu Gly Cys Asp Gly Pro Lys Val
20 25

<210> SEQ ID NO 142
<211> LENGTH: 26
<212> TYPE: PRT
<213> ORGANISM: Artificial Sequence
<220> FEATURE:
<223> OTHER INFORMATION: Av3bM128
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 142

Gly Ser Cys Cys Pro Cys Gly Asp Gly Gly Cys Gln Thr Gly Gln Arg
1 5 10 15

Cys Phe Pro Glu Gly Cys Asp Gly Pro Lys
20 25

<210> SEQ ID NO 143
<211> LENGTH: 26
<212> TYPE: PRT
<213> ORGANISM: Artificial Sequence
<220> FEATURE:
<223> OTHER INFORMATION: Av3bM129
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 143

Gly Ser Cys Cys Pro Cys His Asp Gly Gly Cys Trp Ser Gly Gln Arg
1 5 10 15

Cys Tyr Pro Glu Gly Cys Asp Gly Pro Lys
20 25

<210> SEQ ID NO 144
<211> LENGTH: 26
<212> TYPE: PRT
<213> ORGANISM: Artificial Sequence
<220> FEATURE:
<223> OTHER INFORMATION: Av3bM130
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 144

Gly Ser Cys Cys Pro Cys Gly Gly Gly Gly Cys Pro His Gly Gln Arg
1 5 10 15

Cys Tyr Pro Glu Gly Cys Asp Gly Pro Lys
20 25

<210> SEQ ID NO 145
<211> LENGTH: 26
<212> TYPE: PRT
<213> ORGANISM: Artificial Sequence
<220> FEATURE:
<223> OTHER INFORMATION: Av3bM131
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 145

Gly Ser Cys Cys Pro Cys Gly Asp Gly Gly Cys Gln Trp Gly Gln Arg
1 5 10 15

Cys Tyr Pro Glu Gly Cys Asp Gly Pro Lys
20 25

<210> SEQ ID NO 146
<211> LENGTH: 26
<212> TYPE: PRT
<213> ORGANISM: Artificial Sequence
<220> FEATURE:
<223> OTHER INFORMATION: Av3bM132
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 146

His Ser Cys Cys Pro Cys Trp Trp Gly Gly Cys Ile Trp Gly Gln Arg
1 5 10 15

Cys Tyr Pro Glu Gly Cys Ser Gly Pro Lys
20 25

<210> SEQ ID NO 147
<211> LENGTH: 26
<212> TYPE: PRT
<213> ORGANISM: Artificial Sequence
<220> FEATURE:
<223> OTHER INFORMATION: Av3bM133
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 147

His Ser Cys Cys Pro Cys Gly Asp Gly Gly Cys Pro Asn Gly Gln Arg
1 5 10 15

Cys Tyr Pro Glu Gly Cys Asp Gly Pro Lys
20 25

<210> SEQ ID NO 148
<211> LENGTH: 26
<212> TYPE: PRT
<213> ORGANISM: Artificial Sequence
<220> FEATURE:
<223> OTHER INFORMATION: Av3bM134
<220> FEATURE:
<221> NAME/KEY: VARIANT

```
<222> LOCATION: (1)..(26)
<223> OTHER INFORMATION: Recombinant variant of Anemonia viridis Av3
      peptide

<400> SEQUENCE: 148

His Ser Cys Cys Pro Cys Phe Asp Gly Gly Cys Pro Phe Gly Gln Arg
1               5                   10                  15

Cys Phe Pro Glu Gly Cys Asp Gly Pro Lys
            20                  25


<210> SEQ ID NO 149
<211> LENGTH: 26
<212> TYPE: PRT
<213> ORGANISM: Artificial Sequence
<220> FEATURE:
<223> OTHER INFORMATION: Av3bM135
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 149

His Ser Cys Cys Pro Cys Gly Ala Gly Gly Cys Pro Val Gly Gln Arg
1               5                   10                  15

Cys Tyr Pro Glu Gly Cys Asp Gly Pro Lys
            20                  25


<210> SEQ ID NO 150
<211> LENGTH: 26
<212> TYPE: PRT
<213> ORGANISM: Artificial Sequence
<220> FEATURE:
<223> OTHER INFORMATION: Av3bM136
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 150

Gln Ser Cys Cys Pro Cys Tyr Trp Gly Gly Cys His His Gly Gln Asp
1               5                   10                  15

Cys Gly Pro Glu Gly Cys Ser Gly Pro Lys
            20                  25


<210> SEQ ID NO 151
<211> LENGTH: 26
<212> TYPE: PRT
<213> ORGANISM: Artificial Sequence
<220> FEATURE:
<223> OTHER INFORMATION: Av3bM137
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 151

Lys Ser Cys Cys Pro Cys Trp Trp Gly Gly Cys Asp Trp Gly Gln Asp
1               5                   10                  15

Cys Gly Pro Glu Gly Cys Ser Gly Pro Lys
            20                  25


<210> SEQ ID NO 152
<211> LENGTH: 26
<212> TYPE: PRT
```

<213> ORGANISM: Artificial Sequence
<220> FEATURE:
<223> OTHER INFORMATION: Av3bM138
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 152

Lys Ser Cys Cys Pro Cys Tyr Trp Gly Gly Cys His Thr Gly Gln Asp
1 5 10 15

Cys Gly Pro Glu Gly Cys Ser Gly Pro Lys
20 25

<210> SEQ ID NO 153
<211> LENGTH: 26
<212> TYPE: PRT
<213> ORGANISM: Artificial Sequence
<220> FEATURE:
<223> OTHER INFORMATION: Av3bM143
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 153

His Ser Cys Cys Pro Cys Tyr Trp Gly Gly Cys Pro Trp Gly Gln Asn
1 5 10 15

Cys Tyr Pro Glu Gly Cys Asp Gly Pro Lys
20 25

<210> SEQ ID NO 154
<211> LENGTH: 27
<212> TYPE: PRT
<213> ORGANISM: Artificial Sequence
<220> FEATURE:
<223> OTHER INFORMATION: Av3bM144
<220> FEATURE:
<221> NAME/KEY: VARIANT
<222> LOCATION: (1)..(27)
<223> OTHER INFORMATION: Recombinant variant of Anemonia viridis Av3 peptide

<400> SEQUENCE: 154

Lys Pro Cys Cys Pro Cys Tyr Trp Gly Gly Cys Pro Trp Gly Gln Asn
1 5 10 15

Cys Tyr Pro Glu Gly Cys Ser Gly Pro Lys Val
20 25

<210> SEQ ID NO 155
<211> LENGTH: 27
<212> TYPE: PRT
<213> ORGANISM: Artificial Sequence
<220> FEATURE:
<223> OTHER INFORMATION: Av3bM145
<220> FEATURE:
<221> NAME/KEY: VARIANT
<222> LOCATION: (1)..(27)
<223> OTHER INFORMATION: Recombinant variant of Anemonia viridis Av3 peptide

<400> SEQUENCE: 155

Lys Ser Cys Cys Pro Cys Tyr Trp Gly Gly Cys Pro Trp Gly Gln Asn
1 5 10 15

Cys Tyr Pro Glu Gly Cys Ser Gly Met Lys Val
20 25

<210> SEQ ID NO 156
<211> LENGTH: 27
<212> TYPE: PRT
<213> ORGANISM: Artificial Sequence
<220> FEATURE:
<223> OTHER INFORMATION: Av3bM149
<220> FEATURE:
<221> NAME/KEY: VARIANT
<222> LOCATION: (1)..(27)
<223> OTHER INFORMATION: Recombinant variant of Anemonia viridis Av3 peptide

<400> SEQUENCE: 156

```
Lys Ser Cys Cys Pro Cys Tyr Trp Gly Gly Cys Pro Trp Gly Gln Asn
1               5                   10                  15

Cys Tyr Pro Glu Gly Cys Ser Gly Pro Lys Phe
            20                  25
```

<210> SEQ ID NO 157
<211> LENGTH: 27
<212> TYPE: PRT
<213> ORGANISM: Artificial Sequence
<220> FEATURE:
<223> OTHER INFORMATION: Av3bM150
<220> FEATURE:
<221> NAME/KEY: VARIANT
<222> LOCATION: (1)..(27)
<223> OTHER INFORMATION: Recombinant variant of Anemonia viridis Av3 peptide

<400> SEQUENCE: 157

```
Lys Ser Cys Cys Pro Cys Tyr Trp Gly Gly Cys Pro Trp Gly Gln Asn
1               5                   10                  15

Cys Tyr Pro Glu Gly Cys Ser Gly Pro Lys Ile
            20                  25
```

<210> SEQ ID NO 158
<211> LENGTH: 26
<212> TYPE: PRT
<213> ORGANISM: Artificial Sequence
<220> FEATURE:
<223> OTHER INFORMATION: Av3bM151
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 158

```
Val Ser Cys Cys Pro Cys Tyr Trp Gly Gly Cys Pro Trp Gly Gln Asn
1               5                   10                  15

Cys Tyr Pro Glu Gly Cys Asp Gly Pro Lys
            20                  25
```

<210> SEQ ID NO 159
<211> LENGTH: 26
<212> TYPE: PRT
<213> ORGANISM: Artificial Sequence
<220> FEATURE:
<223> OTHER INFORMATION: Av3bM152
<220> FEATURE:
<221> NAME/KEY: VARIANT
<222> LOCATION: (1)..(26)
<223> OTHER INFORMATION: Recombinant variant of Anemonia viridis Av3 peptide

<400> SEQUENCE: 159

```
Ile Ser Cys Cys Pro Cys Tyr Trp Gly Gly Cys Pro Trp Gly Gln Asn
1               5                   10                  15

Cys Tyr Pro Glu Gly Cys Asp Gly Pro Lys
            20                  25


<210> SEQ ID NO 160
<211> LENGTH: 26
<212> TYPE: PRT
<213> ORGANISM: Artificial Sequence
<220> FEATURE:
<223> OTHER INFORMATION: Av3bM153
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 160

Leu Ser Cys Cys Pro Cys Tyr Trp Gly Gly Cys Pro Trp Gly Gln Asn
1               5                   10                  15

Cys Tyr Pro Glu Gly Cys Asp Gly Pro Lys
            20                  25


<210> SEQ ID NO 161
<211> LENGTH: 26
<212> TYPE: PRT
<213> ORGANISM: Artificial Sequence
<220> FEATURE:
<223> OTHER INFORMATION: Av3bM154
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 161

Lys Ser Cys Cys Pro Cys Tyr Trp Gln Gly Cys Pro Trp Gly Gln Asn
1               5                   10                  15

Cys Tyr Pro Glu Gly Cys Asp Gly Pro Lys
            20                  25


<210> SEQ ID NO 162
<211> LENGTH: 26
<212> TYPE: PRT
<213> ORGANISM: Artificial Sequence
<220> FEATURE:
<223> OTHER INFORMATION: Av3bM155
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 162

Lys Ser Cys Cys Pro Cys Tyr Trp Pro Gly Cys Pro Trp Gly Gln Asn
1               5                   10                  15

Cys Tyr Pro Glu Gly Cys Asp Gly Pro Lys
            20                  25


<210> SEQ ID NO 163
<211> LENGTH: 26
<212> TYPE: PRT
<213> ORGANISM: Artificial Sequence
<220> FEATURE:
<223> OTHER INFORMATION: Av3bM158
<220> FEATURE:
<221> NAME/KEY: VARIANT
<222> LOCATION: (1)..(26)
```

<223> OTHER INFORMATION: Recombinant variant of Anemonia viridis Av3
      peptide

<400> SEQUENCE: 163

Val Ser Cys Cys Pro Cys Tyr Trp Pro Gly Cys Pro Trp Gly Gln Asn
1               5                   10                  15

Cys Tyr Pro Glu Gly Cys Arg Gly Pro Asp
            20                  25

<210> SEQ ID NO 164
<211> LENGTH: 26
<212> TYPE: PRT
<213> ORGANISM: Artificial Sequence
<220> FEATURE:
<223> OTHER INFORMATION: Av3bM159
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 164

Ile Ser Cys Cys Pro Cys Tyr Trp Pro Gly Cys Pro Trp Gly Gln Asn
1               5                   10                  15

Cys Tyr Pro Glu Gly Cys Arg Gly Pro Asp
            20                  25

<210> SEQ ID NO 165
<211> LENGTH: 26
<212> TYPE: PRT
<213> ORGANISM: Artificial Sequence
<220> FEATURE:
<223> OTHER INFORMATION: Av3bM160
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 165

Leu Ser Cys Cys Pro Cys Tyr Trp Pro Gly Cys Pro Trp Gly Gln Asn
1               5                   10                  15

Cys Tyr Pro Glu Gly Cys Arg Gly Pro Asp
            20                  25

<210> SEQ ID NO 166
<211> LENGTH: 26
<212> TYPE: PRT
<213> ORGANISM: Artificial Sequence
<220> FEATURE:
<223> OTHER INFORMATION: Av3bM161
<220> FEATURE:
<221> NAME/KEY: VARIANT
<222> LOCATION: (1)..(26)
<223> OTHER INFORMATION: Recombinant variant of Anemonia viridis Av3
      peptide

<400> SEQUENCE: 166

Val Ser Cys Cys Pro Cys Tyr Trp Pro Gly Cys Pro Trp Gly Gln Asn
1               5                   10                  15

Cys Tyr Pro Glu Gly Cys Thr Gly Pro Thr
            20                  25

<210> SEQ ID NO 167
<211> LENGTH: 26
<212> TYPE: PRT
<213> ORGANISM: Artificial Sequence
<220> FEATURE:
<223> OTHER INFORMATION: Av3bM162
<220> FEATURE:
<221> NAME/KEY: VARIANT
<222> LOCATION: (1)..(26)
<223> OTHER INFORMATION: Recombinant variant of Anemonia viridis Av3
peptide

<400> SEQUENCE: 167

Val Ser Cys Cys Pro Cys Tyr Trp Pro Gly Cys Pro Trp Gly Gln Asn
1 5 10 15

Cys Tyr Pro Glu Gly Cys Thr Gly Pro Lys
20 25

<210> SEQ ID NO 168
<211> LENGTH: 25
<212> TYPE: PRT
<213> ORGANISM: Artificial Sequence
<220> FEATURE:
<223> OTHER INFORMATION: Av3bM163
<220> FEATURE:
<221> NAME/KEY: VARIANT
<222> LOCATION: (1)..(25)
<223> OTHER INFORMATION: Recombinant variant of Anemonia viridis Av3
peptide

<400> SEQUENCE: 168

Lys Ser Cys Cys Pro Cys Tyr Trp Gly Gly Cys Pro Trp Gly Gln Asn
1 5 10 15

Cys Tyr Pro Glu Gly Cys Ser Gly Pro
20 25

<210> SEQ ID NO 169
<211> LENGTH: 24
<212> TYPE: PRT
<213> ORGANISM: Artificial Sequence
<220> FEATURE:
<223> OTHER INFORMATION: Av3bM164
<220> FEATURE:
<221> NAME/KEY: VARIANT
<222> LOCATION: (1)..(24)
<223> OTHER INFORMATION: Recombinant variant of Anemonia viridis Av3
peptide

<400> SEQUENCE: 169

Lys Ser Cys Cys Pro Cys Tyr Trp Gly Gly Cys Pro Trp Gly Gln Asn
1 5 10 15

Cys Tyr Pro Glu Gly Cys Ser Gly
20

<210> SEQ ID NO 170
<211> LENGTH: 28
<212> TYPE: PRT
<213> ORGANISM: Artificial Sequence
<220> FEATURE:
<223> OTHER INFORMATION: Av3bM166
<220> FEATURE:
<221> NAME/KEY: VARIANT
<222> LOCATION: (1)..(28)
<223> OTHER INFORMATION: Recombinant variant of Anemonia viridis Av3
peptide

<400> SEQUENCE: 170

Lys Ser Cys Cys Pro Cys Tyr Trp Gly Gly Cys Pro Trp Gly Gln Asn
1 5 10 15

Cys Tyr Pro Glu Gly Cys Ser Gly Pro Lys Val Gln
20 25

<210> SEQ ID NO 171
<211> LENGTH: 28
<212> TYPE: PRT
<213> ORGANISM: Artificial Sequence
<220> FEATURE:
<223> OTHER INFORMATION: Av3bM167
<220> FEATURE:
<221> NAME/KEY: VARIANT
<222> LOCATION: (1)..(28)
<223> OTHER INFORMATION: Recombinant variant of Anemonia viridis Av3 peptide

<400> SEQUENCE: 171

Lys Ser Cys Cys Pro Cys Tyr Trp Gly Gly Cys Pro Trp Gly Gln Asn
1 5 10 15

Cys Tyr Pro Glu Gly Cys Ser Gly Pro Lys Val Asp
20 25

<210> SEQ ID NO 172
<211> LENGTH: 27
<212> TYPE: PRT
<213> ORGANISM: Anemonia viridis

<400> SEQUENCE: 172

Arg Ser Cys Cys Pro Cys Tyr Trp Gly Gly Cys Pro Trp Gly Gln Asn
1 5 10 15

Cys Tyr Pro Glu Gly Cys Ser Gly Pro Lys Val
20 25

<210> SEQ ID NO 173
<211> LENGTH: 24
<212> TYPE: PRT
<213> ORGANISM: Hordeum vulgare

<400> SEQUENCE: 173

Met Ala Asn Lys His Leu Ser Leu Ser Leu Phe Leu Val Leu Leu Gly
1 5 10 15

Leu Ser Ala Ser Leu Ala Ser Gly
20

<210> SEQ ID NO 174
<211> LENGTH: 27
<212> TYPE: PRT
<213> ORGANISM: Nicotiana plumbaginifolia

<400> SEQUENCE: 174

Glu Met Gly Lys Met Ala Ser Leu Phe Ala Ser Leu Leu Val Val Leu
1 5 10 15

Val Ser Leu Ser Leu Ala Ser Glu Ser Ser Ala
20 25

<210> SEQ ID NO 175
<211> LENGTH: 26
<212> TYPE: PRT
<213> ORGANISM: Nicotiana plumbaginifolia

<400> SEQUENCE: 175

Met Gly Lys Met Ala Ser Leu Phe Ala Thr Phe Leu Val Val Leu Val
1 5 10 15

Ser Leu Ser Leu Ala Ser Glu Ser Ser Ala
20 25

<210> SEQ ID NO 176

<211> LENGTH: 78
<212> TYPE: DNA
<213> ORGANISM: Nicotiana plumbaginifolia

<400> SEQUENCE: 176
atgggtaaga tggcttctct gtttgcttct ctgctggttg ttctggtttc tctgtctctg 60
gcttctgaat cttctgct 78

<210> SEQ ID NO 177
<211> LENGTH: 78
<212> TYPE: DNA
<213> ORGANISM: Nicotiana plumbaginifolia

<400> SEQUENCE: 177
atgggtaaga tggcttctct gtttgctact ttctggttg ttctggtttc tctgtctctg 60
gcttctgaat cttctgct 78

<210> SEQ ID NO 178
<211> LENGTH: 238
<212> TYPE: PRT
<213> ORGANISM: Aequorea victoria

<400> SEQUENCE: 178

Ala Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 179
<211> LENGTH: 224
<212> TYPE: PRT

<213> ORGANISM: Juniperus ashei

<400> SEQUENCE: 179

Lys Phe Asp Ile Lys Asn Gln Cys Gly Tyr Thr Val Trp Ala Ala Gly
1 5 10 15

Leu Pro Gly Gly Gly Lys Arg Leu Asp Gln Gly Gln Thr Trp Thr Val
20 25 30

Asn Leu Ala Ala Gly Thr Ala Ser Ala Arg Phe Trp Gly Arg Thr Gly
35 40 45

Cys Thr Phe Asp Ala Ser Gly Lys Gly Ser Cys Gln Thr Gly Asp Cys
50 55 60

Gly Gly Gln Leu Ser Cys Thr Val Ser Gly Ala Val Pro Ala Thr Leu
65 70 75 80

Ala Glu Tyr Thr Gln Ser Asp Gln Asp Tyr Tyr Asp Val Ser Leu Val
85 90 95

Asp Gly Phe Asn Ile Pro Leu Ala Ile Asn Pro Thr Asn Ala Gln Cys
100 105 110

Thr Ala Pro Ala Cys Lys Ala Asp Ile Asn Ala Val Cys Pro Ser Glu
115 120 125

Leu Lys Val Asp Gly Gly Cys Asn Ser Ala Cys Asn Val Phe Lys Thr
130 135 140

Asp Gln Tyr Cys Cys Arg Asn Ala Tyr Val Asp Asn Cys Pro Ala Thr
145 150 155 160

Asn Tyr Ser Lys Ile Phe Lys Asn Gln Cys Pro Gln Ala Tyr Ser Tyr
165 170 175

Ala Lys Asp Asp Thr Ala Thr Phe Ala Cys Ala Ser Gly Thr Asp Tyr
180 185 190

Ser Ile Val Phe Cys Met Ala Arg Val Ser Glu Leu Ala Phe Leu Leu
195 200 205

Ala Ala Thr Leu Ala Ile Ser Leu His Met Gln Glu Ala Gly Val Val
210 215 220

<210> SEQ ID NO 180
<211> LENGTH: 225
<212> TYPE: PRT
<213> ORGANISM: Juniperus ashei

<400> SEQUENCE: 180

Met Ala Arg Val Ser Glu Leu Ala Phe Leu Leu Ala Ala Thr Leu Ala
1 5 10 15

Ile Ser Leu His Met Gln Glu Ala Gly Val Val Lys Phe Asp Ile Lys
20 25 30

Asn Gln Cys Gly Tyr Thr Val Trp Ala Ala Gly Leu Pro Gly Gly Gly
35 40 45

Lys Arg Leu Asp Gln Gly Gln Thr Trp Thr Val Asn Leu Ala Ala Gly
50 55 60

Thr Ala Ser Ala Arg Phe Trp Gly Arg Thr Gly Cys Thr Phe Asp Ala
65 70 75 80

Ser Gly Lys Gly Ser Cys Gln Thr Gly Asp Cys Gly Gly Gln Leu Ser
85 90 95

Cys Thr Val Ser Gly Ala Val Pro Ala Thr Leu Ala Glu Tyr Thr Gln
100 105 110

Ser Asp Gln Asp Tyr Tyr Asp Val Ser Leu Val Asp Gly Phe Asn Ile
115 120 125

Pro Leu Ala Ile Asn Pro Thr Asn Ala Gln Cys Thr Ala Pro Ala Cys

```
    130                 135                 140

Lys Ala Asp Ile Asn Ala Val Cys Pro Ser Glu Leu Lys Val Asp Gly
145                 150                 155                 160

Gly Cys Asn Ser Ala Cys Asn Val Phe Lys Thr Asp Gln Tyr Cys Cys
                165                 170                 175

Arg Asn Ala Tyr Val Asp Asn Cys Pro Ala Thr Asn Tyr Ser Lys Ile
            180                 185                 190

Phe Lys Asn Gln Cys Pro Gln Ala Tyr Ser Tyr Ala Lys Asp Asp Thr
        195                 200                 205

Ala Thr Phe Ala Cys Ala Ser Gly Thr Asp Tyr Ser Ile Val Phe Cys
    210                 215                 220

Pro
225


<210> SEQ ID NO 181
<211> LENGTH: 4
<212> TYPE: PRT
<213> ORGANISM: Artificial Sequence
<220> FEATURE:
<223> OTHER INFORMATION: IGER
<220> FEATURE:
<221> NAME/KEY: MISC_FEATURE
<222> LOCATION: (1)..(4)
<223> OTHER INFORMATION: Linker

<400> SEQUENCE: 181

Ile Gly Glu Arg
1


<210> SEQ ID NO 182
<211> LENGTH: 5
<212> TYPE: PRT
<213> ORGANISM: Artificial sequence
<220> FEATURE:
<223> OTHER INFORMATION: EEKKN
<220> FEATURE:
<221> NAME/KEY: MISC_FEATURE
<222> LOCATION: (1)..(5)
<223> OTHER INFORMATION: Linker

<400> SEQUENCE: 182

Glu Glu Lys Lys Asn
1               5


<210> SEQ ID NO 183
<211> LENGTH: 8
<212> TYPE: PRT
<213> ORGANISM: Artificial sequence
<220> FEATURE:
<223> OTHER INFORMATION: ETMFKHGL
<220> FEATURE:
<221> NAME/KEY: MISC_FEATURE
<222> LOCATION: (1)..(8)
<223> OTHER INFORMATION: Linker

<400> SEQUENCE: 183

Glu Thr Met Phe Lys His Gly Leu
1               5


<210> SEQ ID NO 184
<211> LENGTH: 6
<212> TYPE: PRT
<213> ORGANISM: Artificial sequence
<220> FEATURE:
<223> OTHER INFORMATION: Linker
<220> FEATURE:
```

<221> NAME/KEY: MISC_FEATURE
<222> LOCATION: (1)..(6)
<223> OTHER INFORMATION: Synthetic peptide linker

<400> SEQUENCE: 184

Ala Leu Lys Phe Leu Val
1               5

<210> SEQ ID NO 185
<211> LENGTH: 6
<212> TYPE: PRT
<213> ORGANISM: Artificial sequence
<220> FEATURE:
<223> OTHER INFORMATION: Linker
<220> FEATURE:
<221> NAME/KEY: MISC_FEATURE
<222> LOCATION: (1)..(6)
<223> OTHER INFORMATION: Synthetic peptide linker

<400> SEQUENCE: 185

Ala Leu Lys Leu Phe Val
1               5

<210> SEQ ID NO 186
<211> LENGTH: 6
<212> TYPE: PRT
<213> ORGANISM: Artificial sequence
<220> FEATURE:
<223> OTHER INFORMATION: Linker
<220> FEATURE:
<221> NAME/KEY: MISC_FEATURE
<222> LOCATION: (1)..(6)
<223> OTHER INFORMATION: Synthetic peptide linker

<400> SEQUENCE: 186

Ile Phe Val Arg Leu Arg
1               5

<210> SEQ ID NO 187
<211> LENGTH: 6
<212> TYPE: PRT
<213> ORGANISM: Artificial sequence
<220> FEATURE:
<223> OTHER INFORMATION: Linker
<220> FEATURE:
<221> NAME/KEY: MISC_FEATURE
<222> LOCATION: (1)..(6)
<223> OTHER INFORMATION: Synthetic peptide linker

<400> SEQUENCE: 187

Leu Phe Ala Ala Pro Phe
1               5

<210> SEQ ID NO 188
<211> LENGTH: 8
<212> TYPE: PRT
<213> ORGANISM: Artificial sequence
<220> FEATURE:
<223> OTHER INFORMATION: Linker
<220> FEATURE:
<221> NAME/KEY: MISC_FEATURE
<222> LOCATION: (1)..(8)
<223> OTHER INFORMATION: Synthetic peptide linker

<400> SEQUENCE: 188

Ala Leu Lys Phe Leu Val Gly Ser
1               5

<210> SEQ ID NO 189

<211> LENGTH: 8
<212> TYPE: PRT
<213> ORGANISM: Artificial sequence
<220> FEATURE:
<223> OTHER INFORMATION: Linker
<220> FEATURE:
<221> NAME/KEY: MISC_FEATURE
<222> LOCATION: (1)..(8)
<223> OTHER INFORMATION: Synthetic peptide linker

<400> SEQUENCE: 189

Ala Leu Lys Leu Phe Val Gly Ser
1               5

<210> SEQ ID NO 190
<211> LENGTH: 8
<212> TYPE: PRT
<213> ORGANISM: Artificial sequence
<220> FEATURE:
<223> OTHER INFORMATION: Linker
<220> FEATURE:
<221> NAME/KEY: MISC_FEATURE
<222> LOCATION: (1)..(8)
<223> OTHER INFORMATION: Synthetic peptide linker

<400> SEQUENCE: 190

Ile Phe Val Arg Leu Arg Gly Ser
1               5

<210> SEQ ID NO 191
<211> LENGTH: 8
<212> TYPE: PRT
<213> ORGANISM: Artificial sequence
<220> FEATURE:
<223> OTHER INFORMATION: Linker
<220> FEATURE:
<221> NAME/KEY: MISC_FEATURE
<222> LOCATION: (1)..(8)
<223> OTHER INFORMATION: Synthetic peptide linker

<400> SEQUENCE: 191

Leu Phe Ala Ala Pro Phe Gly Ser
1               5

<210> SEQ ID NO 192
<211> LENGTH: 8
<212> TYPE: PRT
<213> ORGANISM: Artificial sequence
<220> FEATURE:
<223> OTHER INFORMATION: Linker
<220> FEATURE:
<221> NAME/KEY: MISC_FEATURE
<222> LOCATION: (1)..(8)
<223> OTHER INFORMATION: Synthetic peptide linker

<400> SEQUENCE: 192

Leu Phe Val Arg Leu Arg Gly Ser
1               5

<210> SEQ ID NO 193
<211> LENGTH: 6
<212> TYPE: PRT
<213> ORGANISM: Artificial sequence
<220> FEATURE:
<223> OTHER INFORMATION: Linker
<220> FEATURE:
<221> NAME/KEY: MISC_FEATURE
<222> LOCATION: (1)..(6)
<223> OTHER INFORMATION: Synthetic peptide linker

<400> SEQUENCE: 193

Leu Gly Glu Arg Gly Ser
1 5

<210> SEQ ID NO 194
<211> LENGTH: 23
<212> TYPE: DNA
<213> ORGANISM: Artificial sequence
<220> FEATURE:
<223> OTHER INFORMATION: rt-Klprc1-LB1
<220> FEATURE:
<221> NAME/KEY: misc_feature
<222> LOCATION: (1)..(23)
<223> OTHER INFORMATION: Synthetic primer sequence

<400> SEQUENCE: 194
gtacgcatcg ggccaagatt tcc 23

<210> SEQ ID NO 195
<211> LENGTH: 30
<212> TYPE: DNA
<213> ORGANISM: Artificial sequence
<220> FEATURE:
<223> OTHER INFORMATION: rt-Klprc1-LB2
<220> FEATURE:
<221> NAME/KEY: misc_feature
<222> LOCATION: (1)..(30)
<223> OTHER INFORMATION: Synthetic primer sequence

<400> SEQUENCE: 195
cggttagacc gttaccgata agaacagaag 30

<210> SEQ ID NO 196
<211> LENGTH: 24
<212> TYPE: DNA
<213> ORGANISM: Artificial Sequence
<220> FEATURE:
<223> OTHER INFORMATION: rt-URA3c-LB1
<220> FEATURE:
<221> NAME/KEY: misc_feature
<222> LOCATION: (1)..(24)
<223> OTHER INFORMATION: Synthetic primer sequence

<400> SEQUENCE: 196
ttccaagggt tctctagcac acgg 24

<210> SEQ ID NO 197
<211> LENGTH: 25
<212> TYPE: DNA
<213> ORGANISM: Artificial Sequence
<220> FEATURE:
<223> OTHER INFORMATION: rt-URA3c-LB2
<220> FEATURE:
<221> NAME/KEY: misc_feature
<222> LOCATION: (1)..(25)
<223> OTHER INFORMATION: Synthetic primer sequence

<400> SEQUENCE: 197
cctacacctg gggtcatgat tagcc 25

<210> SEQ ID NO 198
<211> LENGTH: 29
<212> TYPE: DNA
<213> ORGANISM: Artificial Sequence
<220> FEATURE:
<223> OTHER INFORMATION: rt-AmdS-LB1: forward
<220> FEATURE:
<221> NAME/KEY: misc_feature
<222> LOCATION: (1)..(29)
<223> OTHER INFORMATION: Synthetic primer sequence

<400> SEQUENCE: 198
aagggaactc gatgaatact acgcaaagc 29

<210> SEQ ID NO 199
<211> LENGTH: 29
<212> TYPE: DNA
<213> ORGANISM: Artificial sequence
<220> FEATURE:
<223> OTHER INFORMATION: rt-AmdS-LB2: reverse
<220> FEATURE:
<221> NAME/KEY: misc_feature
<222> LOCATION: (1)..(29)
<223> OTHER INFORMATION: Synthetic primer sequence

<400> SEQUENCE: 199
cgtacttgtt tagccatgag atgtagccc 29

<210> SEQ ID NO 200
<211> LENGTH: 1608
<212> TYPE: DNA
<213> ORGANISM: Kluyveromyces lactis

<400> SEQUENCE: 200
atgagaactg ctagtgtttt gtgtgctttg gctggttgcg cgtccgcttt aagcgttcaa 60
aataagttac caggaagaac tgccttggat aaagcaattg acgctttagg gttaagttca 120
tctgatgttt taagctctct tcctaaccat ttgaagaccg cttggaacga aatggggatg 180
ttgttcccac aagaagctgg tcaattggag tttttatcca aaccaagagg taagattacc 240
aagcacgata agtgggatta cgtggtgaaa ccagagagtt tcgtttctac tgcaaacgtt 300
aacaacgata acgttgggaa ctaccaattg cgtgtgaaga agattaagga ccctaaggtc 360
ttgggtgtgg acccagatgt taagcaatac tctggttatt tggacgttga agatgaggat 420
aagcatttct tttattggtt ctttgaatcc agaaacgatc caaagaatga ccctatcatt 480
ctttggttga acggtggccc tggttgttct tctttgaccg gtttgttctt cgaattgggt 540
ccatcttctg ttggtgaaga gattaaacca atttacaacc cacattcttg gaatagtaac 600
gcttctgtga tctttttgga tcaaccagtt aacgttggtt actcttattc ttcctctgaa 660
ggtgtctcaa acaccgttgc tgccggtaaa gacgtttacg cattcttgca attgttcttc 720
caacaattcc cagagtacgc atcgggccaa gatttccata tcgctggtga atcttatgct 780
ggtcattata tcccagtgtt cgctactgaa attttatctc atccaactga agaacgttct 840
ttcaacttga cttctgttct tatcggtaac ggtctaaccg atccattaag ccaatatcca 900
tactacgaac caatggcttg tggtgaaggt ggtgaaccat ccgtattgga accagaacaa 960
tgtgacaata tgttggaaac tttaccaaga tgtctaaact tgatccaatc ctgttacgaa 1020
tacgaatccg tttggtcttg tgttccagcc tccatctatt gtaataacgc tcaaatgggt 1080
ccttatcaaa gtactggtaa gaacgtttac gatattcgta aagaatgtca aggtgaattg 1140
tgttacgatg aaatgaaata catggacgaa tatttgaact tggatttcgt taaggaagcc 1200
gttggtgctg aagttgacaa ctatgaatcg tgtaacttcg acattaacag aaacttctta 1260
tttgcaggtg attggatgaa accataccac aagcacgtta ccgaattgtt ggaacaagat 1320
cttccagttc taatttacgc aggtgacaag gatttcatct gtaactggtt gggtaaccaa 1380
gcttggacca acttattgcc atataaggat gccgaagaat ttgctaaaca accagttaag 1440
aattgggtta cttctgttgg taagaaggcc ggtaaggtta agaactttga caagttcacc 1500

-continued

```
ttcctaagag tatacggtgc tggacacatg gtaccattcg accaaccaga aaatgctttg   1560

gatatggtta atgactgggt taacggtaag tttgacttcg agcattag                1608


<210> SEQ ID NO 201
<211> LENGTH: 1686
<212> TYPE: DNA
<213> ORGANISM: Kluyveromyces lactis

<400> SEQUENCE: 201

atgaagttcg aaaatacatt attgactata accgcattgt ctaccgtggc tactgctttg     60

gttatccctg aagttaatag ggaaaacaag catggtgaca agagcgttgc catcaaagat    120

catgcttctt ctgatttgga taagcctcaa catcatgcta atggcaaggc tcgttctaag    180

tctcgtggtc gctgcgcaga ctccaagaaa ttcgacaagc tacgtccagt cgacgatgct    240

tcagctattt tagctccact ttctacagtt aatgatattg ccaacaagat tcctaatcgt    300

tacatcattg tctttaagaa agatgcctct gcagatgaag tgaagttcca tcaagaacta    360

gtctctgtcg aacatgccaa ggcactaggt tccttagctg acaatgaccc attcttcaca    420

gcaacttccg gtgaacatag tgaatttggt gtcaaagcac actctttgga aggtggtatt    480

caagactctt ttgatattgc cggttccctt tctggttatg ttggctactt cacaaaagaa    540

gttatcgatt tcatcagaag aagcccattg gttgaatttg ttgaagaaga ttctatggtt    600

ttctctaata gtttcaatac ccaaaacagt gctccttggg gtctagctcg tatttctcat    660

cgtgaaaagt tgaatttagg atctttcaac aagtacttgt atgatgatga cgctggtaaa    720

ggtgttactg cttacgttgt tgacactggt gtcaatgtta accataagga ctttgatggc    780

agagctgttt ggggtaagac tattccaaaa gatgatccag atgtagatgg aaatggtcac    840

ggtacccact gtgctggtac catcggttcg gttcattatg gtgttgctaa gaatgctgat    900

atagttgccg ttaaggtttt gagatctaat ggttctggta ccatgtctga tgttgttaaa    960

ggtgtcgaat atgttgccga agcacacaag aaagctgttg aagaacaaaa gaaagggttc   1020

aagggttcaa ctgctaacat gtctttgggt ggtggtaaat ctccagcctt ggatttggcc   1080

gtcaacgccg ctgttaaggc aggtgttcat tttgctgttg ctgccggtaa tgagaaccaa   1140

gatgcttgta acacttcgcc tgccgcggct gagaatgcta tcacggttgg tgcctccaca   1200

ttaagtgatg aaagagctta cttttccaat tggggtaaat gtgtcgacat ctttggtccg   1260

ggtttgaata tcttatctac ctacattggt tctgatactg ctactgctac cttgtctggt   1320

acttctatgg ccactcctca tgttgtcggt ttgctaacat atttcttgtc cttgcaacca   1380

gatgctgata gtgaatattt ccatgccgct ggcggtatta ctccttccca actcaagaag   1440

aagttaattg atttctctac taagaacgta ttgtccgatc tacctgaaga taccgtgaac   1500

tacttgattt acaacggtgg tggtcaagat ttggatgacc tatggggtaa ggattactct   1560

attggaaaag aaccatctgc caaccctgaa ttcagcttgg aaagcttgat taactctttg   1620

gattcaaaga ctgatgctat ctttgacgac gttagacagt tgttggacca atttaatatc   1680

atctaa                                                              1686
```